(12) United States Patent
Liang et al.

(10) Patent No.: US 11,066,464 B2
(45) Date of Patent: Jul. 20, 2021

(54) ANTI-MALARIAL ANTIBODIES THAT BIND CIRCUMSPOROZOITE PROTEIN

(71) Applicants: KYMAB LIMITED, Cambridge (GB); ATRECA, INC., Redwood City, CA (US)

(72) Inventors: Qi Liang, Cambridge (GB); Sean Matthew Carroll, Redwood City, CA (US); Daniel Eric Emerling, Redwood City, CA (US); Allan Bradley, Cambridge (GB); Paul Kellam, Cambridge (GB); Špela Binter, Cambridge (GB); Simon James Watson, Cambridge (GB)

(73) Assignees: KYMAB LIMITED, Cambridge (GB); ATRECA, INC., Redwood City, CA (US)

( * ) Notice: Subject to any disclaimer, the term of this patent is extended or adjusted under 35 U.S.C. 154(b) by 50 days.

(21) Appl. No.: 15/977,762

(22) Filed: May 11, 2018

(65) Prior Publication Data

US 2018/0362628 A1   Dec. 20, 2018

Related U.S. Application Data

(63) Continuation-in-part of application No. PCT/GB2017/050786, filed on Mar. 21, 2017.

(60) Provisional application No. 62/311,059, filed on Mar. 21, 2016, provisional application No. 62/504,863, filed on May 11, 2017, provisional application No. 62/560,971, filed on Sep. 20, 2017, provisional application No. 62/564,066, filed on Sep. 27, 2017.

(51) Int. Cl.
| | |
|---|---|
| C07K 16/20 | (2006.01) |
| A61P 33/06 | (2006.01) |
| C07K 14/445 | (2006.01) |
| G01N 33/569 | (2006.01) |
| A61K 39/00 | (2006.01) |

(52) U.S. Cl.
CPC ............ *C07K 16/205* (2013.01); *A61P 33/06* (2018.01); *C07K 14/445* (2013.01); *G01N 33/569* (2013.01); *A61K 2039/505* (2013.01); *C07K 2317/21* (2013.01); *C07K 2317/34* (2013.01); *C07K 2317/565* (2013.01); *C07K 2317/76* (2013.01); *C07K 2317/92* (2013.01); *G01N 2333/445* (2013.01); *G01N 2469/10* (2013.01)

(58) Field of Classification Search
None
See application file for complete search history.

(56) References Cited

U.S. PATENT DOCUMENTS

| | | | | |
|---|---|---|---|---|
| 2005/0112139 | A1* | 5/2005 | Karp | A61K 9/0014 424/188.1 |
| 2007/0117774 | A1* | 5/2007 | Zanetti | C12N 15/8509 514/44 R |
| 2011/0065902 | A1 | 3/2011 | Sleeman et al. | |
| 2012/0093818 | A1 | 4/2012 | Jackson et al. | |

FOREIGN PATENT DOCUMENTS

| | | |
|---|---|---|
| WO | WO-02060919 A2 | 8/2002 |
| WO | WO-2007003384 A1 | 1/2007 |
| WO | WO-2011004192 A1 | 1/2011 |
| WO | WO-2015075070 A1 | 5/2015 |
| WO | WO-2016033547 A1 | 3/2016 |
| WO | WO-2017163049 A1 | 9/2017 |
| WO | WO-2018209265 A1 | 11/2018 |

OTHER PUBLICATIONS

Foquet et al. The Journal of Clinical Investigation vol. 124, p. 140-144, 2014.*
Nardin et al. Infection and Immunity, Nov. 2004, vol. 72, No. 11, p. 6519-6527.*
Definition of kit: a set of articles or equipment needed for a specific purpose. Retrieved Nov. 25, 2019 from https://www.lexico.com/en/definition/kit.*
Almagro et al. Frontiers in Bioscience 13:1619-1633, 2008.*
Edwards et al. J. Mol. Biol. (2003) 334, 103-118.*
Anker, R., et al., "VH and VL Region Structure of Antibodies That Recognize the (NANP)3 Dodecapeptide Sequence in the Circumsporozoite Protein of Plasmodium Falciparum," European Journal of Immunology 20(12):2757-2761, Wiley-VCH, Germany (Dec. 1990).
Bruna-Romero, O., et al., "Detection of Malaria Liver-stages in Mice Infected Through the Bite of a Single Anopheles Mosquito Using a Highly Sensitive Real-time PCR," International Journal for Parasitology 31(13):1499-1502, Elsevier Science, England (Nov. 2001).
Burkot, T.R., et al., "Fine Specificities of Monoclonal Antibodies against the Plasmodium Falciparum Circumsporozoite Protein: Recognition of both Repetitive and Non-Repetitive Regions," Parasite Immunology 13(2): 161-170, Oxford, Wiley, England (Mar. 1991).

(Continued)

*Primary Examiner* — Oluwatosin A Ogunbiyi
(74) *Attorney, Agent, or Firm* — Sterne, Kessler, Goldstein & Fox P.L.L.C.

(57) ABSTRACT

Antibodies that bind to the circumsporozoite protein (CSP) of *Plasmodium falciparum*. Use of such antibodies as anti-malarial agents, to confer protection against infection by malarial parasites such as *P. falciparum* by insect vector transmission. Diagnosis of malaria using anti-CSP antibodies. Methods of determining efficacy of candidate vaccine compositions in development and testing of anti-malarial vaccines.

13 Claims, 30 Drawing Sheets

Specification includes a Sequence Listing.

(56) References Cited

OTHER PUBLICATIONS

Dall'Acqua, W.F., et al., "Properties of Human IgG1s Engineered for Enhanced Binding to the Neonatal Fc Receptor (FcRn)," The Journal of Biological Chemistry 281(33):23514-23524, American Society for Biochemistry and Molecular Biology, United States (2006).
Database EPO Proteins, "Sequence 253 from Patent W02007120767," Database accession No. FB656442 sequence, accessed from EBI accession No. EPOP:FB656442, accessed on Oct. 31, 2008.
Database Geneseq, "Anti-OprF/Opri antibody heavy chain variable region. SEQ ID 41," Database accession No. BCM88055 sequence, accessed from EBI accession No. GSP:BCM88055, accessed on Mar. 3, 2016.
Del Giudice, G., et al., "Detection of Human Antibodies Against Plasmodium Falciparum Sporozoites Using Synthetic Peptides," Journal of Clinical Microbiology 25(1):91-96, American Society for Microbiology, United States (Jan. 1987).
Douglass, A.N., et al., "Flow Cytometry-based Assessment of Antibody Function Against Malaria Pre-erythrocytic Infection," Methods in Molecular Biology 1325:49-58, Humana Press, United States (2015).
Ejigiri, I., et al., "Shedding of TRAP by a Rhomboid Protease From the Malaria Sporozoite Surface Is Essential for Gliding Motility and Sporozoite Infectivity," PLoS Pathog 8(7):e1002725, Public Library of Science, United States (2012).
Espinosa, D.A., et al., "Development of a Chimeric *Plasmodium berghei* Strain Expressing the Repeat Region of the *P. vivax* Circumsporozoite Protein for in Vivo Evaluation of Vaccine Efficacy," Infection and Immunity 81(8):2882-2887, American Society for Microbiology, United States (Aug. 2013).
Genbank, "Immunoglobulin lambda-1 variable region, partial [*Homo sapiens*]," accession No. CAE18330.1, accessed at https://www.ncbi.nlm.nih.gov/protein/CAE18330, Jul. 2016.
Genbank, "MCT022F09_171091 Ice plant *Lambda* Uni-Zap XR expression library, 5 days 0.5 M NaCl treatment, Crassulacean acid metabolism, phase IV (5:30 PM). *Mesembryanthemum crystallinum* cDNA clone MCT022F09 5, mRNA sequence," accession No. CA838998, accessed at https://www.ncbi.nlm.nih.gov/nucest/26566763/, Dec. 2002.
Genbank, "Plasmodium Falciparum MAL3P2, Complete Sequence," accession No. AL034558.3, accessed at https://www.ncbi.nlm.nih.gov/nuccore/AL034558.3?report=genbank, Apr. 2005.
Goodson, J.M., "Dental Applications," in Medical Applications of Controlled Release, vol. 2, Langer, R.S. and Wise, D.L., eds., pp. 115-138, CRC Press, Inc., United States (1984).
Griffin, J.T., et al., "Gradual Acquisition of Immunity to Severe Malaria With Increasing Exposure," Proceedings. Biological Sciences 282(1801), Royal Society of London, England (Feb. 2015).
Herrera, R., et al., "Reversible Conformational Change in the Plasmodium Falciparum Circumsporozoite Protein Masks Its Adhesion Domains," Infection and Immunity 83(10):3771-3780, American Society for Microbiology, United States (Oct. 2015).
Herrington, D.A., et al., "Safety and Immunogenicity in Man of a Synthetic Peptide Malaria Vaccine Against Plasmodium Falciparum Sporozoites," Nature 328(6127):257-259, Nature Publishing Group, England (Jul. 1987).
Hollingdale, M.R., et al., "Inhibition of Entry of Plasmodium Falciparum and P. Vivax Sporozoites Into Cultured Cells; An in Vitro Assay of Protective Antibodies," Journal of Immunology 132(2):909-913, American Association of Immunologists, United States (Feb. 1984).
Imwong, M., et al., "The Spread of Artemisinin-resistant Plasmodium Falciparum in the Greater Mekong Subregion: A Molecular Epidemiology Observational Study," The Lancet. Infectious Diseases 17(5):491-497, The Lancet Pub. Group, United States (May 2017).
International Search Report and Written Opinion for Application No. PCT/GB2017/050786, European patent office, Rijswijk, dated Jul. 14, 2017, 14 pages.
International Search Report and Written Opinion for Application No. PCT/US2018/32366, dated Aug. 24, 2018, 7 pages.
Kastenmuller, K., et al., "Full-length Plasmodium Falciparum Circumsporozoite Protein Administered With Long-chain Poly(I·c) or the Toll-like Receptor 4 Agonist Glucopyranosyl Lipid Adjuvant-stable Emulsion Elicits Potent Antibody and CD4+ T Cell Immunity and Protection in Mice," Infection and Immunity 81(3):789-800, American Society for Microbiology, United States (Mar. 2013).
Kublin, J.G., et al., "Complete Attenuation of Genetically Engineered Plasmodium Falciparum Sporozoites in Human Subjects," Science Translational Medicine 9(371), American Association for the Advancement of Science, United States (Jan. 2017).
Sanjai, K., et al., "A Chemiluminescent-western Blot Assay for Quantitative Detection of Plasmodium Falciparum Circumsporozoite Protein," Journal of Immunological Methods 390(1-2):99-105, Elsevier, Netherlands (Apr. 2013).
Lee, E.C., et al., "Complete Humanization of the Mouse Immunoglobulin Loci Enables Efficient Therapeutic Antibody Discovery," Nature Biotechnology 32(4):356-363, Nature America Publishing, United States (Apr. 2014).
Nardin, E.H., et al., "Circumsporozoite Proteins of Human Malaria Parasites *Plasmodium falciparum* and *Plasmodium vivax*," The Journal of Experimental Medicine 156(1):20-30, Rockefeller University Press, United States (Jul. 1982).
Porter, M.D., et al., "Transgenic Parasites Stably Expressing Full-length *Plasmodium falciparum* Circumsporozoite Protein as a Model for Vaccine Down-selection in Mice Using Sterile Protection as an Endpoint," Clinical and Vaccine Immunology 20(6):803-810, American Society for Microbiology, United States (Jun. 2013).
Przysiecki, C., et al., "Sporozoite Neutralizing Antibodies Elicited in Mice and Rhesus Macaques Immunized With a *Plasmodium falciparum* Repeat Peptide Conjugated to Meningococcal Outer Membrane Protein Complex," Frontiers in Cellular and Infection Microbiology 2:1-11, Frontiers Media SA, Switzerland (Nov. 2012).
Sack, B.K., et al., "Model for in Vivo Assessment of Humoral Protection Against Malaria Sporozoite Challenge by Passive Transfer of Monoclonal Antibodies and Immune Serum," Infection and Immunity 82(2):808-817, American Society for Microbiology, United States (Feb. 2014).
Sefton, M.V., "Implantable Pumps," Critical Reviews in Biomedical Engineering 14(3):201-240, Begell House, United States (1987).
Zavala, F., et al., "Circumsporozoite Proteins of Malaria Parasites Contain a Single Immunodominant Region With Two or More Identical Epitopes," The Journal of Experimental Medicine 157(6):1947-1957, Rockefeller University Press, United States (Jun. 1983).
Zou, X., et al., "Towards an Optimized Inhibition of Liver Stage Development Assay (ILSDA) for Plasmodium Falciparum," Malaria Journal 12:394, BioMed Central, England (Nov. 2013).
International Preliminary Report on Patentability for Application No. PCT/GB2017/050786, European patent office, Geneva, Switzerland, dated Sep. 25, 2018, 9 pages.
Vaughan, A.M., et al., "A transgenic *Plasmodium falciparum* NF54 strain that expresses GFP-Luciferase throughout the parasite life cycle," Molecular & Biochemical Parasitology 186:143-147, Elsevier, Netherlands (2012).
International Preliminary Report on Patentability for International Application No. PCT/US2018/032366, The International Bureau of WIPO, dated Nov. 12, 2019, 6 pages.

\* cited by examiner

| clone pick | h_v | h_d | h_j | Kymouse | h_c | h_vd_n_nt* | h_dj_n_nt† | l_v | l_j | l_c | l_vj_n_nt‡ |
|---|---|---|---|---|---|---|---|---|---|---|---|
| 666 | IGHV1-3 | IGHD3-10 | IGHJ6 | h1 mice | IGHG1 | TGAA (SEQ ID NO:542) | G | IGLV2-23 | IGLJ3 | IGLC2 | |
| 667 | IGHV1-3 | IGHD3-9 | IGHJ6 | h1 mice | IGHG1 | TTCTTT (SEQ ID NO:543) | GCCAGTCTATC (SEQ ID NO:545) | IGLV2-23 | IGLJ3 | IGLC2 | GC |
| 668 | IGHV1-3 | IGHD4-11 | IGHJ6 | h1 mice | IGHG1 | TGGGTTTGTCCT (SEQ ID NO:544) | ACTTGTTCTGGT (SEQ ID NO:546) | IGLV2-23 | IGLJ3 | IGLC2 | |
| 669 | IGHV1-3 | IGHD2-2 | IGHJ6 | h1 mice | IGHG3 | T | CCG | IGLV2-23 | IGLJ3 | IGLC7 | |

\* non-germline junctional nucleotide additions at the V-D junction in the heavy chain † non-germline junctional nucleotide additions at the D-J junction in the heavy chain ‡ non-germline junctional nucleotide additions at the V-J junction in the light chain

FIG. 4

Mouse infected *P. bergheri* expressing full-length *P. falciparum* Ag A used to 'load' mosquitos Mouse 'loaded' with MAb 667 or 668 infected via mosquito biting

FIG. 5

```
          ClaI      SpeI  PacI                 KpnI  NdeI
      CGAATTGGGGATCGATCCACTAGTTAATTAACGCGATGTAAGGTACCATATGCTGTTTCA SEQ ID NO: 41
  1   ------+---------+---------+---------+---------+---------+
      GCTTAACCCCTAGCTAGGTGATCAATTAATTGCGCTACATTCCATGGTATACGACAAAGT SEQ ID NO: 538
                                                      M  L  F  Q  SEQ ID NO: 42

AGAATATCAGTGCTATGGCAGCAGCAGCAACACCCGTGTGCTGAACGAGCTGAACTATGA SEQ ID NO: 41
  61  ------+---------+---------+---------+---------+---------+
      TCTTATAGTCACGATACCGTCGTCGTCGTTGTGGGCACACGACTTGCTCGACTTGATACT SEQ ID NO: 538
       E  Y  Q  C  Y  G  S  S  S  N  T  R  V  L  N  E  L  N  Y  D  SEQ ID NO: 42

TAACGCGGGCACCAACCTGTATAACGAGCTGGAAATGAACTATTACGGCAAGCAGGAAAA SEQ ID NO: 41
 121  ------+---------+---------+---------+---------+---------+
      ATTGCGCCCGTGGTTGGACATATTGCTCGACCTTTACTTGATAATGCCGTTCGTCCTTTT SEQ ID NO: 538
       N  A  G  T  N  L  Y  N  E  L  E  M  N  Y  Y  G  K  Q  E  N  SEQ ID NO: 42

CTGGTACAGCCTGAAAAAAAACAGCCGTAGCCTGGGCGAAAACGATGATGGCAACAACAA SEQ ID NO: 41
 181  ------+---------+---------+---------+---------+---------+
      GACCATGTCGGACTTTTTTTTGTCGGCATCGGACCCGCTTTTGCTACTACCGTTGTTGTT SEQ ID NO: 538
       W  Y  S  L  K  K  N  S  R  S  L  G  E  N  D  D  G  N  N  N  SEQ ID NO: 42

EagI
      CAACGGCGATAACGGCCGTGAAGGCAAAGATGAAGATAAACGCGACGGCAATAACGAAGA SEQ ID NO: 41
 241  ------+---------+---------+---------+---------+---------+
      GTTGCCGCTATTGCCGGCACTTCCGTTTCTACTTCTATTTGCGCTGCCGTTATTGCTTCT SEQ ID NO: 538
       N  G  D  N  G  R  E  G  K  D  E  D  K  R  D  G  N  N  E  D  SEQ ID NO: 42

TAACGAGAAACTGCGTAAACCGAAACACAAAAAACTGAAACAGCCGGGCGATGGCAATCC SEQ ID NO: 41
 301  ------+---------+---------+---------+---------+---------+
      ATTGCTCTTTGACGCATTTGGCTTTGTGTTTTTTGACTTTGTCGGCCCGCTACCGTTAGG SEQ ID NO: 538
       N  E  K  L  R  K  P  K  H  K  K  L  K  Q  P  G  D  G  N  P  SEQ ID NO: 42

AccI
             SalI
             HincII
      GGACCCTAATGCGAATCCAAATGTCGACCCTAATGCCAATCCGAATGTAGATCCGAACGC SEQ ID NO: 41
 361  ------+---------+---------+---------+---------+---------+
      CCTGGGATTACGCTTAGGTTTACAGCTGGGATTACGGTTAGGCTTACATCTAGGCTTGCG SEQ ID NO: 538
       D  P  N  A  N  P  N  V  D  P  N  A  N  P  N  V  D  P  N  A  SEQ ID NO: 42

BamHI
      GAATCCGAACGTGGATCCAAATGCAAATCCCAATGCCAATCCAAATGCAAACCCAAACGC SEQ ID NO: 41
 421  ------+---------+---------+---------+---------+---------+
      CTTAGGCTTGCACCTAGGTTTACGTTTAGGGTTACGGTTAGGTTTACGTTTGGGTTTGCG SEQ ID NO: 538
       N  P  N  V  D  P  N  A  N  P  N  A  N  P  N  A  N  P  N  A  SEQ ID NO: 42

GAATCCCAATGCCAATCCCAACGCAAATCCAAATGCGAACCCAAATGCAAATCCCAACGC SEQ ID NO: 41
 481  ------+---------+---------+---------+---------+---------+
      CTTAGGGTTACGGTTAGGGTTGCGTTTAGGTTTACGCTTGGGTTTACGTTTAGGGTTGCG SEQ ID NO: 538
       N  P  N  A  N  P  N  A  N  P  N  A  N  P  N  A  N  P  N  A  SEQ ID NO: 42
```

FIG. 6A

```
541  AAATCCCAATGCGAACCCCAATGCCAATCCCAACGCAAATCCAAATGCCAACCCTAATGC  SEQ ID NO: 41
     TTTAGGGTTACGCTTGGGGTTACGGTTAGGGTTGCGTTTAGGTTTACGGTTGGGATTACG  SEQ ID NO: 538
      N  P  N  A  N  P  N  A  N  P  N  A  N  P  N  A  N  P  N  A   SEQ ID NO: 42

601  AAATCCAAATGCTAATCCAAATGTAGATCCTAACGCTAACCCAAATGCTAACCCTAACGC  SEQ ID NO: 41
     TTTAGGTTTACGATTAGGTTTACATCTAGGATTGCGATTGGGTTTACGATTGGGATTGCG  SEQ ID NO: 538
      N  P  N  A  N  P  N  V  D  P  N  A  N  P  N  A  N  P  N  A   SEQ ID NO: 42

661  AAACCCTAATGCAATCCTAATGCCAATCCAAACGCAATCCAACGCGAACCCAAATGC    SEQ ID NO: 41
     TTTGGGATTACGGTTAGGATTACGGTTAGGTTTGCGTTAGGTTGCGCTTGGGTTTACG   SEQ ID NO: 538
      N  P  N  A  N  P  N  A  N  P  N  A  N  P  N  A  N  P  N  A  SEQ ID NO: 42

721  CAACCCTAACGCGAATCCTAATGCCAATCCCAATGCCAATCCAAATGCCAATCCGAACGC  SEQ ID NO: 41
     GTTGGGATTGCGCTTAGGATTACGGTTAGGGTTACGGTTAGGTTTACGGTTAGGCTTGCG  SEQ ID NO: 538
      N  P  N  A  N  P  N  A  N  P  N  A  N  P  N  A  N  P  N  A   SEQ ID NO: 42

781  GAATCCGAATGCAATCCGAATGCTAACCCTAATGCCAACCCCAATGCCAACCCCAATGC   SEQ ID NO: 41
     CTTAGGCTTACGTTAGGCTTACGATTGGGATTACGGTTGGGGTTACGGTTGGGGTTACG   SEQ ID NO: 538
      N  P  N  A  N  P  N  A  N  P  N  A  N  P  N  A  N  P  N  A   SEQ ID NO: 42

841  TAATCCCAACGCAAACCCTAACAAAAACAACCAGGGCAACGGCCAGGGCCATAACATGCC  SEQ ID NO: 41
     ATTAGGGTTGCGTTTGGGATTGTTTTTGTTGGTCCCGTTGCCGGTCCCGGTATTGTACGG  SEQ ID NO: 538
      N  P  N  A  N  P  N  K  N  N  Q  G  N  G  Q  G  H  N  M  P   SEQ ID NO: 42

901  GAACGATCCGAACCCGTAACGTGGATGAAAACGCGAACGCGAACAACGCGGTGAAAAACAA  SEQ ID NO: 41
     CTTGCTAGGCTTGGGCATTGCACCTACTTTTTGCGCTTGCGCTTGTTGCGCCACTTTTTGTT SEQ ID NO: 538
      N  D  P  N  R  N  V  D  E  N  A  N  A  N  N  A  V  K  N  N   SEQ ID NO: 42

961  CAACAACGAAGAACCGAGCGATAAACACATCGAAAAATACCTGAAAAAGATCCAGAACAG  SEQ ID NO: 41
     GTTGTTGCTTCTTGGCTCGCTATTTGTGTAGCTTTTTATGGACTTTTTCTAGGTCTTGTC  SEQ ID NO: 538
      N  N  E  E  P  S  D  K  H  I  E  K  Y  L  K  K  I  Q  N  S   SEQ ID NO: 42

BsaI            BspMI
1021 CCTGAGCACCGAATGGTCTCCGTGCAGCGTGACCTGCGGCAACGGCATTCAGGTGCGTAT  SEQ ID NO: 41
     GGACTCGTGGCTTACCAGAGGCACGTCGCACTGGACGCCGTTGCCGTAAGTCCACGCATA  SEQ ID NO: 538
      L  S  T  E  W  S  P  C  S  V  T  C  G  N  G  I  Q  V  R  I   SEQ ID NO: 42

1081 TAAACCGGGCAGCGCGAACAAACCGAAAGATGAGCTGGATTACGAAAACGACATCGAAAA  SEQ ID NO: 41
     ATTTGGCCCGTCGCGCTTGTTTGGCTTTCTACTCGACCTAATGCTTTTGCTGTAGCTTTT  SEQ ID NO: 538
      K  P  G  S  A  N  K  P  K  D  E  L  D  Y  E  N  D  I  E  K   SEQ ID NO: 42

1141 AAAAATCTGCAAAATGGAAAAATGCAGCAGCGTGTTTAACCTGGTGAACAGCAGCATTGG  SEQ ID NO: 41
     TTTTTAGACGTTTTACCTTTTTACGTCGTCGCACAAATTGGACCACTTGTCGTCGTAACC  SEQ ID NO: 538
      K  I  C  K  M  E  K  C  S  S  V  F  N  V  V  N  S  S  I  G   SEQ ID NO: 42

XhoI      SacI
1201 CCTGATTCTGGAACATCATCATCATCATCACTAACCGCTCGAGCGGAGCTCTTACATCGC SEQ ID NO: 41
     GGACTAAGACCTTGTAGTAGTAGTAGTAGTGATTGGCGAGCTCGCCTCGAGAATGTAGCG SEQ ID NO: 538
      L  I  L  E  H  H  H  H  H  H  *                              SEQ ID NO: 42
```

FIG. 6B

Pf CSP:
MLFQEYQCYGSSSNTRVLNELNYDNAGTNLYNELEMNYYGKQENWYSLK
KNSRSLGENDDGNNNNGDNGREGKDEDKRDGNNEDNEKLRKPKHKKLKQ
PGDGNPDPNANPNVDPNANPNVDPNANPNVDPNANPNANPNANPNANPNA
NPNANPNANPNANPNANPNANPNANPNANPNANPNANPNANPNVDPNANP
NANPNANPNANPNANPNANPNANPNANPNANPNANPNANPNANPNANPN
ANPNANPNANPNANPNANPNANPNKNNQGNGQGHNMPNDPNRNVDENA
NANNAVKNNNNEEPSDKHIEKYLKKIQNSLSTEWSPCSVTCGNGIQVRIKPG
SANKPKDELDYENDIEKKICKMEKCSSVFNVVNSSIGLILEHHHHHH●SEQ ID NO: 42

FIG. 7

AB-000667 Heavy Chain Variable Region (SEQ ID NO: 89)
QVQLVQSGAEVKKPGASVKVSCRASGYTFTNYAMHWVRQAPGQRLEWMGWINAGNGYTKYSQ
KFQDRVTITRDTSATTAYMELSSLRSEDTAMYYCARDSFYDILSGPVYHYYGMDVWGQGTTV
TVSS AB-000667 Light Chain Variable Region (SEQ ID NO: 67)
QSALTQPDSVSGSPGQSITISCTGTSNDVGIYNHVSWYQQHPGKAPKLMIYDVNKRPSGISN
RFSGSKSGDTASLTISGLQAEDEADYYCCSYAGSSAWVFGGGTKLTVL AB-000668 Heavy Chain Variable Region (SEQ ID NO: 126)
QVQLVQSGAEVKKPGASVKVSCKASGFTFTDYAMHWVRQAPGQRLEWMGWINAGNGYTKYSQ
KFQDRLTITRDTFASTVYMELSSLRSEDTTVYYCARDGFCPSNTCSGYYGMDVWGQGTTVTV
SS AB-000668 Light Chain Variable Region (SEQ ID NO: 110)
QSALTQPASVSGSPGQSITISCTGTSSDVGSYNYVSWYQQHPGKAPKLMIYDVNTRPSGVSI
RFSASKSGNTASLTVSGLQAEDEAVYYCSSYAGSSTWVFGGGTKLTVL

FIG. 17

A) ACAATGGCCAGAAAGCTGGCCATCCTGAGCGTGTCCAGCTTCCTGTTCGTGGAAGCCC
TGTTCCAGGAATACCAGTGCTACGGCAGCAGCAGCAACACCAGAGTGCTGAACGAGCT
GAACTACGACAACGCCGGCACCAACCTGTACAACGAGCTGGAAATGAACTACTACGGC
AAGCAGGAAAACTGGTACAGCCTGAAGAAGAACAGCAGAAGCCTGGGCGAGAACGACG
ACGGCAACAACGAGGACAACGAGAAGCTGCGGAAGCCCAAGCACAAGAAGCTGAAGCA
GCCCGCCGACGGCAATCCCGACCCCAACGCCAACCCCAACGTGGACCCTAATGCCAAT
CCTAATGTGGATCCAAACGCTAACCCTAATGTGGACCCCAACGCAAATCCCAATGCCA
ACCCTAACGCTAACCCAAACGCCAATCCAAACGCAAACCCCAACGCTAATCCTAATGC
TAATCCCAATGCAAACCCAAATGCCAATCCCAACGCCAATCCAAATGCAAATCCTAAC
GCCAACCCCAATGCTAACCCCAACGCCAACCCTAATGCAAACCCAAATGCTAACCCTA
ACGCAAATCCCAACGTGGACCCCAACGCAAACCCTAACGCCAATCCAAATGCCAACCC
TAATGCCAATCCTAACGCAAATCCTAATGCTAATCCAAACGCTAATCCCAACGCCAAT
CCTAACGCCAACCCCAACGCCAACCCAAATGCCAACCCCAATGCAAACCCTAACGCTA
ATCCTAACGCTAACCCTAATGCCAATCCCAACGCCAACCCCAATGCTAATCCAAATGC
CAACCCAAACAAGAACAACCAGGGCAACGGCCAGGGCCACAACATGCCCAACGACCCC
AATCGGAACGTGGACGAGAACGCCAATGCCAATAGCGCCGTGAAGAACAACAACAATG
AGGAACCCAGCGACAAGCACATCAAAGAGTACCTGAACAAGATCCAGAACAGCCTGAG
CACCGAGTGGTCCCCCTGCAGCGTGACATGCGGCAATGGAATCCAAGTGCGGATCAAG
CCCGGCAGCGCCAACAAGCCCAAGGATGAGCTGGACTACGCCAATGACATCGAGAAGA
AAATCTGCAAGATGGAAAAGTGCAGCTCT (SEQ ID NO: 539)

B) TMARKLAILSVSSFLFVEALFQEYQCYGSSSNTRVLNELNYDNAGTNLYNELEMNYYG
KQENWYSLKKNSRSLGENDDGNNEDNEKLRKPKHKKLKQPADGNPDPNANPNVDPNAN
PNVDPNANPNVDPNANPNANPNANPNANPNANPNANPNANPNANPNANPNANPNANPN
ANPNANPNANPNANPNANPNANPNVDPNANPNANPNANPNANPNANPNANPNANPNAN
PNANPNANPNANPNANPNANPNANPNANPNANPNANPNKNNQGNGQGHNMPNDP
NRNVDENANANSAVKNNNNEEPSDKHIKEYLNKIQNSLSTEWSPCSVTCGNGIQVRIK
PGSANKPKDELDYANDIEKKICKMEKCSSGAPGS<u>LHHILDAQKMLWNHR</u>DRNLPPLAP
LGP<u>HHHHHH</u>* (SEQ ID NO: 540)

FIG. 22

|  | Antibody ID | | | LCDR1 | |
|---|---|---|---|---|---|
|  |  | 10 | 20 | 30 | 40 |
| SEQ ID NO: 7 | 666 | QSALTQPASVSGSPGQSITISC | TGTSSDVGVYNY | VSWFQQHP |
| SEQ ID NO: 17 | 667 | ....D................ | ....N...I..H. | ..Y.... |
| SEQ ID NO: 22 | 668 | ...................... | ....S......... | ..Y.... |
| SEQ ID NO: 31 | 669 | ...................... | ....S......... | ..Y.... |
|  | CL-141810 | ...................... | ....GSK...... | ..Y.... |
|  | CL-141805 | ...................... | ............. | ....... |
|  | CL-141806 | ...................... | ....S..H..... | ..Y.... |
|  | CL-141795 | ...................... | ....G........ | ..Y.... |
|  | CL-141798 | ...................... | ....G........ | ..Y.... |
|  | CL-141763 | ...................... | ...N.G....... | ..Y.... |
|  | CL-141764 | ...................... | ....G........ | ..Y.... |
|  | CL-141765 | ...................... | ...N.G....... | ..Y.... |
|  | CL-141766 | .............P........ | ....S..H..... | ..Y.... |
|  | CL-141768 | ...................... | ....G........ | ..Y.... |
|  | CL-141799 | ...................... | ....A.K...... | ..Y.... |
|  | CL-141800 | ...................... | ....G.KN..... | ..Y.... |
|  | CL-141802 | ...................... | ....A........ | ..Y.... |
|  | CL-141804 | ...................... | ....G........ | ..Y.... |
|  | CL-141792 | ...................... | ....S..H..... | ..Y.... |
|  | CL-141793 | ...................... | ....G........ | ..Y.... |
|  | CL-141794 | ...................... | ....G........ | ..Y.... |
|  | CL-141769 | ....D................. | ....N...H.... | ..Y.... |
|  | CL-141770 | ...................... | ....S..H..... | ..Y.... |
|  | CL-141772 | ...................... | ....G........ | ..Y.... |
|  | CL-141773 | .....V......L......... | ..I.G........ | ..Y.... |
|  | CL-141776 | ...................... | ....G........ | ..Y.... |
|  | CL-141777 | ...................... | ....S..H..... | ..Y..Y. |
|  | CL-141779 | ...................... | ....G........ | ..Y.... |
|  | CL-141781 | ....D................. | ....N...H.... | ..Y.... |
|  | CL-141783 | ...................... | ....S..H..... | ..Y.... |
|  | CL-141784 | ...................... | ....S..H..... | ..Y.... |
|  | CL-141785 | ...................... | ....S........ | ..Y.... |
|  | CL-141786 | ..V.......P........... | ....N...H.... | ..Y.... |
|  | CL-141787 | ...................... | ....G........ | ..Y.... |
|  | CL-141789 | ...................... | ....S........ | ..Y.... |
|  | CL-141790 | ...................... | ....N...H.... | ..Y.... |
|  | CL-141791 | ......D............... | ....N....H... | ..Y.... |

LCDR3

| Antibody ID | Sequence (80-110) |
|---|---|
| | `........|....|....|....|....|....|..` |
| | `                 90        100       110` |
| SEQ ID NO: 7  666 | `EDEADYYCCSYAGSSTWVFGGGTNLTVL` |
| SEQ ID NO: 17 667 | `...........A........K....` |
| SEQ ID NO: 22 668 | `....V...S...........K....` |
| SEQ ID NO: 31 669 | `...................K....` |
| CL-141810 | `...................K....` |
| CL-141805 | `........................` |
| CL-141806 | `...................K....` |
| CL-141795 | `...................K....` |
| CL-141798 | `..............NT...K....` |
| CL-141763 | `...............R...K....` |
| CL-141764 | `......C.......T....K....` |
| CL-141765 | `...T...........R...K....` |
| CL-141766 | `...................K....` |
| CL-141768 | `...................K....` |
| CL-141799 | `....V...S..........K....` |
| CL-141800 | `...................K....` |
| CL-141802 | `....V..............K....` |
| CL-141804 | `...................K....` |
| CL-141792 | `...................K....` |
| CL-141793 | `...................K....` |
| CL-141794 | `...................K....` |
| CL-141769 | `...S...............K....` |
| CL-141770 | `....E...V..S.L.....K....` |
| CL-141772 | `...................K....` |
| CL-141773 | `...................K....` |
| CL-141776 | `...................K....` |
| CL-141777 | `..........V........K....` |
| CL-141779 | `...................K....` |
| CL-141781 | `..........V.N.A....K....` |
| CL-141783 | `..........V........K....` |
| CL-141784 | `...................KM...` |
| CL-141785 | `...................K....` |
| CL-141786 | `...................K....` |
| CL-141787 | `...................K....` |
| CL-141789 | `.............G.....K....` |
| CL-141790 | `...................K....` |
| CL-141791 | `..........V...A..........` |

FIG. 23C

```
                                                                   HCDR1
                Antibody ID    ....|....|....|....|....|....|....|....|
                                       10        20        30
SEQ ID NO: 7    666            QVQLVQSGAEVKKPGASVKVSCKASGYTFTNY--AMHW
SEQ ID NO: 17   667            ........................R.....----....
SEQ ID NO: 22   668            .........................F...D.--....
SEQ ID NO: 31   669            ........................R....F...S.--....

CI-14180       E....E..GGLVQ..G.LRL..A...F..SS.--..S.
                CI-141805      .....................................--....
                CI-141806      .....................................--.I..
                CI-141795      ..............................S.--....
                CI-141798      E....E..GG.VR..G.LRL..A...F..DD.--G.S.
                CI-141763      E....E..GGLVQ..G.LRL..A..FP.S..--D...
                CI-141764      ....Q...PGLV..SQTLSLT.AI..DSVSSNSA.WN.
                CI-141765      E....E..GGLVQ..G.LRL..AS..FP.S..--D...
                CI-141766      ..............................S.--....
                CI-141768      E....E..GGLVQ..G.LRL..A...F..SS.--..S.
                CI-141799      .............................F...D.--....
                CI-141800      ...............................--TI..
                CI-141802      .......T.....................F..SS.--....
                CI-141804      ....QE..PGLV..SGTLSLT.AV..DSISSS-NWWS.
                CI-141792      ..............................S.--....
                CI-141794      ....Q...PGLV..SQTLSLT.AI..DSVSSNSA.WN.
                CI-141769      ........................R.............
                CI-141770      ...............................--.I..
                CI-141772      .............................FI.I.--..Q.
                CI-141773      .IT.KE..PTLV..TQTLTLT.TFP.FALSTSGVGVG.
                CI-141776      ...........N.................F...--....
                CI-141777      ...............................--....
                CI-141779      ..............................S.--....
                CI-141781      ........................R....S.--....
                CI-141783      .............L.................--....
                CI-141784      ...........N...L................--....
                CI-141785      ........................R....F..IS.--....
                CI-141786      ...L............................--....
                CI-141787      .............................F...SH--.I..
                CI-141789      ........................R..T.F...S.--.IQ.
                CI-141790      ........................R....I..--.I..
                CI-141791      ........................R.......--....
```

FIG. 24A

|  | Antibody ID | HCDR2 |
|---|---|---|
| | | 40        50        60 |
| SEQ ID NO: 7 | 666 | VRQAPGQRLEWMGWINAGNGNTRYSQNFQGR |
| SEQ ID NO: 17 | 667 | .........................Y.....K..D. |
| SEQ ID NO: 22 | 668 | .........................Y.....K..D. |
| SEQ ID NO: 31 | 669 | .........................H.....K..D. |
| | CI-14180 | ......KG...VSG.SGSG.S.Y.ADSEK... |
| | CI-141805 | ............................... |
| | CI-141806 | ..............................K..... |
| | CI-141795 | ..............................K..... |
| | CI-141798 | ...G..KG...VSG..WNG...G.ADSVK... |
| | CI-141763 | ...VT.KG...VSA.GTAGD-.Y.PDSVK... |
| | CI-141764 | I..S.SRG...L.RTYYRSKWYNDYSVSVKS |
| | CI-141765 | ...VT.KG...VSA.GTAGD-.Y.PDSVK... |
| | CI-141766 | ...........................K...G |
| | CI-141768 | ......KG...VSA.SGSG.S.Y.ADSVK... |
| | CI-141799 | .........................Y.....K..D. |
| | CI-141800 | ..V.....................G.......K.... |
| | CI-141802 | ................................K..... |
| | CI-141804 | ...P..KG...I.E.YHSGNTNYNPSL-KS. |
| | CI-141792 | .........................Y........... |
| | CI-141794 | I..S.SRG...L.RTYYRSKWYNDYAVSVKS |
| | CI-141769 | .........................Y.....K..D. |
| | CI-141770 | ........S.V..............Y.....M..D. |
| | CI-141772 | .........................Y.....K..... |
| | CI-141773 | I..P..KA...LAL.YWDDDKRYSPSL-KS. |
| | CI-141776 | .........................H.....K..D. |
| | CI-141777 | .........................Y.....K..... |
| | CI-141779 | ................................K..... |
| | CI-141781 | .........................Y.....K..D. |
| | CI-141783 | ..........S..............Y.....K..... |
| | CI-141784 | .........................Y.....T..... |
| | CI-141785 | ........G................D.H....K..D. |
| | CI-141786 | L........................Y.....K..... |
| | CI-141787 | .........................Y.....K..D. |
| | CI-141789 | ........G................D.H....K..D. |
| | CI-141790 | .........................Y.....K..... |
| | CI-141791 | .........................Y.....K..D. |

|  | Antibody ID | 70         80         90 |
|---|---|---|
| SEQ ID NO: 7 | 666 | VTITR-DTSASTAYMELSSLRSEDTAVYY |
| SEQ ID NO: 17 | 667 | .....-...T................M.. |
| SEQ ID NO: 22 | 668 | L....-..F...V...........T... |
| SEQ ID NO: 31 | 669 | .A...-....T.V..D............ |
|  | CI-14180 | F..S.-.N.KN.L.LQMN...G....... |
|  | CI-141805 | .....-....................... |
|  | CI-141806 | .....-....................... |
|  | CI-141795 | .....-....................... |
|  | CI-141798 | F..S.-.NAKNSL.LQMN...A....L.. |
|  | CI-141763 | F..S.-.NAKNSLFLQMN...AG...... |
|  | CI-141764 | RITINP...KNQFSLQ.N.VTP....... |
|  | CI-141765 | F..S.-.NAKNSLFLQMN...AG...... |
|  | CI-141766 | .....-....................... |
|  | CI-141768 | F..S.-.N.KN.L.LQMN...A....... |
|  | CI-141799 | L....-..F...V...........T... |
|  | CI-141800 | ...N.-....N..............V... |
|  | CI-141802 | .....-....................... |
|  | CI-141804 | ...SV-..R.KNQFSLN.N.VTAA..... |
|  | CI-141792 | .....-....................... |
|  | CI-141794 | RITFNP...KNQFSLQ.N.VTP....... |
|  | CI-141769 | F....-....T.................. |
|  | CI-141770 | .A...-....N.............G.... |
|  | CI-141772 | .....-.I..N.V................ |
|  | CI-141773 | L...K-...KNQVVLTVTNMDPV...T.. |
|  | CI-141776 | .A...-....T.................. |
|  | CI-141777 | ....I-....T.................. |
|  | CI-141779 | .....-....................... |
|  | CI-141781 | .....-....T................M.. |
|  | CI-141783 | .....-....N....D............. |
|  | CI-141784 | .....-..Y.................... |
|  | CI-141785 | .A...-....T.V..D............. |
|  | CI-141786 | .....-....T...D.............. |
|  | CI-141787 | .A...-....................... |
|  | CI-141789 | .V...-....T.V..D............. |
|  | CI-141790 | .....-...TS..L..Y..I......... |
|  | CI-141791 | .....-....T..H.............M.. |

|  | Antibody ID | HCDR3 |
|---|---|---|
| SEQ ID NO: 7 | 666 | CARDEYYASGSYYDYYYYGMDVWGQGTTVTVSS |
| SEQ ID NO: 17 | 667 | ....SF.DIL.GPV.H.............S. |
| SEQ ID NO: 22 | 668 | ....GFCP.NTCSG..GMDVWGQ.TTV..SS |
| SEQ ID NO: 31 | 669 | .T..GFCT.TTCS.H.GMDVWGQ.TTV..SS |
|  | CL-14180 | ...KAY..G..MDVWGQGTTVT.SS |
|  | CL-141805 | ................................ |
|  | CL-141806 | ....NP.G..T.FS.FF.H..........S. |
|  | CL-141795 | ...GGSRDYWGQGTLVTVSS |
|  | CL-141798 | ...GLR.FDWLVGMDVWGQGTTVTVSS |
|  | CL-141763 | ...GGGSGTY...Y..GMDVWGQ.TTV..SS |
|  | CL-141764 | ...KWELLDAFDVWGQGTMVT.SS |
|  | CL-141765 | ...GGGSGTY...Y..GMDVWGQ.TTV..SS |
|  | CL-141766 | ....N..D..................S. |
|  | CL-141768 | ...KEGSGSYYGDWFDPWGQGTLVTVSS |
|  | CL-141799 | ....GFCP.NTCSG..GMDVWGQ.TTV..SS |
|  | CL-141800 | ....Q..YDS.G.FD.WGQGTLVTVSS |
|  | CL-141802 | ....G.CS.T.C.G..GMDVWGQ.TTV..SS |
|  | CL-141804 | ...GRPLSY..GSY.NLNWF.P.....L...S. |
|  | CL-141792 | ....N.FD.SV.DSS..FYYGMDVW.QGT...VSS |
|  | CL-141794 | ...EGVG.IT.HF..WGQ.TL.TVSS |
|  | CL-141769 | ....SP.DILTGPV.H................S. |
|  | CL-141770 | ....QP.ETLTG.YNV..YYGMDVW.QGT..AVSS |
|  | CL-141772 | ....GFCSTTTCS.H.GMDVWGQ.TTV..SS |
|  | CL-141773 | ..LKD.GDYYY.DMDVWGQGTTVTVSS |
|  | CL-141776 | .S..GFCSTTTCS.H.GMDVWGQ.TTV..SS |
|  | CL-141777 | ....N..D.....E.C................S. |
|  | CL-141779 | ....Q..DILTP.Y..................S. |
|  | CL-141781 | .S..SF.DILTGPV.H................S. |
|  | CL-141783 | ....Q..DILKG.YNVD.YYGMDVW.QGT..AVSS |
|  | CL-141784 | .V.....E...SNY...GMDVWGQGT.VTVSS |
|  | CL-141785 | .S..GFCTTTTCS.H.GMDVWGQ.TTV..SS |
|  | CL-141786 | ....N..D.NV.NS..F................S. |
|  | CL-141787 | .T..GFCSTTTCS.H.GMDVWGQ.TTV..SS |
|  | CL-141789 | .T..GFCTTTTCS.H.GMDVWGQ.TTV..SS |
|  | CL-141790 | .V.....D...SNY...GMDVWGQGT.VTVSS |
|  | CL-141791 | ...SP.DILTGPV.H................S. |

FIG. 24D ature of anti-malarial drug patent text

ANTI-MALARIAL ANTIBODIES THAT BIND CIRCUMSPOROZOITE PROTEIN

CROSS-REFERENCE TO RELATED APPLICATIONS

This application claims priority to U.S. Provisional Application Nos. 62/504,863, filed May 11, 2017; 62/560,971, filed Sep. 20, 2017; and 62/564,066, filed Sep. 27, 2017; and is a continuation-in-part of International Application No. PCT/GB2017/050786, filed Mar. 21, 2017, which claims priority to U.S. Provisional Application No. 62/311,059, filed on Mar. 21, 2016, which are incorporated herein by reference in their entireties.

REFERENCE TO SEQUENCING LISTING

The content of the electronically submitted sequence listing (Name: 4010_0040002_Seqlisting_ST25; Size: 368,201 and Date of Creation: Apr. 1, 2020) is incorporated herein by reference in its entirety.

FIELD OF THE INVENTION

This invention relates to treating or preventing malaria, and to antibodies conferring protection against infection by malarial parasites such as *Plasmodium falciparum* by insect vector transmission. The invention also relates to treating, preventing or diagnosing *Plasmodium* infection in a mammal.

BACKGROUND

Malaria causes a large burden of morbidity and mortality, especially in the developing world. The causative agent of malaria is a protozoal parasite, which is transmitted by mosquitos. There are several infectious *Plasmodium* species that cause malaria, the most deadly of which is *Plasmodium falciparum*. Others include *P. vivax, P. ovale* and *P. malariae*.

The life cycle of *Plasmodium* parasites such as *P. falciparum* is shown in FIG. 1. The infective stage is the sporozoite, which is transmitted from the mosquito to the vertebrate host, e.g., human. Preventing infection will involve preventing sporozoite transmission from the insect vector to humans. Decreasing infection by *P. falciparum* will depend on blocking transmission, or inhibiting the pre-erythrocytic phase of infection. Targeting the asexual phases involved in the erythrocytic cycle (and disease) may only mimic naturally acquired immunity—that is, immunity to disease rather than immunity to infection.

Circumsporozoite protein (CSP) is an antigen that is highly expressed on the *P. falciparum* sporozoite. CSP is displayed on the surface of the sporozoite and is involved in key parasite functions. Human antibodies against *P. falciparum* sporozoites have been described. Del Giudice et al synthesised a peptide of about 40 repeats of NANP (Asn-Ala-Asn-Pro) SEQ ID NO: 509 from CSP, (NANP)$_{40}$ (SEQ ID NO: 44). This was recognised by monoclonal antibodies produced against *P. falciparum* sporozoites, and was proposed for use in detecting anti-sporozoite antibodies and for epidemiological studies to obtain baseline data concerning the immune status of individuals before their participation in a sporozoite vaccine trial (del Guidice et al., J. Clin. Microbiol. 25(1):91-96 1987). In a study of the structural diversity of antibodies that bind the NANP (SEQ ID NO: 509) repeat region of CSP, it was found that the murine antibody response to this immunodominant region is heterogeneous. In that study, hybridomas (2E7, 2A10, 3D6, 2C11, 1E9) were created from mice innoculated with whole *P. falciparum* sporozoites, and the VH and VL domains from the hybridoma antibodies were sequenced. It was found that the different antibodies to the NANP (SEQ ID NO: 509) repeat region incorporated a variety of different v, d and j gene segments (Anker, Zavala & Pollok, Eur J Immunol. 20:2757-2761 1990).

The NANP repeat (SEQ ID NO: 509), coupled to Keyhole limpet hemocyanin (KLH), has been used to vaccinate human volunteers and shown to produce an immune response in up to 71% of volunteers (n=35). 3 individuals with the highest anti NANP(SEQ ID NO: 509) antibody titres were challenged by experimental mosquito mediated infection with *Plasmodium falciparum* sporozoites. Compared with controls (n=10) who had not been vaccinated and who all showed blood stage parasitaemia, 2 of the vaccines showed delayed parasitaemia and one showed no parasitaemia (Herington et al, Nature. 328: 257-259 1987), indicating that antibodies to NANP (SEQ ID NO: 509) could be protective to infection.

A first generation vaccine (RTS,S) has been developed using portions of CSP, including part of the NANP (SEQ ID NO: 509) repeats. CSP-based vaccines have consistently shown 30-50% efficacy in prevention of erythrocytic-stage infection. This level of efficacy is not sufficient for eradication and new pre-erythrocytic treatments will need superior efficacy.

Other anti-malarial products include mefloquinine, doxycycline and atovaquone/proguanil, which are used for chemoprophylaxis by travelers and the military. Artemisinin and its derivatives also have anti-malarial action, and artemisinin combination therapies are a standard treatment worldwide for malaria.

In the absence of sufficiently effective vaccines, these drug treatments currently remain at the forefront of anti-malarial medicine. However, resistance to existing anti-malarial treatments is arising. Evidence for resistance to artemisinin in Southeast Asia was first reported in 2008, and more recently it has been reported that *Plasmodium falciparum* resistant to artemisinin were spreading in the Greater Mekong subregion (Imwong et al., The Lancet, 2017; dx.doi.org/10.1016/S1473-3099(17)30048-8).

The development of drug resistant *Plasmodium* follows a familiar pattern. In Thailand, sulphadoxine-pyrimethanime (SP) was initially almost 100% effective in curing malaria when introduced in 1977, but within five years was curing only 10% of cases due to drug resistance. The once-popular chloroquine has lost its effectiveness in almost every part of the world. Between 1999 and 2004, 95% of African children treated for malaria were given chloroquine, even though the drug only cured half of malaria cases in many countries. Resistance to atovaquone developed within one year of introduction in 1997.

Development of resistance can be reduced through use of combination therapies, and the World Health Organisation has discouraged use of artemisinin monotherapy in favour of combination treatments for this reason. The WHO has also urged the global malaria research community and the pharmaceutical industry to invest in the design of the next generation of antimalarial drugs. Use of further categories of active anti-malarials in combination therapies should slow the development of drug resistance and provide treatment options for cases that are resistant to existing anti-malarial drugs.

SUMMARY OF THE INVENTION

The invention provides novel anti-parasitic therapeutic and diagnostic agents, including prophylactic agents, especially antibodies. The antibodies may be employed for diagnosing, treating, or preventing malaria or *Plasmodium* infection in humans and other mammals, or for reducing the risk of malaria or *Plasmodium* infection in humans and other mammals. Methods of diagnosis and treatment are described herein, including methods of administration to a mammal. The antibodies may be used to confer protection against infection by malarial parasites such as *Plasmodium falciparum* by insect vector transmission. Desirable features of the antibodies include inhibiting the pre-erythrocytic stage (e.g., sporozoite) of *Plasmodium* infection, reducing progression of *Plasmodium* infection in a mammal, reducing one or more symptoms of malaria, and reducing transmission or risk of transmission of *Plasmodium* to and/or from a mammal. Inhibition of transmission of malarial *Plasmodium* parasites between mammals (especially humans) is of particular value in lessening spread of disease, limiting malaria and controlling reservoirs of infectious malarial parasites in populations. This invention offers particular advantages for use in countries and regions where malaria is prevalent, and for travelers, military personnel and health workers visiting or operating in such countries or regions.

This invention also relates to the use of antibody sequences as correlates of protection following vaccination to protect from malaria infection, which has utility in vaccine development programs, including pre-clinical and clinical trials, and in determining the level of protection achieved in individuals vaccinated against *Plasmodium* infection. This invention also relates to the use of such antibodies to diagnose malaria infection, and diagnostic methods and kits are described herein. Pharmaceutical compositions comprising the antibodies are also provided. Exemplary embodiments of the invention are set out in the appended claims.

Exemplary antibodies include antibodies 666, 667, 668 and 669, the sequences of which are set out herein. Antibodies having close structural similarity with these antibodies, are also described. These are antibodies 666-1, 666-2, 666-3, 666-4 (antibody 666 lineage), 667-1, 667-2, 667-3 (antibody 667 lineage), 668-1 (antibody 668 lineage) 669-1, 669-2, 669-3, 669-4, 669-5 and 669-6 (antibody 669 lineage), and antibodies having the sets of CDRs shown in Tables 5 to 7. Further exemplary antibodies are described in Example 11 and include antibodies having the sets of CDRs, and optionally the VH domain and/or VL domains, shown in Table 16. Still further exemplary antibodies are described in Example 13 and include antibodies having the sets of CDRs, and optionally the VH domain and/or VL domains, shown in Table 18.

Antibody 667 and antibody 668 are believed to bind the NANP (SEQ ID NO: 509) repeat region of the CSP polypeptide sequence and/or to bind within a region of up to 12 amino acids preceding the NANP (SEQ ID NO: 509) repeat region. The NANP (SEQ ID NO: 509) repeat region starts with a sequence NANPNVDPNANP(SEQ ID NO: 510), which may provide at least part of the epitope recognised by these antibodies. Immediately upstream of the NANP (SEQ ID NO: 509) repeat region is a sequence of 12 amino acids KLKQPGDGNPDP (SEQ ID NO: 511), which may also provide or contribute to the epitope recognised by antibody 667 and antibody 668. For example, the antibodies may bind the NPDP motif within this sequence. The epitope recognised by antibody 667 and antibody 668 may lie within, or include, the 8-mer sequence NPDPNANP (SEQ ID NO:512), i.e., the sequence comprising the first NANP (SEQ ID NO: 509) motif and the residues that immediately precede it.

Antibody 667 and antibody 668 have been characterised both in vitro and in vivo and found to inhibit pathologically relevant sporozoite functions and to protect against sporozoite infection as described in the appended Examples. Antibody 666 and antibody 669 are related in sequence to both antibody 667 and antibody 668, indicating they may share useful functional properties in common and that they may also bind the same region(s) of CSP, e.g., the NANP (SEQ ID NO: 509) region and/or upstream sequences of CSP as described above. Targeting an epitope within the NANP (SEQ ID NO: 509) repeat region and/or upstream sequence as described may confer particular advantages for inhibiting sporozoite infection. Antibodies that bind the same part of the CSP polypeptide that is recognised by antibodies 667 and 668, e.g., the NANP (SEQ ID NO: 509) repeat region and/or upstream sequences, and the use of such antibodies in therapeutic and prophylactic methods described herein, thus represent an aspect of the present invention. The invention also relates to antibodies that neutralise CSP.

An antibody according to the invention may be one that competes for binding to CSP of *Plasmodium falciparum* with an antibody (e.g., human IgG1, or an scFv) comprising the heavy and light chain complementarity determining regions (CDRs) of antibody 666, antibody 667, antibody 668 or antibody 669.

An antibody according to the present invention may comprise one or more CDRs of any of antibody 666, 667, 668 or 669 (e.g., all 6 CDRs of any such antibody, or a set of HCDRs and/or LCDRs) or variants thereof as described herein.

An antibody according to the present invention may comprise one or more CDRs of an antibody of the "antibody 666 lineage", an antibody of the "antibody 667 lineage", an antibody of the "antibody 668 lineage" or an antibody of the "antibody 669 lineage" (e.g., all 6 CDRs of any such antibody, or a set of HCDRs and/or LCDRs) or variants thereof as described herein.

The "antibody 666 lineage" comprises antibody 666, antibody 666-1, antibody 666-2, antibody 666-3 and antibody 666-4.

The "antibody 667 lineage" comprises antibody 667, antibody 667-1, antibody 667-2 and antibody 667-3.

The "antibody 668 lineage" comprises antibody 668 and antibody 668-1.

The "antibody 669 lineage" comprises antibody 669, antibody 669-1, antibody 669-2, antibody 669-3, antibody 669-4, antibody 669-5 and antibody 669-6.

An antibody according to the present invention may comprise one or more CDRs as shown in Tables 5 to 7. For example, the antibody may comprise a set of 6 CDRs shown in Table 5 or Table 6, it may comprise a VH domain having a set of HCDRs as indicated in any of Tables 5 to 7, and/or it may comprise a VL domain having a set of LCDRs as indicated in Table 5 or Table 6.

An antibody according to the present invention may comprise one or more CDRs as shown in Table 16. The antibody may comprise HCDR1, HCDR2, HCDR3, LCDR1, LCDR2 and LCDR3 as shown in Table 16, it may comprise a VH domain having the HCDR1, HCDR2 and HCDR3 shown in Table 16 and/or it may comprise a VL domain having the LCDR1, LCDR2 and LCDR3 shown in Table 16.

An antibody according to the present invention may comprise one or more CDRs as shown in Table 18. The antibody may comprise HCDR1, HCDR2, HCDR3, LCDR1, LCDR2 and LCDR3 as shown in Table 18, it may comprise a VH domain having the HCDR1, HCDR2 and HCDR3 shown in Table 18 and/or it may comprise a VL domain having the LCDR1, LCDR2 and LCDR3 shown in Table 18.

The antibody may comprise an antibody VH domain comprising CDRs HCDR1, HCDR2 and HCDR3 and an antibody VL domain comprising CDRs LCDR1, LCDR2 and LCDR3, wherein the HCDR3 is an HCDR3 of an antibody selected from antibody 666, 667, 668 or 669 or comprises that HCDR3 with 1, 2, 3, 4 or 5 amino acid alterations. The HCDR2 may be the HCDR2 of the selected antibody or it may comprise that HCDR2 with 1, 2, 3, 4 or 5 amino acid alterations. The HCDR1 may be the HCDR1 of the selected antibody or it may comprise that HCDR1 with 1, 2, 3, 4 or 5 amino acid alterations.

The antibody may comprise an antibody VL domain comprising CDRs HCDR1, HCDR2 and HCDR3 and an antibody VL domain comprising CDRs LCDR1, LCDR2 and LCDR3, wherein the LCDR3 is an LCDR3 of an antibody selected from antibody 666, 667, 668 or 669 or comprises that LCDR3 with 1, 2, 3, 4 or 5 amino acid alterations. The LCDR2 may be the LCDR2 of the selected antibody or it may comprise that LCDR2 with 1, 2, 3, 4 or 5 amino acid alterations. The LCDR1 may be the LCDR1 of the selected antibody or it may comprise that LCDR1 with 1, 2, 3, 4 or 5 amino acid alterations.

An antibody may comprise:

an antibody VH domain comprising complementarity determining regions HCDR1, HCDR2 and HCDR3, and an antibody VL domain comprising complementarity determining regions LCDR1, LCDR2 and LCDR3, wherein the heavy chain complementarity determining regions are those of antibody 666, antibody 667, antibody 668 or antibody 669, or comprise the antibody 666, 667, 668 or 669 heavy chain complementarity determining regions with 1, 2, 3, 4 or 5 amino acid alterations; and/or wherein the light chain complementarity determining regions are those of antibody 666, antibody 667, antibody 668 or antibody 669, or comprise the antibody 666, 667, 668 or 669 light chain complementarity determining regions with 1, 2, 3, 4 or 5 amino acid alterations.

The antibody may comprise an antibody VH domain comprising CDRs HCDR1, HCDR2 and HCDR3 and an antibody VL domain comprising CDRs LCDR1, LCDR2 and LCDR3, wherein the HCDR1, HCDR2 and HCDR3 are each independently selected from an antibody of the antibody 666 lineage, and/or wherein the LCDR1, LCDR2 and LCDR3 are each independently selected from an antibody of the antibody 666 lineage.

Thus, the HCDR1 may be the HCDR1 of any of antibodies 666, 666-1, 666-2, 666-3 or 666-4, the HCDR2 may be the HCDR2 of any of antibodies 666, 666-1, 666-2, 666-3 or 666-4, the HCDR3 may be the HCDR3 of any of antibodies 666, 666-1, 666-2, 666-3 or 666-4. Similarly, the LCDR1 may be the LCDR1 of any of antibodies 666, 666-1, 666-2, 666-3 or 666-4, the LCDR2 may be the LCDR2 of any of antibodies 666, 666-1, 666-2, 666-3 or 666-4, and the LCDR3 may be the LCDR3 of any of antibodies 666, 666-1, 666-2, 666-3 or 666-4.

Optionally, the antibody comprises a set of HCDRs (HCDR1, HCDR2 and HCDR3) from antibody 666-1, antibody 666-2, antibody 666-3 or antibody 666-4. The antibody optionally comprises a set of LCDRs (LCDR1, LCDR2 and LCDR3) from the same antibody.

An antibody may comprise an antibody VH domain comprising CDRs HCDR1, HCDR2 and HCDR3 and an antibody VL domain comprising CDRs LCDR1, LCDR2 and LCDR3, wherein the HCDR1, HCDR2 and HCDR3 are each independently selected from an antibody of the antibody 667 lineage, and/or wherein the LCDR1, LCDR2 and LCDR3 are each independently selected from an antibody of the antibody 667 lineage.

Optionally, the antibody comprises a set of HCDRs from antibody 667-1, antibody 667-2 or antibody 667-3. The antibody optionally comprises a set of LCDRs from the same antibody.

An antibody may comprise an antibody VH domain comprising CDRs HCDR1, HCDR2 and HCDR3 and an antibody VL domain comprising CDRs LCDR1, LCDR2 and LCDR3, wherein the HCDR1, HCDR2 and HCDR3 are each independently selected from an antibody of the antibody 668 lineage, and/or wherein the LCDR1, LCDR2 and LCDR3 are each independently selected from an antibody of the antibody 668 lineage.

Optionally, the antibody comprises a set of HCDRs from antibody 668-1. The antibody optionally also comprises a set of LCDRs from antibody 668-1.

An antibody may comprise an antibody VH domain comprising CDRs HCDR1, HCDR2 and HCDR3 and an antibody VL domain comprising CDRs LCDR1, LCDR2 and LCDR3, wherein the HCDR1, HCDR2 and HCDR3 are each independently selected from an antibody of the antibody 669 lineage, and/or wherein the LCDR1, LCDR2 and LCDR3 are each independently selected from an antibody of the antibody 669 lineage.

Optionally, the antibody comprises a set of HCDRs from antibody 669-1, 669-2, 669-3, 669-4, 669-5 or 669-6. The antibody optionally comprises a set of LCDRs from the same antibody.

Example antibody CDR sequences for antibodies of the invention are as follows:

```
                                     SEQ ID NO: 134
    HCDR1  G(Y/F)TFT(N/D)YAMH

SEQ ID NO: 14
    HCDR2  WINAGNGYTKYSQKFQD

SEQ ID NO: 15
    HCDR3  DSFYDILSGPVYHYYGMDV

SEQ ID NO: 135
    LCDR1  TGTS(N/S)DVG(I/S)YN (H/YV)S

SEQ ID NO: 136
    LCDR2  DVN(T/K)RPS

SEQ ID NO: 137
    LCDR3  (C/S)SYAGSS(A/T)WV, e.g., CSYAGSSAWV (SEQ ID NO: 20) or SSYAGSSTWV
(SEQ ID NO: 30).
```

Residues shown in brackets are alternatives at a given position. Thus, position 2 of a sequence Z(X/Y)Z has either residue X or residue Y, so that Z(X/Y)Z designates the sequences ZXZ and ZYZ.

Thus, in some embodiments, the antibody has a HCDR3 sequence DSFYDILSGPVYHYYGMDV(SEQ ID NO: 15) or DGFCPSNTCSGYYGMDV (SEQ ID NO: 25), a HCDR1 sequence G(Y/F)TFT(N/D)YAMH (SEQ ID NO: 134), and a HCDR2 sequence WINAGNGYTKYSQKFQD (SEQ ID NO: 24). In some embodiments, the antibody has an LCDR3 sequence CSYAGSSAVVV (SEQ ID NO: 20) or SSYAGSSTVVV (SEQ ID NO: 30), an LCDR1 sequence TGTS(N/S)DVG(I/S)YN (H/YV)S(SEQ ID NO: 135), and an LCDR2 sequence DVN(T/K)RPS (SEQ ID NO: 136).

Antibodies of the invention may comprise VH and/or VL domain framework regions corresponding to human germline gene segment sequences. For example, it may comprise one or more framework regions of antibody 666, antibody 667, antibody 668 or antibody 669. The framework region or framework regions may be a FR1, FR2, FR3 and/or FR4.

An antibody of the invention may comprise an antibody VH domain which
(i) is derived from recombination of a human heavy chain V gene segment, a human heavy chain D gene segment and a human heavy chain J gene segment, wherein
    the V segment is IGHV1-3;
    the D gene segment is IGHD3-10, IGHD3-9, IGHD4-11 or IGHD2-2; and/or
    the J gene segment is IGHJ6, or
(ii) comprises framework regions FR1, FR2, FR3 and FR4, wherein
    FR1 aligns with human germline V gene segment IGHV1-3 with up to 5 amino acid alterations, e.g., 1, 2, 3, 4 or 5 amino acid alterations,
    FR2 aligns with human germline V gene segment IGHV1-3 with up to 5 amino acid alterations, e.g., 1, 2, 3, 4 or 5 amino acid alterations,
    FR3 aligns with human germline V gene segment IGHV1-3 with up to 5 amino acid alterations, e.g., 1, 2, 3, 4 or 5 amino acid alterations, and/or
    FR4 aligns with human germline J gene segment IGHJ6 with up to 5 amino acid alterations, e.g., 1, 2, 3, 4 or 5 amino acid alterations. Optionally, a FR1, FR2, FR3 or FR4 segment may align perfectly with the germline gene segment, i.e., with no amino acid alterations.

Thus, for example, the antibody may comprise a VH domain derived from recombination of human heavy chain V gene segment IGHV1-3, a human heavy chain D gene segment and a human heavy chain J gene segment IGHJ6. An antibody may comprise VH domain framework regions FR1, FR2, FR3 and FR4, wherein FR1, FR2 and FR3 each align with human germline V gene segment IGHV1-3 with 1, 2, 3, 4 or 5 amino acid alterations, and a FR4 that aligns with human germline J gene segment IGHJ6 with 1, 2, 3, 4 or 5 amino acid alterations.

An antibody of the invention may comprise an antibody VL domain which
(i) is derived from recombination of a human light chain V gene segment and a human light chain J gene segment, wherein
    the V segment is IGLV2-23, and/or
    the J gene segment is IGLJ3; or
(ii) comprises framework regions FR1, FR2, FR3 and FR4, wherein
    FR1 aligns with human germline V gene segment IGLV2-23 with up to 5 amino acid alterations, e.g., 1, 2, 3, 4 or 5 amino acid alterations,
    FR2 aligns with human germline V gene segment IGLV2-23 with up to 5 amino acid alterations, e.g., 1, 2, 3, 4 or 5 amino acid alterations,
    FR3 aligns with human germline V gene segment IGLV2-23 with up to 5 amino acid alterations, e.g., 1, 2, 3, 4 or 5 amino acid alterations, and/or
    FR4 aligns with human germline J gene segment IGLJ3 with up to 5 amino acid alterations, e.g., 1, 2, 3, 4 or 5 amino acid alterations. Optionally, a FR1, FR2, FR3 or FR4 segment may align perfectly with the germline gene segment, i.e., with no amino acid alterations.

An antibody according to the invention may comprise an antibody VH domain which is the VH domain of antibody 666, antibody 667, antibody 668 or antibody 669, or which has an amino acid sequence at least 90% identical to the antibody VH domain sequence of antibody 666, antibody 667, antibody 668 or antibody 669. Optionally, the VH domain is the VH domain of an antibody in the antibody 666 lineage, an antibody in the antibody 667 lineage, an antibody in the antibody 668 lineage or an antibody in the antibody 669 lineage.

The antibody may comprise an antibody VL domain which is the VL domain of antibody 666, antibody 667, antibody 668 or antibody 669, or which has an amino acid sequence at least 90% identical to the antibody VL domain sequence of antibody 666, antibody 667, antibody 668 or antibody 669. Optionally, the VL domain is the VL domain of an antibody in the antibody 666 lineage, an antibody in the antibody 667 lineage, an antibody in the antibody 668 lineage or an antibody in the antibody 669 lineage.

An antibody VH domain having the HCDRs of antibody 666, antibody 667, antibody 668 or antibody 669, or having a variant of those CDRs, may be paired with an antibody VL domain having the LCDRs of the same antibody, or having a variant of those CDRs. Similarly, the VH domain of any of antibody 666, antibody 667, antibody 668 or antibody 669, or a variant of that VH domain, may be paired with a VL domain of the same antibody, or a VL domain variant of the same antibody.

For instance, the antibody may comprise the antibody 667 VH domain and the antibody 667 VL domain. In another example, the antibody may comprise the antibody 668 VH domain and the antibody 668 VL domain.

Antibodies may include constant regions, optionally human heavy and/or light chain constant regions. An exemplary isotype is IgG, e.g., human IgG1.

Antibodies according to the present invention may be administered to human patients, optionally paediatric patients (under 18 years of age), including young children (5 years of age and under), such as to babies and infants (under 36 months of age, e.g., under 24 months of age). Young patients may have greatest need of prevention by prophylaxis or treatment with the antibodies, as they have been reported to have the highest rates of severe malaria (Griffin et al., Proc. R. Soc. B 282:20142657). The antibodies can also be used in adults of any age. For example, the patient may be a male or female aged 50 years or under, e.g., 40 or under, or 30 or under.

The antibodies may be optimally used at time of peak malaria transmission, which coincides with the rain seasons in many target populations. Antibodies may be administered to individuals during the rain season in tropical regions where malaria transmission is ongoing, including sub-Saharan Africa, South-East Asia, Latin America or the Middle East. Antibody may also be administered to travellers outside these regions, in preparation for travel to tropical regions affected by malaria.

Further aspects of the invention include nucleic acid molecules encoding sequences of the antibodies described herein, host cells containing such nucleic acids, and methods of producing the antibodies by culturing the host cells and expressing and optionally isolating or purifying the antibodies. The expressed antibody is thereby obtained. VH and VL domains of antibodies described herein may similarly be produced and are aspects of the present invention. Suitable production methods of antibodies include large-scale expression from host cells (e.g, mammalian cells) in a bioreactor by continuous or batch culture (e.g., fed batch culture).

BRIEF DESCRIPTION OF THE DRAWINGS

FIG. 4 is a table of data relating to selected anti-malarial antibodies.

FIG. 5 illustrates a model to test protection of mice from mosquito transmission of *Plasmodium*.

FIG. 6A-B shows the synthetic nucleotide sequence for Pf CSP (SEQ ID NO: 41, encoding SEQ ID NO: 42).

FIG. 7 shows the amino acid sequence of Pf CSP (SEQ ID NO: 42) used for reverse translation of a synthetic nucleotide sequence. The illustrated sequence includes a hexa-histidine C-terminal tag. The sequence without the his tag is *Plasmodium falciparum* CSP SEQ ID NO: 43.

FIG. 9 shows results obtained for Antibody 667 and Antibody 668 in a murine malaria challenge model as described in Examples 4a and 4b. Protection data is displayed in terms of liver-stage parasite burden, determined by the number of *P. berghei* 18s RNA copies detected in mouse liver homogenates.

FIG. 10 shows results obtained in the in vivo mouse protection assay described in Examples 4a and 4b. Results are expressed as percent inhibition compared with naïve infected mice.

FIG. 11 shows further results from the work described in Examples 4a and 4b, in terms of parasitemia following sporozoite challenge of mice receiving passive transfer of anti-CSP mAbs. 17 days after blood feeding on Pb-Pf FULL CSP infected mice, the proportion of infected mosquitoes was ~85% (26 out of 30 infected salivary glands). Based on this calculation, it was determined that 6 mosquitoes were needed to challenge mice with 5 infected mosquito bites. Upon passive transfer of monoclonal antibodies, mice were anesthetised with 2% Avertin and mosquitoes allowed to feed on mice for ~10 minutes. After feeding, we determined the number of mosquitoes positive for a blood meal. Upper panel data are for mAb667; lower panel data are for mAb668.

FIG. 12 shows data from the gliding motility assay described in Example 5. *P. falciparum* sporozoites were pre-incubated with the indicated antibodies for 30 min and then added to wells in the presence of bovine serum albumin and incubated at 37 degrees C. for 1 hr. They were then fixed and trails were stained with anti-CSP antibody and counted using a fluorescence microscope. 100 sporozoites were counted and shown is the number associated with the indicated number of circular trails, indicative of their motility.

FIG. 13 shows ILSDA data from the work described in Example 6. 25k Pf sporozoites were mixed with the indicated mAbs at 20 μg/ml and inoculated into CPHH. CPHH were harvested after 96 hours incubation. Pf 18s rRNA copy numbers were measured by qRT-PCR. Y axis is copies of Pf18s per well compared to standards. Error bars represent standard deviation. 3 separate wells were tested for each mAb. The tested anti-CSP antibodies are Ab640, Ab643, Ab646, Ab649, Ab662, Ab667 (second from right), Ab668 (far right) and the reference anti-CSP antibody 2A10 (second from left).

FIG. 14 shows data on inhibition of hepatocyte traversal as described in Example 7. Graph represents traversal inhibition conferred by anti-CSP Antibodies 640, 643, 646, 649, 667 and 668 and antibodies to another antigen (Antibodies 605, 612, 628, 629, 632) tested in this assay at 10 μg/mL (right hand bar) and 100 μg/mL (left hand bar). The means of two independent experiments are shown. Only anti-CSP mAbs 667 and 668 appear to mediate traversal.

FIG. 15 shows data on inhibition of sporozoite invasion as described in Example 7. Graph represents invasion inhibition conferred by anti-CSP Antibodies 640, 643, 646, 649, 667 and 668 and antibodies to another antigen (Antibodies 605, 612, 628, 629, 632) tested in this assay at 10 μg/mL. The means of two independent experiments are shown.

FIG. 16 shows in vivo protection mediated by passive transfer of antibodies 667 and 668 in challenge of FRG humanized liver (Hu-Hep) mice with Pf-infected mosquito bites as described in Example 8. Ab667 and Ab668 exhibit robust and dose dependent protection from Pf sporozoite liver infection.

FIG. 17 shows amino acid sequences of the VH and VL domains of Antibody 667 and Antibody 668 with CDR sequences boxed. In the Ab667 VH domain (SEQ ID NO: 12) the HCDR1 (SEQ ID NO: 13), HCDR2 (SEQ ID NO: 14) and HCDR3 (SEQ ID NO: 15) sequences are boxed. In the Ab667 VL domain (SEQ ID NO: 17), the LCDR1 (SEQ ID NO: 18), LCDR2 (SEQ ID NO: 19) and LCDR3 (SEQ ID NO: 20) sequences are boxed. In the Ab668 VH domain (SEQ ID NO: 22), the HCDR1 (SEQ ID NO: 23), HCDR2 (SEQ ID NO: 24) and HCDR3 (SEQ ID NO: 25) sequences are boxed. In the Ab668 VL domain (SEQ ID NO: 27), the LCDR1 (SEQ ID NO: 28), LCDR2 (SEQ ID NO: 29) and LCDR3 (SEQ ID NO: 30) sequences are boxed.

FIG. 18 is an antibody lineage tree for Ab666, showing the inferred relationship between Ab666 and Ab666-1, Ab666-2, Ab666-3 and Ab666-4.

FIG. 19 is an antibody lineage tree for Ab667, showing the inferred relationship between Ab667 and Ab667-1, Ab667-2 and Ab667-3.

FIG. 20 is an antibody lineage tree for Ab668, showing the inferred relationship between Ab668 and Ab668-1.

FIG. 21 is an antibody lineage tree for Ab669, showing the inferred relationship between Ab669 and Ab669-1, Ab669-2, Ab669-3, Ab669-4, Ab669-5 and Ab669-6.

FIG. 22 shows (a) the nucleotide sequence and (b) the amino acid sequence of recombinant CSP used for the experimental work in Example 10.

Figure 1:
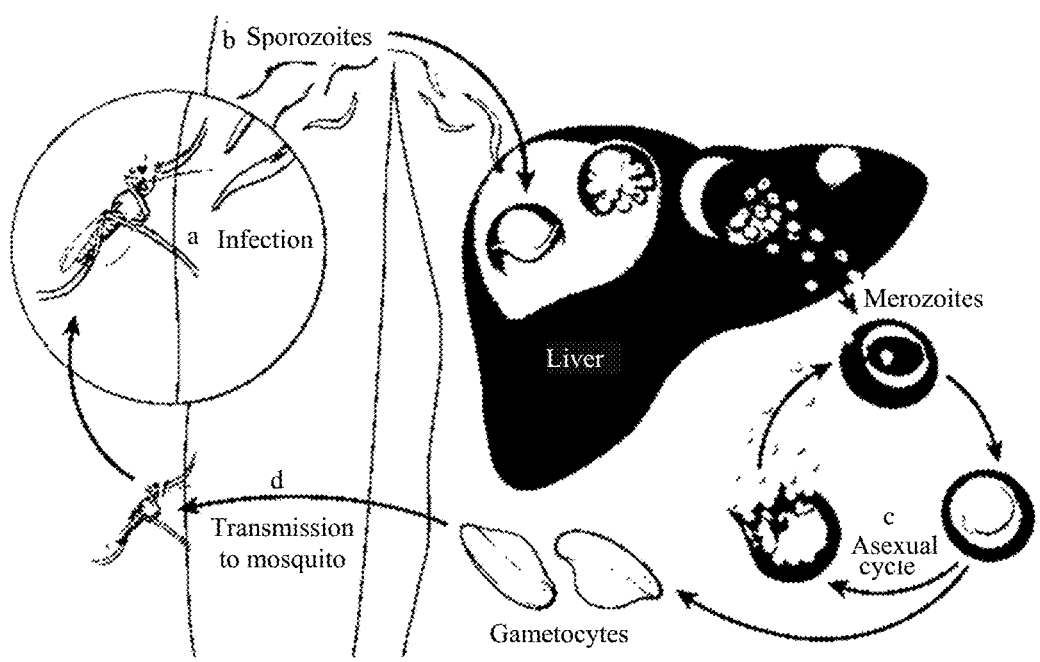
FIG. 1 illustrates the life cycle of malarial *Plasmodium* parasites such as *P. falciparum*.

The amino acid sequence includes, besides the CSP ectodomain:
LHHILDAQKMLWNHR=Biotinylation tag BirA enzyme substrate peptide (SEQ ID NO: 513)
DRNLPPLAPLGP=Biolinker (SEQ ID NO: 514)
HHHHHH=Histidine tag (SEQ ID NO: 515)

Figure 23B:
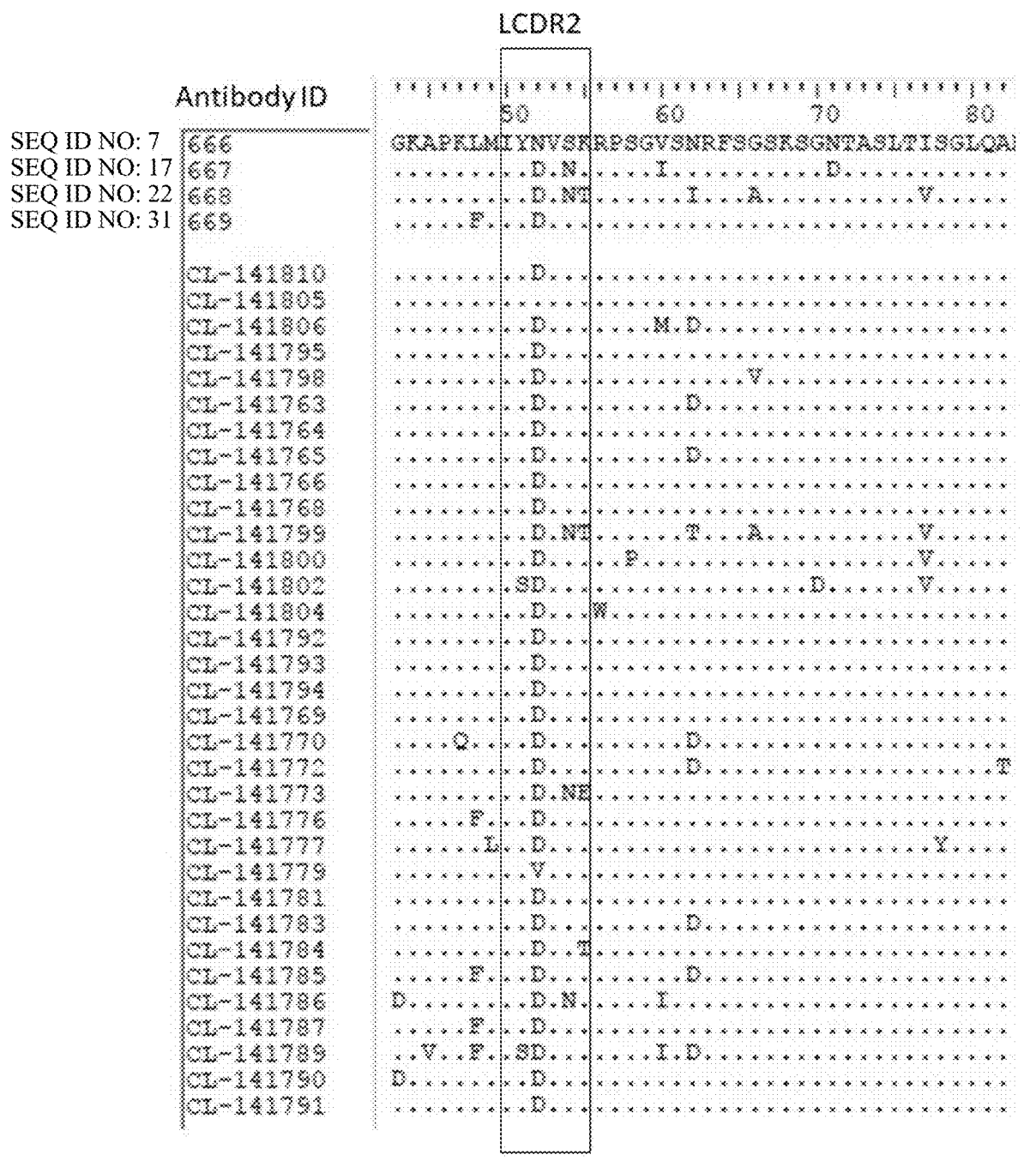

FIG. 23A-C is a multiple sequence alignment of the light chain for all antibodies containing the common IGLV2-23 IGLJ3 genotype. CDRs are highlighted by boxes. Identical amino acids are indicated by a dot.

FIG. 24A-D is a multiple sequence alignment of the heavy chain for all antibodies containing the common IGLV2-23 IGLJ3 genotype. CDRs of Ab666, Ab667, Ab668 and Ab669 are highlighted by boxes. Due to differences in CDR lengths, the sequences have different overall lengths. Identical amino acids are indicated by a dot.

DETAILED DESCRIPTION

As described in more detail in the Examples, we isolated and characterised antibodies of particular interest, numbered 666, 667, 668 and 669. Sequences of each of these antibodies are provided in the appended sequence listing, wherein for each antibody the following sequences are shown in order: nucleotide sequence encoding VH domain; amino acid sequence of VH domain; VH CDR1 amino acid sequence, VH CDR2 amino acid sequence; VH CDR3 amino acid sequence; nucleotide sequence encoding VL domain; amino acid sequence of VL domain; VL CDR1 amino acid sequence; VL CDR2 amino acid sequence; and VL CDR3 amino acid sequence, respectively. In addition, the sequence listing includes VH and VL domain sequences for antibodies that were identified as being in the same lineages as antibody 666, 667, 668 and 669 and having different CDR sequences, namely antibodies 666-3, 666-4 (antibody 666 lineage), 667-1, 667-2, 667-3 (antibody 667 lineage), 668-1 (antibody 668 lineage) 669-1, 669-2, 669-3, 669-4, 669-5 and 669-6 (antibody 669 lineage). Further sets of antibody CDRs are shown in Table 5, Table 6 and Table 7. Still further sets of antibody CDRs, and antibody VH and VL domains, are shown in Table 16 and Table 18.

It is recognised that different conventions exist for identifying CDR sequences within antibody variable domains, and that CDRs may for example be determined according to the Kabat system, Chothia system, IMGT system, or others. In the appended Antibody CDR sequence tables we therefore show CDRs for the antibodies, including their CDRs as determined by the Kabat and Chothia systems respectively.

Desirable Properties

Antibodies according to the present invention are intended for medical use, particularly as anti-malarials, and for diagnostic use.

Desirable properties for antibodies according to examples of the present invention include one or more of:
(i) binding to the NANP (SEQ ID NO: 509) repeat region of CSP and/or to a region of 12 or 15 amino acids immediately preceding the NANP (SEQ ID NO: 509) repeat region;
(ii) reducing the risk of malaria in a mammal;
(iii) reducing one or more symptoms of malaria in a mammal;
(v) reducing progression of *Plasmodium* infection in a mammal; and
(vi) reducing transmission, or reducing the risk of transmission, of *Plasmodium* to and/or from a mammal.

Thus, an antibody of the present invention may have any one or more, for example all, of these properties.

An antibody according to the invention may be a neutralising antibody, neutralising one or more functions of CSP.

Anti-CSP antibodies according to the invention may inhibit sporozoite functions in assays in vitro, including gliding motility (Example 5), liver stage development (Example 6) and hepatocyte traversal and/or invasion (Example 7).

An antibody of the invention may inhibit the pre-erythrocytic stage of a *Plasmodium* parasite infection, e.g., *P. falciparum* infection, thereby reducing infection by mosquito transmitted malaria. An antibody may provide protection from challenge in a malaria challenge mouse model (e.g., in which mice are infected with recombinant *Plasmodium berghei* expressing *Plasmodium falciparum* CPS) and the equivalent human challenge model. An illustrative protocol for such a mouse model is set out in Example 4. Protection from challenge may be quantified as % reduction in liver-stage parasite load determined by the number of *P. berghei* 18s RNA copies detected in mouse liver homogenates in such a model where the murine *P. berghei* has been engineered to express *P. falciparum* CSP. Protection from challenge may be at least 50%, at least 60%, at least 70%, at least 80%, at least 90%, at least 95%, at least 98% or at least 99%. Full protection from challenge may be obtained, i.e., liver-stage parasite load may be eliminated or entirely prevented through treatment.

Examples 4 and 8 herein describe in detail two different in vivo mouse challenge models that were used to assess the ability of passively-transferred anti-CSP mAbs to protect mice from sporozoite challenge: a transgenic (Pb-Pf CSP) sporozoite challenge and a human liver (Hu-Hep) mouse challenge model.

Protocols for challenge models are also described in:
Development of a chimeric *Plasmodium berghei* strain expressing the repeat region of the *P. vivax* circumsporozoite protein for in vivo evaluation of vaccine efficacy. Espinosa DA1, Yadava A, Angov E, Maurizio P L, Ockenhouse C F, Zavala F. Infect Immun. 2013 August; 81(8):2882-7. doi: 10.1128/IAI.00461-13. Epub 2013 May 28.
Full-length *Plasmodium falciparum* circumsporozoite protein administered with long-chain poly(I•C) or the Toll-like receptor 4 agonist glucopyranosyl lipid adjuvant-stable emulsion elicits potent antibody and CD4+ T cell immunity and protection in mice. Kastenmüller K, Espinosa D A, Trager L, Stoyanov C, Salazar A M, Pokalwar S, Singh S, Dutta S, Ockenhouse C F, Zavala F, Seder R A. Infect Immun. 2013 March; 81(3):789-800. doi: 10.1128/IAI.01108-12. Epub 2012 Dec. 28.
Transgenic Parasites Stably Expressing Full-Length *Plasmodium falciparum* Circumsporozoite Protein as a Model for Vaccine Down-Selection in Mice Using Sterile Protection as an Endpoint. Porter et al., Clin Vaccine Immunol. 20(6):803-810 2013.

Antibodies according to the present invention bind CSP. As described in Example 1, exemplary antibodies were raised in Kymice™ immunised with CSP from *P. falciparum*. The nucleotide and amino acid sequences of CSP are shown in FIGS. 6 and 7. An antibody may bind the four amino acid repeat region (NANP) (SEQ ID NO: 47) of CSP. It may bind one or more residues encoded by nucleotides 368 to 862 as shown in FIG. 6. The NANP (SEQ ID NO: 509) region is the region of the CSP polypeptide that is characterised by multiple tandem repeats of the amino acid sequence NANP (SEQ ID NO: 47) i.e., Asn-Ala-Asn-Pro. The NANP (SEQ ID NO: 509) repeat region starts with a sequence NANPNVDPNANP (SEQ ID NO: 510), which may provide at least part of the epitope for antibodies according to the invention. Thus, an antibody may bind one or more residues of this sequence. An antibody may for example bind the initial (N-terminal) NANP (SEQ ID NO: 509) motif of this sequence, i.e., it may bind one or more residues of the NANP (SEQ ID NO: 509) motif.

An antibody according to the present invention may bind the second and or third amino acid residue within a "NANP" (SEQ ID NO: 509) motif, i.e., it may bind the Ala or the second Asn residue, as may be determined for example by measuring binding to a peptide comprising the NANP (SEQ ID NO: 509) motif and a loss of binding or reduction in binding to a corresponding peptide in which the NANP (SEQ ID NO: 509) motif is mutated at the second or third amino acid residue. Peptide mapping methods are described below and in Example 10. Points of contact between antibody and antigen may be determined in other ways, such as by x-ray crystallography.

In addition, or as an alternative, to binding the NANP (SEQ ID NO: 509) repeat region of the CSP polypeptide sequence, antibodies may bind CSP within a region of up to 12 amino acids preceding the NANP (SEQ ID NO: 509) repeat region, in the sequence KLKQPGDGNPDP (SEQ ID NO: 511). For example, antibodies may bind the NPDP motif within this sequence.

An antibody may bind to CSP at one or more residues of the sequence NPDPNANP (SEQ ID NO: 512), which is the sequence comprising the first NANP (SEQ ID NO: 509) motif and the residues that immediately precede it. Thus, optionally the antibody may bind the NPDP motif immediately preceding the NANP (SEQ ID NO: 509) repeat region, and/or may bind the first NANP (SEQ ID NO: 509) motif of the NANP (SEQ ID NO: 509) repeat region.

In addition, or as an alternative, to binding the NANP (SEQ ID NO: 509) repeat region of the CSP sequence, antibodies may bind CSP within a region of up to 15 amino acids preceding the NANP (SEQ ID NO: 509) repeat region, in the sequence KHKKLKQPGDGNPDP (SEQ ID NO: 516). An antibody may bind one or more residues within the sequence KHKKLKQPG (SEQ ID NO: 517).

An antibody may bind a polypeptide or peptide comprising or consisting of a NANP (SEQ ID NO: 509) repeat region (NANP)n where n is 1 to 40, e.g., 1, 2, 3, 4, 5, 6, 7, 8, 9, 10, 20, 30 or 40, e.g., (NANP)4 (SEQ ID NO: 44).

Any suitable method may be used to determine whether an antibody binds to an antigen such as CSP, a fragment thereof (e.g., the NANP (SEQ ID NO: 509) region or a fragment comprising the NANP (SEQ ID NO: 509) region or a sequence or motif mentioned above), or a polypeptide or peptide comprising a NANP (SEQ ID NO: 509) repeat region. Such a method may comprise surface plasmon resonance (SPR), bio-layer interferometry, or an ELISA to determine specificity of antibodies. An antibody may be said to bind its antigen if the level of binding to antigen is at least 2.5 fold greater, e.g., at least 10 fold greater, than binding to a control antigen. Binding between an antibody and its cognate antigen is often referred to as specific binding. Precise identification of the residues bound by an antibody can usually be obtained using x-ray crystallography. This technique may be used to determine that an antibody of the invention binds one or more residues of the NANP (SEQ ID NO: 509) repeat region of CSP and/or other sequences as mentioned above. The antibody epitope may comprise or consist of residues within the NANP (SEQ ID NO: 509) repeat region.

Antibody binding epitopes can be mapped using one or more of the following methods:

ELISA binding of antibodies to linear peptides synthesised chemically can be used for linear epitope identification, with fine mapping achieved through the use of overlapping peptides where each peptide is offset by a minimum of one amino acid.

Single alanine substitutions of the binding peptide can be used to fine map internal amino acid contributions to the minimal binding peptide.

Full length CSP can be used together with progressive deletions from the N or C-terminus or expression of CSP sub-domains to identify antibody binding epitopes.

Site directed mutagenesis of full length CSP, N or C terminal deletions or sub-domains can be used to identify the precise epitope in the native protein.

Co-crystallisation, scanning and/or cryoEM can be used to give structural information of antibody bound to CSP including the precise atomic resolution of antibody and CSP binding using either CSP or linear peptides.

Biolayer interferometry can be used to analyse binding of antibodies to CSP peptides. Illustrative methods using biolayer interferometry, including fine mapping using single residue substitutions in peptide fragments, are presented in Example 10.

Any of these techniques, alone or in combination, can be used to determine whether an antibody binds to a CSP sequence of interest, including those mentioned above such as NANPNVDPNANP (SEQ ID NO: 510) and/or KLKQPGDGNPDP (SEQ ID NO: 511).

Binding to CSP or peptides or residues thereof may be determined with respect to the CSP amino acid sequence shown in FIG. 6 or FIG. 7 or a fragment thereof. Variant CSP sequences are known, including naturally occurring variants. FIG. 23 shows an alternative CSP sequence. An antibody of the present invention may bind CSP having an amino acid sequence shown in FIG. 6 or FIG. 7. The antibody may additionally bind CSP having an amino acid sequence shown in FIG. 22.

The invention provides antibodies that compete with antibody 666, 667, 668 or 669 for binding to CSP or a fragment thereof. An antibody may compete with a human IgG1 or with an scFv antibody comprising the VH and VL domain of an antibody selected from 666, 667, 668 or 669, or a human IgG1 or with an scFv antibody comprising the heavy and light chain CDRs of antibody 666, 667, 668 or 669. Competition between antibodies may be assayed in vitro, for example using ELISA and/or by tagging a specific reporter molecule to one antibody, which can be detected in the presence of one or more other untagged antibodies, to enable identification of antibodies that bind the same epitope or an overlapping epitope. One standard assay for competition between antibodies is a competitive cross-blocking assay using surface plasmon resonance—see Example 3.

In assay methods and methods of administration described herein relating to the CSP antigen, it is optional to use full length CSP. Alternatives to full length CSP include the isolated NANP (SEQ ID NO: 509) repeat region, a fragment of CSP comprising this region, or a synthetically generated NANP (SEQ ID NO: 509) repeat peptide such as (NANP)n, where n=4 to 40, e.g., (NANP)40, (NANP)10 or (NANP)4, may be employed. These CSP fragments or synthetic peptides may be provided as isolated sequences, contained within longer polypeptide sequences, and/or provided with one or more tags or detectable labels, as appropriate.

Ability of an antibody to bind its target antigen, and the specificity and affinity of that binding (Kd, Koff and/or Kon) can be determined by any routine method in the art, including SPR. The term "Kd", as used herein, is intended to refer to the equilibrium dissociation constant of a particular antibody-antigen interaction. Affinity of antibody-antigen binding may be determined, e.g., by surface plasmon resonance. Affinity may also be determined by bio-layer interferometry. An example of affinity determination by bio-layer interferometry is provided in Example 3 herein. An antibody may bind to CSP with an affinity (Kd) of 1 mM or less, usually 1 nM or less, e.g., 0.9 nM or less, 0.8 nM or less, 0.7 nM or less, 0.5 nM or less, or 0.4 nM or less.

Determining affinity (Kd) by bio-layer interferometry may comprise:
- immobilising antibody on biosensors (e.g., at a concentration of 20 μg/mL) for a first time period, e.g., 60 seconds;
- contacting the antibody-loaded biosensors with a dilution series of antigen (Pf CSP), e.g., starting at 1000 nM, 1:3 diluted down;
- observing association for a second time period, e.g., 120 seconds, followed by a dissociation period, e.g., 180 seconds of dissociation;
- characterising the antibody-antigen binding affinity by fitting kinetic sensorgrams to a monovalent binding model (1:1 binding).

A baseline measurement may be established using dissociation buffer after loading the biosensors (e.g., for 30 seconds). Parallel references may be set up by using unloaded bare sensor and sensor contacted with the dilution series of the antigen, and the parallel reference used for normalisation in data processing.

In an alternative set-up, antigen is immobilised on the biosensors and contacted with a dilution series of the antibody (e.g., starting at 33 nM or 133 nM, 1:3 diluted down). In each case, suitable concentrations for the dilution series can be determined depending on the strength of the affinity being measured. Any suitable bio-layer interferometry machine may be used.

An alternative is to use SPR. Optionally, SPR is carried out at 25° C. An alternative is 37° C. SPR may be performed at physiological pH, such as about pH 7 or at pH 7.6 (e.g., using Hepes buffered saline at pH 7.6 (also referred to as HBS-EP)). SPR may be carried out at a physiological salt level, eg, 150 mM NaCl. SPR may be carried out at a detergent level of no greater than 0.05% by volume, e.g., in the presence of P20 (polysorbate 20; eg, Tween-20®) at 0.05% and EDTA at 3 mM. In one example, the SPR is carried out at 25° C. or 37° C. in a buffer at pH 7.6, 150 mM NaCl, 0.05% detergent (e.g., P20) and 3 mM EDTA. The buffer can contain 10 mM Hepes. In one example, the SPR is carried out at 25° C. or 37° C. in HBS-EP. HBS-EP is available from Teknova Inc (California; catalogue number H8022).

In an example, the affinity of the antibody is determined using SPR by
1. Coupling anti-mouse (or other relevant human, rat or non-human vertebrate antibody constant region species-matched) IgG (e.g., Biacore® BR-1008-38) to a biosensor chip (e.g., GLM chip) such as by primary amine coupling;
2. Exposing the anti-mouse IgG (or other matched species antibody) to a test IgG antibody to capture test antibody on the chip;
3. Passing the test antigen over the chip's capture surface at 1024 nM, 256 nM, 64 nM, 16 nM, 4 nM with a 0 nM (i.e. buffer alone); and
4. Determining the affinity of binding of test antibody to test antigen using surface plasmon resonance, eg, under an SPR condition discussed above (e.g., at 25° C. in physiological buffer).

SPR can be carried out using any standard SPR apparatus, such as by Biacore® using the ProteOn XPR36® (Bio-Rad®).

Regeneration of the capture surface can be carried out with 10 mM glycine at pH 1.7. This removes the captured antibody and allows the surface to be used for another interaction. The binding data can be fitted to 1:1 model inherent using standard techniques, e.g., using a model inherent to the ProteOn XPR36® analysis software.

Antibodies

Antibodies according to the present invention are immunoglobulins or molecules comprising immunoglobulin domains, whether natural or partly or wholly synthetically produced. Antibodies may be IgG, IgM, IgA, IgD or IgE molecules or antigen-specific antibody fragments thereof (including, but not limited to, a Fab, F(ab')2, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria. Antibodies can be humanised using routine technology. The term antibody covers any polypeptide or protein comprising an antibody antigen-binding site. An antigen-binding site (paratope) is the part of an antibody that binds to and is complementary to the epitope of its target antigen (NANP SEQ ID NO: 510), eg, comprised by CSP).

The term "epitope" refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The antigen binding site is a polypeptide or domain that comprises one or more CDRs of an antibody and is capable of binding the antigen. For example, the polypeptide comprises a CDR3 (e.g., HCDR3). For example the polypeptide comprises CDRs 1 and 2 (e.g., HCDR1 and 2) or CDRs 1-3 of a variable domain of an antibody (e.g., HCDRs1-3).

An antibody antigen-binding site may be provided by one or more antibody variable domains. In an example, the antibody binding site is provided by a single variable domain, e.g., a heavy chain variable domain (VH domain) or a light chain variable domain (VL domain). In another example, the binding site comprises a VH/VL pair or two or more of such pairs. Thus, an antibody antigen-binding site may comprise a VH and a VL.

The antibody may be a whole immunoglobulin, including constant regions, or may be an antibody fragment. An antibody fragment is a portion of an intact antibody, for example comprising the antigen binding and/or variable region of the intact antibody. Examples of antibody fragments include:
(i) a Fab fragment, a monovalent fragment consisting of the VL, VH, CL and CH1 domains;
(ii) a F(ab')2 fragment, a bivalent fragment including two Fab fragments linked by a disulfide bridge at the hinge region;
(iii) an Fd fragment consisting of the VH and CH1 domains;

(iv) an Fv fragment consisting of the VL and VH domains of a single arm of an antibody,
(v) a dAb fragment (Ward et al., (1989) Nature 341:544-546; which is incorporated by reference herein in its entirety), which consists of a VH or VL domain; and
(vi) an isolated complementarity determining region (CDR) that retains specific antigen-binding functionality.

Single-chain antibodies (e.g., scFv) are a commonly used fragment. Multispecific antibodies may be formed from antibody fragments. An antibody of the invention may employ any such format, as appropriate.

An antibody normally comprises an antibody VH and/or VL domain. Isolated VH and VL domains of antibodies are also part of the invention. The antibody variable domains are the portions of the light and heavy chains of antibodies that include amino acid sequences of complementarity determining regions (CDRs; ie., CDR1, CDR2, and CDR3), and framework regions (FRs). Thus, within each of the VH and VL domains are CDRs and FRs. A VH domain comprises a set of HCDRs, and a VL domain comprises a set of LCDRs. VH refers to the variable domain of the heavy chain. VL refers to the variable domain of the light chain. Each VH and VL is typically composed of three CDRs and four FRs, arranged from amino-terminus to carboxy-terminus in the following order: FR1, CDR1, FR2, CDR2, FR3, CDR3, FR4. According to the methods used in this invention, the amino acid positions assigned to CDRs and FRs may be defined according to Kabat (Sequences of Proteins of Immunological Interest (National Institutes of Health, Bethesda, Md., 1987 and 1991)) or according to IMGT nomenclature. An antibody may comprise an antibody VH domain comprising a VH CDR1, CDR2 and CDR3 and a framework. It may alternatively or also comprise an antibody VL domain comprising a VL CDR1, CDR2 and CDR3 and a framework. Examples of antibody VH and VL domains and CDRs according to the present invention are as listed in the appended sequence listing that forms part of the present disclosure. All VH and VL sequences, CDR sequences, sets of CDRs and sets of HCDRs and sets of LCDRs disclosed herein represent aspects and embodiments of the invention. As described herein, a "set of CDRs" comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a "set of CDRs" includes HCDRs and LCDRs. An antibody the invention may comprise one or more CDRs as described herein, e.g. a CDR3, and optionally also a CDR1 and CDR2 to form a set of CDRs. The CDR or set of CDRs may be a CDR or set of CDRs of any of antibodies 666, 667 668 or 669, or may be a variant thereof as described herein.

The invention provides antibodies comprising an HCDR1, HCDR2 and/or HCDR3 of any of antibodies 666, 667, 668 and 669 and/or an LCDR1, LCDR2 and/or LCDR3 of any of these antibodies, e.g. a set of CDRs. The antibody may comprise a set of VH CDRs of one of these antibodies. Optionally it may also comprise a set of VL CDRs of one of these antibodies, and the VL CDRs may be from the same or a different antibody as the VH CDRs.

A VH domain comprising a disclosed set of HCDRs, and/or a VL domain comprising a disclosed set of LCDRs, are also provided by the invention.

Typically, a VH domain is paired with a VL domain to provide an antibody antigen-binding site, although as discussed further below a VH or VL domain alone may be used to bind antigen. The antibody 667 VH domain may be paired with the antibody 667 VL domain, so that an antibody antigen-binding site is formed comprising both the antibody 667 VH and VL domains. Analogous embodiments are provided for the other VH and VL domains disclosed herein. In other embodiments, the antibody 667 VH is paired with a VL domain other than the antibody 667 VL. Light-chain promiscuity is well established in the art. Again, analogous embodiments are provided by the invention for the other VH and VL domains disclosed herein.

Thus, the VH of any of antibodies 666 to 669 may be paired with the VL of any of antibodies 666 to 669. In particular, antibody 667 VH may be paired with antibody 668 VL, and antibody 668 VH may be paired with antibody 667 VL.

An antibody VH domain may optionally be paired with a VH domain of another antibody in the same lineage. For example, the VH domain of antibody 666 may be paired with the VL domain of any of antibodies 666-1, 666-2, 666-3 and 666-4, the VH domain of antibody 666-1 may be paired with the VL domain of any of antibodies 666, 666-2, 666-3 and antibody 666-4, and so on.

An antibody may comprise one or more CDRs, e.g. a set of CDRs, within an antibody framework. The framework regions may be of human germline gene segment sequences. Thus, the antibody may be a human antibody having a VH domain comprising a set of HCDRs in a human germline framework. Normally the antibody also has a VL domain comprising a set of LCDRs, e.g. in a human germline framework. FIG. 4 identifies human germline gene segment sequences that align to the variable domains of antibodies 666, 667, 668 and 669, indicating that these antibodies were derived from recombination of the identified gene segments. Table 17 provides the corresponding information for the antibodies referenced in Table 16 and Example 11 and for the antibodies referenced in Table 18 and Example 13. An antibody "gene segment", e.g., a VH gene segment, D gene segment, or JH gene segment refers to oligonucleotide having a nucleic acid sequence from which that portion of an antibody is derived, e.g., a VH gene segment is an oligonucleotide comprising a nucleic acid sequence that corresponds to a polypeptide VH domain from FR1 to part of CDR3. Human V, D and J gene segments recombine to generate the VH domain, and human V and J segments recombine to generate the VL domain. The D domain or region refers to the diversity domain or region of an antibody chain. J domain or region refers to the joining domain or region of an antibody chain. Somatic hypermutation may result in an antibody VH or VL domain having framework regions that do not exactly match or align with the corresponding gene segments, but sequence alignment can be used to identify the closest gene segments and thus identify from which particular combination of gene segments a particular VH or VL domain is derived. When aligning antibody sequences with gene segments, the antibody amino acid sequence may be aligned with the amino acid sequence encoded by the gene segment, or the antibody nucleotide sequence may be aligned directly with the nucleotide sequence of the gene segment.

An antibody of the invention may comprise an antibody VH domain derived from recombination of a human heavy chain V gene segment, a human heavy chain D gene segment and a human heavy chain J gene segment, wherein
  the V segment is IGHV1-3;
  the D gene segment is IGHD3-10, IGHD3-9, IGHD4-11 or IGHD2-2; and/or
  the J gene segment is IGHJ6.

IGHV1-3 is a particularly preferred V gene segment in antibodies and VH domains of the present invention. The selection of IGHV1-3 for recombination to generate antibody VH domains is believed to represent a particularly effective "choice" when the human immune repertoire is challenged with CSP antigen, as shown in the present Examples. Populations of transgenic mice immunised with CSP may generate anti-NANP (SEQ ID NO: 509) repeat antibodies utilising the IGHV1-3 gene segment, these antibodies being effective for neutralising CSP. Thus, in one example the antibody of the invention comprises an antibody VH domain derived from recombination of a human heavy chain V gene segment, a human heavy chain D gene segment and a human heavy chain J gene segment, wherein the V segment is IGHV1-3 and the antibody neutralises NANP (SEQ ID NO: 509) (e.g., neutralises CSP comprising (NANP)$_4$ (SEQ ID NO: 46)). In an example, neutralisation is with an IC$_{50}$ of 500M or less.

An antibody of the invention may comprise an antibody VL domain derived from recombination of a human light chain V gene segment and a human light chain J gene segment, wherein the V segment is IGLV2-23, and/or the J gene segment is IGLJ3.

An antibody of the invention may be a human antibody or a chimaeric antibody comprising human variable regions and non-human (e.g., mouse) constant regions. The antibody of the invention for example has human variable regions, and optionally also has human constant regions.

Thus, antibodies optionally include constant regions or parts thereof, e.g., human antibody constant regions or parts thereof. For example, a VL domain may be attached at its C-terminal end to antibody light chain kappa or lambda constant domains. Similarly, an antibody VH domain may be attached at its C-terminal end to all or part (e.g. a CH1 domain or Fc region) of an immunoglobulin heavy chain constant region derived from any antibody isotype, e.g. IgG, IgA, IgE and IgM and any of the isotype sub-classes, such as IgG1 or IgG4.

Antibody constant regions may be engineered to have an extended half life in vivo. Examples include "YTE" mutations and other half-life extending mutations (Dall'Acqua, Kiener & Wu, JBC 281(33):23514-23524 2006 and WO02/060919, incorporated by reference herein). The triple mutation YTE is a substitution of 3 amino acids in the IgG CH2 domain, these mutations providing tyrosine at residue 252, threonine at residue 254 and glutamic acid at residue 256, numbered according to the EU index of Kabat. As described in the referenced publications, the YTE modification increases the half-life of the antibody compared with the half-life of a corresponding antibody having a human CH2 wild type domain. To provide an increased duration of efficacy in vivo, antibodies of the present invention may include antibody constant regions (e.g., IgG constant regions, e.g., IgG CH2 domains) that have one or more mutations that increase the half life of the antibody compared with the corresponding wild type human constant region (e.g., IgG, e.g., IgG CH2 domain). Half-life may be determined by standard methods, such as are described in WO02/060919.

Constant regions of antibodies of the invention may alternatively be non-human constant regions. For example, when antibodies are generated in transgenic animals (examples of which are described elsewhere herein), chimaeric antibodies may be produced comprising human variable regions and non-human (host animal) constant regions. Some transgenic animals generate fully human antibodies. Others have been engineered to generate antibodies comprising chimaeric heavy chains and fully human light chains. Where antibodies comprise one or more non-human constant regions, these may be replaced with human constant regions to provide antibodies more suitable for administration to humans as therapeutic compositions, as their immunogenicity is thereby reduced.

Generating and Modifying Antibodies

Methods for identifying and preparing antibodies are well known. Antibodies may be generated using transgenic mice (eg, the Kymouse™, Velocimouse®, Omnimouse®, Xenomouse®, HuMab Mouse® or MeMo Mouse®), rats (e.g., the Omnirat®), camelids, sharks, rabbits, chickens or other non-human animals immunised with CSP or a fragment thereof or a synthetic peptide comprising NANP (SEQ ID NO: 509) tandem repeats (as described elsewhere herein), followed optionally by humanisation of the constant regions and/or variable regions to produce human or humanised antibodies. In an example, display technologies can be used, such as yeast, phage or ribosome display, as will be apparent to the skilled person. Standard affinity maturation, e.g., using a display technology, can be performed in a further step after isolation of an antibody lead from a transgenic animal, phage display library or other library. Representative examples of suitable technologies are described in US20120093818 (Amgen, Inc), which is incorporated by reference herein in its entirety, eg, the methods set out in paragraphs [0309] to [0346].

Generally, a Kymouse™, VELOCIMMUNE® or other mouse or rat can be challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimaeric antibodies or the variable domains of the light and heavy chains may be isolated directly from antigen-specific lymphocytes.

Initially, high affinity chimaeric antibodies are isolated having a human variable region and a mouse constant region. The antibodies are characterised and selected for desirable characteristics, including affinity, selectivity, epitope, etc. The mouse constant regions are optionally replaced with a desired human constant region to generate the fully human antibody of the invention, for example wild-type or modified IgG1 or IgG4 (for example, SEQ ID NO: 751, 752, 753 in US2011/0065902 (which is incorporated by reference herein in its entirety). While the constant region selected may vary according to specific use, high affinity antigen-binding and target specificity characteristics reside in the variable region.

Variable domain amino acid sequence variants of any of the VH and VL domains or CDRs whose sequences are specifically disclosed herein may be employed in accordance with the present invention, as discussed.

An antibody may comprise a set of H and/or L CDRs of any of the disclosed antibodies with one or more amino acid mutations within the disclosed set of H and/or L CDRs. The mutation may be an amino acid substitution, deletion or insertion. Thus for example there may be one or more amino acid substitutions within the disclosed set of H and/or L CDRs. For example, there may be up to 12, 11, 10, 9, 8, 7, 6, 5, 4, 3 or 2 mutations e.g. substitutions, within the set of H and/or L CDRs. For example, there may be up to 6, 5, 4, 3 or 2 mutations, e.g. substitutions, in HCDR3 and/or there may be up to 6, 5, 4, 3, or 2 mutations, e.g. substitutions, in LCDR3.

An antibody may comprise a VH domain that has at least 60, 70, 80, 85, 90, 95, 98 or 99% amino acid sequence identity with a VH domain of any of the antibodies shown in the appended sequence listing, and/or comprising a VL domain that has at least 60, 70, 80, 85, 90, 95, 98 or 99% amino acid sequence identity with a VL domain of any of those antibodies. Algorithms that can be used to calculate % identity of two amino acid sequences include e.g. BLAST, FASTA, or the Smith-Waterman algorithm, e.g. employing default parameters. Particular variants may include one or more amino acid sequence alterations (addition, deletion, substitution and/or insertion of an amino acid residue).

Alterations may be made in one or more framework regions and/or one or more CDRs. Variants are optionally provided by CDR mutagenesis. The alterations normally do not result in loss of function, so an antibody comprising a thus-altered amino acid sequence may retain an ability to bind CSP. It may retain the same quantitative binding ability as an antibody in which the alteration is not made, e.g. as measured in an assay described herein. The antibody comprising a thus-altered amino acid sequence may have an improved ability to bind CSP.

Alteration may comprise replacing one or more amino acid residue with a non-naturally occurring or non-standard amino acid, modifying one or more amino acid residue into a non-naturally occurring or non-standard form, or inserting one or more non-naturally occurring or non-standard amino acid into the sequence. Examples of numbers and locations of alterations in sequences of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring.

The term "variant" as used herein refers to a peptide or nucleic acid that differs from a parent polypeptide or nucleic acid by one or more amino acid or nucleic acid deletions, substitutions or additions, yet retains one or more specific functions or biological activities of the parent molecule. Amino acid substitutions include alterations in which an amino acid is replaced with a different naturally-occurring amino acid residue. Such substitutions may be classified as "conservative", in which case an amino acid residue contained in a polypeptide is replaced with another naturally occurring amino acid of similar character either in relation to polarity, side chain functionality or size. Such conservative substitutions are well known in the art. Substitutions encompassed by the present invention may also be "non-conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a non-conventional amino acid. In some embodiments amino acid substitutions are conservative. Also encompassed within the term variant when used with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide).

In some aspects, one can use "synthetic variants", "recombinant variants", or "chemically modified" polynucleotide variants or polypeptide variants isolated or generated using methods well known in the art. "Modified variants" can include conservative or non-conservative amino acid changes, as described below. Polynucleotide changes can result in amino acid substitutions, additions, deletions, fusions and truncations in the polypeptide encoded by the reference sequence. Some aspects use include insertion variants, deletion variants or substituted variants with substitutions of amino acids, including insertions and substitutions of amino acids and other molecules) that do not normally occur in the peptide sequence that is the basis of the variant, for example but not limited to insertion of ornithine which do not normally occur in human proteins. The term "conservative substitution," when describing a polypeptide, refers to a change in the amino acid composition of the polypeptide that does not substantially alter the polypeptide's activity. For example, a conservative substitution refers to substituting an amino acid residue for a different amino acid residue that has similar chemical properties (e.g., acidic, basic, positively or negatively charged, polar or nonpolar, etc.). Conservative amino acid substitutions include replacement of a leucine with an isoleucine or valine, an aspartate with a glutamate, or a threonine with a serine. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984), incorporated by reference in its entirety.) In some embodiments, individual substitutions, deletions or additions that alter, add or delete a single amino acid or a small percentage of amino acids can also be considered "conservative substitutions" if the change does not reduce the activity of the peptide. Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

One can select the amino acid that will substitute an existing amino acid based on the location of the existing amino acid, including its exposure to solvents (i.e., if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, J. Mol Biol, 1999, 217, 721-739 and Taylor et al, J. Theor. Biol. 119(1986); 205-218 and S. French and B. Robson, J. Mol. Evol. 19(1983)171. Accordingly, one can select conservative amino acid substitutions suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids is on the interior of a protein or peptide (i.e. the amino acids are not exposed to a solvent), for example but not limited to, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, non-conservative amino acid substitutions are also encompassed within the term of variants.

The invention includes methods of producing antibodies containing VH and/or VL domain variants of the antibody VH and/or VL domains shown in the appended sequence listing. Such antibodies may be produced by a method comprising
(i) providing, by way of addition, deletion, substitution or insertion of one or more amino acids in the amino acid sequence of a parent antibody VH domain, an antibody VH domain that is an amino acid sequence variant of the parent antibody VH domain,
wherein the parent antibody VH domain is the VH domain of any of antibodies 666, 667, 668 and 669 or a VH domain comprising the heavy chain complementarity determining regions of any of those antibodies,
(ii) optionally combining the VH domain thus provided with a VL domain, to provide a VH/VL combination, and
(iii) testing the VH domain or VH/VL domain combination thus provided to identify an antibody with one or more desired characteristics.

Desired characteristics include binding to CSP, for example binding to the four amino acid repeat region NANP (SEQ ID NO: 509) of the circumsporozoite protein (CSP) of *Plasmodium* parasites such as *Plasmodium falciparum* and optionally other malarial *Plasmodium* species as mentioned herein. Antibodies with comparable or higher affinity for binding CSP may be identified. Other desired characteristics include inhibiting the pre-erythrocytic stage of infection by *Plasmodium*, e.g, *P. falciparum*, which may be determined in an assay as described herein.

When VL domains are included in the method, the VL domain may be a VL domain of any of antibodies 666, 667, 668 or 669, or may be a variant provided by way of addition, deletion, substitution or insertion of one or more amino acids in the amino acid sequence of a parent VL domain, wherein the parent VL domain is the VL domain of any of antibodies 666, 667, 668 and 669 or a VL domain comprising the light chain complementarity determining regions of any of those antibodies.

An amino acid mutation (addition, deletion, substitution or insertion) may be introduced in an antibody variable domain at a position corresponding to a point of sequence variation across multiple antibodies in an antibody lineage. Thus, for example, an amino acid in a variable domain (VH or VL domain) of an antibody in a lineage (e.g., 666 lineage, 667 lineage, 668 lineage or 669 lineage) may be substituted with a different amino acid that is present at the corresponding position in another antibody of the same lineage. For instance, the antibody 666 VH domain comprises a C terminal sequence VTS, whereas certain other antibodies of the same lineage (666 lineage) comprise C terminal sequence VSS. The 666 VH domain may be engineered to have the substitution T>S in this C terminal motif. Comparison of antibody variable domain sequences with human germline gene segment sequences can also identify amino acid residues (e.g., within framework regions) that differ from the germline sequence and may optionally be reverted. Such "germlining" methods are known in the art and comparison with germline gene segment sequences is discussed elsewhere herein.

Further examples of changes that may be introduced in antibody variable domains can be identified by reference to FIGS. 23 and 24 in which sequences of multiple antibodies are aligned. When introducing one or more amino acid alterations into an antibody variable domain sequence at a given residue position, the alteration or alterations may optionally be designed by reference to the corresponding residue at that position in another antibody shown in the alignment.

Methods of generating variant antibodies may optionally comprise producing copies of the antibody or VH/VL domain combination. Methods may further comprise expressing the resultant antibody. It is possible to produce nucleotide sequences corresponding to a desired antibody VH and/or VL domain, optionally in one or more expression vectors. Suitable methods of expression, including recombinant expression in host cells, are set out in detail herein.
Encoding Nucleic Acids and Methods of Expression Isolated nucleic acid may be provided, encoding antibodies according to the present invention. Nucleic acid may be DNA and/or RNA. Genomic DNA, cDNA, mRNA or other RNA, of synthetic origin, or any combination thereof can encode an antibody.

The present invention provides constructs in the form of plasmids, vectors, transcription or expression cassettes which comprise at least one polynucleotide as above.

Exemplary nucleotide sequences are included in the sequence listing. Reference to a nucleotide sequence as set out herein encompasses a DNA molecule with the specified sequence, and encompasses a RNA molecule with the specified sequence in which U is substituted for T, unless context requires otherwise.

The present invention also provides a recombinant host cell that comprises one or more nucleic acids encoding the antibody. Methods of producing the encoded antibody may comprise expression from the nucleic acid, e.g., by culturing recombinant host cells containing the nucleic acid. The antibody may thus be obtained, and may be isolated and/or purified using any suitable technique, then used as appropriate. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, filamentous fungi, yeast and baculovirus systems and transgenic plants and animals.

The expression of antibodies and antibody fragments in prokaryotic cells is well established in the art. A common bacterial host is *E. coli*. Expression in eukaryotic cells in culture is also available to those skilled in the art as an option for production. Mammalian cell lines available in the art for expression of a heterologous polypeptide include Chinese hamster ovary (CHO) cells, HeLa cells, baby hamster kidney cells, NSO mouse melanoma cells, YB2/0 rat myeloma cells, human embryonic kidney cells, human embryonic retina cells and many others.

Vectors may contain appropriate regulatory sequences, including promoter sequences, terminator sequences, polyadenylation sequences, enhancer sequences, marker genes and other sequences as appropriate. Nucleic acid encoding an antibody can be introduced into a host cell. Nucleic acid can be introduced to eukaryotic cells by various methods, including calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques include calcium chloride transformation, electroporation and transfection using bacteriophage. The introduction may be followed by expressing the nucleic acid, e.g., by culturing host cells under conditions for expression of the gene, then optionally isolating or purifying the antibody.

Nucleic acid of the invention may be integrated into the genome (e.g. chromosome) of the host cell. Integration may be promoted by inclusion of sequences that promote recombination with the genome, in accordance with standard techniques.

The present invention also provides a method that comprises using nucleic acid described herein in an expression system in order to express an antibody.

To provide medicines suitable for global treatment, antibodies can be produced on a large scale, for instance in cell culture volumes of at least 100 litres or at least 200 litres, e.g., between 100-250 litres. Batch culture, particularly fed-batch culture, is now commonly used for production of biotherapeutics for clinical and commercial use, and such methods may suitably be used in the present invention to generate the antibodies, followed by purification and formulation steps as noted herein. Bioreactors may be metal (e.g., stainless steel) vessels or may be single-use bioreactors.

Formulations and Therapeutic Use

Antibodies may be monoclonal or polyclonal, but are preferably provided as monoclonal antibodies for therapeutic use. They may be provided as part of a mixture of other antibodies, optionally including antibodies of different binding specificity, such as one or more antibodies that bind to different antigens of a *Plasmodium* parasite, e.g., *P. falciparum*.

Antibodies according to the invention, and encoding nucleic acid, will usually be provided in isolated form. Thus, the antibodies, VH and/or VL domains, and nucleic acids may be provided purified from their natural environment or their production environment. Isolated antibodies and isolated nucleic acid will be free or substantially free of material with which they are naturally associated, such as other polypeptides or nucleic acids with which they are found in vivo, or the environment in which they are prepared (e.g. cell culture) when such preparation is by recombinant DNA technology in vitro. Optionally an isolated antibody or nucleic acid (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature.

Antibodies or nucleic acids may be formulated with diluents or adjuvants and still for practical purposes be isolated—for example they may be mixed with carriers if used to coat microtitre plates for use in immunoassays, and may be mixed with pharmaceutically acceptable carriers or diluents when used in therapy. As described elsewhere herein, other active ingredients may also be included in therapeutic preparations. Antibodies may be glycosylated, either naturally in vivo or by systems of heterologous eukaryotic cells such as CHO cells, or they may be (for example if produced by expression in a prokaryotic cell) unglycosylated. The invention encompasses antibodies having a modified glycosylation pattern. In some applications, modification to remove undesirable glycosylation sites may be useful, or e.g., removal of a fucose moiety to increase antibody dependent cellular cytotoxicity (ADCC) function (see Shields et al. (2002) JBC 277:26733). In other applications, modification of galactosylation can be made in order to modify complement dependent cytotoxicity (CDC).

Typically, an isolated product constitutes at least about 5%, at least about 10%, at least about 25%, or at least about 50% of a given sample. An antibody may be substantially free from proteins or polypeptides or other contaminants that are found in its natural or production environment that would interfere with its therapeutic, diagnostic, prophylactic, research or other use.

An antibody may have been identified, separated and/or recovered from a component of its production environment (eg, naturally or recombinantly). The isolated antibody may be free of association with all other components from its production environment, eg, so that the antibody has been isolated to an FDA-approvable or approved standard. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In some embodiments, the antibody will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or silver stain. Isolated antibody includes the antibody in situ within recombinant cells since at least one component of the antibody's natural environment will not be present. Ordinarily, however, an isolated antibody or its encoding nucleic acid will be prepared by at least one purification step.

The invention provides therapeutic compositions comprising the antibodies described herein. Therapeutic compositions comprising nucleic acid encoding such antibodies are also provided. Encoding nucleic acids are described in more detail elsewhere herein and include DNA and RNA, e.g., mRNA. Nucleic acid encoding the antibody of the invention may be provided as naked DNA, mRNA, replicon RNA or in a viral vector (e.g., adenoviral vector or lentiviral vector, or retroviral vector or poxvirus vector or herpesvirus vector) for administration in a therapeutic method that allows direct expression of the antibody. The nucleic acid will then be expressed in vivo by the recipient eukaryotic cells, providing an in vivo source of the therapeutic antibody, suitable for provision of long term protection against the malarial parasite. Various methods are known for administering nucleic acid for stable expression in vivo. For example, a nucleic acid composition (optionally naked DNA, mRNA, replicon RNA) may be administered by intramuscular injection, or via a 'gene gun'. For viral delivery, a range of viral vectors are known in the art (including gene therapy vectors) and any suitable vector may be used for transient expression, episomal expression (persistent but not integrated into the host genome) or integration of the encoding nucleic acid into cells of the recipient (e.g., liver cells and/or cells of the haematopoietic system).

Compositions may contain suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPO-FECTINT™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311. Compositions may comprise the antibody or nucleic acid in combination with medical injection buffer and/or with adjuvant. A composition may comprise the antibody in an aqueous buffered solution at a pH of between 6 and 8, e.g., 6.0 to 6.6, 6.4 to 7.1, 6.9 to 7.6 or 7.4 to 8.0. Such compositions can be included in medical containers and/or in kits.

Antibodies, or their encoding nucleic acids, may be formulated for the desired route of administration to a patient, e.g., in liquid (optionally aqueous solution) for injection. Various delivery systems are known and can be used to administer the pharmaceutical composition of the invention. Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see Langer (1990) Science 249:1527-1533; Treat et al. (1989) in Liposomes in the Therapy of Infectious Disease and Cancer, Lopez Berestein and Fidler (eds.), Liss, New York, pp. 353-365; Lopez-Berestein, ibid., pp. 317-327; see generally ibid.).

In certain situations, the pharmaceutical composition can be delivered in a controlled release system. In one embodiment, a pump may be used (see Langer, supra; Sefton (1987) CRC Crit. Ref. Biomed. Eng. 14:201). In another embodiment, polymeric materials can be used; see, Medical Applications of Controlled Release, Langer and Wise (eds.), CRC Pres., Boca Raton, Fla. (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule. A pharmaceutical composition of the present invention can be delivered subcutaneously or intravenously with a standard needle and syringe. It is envisaged that treatment will not be restricted to use in the clinic. Therefore, subcutaneous injection using a needle-free device is also advantageous. With respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded. Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPENT™, OPTIPEN PRO™, OPTIPEN STARLET™, and OPTICLIKT™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly).

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, the aforesaid antibody may be contained in about 5 to about 100 mg and in about 10 to about 250 mg for the other dosage forms.

The antibody, nucleic acid, or composition comprising it, may be contained in a medical container such as a phial, syringe, IV container or an injection device. In an example, the antibody, nucleic acid or composition is in vitro, and may be in a sterile container. In an example, a kit is provided comprising the antibody, packaging and instructions for use in a therapeutic method as described herein. The kit may comprise an insert (e.g., paper) and/or a label on a container containing the antibody or on the outer packaging of the kit, carrying the instructions for use in the therapeutic method, for example specifying use for prevention or treatment of malaria or of infection by *Plasmodium* such as *P. falciparum*. The insert or label may bear a marketing authorisation number, e.g., an FDA or EMA authorisation number. The antibody may be within a medical container comprising plastics material. Alternative medical grade materials include metal or glass. The medical container (e.g., phial, syringe, intravenous container or injection device) may comprise the antibody in a fluid form, optionally aqueous solution or in a composition comprising a pharmaceutically acceptable excipient as described herein.

One aspect of the invention is a composition comprising an antibody or nucleic acid of the invention and one or more pharmaceutically acceptable excipients, examples of which are listed above. "Pharmaceutically acceptable" refers to approved or approvable by a regulatory agency of the USA Federal or a state government or listed in the U.S. Pharmacopeia or other generally recognized pharmacopeia for use in animals, including humans. A pharmaceutically acceptable carrier, excipient, or adjuvant can be administered to a patient, together with an agent, e.g., any antibody or antibody chain described herein, and does not destroy the pharmacological activity thereof and is nontoxic when administered in doses sufficient to deliver a therapeutic amount of the agent.

Compositions according to the present invention optionally include one or more additional active ingredients. Further therapeutic agents may be anti-malarial agents such as other antibodies that bind antigens of *P. falciparum* or other malarial *Plasmodium* species. Optionally, such compositions contain multiple antibodies (or encoding nucleic acids) in a combined preparation, e.g., a single formulation comprising the anti-CSP antibody and one or more other antibodies to the same or different antigens of malarial *Plasmodium* species such as *P. falciparum*. For example, a composition may include an antibody to Pfs25, an antigen of *P. falciparum*. Other example antibodies to *Plasmodium* antigens are antibodies to MSP-1, MSP-2, TRAP, CelTOS, AMA1, Rh5 or LSA1, e.g., from *P. falciparum*. Other anti-malarial agents include chemoprophylactic drugs such as mefloquinine, doxycycline, atovaquone, proguanil, quinine, artemether, lumefantrine, clindamycin, primaquine, artemisinin, sulphadoxine-pyrimethamine and chloroquine. Atovaquone and proguanil are usually administered in combination. Further anti-malarial drug combinations include artemether with lumefantrine, quinine plus doxycycline, and quinine plus clindamycin. Other therapeutic agents that it may be desirable to administer with antibodies or nucleic acids according to the present invention include antibiotics such as amikacin, and analgaesic agents. Any such agent or combination of agents may be administered in combination with, or provided in compositions with antibodies or nucleic acids according to the present invention, whether as a combined or separate preparation. The antibody or nucleic acid according to the present invention may be administered separately and sequentially, or concurrently and optionally as a combined preparation, with another therapeutic agent or agents such as those mentioned.

Multiple compositions can be administered separately or simultaneously. Separate administration refers to the two compositions being administered at different times, e.g. at least 10, 20, 30, or 10-60 minutes apart, or 1, 2, 3, 4, 5, 6, 7, 8, 9, 10, 12 hours apart. One can also administer compositions at 24 hours apart, or even longer apart. Alternatively, two or more compositions can be administered simultaneously, e.g. less than 10 or less than 5 minutes apart. Compositions administered simultaneously can, in some aspects, be administered as a mixture, with or without similar or different time release mechanism for each of the components.

Antibodies, and their encoding nucleic acids, can be used as anti-malarial agents. They may be used for passive immunisation of mammals. An antibody or nucleic acid may be administered to a mammal, e.g., by any route of administration mentioned herein. Mammals may be humans, including humans at risk of malaria or humans diagnosed with malaria. The human or other mammal to whom the composition is administered may be one who has been, or is suspected of having been, infected with a malarial *Plasmodium* parasite, and/or who exhibits one or more symptoms of malaria.

An antibody molecule of the present invention, or a composition comprising such an antibody molecule or its encoding nucleic acid, may be provided for use in a method of:

treating or preventing malaria in a mammal;
reducing risk of malaria in a mammal;
reducing one or more symptoms of malaria in a mammal;
inhibiting the pre-erythrocytic stage of a *Plasmodium* infection in a mammal
reducing progression of *Plasmodium* infection in a mammal; and/or
reducing transmission, or reducing risk of transmission, of *Plasmodium* to and/or from a mammal;
wherein the method comprises administering the antibody or composition to a mammal.

The invention also provides a method of:
treating, or preventing or reducing risk of malaria in a mammal;
reducing one or more symptoms of malaria in a mammal;
reducing risk of malaria in a mammal;
inhibiting the pre-erythrocytic stage of *Plasmodium* infection in a mammal;
reducing progression of *Plasmodium* infection in a mammal; and/or
reducing transmission, or reducing risk of transmission, of *Plasmodium* to and/or from a mammal;
the method comprising administering an antibody of the invention, or a composition comprising the antibody or its encoding nucleic acid, to the mammal Administration is normally in a "therapeutically effective amount", this being an amount that produces the desired effect for which it is administered, sufficient to show benefit to a patient. The exact amount will depend on the purpose of the treatment, and will be ascertainable by one skilled in the art using known techniques (see, for example, Lloyd (1999) The Art, Science and Technology of Pharmaceutical Compounding). Benefit to the patient may be at least amelioration of at least one symptom of malaria, e.g., reduction in liver-stage parasite load, or protection against malaria or infection by malarial *Plasmodium* species such as *P. falciparum*. Prescription of treatment, e.g. decisions on dosage etc, is within the responsibility of general practitioners and other medical doctors and may depend on the severity of the symptoms and/or progression of a disease being treated. A therapeutically effective amount or suitable dose of antibody or nucleic acid can be determined by comparing its in vitro activity and in vivo activity in an animal model. Methods for extrapolation of effective dosages in mice and other test animals to humans are known.

In methods of treatment described herein, one or more doses may be administered. In some cases, a single dose may be effective to achieve a long-term benefit. Thus, the method may comprise administering a single dose of the antibody, its encoding nucleic acid, or the composition. Alternatively, multiple doses may be administered, usually sequentially and separated by a period of days, weeks or months.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilised (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment). For treatment to be effective a complete cure is not contemplated. The method can in certain aspects include cure as well. In the context of the invention, treatment may be preventative treatment, optionally the prevention or reduction of infection by *Plasmodium* such as *P. falciparum*, and/or the prevention of malaria, or reduction of at least one symptom of malaria.

Diagnostics

A further aspect of the invention relates to diagnostic uses of the antibodies described herein. The antibodies offer advantages for point of care diagnostics in mammals, and are especially envisaged for use in humans, where rapid diagnosis of malaria and/or *Plasmodium* infection is of significant clinical benefit. An antibody according to the invention may be used to detect *Plasmodium*, e.g., *Plasmodium falciparum*.

For diagnostic purposes, an antibody may comprise or be conjugated to a detectable label, such as a radioisotope or a fluorescent label. An antibody according to the invention may be used for determining the presence or absence of CSP or *Plasmodium* in a sample.

A method of determining the presence or absence of CSP or *Plasmodium* in a sample may comprise
contacting the sample with the antibody; and
testing for binding between the antibody and CSP or *Plasmodium* in the sample.
Detection of binding indicates the presence of CSP or *Plasmodium* in the sample, whereas absence of binding indicates the absence of CSP or *Plasmodium* in the sample.

Methods may further comprise quantifying the level of binding, for example by comparing the level of binding with a control. Control assays may be run in parallel, or the level of binding may be compared with previously obtained control values. Suitable controls include negative control samples in which no CSP or *Plasmodium* is present, thus establishing a level of background signal, which can be subtracted from the signal obtained from the test assay. Positive controls may also be conducted, by contacting the antibody with a sample known to contain a pre-determined amount of CSP or *Plasmodium*. Determining the level of binding in the test sample compared with the level of binding in one or more positive controls is one method of quantifying the amount of CSP or *Plasmodium* in the sample.

The sample may be one that has been obtained from a mammal who has been, or is suspected of having been, infected with a malarial *Plasmodium* parasite, and/or who exhibits one or more symptoms of malaria. It may be a blood sample, e.g., serum or whole blood. Peripheral blood samples are routinely obtainable from mammals, including human patients, in a clinical setting.

Antibodies may be provided in diagnostic kits. A kit may comprise the antibody, or a composition as described herein, and optionally one or more buffering solutions. As noted, the antibody may comprise or be conjugated to a detectable label. Labelled antibodies allow for detection of the antibody, facilitating detection of binding of the antibody to its target. Alternatively, an antibody may be used in combination with a secondary antibody or other labelled agent, the secondary antibody comprising or carrying a detectable label. Thus a kit may comprise a first reagent comprising an antibody according to the present invention, plus a second reagent comprising a detector molecule that binds to the first reagent. The detector molecule may be an antibody that comprises or is conjugated to a detectable label.

Mammals and Transgenic Animals

In the context of the present invention, mammals may be humans or other mammalian subjects such as wild animals, livestock or test (laboratory) animals. The mammal may be one who has been, or is suspected of having been, infected with a malarial *Plasmodium* parasite, and/or who exhibits one or more symptoms of malaria. Such mammals represent potential subjects for treatment with antibodies and compositions of the invention, and subjects from whom it may be of value to obtain samples for performing the diagnostic methods described herein.

In a research context, laboratory mammals have been engineered to express antibodies comprising human variable regions. A mammal may be a non-human mammal comprising a human immunoglobulin variable region that is capable of generating antibodies comprising human variable regions. The Kymouse™ is a transgenic mouse containing a humanised antibody heavy chain locus and a humanised antibody light chain locus. It is described in Lee et al., Nature Biotechnology 32(4): 356-367 2014 and in WO2011004192. A number of different Kymice™ have been developed, including mice with humanised kappa light chain variable regions, humanised lambda light chain variable regions, and mice in which the heavy chain variable regions and both lambda and kappa light chain variable regions are fully humanised and comprise the full repertoire of human immunoglobulin gene segments, reflecting the full diversity of the human antibody repertoire.

In addition to the Kymouse™, other transgenic animals have been created for production of antibodies comprising human variable regions. These include other mice, such as Velocimouse®, Omnimouse®, Xenomouse®, HuMab Mouse® and MeMo Mouse®, and rats such as the Omnirat®.

Owing to their ability to mirror aspects of the human antibody immune response, these animals—especially the Kymouse™—are of particular value in a pre-clinical setting for the development of vaccines and for testing compositions to determine efficacy of immunisation against infection by malarial *Plasmodium* parasites. They find use in many aspects of the invention, such as in testing anti-malarial vaccines as described in more detail elsewhere herein.

Plasmodium

*Plasmodium* is a genus of parasitic protozoa. Infection with *Plasmodium* results in the disease malaria, which can be fatal. The malarial *Plasmodium* parasite has two hosts in its life cycle—a Dipteran insect host and a vertebrate host. The life-cycle is complex, involving a sequence of different stages both in the vector and the vertebrate host. These stages include sporozoites, which are injected by the insect vector into the vertebrate host's blood; latent hypnozoites, which may rest undetected in the liver for up to 30 years; merosomes and merozoites, which infect the red cells (erythrocytes) of the blood; trophozoites, which grow in the red cells, and schizonts, which divide in red blood cells. Schizonts produce merozoites, which leave to infect more red cells. The sexual forms, gametocytes, are taken up by other insect hosts during feeding. Gametocytes develop into gametes in the insect midgut, and then fertilise each other to form motile zygotes, which escape the gut. Zygotes grow into new sporozoites, which move to the insect's salivary glands. Sporozoites are injected into vertebrate hosts during insect feeding, thus completing the cycle of infection. Biting mosquitos are a common route of transmission between mammals, including humans. See FIG. 1.

In the present invention, unless the context requires otherwise, *Plasmodium* may be any *Plasmodium* species, such as *P. falciparum, P. vivax, P. ovale*, or *P. malariae*. It may be a naturally occurring *Plasmodium* species, or a laboratory-engineered *Plasmodium* such as *P. berghei* that has been engineered to express CSP from *Plasmodium falciparum*. Such engineered protozoa are useful in animal models, especially with mice as described herein.

Antibodies according to the present invention may target or bind *Plasmodium* sporozoites. Antibodies may inhibit or reduce the risk of *Plasmodium* infection, specifically the pre-erythrocytic or sporozoite stage of infection. This provides the advantage of targeting the *Plasmodium* at an early stage of entry to the vertebrate host body, offering the possibility of preventing infection from taking place. Where a body is already infected with *Plasmodium*, inhibition of sporozoites nevertheless has the advantage of reducing progression of *Plasmodium* infection and of inhibiting sporozoites in the blood stream, thereby lessening the risk of transmission of *Plasmodium* from that individual to another via insect feeding e.g., mosquito bite or via contact with infected blood.

Anti-Malarial Vaccines and Immunisation

Efforts to produce effective vaccines against malarial *Plasmodium* parasites are ongoing. It is desirable to eradicate malaria, or at least to reduce its prevalence, and improving the efficacy of anti-malarial vaccines offers a route to achieving this goal.

CSP, fragments of CSP comprising the NANP (SEQ ID NO: 509) repeat region, or synthetic NANP (SEQ ID NO: 509) repeat peptide such as (NANP)n, where n=4 to 40, e.g., (NANP)40, (NANP)10 or (NANP)4, (SEQ ID NO: 44, SEQ ID NO: 45 and SEQ ID NO: 46, respectively) may be used for immunisation of a mammal against infection by a malarial *Plasmodium* parasite, and represent potential components for vaccine compositions. Fragments of CSP or synthetic peptides comprising other epitopes identified herein, e.g., NPDPNANP (SEQ ID NO: 512), may be used for such immunisations and also represent potential components for vaccine compositions. A synthetic repeat peptide may be generated, comprising repeats of the motif NPDPNANP (SEQ ID NO: 512), optionally including one or more additional amino acids at one or both ends of the repeated motif. A vaccine composition may optionally include part but not all of the NANP (SEQ ID NO: 509) repeat region, e.g., may be a fragment or C-terminal truncated CSP, including the sequence NPDPNANP (SEQ ID NO: 512) and optionally upstream sequence, but lacking a C-terminal and/or central portion of the NANP (SEQ ID NO: 509) repeat region. Such peptide vaccines could be coupled to carrier proteins or virus like nanoparticles to achieve a more optimal and long lived immune response. Advantageously, compositions may further comprise one or more additional antigens or antigen fragments from one or more malarial *Plasmodium* parasites, optionally *P. falciparum*.

When developing vaccines, candidate compositions must be tested for efficacy. Efficacy may be measured in preclinical models, such as in mice, and in human clinical trials. One way to measure the ability of a composition to confer protection against a malarial *Plasmodium* parasite is to administer the composition to a mammal and determine the efficacy of immunisation of that mammal resulting from the administration. Measures of efficacy of immunisation include strength of immune response generated, e.g., antibody titre, and quality of antibodies generated, e.g., in terms of their binding specificity, neutralising ability, or sequence and/or epitope-binding diversity. Efficacy of immunisation can also be determined by subsequently challenging the individual with a malarial *Plasmodium* parasite and observing the degree to which the individual develops, or is protected from, *Plasmodium* infection and/or symptoms of malaria. It is useful to measure efficacy of immunisation in populations of individuals, such as cohorts of mice, and to determine protection against challenge in terms of length of survival of the individuals following challenge. It will be appreciated that individuals, or populations of individuals, will usually be compared with control individuals or populations of individuals that receive the same challenge without having previously been immunised with the candidate composition. Control individuals may be placed in the same experimental conditions except that they do not receive the administration of candidate composition. They may for example receive a mock injection-injection of buffer/saline in place of an injection of the test composition. Efficacy of immunisation, and protection from challenge, are thus usually compared with control data.

Antibodies according to the present invention may be used to determine the efficacy of immunisation against a malarial *Plasmodium* parasite. They may be used as diagnostic reagents for determining the level of CSP or *Plasmodium* in a sample, this being indicative of the level of *P. falciparum* (or of other *Plasmodium* species that express CSP, such as *P. berghei* engineered to express *P. falciparum* CSP) in the sample, and thus the level of infection in the mammal from whom the sample is obtained, particularly the pre-erythrocytic or sporozoite stage of the parasite. Methods of detecting CSP or *Plasmodium* with antibodies are described in detail elsewhere herein.

A method of determining efficacy of immunisation of a mammal against a malarial *Plasmodium* parasite may comprise:

administering CSP, a fragment thereof comprising the NANP (SEQ ID NO: 509) repeat region, or a synthetic NANP (SEQ ID NO: 509) repeat peptide, and optionally one or more other antigens of the *Plasmodium* parasite, to a mammal, allowing time for development of an immune response in the mammal;

challenging the mammal with a malarial *Plasmodium* parasite, for example by exposing the mammal to biting by a mosquito infected with the parasite, and allowing time for development of an immune response in the mammal, to provide a challenged mammal;

obtaining a sample from the challenged mammal;

contacting the sample with the antibody; and determining the level of binding between the antibody and CSP or *Plasmodium* in the sample;

the level of binding being negatively correlated with the efficacy of immunisation.

Alternatively, a method of determining efficacy of immunisation of a mammal against a malarial *Plasmodium* parasite may comprise:

providing a sample obtained from a challenged mammal provided as described above;

contacting the sample with the antibody; and determining the level of binding between the antibody and CSP or *Plasmodium* in the sample;

the level of binding being negatively correlated with the efficacy of immunisation.

Any suitable diagnostic method, as described elsewhere herein, may be used to determine the level of binding. As noted, binding may be quantified relative to binding in samples obtained from control individuals, or relative to positive and/or negative control samples.

The CSP (or fragment thereof, or NANP (SEQ ID NO: 509) repeat peptide) or the *Plasmodium* may be administered by any method suitable to generate an immune response in the mammal. Common methods of delivering vaccines include by intramuscular, subcutaneous or intravenous injection, and any such method may be used here. Other possible methods of administration are described elsewhere herein, and may be applied to methods of administering the CSP (or fragment thereof, or NANP (SEQ ID NO: 509) repeat peptide) or the *Plasmodium*. Administering the candidate vaccine composition comprising the antigen or antigens may comprise injecting live or killed *Plasmodium*, or antigen or antigens purified from *Plasmodium* or recombinantly expressed, into the mammal. The antigen or antigens may be administered in combination with an adjuvant.

Mice are a suitable test animal for vaccine development. The mammal in these methods may thus be a mouse. In a mouse model, a suitable *Plasmodium* parasite is *P. berghei*, which can be engineered to express *P. falciparum* CSP or a fragment thereof comprising the NANP (SEQ ID NO: 509) repeat region, ensuring that the *P. berghei* is bound by antibodies according to the present invention. Where transgenic mice containing a human antibody repertoire are employed, this provides a model of infection of humans by *P. falciparum*, the antibody response in the mice representing a model antibody response generated by the human immune system.

The Kymouse™ is especially suitable for use in such models. It is possible to use other transgenic mice or other test animals engineered to express antibodies with human variable regions, and examples of these are mentioned elsewhere herein.

When challenging such mice with malarial *Plasmodium* parasites (e.g., *P. berghei* engineered to express *P. falciparum* CSP or a fragment thereof comprising the NANP (SEQ ID NO: 509) region), the generation of antibodies according to the present invention provides an indication that the mouse generates an effective immune response. Equally, in humans, generation of antibodies according to the present invention is an indication that the human generates an effective immune response against *P. falciparum*. Antibodies according to the invention may thus be used as a measure of vaccine efficacy in anti-malarial vaccine trials, whether pre-clinical (e.g., in transgenic animals expressing antibodies with human variable domains) or clinical (in humans).

A method of determining efficacy of immunisation of a mammal against a malarial *Plasmodium* parasite may comprise:

administering CSP, a fragment thereof comprising the NANP (SEQ ID NO: 509) repeat region, or a NANP (SEQ ID NO: 509) repeat peptide, and optionally one or more other antigens of the *Plasmodium* parasite, to a mammal, allowing time for development of an immune response in the mammal, and obtaining a sample from the mammal; and assaying for the presence of an antibody according to the present invention in the sample;

wherein the presence of one or more such antibodies is indicative of effective immunisation.

Alternatively, a method of determining efficacy of immunisation of a mammal against a malarial *Plasmodium* parasite may comprise:

providing a sample obtained from a mammal, wherein the mammal has received an administration of CSP, a fragment thereof comprising the NANP (SEQ ID NO: 509) repeat region, or a NANP (SEQ ID NO: 509) repeat peptide, and optionally one or more other antigens of the *Plasmodium* parasite, and wherein the sample has been obtained after allowing time for development of an immune response; and assaying for the presence of an antibody according to the present invention in the sample;

wherein the presence of one or more such antibodies is indicative of effective immunisation.

As noted above, fragments of CSP or synthetic peptides comprising epitopes identified herein, e.g., NPDPNANP (SEQ ID NO: 512), may be administered. A synthetic repeat peptide may be generated, comprising repeats of the motif NPDPNANP (SEQ ID NO: 512), optionally including one or more additional amino acids at one or both ends of the repeated motif. A vaccine composition or a composition used for immunisation or administration to a mammal may optionally contain part but not all of the NANP (SEQ ID NO: 510) repeat region, e.g., may be a fragment or C-terminal truncated CSP, including the sequence NPDPNANP (SEQ ID NO: 512) and optionally upstream sequence, but lacking a C-terminal and/or central portion of the NANP (SEQ ID NO: 509) repeat region. Such vaccines could be coupled to carrier proteins or virus like nanoparticles to achieve a more optimal and long lived immune response.

Thus, further methods of the invention include methods of determining efficacy of immunisation of a mammal against a malarial *Plasmodium* parasite, comprising:

administering a composition comprising CSP, or comprising a fragment of CSP or a synthetic peptide comprising NPDPNANP (SEQ ID NO: 512), to a mammal, allowing time for development of an immune response in the mammal, and obtaining a sample from the mammal; and assaying for the presence of an antibody according to the present invention in the sample;

wherein the presence of one or more such antibodies is indicative of effective immunisation.

A method of determining efficacy of immunisation of a mammal against a malarial *Plasmodium* parasite may comprise:

providing a sample obtained from a mammal, wherein the mammal has received an administration of the said composition as defined above, and wherein the sample has been obtained after allowing time for development of an immune response; and assaying for the presence of an antibody according to the present invention in the sample;

wherein the presence of one or more such antibodies is indicative of effective immunisation.

As noted, the administered compositions may optionally further comprise one or more other antigens of the *Plasmodium* parasite.

Exemplary antibodies are antibodies comprising the antibody 667 or antibody 668 CDRs, and variants thereof, as described herein.

Methods of determining efficacy of immunisation may comprise assaying for the presence of, or determining enrichment of, antibody comprising the structural motif as defined herein. Thus, the antibody may comprise a VH domain comprising HCDR1, HCDR2 and HCDR3 in a framework, and a VL domain comprising LCDR1, LCDR2 and LCDR3 in a framework, wherein LCDR1, LCDR3, HCDR2 and HCDR3 are as follows:

LCDR1 contains an N and a hydrophobic residue. Preferably, the N is at position 31. Preferably, the N is either directly preceded or followed by the hydrophobic residue. The hydrophobic residue is preferably Y.

LCDR3 contains a Y residue and a W residue. Preferably, the Y precedes W (in the N to C direction). Preferably, Y is at position 91. Preferably, W is at position 96.

HCDR2 contains W and N. Preferably, the W precedes N (in the N to C direction). Preferably, W is at position 50. Preferably, N is at position 52.

HCDR3 contains at least one Y residue. Y may be present at any position in the HCDR3.

Assaying for the presence of an antibody molecule may comprise identifying whether any B cells in the mammal encode antibodies according to the present invention, for example by sequencing nucleic acid from the B cells. Methods may comprise determining whether antibodies (e.g., VH and VL domains comprising the defined structural motif) according to the present invention are enriched in the mammal following administration of the composition. For example, a method may comprise determining whether such antibodies are enriched over background frequencies by at least 0.1%, at least 1%, at least 2%, at least 5% or at least 10% in the sample from the mammal, compared with a control sample (e.g., from a mammal who has not received the administered composition, e.g., a sample obtained from the same mammal prior to the administration). As noted previously, a sample may be a blood sample, e.g., serum or whole blood. Peripheral blood samples are routinely obtainable from mammals, including human patients, in a clinical setting. The presence of, and especially the enrichment of, the antibody or antibody sequence according to the invention in the sample provides an indication that the administered composition generates a protective immune response against the malarial *Plasmodium* parasite (e.g., protecting against infection by *P. falciparum*).

Suitable methods of administering the composition to a mammal are set out above. The administered composition may be a vaccine or a candidate vaccine, and may comprise one or more adjuvants. The methods described here may be used to determine efficacy of vaccination of a mammal, for example to confirm, predict or test for protection of a vaccinated human individual against infection by a malarial *Plasmodium* parasite. The methods may also be used in the context of pre-clinical or clinical trials involving a candidate vaccine composition.

The method may further comprise challenging the mammal with a malarial *Plasmodium* parasite by exposing the mammal to biting by a *Plasmodium*-infected mosquito, and determining the degree of protection against challenge, as described.

EXAMPLES

The following examples report experimental work underlying the present invention and serve to illustrate aspects of various embodiments.

This work was funded in whole or in part by the PATH Malaria Vaccine Initiative, in a collaboration between PATH, the Bill and Melinda Gates Foundation, Kymab Limited and Atreca, Inc. Kymice™ were used in the United Kingdom.

Example 1: Generation of Antibodies

Kymice™, a transgenic mouse platform capable of generating antibodies with human variable domains, were immunised with CSP to generate anti-CSP antibodies.

The Kymouse™ platform used in this study is composed of two strains of mice, Kymouse HK and Kymouse HL, both of which carry human variable domains and mouse constant domains. The antibody repertoire of these mice are composed of human V, D and J segments. The endogenous mouse variable genes have been silenced and make up a very small portion of the repertoire (less than 0.5% of all heavy chain variable regions are of mouse origin). The mice display normal B-cell signalling and development. These mice respond robustly to antigen challenge and produce high affinity antibodies with human-like HCDR3 lengths.

Kymouse HK includes engineered IgH and IgK loci. It includes inserted human VH-gene segments and human V-kappa gene segments. It has normal mouse heavy and light constant regions.

Kymouse HL includes engineered IgH and IgL loci. It includes inserted human VH-gene segments and V-lambda gene segments. It has normal mouse heavy regions and human light constant regions.

CSP used for this experiment was sourced from Gennova through the Malaria Vaccine Initiative (MVI). Protein was provided in lyophilised form. The antigen is a 58 kDa protein from *P. falciparum* strain 3D7; GenBank accession number AL034558. A synthetic nucleotide sequence encoding the full-length, mature translated protein sequence for PfCSP (3D7 strain; GenBank accession number AL034558) was commercially synthesised with codons optimised for maximizing expression of the heterologous gene in *E. coli*. This synthetic gene encoded the predicted full-length mature protein with a carboxy-terminal hexa-histidine tag, without the signal sequence and putative GPI anchor sequence. Expression system: *E. coli* BL21 (DE3). These host cells contain a chromosomal copy of T7 RNA polymerase gene under the control of lacUV5 promoter which is induced by addition of lactose analogue such as isopropyl-β-D-thiogalactopyranoside (IPTG). IPTG induces production of T7 RNA polymerase allowing transcription of the target DNA in the plasmid. BL21 (DE3) strain is deficient in both lon and ompT proteases, thus improving stability of the recombinant protein expressed in these host cells. The purified antigen has been show to elicit a strong T-cell immune response by Elispot. Nucleotide and amino acid sequences of CSP are shown in FIGS. 6 and 7. The antigen has also previously been shown to be immunogenic in immunisations in animals (Kastenmüller K, Espinosa D A, Trager L, Stoyanov C, Salazar A M, Pokalwar S, Singh S, Dutta S, Ockenhouse C F, Zavala F, Seder RA. Infect Immun. 2013 March; 81(3):789-800. doi: 10.1128/IAI.01108-12. Epub 2012 Dec. 28).

Figure 2:
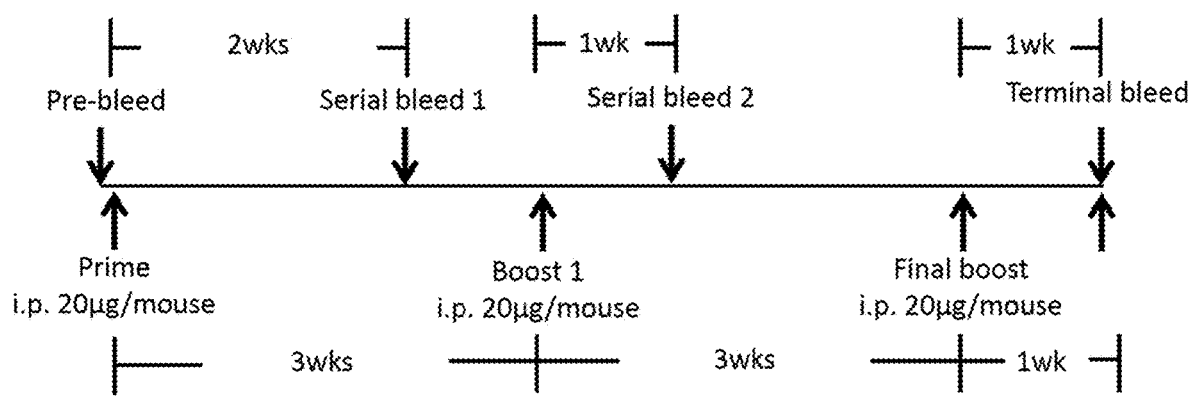
FIG. 2 is an immunisation schedule for Kymice to produce anti-malarial antibodies.

Immunisations were carried out according to the schedule in FIG. 2 using 20 μg of *E. coli* expressed full length Pf-CSP and Montanide ISA720 adjuvant 70/30% v/v. Details of the animals used for immunisation are presented in Table 1.

TABLE 1

Animals used for CSP immunisation.

| Exp ID | Mouse ID | Sex | Adjuvant | Immunisation procedure | Amount 1st inject | Age at start |
|---|---|---|---|---|---|---|
| KG007 | KMCF 80.5a | Male | Montanide 720 | ip/ip/iv | 20 ug | 10.4 w |
|  | KMCF 80.5b | Male | Montanide 720 | ip/ip/iv | 20 ug | 10.4 w |
|  | KMCF 80.5c | Male | Montanide 720 | ip/ip/iv | 20 ug | 10.4 w |
|  | KMCF 80.5d | Female | Montanide 720 | ip/ip/iv | 20 ug | 10.4 w |
|  | KMCF 80.5e | Female | Montanide 720 | ip/ip/iv | 20 ug | 10.4 w |
|  | KMCF 80.5f | Female | Montanide 720 | ip/ip/iv | 20 ug | 10.4 w |
|  | KMCF 80.5g | Female | Montanide 720 | ip/ip/iv | 20 ug | 10.4 w |
| KG007 | KMCE 73.5a | Male | Montanide 720 | ip/ip/iv | 20 ug | 10.1 w |
|  | KMCE 73.5b | Male | Montanide 720 | ip/ip/iv | 20 ug | 10.1 w |
|  | KMCE 73.5c | Male | Montanide 720 | ip/ip/iv | 20 ug | 10.1 w |
|  | KMCE 73.5d | Male | Montanide 720 | ip/ip/iv | 20 ug | 10.1 w |
|  | KMCE 73.5e | Male | Montanide 720 | ip/ip/iv | 20 ug | 10.1 w |
|  | KMCE 73.5f | Female | Montanide 720 | ip/ip/iv | 20 ug | 10.1 w |
|  | KMCE 73.5g | Female | Montanide 720 | ip/ip/iv | 20 ug | 10.1 w |

Immunisation progress was monitored via serial bleed titres. Following sacrifice, sera were collected for terminal bleed titre via a CSP-ELISA assay. All mice responded to CSP-antigen challenge with >10^4 final titre.

Example 2: Expression of Selected Antibody Sequences

Post-immunisation antibody responses in the Kymice™ were identified from blasting B cells using the IRC™ sequencing technology. IRC™ technology has been described by Atreca, Inc. in published patent applications. This platform captures full length sequences, enabling detection of somatic mutations across the entire antibody variable region. Natively paired heavy and light chain IgG variable regions are analysed, and constant region isotype assignments can be made. IRC corrects for sequence errors introduced at all steps of a single-cell analysis process and provides unbiased output by correcting for biases from PCR amplification and other sources. IRC can be applied to any B cell type, other isotypes, and any species for which constant region sequences are known, including blasted B cells (e.g. human plasmablasts, mouse splenocytes, etc.) and antigen sorted B cells (e.g. antigen-binding memory B cells). IRC was used here to provide the signal peptide, full variable region, and a portion of the constant region of natively-paired heavy and light chain sequences from individual B cells of the immunised Kymice.

Candidate antibody lineages for expression and testing were chosen based on sequence-features such as the degree of lineage dominance, somatic hypermutation levels, and apparent convergence of lineages across multiple CSP-immunised Kymice. Forty-eight antibody sequences representing thirty-seven diverse, putative antibody lineages were produced via gene synthesis and recombinant expression as fully human antibodies.

Methods of Vector Construction and Recombinant Antibody Expression

Subcloning of Antibody Sequences into Expression Vectors:

DNA sequences for paired heavy chain (HC) and light chain (LC) IgG variable regions were synthesised and subcloned into expression vector pLEV123 (LakePharma, Inc.). Heavy chain variable region sequences were fused to the signal peptide MDPKGSLSWRILLFLSLAFELSYG (SEQ ID NO: 51) and human IgG1 constant regions. The light chain variable region sequences were fused to the signal peptide MSVPTQVLGLLLLWLTDARC (SEQ ID NO: 52) for the lambda light chain, or METDTLLLWVLLLWVPGSTG (SEQ ID NO: 53) for the kappa light chain, followed by the compatible human kappa or lambda light chain constant regions.

Small Scale Transient Transfection:

HEK293 cells were seeded in shake flasks one day before transfection, and were grown using serum-free chemically defined media. The DNA expression plasmids were scaled up and transiently transfected into 10-30 ml of suspension HEK293 cells using LakePharma's standard operating procedure for transient transfection. After 20 hours, cultures were fed and production continued for 5 days. Cells were sampled to obtain the viabilities and viable cell counts, and titers were measured (Octet QKe, ForteBio). On day 5, cells were sampled to obtain the viabilities and viable cell counts, and titers were measured (Octet QKe, ForteBio) before harvesting the cell cultures.

Protein a Affinity Purification:

The conditioned media from HEK293 cells expressing antibody were harvested from the transient transfection production run by centrifugation. The supernatant was run over a Protein A column and eluted with a low pH buffer. Filtration using a 0.2 μm membrane filter was performed before aliquoting. After purification and filtration, the protein concentration was calculated from the OD280 and the extinction coefficient. Antibodies were formulated in HEPES buffer (200 mM HEPES, 100 mM NaCl, 50 mM NaOac, pH 7.) CE-SDS analysis was performed (LabChip GXII, Perkin Elmer) to ensure antibody quality.

Example 3: CSP-Binding Characterisation

Nine antibody lineages were found to bind CSP when tested by ELISA. Of these, seven bound to native CSP epitopes presented on the surface of whole sporozoites.

Seven of nine ELISA positive lineages were expressed as full-length antibodies with human IgG1 constant region and further characterised using bio-layer interferometry and competitive binding assays to identify distinct binding sites.

TABLE 2

Dissociation constants were determined via Octet affinity analysis at LakePharma, Inc.. CSP binding site was determined via ELISA with CSP fragments.

| Antibody | Putative Lineage # | # mAbs in lineage | $K_d$ (nM) | CSP Binding Site |
|---|---|---|---|---|
| AB-000640 | CSP-36 | 36 | 307 | C-term |
| AB-000643 | CSP-14 | 14 | 15.9 | C-term |
| AB-000646 | CSP-53 | 53 | 10.2 | C-term |
| AB-000649 | CSP-04 | 20 | 13.2 | not determined |
| AB-000662 | CSP-02 | 37 | 18.1 | C-term |
| AB-000667 | CSP-06 | 13 | 0.34 | NANP (SEQ ID NO: 509) repeat region |
| AB-000668 | CSP-07 | 12 | 0.57 | NANP (SEQ ID NO: 509) repeat region |

Binding affinities against rCSP were measured via ForteBio Octet Red69 using two different assay formats. By changing the Octet assay antibody-antigen orientation (see methods section below for two formats), the dose-dependent responses of Ab667 and Ab668 toward Streptavidin-sensor captured biotin/rCSP were obtained and the kinetics constants were calculated. The kinetic analysis of Ab667 and Ab668 binding toward biotin/rCSP by Octet was used to generate the kinetic constants shown in Table 3 and illustrate the high affinity of antibodies 667 and 668 to the CSP antigen.

TABLE 3

Kinetic constants of AB-000667 and AB-000668 to biotin/rCSP

| Loading Sample ID | Sample ID | KD (M) | kon (1/Ms) | kdis (1/s) | Full R^2 | Full X^2 |
|---|---|---|---|---|---|---|
| Biotin-rCSP | AB-000667 | 3.41E−10 | 1.66E+05 | 5.67E−05 | 0.999447 | 0.008402 |
| Biotin-rCSP | AB-000668 | 5.70E−10 | 1.25E+05 | 7.10E−05 | 0.999348 | 0.084204 |

Figure 8A:
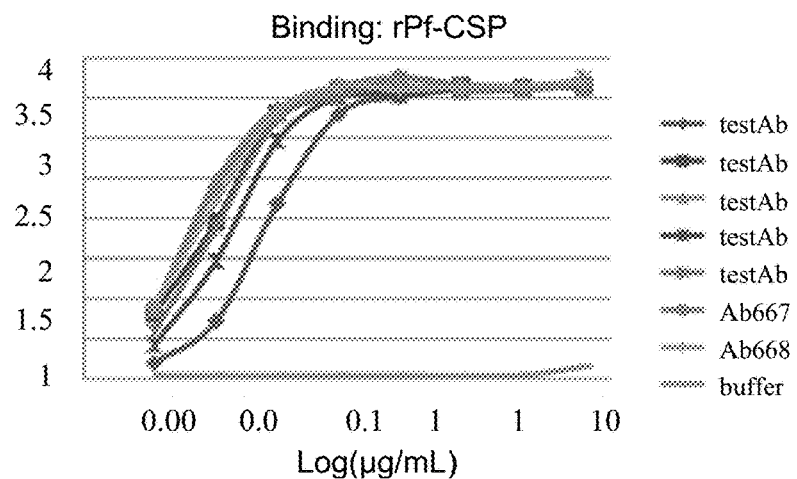
FIG. 8 shows the results of epitope mapping experiments for antibodies 667 and 668 and reference data from other test antibodies. A: Dose-dependent ELISA binding towards recombinant CSP from *P. falciparum*. B: Dose-dependent ELISA binding towards EP070034 (NANP peptide)(SEQ ID NO: 47). C: Dose-dependent ELISA binding towards Pf16 (C-terminal peptide of CSP).
Figure 8B:
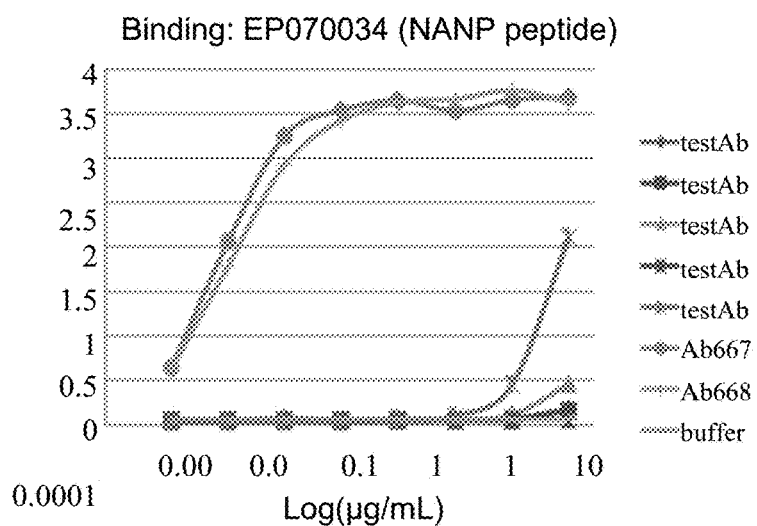
Figure 8C:
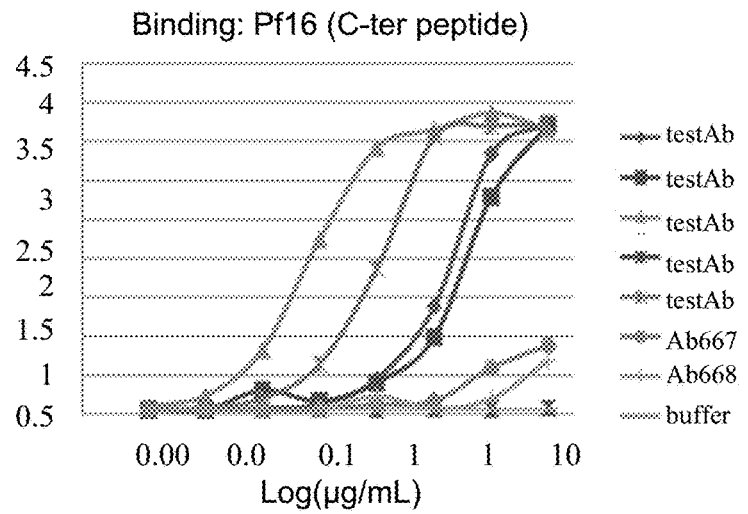

A direct binding ELISA of the anti-CSP mAbs to two different peptides and the rPf-CSP control antigen (Gennova) was performed. Anti-CSP mAbs 667 and 668 were shown to bind to rPF-CSP and to the NANP (SEQ ID NO: 509) repeat region, while lacking binding capacity to the Pf16 motif at the C-terminus region of CSP. See FIG. 8.

Figure 3:
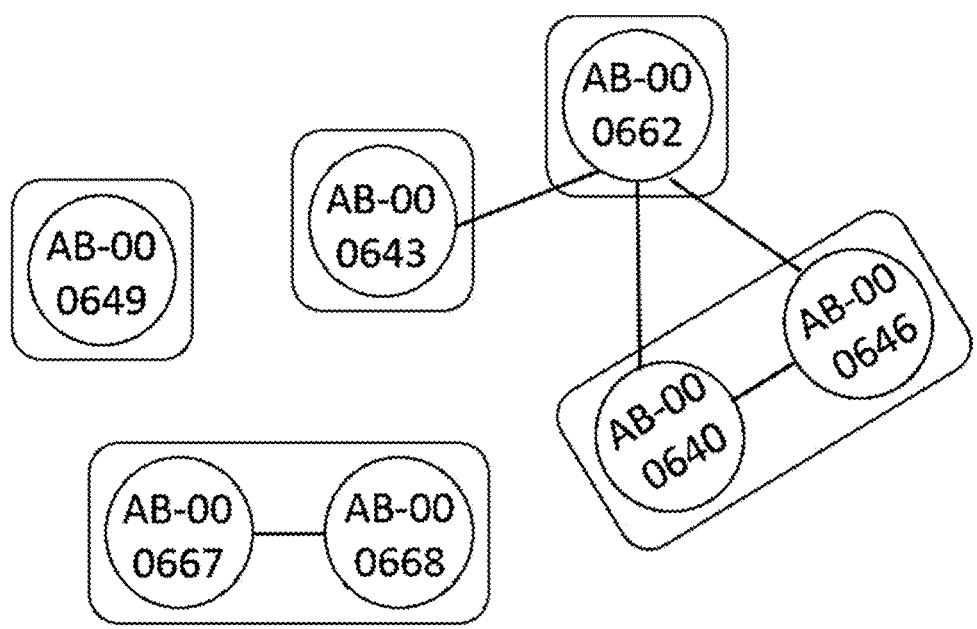
FIG. 3 is a schematic diagram of antigen binding cross-blocking between antibodies.

Competitive binding assays were performed with the ForteBio Octet™ system, in which anti-human Fc coated sensors were sequentially incubated with first antibody, antigen, then second antibody. Binding of each component was monitored by SPR. Results are illustrated in FIG. 3, in which a chord between two mAbs indicates a blocking relationship and no chord indicates no blocking.

In order for two antibodies to belong to the same bin, they must block one another and exhibit similar blocking profiles when each is paired with the other antibodies in the test panel. In this project, both assay formats (see methods below) agree that AB-000649 has a unique epitope than the other antibodies, and AB-000667 and AB-000668 are in the same epitope bin. AB000643 and AB-000646 are in different bins because they do not block each other. Whether AB-00640 is in the same bin as AB-000646 or AB-000662 depends on the blocking relationship of AB-000640 and AB-000643. From the kinetics analysis results, AB-000640 is a relatively weaker antibody with a slower on-rate and a fast off-rate. This may contribute to the uncertainty into its bin assignment.

Methods:

Epitope binning tests antibodies in a pairwise manner; antibodies competing for the same binding region are grouped together into bins. In this project, epitope binning was performed on Octet QKe system (ForteBio) using two assay formats. The biosensors were hydrated in sample diluent (0.1% BSA in PBS and 0.02% Tween 20) and preconditioned in pH 1.9 Glycine. The first assay format (Assay Format 1) used Anti-hFc (AHC) kinetic grade biosensors (ForteBio, #18-5060) to capture rCSP/Ab1 mix (rCSP 100 nM, Ab1 300 nM, 60 seconds); the sensors were then dipped into high concentration of hFc (150 ug/mL) for 300 seconds to saturate the AHC sensor. Ab1 of 300 nM was loaded again for 300 seconds to check for unsaturated Ab1 binding epitope. Lastly, the sensors were dipped into Ab2 (100 nM, 120 seconds) to capture the association.

A second assay format (Assay Format 2) used Streptavidin (SA) kinetic grade biosensors (ForteBio, #18-5021) to immobilize biotinylated rCSP at a concentration of 20 µg/ml for 120 seconds. The antigen-loaded SA biosensors were then dipped into Ab1 ("saturating antibody") at 20 ug/ml for 600 seconds. A short baseline (30 seconds) was observed using dissociation buffer after the Ab1 loading. The sensor was then dipped into Ab2 ("competing antibody") at 5 ug/mL and the association was observed for 120 seconds, followed by 120 seconds of dissociation. Parallel references were set up by repeating all the steps except for the saturating antibody step. Instead, the biosensors were dipped into the dissociation buffer directly. The Ab2 binding sensorgram captured the difference between the SA sensor-antigen-Ab1 and the SA sensor-antigen-buffer.

Methods for Enzyme-Linked Immunosorbent Assays (ELISA)

Ninety-six-well EIA plates were coated with 100 µL/well, 2 µg/mL Pf CSP antigen and incubated at 4° C. overnight. Antigen was diluted in 1× phosphate buffer (PB), pH 6.5. Coated plates were then blocked with 1×PBS, 2.5% BSA the next morning at room temperature for 2 hrs. Two serial dilutions (1:10 and 1:100) of each conditioned HEK 293 cell culture medium sample was prepared with 1×PBS, 1% BSA assay diluent. Duplicate 100 µL samples were added to each well; plates were then incubated at room temperature for 1 hour on a microplate shaker and then washed three times in 1×PBS. Secondary antibody (100 µL of 1:5,000 dilution) was added to each well: goat anti-mouse Fc-HRP was used for controls and anti-human Fc-HRP was used for the test sample wells. Plates were shaken at room temperature for 1 hour, followed by three washes with 1×PBS. Plates were then developed using TMB; the OD450 of each well was determined and recorded with a BMG POLARstar Omega Microplate reader.

Methods for Peptide ELISA for Epitope Mapping Studies

For determination of the specific Pf CSP epitope these antibodies bind to, ELISAs were performed using two different CSP-specific peptides, Pf 16 (C-terminus) and EP070034 (NANP (SEQ ID NO: 509) repeat region). Peptide Pf16 was reconstituted with DMSO to 20 mg/mL and then diluted with sterile water to obtain a final concentration of 5 mg/mL. EP070034 was reconstituted with sterile water to obtain a final concentration of 5 mg/mL. 96-well plates were coated overnight with the three antigens (including the full-length Pf CSP antigen) at a final concentration of 1 µg/mL. The plate was blocked with 1×PBS, 2.5% BSA for 2 hours the next morning at room temperature. Antibody samples were prepared in an 8-point 1:5 serial dilution series with 1×PBS, 1% BSA with a starting concentration of 50 µg/mL. The HRP-goat anti-human Fc was diluted 1:5,000 for detection as described above.

Methods for Octet Affinity Analyses

Affinity determination was performed on an Octet QKe system (ForteBio). Anti-hFc (AHC) kinetic grade biosensors (ForteBio, #18-5060) were hydrated in sample diluent (0.1% BSA in PBS and 0.02% Tween 20) and preconditioned in pH 1.9 Glycine. Antibody was immobilised onto AHC biosensors at a concentration of 20 µg/mL for 60 seconds. The antibody-loaded AHC biosensors were then dipped into an 8-point dilution series of the Pf CSP antigen (starting at 1000 nM, 1:3 diluted down). Association was observed for 120 seconds, followed by 180 seconds of dissociation. A short baseline (30 seconds) was established using dissociation buffer after AHC loading. Parallel references were set up by using unloaded bare sensor and sensor dipped into an 8-point dilution series of the antigen. During data processing, the parallel reference was used for normalization. The binding affinity of Pf CSP to each antibody was characterized by fitting kinetic sensorgrams to a monovalent binding model (1:1 binding). This assay set up was used for five related antibodies (AB-000662, AB-000640, AB-000649, AB000646 and AB000643). However, the binding affinity of AB-000667 and AB-000668 was near the level of detection in this format. To confirm the binding affinity of AB-000667 and AB-000668 to PF CSP, another assay orientation was conducted using Streptavidin kinetic grade biosensors (ForteBio, #18-5021) to capture biotinylated rCSP. The biotin/Pf CSP loaded SA sensor was then dipped into an 8-point dilution series of the AB-000667 or AB-000668 (starting at 33 nM or 133 nM, 1:3 diluted down).

Example 4a: In Vivo Protection Studies Using Mouse Malaria Challenge Model

Candidate antibodies are tested in a mouse malaria challenge model. This in vivo mouse protection assay uses intravenous passive transfer of selected antibodies (300 µg/mouse) followed by challenge with chimeric *P. berghei* encoding full-length *P. falciparum* CSP.

In an initial experiment, antibodies are injected intravenously. Sporozoites are injected 30 minutes later by intravenous challenge. Parasite liver burden (measured by PCR) is used as a readout. Antibodies that show protection in this IV challenge are then further tested in a second experiment, using mosquito bite challenge. Parasitaemia can be used as a readout to assess sterile protection.

FIG. 5 illustrates principles of the challenge model.

40 h after challenge with chimeric sporozoites, livers are extracted and RNA is isolated from liver homogenates. Real-time PCR, targeting the parasite 18S rRNA sequence, is used to measure the relative level of liver-stage parasites. Liver-stage parasite load can be quantified in terms of the number of *P. berghei* 18S rRNA copies in liver. % reduction of parasite load can be determined relative to control mice who do not receive the candidate antibody or who receive a control antibody (naive mice).

Another measure of protection is the % of challenged mice remaining free of blood-stage parasites for a period following challenge. Mice may be monitored for a period of, e.g., 7 or 14 days, and % mice remaining free of blood-stage parasites is determined for challenged mice and control mice.

Example 4b

The mouse challenge described in Example 4a was performed to assess the ability of passively-transferred anti-CSP mAbs to protect mice from sporozoite challenge. As noted, these in vivo protection studies involving transgenic sporozoites comprised initial screening by IV injection of 300 ug of Ab per animal followed by measurement of liver stage burden. Aspects of the methodology have been previously described in Bruna-Romero et al 2001 Int. J. Parasitol. 31:1499-1502. The anti-CSP mAb 2A10 (Anker, Zavala & Pollok, Eur J Immunol. 20:2757-2761 1990) was used as a positive control.

Figure 9:
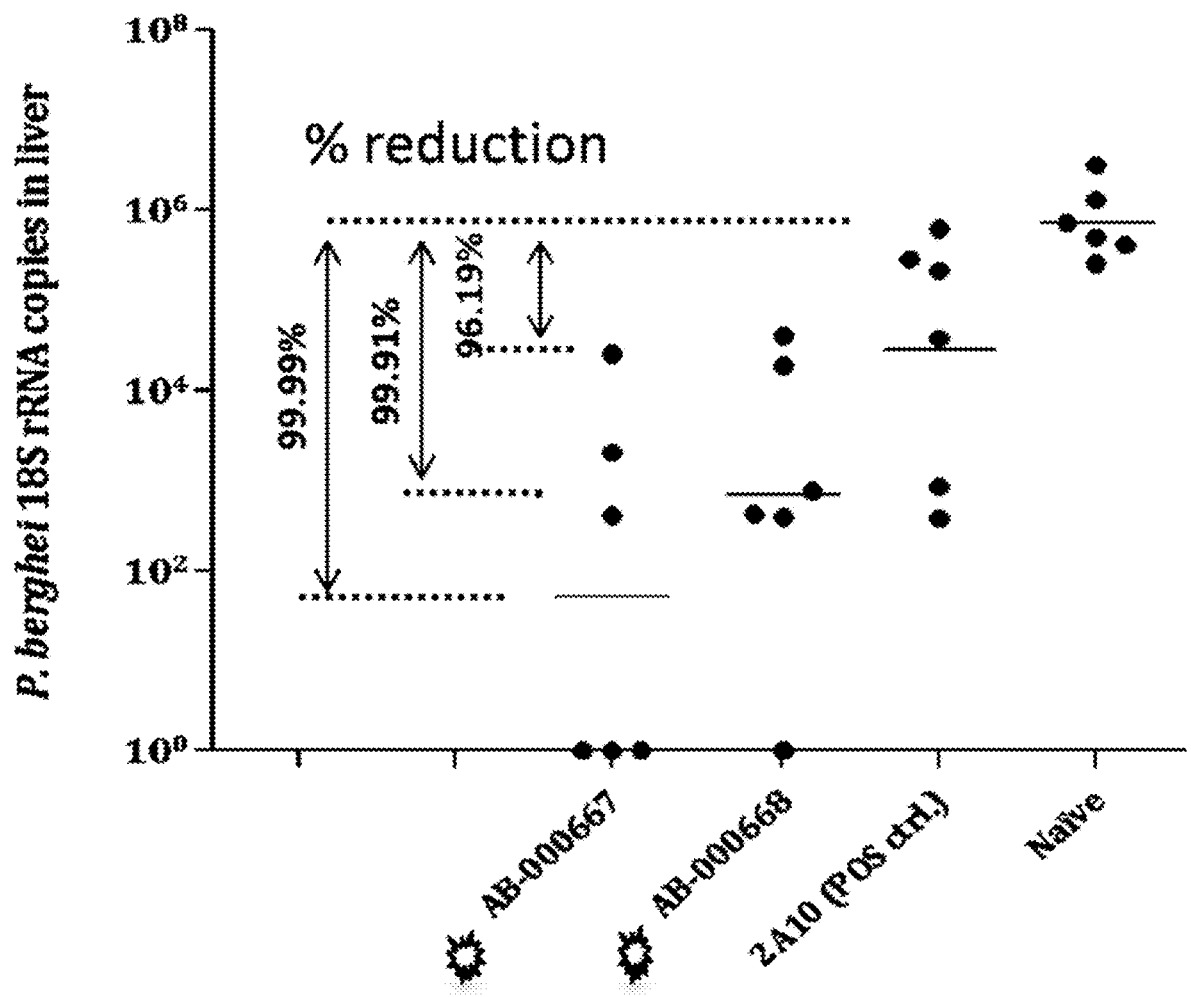
Figure 10:
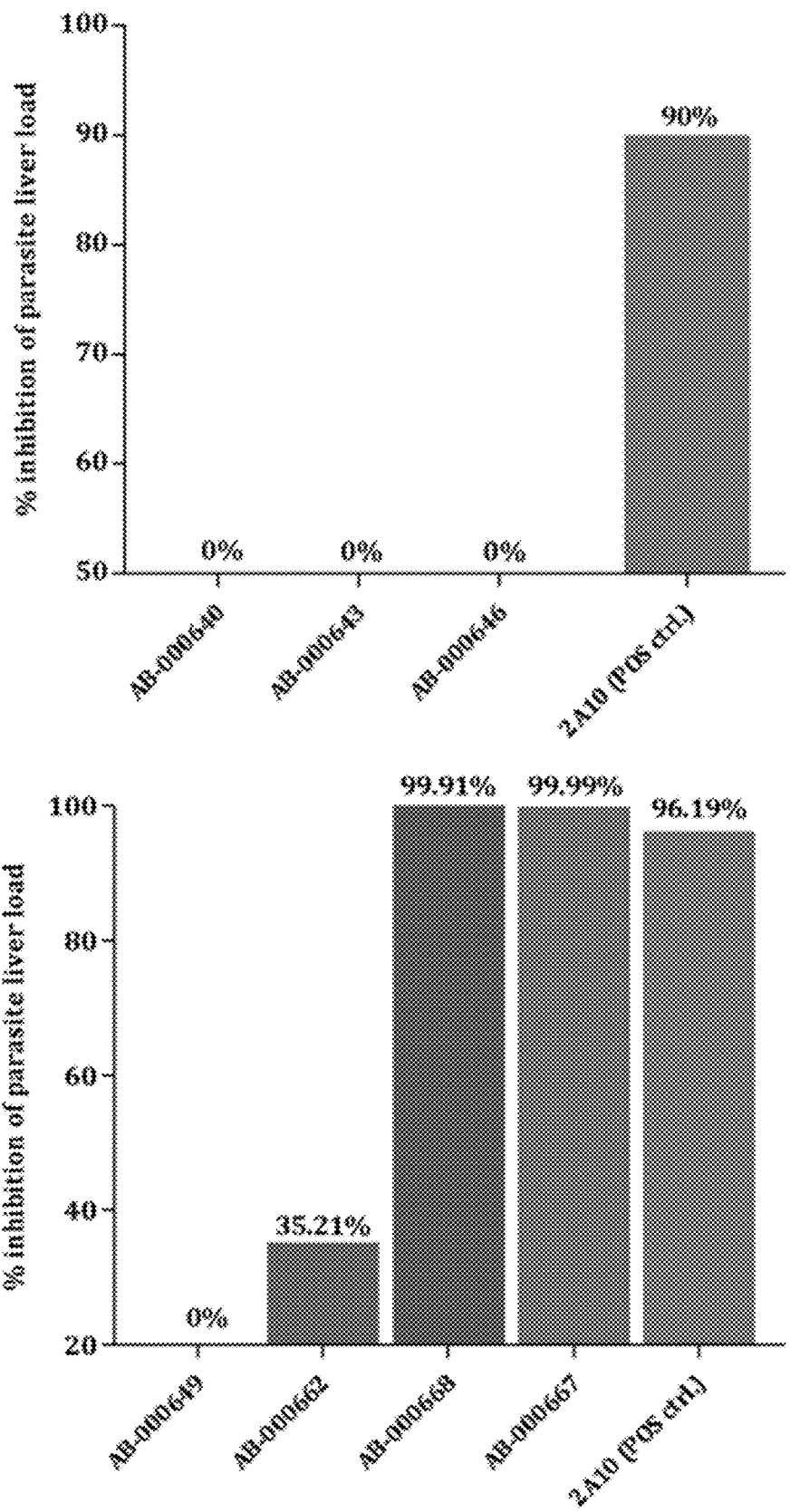

Results are shown in FIG. 9 and FIG. 10. The data indicate that antibodies 667 and 668 confer significant and very strong protection relative to the 2A10 positive control.

To confirm that mAbs 667 and 668 confer protection from transgenic sporozoite challenge and evaluate whether such protection could be sterilising, a second challenge was performed using three different concentrations of antibody. The outcome was evaluated by determination of parasitemia at various time points post-challenge.

TABLE 4

| Cohort | Infected/ challenged (mice) | Pre-patent period (days) | Protection | Logrank Test (vs. Naïve) |
|---|---|---|---|---|
| AB-000667 - 300 µg | 1/7 | 6 | 86% | 0.0003 (***) |
| AB-000667 - 150 µg | 4/6 | 6 | 33% | 0.0001 (***) |
| AB-000667 - 30 µg | 4/7 | 5 | 43% | 0.0001 (***) |
| AB-000668 - 300 µg | 2/7 | 6 | 71% | 0.0002 (***) |
| AB-000668 - 150 µg | 3/7 | 5.3 | 57% | 0.0001 (***) |
| AB-000668 - 30 µg | 7/7 | 5.3 | 0% | 0.0004 (***) |
| 2A10 - 300 µg | 6/7 | 5.2 | 14% | 0.0072 (**) |
| Naïve | 7/7 | 4 | 0% | — |

Figure 11:
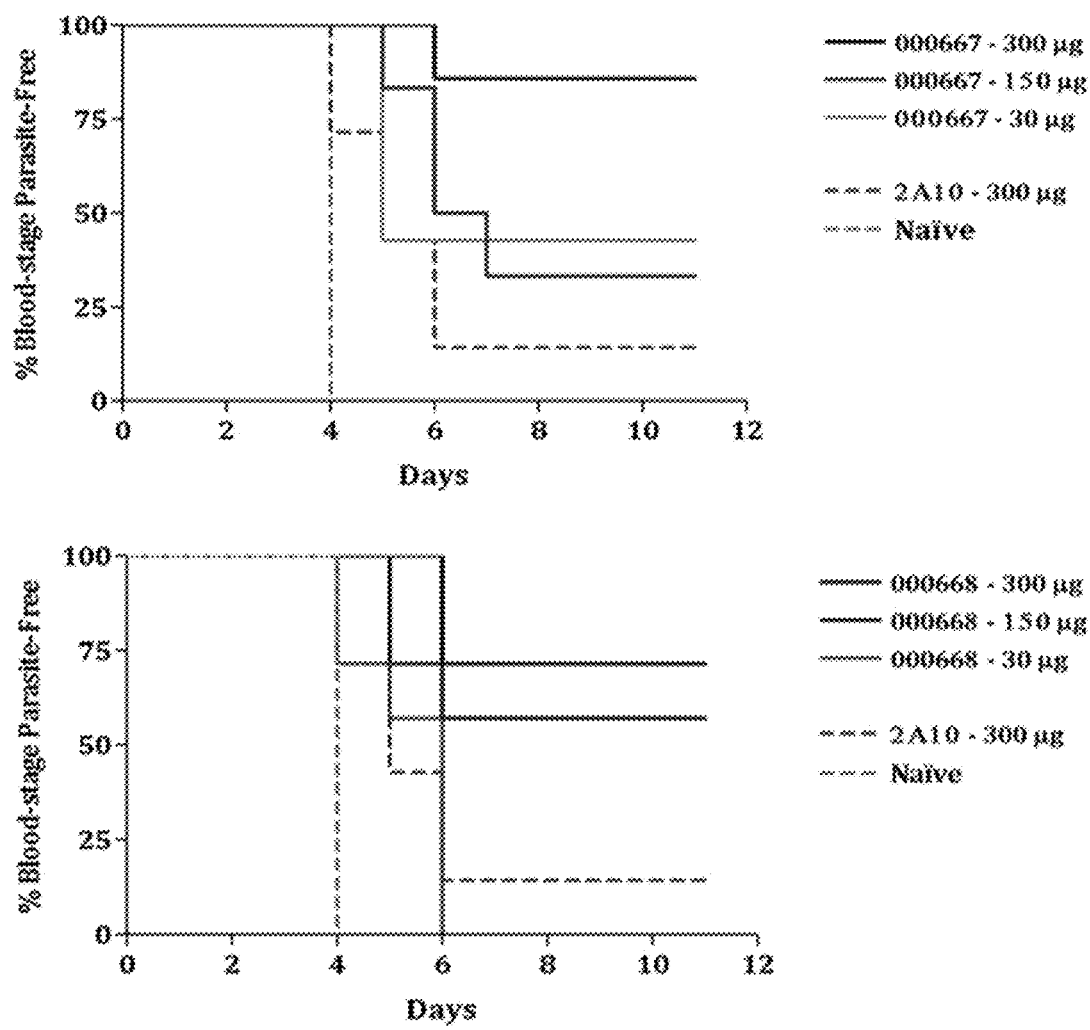

Results shown in FIG. 11 and in Table 4 demonstrate that
i) parasitemia data confirm the previously observed protection seen in the liver,
ii) protection is fully sterilising in a significant fraction of the animals, and
iii) protection is dose-dependent but is still higher at the lower dose of antibodies 667 and 668 than for 2A10 at the highest dose.

For assays culminating in a parasitemia endpoint, challenge is administered by 5 infected mosquito bites. In order to determine how many mosquitoes are needed to challenge mice with 5 infected mosquito bites, 17 days after blood feeding on mice infected with chimeric *P. berghei* parasites encoding full-length *P. falciparum* CSP, the proportion of infected mosquitoes was calculated, in this case, ~85% (26 out of 30 infected salivary glands). Based on this calculation, it was determined that 6 mosquitoes were needed to challenge mice with 5 infected mosquito bites. Cohorts of seven mice per group underwent treatment, either passive transfer of experimental mAbs or positive control mAb, or in the case of the negative control, were not treated and merely challenged. Upon passive transfer of monoclonal antibodies, mice were anesthetized with 2% Avertin and mosquitoes allowed to feed on mice for ~10 minutes. After feeding, the number of mosquitoes positive for a blood meal was determined. On days 4-11 after challenge, blood smears were taken from mice to determine parasitemia. % sterile protection was determined by dividing the number of uninfected mice by the total number of mice challenged. Pre-patent period, the number of days prior to detection of parasites in the blood, was also recorded.

Example 5: Inhibition of Gliding Motility

*Plasmodium* sporozoites move by gliding motility, a unique form of locomotion, which is required for tissue migration and host cell invasion. The impact of anti-CSP antibodies on sporozoites' gliding motility was assessed using methods previously described by Ejigiri et al. (Ejigiri et al., Shedding of TRAP by a Rhomboid Protease from the Malaria Sporozoite Surface is Essential for Gliding Motility and Sporozoite Infectivity, PLoS Pathog 8(7), 2012). Briefly, *P. falciparum* sporozoites were pre-incubated with the indicated antibodies (100 ug/ml) for 30 min and then added to wells in the presence of bovine serum albumin and incubated at 37° C. for 1 hr. They were then fixed and trails were stained with anti-CSP antibody and counted using a fluorescence microscope.

Figure 12:
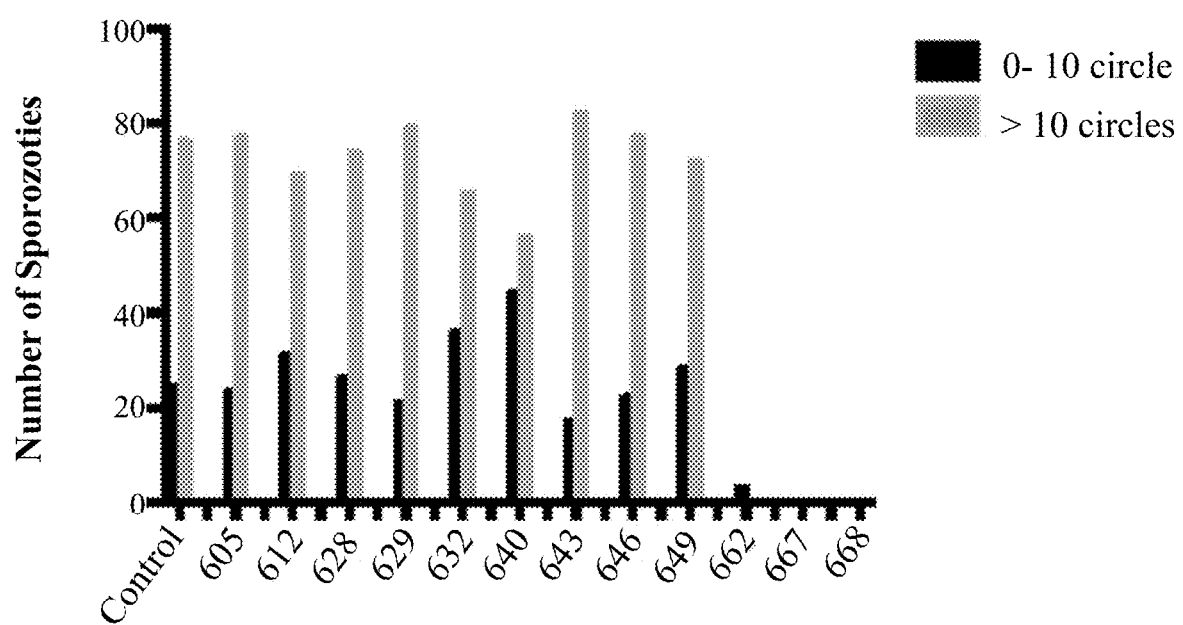

Anti-CSP antibodies mAb667 and mAb668 abolished gliding motility of the sporozoites in this assay. Data are shown in FIG. 12.

Example 6: Inhibition of Liver Stage Development

The inhibition of liver stage development assay (ILSDA) tests antibodies for the ability to block sporozoite development in hepatocytes. As such the ILSDA is an excellent candidate assay to identify correlates of humoral protection, particularly against the liver stage of malaria infection.

Figure 13:
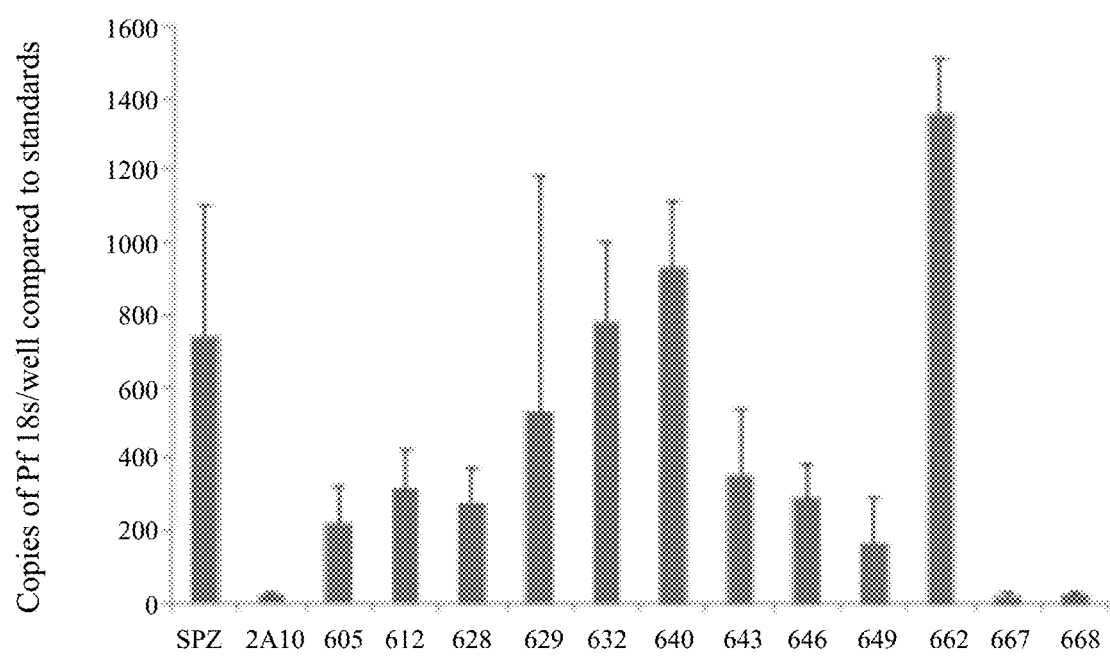

The Inhibition of Liver Stage Development Assay (ILSDA) was performed as previously described by Zou et al. (Zou et al, Towards an optimized inhibition of liver stage development assay (ILDSA) for *Plasmodium falciparum*, Malaria Journal 12:394, 2013). In brief, the NF54 strain of *Plasmodium falciparum* (Pf) sporozoites (obtained from salivary gland dissections) were mixed with monoclonal antibodies (mAbs) and incubated at room temperature for 20 minutes. The sporozoites-mAbs mixtures were then introduced into the wells containing cryopreserved human hepatocytes (CPHH; BioReclamation IVT, Baltimore Md.) and incubated at 37° C. for 3 hours to allow sporozoites to infect hepatocytes. The anti-CSP mAb 2A10 was used as a positive control. After the 3 hour incubation period, CPHH were washed with fresh hepatocyte culture media to remove non-invaded sporozoites and incubated at 37° C. for 96 hours. The RNA from the cells was then harvested for downstream quantitative real-time PCR (qRT-PCR) analysis. Pf 18s rRNA level were quantified to determine the inhibitive ability of the tested mAbs.

mAb 667 and mAb668 effectively blocked sporozoite development in hepatocytes in this assay (FIG. 13).

Example 7: Inhibition of Sporozoite Traversal and Invasion (ISTI)

Monoclonal antibodies were tested for their ability to inhibit invasion and traversal using the ISTI assay as previously published (A. N. Douglass, P. G. Metzger, S. H. Kappe, A. Kaushansky, Flow Cytometry-Based Assessment of Antibody Function Against Malaria Pre-erythrocytic Infection. Methods Mol Biol 1325, 49-58 (2015), and J. G. Kublin et al., Complete attenuation of genetically engineered *Plasmodium falciparum* sporozoites in human subjects. Sci Transl Med 9, (2017).). Briefly, freshly-dissected PfNF54 salivary gland sporozoites were pre-incubated with 10 μg/mL of mAb or non-specific murine IgG (mock) in complete DMEM containing FITC-dextran for 15 minutes. Sporozoites were then directly added to 100,000 HC04 cells in a 96 well plate at an MOI of 1:3 (sporozoites:HCO4 cells) in triplicate, centrifuged at 500×g for 5 minutes and returned to 37 degrees C. After 90 minutes, cells were fixed and stained for presence of CSP with AlexaFluor-647-conjugated mAb clone 2A10. Cells were then analyzed for invasion (CSP+) or traversal (FITC-dextran+) via flow cytometry. Both invasion and traversal for each well was normalized to the average of mock-treated wells and expressed as "% of mock".

Figure 14:
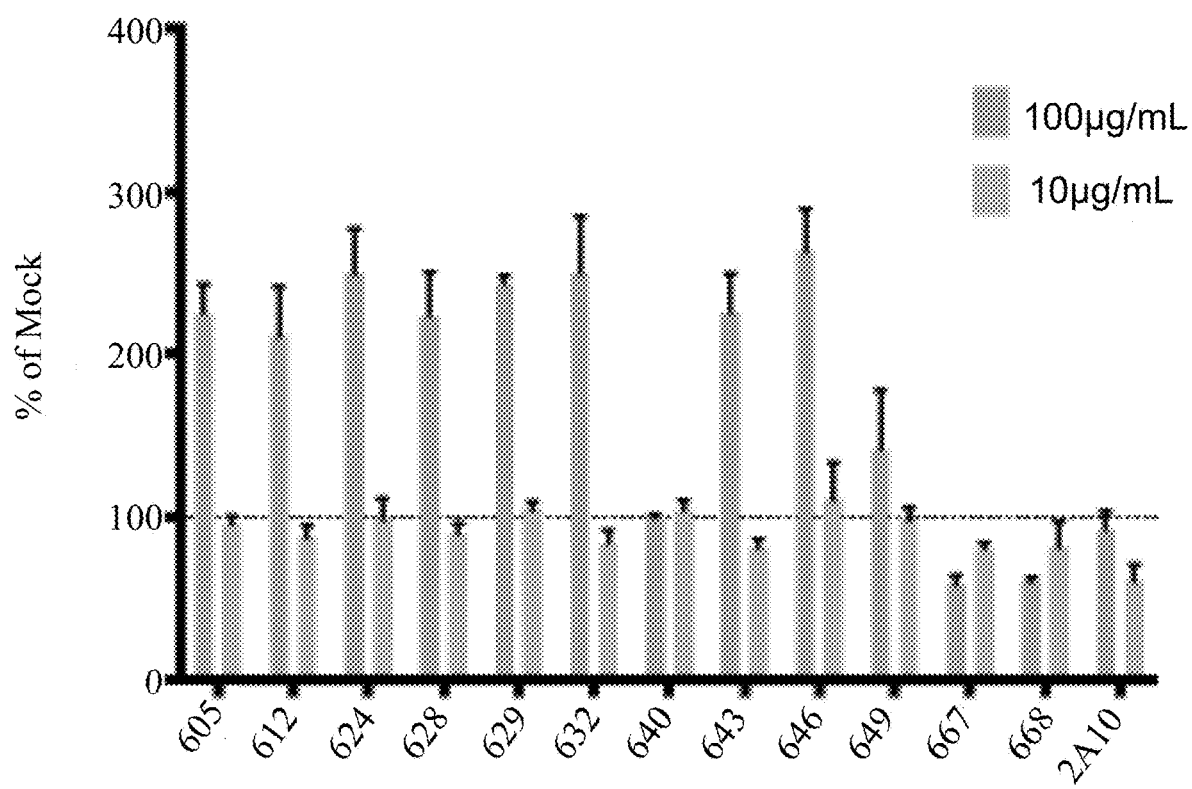
Figure 15:
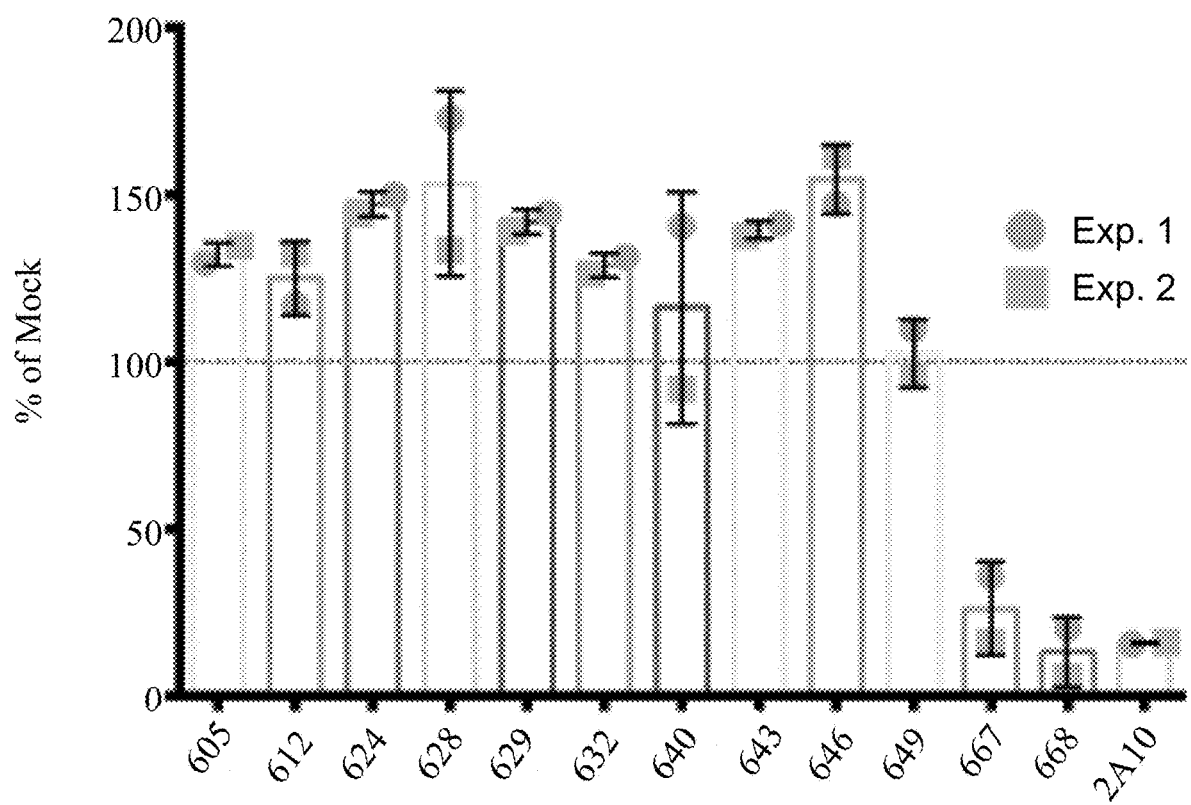

Anti-CSP antibodies mAb667 and mAb668 dramatically reduced both hepatocyte traversal (FIG. 14) and hepatocyte invasion (FIG. 15) in this assay.

Antibody 666 and antibody 669 were also tested and were confirmed to be functional hits in the ISTI assay.

Example 8: Sporozoite Challenge into FRG Hu-Hep Mice

In addition to the challenge model described in Example 4, a human liver (Hu-Hep) mouse challenge model was used to assess the ability of passively-transferred anti-CSP mAbs to protect mice from sporozoite challenge.

FRG Hu-Hep mice were purchased from Yecuris, Inc. and used in passive transfer experiments as previously described (K. Sack et al., Model for in vivo assessment of humoral protection against malaria sporozoite challenge by passive transfer of monoclonal antibodies and immune serum. Infect Immun 82, 808-817 (2014), and Sack et al., submitted). Briefly, mice were intravenously injected with 150 μg of mAb or non-specific murine IgG (mock) 16-24 hours prior to infection by bite of 50 mosquitos infected with Pf GFP-luciferase parasites (Vaughan et al. 2012) for 10 minutes. Six days after infection, parasite liver burden was assessed by bioluminescent imaging. Percent of mock liver burden was calculated by normalizing all liver burdens to the average of the mock-injected group within each independent experiment. The 3C1 anti-CSP mAb (Zavala et al., J Exp Med 157:1947-1957 1983) had previously been shown in this model to mediate higher inhibition of infection than the 2A10 positive control and was therefore used as the positive control in the present experiment.

Figure 16:
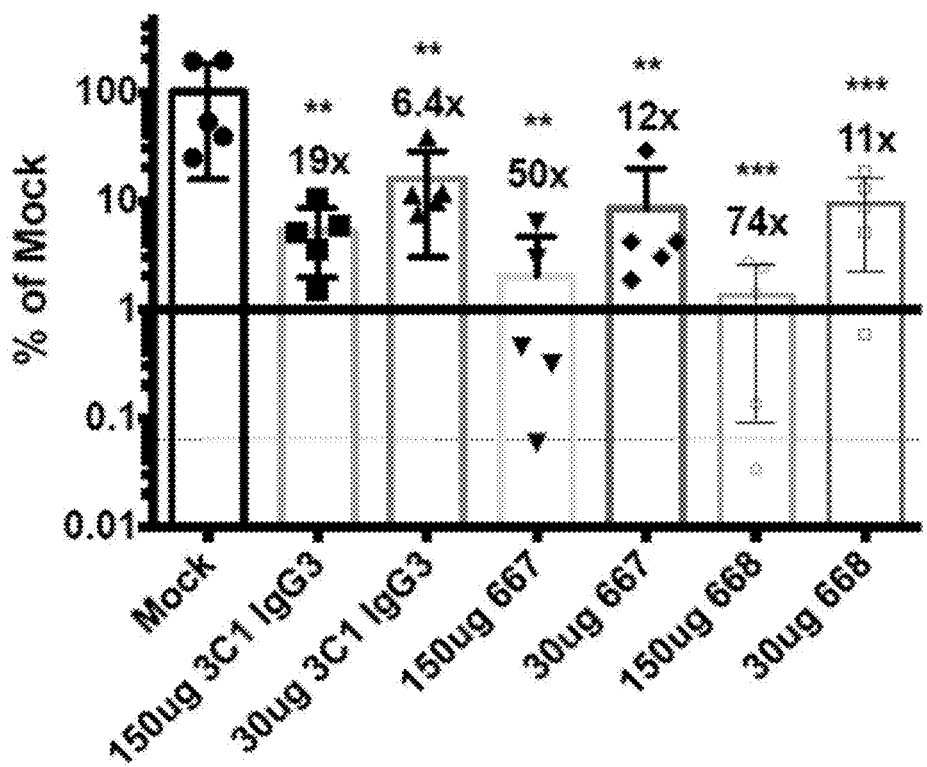

Data from this experiment confirmed the observations made in the transgenic sporozoite model (Example 4), that the two anti-CSP antibodies tested provide robust and dose-dependent protection from liver-stage infection. See FIG. 16.

Example 9: Informatics

In view of the encouraging performance of the anti-CSP antibodies 666, 667, 668 and 669 as described herein, informatics analysis was undertaken to identify related antibodies generated by the immunised mice, as structurally-related antibodies derived from the same lymphocyte lineage would be expected to share specificity for the same epitope and to display similar functional properties.

Bioinformatics indicated that the antibodies 667 and 668 belonged to families of phylogenetically similar antibodies, antibodies within each family being recombined from the same heavy chain v and j gene segments and the same or similar light chain germline genes. There is a high probability that other members of those families are functionally active and may demonstrate in vivo activity comparable to that of Ab667 and Ab668.

The phylogenetic family of Ab667 contains Ab666 and a number of further antibodies, as shown in Table 5.

TABLE 5

Atreca identification of CDRs of antibodies related to Ab666 and Ab667.

| h_cdr3 | h_cdr2 | h_cdr1 | l_cdr3 | l_cdr2 | l_cdr1 |
|---|---|---|---|---|---|
| DNFFESSGYYSYYFYGMDV SEQ ID NO: 152 | WINAGNGYTKYSQRFQG SEQ ID NO: 153 | GYTFTSYAMH SEQ ID NO: 60 | CSYVGSSTWI SEQ ID NO: 154 | DVSKRPS SEQ ID NO: 39 | TGTSSDVGSYNHVS SEQ ID NO: 63 |
| DEYYASGSYYDYYYYGMDV SEQ ID NO: 404 | WINAGNGNTKYSQNFQG SEQ ID NO: 403 | GYTFTNYAMH SEQ ID NO: 3 | CSYAGSSTWV SEQ ID NO: 10 | NVSKRPS SEQ ID NO: 411 | TGTSSDVGVYNYVS SEQ ID NO: 8 |
| DEYYASGSYYDYYYYGMDV SEQ ID NO: 404 | WINAGNGNTKYSQNFQG SEQ ID NO: 403 | GYTFTNYAMH SEQ ID NO: 3 | CSYAGSSTWV SEQ ID NO: 10 | NVSKRPS SEQ ID NO: 411 | TGTSSDVGVYNYVS SEQ ID NO: 8 |
| DEYYASGSYYDYYYYGMDV SEQ ID NO: 404 | WINAGNGNTKYSQNFQG SEQ ID NO: 403 | GYTFTNYAMH SEQ ID NO: 3 | CSYAGSSTWV SEQ ID NO: 10 | NVSKRPS SEQ ID NO: 411 | TGTSSDVGVYNYVS SEQ ID NO: 8 |
| DNFYGSGTYFSYFFYHMDV SEQ ID NO: 155 | WINAGNGNTKYSQKFQG SEQ ID NO: 403 | GYTFTNYAIH SEQ ID NO: 156 | CSYAGSSTWV SEQ ID NO: 10 | DVSKRPS SEQ ID NO: 39 | TGTSSDVGSYNHVS SEQ ID NO: 63 |
| DNYYDSGSYYDYYYYGMDV SEQ ID NO: 62 | WINAGNGNTKYSQKFQG SEQ ID NO: 419 | GYTFTSYAMH SEQ ID NO: 60 | CSYAGSSTWV SEQ ID NO: 10 | DVSKRPS SEQ ID NO: 39 | TGTSSDVGSYNHVS SEQ ID NO: 63 |
| DNYYDSGSYYEYCYYGMDV SEQ ID NO: 69 | WINAGNGYTKYSQKFQG SEQ ID NO: 499 | GYTFTNYAMH SEQ ID NO: 3 | CSYVGSSTWV SEQ ID NO: 70 | DVSKRPS SEQ ID NO: 39 | TGTSSDVGSYNHVS SEQ ID NO: 63 |
| DNYYDSNVYNSYYFYGMDV SEQ ID NO: 163 | WINAGNGYTKYSQKFQG SEQ ID NO: 499 | GYTFTNYAMH SEQ ID NO: 3 | CSYAGSSTWV SEQ ID NO: 10 | DVNKRPS SEQ ID NO: 19 | TGTSSDVGNYNHVS SEQ ID NO: 164 |
| DQYYDILTPYYYYYYGMDV SEQ ID NO: 165 | WINAGNGNTKYSQKFQG SEQ ID NO: 419 | GYTFTSYAMH SEQ ID NO: 60 | CSYAGSSTWV SEQ ID NO: 10 | VVSKRPS SEQ ID NO: 157 | TGTSSDVGGYNYVS SEQ ID NO: 426 |
| DSFYDILSGPVYHYYGMDV SEQ ID NO: 15 | WINAGNGYTKYSQKFQD SEQ ID NO: 24 | GYTFTNYAMH SEQ ID NO: 3 | CSYAGSSAWV SEQ ID NO: 20 | DVNKRPS SEQ ID NO: 19 | TGTSNDVGIYNHVS SEQ ID NO: 18 |
| DSFYDILTGPVYHYYGMDV SEQ ID NO: 76 | WINAGNGYTKYSQKFQD SEQ ID NO: 14 | GYTFTNYAMH SEQ ID NO: 3 | CSYAGSSTWV SEQ ID NO: 10 | DVSKRPS SEQ ID NO: 39 | TGTSNDVGVYNHVS SEQ ID NO: 77 |
| DSFYDILTGPVYHYYGMDV SEQ ID NO: 76 | WINAGNGYTKYSQKFQD SEQ ID NO: 14 | GYTFSNYAMH SEQ ID NO: 75 | CSYVGNSAWV SEQ ID NO: 78 | DVSKRPS SEQ ID NO: 39 | TGTSNDVGVYNHVS SEQ ID NO: 77 |
| DSFYDILTGPVYHYYGMDV SEQ ID NO: 76 | WINAGNGYTKYSQKFQD SEQ ID NO: 24 | GYTFTNYAMH SEQ ID NO: 3 | CSYVGSSAWV SEQ ID NO: 83 | DVSKRPS SEQ ID NO: 39 | TGTSNDVGVYNHVS SEQ ID NO: 77 |

The phylogenetic family of Ab668 contains Ab669 and a number of further antibodies, as shown in Table 6.

TABLE 6

Atreca identification of CDRs of antibodies related to Ab668 and Ab669.

| h_cdr3 | h_cdr2 | h_cdr1 | l_cdr3 | l_cdr2 | l_cdr1 |
|---|---|---|---|---|---|
| DGFCPSTTCSGYYGMDV SEQ ID NO: 468 | WINAGNGYTKYSQKFQV SEQ ID NO: 467 | GFTFTDYAMH SEQ ID NO: 23 | SSYAGSSTWI SEQ ID NO: 473 | DVNTRPS SEQ ID NO: 29 | TGTSSDVGAYNYVS SEQ ID NO: 474 |
| DGFCPSTTCSGYYGMDV SEQ ID NO: 468 | WINAGNGYTKYSQQFQV SEQ ID NO: 483 | GFTFTDYAMH SEQ ID NO: 23 | SSYAGSSTWI SEQ ID NO: 473 | DVNTRPS SEQ ID NO: 29 | TGTSSDVGAYNYVS SEQ ID NO: 474 |
| DGFCPSNTCSGYYGMDV SEQ ID NO: 25 | WINAGNGYTKYSQKFQD SEQ ID NO: 24 | GFTFTDYAMH SEQ ID NO: 23 | SSYAGSSTWV SEQ ID NO: 30 | DVNTRPS SEQ ID NO: 29 | TGTSSDVGSYNYVS SEQ ID NO: 28 |
| DGFCPSNTCSGYYGMDV SEQ ID NO: 25 | WINAGNGYTKYSQKFQD SEQ ID NO: 24 | GFTFTDYAMH SEQ ID NO: 23 | SSYAGSSTWV SEQ ID NO: 30 | DVNTRPS SEQ ID NO: 29 | TGTSSDVGAYKYVS SEQ ID NO: 92 |
| DGFCRTTSCSDHYGMDV SEQ ID NO: 123 | WINAGNGYTKYSQKFQG SEQ ID NO: 68 | GYIFINYAMQ SEQ ID NO: 122 | CSYAGSSTWV SEQ ID NO: 10 | DVSKRPS SEQ ID NO: 39 | TGTSSDVGGYNYVS SEQ ID NO: 426 |
| DGFCSTTTCSDHYGMDV SEQ ID NO: 111 | WINAGNGYTKYSQKFQG SEQ ID NO: 68 | GFIFINYAMQ SEQ ID NO: 128 | CSYAGSSTWV SEQ ID NO: 10 | DVSKRPS SEQ ID NO: 39 | TGTSSDVGGYNYVS SEQ ID NO: 426 |
| DGFCSTTTCSDHYGMDV SEQ ID NO: 111 | WINAGNGHTKYSQKFQD SEQ ID NO: 34 | GFTFTNYAMH SEQ ID NO: 110 | CSYAGSSTWV SEQ ID NO: 10 | DVSKRPS SEQ ID NO: 39 | TGTSSDVGGYNYVS SEQ ID NO: 426 |
| DGFCSTTTCSDHYGMDV SEQ ID NO: 111 | WINAGNGYTKYSQKFQD SEQ ID NO: 24 | GFTFTSHAIH SEQ ID NO: 117 | CSYAGSSTWV SEQ ID NO: 10 | DVSKRPS SEQ ID NO: 39 | TGTSSDVGGYNYVS SEQ ID NO: 426 |
| DGFCSTTTCSDHYGMDV SEQ ID NO: 35 | WINAGNGHTKYSQKFQD SEQ ID NO: 34 | GFTFTSYAMH SEQ ID NO: 33 | CSYAGSSTWV SEQ ID NO: 10 | DVSKRPS SEQ ID NO: 39 | TGTSSDVGSYNYVS SEQ ID NO: 28 |
| DGFCTTTTCSDHYGMDV SEQ ID NO: 99 | WINAGDGHTKYSQKFQD SEQ ID NO: 98 | GFTFTSYAIQ SEQ ID NO: 104 | CSYAGGSTWV SEQ ID NO: 10 | DVSKRPS SEQ ID NO: 39 | TGTSSDVGSYNYVS SEQ ID NO: 28 |
| DGFCTTTTCSDHYGMDV SEQ ID NO: 99 | WINAGDGHTKYSQKFQD SEQ ID NO: 98 | GFTFISYAMH SEQ ID NO: 97 | CSYAGSSTWV SEQ ID NO: 10 | DVSKRPS SEQ ID NO: 39 | TGTSSDVGSYNYVS SEQ ID NO: 28 |
| DGYCSSTSCYGYYGMDV SEQ ID NO: 166 | WINAGNGNTKYSQKFQG SEQ ID NO: 419 | GFTFSSYAMH SEQ ID NO: 167 | CSYAGSSTWV SEQ ID NO: 10 | DVSKRPS SEQ ID NO: 39 | TGTSSDVGAYNYVS SEQ ID NO: 474 |

In addition, bioinformatics analysis indicated that the phylogenetic branch containing the family of antibody 667 and antibody 668 also contained other individual antibody VH-VL pairs that use the same v gene segments and have light chains with high identity to those of Ab667 and Ab668 respectively.

Antibody heavy chains having the following sets of CDRs were identified:

TABLE 7

Atreca identification of HCDRs of additional antibodies in the phylogenetic branch.

| | HC CDR3 | HC CDR2 | HC CDR1 |
|---|---|---|---|
| AB-000666 | DEYYASGSYYDYYYGMDV (SEQ ID NO: 5) | WINAGNGNTKYSQNFQG (SEQ ID NO: 403) | GYTFTNYAMH (SEQ ID NO: 13) |
| AB-000667 | DSFYDILSGPVYHYYGMDV (SEQ ID NO: 15) | WINAGNGYTKYSQKFQD (SEQ ID NO: 24) | GYTFTNYAMH (SEQ ID NO: 13) |

TABLE 7-continued

Atreca identification of HCDRs of additional antibodies in the phylogenetic branch.

| | HC CDR3 | HC CDR2 | HC CDR1 |
|---|---|---|---|
| AB-000668 | DGFCPSNTCSGYYGMDV (SEQ ID NO: 25) | WINAGNGYTKYSQKFQD (SEQ ID NO: 24) | GFTFTDYAMH (SEQ ID NO: 23) |
| AB-000669 | DGFCTSTTCSDHYGMDV (SEQ ID NO: 35) | WINAGNGHTKYSQKFQD (SEQ ID NO: 34) | GFTFTSYAMH (SEQ ID NO: 23) |
| | DQYYDILKGYYNVDYYYGMDV (SEQ ID NO: 168) | WINAGNGYTKYSQKFQG (SEQ ID NO: 499) | GYTFTNYAMH (SEQ ID NO: 13) |
| | DNYFDSSVYDSSYYFYYGMDV (SEQ ID NO: 169) | WINAGNGYTKYSQNFQG (SEQ ID NO: 170) | GYTFTSYAMH (SEQ ID NO: 60) |
| | DEYYESGSSNYYYYGMDV (SEQ ID NO: 171) | WINAGNGYTKYSQTFQG (SEQ ID NO: 172) | GYTFTNYAMH (SEQ ID NO: 13) |
| | DQFYETLTGYYNVYYYYGMDV (SEQ ID NO: 173) | WINAGNGYTKYSQMFQD (SEQ ID NO: 174) | GYTFTNYAIH (SEQ ID NO: 156) |
| | DEYYDSGSSNYYYYGMDV (SEQ ID NO: 175) | WINAGNGYTKYSQKFQG (SEQ ID NO: 499) | GYTFTNYAIH (SEQ ID NO: 156) |

These antibodies have the same germline gene usage, high identity light chains and high identity in the HCDR1 and HCDR2. It is believed that antibodies comprising VH domains having these CDRs may be functionally active in a similar way to Ab666, 667, 668 and 669. This may be confirmed through assays as described in the above Examples.

Separately, further bioinformatic analysis was undertaken to infer lineage trees for antibodies Ab666, Ab667, Ab668 and Ab669. Each tree connects antibody clones predicted to have been derived from the same naïve B cell clonal expansion lineage, and shows how they relate to each other, and to the germline sequence. The identified antibody families were as follows:

Ab666 lineage: Ab666, Ab666-1, Ab666-2, Ab666-3, Ab666-4.

Ab667 lineage: Ab667, Ab667-1, Ab667-2, Ab667-3.

Ab668 lineage: Ab668, Ab668-1.

Ab669 lineage: Ab669, Ab669-1, Ab669-2, Ab669-3, Ab669-4, Ab669-5, Ab669-6.

Figure 18:
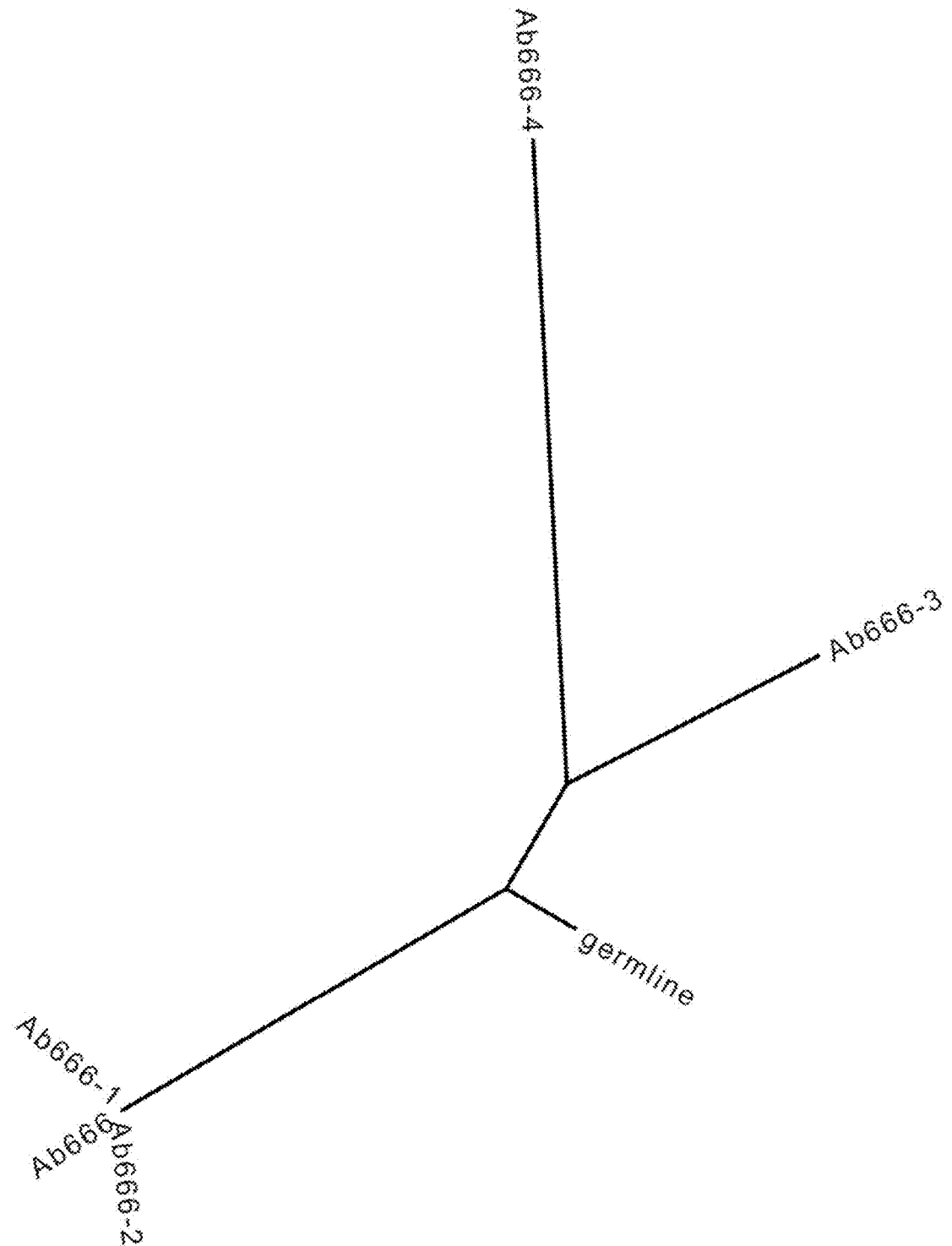
Figure 19:
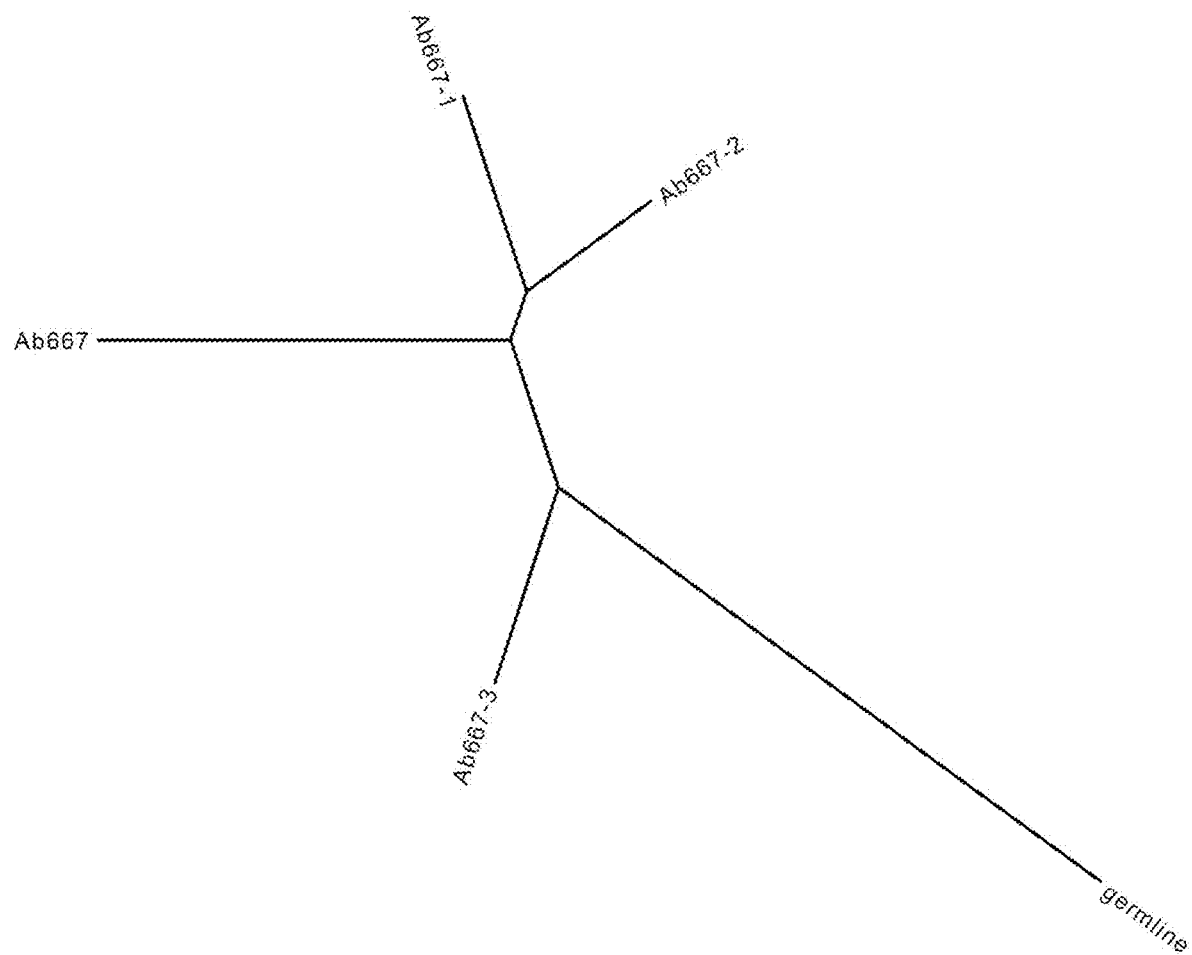
Figure 20:
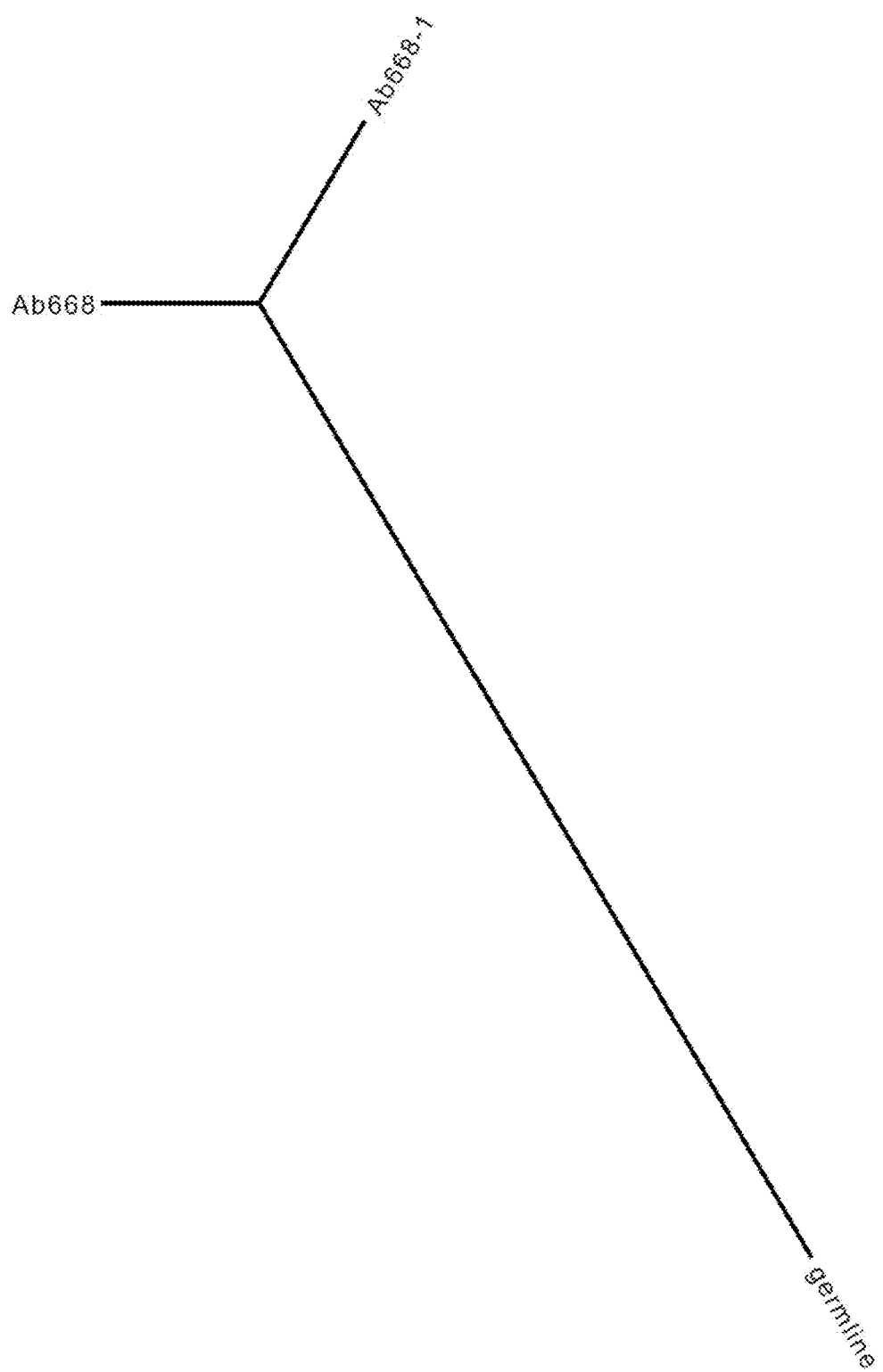
Figure 21:
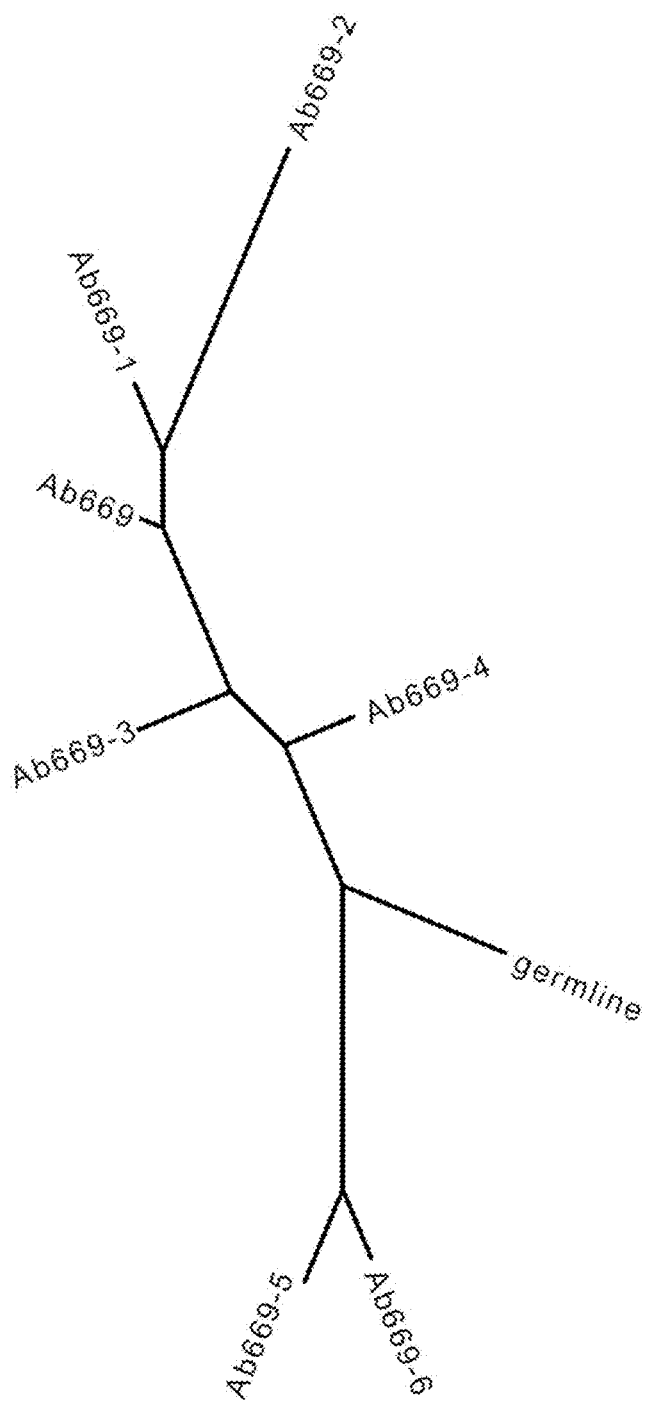

Lineage trees are shown in FIG. 18 (Ab666 lineage), FIG. 19 (Ab667 lineage), FIG. 20 (Ab668 lineage) and FIG. 21 (Ab669 lineage).

The antibodies in each given lineage were inferred to have been derived from recombination of the same v, d and j gene segment sequences (heavy chain) and the same v and j gene segments (light chain). See FIG. 4 for gene segment identification of antibodies in these lineages.

Example 10: Further Characterisation of Anti-CSP Antibodies by Surface Plasmon Resonance In Example 3 we reported measurements of the affinity of binding between anti-CSP antibodies and the CSP antigen, and showed that binding sites for antibody 667 and antibody 668 were found in the NANP (SEQ ID NO: 509) repeat region of the CSP antigen. Here, we further characterise the interaction of the antibodies (666, 667, 668 and 669) with CSP, including measuring the kinetics of binding using SPR and determining binding to an array of CSP peptides to provide additional information on epitope recognition by these antibodies.

Materials & Methods—Expression and SPR

Amino acid sequences of antibodies 666, 667, 668 and 669 are shown in the appended sequence listing. For expression, silent mutations were introduced in certain VH domain nucleotide sequences to remove an AarI restriction site.

Antibodies 667, 668 and 669 were expressed as human IgG1 in HEK cells (Expi293F, Gibco Life Technologies), and antibody 666 was expressed as human IgG1 in CHO cells (ExpiCHO, Gibco Life Technologies). The IgG1 were purified by Protein A and desalting and formulated at a concentration of 1 mg/mL in PBS at pH 7.4. Purity from size exclusion chromatography (SEC) was 92-95%.

Antibodies 666, 667, 668 and 669 were expressed as Fabs in CHO cells (CHO-3E7, National Research Council Canada), purified on HiTrap nickel columns (GE Healthcare) eluted using 250 nM imidazole in PBS, and formulated at a concentration of 1 mg/mL in PBS at pH 7.4. Purity from SEC was >95%.

Recombinant CSP (FIG. 22) was provided by the Wellcome Trust Sanger Institute. *P. falciparum* strain 3D7 (GenBank accession number: CAB38998.2), molecular weight 45 kDa. The gene construct encoded CSP without the final 21 amino acids (GPI-anchor) to allow for soluble expression. A biotinylation site (BirA enzyme substrate peptide BSP) and histidine tag was also added.

Recombinant CSP was expressed in HEK293 cells using a mouse variable K light chain peptide signal sequence for secretion into the culture medium, nickel-affinity purified and dialyzed into DPBS.

SPR experiments were performed as follows:

(i) Binding of antibody 666, 667, 668 and 669 Fabs to CSP, 25 degrees C., 900s dissociation time. The biotinylated recombinant CSP was diluted to 5 µg/mL in running buffer (1×HBS-EP+ Buffer Technova, cat. No. H8022) and captured on an NLC sensor chip (Bio-Rad, cat No 1765021). The surface was then blocked using biocytin (Sigma Aldrich, cat No B1758) at 1 mg/mL to prevent non-specific interaction with the chip surface. The recombinant human Fabs were used as analyte at 1024 nM, 256 nM, 64 nM, 16 nM and 0 nM and injected over recombinant CSP. The assay was carried out at 25° C., with an association step of 240 sec and a dissociation step of 900 sec. Buffer injection (0 nM) was used to double reference the sensorgrams. The analysis was carried out using the 1:1 binding model inherent to the Bio-Rad ProteOn's analysis software.

(ii) Binding of antibody 666, 667, 668 and 669 IgG to CSP, 40 degrees C. Five concentrations of CSP (64, 16, 4, 1 and 0.25 nM) were used as analyte over each human IgG1 construct captured at 0.3 μg/mL.

(iii) Binding of reference antibody 2A10 to CSP. Mouse monoclonal antibody 2A10 recognises the minimal epitope (NANP)3 (SEQ ID NO: 510) of the *Plasmodium falciparum* (*P. falciparum*) circumsporozoite protein (CSP) repeat. It cross-reacts with the variant repeat sequence (NANPNVDPNANP) (SEQ ID NO: 510) contained in the 5' repeat region of CSPs of all *P. falciparum* isolates.

Monoclonal antibody 2A10 (IgG2aκ) was obtained through BEI Resources, NIAID, NIH (MRA-183A, contributed by E. Nardin). 2A10 was diluted to 5 μg/mL in running buffer (1×HBS-EP+ Buffer: Technova, cat. No. H8022) and captured on the anti-mouse capture surface. Recombinant CSP was used as analyte at 64 nM, 16 nM, 4 nM, 1 nM, 0.25 nM and 0 nM, and injected over the monoclonal mouse IgG2a construct. The assay was carried out at 25° C., with an association step of 240 sec and a dissociation step of 600 sec. Buffer injection (0 nM) was used to double reference the sensorgrams. The analysis was carried out using the 1:1 binding model inherent to the Bio-Rad ProteOn's analysis software.

(iv) Anti-CSP reference antibody 2A10, mouse IgG2aκ, 40 degrees C., with recombinant CSP. The concentration of antibody captured on the anti-mouse surface was varied from 5 ug/mL-0.3125 ug/mL. Varying concentrations of recombinant CSP (64 nM-0 nM) were passed over the captured antibody.

SPR Results (i)

TABLE 8

SPR determination of CSP binding by antibody 666, 667, 668 and 669 Fabs, 25 degrees C.

| Sample | ka (1/Ms) | kd (1/s) | KD (M) | KD (nM) |
|---|---|---|---|---|
| 666 Fab | 4.80E+04 | 2.49E−03 | 5.20E−08 | 52 |
| 667 Fab | 2.50E+04 | 7.90E−04 | 3.16E−08 | 31.6 |
| 668 Fab | 3.79+04 | 4.73E−04 | 1.25E−08 | 12.5 |
| 669 Fab | 1.68E+04 | 2.11E−03 | 1.26E−07 | 126 |

(ii)

TABLE 9

SPR determination of CSP binding by antibody 666, 667, 668 and 669 IgG1, 40 degrees C.

| | ka (1/Ms) | kd (1/s) | KD (nM) |
|---|---|---|---|
| 666 human IgG1 | 9.70E+04 | 1.70E−05 | 0.18 |
| 667 human IgG1 | 2.15E+05 | 6.46E−05 | 0.31 |
| 668 human IgG1 | 5.40E+05 | 2.47E−05 | 0.05 |
| 669 human IgG1 | 2.65E+05 | 1.25E−04 | 0.47 |

Here a higher temperature (40° C.) was used to increase dissociation and lower capture. Considering the difference of affinities between human Fab and IgG1, results suggest that the binding of the human IgG1 constructs to recombinant CSP is driven by avidity. This correlates with the apparent recognition by these antibodies of sequence NPDPNANP (SEQ ID NO: 512), which is heavily repeated in CSP. The KD values generated for the human IgG1 constructs are therefore considered as apparent affinities for CSP.

(iii)

TABLE 10

SPR determination of CSP binding by antibody 2A10 IgG, 25 degrees C.

| | ka (1/Ms) | kd (1/s) | KD (nM) |
|---|---|---|---|
| 2A10 | 2.23E+06 | 9.41E−05 | 0.04 |

(iv) The on-rate/off-rate could not be resolved for any of the 2A10 samples at 40° C. and hence no KD values could be generated. Increasing the temperature to 40° C. for this analysis did not have an effect on the off-rate.

Materials & Methods—Peptide Binding Assay with Antibody 666, 667, 668 and 669 IgG1

A biolayer interferometry assay was performed to analyse binding of monoclonal human IgG1 antibodies to CSP peptides.

Sensors coated with a commercial streptavidin ligand (Pall ForteBio, cat No 18-5019) were hydrated for 10 min in running buffer (1×HBS-EP+ Buffer: Technova, cat. No. H8022).

The monoclonal human IgG1 Abs were diluted to 30 μg/mL in running buffer. Commercial CSP peptides and biotinylated recombinant CSP were diluted to 20 μg/mL in running buffer. A first set of peptides (#1 to #4) was designed to cover 22 amino acids around the first occurrence of the epitope NPDPNANP (SEQ ID NO: 512), and a second set of peptides (#5 to #17) was designed as an alanine scan replacing one by one all amino acids in the DGNPDPNANPNV (SEQ ID NO: 541) sequence by an alanine (or a lysine if the amino acid is already an alanine).

TABLE 11

Biotinylated CSP peptides.

| No in Assay | Sequence | Purity |
|---|---|---|
| Peptide #1 | Biotin-SGSGKPKHKKLKQPGDGNPDPNANP (SEQ ID NO: 518) | 97.66% |
| Peptide #2 | Biotin-SGSGKHKKLKQPG (SEQ ID NO: 519) | 99.50% |
| Peptide #3 | Biotin-SGSGHKKLKQPGDGNPDPNANPN (SEQ ID NO: 520) | 98.62% |

TABLE 11-continued

Biotinylated CSP peptides.

| No in Assay | Sequence | Purity | |
|---|---|---|---|
| Peptide #4 | Biotin-SGSGNPDPNANP (SEQ ID NO: 521) | 99.25% | |
| Peptide #5 | Biotin-SGSGDGNPDPNANPNV (SEQ ID NO: 522) | 98.07% | Original |
| Peptide #6 | Biotin-SGSGAGNPDPNANPNV (SEQ ID NO: 523) | 98.79% | Alanine Scan |
| Peptide #7 | Biotin-SGSGDANPDPNANPNV (SEQ ID NO: 524) | 96.86% | |
| Peptide #8 | Biotin-SGSGDGAPDPNANPNV (SEQ ID NO: 525) | 96.76% | |
| Peptide #9 | Biotin-SGSGDGNADPNANPNV (SEQ ID NO: 526) | 97.93% | |
| Peptide #10 | Biotin-SGSGDGNPAPNANPNV (SEQ ID NO: 527) | 98.87% | |
| Peptide #11 | Biotin-SGSGDGNPDANANPNV (SEQ ID NO: 528) | 98.08% | |
| Peptide #12 | Biotin-SGSGDGNPDPAANPNV (SEQ ID NO: 529) | 98.13% | |
| Peptide #13 | Biotin-SGSGDGNPDPNKNPNV (SEQ ID NO: 530) | 98.83% | |
| Peptide #14 | Biotin-SGSGDGNPDPNAAPNV (SEQ ID NO: 531) | 97.20% | |
| Peptide #15 | Biotin-SGSGDGNPDPNANANV (SEQ ID NO: 532) | 95.57% | |
| Peptide #16 | Biotin-SGSGDGNPDPNANPAV (SEQ ID NO: 533) | 98.81% | |
| Peptide #17 | Biotin-SGSGDGNPDPNANPNA (SEQ ID NO: 534) | 97.79% | |

The biotinylated peptides and recombinant CSP were captured at 20 μg/mL on the streptavidin sensors and then the sensors were dipped into the antibody solutions at 30 μg/mL. Fresh streptavidin sensors were used for each peptide-antibody interaction. The assay was carried out at 25° C. Binding signals were double referenced using a well reference and a sensor reference.

For the analysis, the limit of detection of a binding event (LOD) was defined as:

LOD=Average of Buffer Signals+(3×Standard Deviation of Buffer Signals)

Any interaction with a response signal below the LOD was considered as non-binding.

Peptide Binding Results

TABLE 12

Summary of 667 human IgG1 interactions with peptides

| Sample ID | Loading Sample ID | Response (nm) | Binding |
|---|---|---|---|
| 667 human IgG1 | Peptide #1 44286 | 0.6454 | Yes |
| | Peptide #2 44287 | −0.0438 | No |
| | Peptide #3 44288 | 0.8137 | Yes |
| | Peptide #4 44285 | 0.1631 | Yes |
| | Peptide #5 44289 | 0.6346 | Yes |

TABLE 12-continued

Summary of 667 human IgG1 interactions with peptides

| Sample ID | Loading Sample ID | Response (nm) | Binding |
|---|---|---|---|
| | Peptide #6 44290 | 0.9073 | Yes |
| | Peptide #7 44291 | 0.951 | Yes |
| | Peptide #8 44292 | 0.6919 | Yes |
| | Peptide #9 44293 | 0.6956 | Yes |
| | Peptide #10 44294 | 3.2183 | Yes |
| | Peptide #11 44295 | 0.0953 | Yes |
| | Peptide #12 44296 | 0.0529 | Yes |
| | Peptide #13 44297 | −0.0102 | No |
| | Peptide #14 44298 | −0.0141 | No |
| | Peptide #15 44299 | 0.2132 | Yes |
| | Peptide #16 44300 | 0.6506 | Yes |
| | Peptide #17 44301 | 1.086 | Yes |
| | Recombinant CSP | 0.5284 | Yes |
| | Running Buffer | 0.0209 | |
| | Running Buffer | Sensor Error | |
| | Running Buffer | 0.0169 | |
| Buffer Average | 0.0189 | | |
| Buffer St. Dev | 0.0028 | | |
| LOD | 0.027 | | |

TABLE 13

Summary of 668 human IgG1 interactions with peptides

| Sample ID | Loading Sample ID | Response (nm) | Binding |
|---|---|---|---|
| 668 human IgG1 | Peptide #1 44286 | 6.4733 | Yes |
| | Peptide #2 44287 | −0.0533 | No |
| | Peptide #3 44288 | 6.341 | Yes |
| | Peptide #4 44285 | 4.6934 | Yes |
| | Peptide #5 44289 | 4.7146 | Yes |
| | Peptide #6 44290 | 4.8958 | Yes |
| | Peptide #7 44291 | 4.8788 | Yes |
| | Peptide #8 44292 | 4.8627 | Yes |
| | Peptide #9 44293 | 4.7189 | Yes |
| | Peptide #10 44294 | 5.8228 | Yes |
| | Peptide #11 44295 | 6.006 | Yes |
| | Peptide #12 44296 | 4.7362 | Yes |
| | Peptide #13 44297 | 0.0033 | No |
| | Peptide #14 44298 | 0.5966 | Yes |
| | Peptide #15 44299 | 5.6891 | Yes |
| | Peptide #16 44300 | 4.7153 | Yes |
| | Peptide #17 44301 | 4.86 | Yes |
| | Recombinant CSP | 0.6534 | Yes |
| | Running Buffer | 0.1213 | |
| | Running Buffer | 0.1003 | |
| | Running Buffer | 0.0739 | |
| Buffer Average | | | |
| Buffer St. Dev | 0.024 | | |
| LOD | 0.170 | | |

TABLE 14

Summary of 669 human IgG1 interactions with peptides

| Sample ID | Loading Sample ID | Response (nm) | Binding |
|---|---|---|---|
| 669 human IgG1 | Peptide #1 44286 | 5.8313 | Yes |
| | Peptide #2 44287 | −0.0428 | No |
| | Peptide #3 44288 | 5.0648 | Yes |
| | Peptide #4 44285 | 5.2674 | Yes |
| | Peptide #5 44289 | 3.7565 | Yes |
| | Peptide #6 44290 | 3.8156 | Yes |
| | Peptide #7 44291 | 3.8607 | Yes |
| | Peptide #8 44292 | 3.7931 | Yes |
| | Peptide #9 44293 | 3.6832 | Yes |
| | Peptide #10 44294 | 4.4782 | Yes |
| | Peptide #11 44295 | 2.1841 | Yes |
| | Peptide #12 44296 | 2.8081 | Yes |
| | Peptide #13 44297 | −0.0024 | No |
| | Peptide #14 44298 | 0.0239 | No |
| | Peptide #15 44299 | 2.8174 | Yes |
| | Peptide #16 44300 | 3.6625 | Yes |
| | Peptide #17 44301 | 3.8523 | Yes |
| | Recombinant CSP | 0.5456 | Yes |
| | Running Buffer | 0.0674 | |
| | Running Buffer | 0.0879 | |
| | Running Buffer | 0.0507 | |
| Buffer Average | 0.069 | | |
| Buffer St. Dev | 0.0186 | | |
| LOD | 0.125 | | |

TABLE 15

Summary of 666 human IgG1 interactions with peptides

| Sample ID | Loading Sample ID | Response (nm) | Binding |
|---|---|---|---|
| 666 human IgG1 | Peptide #1 44286 | 9.0618 | Yes |
| | Peptide #2 44287 | 0.3243 | Yes |
| | Peptide #3 44288 | 6.5328 | Yes |
| | Peptide #4 44285 | 7.0613 | Yes |
| | Peptide #5 44289 | 2.4017 | Yes |
| | Peptide #6 44290 | 3.1362 | Yes |
| | Peptide #7 44291 | 2.9882 | Yes |
| | Peptide #8 44292 | 2.2319 | Yes |
| | Peptide #9 44293 | 1.7451 | Yes |
| | Peptide #10 44294 | 5.178 | Yes |
| | Peptide #11 44295 | 0.9817 | Yes |
| | Peptide #12 44296 | 0.0943 | Yes |
| | Peptide #13 44297 | −0.0028 | No |
| | Peptide #14 44298 | 0.0116 | No |
| | Peptide #15 44299 | 0.862 | Yes |
| | Peptide #16 44300 | 2.6993 | Yes |
| | Peptide #17 44301 | 2.9455 | Yes |
| | Recombinant CSP | 0.2954 | Yes |
| | Running Buffer | −0.0038 | |
| | Running Buffer | −0.012 | |
| | Running Buffer | −0.0265 | |
| Buffer Average | −0.0141 | | |
| Buffer St. Dev | 0.011494781 | | |
| LOD | 0.020 | | |

Considering the first set of peptides, all four monoclonal human IgG1s bind the peptide #4 (NPDPNANP) (SEQ ID NO: 512) and the longest peptides (#1 and #3) that are including this sequence. 667, 668 and 669 do not bind the peptide #2 which covers the same sequence except for the NPDPNANP sequence (SEQ ID NO: 512). The four tested monoclonal human IgG1s show the same results that correlate with an epitope involving the NPDPNANP sequence (SEQ ID NO: 512). However, 666 IgG1 did show weak binding to peptide #2 which suggests the epitope for this antibody extends into the region further upstream, binding an epitope comprising one or more residues of the sequence KHKKLKQPG (SEQ ID NO: 517).

Considering the second set of peptides, the binding of the four monoclonal human IgG1s is disrupted on peptide #13 (DGNPDPNKNPNV) (SEQ ID NO: 535) and the binding of 666, 667 and 669 human IgG1s is disrupted on the following peptide as well (DGNPDPNAAPNV) (SEQ ID NO: 536). This suggests a refined epitope where the alanine in the NPDPNANP (SEQ ID NO: 512) sequence has a role in the binding of the four monoclonal human IgG1s, and the following asparagine is involved in the binding of 666, 667 and 669 human IgG1s.

Example 11: Additional Anti-CSP Antibody Sequences

Further computational analysis of the antibody lineages identified in Example 2 was performed to group antibodies into evolutionarily-related lineages from their nucleotide sequences. Bioinformatics analysis was used to infer phylogenetic trees of antibodies derived from the same B cell clonal lineage.

Antibodies 666, 667, 668 and 669 are derived from IGLV2-23 and IGLJ3 germline genes. An additional 33 antibody sequences were identified which contain the common IGLV2-23 IGLJ3 genotype. These antibodies may therefore also be active against CSP. Alignments of the light and heavy chains of these antibodies are shown in FIGS. 23 and 24. An additional six antibodies were also selected as they were identified as members of the largest lineages. A large lineage is suggestive of a favoured evolutionary trajectory against an antigen and therefore of greater potential to contain strong antigen binding antibodies. Sequence information for these antibodies is provided in Table 16 and Table 17.

Example 12: SPR Characterisaton of Additional Antibodies

The antibodies identified in Example 11 were expressed as human IgG1 in HEK cells (Expi293F, Gibco Life Technologies) having the VH and VL domains shown in Table 16 and cell culture supernatants were tested for binding to CSP by SPR at 25 degrees C. Antibody 666 was included as a positive control. Positive binding data were obtained for antibody 666 and for 21 of the Table 16 antibodies.

Off-rates could not be resolved so kd (1/s) and KD (nM) values were not calculated. On-rates as represented by ka (1/Ms) were as follows:

TABLE 18

On-rates of antibodies identified in Example 11.

| Antibody | ka (1/Ms) |
|---|---|
| CL-141805 | 1.19E+06 |
| CL-141806 | 2.84E+05 |
| CL-141766 | 5.28E+05 |
| CL-141799 | 4.86E+05 |
| CL-141802 | 3.13E+05 |
| CL-141792 | 5.13E+04 |
| CL-141769 | 1.56E+05 |
| CL-141770 | 5.67E+05 |
| CL-141772 | 3.38E+05 |
| CL-141776 | 1.43E+05 |
| CL-141777 | 2.10E+01 |
| CL-141779 | 2.98E+05 |
| CL-141781 | 2.21E+05 |
| CL-141783 | 1.28E+05 |
| CL-141784 | 5.41E+05 |
| CL-141785 | 5.73E+05 |
| CL-141786 | 4.57E+05 |
| CL-141787 | 3.37E+01 |
| CL-141789 | 2.93E+05 |
| CL-141790 | 4.28E+05 |
| CL-141791 | 2.53E+05 |
| 666 | 1.00E+08 |

Kinetic Assay Method:

The human IgG1s were transiently expressed in HEK293 cells over a week. The supernatants containing the human IgG1s were diluted 1/100 in running buffer (1×HBS-EP+ Buffer Technova, cat. No. H8022) and captured on an anti-human IgG capture surface. The full CSP protein was used as analyte at 64 nM, 16 nM, 4 nM, 1 nM, 0.25 nM and 0 nM, and injected over the captured human IgG1s. Finally, the surface was regenerated between each human IgG1 construct using 100 mM PO4. The assay was carried out at 25° C., with an association step of 210 sec and a dissociation step of 600 sec.

The buffer injection (i.e. 0 nM) was used to double reference the sensorgrams. The analysis was carried out using the 1:1 binding model inherent to the Bio-Rad ProteOn's analysis software.

Example 13: Selection of Further Protective Anti-CSP Antibodies with Structural Motif for NPDPNANp (SEQ ID NO: 512) Binding Through sequence analysis of antibodies that showed strong binding to CSP and effective inhibition in biological assays described herein, and considering their structural interface with the NPDPNANP (SEQ ID NO: 512) epitope identified herein, we uncovered a structural pattern that may be considered a structural "signature" or motif indicative of a class of antibodies that confer protection against sporozoite infection. Such antibodies are strong candidates for preventing malaria and may thus be administered to a mammal (e.g., human) to reduce risk of malaria in that mammal, methods for which are described in more detail elsewhere herein.

In particular, with reference to the structure of antibody AB-00068, we identified residues that contribute hydrophobic or electrostatic interactions with the CSP epitope. Furthermore, we ran simulated molecular dynamics to model each of these structures dynamically, to further identify the electrostatically-important residues. This led to the identification of the following structural motif (all numbers are from the Kabat numbering scheme):

LCDR1 containing an N and a hydrophobic residue. Preferably, the N is at position 31. Preferably, the N is either directly preceded or followed by the hydrophobic residue. The hydrophobic residue is preferably Y.

LCDR3 containing a Y residue and a W residue. Preferably, the Y precedes W (in the N to C direction). Preferably, Y is at position 91. Preferably, W is at position 96.

HCDR2 containing W and N. Preferably, the W precedes N (in the N to C direction). Preferably, W is at position 50. Preferably, N is at at position 52.

HCDR3 containing at least one Y residue. Y may be present at any position in the HCDR3.

Antibodies comprising this structural motif represent preferred embodiments of the present invention.

Having identified this structural motif with reference to Ab-000668, we confirmed presence of this motif in numerous other antibodies described in the preceding Examples, and through analysis of other antibody sequences from the immunised mice we were able to further select the additional antibodies presented in Table 18, which contain this structural motif and are thus believed to represent candidate therapeutics according to the present invention.

```
Antibody sequences
Antibody 666:
Ab666 H contig nucleotide sequence
                                            SEQ ID NO: 1
ATGGACTGGACCTGGAGGATCCTCTTTTTGGTGGCAGCAGCCACAGGTGCCCACTCCC

AGGTCCAGCTTGTGCAGTCTGGGGCTGAGGTGAAGAAGCCTGGGGCCTCAGTGAAGG

TTTCCTGCAAGGCTTCTGGATACACCTTCACAAACTATGCTATGCATTGGGTGCGCCAG

GCCCCCGGACAAAGGCTTGAGTGGATGGGATGGATCAACGCTGGCAATGGTAATACAA

AATATTCACAAAATTTCCAGGGCAGAGTCACCATTACCAGGGACACATCCGCGAGCACA

GCCTACATGGAGCTGAGCAGCCTGAGATCTGAAGACACGGCTGTGTATTACTGTGCGA

GAGATGAATACTATGCTTCGGGGAGTTATTATGACTACTACTACTACGGTATGGACGTC

TGGGGCCAAGGGACCACGGTCACCGTCACCTCAGC
```

Ab666 H contig amino acid sequence
VH domain sequence encoded by the nucleotide sequence above:
SEQ ID NO: 2
QVQLVQSGAEVKKPGASVKVSCKASGYTFTNYAMHVWRQAPGQRLEWMGWINAGNGNT

KYSQNFQGRVTITRDTSASTAYMELSSLRSEDTAVYYCARDEYYASGSYYDYYYYGMDVW

GQGTTVTVTS

Ab666 HCDR1
SEQ ID NO: 3
GYTFTNYAMH

Ab666 HCDR2
SEQ ID NO: 4
WINAGNGNTKYSQNFQG

Ab666 HCDR3
SEQ ID NO: 5
DEYYASGSYYDYYYYGMDV

Ab666 L contig nucleotide sequence
SEQ ID NO: 6
ATGGCCTGGGCTCTGCTGCTCCTCAACCTCCTCACTCAGGACACAGGGTCCTGGGCCC

AGTCTGCCCTGACTCAGCCTGCCTCCGTGTCTGGGTCTCCTGGACAGTCGATCACCAT

CTCCTGCACTGGAACCAGCAGTGATGTTGGTGTTTATAACTATGTCTCCTGGTTCCAAC

AGCACCCAGGCAAAGCCCCCAAACTCATGATTTATAATGTCAGTAAGCGGCCCTCAGG

GGTTTCTAATCGCTTCTCTGGCTCCAAGTCTGGCAACACGGCCTCCCTGACAATCTCTG

GGCTCCAGGCTGAGGACGAGGCTGATTATTACTGCTGCTCATATGCAGGTAGTAGCAC

TTGGGTGTTCGGCGGAGGGACCAACCTGACCGTCCTAGG

Ab666 L contig amino acid sequence
VL domain sequence encoded by the nucleotide sequence above:
SEQ ID NO: 7
QSALTQPASVSGSPGQSITISCTGTSSDVGVYNYVSWFQQHPGKAPKLMIYNVSKRPSGVS

NRFSGSKSGNTASLTISGLQAEDEADYYCCSYAGSSTWVFGGGTNLTVL

Ab666 LCDR1
SEQ ID NO: 8
TGTSSDVGVYNYVS

Ab666 LCDR2
SEQ ID NO: 9
NVSKRPS

Ab666 LCDR3
SEQ ID NO: 10
CSYAGSSTWV

Antibody 667:
Ab667 H contig nucleotide sequence
SEQ ID NO: 11
ATGGACTGGACCTGGAGGGTCCTCTTTTTGGTGGCAGCAGCCACAGGTGCCCACTCCC

AGGTCCAGCTTGTGCAGTCTGGGGCTGAGGTGAAGAAGCCTGGGGCCTCAGTGAAGG

TTTCCTGCAGGGCTTCTGGATACACCTTCACTAACTATGCTATGCATTGGGTGCGCCAG

GCCCCCGGACAAAGGCTTGAGTGGATGGGATGGATCAACGCTGGCAATGGTTACACAA

AATATTCACAGAAGTTCCAGGACAGAGTCACCATTACCAGGGACACATCCGCGACCAC

AGCCTACATGGAGCTGAGCAGCCTGAGATCTGAAGACACGGCTATGTATTACTGTGCG

AGAGATTCTTTTTACGATATTTTGAGTGGGCCAGTCTATCACTACTACGGTATGGACGTC

TGGGGCCAAGGGACCACGGTCACCGTCTCCTCAGC

```
Ab667 H contig amino acid sequence
VH domain sequence encoded by the nucleotide sequence above:
                                                      SEQ ID NO: 12
QVQLVQSGAEVKKPGASVKVSCRASGYTFTNYAMHWVRQAPGQRLEWMGWINAGNGYT

KYSQKFQDRVTITRDTSATTAYMELSSLRSEDTAMYYCARDSFYDILSGPVYHYYGMDVW

GQGTTVTVSS

Ab667 HCDR1
                                                      SEQ ID NO: 13
GYTFTNYAMH

Ab667 HCDR2
                                                      SEQ ID NO: 14
WINAGNGYTKYSQKFQD

Ab667 HCDR3
                                                      SEQ ID NO: 15
DSFYDILSGPVYHYYGMDV

Ab667 L contig nucleotide sequence
                                                      SEQ ID NO: 16
ATGGCCTGGGCTCTGCTGCTCCTCAACCTCCTCACTCAGGCCACAGGGTCCTGGGCCC

AGTCTGCCCTGACTCAGCCTGACTCCGTGTCTGGGTCTCCTGGACAGTCGATCACCAT

CTCCTGCACTGGAACCAGCAATGATGTTGGTATTTATAACCATGTCTCCTGGTACCAAC

AGCACCCAGGCAAAGCCCCCAAACTCATGATTTATGATGTCAATAAGCGGCCCTCAGG

GATTTCTAATCGCTTCTCTGGCTCCAAGTCTGGCGACACGGCCTCCCTGACAATCTCTG

GGCTCCAGGCTGAGGACGAGGCTGATTATTACTGCTGCTCATATGCAGGTAGTAGCGC

TTGGGTGTTCGGCGGAGGGACCAAATTGACCGTCCTTGG

Ab667 L contig amino acid sequence
VL domain sequence encoded by the nucleotide sequence above:
                                                      SEQ ID NO: 17
QSALTQPDSVSGSPGQSITISCTGTSNDVGIYNHVSWYQQHPGKAPKLMIYDVNKRPSGIS

NRFSGSKSGDTASLTISGLQAEDEADYYCCSYAGSSAWVFGGGTKLTVL

Ab667 LCDR1
                                                      SEQ ID NO: 18
TGTSNDVGIYNHVS

Ab667 LCDR2
                                                      SEQ ID NO: 19
DVNKRPS

Ab667 LCDR3
                                                      SEQ ID NO: 20
CSYAGSSAWV

Antibody 668:
Ab668 H contig nucleotide sequence
                                                      SEQ ID NO: 21
ATGGACTGGACCTGGAGGATCCTCTTTTTGGTGGCAGCAGCCGCAGGTGCCCACTCCC

AGGTCCAGCTTGTGCAGTCTGGGGCTGAGGTGAAGAAGCCTGGGGCCTCAGTGAAGG

TTTCCTGCAAGGCTTCTGGATTCACCTTCACTGACTATGCTATGCATTGGGTGCGCCAG

GCCCCCGGACAAAGGCTTGAGTGGATGGGCTGGATCAACGCTGGCAATGGTTACACAA

AATATTCACAGAAGTTCCAGGACAGACTCACCATTACCAGGGACACATTCGCGAGCACA

GTCTACATGGAGCTGAGCAGCCTGAGATCTGAAGACACGACTGTGTATTACTGTGCGA

GAGATGGGTTTTGTCCTAGTAACACTTGTTCTGGTTACTACGGTATGGACGTCTGGGGC

CAAGGGACCACGGTCACCGTCTCCTCAGC
```

Ab668 H contig amino acid sequence
VH domain sequence encoded by the nucleotide sequence above:
SEQ ID NO: 22
QVQLVQSGAEVKKPGASVKVSCKASGFTFTDYAMHWVRQAPGQRLEWMGWINAGNGYT

KYSQKFQDRLTITRDTFASTVYMELSSLRSEDTTVYYCARDGFCPSNTCSGYYGMDVWGQ

GTTVTVSS

Ab 668 HCDR1
SEQ ID NO: 23
GFTFTDYAMH

Ab668 HCDR2
SEQ ID NO: 24
WINAGNGYTKYSQKFQD

Ab668 HCDR3
SEQ ID NO: 25
DGFCPSNTCSGYYGMDV

Ab668 L contig nucleotide sequence
SEQ ID NO: 26
ATGGCCTGGGCTCTGCTGCTCCTCAACCTCCTCACTCAGGACACAGGGTCCTGGGCCC

AGTCTGCCCTGACTCAGCCTGCCTCCGTGTCTGGGTCTCCTGGACAGTCGATCACCAT

CTCCTGCACTGGAACCAGCAGTGATGTTGGTTCTTATAACTATGTCTCCTGGTACCAAC

AGCACCCAGGCAAAGCCCCCAAACTCATGATTTATGATGTCAATACGCGGCCCTCAGG

GGTTTCTATTCGCTTCTCTGCCTCCAAGTCTGGCAACACGGCCTCCCTGACAGTCTCTG

GGCTCCAGGCTGAGGACGAGGCTGTTTATTACTGCTCCTCATATGCAGGTAGTAGCAC

TTGGGTGTTCGGCGGAGGGACCAAGCTGACCGTCCTAGG

Ab668 L contig amino acid sequence
VL domain sequence encoded by the nucleotide sequence above:
SEQ ID NO: 27
QSALTQPASVSGSPGQSITISCTGTSSDVGSYNYVSWYQQHPGKAPKLMIYDVNTRPSGV

SIRFSASKSGNTASLTVSGLQAEDEAVYYCSSYAGSSTWVFGGGTKLTVL

Ab668 LCDR1
SEQ ID NO: 28
TGTSSDVGSYNYVS

Ab668 LCDR2
SEQ ID NO: 29
DVNTRPS

Ab668 LCDR3
SEQ ID NO: 30
SSYAGSSTWV

Antibody 669:
Ab669 H contig nucleotide sequence
SEQ ID NO: 31
ATGGACTGGACCTGGAGGATCCTCTTTTTGGTGGCAGCAGCCACAGGTGCCCACTCCC

AGGTCCAGCTTGTGCAGTCTGGGGCTGAGGTGAAGAAGCCTGGGGCCTCAGTGAGGG

TTTCCTGCAAGGCTTCTGGATTCACCTTCACTAGTTATGCTATGCATTGGGTGCGCCAG

GCCCCCGGACAAAGGCTTGAGTGGATGGGATGGATCAACGCTGGCAATGGTCACACA

AAATATTCACAGAAGTTCCAGGACAGAGTCGCCATTACCAGGGACACATCCGCGACCA

CAGTCTACATGGACCTGAGCAGCCTGAGATCTGAAGACACGGCTGTGTATTACTGTAC

GAGAGATGGATTTTGTACTAGTACCACCTGCTCCGACCACTACGGTATGGACGTCTGG

GGCCAAGGGACCACGGTCACCGTCTCCTCAGC

Ab669 H contig amino acid sequence
VH domain sequence encoded by the nucleotide sequence above:
SEQ ID NO: 32
QVQLVQSGAEVKKPGASVRVSCKASGFTFTSYAMHWVRQAPGQRLEWMGWINAGNGHT

KYSQKFQDRVAITRDTSATTVYMDLSSLRSEDTAVYYCTRDGFCTSTTCSDHYGMDVWGQ

GTTVTVSS

Ab669 HCDR1
SEQ ID NO: 33
GFTFTSYAMH

Ab669 HCDR2
SEQ ID NO: 34
WINAGNGHTKYSQKFQD

Ab669 HCDR3
SEQ ID NO: 35
DGFCTSTTCSDHYGMDV

Ab669 L contig nucleotide sequence
SEQ ID NO: 36
ATGGCCTGGGCTCTGCTGCTCCTCAACCTCCTCACTCAGGACACAGGGTCCTGGGCCC

AGTCTGCCCTGACTCAGCCTGCCTCCGTGTCTGGGTCTCCTGGACAGTCGATCACCAT

CTCCTGCACTGGAACCAGCAGTGATGTTGGTAGTTATAACTATGTCTCCTGGTACCAAC

AGCACCCAGGCAAAGCCCCCAAATTCATGATTTATGATGTCAGTAAGCGGCCCTCAGG

GGTTTCTAATCGCTTCTCTGGCTCCAAGTCTGGCAACACGGCCTCCCTGACAATCTCTG

GGCTCCAGGCTGAGGACGAGGCTGATTATTACTGCTGCTCATATGCAGGTAGTAGCAC

TTGGGTGTTCGGCGGAGGGACCAAGCTGACCGTCCTTGG

Ab669 L contig amino acid sequence
VL domain sequence encoded by the nucleotide sequence above:
SEQ ID NO: 37
QSALTQPASVSGSPGQSITISCTGTSSDVGSYNYVSWYQQHPGKAPKFMIYDVSKRPSGV

SNRFSGSKSGNTASLTISGLQAEDEADYYCCSYAGSSTWVFGGGTKLTVL

Ab669 LCDR1
SEQ ID NO: 38
TGTSSDVGSYNYVS

Ab669 LCDR2
SEQ ID NO: 39
DVSKRPS

Ab669 LCDR3
SEQ ID NO: 40
CSYAGSSTWV

Antibody 666-3
Ab666-3 H contig nucleotide sequence
SEQ ID NO: 64
ATGGACTGGACCTGGAGGATCCTCTTTTTGGTGGCAGCAGCCACAGGTGCCCACTCCC

AGGTCCAGCTTGTGCAGTCTGGGGCTGAGGTGAAGAAGCCTGGGGCCTCAGTGAAGG

TTTCCTGCAAGGCTTCTGGATACACCTTCACTAGTTATGCTATGCATTGGGTGCGCCAG

GCCCCCGGACAAAGGCTTGAGTGGATGGGATGGATCAACGCTGGCAATGGTAACACAA

AATATTCACAGAAGTTCCAGGGCGGAGTCACCATTACCAGGGACACATCCGCGAGCAC

AGCCTACATGGAGCTGAGCAGCCTGAGATCTGAAGACACGGCTGTATATTACTGTGCG

AGAGACAATTACTATGATTCGGGGAGTTATTATGACTACTACTACTACGGTATGGACGT

CTGGGGCCAAGGGACCACGGTCACCGTCTCCTCAGC

Ab666-3 H contig amino acid sequence
VH domain encoded by the nucleotide sequence above:
SEQ ID NO: 65
QVQLVQSGAEVKKPGASVKVSCKASGYTFTSYAMHWVRQAPGQRLEWMGWINAGNGNT

KYSQKFQGGVTITRDTSASTAYMELSSLRSEDTAVYYCARDNYYDSGSYYDYYYYGMDVW

GQGTTVTVSS

Ab666-3 L contig nucleotide sequence
SEQ ID NO: 66
ATGGCCTGGGCTCTGCTGCTCCTCAACCTCCTCACTCAGGACACAGGGTCCTGGGCCC

AGTCTGCCCTGACTCAGCCTGCCTCCGTGTCTGGGTCTCCTGGACAGTCGATCACCTT

CTCCTGCACTGGAACCAGCAGTGATGTTGGTAGTTATAATCATGTCTCCTGGTACCAAC

AGCACCCAGGCAAAGCCCCCAAACTCATGATTTATGATGTCAGTAAGCGGCCCTCAGG

GGTTTCTAATCGCTTCTCTGGCTCCAAGTCTGGCAACACGGCCTCCCTGACAATCTCTG

GCTCCAGGCTGAGGACGAGGCTGATTATTACTGCTGCTCATATGCAGGTAGTAGCAC

TTGGGTGTTCGGCGGAGGGACCAAGCTGACCGTCCTAGG

Ab666-3 L contig amino acid sequence
VL domain encoded by the nucleotide sequence above:
SEQ ID NO: 67
QSALTQPASVSGSPGQSITFSCTGTSSDVGSYNHVSWYQQHPGKAPKLMIYDVSKRPSGV

SNRFSGSKSGNTASLTISGLQAEDEADYYCCSYAGSSTWVFGGGTKLTVL

Antibody 666-4
Ab666-4 H contig nucleotide sequence
SEQ ID NO: 71
ATGGACTGGACCTGGAGGATCCTCTTTTTGGTGGCAGCAGCCACAGGTGCCCACTCCC

AGGTCCAGCTTGTGCAGTCTGGGGCTGAGGTGAAGAAGCCTGGGGCCTCAGTGAAGG

TTTCCTGCAAGGCGTCTGGATACACCTTCACGAACTATGCTATGCATTGGGTGCGCCAG

GCCCCCGGACAAAGGCTTGAGTGGATGGGATGGATCAACGCTGGCAATGGTTACACAA

AATATTCACAGAAGTTCCAGGGCAGAGTCACCATTATCAGGGACACATCTGCGACCACA

GCCTATATGGAGCTGAGCAGCCTGAGATCTGAAGACACGGCTGTGTATTACTGTGCGA

GAGATAATTATTATGATTCGGGGAGTTATTATGAATACTGCTACTACGGTATGGACGTCT

GGGGCCAAGGGACCACGGTCACCGTCTCCTCAGC

Ab666-4 H contig amino acid sequence
VH domain encoded by the nucleotide sequence above:
SEQ ID NO: 72
QVQLVQSGAEVKKPGASVKVSCKASGYTFTNYAMHWVRQAPGQRLEWMGWINAGNGYT

KYSQKFQGRVTIIRDTSATTAYMELSSLRSEDTAVYYCARDNYYDSGSYYEYCYYGMDVW

GQGTTVTVSS

Ab666-4 L contig nucleotide sequence
SEQ ID NO: 73
ATGGCCTGGGCTCTGCTGCTCCTCAACCTCCTCACTCAGGACACAGGGTCCTGGGCCC

AGTCTGCCCTGACTCAGCCTGCCTCCGTGTCTGGGTCTCCTGGACAGTCGATCACCAT

CTCCTGCACTGGAACCAGCAGTGATGTTGGTAGTTATAACCATGTCTCCTGGTACCAAC

AATACCCAGGCAAAGCCCCCAAACTCCTGATTTATGATGTCAGTAAGCGGCCCTCAGG

```
GGTTTCTAATCGCTTCTCTGGCTCCAAGTCTGGCAACACGGCCTCCCTGACAATCTATG

GGCTCCAGGCTGAGGACGAGGCTGATTATTACTGCTGCTCATATGTAGGTAGCAGCAC

TTGGGTGTTCGGCGGAGGGACCAAGCTGACCGTCCTAGG
```

Ab666-4 L contig amino acid sequence
VL domain encoded by the nucleotide sequence above:
```
                                                  SEQ ID NO: 74
QSALTQPASVSGSPGQSITISCTGTSSDVGSYNHVSWYQQYPGKAPKLLIYDVSKRPSGVS

NRFSGSKSGNTASLTIYGLQAEDEADYYCCSYVGSSTWVFGGGTKLTVL
```

Antibody 667-1
Ab667-1 H contig nucleotide sequence
```
                                                  SEQ ID NO: 79
ATGGACTGGACCTGGAGGGTCCTCTTTTTGGTGGCAGCAGCCACAGGTGCCCACTCCC

AGGTCCAGCTTGTGCAGTCTGGGGCTGAGGTGAAGAAGCCTGGGGCCTCAGTGAAGG

TTTCCTGCAGGGCTTCTGGATACACCTTCAGTAATTATGCTATGCATTGGGTGCGCCAG

GCCCCCGGACAAAGGCTTGAGTGGATGGGATGGATCAACGCTGGCAATGGTTACACAA

AATATTCACAGAAGTTCCAGGACAGAGTCACCATTACCAGGGACACATCCGCGACCAC

AGCCTACATGGAACTGAGCAGCCTGAGATCTGAAGACACGGCTATGTATTACTGTTCGA

GAGATTCTTTTTACGATATTTTGACTGGGCCAGTCTATCACTACTACGGTATGGACGTCT

GGGGCCAAGGGACCACGGTCACCGTCTCCTCAGC
```

Ab667-1 H contig amino acid sequence
VH domain encoded by the nucleotide sequence above:
```
                                                  SEQ ID NO: 80
QVQLVQSGAEVKKPGASVKVSCRASGYTFSNYAMHWVRQAPGQRLEWMGWINAGNGYT

KYSQKFQDRVTITRDTSATTAYMELSSLRSEDTAMYYCSRDSFYDILTGPVYHYYGMDVW

GQGTTVTVSS
```

Ab667-1 L contig nucleotide sequence
```
                                                  SEQ ID NO: 81
ATGGCCTGGGCTCTGCTGCTCCTCAACCTCCTCACTCAGGACACAGGGTCCTGGGCCC

AGTCTGCCCTGACTCAGCCTGACTCCGTGTCTGGGTCTCCTGGACAGTCGATCACCAT

CTCCTGCACTGGAACCAGCAATGATGTTGGTGTTTATAACCATGTCTCCTGGTACCAAC

AGCACCCAGGCAAAGCCCCCAAACTCATGATTTATGATGTCAGTAAGCGGCCCTCAGG

GGTTTCTAATCGCTTCTCTGGCTCCAAGTCTGGCAACACGGCCTCCCTGACAATCTCTG

GCTCCAGGCTGAGGACGAGGCTGATTATTACTGCTGCTCATATGTAGGTAATAGCGC

TTGGGTGTTCGGCGGAGGGACCAAACTGACCGTCCTAGG
```

Ab667-1 L contig amino acid sequence
VL domain encoded by the nucleotide sequence above:
```
                                                  SEQ ID NO: 82
QSALTQPDSVSGSPGQSITISCTGTSNDVGVYNHVSWYQQHPGKAPKLMIYDVSKRPSGV

SNRFSGSKSGNTASLTISGLQAEDEADYYCCSYVGNSAWVFGGGTKLTVL
```

Antibody 667-2
Ab667-2 H contig nucleotide sequence
```
                                                  SEQ ID NO: 84
ATGGACTGGACCTGGAGGGTCCTCTTTTTGGTGGCAGCAGCCACAGGTGCCCACTCCC

AGGTCCAGCTTGTGCAGTCTGGGGCTGAGGTGAAGAAGCCTGGGGCCTCAGTGAAGG

TTTCCTGCAGGGCTTCTGGATACACCTTCACTAACTATGCTATGCATTGGGTGCGCCAG

GCCCCCGGACAAAGGCTTGAGTGGATGGGATGGATCAACGCTGGCAATGGTTACACAA

AGTATTCACAGAAGTTCCAGGACAGAGTCACCATTACCAGGGACACATCCGCGACCAC
```

-continued

AGCCCACATGGAACTGAGCAGCCTGAGATCTGAAGACACGGCTATGTATTACTGTGCG

AGAGATTCTTTTTACGATATTTTGACTGGGCCAGTCTATCACTACTACGGTATGGACGTC

TGGGGCCAAGGGACCACGGTCACCGTCTCCTCAGC

Ab667-2 H contig amino acid sequence
VH domain encoded by the nucleotide sequence above:
SEQ ID NO: 85
QVQLVQSGAEVKKPGASVKVSCRASGYTFTNYAMHWVRQAPGQRLEWMGWINAGNGYT

KYSQKFQDRVTITRDTSATTAHMELSSLRSEDTAMYYCARDSFYDILTGPVYHYYGMDVW

GQGTTVTVSS

Ab667-2 L contig nucleotide sequence
SEQ ID NO: 86
ATGGCCTGGGCTCTGCTGCTCCTCAACCTCCTCACTCAGGACACAGGGTCCTGGGCCC

AGTCTGCCCTGACTCAGCCTGACTCCGTGTCTGGGTCTCCTGGACAGTCGATCACCAT

CTCCTGCACTGGAACCAGCAATGATGTTGGTGTTTATAACCATGTCTCCTGGTACCAAC

AGCACCCAGGCAAAGCCCCCAAACTCATGATTTATGATGTCAGTAAGCGGCCCTCAGG

GGTTTCTAATCGCTTCTCTGGCTCCAAGTCTGGCAACACGGCCTCCCTGACAATCTCTG

GGCTCCAGGCTGAGGACGAGGCTGATTATTACTGCTGCTCATATGTAGGTAGTAGCGC

TTGGGTGTTCGGCGGAGGGACCAATCTGACCGTCCTAGG

Ab667-2 L contig amino acid sequence
VL domain encoded by the nucleotide sequence above:
SEQ ID NO: 87
QSALTQPDSVSGSPGQSITISCTGTSNDVGVYNHVSWYQQHPGKAPKLMIYDVSKRPSGV

SNRFSGSKSGNTASLTISGLQAEDEADYYCCSYVGSSAWVFGGGTNLTVL

Antibody 667-3
Ab667-3 H contig nucleotide sequence
SEQ ID NO: 88
ATGGACTGGACCTGGAGGGTCCTCTTTTTGGTGGCAGCAGCCACAGGTGCCCACTCCC

AGGTCCAGCTTGTGCAGTCTGGGGCTGAGGTGAAGAAGCCTGGGGCCTCAGTGAAGG

TTTCCTGCAGGGCTTCTGGATACACCTTCACTAACTATGCTATGCATTGGGTGCGCCAG

GCCCCCGGACAAAGGCTTGAGTGGATGGGATGGATCAACGCTGGCAATGGTTACACAA

AATATTCACAGAAGTTCCAGGACAGATTCACCATTACCAGGGACACATCCGCGACCACA

GCCTACATGGAACTGAGCAGCCTGAGATCTGAAGACACGGCTGTATATTACTGTGCGA

GAGATTCTTTTTACGATATTTTGACTGGGCCAGTCTATCACTACTACGGTATGGACGTCT

GGGGCCAAGGGACCACGGTCACCGTCTCCTCAGC

Ab667-3 H contig amino acid sequence
VH domain encoded by the nucleotide sequence above:
SEQ ID NO: 89
QVQLVQSGAEVKKPGASVKVSCRASGYTFTNYAMHWVRQAPGQRLEWMGWINAGNGYT

KYSQKFQDRFTITRDTSATTAYMELSSLRSEDTAVYYCARDSFYDILTGPVYHYYGMDVWG

QGTTVTVSS

Ab667-3 L contig nucleotide sequence
SEQ ID NO: 90
ATGGCCTGGGCTCTGCTGCTCCTCAACCTCCTCACTCAGGACACAGGGTCCTGGGCCC

AGTCTGCCCTGACTCAGCCTGACTCCGTGTCTGGGTCTCCTGGACAGTCGATCACCAT

CTCCTGCACTGGAACCAGCAATGATGTTGGTGTTTATAACCATGTCTCCTGGTACCAAC

AGCACCCAGGCAAAGCCCCCAAACTCATGATTTATGATGTCAGTAAGCGGCCCTCAGG

GGTTTCTAATCGCTTCTCTGGCTCCAAGTCTGGCAACACGGCCTCCCTGACAATCTCTG

GGCTCCAGGCTGAGGACGAGAGTGATTATTACTGCTGCTCATATGCAGGTAGTAGCAC

TTGGGTGTTCGGCGGAGGGACCAAGCTGACCGTCCTAGG

Ab667-3 L contig amino acid sequence
VL domain encoded by the nucleotide sequence above:
                                          SEQ ID NO: 91
QSALTQPDSVSGSPGQSITISCTGTSNDVGVYNHVSWYQQHPGKAPKLMIYDVSKRPSGV

SNRFSGSKSGNTASLTISGLQAEDESDYYCCSYAGSSTWVFGGGTKLTVL

Antibody 668-1
Ab668-1 H contig nucleotide sequence
                                          SEQ ID NO: 93
ATGGACTGGACCTGGAGGATCCTCTTTTTGGTGGCAGCAGCCGCAGGTGCCCACTCCC

AGGTCCAGCTTGTGCAGTCTGGGGCTGAGGTGAAGAAGCCTGGGGCCTCAGTGAAGG

TTTCCTGCAAGGCTTCTGGATTCACCTTCACTGACTACGCTATGCATTGGGTGCGCCAG

GCCCCCGGACAAAGGCTTGAGTGGATGGGTTGGATCAACGCTGGCAATGGTTACACAA

AATATTCACAGAAGTTCCAGGACAGACTCACCATTACCAGGGACACATTCGCGAGCACA

GTCTACATGGAGCTGAGCAGCCTGAGATCTGAAGACACGACTGTGTATTACTGTGCGA

GAGATGGGTTTTGTCCTAGTAACACTTGTTCTGGTTACTACGGTATGGACGTCTGGGGC

CAAGGGACCACGGTCACCGTCTCCTCAGC

Ab668-1 H contig amino acid sequence
VH domain encoded by the nucleotide sequence above:
                                          SEQ ID NO: 94
QVQLVQSGAEVKKPGASVKVSCKASGFTFTDYAMHWVRQAPGQRLEWMGWINAGNGYT

KYSQKFQDRLTITRDTFASTVYMELSSLRSEDTTVYYCARDGFCPSNTCSGYYGMDVWGQ

GTTVTVSS

Ab668-1 L contig nucleotide sequence
                                          SEQ ID NO: 95
ATGGCCTGGGCTCTGCTGCTCCTCAACCTCCTCACTCAGGACACAGGGTCCTGGGCCC

AGTCTGCCCTGACTCAGCCTGCCTCCGTGTCTGGGTCTCCTGGACAGTCGATCACCAT

CTCCTGCACTGGAACCAGCAGTGATGTTGGTGCTTATAAGTATGTCTCCTGGTACCAAC

AGCACCCAGGCAAAGCCCCCAAACTCATGATTTATGATGTCAATACGCGGCCCTCAGG

GGTTTCTACTCGCTTCTCTGCCTCCAAGTCTGGCAACACGGCCTCCCTGACAGTCTCTG

GGCTCCAGGCTGAGGACGAGGCTGTTTATTACTGCTCCTCATATGCAGGTAGTAGCAC

TTGGGTGTTCGGCGGAGGGACCAAGCTGACCGTCCTAGG

Ab668-1 L contig amino acid sequence
VL domain encoded by the nucleotide sequence above:
                                          SEQ ID NO: 96
QSALTQPASVSGSPGQSITISCTGTSSDVGAYKYVSWYQQHPGKAPKLMIYDVNTRPSGVS

TRFSASKSGNTASLTVSGLQAEDEAVYYCSSYAGSSTWVFGGGTKLTVL

Antibody 669-1
Ab669-1 H contig nucleotide sequence
                                          SEQ ID NO: 100
ATGGACTGGACCTGGAGGATCCTCTTTTTGGTGGCAGCAGCCACAGGTGCCCACTCCC

AGGTCCAGCTTGTGCAGTCTGGGGCTGAGGTGAAGAAGCCTGGGGCCTCAGTGAGGG

TTTCCTGCAAGGCTTCTGGATTCACCTTCATTAGTTATGCTATGCATTGGGTGCGCCAG

GCCCCCGGACAAGGGCTTGAGTGGATGGGATGGATCAACGCTGGCGATGGTCACACA

AAATATTCACAGAAGTTCCAGGACAGAGTCGCCATTACCAGGGACACATCCGCGACCA

CAGTCTACATGGACCTGAGCAGCCTGAGATCTGAAGACACGGCTGTGTATTACTGTTC

-continued

GAGAGATGGATTTTGTACTACTACCACCTGTTCCGACCACTACGGTATGGACGTCTGGG

GCCAAGGGACCACGGTCACCGTCTCCTCAGC

Ab669-1 H contig amino acid sequence
VH domain encoded by the nucleotide sequence above:
SEQ ID NO: 101
QVQLVQSGAEVKKPGASVRVSCKASGFTFISYAMHWVRQAPGQGLEWMGWINAGDGHT

KYSQKFQDRVAITRDTSATTVYMDLSSLRSEDTAVYYCSRDGFCTTTTCSDHYGMDVWGQ

GTTVTVSS

Ab669-1 L contig nucleotide sequence
SEQ ID NO: 102
ATGGCCTGGGCTCTGCTGCTCCTCAACCTCCTCACTCAGGACACAGGGTCCTGGGCCC

AGTCTGCCCTGACTCAGCCTGCCTCCGTGTCTGGGTCTCCTGGACAGTCGATCACCAT

CTCCTGCACTGGAACCAGCAGTGATGTTGGTAGTTATAACTATGTCTCCTGGTACCAAC

AGCACCCAGGCAAAGCCCCCAAATTCATGATTTATGATGTCAGTAAGCGGCCCTCAGG

GGTTTCTGATCGCTTCTCTGGCTCCAAGTCTGGCAACACGGCCTCCCTGACAATCTCTG

GGCTCCAGGCTGAGGACGAGGCTGATTATTACTGCTGCTCATATGCAGGTAGTAGCAC

TTGGGTGTTCGGCGGAGGGACCAAGCTGACCGTCCTTGG

Ab669-1 L contig amino acid sequence
VL domain encoded by the nucleotide sequence above:
SEQ ID NO: 103
QSALTQPASVSGSPGQSITISCTGTSSDVGSYNYVSWYQQHPGKAPKFMIYDVSKRPSGV

SDRFSGSKSGNTASLTISGLQAEDEADYYCCSYAGSSTWVFGGGTKLTVL

Antibody 669-2
Ab669-2 H contig nucleotide sequence
SEQ ID NO: 106
ATGGACTGGACCTGGAGGATCCTCTTTTTGGTGGCAGCAGCCACAGGTGCCCACTCCC

AGGTCCAGCTTGTGCAGTCTGGGGCTGAGGTGAAGAAGCCTGGGGCCTCAGTGAGGG

TTTCCTGCAAGACTTCTGGATTCACCTTCACTAGTTATGCTATACAGTGGGTGCGCCAG

GCCCCCGGACAAGGGCTTGAGTGGATGGGATGGATCAACGCTGGCGATGGTCACACG

AAATATTCACAGAAGTTCCAGGACAGAGTCGTCATTACCAGGGACACATCCGCGACCA

CAGTCTACATGGACCTGAGCAGCCTGAGATCTGAAGACACGGCTGTGTATTACTGTAC

GAGAGATGGATTTTGTACTACGACCACCTGCTCCGACCACTACGGTATGGACGTCTGG

GGCCAAGGGACCACGGTCACCGTCTCCTCAGC

Ab669-2 H contig amino acid sequence
VH domain encoded by the nucleotide sequence above:
SEQ ID NO: 107
QVQLVQSGAEVKKPGASVRVSCKTSGFTFTSYAIQWVRQAPGQGLEWMGWINAGDGHTK

YSQKFQDRVVITRDTSATTVYMDLSSLRSEDTAVYYCTRDGFCTTTTCSDHYGMDVWGQG

TTVTVSS

Ab669-2 L contig nucleotide sequence
SEQ ID NO: 108
ATGGCCTGGGCTCTGCTGCTCCTCAACCTCCTCACTCAGGACACAGGGTCCTGGGCCC

AGTCTGCCCTGACTCAGCCTGCCTCCGTGTCTGGGTCTCCTGGACAGTCGATCACCAT

CTCCTGCACTGGAACCAGCAGTGATGTTGGTAGTTATAACTATGTCTCCTGGTACCAAC

AGCACCCAGGCAAAGTCCCCAAATTCATGATTTCTGATGTCAGTAAGCGGCCCTCAGG

AATTTCTGATCGCTTCTCTGGCTCCAAGTCTGGCAATACGGCCTCCCTGACAATCTCTG

GGCTCCAGGCTGAGGACAGAGGCTGATTATTACTGCTGCTCATATGCAGGTGGTAGTAC

TTGGGTGTTCGGCGGAGGGACCAAGCTGACCGTCCTTGG

```
Ab669-2 L contig amino acid sequence
VL domain encoded by the nucleotide sequence above:
                                            SEQ ID NO: 109
QSALTQPASVSGSPGQSITISCTGTSSDVGSYNYVSWYQQHPGKVPKFMISDVSKRPSGIS

DRFSGSKSGNTASLTISGLQAEDEADYYCCSYAGGSTWVFGGGTKLTVL

Antibody 669-3
Ab669-3 H contig nucleotide sequence
                                            SEQ ID NO: 113
ATGGACTGGACCTGGAGGATCCTCTTTTTGGTGGCAGCAGCCACAGGTGCCCACTCCC

AGGTCCAGCTTGTGCAGTCTGGGGCTGAGGTGAAGAACCCTGGGGCCTCAGTGAAGG

TTTCCTGCAAGGCTTCTGGATTCACCTTCACTAACTATGCTATGCATTGGGTGCGCCAG

GCCCCCGGACAAAGGCTTGAGTGGATGGGATGGATCAACGCTGGCAATGGTCACACA

AAATATTCACAGAAGTTCCAGGACAGAGTCGCCATTACCAGGGACACATCCGCGACCA

CAGCCTACATGGAACTGAGCAGCCTGAGATCTGAAGACACGGCTGTGTATTACTGTTC

GAGAGATGGATTTTGTAGTACTACCACCTGCTCCGACCACTACGGTATGGACGTCTGG

GGCCAAGGGACCACGGTCACCGTCTCCTCAGC

Ab669-3 H contig amino acid sequence
VH domain encoded by the nucleotide sequence above:
                                            SEQ ID NO: 114
QVQLVQSGAEVKNPGASVKVSCKASGFTFTNYAMHWVRQAPGQRLEWMGWINAGNGHT

KYSQKFQDRVAITRDTSATTAYMELSSLRSEDTAVYYCSRDGFCSTTTCSDHYGMDVWGQ

GTTVTVSS

Ab669-3 L contig nucleotide sequence
                                            SEQ ID NO: 115
ATGGCCTGGGCTCTGCTGCTCCTCAACCTCCTCACTCAGGACACAGGGTCCTGGGCCC

AGTCTGCCCTGACTCAGCCTGCCTCCGTGTCTGGGTCTCCTGGACAGTCGATCACCAT

CTCCTGCACTGGAACCAGCAGTGATGTTGGTGGTTATAACTATGTCTCCTGGTACCAAC

AGCACCCAGGCAAAGCCCCCAAATTCATGATTTATGATGTCAGTAAGCGGCCCTCAGG

GGTTTCCAATCGCTTCTCTGGCTCCAAGTCTGGCAACACGGCCTCCCTGACAATCTCTG

GGCTCCAGGCTGAGGACGAGGCTGATTATTACTGCTGCTCATATGCAGGTAGTAGCAC

TTGGGTGTTCGGCGGAGGGACCAAGCTGACCGTCCTAGG

Ab669-3 L contig amino acid sequence
VL domain encoded by the nucleotide sequence above:
                                            SEQ ID NO: 116
QSALTQPASVSGSPGQSITISCTGTSSDVGGYNYVSWYQQHPGKAPKFMIYDVSKRPSGV

SNRFSGSKSGNTASLTISGLQAEDEADYYCCSYAGSSTWVFGGGTKLTVL

Antibody 669-4
Ab669-4 H contig nucleotide sequence
                                            SEQ ID NO: 118
ATGGACTGGACCTGGAGGATCCTCTTTTTGGTGGCAGCAGCCACAGGTGCCCACTCCC

AGGTCCAGCTTGTGCAGTCTGGGGCTGAGGTGAAGAAGCCTGGGGCCTCAGTGAAGG

TTTCCTGCAAGGCTTCTGGATTCACCTTCACTAGCCATGCTATACATTGGGTGCGCCAG

GCCCCCGGACAAAGGCTTGAGTGGATGGGATGGATCAACGCTGGCAATGGTTACACAA

AATATTCACAGAAGTTCCAGGACAGAGTCGCCATTACCAGGGACACATCCGCGAGCAC

AGCCTACATGGAGCTGAGCAGCCTGAGATCTGAAGACACGGCTGTGTATTACTGTACG

AGAGATGGATTTTGTAGTACTACCACCTGCTCCGACCACTACGGTATGGACGTCTGGG

GCCAAGGGACCACGGTCACCGTCTCCTCAGC
```

Ab669-4 H contig amino acid sequence
VH domain encoded by the nucleotide sequence above:
SEQ ID NO: 119
QVQLVQSGAEVKKPGASVKVSCKASGFTFTSHAIHWVRQAPGQRLEWMGWINAGNGYTK

YSQKFQDRVAITRDTSASTAYMELSSLRSEDTAVYYCTRDGFCSTTTCSDHYGMDVWGQG

TTVTVSS

Ab669-4 L contig nucleotide sequence
SEQ ID NO: 120
ATGGCCTGGGCTCTGCTGCTCCTCAACCTCCTCACTCAGGACACAGGGTCCTGGGCCC

AGTCTGCCCTGACTCAGCCTGCCTCCGTGTCTGGGTCTCCTGGACAGTCGATCACCAT

CTCCTGCACTGGAACCAGCAGTGATGTTGGCGGTTATAACTATGTCTCCTGGTACCAAC

AGCACCCAGGCAAAGCCCCCAAATTCATGATTTATGATGTCAGTAAGCGGCCCTCAGG

GGTTTCTAATCGCTTCTCTGGCTCCAAGTCTGGCAACACGGCCTCCCTGACAATCTCTG

GGCTCCAGGCTGAGGACGAGGCTGATTATTACTGCTGCTCATATGCAGGTAGTAGCAC

TTGGGTGTTCGGCGGAGGGACCAAGCTGACCGTCCTAGG

Ab669-4 L contig amino acid sequence
VL domain encoded by the nucleotide sequence above:
SEQ ID NO: 121
QSALTQPASVSGSPGQSITISCTGTSSDVGGYNYVSWYQQHPGKAPKFMIYDVSKRPSGV

SNRFSGSKSGNTASLTISGLQAEDEADYYCCSYAGSSTWVFGGGTKLTVL

Antibody 669-5
Ab669-5 H contig nucleotide sequence
SEQ ID NO: 124
ATGGACTGGACCTGGAGGATCCTCTTTTTGGTGGCAGCAGCCACAGGTGCCCACTCCC

AGGTCCAGCTTGTGCAGTCTGGGGCTGAGGTGAAGAAGCCTGGGGCCTCAGTGAAGG

TTTCCTGTAAGGCTTCTGGATACATCTTTATTAACTATGCTATGCAATGGGTGCGCCAG

GCCCCCGGACAAAGGCTTGAGTGGATGGGATGGATCAACGCTGGCAACGGTTACACA

AAATATTCACAGAAGTTCCAGGGCAGAGTCACCATCACCAGGGACATATCCGCGAGCA

CAGTCTACATGGAGCTGAGCAGCCTGAGATCTGAAGACACGGCTGTGTATTACTGTGC

GAGAGATGGATTTTGTAGGACAACCAGCTGCTCCGACCACTACGGTATGGACGTCTGG

GGCCAAGGGACCACGGTCACCGTCTCCTCAGC

Ab669-5 H contig amino acid sequence
VH domain encoded by the nucleotide sequence above:
SEQ ID NO: 125
QVQLVQSGAEVKKPGASVKVSCKASGYIFINYAMQWVRQAPGQRLEWMGWINAGNGYTK

YSQKFQGRVTITRDISASTVYMELSSLRSEDTAVYYCARDGFCRTTSCSDHYGMDVWGQG

TTVTVSS

Ab669-5 L contig nucleotide sequence
SEQ ID NO: 126
ATGGCCTGGGCTCTGCTGCTCCTCAACCTCCTCACTCAGGACACAGGGTCCTGGGCCC

AGTCTGCCCTGACTCAGCCTGCCTCCGTGTCTGGGTCTCCTGGACAGTCGATCACCAT

CTCCTGCACTGGAACCAGCAGTGATGTTGGTGGTTATAACTATGTCTCCTGGTACCAAC

-continued

```
AACACCCAGGCAAAGCCCCCAAACTCATGATTTATGATGTCAGTAAGCGGCCCTCAGG

GGTTTCTGATCGCTTCTCTGGCTCCAAGTCTGGCAACACGGCCTCCCTGACAATCTCTG

GGCTCCAGACTGAGGACGAGGCTGATTTTTACTGCTGCTCATATGCAGGTAGTAGCAC

TTGGGTGTTCGGCGGAGGGACCAAGCTGACCGTCCTAGG
```

Ab669-5 L contig amino acid sequence
VL domain encoded by the nucleotide sequence above:
                                                        SEQ ID NO: 127
QSALTQPASVSGSPGQSITISCTGTSSDVGGYNYVSWYQQHPGKAPKLMIYDVSKRPSGV

SDRFSGSKSGNTASLTISGLQTEDEADFYCCSYAGSSTWVFGGGTKLTVL

Antibody 669-6
Ab669-6 H contig nucleotide sequence
                                                        SEQ ID NO: 130
```
ATGGACTGGACCTGGAGGATCCTCTTTTTGGTGGCAGCAGCCACAGGTGTCCACTCCC

AGGTCCAGCTTGTGCAGTCTGGGGCTGAGGTGAAGAAGCCTGGGGCCTCAGTGAAGG

TTTCCTGCAAGGCTTCTGGATTCATCTTTATTAACTATGCTATGCAATGGGTGCGCCAG

GCCCCCGGACAAAGGCTTGAGTGGATGGGATGGATCAACGCTGGCAACGGTTACACA

AAATATTCACAGAAATTCCAGGGCAGAGTCACCATCACCAGGGACATATCCGCGAACAC

AGTCTACATGGAGCTGAGCAGCCTGAGATCTGAAGACACGGCTGTGTATTACTGTGCG

AGAGATGGATTTTGTAGTACAACCACCTGCTCCGACCACTACGGTATGGACGTCTGGG

GCCAAGGGACCACGGTCACCGTCTCCTCAGC
```

Ab669-6 H contig amino acid sequence
VH domain encoded by the nucleotide sequence above:
                                                        SEQ ID NO: 131
QVQLVQSGAEVKKPGASVKVSCKASGFIFINYAMQWVRQAPGQRLEWMGWINAGNGYTK

YSQKFQGRVTITRDISANTVYMELSSLRSEDTAVYYCARDGFCSTTTCSDHYGMDVWGQG

TTVTVSS

Ab669-6 L contig nucleotide sequence
                                                        SEQ ID NO: 132
```
ATGGCCTGGGCTCTGCTGCTCCTCAACCTCCTCACTCAGGACACAGGGTCCTGGGCCC

AGTCTGCCCTGACTCAGCCTGCCTCCGTGTCTGGGTCTCCTGGACAGTCGATCACCAT

CTCCTGCACTGGAACCAGCAGTGATGTTGGTGGTTATAACTATGTCTCCTGGTACCAAC

AACACCCAGGCAAAGCCCCCAAACTCATGATTTATGATGTCAGTAAGCGGCCCTCAGG

GGTTTCTGATCGCTTCTCTGGCTCCAAGTCTGGCAACACGGCCTCCCTGACAATCTCTG

GGCTCCAGACTGAGGACGAGGCTGATTATTACTGCTGCTCATATGCAGGTAGTAGCAC

TTGGGTGTTCGGCGGAGGGACCAAGCTGACCGTCCTAGG
```

Ab669-6 L contig amino acid sequence
VL domain encoded by the nucleotide sequence above:
                                                        SEQ ID NO: 133
QSALTQPASVSGSPGQSITISCTGTSSDVGGYNYVSWYQQHPGKAPKLMIYDVSKRPSGV

SDRFSGSKSGNTASLTISGLQTEDEADYYCCSYAGSSTWVFGGGTKLTVL

Antibody CDR Sequence Tables

| Ab666, Ab666-1, Ab666-2 | Atreca | Kabat | Chothia |
|---|---|---|---|
| HCDR1 | GYTFTNYAMH SEQ ID NO: 3 | NYAMH SEQ ID NO: 54 | GYTFTNY SEQ ID NO: 55 |
| HCDR2 | WINAGNGNTKYSQNFQG SEQ ID NO: 4 | NAGNGN SEQ ID NO: 56 | |
| HCDR3 | DEYYASGSYYDYYYYGMDV SEQ ID NO: 5 | SEQ ID NO: 5 | SEQ ID NO: 5 |
| LCDR1 | TGTSSDVGVYNYVS SEQ ID NO: 8 | SEQ ID NO: 8 | SEQ ID NO: 8 |

| Ab666, Ab666-1, Ab666-2 | Atreca | Kabat | Chothia |
|---|---|---|---|
| LCDR2 | NVSKRPS SEQ ID NO: 9 | SEQ ID NO: 9 | SEQ ID NO: 9 |
| LCDR3 | CSYAGSSTWV SEQ ID NO: 10 | SEQ ID NO: 10 | SEQ ID NO: 10 |

| Ab666-3 | Atreca | Kabat | Chothia |
|---|---|---|---|
| HCDR1 | GYTFTSYAMH SEQ ID NO: 60 | SYAMH SEQ ID NO: 59 | GYTFTSY SEQ ID NO: 58 |
| HCDR2 | WINAGNGNTKYSQKF QG SEQ ID NO: 61 | SEQ ID NO: 61 | NAGNGN SEQ ID NO: 56 |
| HCDR3 | DNYYDSGSYYDYYYY GMDV SEQ ID NO: 62 | SEQ ID NO: 62 | SEQ ID NO: 62 |
| LCDR1 | TGTSSDVGSYNHVS SEQ ID NO: 63 | SEQ ID NO: 63 | SEQ ID NO: 63 |
| LCDR2 | DVSKRPS SEQ ID NO: 39 | SEQ ID NO: 39 | SEQ ID NO: 39 |
| LCDR3 | CSYAGSSTWV SEQ ID NO: 10 | SEQ ID NO: 10 | SEQ ID NO: 10 |

| Ab666-4 | Atreca | Kabat | Chothia |
|---|---|---|---|
| HCDR1 | GYTFTNYAMH SEQ ID NO: 3 | NYAMH SEQ ID NO: 54 | GYTFTNY SEQ ID NO: 55 |
| HCDR2 | WINAGNGYTKYSQK FQG SEQ ID NO: 68 | SEQ ID NO: 68 | NAGNGY SEQ ID NO: 138 |
| HCDR3 | DNYYDSGSYYEYCY YGMDV SEQ ID NO: 69 | SEQ ID NO: 69 | SEQ ID NO: 69 |
| LCDR1 | TGTSSDVGSYNHVS SEQ ID NO: 63 | SEQ ID NO: 63 | SEQ ID NO: 63 |
| LCDR2 | DVSKRPS SEQ ID NO: 39 | SEQ ID NO: 39 | SEQ ID NO: 39 |
| LCDR3 | CSYVGSSTWV SEQ ID NO: 70 | SEQ ID NO: 70 | SEQ ID NO: 70 |

| Ab667 | Atreca | Kabat | Chothia |
|---|---|---|---|
| HCDR1 | GYTFTNYAMH SEQ ID NO: 13 | NYAMH SEQ ID NO: 54 | GYTFTNY SEQ ID NO: 55 |
| HCDR2 | WINAGNGYTKYSQKFQD SEQ ID NO: 14 | SEQ ID NO: 14 | NAGNGY SEQ ID NO: 138 |
| HCDR3 | DSFYDILSGPVYHYGM DV SEQ ID NO: 15 | SEQ ID NO: 15 | SEQ ID NO: 15 |
| LCDR1 | TGTSNDVGIYNHVS SEQ ID NO: 18 | SEQ ID NO: 18 | SEQ ID NO: 18 |

| Ab667 | Atreca | Kabat | Chothia |
|---|---|---|---|
| LCDR2 | DVNKRPS SEQ ID NO: 19 | SEQ ID NO: 19 | SEQ ID NO: 19 |
| LCDR3 | CSYAGSSAWV SEQ ID NO: 20 | SEQ ID NO: 20 | SEQ ID NO: 20 |

| Ab667-1 | Atreca | Kabat | Chothia |
|---|---|---|---|
| HCDR1 | GYTFSNYAMH SEQ ID NO: 75 | NYAMH SEQ ID NO: 54 | GYTFSNY SEQ ID NO: 139 |
| HCDR2 | WINAGNGYTKYSQK FQD SEQ ID NO: 14 | SEQ ID NO: 14 | NAGNGY SEQ ID NO: 138 |
| HCDR3 | DSFYDILTGPVYHY YGMDV SEQ ID NO: 76 | SEQ ID NO: 76 | SEQ ID NO: 76 |
| LCDR1 | TGTSNDVGVYNHVS SEQ ID NO: 77 | SEQ ID NO: 77 | SEQ ID NO: 77 |
| LCDR2 | DVSKRPS SEQ ID NO: 39 | SEQ ID NO: 39 | SEQ ID NO: 39 |
| LCDR3 | CSYVGNSAWV SEQ ID NO: 78 | SEQ ID NO: 78 | SEQ ID NO: 78 |

| Ab667-2 | Atreca | Kabat | Chothia |
|---|---|---|---|
| HCDR1 | GYTFTNYAMH SEQ ID NO: 13 | NYAMH SEQ ID NO: 54 | GYTFTNY SEQ ID NO: 55 |
| HCDR2 | WINAGNGYTKYSQK FQD SEQ ID NO: 14 | SEQ ID NO: 14 | NAGNGY SEQ ID NO: 138 |
| HCDR3 | DSFYDILTGPVYHY YGMDV SEQ ID NO: 76 | SEQ ID NO: 76 | SEQ ID NO: 76 |
| LCDR1 | TGTSNDVGVYNHVS SEQ ID NO: 77 | SEQ ID NO: 77 | SEQ ID NO: 77 |
| LCDR2 | DVSKRPS SEQ ID NO: 39 | SEQ ID NO: 39 | SEQ ID NO: 39 |
| LCDR3 | CSYVGSSAWV SEQ ID NO: 83 | SEQ ID NO: 83 | SEQ ID NO: 83 |

| Ab667-3 | Atreca | Kabat | Chothia |
|---|---|---|---|
| HCDR1 | GYTFTNYAMH SEQ ID NO: 13 | NYAMH SEQ ID NO: 54 | GYTFTNY SEQ ID NO: 55 |
| HCDR2 | WINAGNGYTKYSQK FQD SEQ ID NO: 14 | SEQ ID NO: 14 | NAGNGY SEQ ID NO: 138 |
| HCDR3 | DSFYDILTGPVYHY YGMDV SEQ ID NO: 76 | SEQ ID NO: 76 | SEQ ID NO: 76 |
| LCDR1 | TGTSNDVGVYNHVS SEQ ID NO: 77 | SEQ ID NO: 77 | SEQ ID NO: 77 |
| LCDR2 | DVSKRPS SEQ ID NO: 39 | SEQ ID NO: 39 | SEQ ID NO: 39 |

| Ab667-3 | Atreca | Kabat | Chothia |
|---|---|---|---|
| LCDR3 | CSYAGSSTWV SEQ ID NO: 10 | SEQ ID NO: 10 | SEQ ID NO: 10 |

| Ab668 | Atreca | Kabat | Chothia |
|---|---|---|---|
| HCDR1 | GFTFTDYAMH SEQ ID NO: 23 | DYAMH SEQ ID NO: 57 | GFTFTDY SEQ ID NO: 140 |
| HCDR2 | WINAGNGYTKYSQKFQD SEQ ID NO: 24 | SEQ ID NO: 24 | NAGNGY SEQ ID NO: 138 |
| HCDR3 | DGFCPSNTCSGYYGMDV SEQ ID NO: 25 | SEQ ID NO: 25 | SEQ ID NO: 25 |
| LCDR1 | TGTSSDVGSYNYVS SEQ ID NO: 28 | SEQ ID NO: 28 | SEQ ID NO: 28 |
| LCDR2 | DVNTRPS SEQ ID NO: 29 | SEQ ID NO: 29 | SEQ ID NO: 29 |
| LCDR3 | SSYAGSSTWV SEQ ID NO: 30 | SEQ ID NO: 30 | SEQ ID NO: 30 |

| Ab668-1 | Atreca | Kabat | Chothia |
|---|---|---|---|
| HCDR1 | GFTFTDYAMH SEQ ID NO: 23 | DYAMH SEQ ID NO: 57 | GFTFTDY SEQ ID NO: 140 |
| HCDR2 | WINAGNGYTKYSQKFQD SEQ ID NO: 24 | SEQ ID NO: 24 | NAGNGY SEQ ID NO: 138 |
| HCDR3 | DGFCPSNTCSGYYGMDV SEQ ID NO: 25 | SEQ ID NO: 25 | SEQ ID NO: 25 |
| LCDR1 | TGTSSDVGAYKYVS SEQ ID NO: 92 | SEQ ID NO: 92 | SEQ ID NO: 92 |
| LCDR2 | DVNTRPS SEQ ID NO: 29 | SEQ ID NO: 29 | SEQ ID NO: 29 |
| LCDR3 | SSYAGSSTWV SEQ ID NO: 30 | SEQ ID NO: 30 | SEQ ID NO: 30 |

| Ab669 | Atreca | Kabat | Chothia |
|---|---|---|---|
| HCDR1 | GFTFTSYAMH SEQ ID NO: 33 | SYAMH SEQ ID NO: 59 | GFTFTSY SEQ ID NO: 141 |
| HCDR2 | WINAGNGHTKYSQKFQD SEQ ID NO: 34 | SEQ ID NO: 34 | NAGNGH SEQ ID NO: 142 |
| HCDR3 | DGFCSTTCSDHYGMDV SEQ ID NO: 35 | SEQ ID NO: 35 | SEQ ID NO: 35 |
| LCDR1 | TGTSSDVGSYNYVS SEQ ID NO: 38 | SEQ ID NO: 38 | SEQ ID NO: 38 |

| Ab669 | Atreca | Kabat | Chothia |
|---|---|---|---|
| LCDR2 | DVSKRPS SEQ ID NO: 39 | SEQ ID NO: 39 | SEQ ID NO: 39 |
| LCDR3 | CSYAGSSTWV SEQ ID NO: 40 | SEQ ID NO: 40 | SEQ ID NO: 40 |

| Ab669-1 | Atreca | Kabat | Chothia |
|---|---|---|---|
| HCDR1 | GFTFISYAMH SEQ ID NO: 97 | SYAMH SEQ ID NO: 59 | GFTFISY SEQ ID NO: 143 |
| HCDR2 | WINAGDGHTKYSQK FQD SEQ ID NO: 98 | SEQ ID NO: 98 | NAGDGH SEQ ID NO: 144 |
| HCDR3 | DGFCTTTTCSDHYG MDV SEQ ID NO: 99 | SEQ ID NO: 99 | SEQ ID NO: 99 |
| LCDR1 | TGTSSDVGSYNYVS SEQ ID NO: 38 | SEQ ID NO: 38 | SEQ ID NO: 38 |
| LCDR2 | DVSKRPS SEQ ID NO: 39 | SEQ ID NO: 39 | SEQ ID NO: 39 |
| LCDR3 | CSYAGSSTWV SEQ ID NO: 40 | SEQ ID NO: 40 | SEQ ID NO: 40 |

| Ab669-2 | Atreca | Kabat | Chothia |
|---|---|---|---|
| HCDR1 | GFTFTSYAIQ SEQ ID NO: 104 | SYAIQ SEQ ID NO: 145 | GFTFTSY SEQ ID NO: 141 |
| HCDR2 | WINAGDGHTKYSQK FQD SEQ ID NO: 98 | SEQ ID NO: 98 | NAGDGH SEQ ID NO: 144 |
| HCDR3 | DGFCTTTTCSDHYG MDV SEQ ID NO: 99 | SEQ ID NO: 99 | SEQ ID NO: 99 |
| LCDR1 | TGTSSDVGSYNYVS SEQ ID NO: 38 | SEQ ID NO: 38 | SEQ ID NO: 38 |
| LCDR2 | DVSKRPS SEQ ID NO: 39 | SEQ ID NO: 39 | SEQ ID NO: 39 |
| LCDR3 | CSYAGGSTWV SEQ ID NO: 105 | SEQ ID NO: 105 | SEQ ID NO: 105 |

| Ab669-3 | Atreca | Kabat | Chothia |
|---|---|---|---|
| HCDR1 | GFTFTNYAMH SEQ ID NO: 110 | NYAMH SEQ ID NO: 54 | GFTFTNY SEQ ID NO: 146 |
| HCDR2 | WINAGNGHTKYSQK FQD SEQ ID NO: 34 | SEQ ID NO: 34 | NAGNGH SEQ ID NO: 142 |
| HCDR3 | DGFCSTTCSDHYG MDV SEQ ID NO: 111 | SEQ ID NO: 111 | SEQ ID NO: 111 |
| LCDR1 | TGTSSDVGGYNYVS SEQ ID NO: 112 | SEQ ID NO: 112 | SEQ ID NO: 112 |

-continued

| Ab669-3 | Atreca | Kabat | Chothia |
|---|---|---|---|
| LCDR2 | DVSKRPS SEQ ID NO: 39 | SEQ ID NO: 39 | SEQ ID NO: 39 |
| LCDR3 | CSYAGSSTWV SEQ ID NO: 40 | SEQ ID NO: 40 | SEQ ID NO: 40 |

| Ab669-4 | Atreca | Kabat | Chothia |
|---|---|---|---|
| HCDR1 | GFTFTSHAIH SEQ ID NO: 117 | SHAIH SEQ ID NO: 147 | GFTFTSH SEQ ID NO: 148 |
| HCDR2 | WINAGNGYTKYSQKFQD SEQ ID NO: 14 | SEQ ID NO: 14 | NAGNGY SEQ ID NO: 138 |
| HCDR3 | DGFCSTTTCSDHYGMDV SEQ ID NO: 111 | SEQ ID NO: 111 | SEQ ID NO: 111 |
| LCDR1 | TGTSSDVGGYNYVS SEQ ID NO: 112 | SEQ ID NO: 112 | SEQ ID NO: 112 |
| LCDR2 | DVSKRPS SEQ ID NO: 39 | SEQ ID NO: 39 | SEQ ID NO: 39 |
| LCDR3 | CSYAGSSTWV SEQ ID NO: 40 | SEQ ID NO: 40 | SEQ ID NO: 40 |

| Ab669-5 | Atreca | Kabat | Chothia |
|---|---|---|---|
| HCDR1 | GYIFINYAMQ SEQ ID NO: 122 | NYAMQ SEQ ID NO: 149 | GYIFINY SEQ ID NO: 150 |
| HCDR2 | WINAGNGYTKYSQKFQG SEQ ID NO: 68 | SEQ ID NO: 68 | NAGNGY SEQ ID NO: 138 |
| HCDR3 | DGFCRTTSCSDHYGMDV SEQ ID NO: 123 | SEQ ID NO: 123 | SEQ ID NO: 123 |
| LCDR1 | TGTSSDVGGYNYVS SEQ ID NO: 112 | SEQ ID NO: 112 | SEQ ID NO: 112 |
| LCDR2 | DVSKRPS SEQ ID NO: 39 | SEQ ID NO: 39 | SEQ ID NO: 39 |
| LCDR3 | CSYAGSSTWV SEQ ID NO: 40 | SEQ ID NO: 40 | SEQ ID NO: 40 |

| Ab669-6 | Atreca | Kabat | Chothia |
|---|---|---|---|
| HCDR1 | GFIFINYAMQ SEQ ID NO: 128 | NYAMQ SEQ ID NO: 149 | GFIFINY SEQ ID NO: 151 |
| HCDR2 | WINAGNGYTKYSQKFQG SEQ ID NO: 68 | SEQ ID NO: 68 | NAGNGY SEQ ID NO: 138 |
| HCDR3 | DGFCSTTTCSDHYGMDV SEQ ID NO: 129 | SEQ ID NO: 129 | SEQ ID NO: 129 |
| LCDR1 | TGTSSDVGGYNYVS SEQ ID NO: 112 | SEQ ID NO: 112 | SEQ ID NO: 112 |
| LCDR2 | DVSKRPS SEQ ID NO: 39 | SEQ ID NO: 39 | SEQ ID NO: 39 |
| LCDR3 | CSYAGSSTWV SEQ ID NO: 40 | SEQ ID NO: 40 | SEQ ID NO: 40 |

TABLE 16

Variable region sequences of further antibodies. CDRs are as identified by IMGT.

| Ab name | VH nucleotide | VH amino acid | HCDR1 | HCDR2 | HCDR3 |
|---|---|---|---|---|---|
| CL-141810 | ATGGAGTTTGGGCTGAGCTGGCTTTTTCTTGTGGCTAT TTTAAAGGTTCCAGTGTGAGGTGCAGCTGGTGGAGT CTGGGGGAGGCTTGGTCACAGCCTGGGGGGTCCCTGAGA CTCTCCTGTGCAGCCTCTGATTCACCTTTAGCAGCTA CTCCATGAGCTGGGTCCGCCAGGCTCCAGGGAAGGGC TGGAGTGGGTCTCAGTGATTAGTGGTGGTAGC ACATACTACGCAGACTCCGAGAAGGGCCGGTTCACCAT CTCCAGAGACAATTCCAAGAACACGCTGTATCTGCAAA TGAACAGCCTGAGAGGCGAGGACACGGCCGTATATTAT TGTGCGAAAGCCTATTACTATGGTTCGGGGATGGACGT CTGGGGCCAAGGGACCACGGTCACCGTCTCCTCAGC SEQ ID NO: 176 | MEFGLSWLFLVAILK GVQCEVQLVESGGGL VQPGGSLRLSCAASG FTFSSYAMSWVRQAP GKGLEWVSGISGSGG STYYADSEKGRFTIS RDNSKNTLYLQMNSL RGEDTAVYYCAKAYY YGSGMDVWGQGTTVT VSS SEQ ID NO: 177 | GFTFSSYAMS SEQ ID NO: 178 | GISGSGGSTYYADSEKG SEQ ID NO: 179 | AYYYGSGMDV SEQ ID NO: 180 |
| CL-141805 | ATGGACTGGACCTGGAGGATCCTCTTTTTGGTGGCAGC AGCCACAGGTGCCCACTCCCAGGTCCAGCTTGTGCAGT CTGGGGCTGAGGTGAAGAAGCCTGGGGCTCAGTGAAG GTTCCTGCAAGGCTTCTGGATACACCTTCACAAACTA TGCTATGCATTGGGTGCGCCAGGCCCCCGGACAAAGGC TTGGAGTGGATGGGATGGATCAACGCTGGCAATGGTAAT ACAAAATATTCACAAAATTTCCAGGCAGAGTCACCAT TACCAGGGACACATCCGCAGCAGCCTACATGGAGC TGCGCAGCCTGAGATCTGAAGACACGGCTGTATTAC TGTGCGAGAGATGAATACTATGCTTCGGGAGTTATTA CGACTACTACTACGGTATGGACGTCTGGGGCCAAG GGACCACGGTCACCGTCTCCTCAGC SEQ ID NO: 181 | MDWTWRILFLVAAAT GAHSQVQLVQSGAEV KKPGASVKVSCKASG YTFTNYAMHWVRQAP GQRLEWMGWINAGNG NTKYSQNFQGRVTIT RDTSASTAYMELSSL RSEDTAVYYCARDEY YASGSYYDYYYGMD VWGQGTTVTVTS SEQ ID NO: 182 | GYTFTNYAMH SEQ ID NO: 3 | WINAGNGNTKYSQNFQG SEQ ID NO: 403 | DEYYASGSYYDYYYGMDV SEQ ID NO: 404 |
| CL-141806 | ATGGACTGGACCTGGAGGATCCTCTTTTTGGTGGCAGC AGCCACAGGTGCCCACTCCCAGGTCCAGCTTGTGCAGT CTGGGGCTGAGGTGAAGAAGCCTGGGGCCTCAGTGAAG GTTCCTGCAAGGCTTCTGGATACACCTTCACTAACTA TGCTATACATTGGGTGCGCCAGGCCCCCGGACAAAGGC TTGAGTGGATGGGATGGATCAACGCTGGCAATGGTAAC ACAAAATATTCACAGAAGTTTCAGGGCAGAGTCACCAT TACCAGGACACATCCGCGGACACAGCCTACATGGAGC TGAGCAGCCTGAGATCTGAAGACACGGCTGTATTAC TGTGCGAGAGATAATTTCTACCATATGACGTCTGTATTAT TGTGCGAGAGATAATTTCTACCATATGACGTCTGGGGCCAAG GGACCACGGTCACCGTCTCCTCAGC SEQ ID NO: 183 | MDWTWRILFLVAAAT GAHSQVQLVQSGAEV KKPGASVKVSCKASG YTFTNYAIHWVRQAP GQRLEWMGWINAGNG NTKYSQKFQGRVTIT RDTSASTAYMELSSL RSEDTAVYYCARDNF YGSGTYFSYFYHMD VWGQGTTVTVSS SEQ ID NO: 184 | GYTFTNYAIH SEQ ID NO: 156 | WINAGNGNTKYSQKFQG SEQ ID NO: 419 | DNFYGSGTYFSYFYHMDV SEQ ID NO: 155 |
| CL-141795 | ATGGACTGGACCTGGAGGATCCTCTTTTTGGTGGCAGC AGCCACAGGTGCCCCACTCCCAGGTCCAGCTTGTGCAGT CTGGGGCTGAGGTGAAGAAGCCTGGGGCCTCAGTGAAG GTTTCGTGCAAGGCTTCTGGATACACCCCCCCACTAGCTA TGCTATGCATTGGGTGCGCCAGGCCCCCCGGACAAAGGC TTGAGTGGATGGGATGGATCAACGCTGGCAATGGTAAC | MDWTWRILFLVAAAT GAHSQVQLVQSGAEV KKPGASVKVSCKASG YTFTSYAMHWVRQAP GQRLEWMGWINAGNG NTKYSQKFQGRVTIT | GYTFTSYAMH SEQ ID NO: 60 | WINAGNGNTKYSQKFQG SEQ ID NO: 419 | GGSRDY SEQ ID NO: 187 |

TABLE 16-continued

Variable region sequences of further antibodies. CDRs are as identified by IMGT.

| Ab name | VH nucleotide | VH amino acid | HCDR1 | HCDR2 | HCDR3 |
|---|---|---|---|---|---|
| | ACAAAATATTCACAGAAGTTCCAGGCAGAGTCACCAT<br>TACCAGGGACACATCCGCGAGCAGCCTACATGAGC<br>TGAGCAGCCTGAGATCTGAAGACACGGCTGTATTAC<br>TGTGCCAGAGGGGGATCGAGGGACTACTGGGGCCAGGG<br>AACCCTGGTCACCGTCTCCTCAGC<br>SEQ ID NO: 185 | RDTSASTAYMELSSL<br>RSEDTAVYYCARGGS<br>RDYWGQGTLVTVSS<br>SEQ ID NO: 186 | | | |
| CL-141798 | ATGGAGTTTGGGCTGAGCTGGGTTTTCCTTGTTGCTAT<br>TTTAAAGGTGTCCAGTGTGAGGTGCAGCTGGTGGAGT<br>CTGGGGGAGGTGTGTACGGCCTGGGGGTCCCTGAGA<br>CTCTCCTGTGCAGCCTCCGGATTCACCTTTGATGATTA<br>TGGCATGAGCTGGGTCTCCGCCAAGTCCAGGGAAGGGC<br>TGGAGTGGGTCTCTGGTATTAATTGGAATGGTGTAAC<br>ACAGGTTATGCAGACTCTGTGAAGGGCCGATTCACCAT<br>CTCCAGAGACAACGCCAAGAACTCCCTGTATTTGCAAA<br>TGAATAGTCTGAGAGCCGAGGACACGGCCTGTATTAC<br>TGTGCGAGAGGGTTACGATATTTTGACTGGTTAGTCGG<br>TATGGACGTCTGGGGCCAAGGGACACCGGTCACCGTCT<br>CCTCAGC<br>SEQ ID NO: 188 | MEFGLSWVFLVAILK<br>GVQCEVQLVESGGGV<br>VRPGGSLRLSCAASG<br>FTFDDYGMSWVRQGP<br>GKGLEWVSGINWNGG<br>NTGYADSVKGRFTIS<br>RDNAKNSLYLQMNSL<br>RAEDTALYYCARGLR<br>YFDWLVGMDVWGQGT<br>TVTVSS<br>SEQ ID NO: 189 | GFTFDDYGMS<br>SEQ ID NO: 190 | GINWNGGNTGYADSVKG<br>SEQ ID NO: 191 | GLRYFDWLVGMDV<br>SEQ ID NO: 192 |
| CL-141763 | ATGGAGTTGGGGCTGAGCTGGGTTTTCCTTGTTGCTAT<br>ATTAGAAGGTGTCCAGTGTGAGGTGCAGCTGGTGGAGT<br>CTGGGGGAGGCTTGGTACAGCCTGGGGGGTCCCTGAGA<br>CTCTCCTGTGCAGCCTCTGGATTCCCCTTCAGTAACTA<br>CGACATGCACTGGGTCCGCCAAGTTACAGGAAAAGGTC<br>TGGAGTGGGTCTCAGCTATTGGTACTGCTGGTGACCA<br>TACTATCCAGACTCCGTGAAGGGCCGATTCACCATCTC<br>CAGAGACAATGCCAAGAACTCCTTGTTTTCTTCAAATGA<br>ACAGCCTGAGAGCCGGGACACGGCTGTATTACTGT<br>GCAAGAGGGGGGACTTCGGGGACTTATTCCTACTACTA<br>CTACTACGGTATGGACGTCTGGGGCCAAGGGACCACGG<br>TCACCGTCTCCTCAGC<br>SEQ ID NO: 193 | MELGLSWVFLVAILE<br>GVQCEVQLVESGGGL<br>VQPGGSLRLSCAASG<br>FPFSNYDMHWVRQVT<br>GKGLEWSAIGTAGD<br>TYYPDSVKGRFTISR<br>DNAKNSLFLQMNSLR<br>AGDTAVYYCARGGGS<br>GTYSYYYYGMDVWG<br>QGTTVTVSS<br>SEQ ID NO: 194 | GFPFSNYDMH<br>SEQ ID NO: 195 | AIGTAGDTYYPDSVKG<br>SEQ ID NO: 196 | GGGSGTYSYYYYGMDV<br>SEQ ID NO: 197 |
| CL-141764 | ATGTCTGTCTTCCTTCATCTTCTGCCCGTGCTGGG<br>CCTCCATGGGGTGTCCTGTCACAGGTACAGCTGCAGC<br>AGTCAGGTCCAGGACTGGTGAAGCCCTCGCAGACCCTC<br>ACTCACCTGTGCCATCTGCGGGGACAGTGTCTTAG<br>CAACAGTGCTGCTTGGAACTGGATCAGGCAGTCCCCAT<br>CGAGAGGCCTTGAGTATGGCTGGGAAGGACATATCTACAGG<br>TCCAAGTGGTATAATGATTATTCAGTATCTGTGAAAAG<br>TCGAATAACCATCAACCCAGACACATCCCAAGAACCAGT<br>TCTCCTGCAACTGACCTCTGACTCCCGAGGACACG<br>GCTGTGTATTACTGTGCAAGAAAGTGGGAGCTACTTGA<br>TGCTTTTGATGTCTGGGGCCAAGGGACAATGGTCACCG<br>TCTCTTCAGC<br>SEQ ID NO: 198 | MSVSFLIFLPVLGLP<br>WGVLSQVQLQQSPG<br>LVKPSQTLSLTCAIS<br>GDSVSSNSAAWNWIR<br>QSPSRGLEWLGRTYY<br>RSKWYNDYSVSVKSR<br>ITINPDTSKNQFSLQ<br>LNSVTPEDTAVYYCA<br>RKWELLDAFDVWGQG<br>TMVTVSS<br>SEQ ID NO: 199 | GDSVSSNSAAWN<br>SEQ ID NO: 200 | RTYYRSKWYNDYSVSVKS<br>SEQ ID NO: 201 | KWELLDAFDV<br>SEQ ID NO: 202 |

TABLE 16-continued

Variable region sequences of further antibodies. CDRs are as identified by IMGT.

| Ab name | VH nucleotide | VH amino acid | HCDR1 | HCDR2 | HCDR3 |
|---|---|---|---|---|---|
| CL-141765 | ATGGAGTTGGGGCTGAGCTGGGTTTTCCTTGTTGCTAT ATTAGAAGGTGTCCAGTGTGAGGTGCAGCTGGTGGAGT CTGGGGGAGGCTTGGTACAGCCGGGGGGTCCCTGAGA CTCTCCTGTGCATCCTCTGGATTCCCCTTCAGTAACTA CGACATGCACTGGGTCCGCCAAGTTACAGGAAAAGGTC TGGAGTGGGTCTCAGCTATTGGTACTGCTGGTGACCA TACTATCCAGATCCGTGAAGGGCCGATTCACCATCTC CAGAGACAATGCCAAGAACTCCTTGTTTCTTCAAATGA ACAGCCTGAGAGCCGGGACACGGCTGTGTATTACTGT GCAAGAGGGGGGTTCGGGGACTTATTCCTACTACTA CTACTACGGTATGGACGTCTGGGGCCAAGGGACCACGG TCACCGTCTCCTCAGC SEQ ID NO: 203 | MELGLSWMVFLVAILE GVQCEVQLVESGGGL VQPGGSLRLSCASSG FPFSNYDMHWVRQVT GKGLEWVSAIGTAGD TYYPDSVKGRFTISR DNAKNSLFLQMNSLR AGDTAVYYCARGGGS GTYSYYYYGMDVWG QGTTVTVSS SEQ ID NO: 204 | GFPFSNYDMH SEQ ID NO: 195 | AIGTAGDTYYPDSVKG SEQ ID NO: 196 | GGGSGTYSYYYYGMDV SEQ ID NO: 197 |
| CL-141766 | ATGGACTGGACCTGGAGGATCCTCTTTTTGGTGGCAGC AGCCACAGGTGCCCACTCCCAGGTCCAGCTTGTGCAGT CTGGGGCTGAGGTGAAGAAGCCTGGGGCTCAGTGAAG GTTCCTGCAAGGCTTCTGGATACACCTTCACTAGTTA TGCTATGCATTGGGTGCGCCAGGCCCCCGGACAAAGGC TTGAGTGGATGGGATGGATCAACGCTGGCAATGGTAAC ACAAAATATTCACAGAAGTTCCAGGGCAGAGTCACCAT TACCAGGGACACATCCGCGAGCACGCTACATGGAGC TGCAGCCTGAGTCTGAAGACACGGCTGTGTATTACTGT GTGCGAGAGACAATTACTACGGTATGATGACGTCTGG GGCCAAG GGACCACGGTCACCGTCTCCTCAGC SEQ ID NO: 205 | MDWTWRILFLVAAAT GAHSQVQLVQSGAEV KKPGASVKVSCKASG YTFTSYAMHWVRQAP GQRLEWMGWINAGNG NTKYSQKFQGGVTIT RDTSASTAYMELSSL RSEDTAVYYCARDNY YDSGSYDYYYGMD VWGQGTTVTVSS SEQ ID NO: 206 | GYTFTSYAMH SEQ ID NO: 60 | WINAGNGNTKYSQKFQG SEQ ID NO: 419 | DNYYDSGSYYDYYYGMDV SEQ ID NO: 62 |
| CL-141768 | ATGGAGTTTGGGCTGAGCTGGCTTTTTTCTTGTGGCTAT TTTAAAAGGTGTCCAGTGTGAGGTGCAGCTGGTGGAGT CTGGGGAAGGCTTGGTACAGCCTGGGGGGTCCCTGAGA CTCTCCTGTGCAGCCTCTGGATTCACCTTTAGTAGCTA TGCCATGAGCTGGGTCCGCCAGGCTCCAGGGAAGGGGC TGGAGTGGGTCTCAGCTATTAGTGGTAGTGGTGGTAGC ACATACTACGCAGACTCCGTGAAGGGCCGGTTCACCAT CTCCAGAGACAATTCCAAGAACACGCTGTATCTGCAAA TGAACAGCCTGAGAGAGGGAGTGGAGCTACACGGAGACTG TGTGCGAAAGAGGGCCCCTGGGGCCAGGGAACCCTGGTCACCGTCT CCTCAGC SEQ ID NO: 207 | MEFGLSWLFLVAILK GVQCEVQLVESGGGL VQPGGSLRLSCAASG FTFSSYAMSWVRQAP GKGLEWVSAISGSGG STYYADSVKGRFTIS RDNSKNTLYLQMNSL RAEDTAVYYCAKEGS GSYYGDWFDPWGQGT LVTVSS SEQ ID NO: 208 | GFTFSSYAMS SEQ ID NO: 178 | AISGSGGSTYYADSVKG SEQ ID NO: 209 | EGSGSYYGDWFDP SEQ ID NO: 210 |
| CL-141799 | ATGGACTGGACCTGGAGGATCCTCTTTTTGGTGGCAGC AGCCACAGGTGCCCACTCCCAGGTCCAGCTTGTGCAGT CTGGGGCTGAGGTGAAGAAGCCTGGGGCCTCAGTGAAG GTTTCCTGCAAGGCTTCTGGATTCACCTTCACTGACTA CGCTATGCATTGGGTGCGACAGGCCCCCGGACAAGGC TTGAGTGGATGGGTTGGATCAACGCTGGCAATGGTTAC ACAAAATATTCACAGAAGTTCCAGGACAGACTCACCAT | MDWTWRILFLVAAAA GAHSQVQLVQSGAEV KKPGASVKVSCKASG FTFTDYAMHWVRQAP GQRLEWMGWINAGNG YTKYSQKFQDRLTIT RDTFASTVYMELSSL | GFTFTDYAMH SEQ ID NO: 23 | WINAGNGYTKYSQKFQD SEQ ID NO: 24 | DGFCPSNTCSGYYGMDV SEQ ID NO: 25 |

TABLE 16-continued

Variable region sequences of further antibodies. CDRs are as identified by IMGT.

| Ab name | VH nucleotide | VH amino acid | HCDR1 | HCDR2 | HCDR3 |
|---|---|---|---|---|---|
| | TACCAGGGACACATTCGCGAGCACAGTCTACATGAGC TGAGCAGCCTGAGATCTGAAGACACGACTGTATTAC TGTGCGAGAGATGGGTTTTGTCCTAGTAACACTTGTTC TGGTTACTACGGTATGGACGTCTGGGGCCAAGGGACCA CGGTCACCGTCTCCTCAGC SEQ ID NO: 211 | RSEDTVYYCARDGF CPSNTCSGYYGMDVW GQGTTVTVSS SEQ ID NO: 212 | | | |
| CL-141800 | ATGGACTGGACCTGGAGGATCCTCTTCTTGGTGGCAGC AGCCACAGTGACCTGAGATCTCCAGGTCCAGCTTGTGCAGT CTGGGGCTGAGGTGAAGAAGCCTGGGGCTCAGTGAAG GTTTCCTGCAAGGCTGTGACATACCTTCACAAACTA TACTATACATTGGGTGCGCCAGGCTCCCGGACAAAGGC TTGAGTGGATGGGATGGATCAACGGTGGCAATGGTAAC ACAAAATATTCACAGAAGTTCCAGGGCAGAGTCACTAT TAACAGGGACACATCCGCGACACCTACATGGAGC TGAGCAGCCTGAGATCTGAAGACACGGTTGTATTAC TGTGCGAGAGATCAGTATTACTATGATAGTAGTGGTTA TTTTGACTACTGGGGCCAGGGAACCCTGGTCACCGTCT CCTCAGC SEQ ID NO: 213 | MDWTWRILFLVAAAT GDHSQVQLVQSGAEV KKPGASVKVSCKASG YTFTNYTIHWVRQVP GQRLEWMGWINGGNG NTKYSQKFQGRVTIN RDTSANTAYMELSSL RSEDTVYYCARDQY YYDSSGYFDYWGQGT LVTVSS SEQ ID NO: 214 | GYTFTNYTIH SEQ ID NO: 215 | WINGGNGNTKYSQKFQG SEQ ID NO: 216 | DQYYYDSSGYFDY SEQ ID NO: 217 |
| CL-141802 | ATGGACTGGACCTGGAGGATCCTCTTTTTGGTGGCAGC AGCCCCAGTGACCCCACCTCCAGCTTGTGCAGT CTGGGGCTGAGGTGAAGAAGCCTGGGGCTCAGTGAAG GTTTCCTGCAAGGCTTCTGATTCACCTTCAGTAGCTA TGCATGGCATTGGGTGCGCCAGGCTCCCCAGGACAAAGGC TTGAGTGGATGGGATGGATCAACGCTGGCAATGGCAAC ACAAAATATTCACAGAAGTTCCAGGGCAGAGTCACCAT TACCAGGGACACGTCCGCGAGCACAGCCTACATGGAGC TGAGCAGCCTGAGATCTGAAGACACGGCTGTGTATTAC TGCGCTACGACTATGGACGTCTGGGGCCAAGGGACCA CGGTCACCGTCTCCTCAGC SEQ ID NO: 218 | MDWTWRILFLVAAAA GAHSQVQLVQSGTEV KKPGASVKVSCKASG FTFSSYAMHWVRQAP GQRLEWMGWINAGNG NTKYSQKFQGRVTIT RDTSASTAYMELSSL RSEDTAVYYCARDGY CSSTSCYGYYGMDVW GQGTTVTVSS SEQ ID NO: 219 | GFTFSSYAMH SEQ ID NO: 167 | WINAGNGNTKYSQKFQG SEQ ID NO: 419 | DGYCSSTSCYGYYGMDV SEQ ID NO: 166 |
| CL-141804 | ATGAAACACCTGTGTTCTTCCTCCTGGTGGCAGC TCCCAGATGGGTCCTGTCTGTCAGCTGCAGGAGT CGGGCCCAGGACTGGTGAAGCCTTCGGGACCCTGTCC CTCACCTGCGCTGTCTCTGGTGACTCCATCAGCAGTAG TAACTGGTGGAGTTGGATCCGCCAGCCCCCAGGGAAGG GGCTGGAGTGGATTGGGGAAATCTATCATAGTGGGAAC ACCAACTACAACCCGTCCCTCAAGAGTCGAGTCACCAT ATCAGTAGACAGGTCCAAGAACCAGTTCTCCCTGAACC TGAGCTCTGTGACCGCCGCGGACACGGCCGTGTATTAC TGTGCGAGAGGACGCCCCCTCTCTTATGGTTCGGGCAG TTATTATAACCTCAACTGGTTCGACCCCTGGGGCCAGG GAACCCTGGTCACCGTCTCCTCAGC SEQ ID NO: 220 | MKHLWFFLLLVAAPR WLSQVQLQESGPGL VKPSGTLSLTCAVSG DSISSSNWWSWRQP PGKGLEWIGEIYHSG NTNYNPSLKSRVTIS VDRSKNQFSLNLNSV TAADTAVYYCARGRP LSYGSGSYYNLNWFD PWGQGTLVTVSS SEQ ID NO: 221 | GDSISSSNWWS SEQ ID NO: 222 | EIYHSGNTNYNPSLKS SEQ ID NO: 223 | GRPLSYGSGSYYNLNWFDP SEQ ID NO: 224 |

TABLE 16-continued

Variable region sequences of further antibodies. CDRs are as identified by IMGT.

| Ab name | VH nucleotide | VH amino acid | HCDR1 | HCDR2 | HCDR3 |
|---|---|---|---|---|---|
| CL-141792 | ATGGACTGGACCTGGAGGATCCTCTTCTTGGTGGCAGC AGCCACAGGTGCCCACTCCCAGGTCCAGCTTGTCCAGT CTGGGGCTGAGGTGAAGAAGCCTGGGGCCTCAGTGAAG GTTTCCTGCAAGGCTTCTGGATACACCTTCACTAGTTA TGCTATGCATTGGGTGCGCCAGGCCCCCGGACAAAGGC TTGAGTGGATGGGATGGATCAACGCTGGCAATGGTTAC ACAGAATATTCACAGAACTTCCAGGGCAGAGTCACCAT TACCAGGGACACATCCGCGAGCACAGCCTACATGGAGC TGAGCAGCCTGAGATCTGAAGACACGGCTGTGTATTAC TGTGCGAGAGATAATTACTTTGATAGTAGTGTTTATGA CTCTTCTTACTACTACTACGGTATGGACGTCTGGG GCCAAGGGACCACGGTCACCGTCTCCTCAGC SEQ ID NO: 225 | MDWTWRILFLVAAT GAHSQVQLVQSGAEV KKPGASVKVSCKASG YTFTSYAMHWVRQAP GQRLEWMGWINAGNG YTKYSQNFQGRVTIT RDTSASTAYMELSSL RSEDTAVYYCARDNY FDSSVVDSSYYYYG MDVWGQGTTVTVSS SEQ ID NO: 226 | GYTFTSYAMH SEQ ID NO: 60 | WINAGNGYTKYSQNFQG SEQ ID NO: 170 | DNYFDSSVVDSSYYFYYGMDV SEQ ID NO: 169 |
| CL-141793 | ATGTCTGTCTCCTTCCTCATCTTCCTGCCCGTGCTGGG CCTCCCATGGGGTGTCCTGTCACAGGTACAGCTGCAGC AGTCAGGTCCAGGACTGGTGAAGCCCTCGCAGACCCTC TCACTCACCTGTGCCATCTCCGGGGACAGTGTCTCTAG CAACAGTGCTGCTTGGAACTGGATCAGGCAGTCTCCAT CGAGAGGCCTTGAGTGGCTGGGAAGGACATATCTAGG TCCAAGTGGTATAATGATTATGCAGTATCTGTGAAAAG TCGAATAACCTTCAACCCAGACACTTCTAAGAACCAGT TCTCCCTGCAGCTGAACTCTGTGACTCCCGAGGACACG GCTGTGTATTACTGTGCAAGAGAGGGGGGGCAGGGAGCTAT TACGTCTCACTTTGACTACTGGGGCCAGGGAACCCTGG TCACCGTCTCCTCAGC SEQ ID NO: 227 | MSVSFLIFLPVLGLP WGVLSQVQLQQSGPG LVKPSQTLSLTCAIS GDSVSSNSAAWNWIR QSPSRGLEWLGRTYY RSKWYNDYAVSVKSR ITFNPDTSKNQFSLQ LNSVTPEDTAVYYCA REGVGAITSHFDYWG QGTLVTVSS SEQ ID NO: 228 | GDSVSSNSAAWN SEQ ID NO: 200 | RTYYRSKWYNDYAVSVKS SEQ ID NO: 233 | EGVGAITSHFDY SEQ ID NO: 229 |
| CL-141794 | ATGTCTGTCTCCTTCCTCATCTTCCTGCCCGTGCTGGG CCTCCCATGGGGTGTCCTGTCACAGGTACAGCTGCAGC AGTCAGGTCCAGGACTGGTGAAGCCCTCGCAGACCCTC TCACTCACCTGTGCCATCTCCGGGGACAGTGTCTCTAG CAACCGTGCTGCTTGGAACTGGATCAGGCAGTCCCCAT CGAGAGGCCTTGAGTGGCTGGGAAGGACATATCTAGG TCCAAGTGGTATAATGATTATGCAGTATCTGTGAAAAG TCGAATAACCTTCAACCCAGACACTTCTAAGAACCAGT TCTCCCTGCAGCTGAACTCTGTGACTCCCGAGGACACG GCTGTGTATTACTGTGCAAGAGAGGGGGTGGGAGCTCTGG TCACCGTCTCACTTTGACTACTGGGGCCAGGGAACCCTGG SEQ ID NO: 230 | MSVSFLIFLPVLGLP WGVLSQVQLQQSGPG LVKPSQTLSLTCAIS GDSVSSNRAAWNWIR QSPSRGLEWLGRTYY RSKWYNDYAVSVKSR ITFNPDTSKNQFSLQ LNSVTPEDTAVYYCA REGVGAITSHFDYWG QGTLVTVSS SEQ ID NO: 231 | GDSVSSNRAAWN SEQ ID NO: 232 | RTYYRSKWYNDYAVSVKS SEQ ID NO: 233 | EGVGAITSHFDY SEQ ID NO: 229 |
| CL-141769 | ATGGACTGGACCTGGAGGGTCCTCTTTTTGGTGGCAGC AGCCACAGGTGCCCACTCCCAGGTCCAGCTTGTGCAGT CTGGGGCTGAGGTGAAGAAGCCTGGGGCCTCAGTGAAG GTTTCCTGCAGGGCTTCTGGATACACCTTCACTAACTA TGCTATGCATTGGGTGCGCCAGGCCCAGGACAAAGGC TTGAGTGGATGGGATGGATCAACGCTGGCAATGGTTAC ACAAAATATTCACAGAAGTTCCAGGACAGATTCACCAT | MDWTWRVLFLVAAA GAHSQVQLVQSGAEV KKPGASVKVSCRASG YTFTNYAMHWVRQAP GQRLEWMGWINAGNG YTKYSQKFQDRFTIT RDTSATTAYMELSSL | GYTFTNYAMH SEQ ID NO: 3 | WINAGNGYTKYSQKFQD SEQ ID NO: 24 | DSFYDILTGPVYHYGMDV SEQ ID NO: 76 |

TABLE 16-continued

Variable region sequences of further antibodies. CDRs are as identified by IMGT.

| Ab name | VH nucleotide | VH amino acid | HCDR1 | HCDR2 | HCDR3 |
|---|---|---|---|---|---|
| | TACCAGGGACACACATCCGCGACCAGCCAGCCTACATGAAAC<br>TGAGCAGCCTGAGATCTGAAGACACGGCTGTATATTAC<br>TGTGCGAGAGAATTCTTTTACGATATTTTGACTGGGCC<br>AGTCTATCACTACTACGGTATGGACGTCTGGGGCCAAG<br>GGACCACGGTCACCGTCTCCTCAGC<br>SEQ ID NO: 234 | RSEDTAVYYCARDSF<br>YDILTGPVYHYYGMD<br>VWGQGTTVTVSS<br>SEQ ID NO: 235 | | | |
| CL-141770 | ATGGACTGGACCTGGAGGATCCTCTTTTTGTGGCAGC<br>AGCCACAGGTGCCCACTCCCAGGTCCAACTTGTGCAGT<br>CTGGGGCTGAGGTGAAGAAGCCTGGGGCCTCAGTGAAG<br>GTTTCCTGCAAGGCTGTCGGATACACCTTCACTAACTA<br>TGCTATACATTGGGTGCGCCAGGCCCCTGGACAAAGTC<br>TTGTGTGGATGGGATGGATCAACGCTGGCAATGGTTAC<br>ACAAAATATTCACAGATGTTCCAGGACAGAGTCGCCAT<br>TACTAGGGACGACACATCCGCGAACAGCCTACATGAGC<br>TGAGCAGCCTGAGATCTGAGGACACGGCTGTATTAC<br>TGTGCGAGAGATCAGTTTTACGAGACTTTGACTGGTTA<br>TTATAACGTGTACTACTACGGTATGGACGTCTGGGG<br>GCCAAGGGACCACGGTCACCGTCTCCTCAGC<br>SEQ ID NO: 238 | MDWTWRILFLVAAAT<br>GAHSQVQLVQSGAEV<br>KKPGASVKVSCKASG<br>YTFTNYAIHWVRQAP<br>GQSLVWMGWINAGNG<br>YTKYSQMFQDRVAIT<br>RDTSANTAYMELSSL<br>RSGDTAVYYCARDQF<br>YETLTGYNVYYYG<br>MDVWGQGTTVAVSS<br>SEQ ID NO: 237 | GYTFTNYAIH<br>SEQ ID NO: 156 | WINAGNGYTKYSQMFQD<br>SEQ ID NO: 174 | DQFYETLTGYNVYYYGMDV<br>SEQ ID NO: 173 |
| CL-141772 | ATGGACTGGACCTGGAGGATCCTCTTTTTGTGGCAGC<br>AGCCACAGGTGCCTCCACTCCCAGGTCCAGCTTGTGCAGT<br>CTGGGGCTGAGGTGAAGAAGCCTGGGGCCTCAGTGAAG<br>GTTTCCTGCAAGGCTTCTGGATTCATCTTTATTAACTA<br>TGCTATGCAATGGGTGCGCCAGGCCCCCGGACAAAGGC<br>TTGAGTGGATGGGATGGATCAACGCTGGCAACGGTTAC<br>ACAAAATATTCACAGAAATTCCGGAACAGTCTACGAGC<br>CACCAGGGACATATCCGGAACAGTCTACATGGAGC<br>TGAGCAGCCTGAGATCTGAAGACACGGCTGTGTATTAC<br>TGTGCGAGAGATGGATTTTGTAGTACAACCACCTGCTC<br>CGACCACTACGGTATGGACGTCTGGGGCCAAGGGACCA<br>CGGTCACCGTCTCCTCAGC<br>SEQ ID NO: 240 | MDWTWRILFLVAAAT<br>GVHSQVQLVQSGAEV<br>KKPGASVKVSCKASG<br>FIFINYAMQWVRQAP<br>GQRLEWMGWINAGNG<br>YTKYSQKFQGRVTIT<br>RDISANTVYMELSSL<br>RSEDTAVYYCARDGF<br>CSTTTCSDHYGMDVW<br>GQGTTVTVSS<br>SEQ ID NO: 239 | GFIFINYAMQ<br>SEQ ID NO: 128 | WINAGNGYTKYSQKFQG<br>SEQ ID NO: 68 | DGFCSTTTCSDHYGMDV<br>SEQ ID NO: 129 |
| CL-141773 | ATGGACACACTTGCTCTGCTCTGCTGCTGACCAT<br>CCCTTCATGGGTCTTGTCCAGATCCAGCACCTTGAAGGAGT<br>CTGGTCCTACGCTGTGAAACCCACACAGACCCTCACG<br>CTGACCTGCACCTTCTCTGGGTTCGCACTCAGTACTAG<br>TGGAGTGGGTGTGGGCTGGATCCGTCAGCCCCCGGAA<br>AGGCCCTGGAGTGGCTTGCACTCATTTATTGGATGAT<br>GATAAGCGTTACAGCCCATCTCTGAAGAGCAGGTCAC<br>CATCACCAAGGACACCTCCAAAAACCAGGTGGTCCTTA<br>CAGTGACCAACATGGACCCTGTGGACACAGCCACATAT<br>TACTGTGCACTTAAGGACTACGGTGACTACTACTA<br>CGATATGGACGTCTGGGGCCAAGGGACCACGGTCACCG<br>TCTCCTCAGC<br>SEQ ID NO: 245 | MDTLCSTLLLITIPS<br>WVLSQITLKESGPTL<br>VKPTQTLTLTCTFPG<br>FALSTSGVGWIRQ<br>PPGKALEWLALIYWD<br>DDKRYSPSLKSRLTI<br>TKDTSKNQVVLTVTN<br>MDPVDTATYYCALKD<br>YGDYYYDMDVWGQG<br>TTVTVSS<br>SEQ ID NO: 537 | GFALSTSGVGVG<br>SEQ ID NO: 242 | LIYWDDDKRYSPSLKS<br>SEQ ID NO: 243 | KDYGDYYYDMDV<br>SEQ ID NO: 244 |

TABLE 16-continued

Variable region sequences of further antibodies. CDRs are as identified by IMGT.

| Ab name | VH nucleotide | VH amino acid | HCDR1 | HCDR2 | HCDR3 |
|---|---|---|---|---|---|
| CL-141776 | ATGGACTGGACCTGGAGGATCCTCTTTTTGGTGGCAGC AGCCACAGGTGCCCACTCCCAGGTCCAGCTTGTGCAGT CTGGGGCTGAGGTGAAGAACCCTGGGGCCTCAGTGAAG GTTTCCTGCAAGGCTTCTGGATTCACCTTCACTAACTA TGCTATGCATTGGGTGCGCCAGGCCCCCGGACAAAGGC TTGAGTGGATGGGATGGATCAACGCTGGCAATGGTCAC ACAAAATATTCACAGAAGTTCCAGGACAGAGTCGCCAT TACCAGGGACACATCCGCCACCAGCTGTATGGAAC TGAGCAGCCTGAGATCTGAAGACACGGCTGTGTATTAC TGTTCGAGAGATGATTTGTAGTACTACCACCTGCTC CGACCACTACGGTATGGACGTCTGGGGCCAAGGGACCA CGGTCACCGTCTCCTCAGC SEQ ID NO: 246 | MDWTWRILFLVAAAT GAHSQVQLVQSGAEV KNPGASVKVSCKASG FTFTNYAMHWVRQAP GQRLEWMGWINAGNG HTKYSQKFQDRVAIT RDTSATTAYMELSSL RSEDTAVYYCSRDGF CSTTTCSDHYGMDVW GQGTTVTVSS SEQ ID NO: 241 | GFTFTNYAMH SEQ ID NO: 110 | WINAGNGHTKYSQKFQD SEQ ID NO: 34 | DGFCSTTTCSDHYGMDV SEQ ID NO: 111 |
| CL-141777 | ATGGACTGGACCTGGAGGATCCTCTTTTTGGTGGCAGC AGCCACAGGTGCCCACTCCCAGGTCCAGCTTGTGCAGT CTGGGGCTGAGGTGAAGAAGCCTGGGGCCTCAGTGAAG GTTTCCTGCAAGGCGTCTGGATACACCTTCACGAACTA TGCTATGCATTGGGTGCGCCAGGCCCCCGGACAAAGGC TTGAGTGGATGGGATGGATCAACGCTGGCAATGGTTAC ACAAAATATTCACAGAAGTTCCAGGGCAGAGTCACCAT TATCAGGGACACATCCTGCGACACAGCCTATATGGAGC TGAGCAGCCTGAGATCTGAAGACACGGCTGTGTATTAC TGTGCGAGATATGATAGCGGTATGATTATGAGC GAATACTGCTACTACGGTATGGACGTCTGGGGCCAAG GGACCACGGTCACCGTCTCCTCAGC SEQ ID NO: 248 | MDWTWRILFLVAAAT GAHSQVQLVQSGAEV LGASVKVSCKASG YTFTNYAMHWVRQAP GQRLEWMGWINAGNG YTKYSQKFQGRVTII RDTSATTAYMELSSL RSEDTAVYYCARDNY YDSGSYYEYCYYGMD VWGQGTTVTVSS SEQ ID NO: 247 | GYTFTNYAMH SEQ ID NO: 3 | WINAGNGYTKYSQKFQG SEQ ID NO: 68 | DNYDSGSYYEYCYYGMDV SEQ ID NO: 69 |
| CL-141779 | ATGGACTGGACCTGGAGGATCCTCTTTTTGGTGGCAGC AGCCACAGGTGCCCACTCCCAGGTCCAGCTTGTGCAGT CTGGGGCTGAGGTGAAGAAGCCTGGGGCCTCAGTGAAG GTTTCCTGCAAGGCTTCTGGATACACCTTCACTAGCTA TGCTATGCATTGGGTGCGCCAGGCCCCCGGACAAAGGC TTGAGTGGATGGGATGGATCAACGCTGGCAATGGTAAC ACAAAATATTCACAGAAGTTCCAGGGCAGAGTCACCAT TACCAGGGACACATCCGCCACCAGCTACATGGAGC TGAGCAGCCTGAGATCTGAAGACACGGCTGTGTATTAC TGTGCGAGAGATCAGTATTACGATATTTTGACTCCATA TTACTACTACGGTATGGACGTCTGGGGCCAAG GGACCACGGTCACCGTCTCCTCAGC SEQ ID NO: 252 | MDWTWRILFLVAAAT GAHSQVQLVQSGAEV KKPGASVKVSCKASG YTFTSYAMHWVRQAP GQRLEWMGWINAGNG NTKYSQKFQGRVTIT RDTSASTAYMELSSL RSEDTAVYYCARDQY YDILTPYYYYYGMD VWGQGTTVTVSS SEQ ID NO: 249 | GYTFTSYAMH SEQ ID NO: 60 | WINAGNGNTKYSQKFQG SEQ ID NO: 419 | DQYYDILTPYYYYYGMDV SEQ ID NO: 165 |
| CL-141781 | ATGGACTGGACCTGGAGGGTCCTCTTTTTGGTGGCAGC AGCCACAGGTGCCCACTCCCAGGTCCAGCTTGTGCAGT CTGGGGCTGAGGTGAAGAAGCCTGGGGCCTCAGTGAAG GTTTCCTGCAGGGCTTCTGATAACCTTCAGTAATTA TGCTATGCATTGGGTGCGCCAGGCCCCCGGACAAAGGC TTGAGTGGATGGGATGGATCAACGCTGGCAATGGTTAC ACAAAATATTCACAGAAGTTCCAGGACAGAGTCACCAT | MDWTWRILFLVAAAT GAHSQVQLVQSGAEV KKPGASVKVSCRASG YTFSNYAMHWVRQAP GQRLEWMGWINAGNG YTKYSQKFQDRVTIT RDTSATTAYMELSSL | GYTFSNYAMH (SEQ ID NO: 75) | WINAGNGYTKYSQKFQD SEQ ID NO: 24 | DSFYDILTGPVHYHYGMDV SEQ ID NO: 76 |

TABLE 16-continued

Variable region sequences of further antibodies. CDRs are as identified by IMGT.

| Ab name | VH nucleotide | VH amino acid | HCDR1 | HCDR2 | HCDR3 |
|---|---|---|---|---|---|
| | TACCAGGGGACACATCCGCGACCAGCAGCCTACATGAAAC TGAGCAGCCTGAGATCTGAAGACACGGCTGTATTAC TGTTCGAGAGATTCTTTTACGATATTTTGACTGGGCC AGTCTATCACTACTACGGTATGGACGTCTGGGGCCAAG GGACCACGGTCACCGTCTCCTCAGC SEQ ID NO: 254 | RSEDTAMYYCSRDSF YDILTGPVYHYYGMD VWGQGTTVTVSS SEQ ID NO: 251 | | | |
| CL-141783 | ATGGACTGGACCTGGAGGATCCTCTTTTTGGTGGCAGC AGCCACAGGTGTCCACTCCCAGGTCCAACTTGTGCAGT CTGGGGCTGAGGTGAAGAAGCCTGGGGCCTCAGTAAAG CTTTCCTGCAAGGCTGTCTGATACACCTTCACTAACTA TGCTATGCATTGGGTGCGCCAGGCCCCCGGACAAAGTC TTGAGTGGATGGGATGGATCAACGCTGGCAATGGTTAC ACAAAATATTCACAGAAGTTCCAGGGCAGAGTCACCAT TACTAGGGACACCCGAGACGTCACTGATC TGAGCAGCCTGAGATCTGAAGACACGGCTGTGTATTAC TGTGCAGAGATCAGTATTACGATATTTTGAAAGGTTA GCCAAGGGACCACGGTCGCCGTCTCCTCAGC SEQ ID NO: 256 | MDWTWRILFLVAAAT GVHSQVQLVQSGAEV KKPGASVKLSCKASG YTFTNYAMHWVRQAP GQSLEWMGWINAGNG YTKYSQKFQGRVTIT RDTSANTAYMDLSSL RSEDTAVYYCARDQY YDILKGYNVDYYYG MDVWGQGTTVAVSS SEQ ID NO: 253 | GYTFTNYAMH SEQ ID NO: 3 | WINAGNGYTKYSQKFQG SEQ ID NO: 499 | DQYYDILKGYNVDYYYGMDV SEQ ID NO: 168 |
| CL-141784 | ATGGACTGGACCTGGAGGATCCTCTTTTTGGTGGCAGC AGCCACAGGTGCCCCACTCCCAGGTCCAGCTTGTGCAGT CTGGGGCTGAGGTGAAGAACCCTGGGGCCTCAGTGAAA GTTTCCTGCAAGGCTTCTGGATACACCTTCACTAATTA TGCTATGCATTGGGTGCGCCAGGCCCCCGGACAAAGGC TTGAGTGGATGGGATGGATCAACGCTGGCAATGGTTAC ACAAAATATTCACAGACCTTCCAGGGCAGAGTCACCAT TACCAGGGACACCATACGGAGTACAGCCTACATGGAGC TGAGCAGCCTGAGATCTGAAGACACGGCTGTATATTAC TGTGTGAGAGATGAATATATGAGTCGGGGAGTTCCAA CTACTACTACTATGGTATGGACGTCTGGGGCCAAGGGA CCACGGTCACCGTCTCCTCAGC SEQ ID NO: 258 | MDWTWRILFLVAAAT GAHSQVQLVQSGAEV KNPGASLKVSCKASG YTFTNYAMHWVRQAP GQRLEWMGWINAGNG YTKYSQTFQGRVTIT RDTYASTAYMELSSL RSEDTAVYYCVRDEY YESGSSNYYYYGMDV WGQGTTVTVSS SEQ ID NO: 255 | GYTFTNYAMH SEQ ID NO: 3 | WINAGNGYTKYSQTFQG SEQ ID NO: 172 | DEYYESGSSNYYYYGMDV SEQ ID NO: 171 |
| CL-141785 | ATGGACTGGACCTGGAGGATCCTCTTTTTGGTGGCAGC AGCCACAGGTGCCCACTCCCAGGTCCAGCTTGTGCAGT CTGGGGCTGAGGTGAAGAAGCCTGGGGCCTCAGTGAGG GTTTCCTGCAAGGCTTCTGGATTCACCTTCATTAGTTA TGCTATGCATTGGGTGCGCCAGGCCCCCGGACAAGGGC TTGAGTGGATGGGATGGATCAACGCTGGCGATGGTCAC ACAAAATATTCACAGAAGTTCCAGGACAGAGTCGCCAT TACCAGGGACACATCCGCGACCAGTCTACATGGTTAC TGAGCAGCCTGAGATCTGAAGACACGGCTGTGTATTAC TGTTCGAGAGATGGATTTTGTACTACTACCACCGTTTC CGACCACTACGGTATGGACGTCTGGGGCCAAGGGACCA CGGTCACCGTCTCCTCAGC SEQ ID NO: 260 | MDWTWRILFLVAAAT GAHSQVQLVQSGAEV KKPGASVRVSCKASG FTFISYAMHWVRQAP GQGLEWMGWINAGDG HTKYSQKFQDRVAIT RDTSATTVYMDLSSL RSEDTAVYYCSRDGF CTTTTCSDHYGMDVW GQGTTVTVSS SEQ ID NO: 257 | GFTFISYAMH SEQ ID NO: 97 | WINAGDGHTKYSQKFQD SEQ ID NO: 98 | DGFCTTTTCSDHYGMDV SEQ ID NO: 99 |

TABLE 16-continued

Variable region sequences of further antibodies. CDRs are as identified by IMGT.

| Ab name | VH nucleotide | VH amino acid | HCDR1 | HCDR2 | HCDR3 |
|---|---|---|---|---|---|
| CL-141786 | ATGGACTGGACCTGGAGGATCCTCTTTTTGGTGGCAGC AGCCACAGGTGCCCACTCCCAGGTCCAGCTTGTGCAGT CTGGGGCTGAGGTGAAGAAGCCTGGGGCCTCAGTGAAG GTTTCCTGCAAGGCTTCTGGATACACCTTCACTAACTA TGCTATGCATTGGTTGCGCCAGGCCCCCGGACAAAGGC TTGAGTGGATGGGATGGATCAACGCTGGCAATGGTTAC ACAAAATATTCACAGAAGTTCCAGGGCAGAGTCACCAT AACCAGGGACACATCCGCACCACAGCCTACATGGACC TGAGCAGCCTGAGATCTGAAGACACGGCTGTTTACTAC TGTGCGAGAGATAATTACTATGATAGTAATGTTTATAA TTCTTACTACTTCTACGGTATGGACGTCTGGGGCCAAG GGACCACGGTCACCGTCTCCTCAGC SEQ ID NO: 262 | MDWTWRILFLVAAAT GAHSQVQLLQSGAEV KKPGASVKVSCKASG YTFTNYAMHWLRQAP GQRLEWMGWINAGNG YTKYSQKFQGRVTIT RDTSATTAYMDLSSL RSEDTAVYYCARDNY YDSNVYNSYYFYGMD VWGQGTTVTVSS SEQ ID NO: 261 | GYTFTNYAMH SEQ ID NO: 3 | WINAGNGYTKYSQKFQG SEQ ID NO: 68 | DNYYDSNVYNSYYFYGMDV SEQ ID NO: 163 |
| CL-141787 | ATGGACTGGACCTGGAGGATCCTCTTTTTGGTGGCAGC AGCCACAGGTGCCCACTCCCAGGTCCAGCTTGTGCAGT CTGGGGCTGAGGTGAAGAAGCCTGGGGCCTCAGTGAAG GTTTCCTGCAAGGCTTCTGGATTCACCTTCACTAGCCA TGCTATACATTGGGTGCGCCAGGCCCCCGGACAAAGGC TTGAGTGGATGGGATGGATCAACGCTGGCAATGGTTAC ACAAAATATTCACAGAAGTTCCAGGACAGAGTCGCCAT TACCAGGGACACATCCGCGAGCACAGCCTACATGGAGC TGAGCAGCCTGAGATCTGAAGACACGGCTGTGTATTAC TGTACAGAGATGATGGATTTGTAGTACTACCACCTGCTC CGACCACTACGGTATGGACGTCTGGGGCCAAGGGACCA CGGTCACCGTCTCCTCAGC SEQ ID NO: 264 | MDWTWRILFLVAAAT GAHSQVQLVQSGAEV KKPGASVKVSCKASG FTFTSHAIHWVRQAP GQRLEWMGWINAGNG YTKYSQKFQDRVAIT RDTSASTAYMELSSL RSEDTAVYYCTRDGF CSTTTCSDHYGMDVW GQGTTVTVSS SEQ ID NO: 265 | GFTFTSHAIH SEQ ID NO: 117 | WINAGNGYTKYSQKFQD SEQ ID NO: 24 | DGFCSTTTCSDHYGMDV SEQ ID NO: 111 |
| CL-141789 | ATGGACTGGACCTGGAGGATCCTCTTTTTGGTGGCAGC AGCCACAGGTGCCCACTCCCAGTCCAGCTTGTGCAGT CTGGGGCTGAGGTGAAGAAGCCTGGGGCCTCAGTGAAG GTTTCCTGCAAGACTTCTGGATTCACCTTCACTAGTTA TGCTATACAGTGGGTGCGCCAGGCCCCCGGACAAGGGC TTGAGTGGATGGGATGGATCAACGCTGGCGATGGTCAC ACGAAATATTCACAGAAGTTCCAGGACAGAGTCGTCAT TACCAGGGACACATCCGCGAGTACAGCCTACATGGAGC TGAGCAGCCTGAGATCTGAAGACACGGCTGTGTATTAC TGTACGAGAGATGGATTTTGTACTACGACACCTGCTC CGACCACTACGGTATGGACGTCTGGGGCCAAGGGACCA CGGTCACCGTCTCCTCAGC SEQ ID NO: 266 | MDWTWRILFLVAAAT GAHSQVQLVQSGAEV KKPGASVRVSCKTSG FTFTSYAIQWVRQAP GQGLEWMGWINAGDG HTKYSQKFQDRVVIT RDTSATTVYMDLSSL RSEDTAVYYCTRDGF CTTTTCSDHYGMDVW GQGTTVTVSS SEQ ID NO: 263 | GFTFTSYAIQ SEQ ID NO: 104 | WINAGDGHTKYSQKFQD SEQ ID NO: 98 | DGFCTTTTCSDHYGMDV SEQ ID NO: 99 |
| CL-141790 | ATGGACTGGACCTGGAGGATCCTCTTTTTGGTGGCAGC AGCCACAGGTGCCCACTCCCAGTCCAGCTTGTGCAGT CTGGGGCTGAGGTGAAGAGGCCTGGGGCCTCAGTGAAA ATTTCCTGCAAGGCTTCTGGATACACCTTCACTAACTA TGCTATACATTGGGTGCGACAGGCCCCCGGACAAAGGC TTGAGTGGATGGGATGGATCAACGCTGGCAATGGTTAC ACAAAATATTCACAGAAGTTCCAGGGCAGAGTCACCAT | MDWTWRILFLVAAAT GAHSQVQLVQSGAEV KRPGASVKISCKASG YTFTNYAIHWVRQAP GQRLEWMGWINAGNG YTKYSQKFQGRVTIT RDTSATSAYLELYSL | GYTFTNYAIH SEQ ID NO: 156 | WINAGNGYTKYSQKFQG SEQ ID NO: 68 | DEYYDSGSNYYYYGMDV SEQ ID NO: 175 |

TABLE 16-continued

Variable region sequences of further antibodies. CDRs are as identified by IMGT.

| Ab name | VH nucleotide | VH amino acid | HCDR1 | HCDR2 | HCDR3 |
|---|---|---|---|---|---|
| | TACCAGGGACACATCCGCGACCTCAGCCTACCTGGAGC TGTACAGCCTGATATCTGAAGACACGGCTGTATATTAC TGTGTGAGAGATGAATACTATGGTATGGACGTTCGGGGAGTTCCAA CTACTACTACTATGGTATGGACGTCTGGGGCCAAGGGA CCACGGTCACCGTCTCCTCAGC SEQ ID NO: 268 | ISEDTAVYYCVRDEY YDSGSSNYYYGMDV WGQGTTVTVSS SEQ ID NO: 265 | | | DSFYDILTGPVYHYYGMDV SEQ ID NO: 76 |
| CL-141791 | ATGGACTGGACCTGGAGGGTTCCTCTTTTTGTGGCAGC AGCCACAGGTGCCCACTCCCAGGTCCAGCTTGTGCAGT CTGGGGCTGAGGTGAAGAAGCCTGGGGGCTCAGTGAAG GTTTCCTGCAGGGCTTCTGGATACACCTTCACTAACTA TGCTATGCATTGGGTGCGCCAGGCCCCCGGACAAAGGC TTGAGTGGATGGGATGGATCAACGCTGGCAATGGTTAC ACAAAGTATTCACAGAAGTTCCAGGACAGAGTCACCAT TACCAGGGACACATCCGCGACCCCACATGGAAC TGAGCAGCCTGAGATCTGAAGACACGGCTATGTATTAC TGTGCCAGAGATTCTTTACGGTATGGACGTCTGGGGCC AAGGGACCACGGTCACCGTCTCCTCAGC SEQ ID NO: 269 | MDWTWRVLFLVAAAT GAHSQVQLVQSGAEV KKPGASVKVSCRASG YTFTNYAMHWVRQAP GQRLEWMGWINAGNG YTKYSQKFQDRVTIT RDTSATTAHMELSSL RSEDTAMYYCARDSF YDILTGPVYHYYGMD VWGQGTTVTVSS SEQ ID NO: 267 | GYTFTNYAMH SEQ ID NO: 3 | WINAGNGYTKYSQKFQD SEQ ID NO: 24 | |
| CL-141778 | ATGGAGTTTGGGCTGAGTTGGATTTACCTTGCTGCTAT TTTAAAAGGTGTCCAGTGTGAGGTGCAGCTGGTGGAGT CTGGGGGGGGCTTGGTACAGCCTGGGGGGTCCCTTAGT CTCTCCTGTACAGCCTCTGGATTCACTTTCAATAACGC CTGGATGAGCTGGGTCCGCCAGGCTCCAGGGAAGGGGC TGGAGTGGGTTGGCCGTATTAAAAGCAAAACTGATGGT GGGACAACAGACTACGCTGCCCCTGTGAAAGGCAGATT CACCATCTCAAGAGATGATTCAAAAACCACGCTGTCTC TGCAATGAACAGCCTGAAACCCGAGGACACGGCCGTG TATTACTGTGCCACAGGCAGTGGTTGGTCCCACTTTGA CTACTGGGGGCCAGGGAACCCTGGTCACCGTCTCCTCAG C SEQ ID NO: 269 | MEFGLSWIYLAAILK GVQCEVQLVESGGGL VKPGGSLSLSCTASG FTFNNAWMSWVRQAP GKGLEWVGRIKSKTD GTTDYAAPVKGRFT ISRDDSKTTLSLRMN SLKTEDTAVYYCATG SGWSHFDYWGQGTLV TVSS SEQ ID NO: 270 | GFTFNNAWMS SEQ ID NO: 271 | RIKSKTDGGTTDYAAPVKG SEQ ID NO: 272 | GSGWSHFDY SEQ ID NO: 273 |
| CL-141780 | ATGGAGTTTGGGCTGAGCTGGATTTTCCTTACTGCTAT TTTAAAAGGTGTCCAGTGTGAGGTGCAGCTGGTGGAGT CTGGGGGAGGCTTGGTACAGCCTGGGGGGTCCCTTAGA CTCTCCTGTGCAGCCTCTGGATTCACTTTCAGTAACGC CTGGATGAGCTGGGTCCGCCAGGCTCCAGGGAAGGGGC TGGAGTGGGTTGGCCGTGTTAAAAGCAAAACTGATGGT GGGACAACAGACTACGCTGCCCCTGTGAAAGGCAGATT CACCATCTCAAGAGATGATTCAAAAAACACGCTGTATC TGCAAATGAACAGTGTGAAAACAGGAGGACACGGCCGTG TATTACTGTACCACAGGCAGTGACTGGTCCCACTTTGA CTACTGGGGCCAGGGAACCCTGGTCACCGTCTCCTCAG SEQ ID NO: 274 | MEFGLSWIFLTAILK GVQCEVQLVESGGGL VKPGGSLRLSCAASG FTFSNAWMSWVRQAP GKGLEWVGRVKSKTD GGTTDYAAPVKGRFT ISRDDSKNTLYLQMN SLKTEDTAVYYCTTG SDWSHFDYWGQGTLV TVSS SEQ ID NO: 275 | GFTFSNAWMS SEQ ID NO: 276 | RVKSKTDGGTTDYAAPVKG SEQ ID NO: 277 | GSDWSHFDY SEQ ID NO: 278 |

TABLE 16-continued

Variable region sequences of further antibodies. CDRs are as identified by IMGT.

| Ab name | VH nucleotide | VH amino acid | HCDR1 | HCDR2 | HCDR3 |
|---|---|---|---|---|---|
| CL-141771 | ATGGAGTTTGGGCTGAGCTGGATTTTCCTTGCTGTAT TTTAAAAGGTGTCCAGTGTGAGGTGCAGCTGGTGGAGT CTGGGGGAGGCTTGGTGAAGCCTGGGGGGTCCCTTAGA CTCCTCTGTGCAGCCTCTGGATTCACTTTCAGTAACGC CTGGATGAACTGGGTCCGCCAGGCCCCAGGAAGGGGC TGGAGTGGGTTGGCCGTATTAAAGCAAAACTGAAGGT GGGACAACAGACTACGCTGCACCCTGAAAGCCAGATT CACCATCTCAAGAGATGATTCAAAAACACGCTGTATC TGCAAATGAATAGCCTGAAACCTGAAGACACAGCCGTG TATTACTGTACCACAGGCAGTGACTGGACCCACTTTGA CTACTGGGGCCAGGGAACCCTGGTCACCGTCTCCTCAG C SEQ ID NO: 279 | MEFGLSWIFLAGILK GVQCEVQLVESGGGL VKPGGSLRLSCAASG FTFSNAWMNWVRQAP GKGLEWVGRIKSKTE GTTDYAAPVKGRFT ISRDDSKNTLYLQMN SLKTEDTAVYYCTTG SDWTHFDYWGQGTLV TVSS SEQ ID NO: 280 | GFTFSNAWMN SEQ ID NO: 281 | RIKSKTEGGTTDYAAPVKG SEQ ID NO: 282 | GSDWTHFDY SEQ ID NO: 283 |
| CL-141814 | ATGGAGTTTGGGCTGAGCTGGATTTTCCTTGCTCTAT TTTAAAAGGTGTCCAGTGTGAGGTGCAACTGGTGGAGT CTGGGGGAGGCTTGGTGAAGCCTGGGGGGTCCCTTAGA CTGTCCTGTGCAGCCTCTGGATTCACTTTCAGTGACGC CTGGATGACCTGGGTCCGCCAGGCTCCAGGGAAGGGGC TGGAGTGGGTTGGCCGTATTAAAGCAAAACTGATGAT GGGACAACAGACTACGCTGCACCCTGAAAGGCAGATT CACCATCTCAAGAGATGATTCAAAAACACGCTGTATC TGCAAATGAACAGCCTGAAACCTGAAGACACAGCCGTT TATTACTGTACCTCCCTATTACTATGGTTCGGGAGTT AAGGGACTACTGGGGCCAGGGAACCCTGGTCACCGTCT CCTCAGC SEQ ID NO: 284 | MEFGLSWIFLAAILK GVQCEVQLVESGGGL VKPGGSLRLSCAASG FTFSDAWMTWVRQAP GKGLEWVGRIKSKTD GTTDYAAPVKGRFT ISRDDSKNTLYLQMN SLKTEDTAVYYCTSL LLWFGELRDYWGQGT LVTVSS SEQ ID NO: 285 | GFTFSDAWMT SEQ ID NO: 286 | RIKSKTDDGTTDYAAPVKG SEQ ID NO: 287 | LLLWFGELRDY SEQ ID NO: 288 |
| CL-141813 | ATGGAGTTTGGGCTGAGCTGGATTTTCCTTGCTGCTAT TTTAAAAGGTGTCCAGTGTGAGGTGCAGCTGGTGGAAT IKPGGSLRLSCAASG CTGGGGGAGGCTTGATAAAGCCTGGGGGGTCCCTTAGA CTCTCCTGTGCAGCCTCTGGATTCACTTTCAGTAACGC CTGGATGACCTGGGTCCGCCAGGCTCCAGGGAAGGGGC TGGAGTGGGTTGGCCGTATTAAAGCAAAACTGATGAT GGGACAACCGACTACGCTGCACCCTGAAAGGCAGATT CACCATCTCAAGAGAATGATTCAAAAACACGCTGTATC TGCAAATGAACAGCCTCCTATTACTCTGGTTCGGGAGTT AAGGGACTACTGGGGCCAGGGAACCCTGGTCACCGTCT CCTCAGC SEQ ID NO: 289 | MEFGLSWIFLAAILK GVQCEVQLVESGGGL IKPGGSLRLSCAASG FTFSNAWMTWVRQAP GKGLEWVGRIKSKTD GTTDYAAPVKGRFT ISRNDSKNTLYLQMN SLKTEDTAVYYCTSL LLWFGELRDYWGQGT LVTVSS SEQ ID NO: 290 | GFTFSNAWMT SEQ ID NO: 291 | RIKSKTDDGTTDYAAPVKG SEQ ID NO: 287 | LLLWFGELRDY SEQ ID NO: 288 |
| CL-141812 | ATGGACTTTGGGCTGAGCTGGATTTTCCTTGCTGCTAT TTTAAAAGGTGTCCCGTGTGAGGTGCAGTTGGTGGAGT CTGGGGGAGGCTTGGTAAAGCCTGGGGGGTCCCTTAGA CTCTCCTGTGCAGCCTCTGGATTCACTTTCAATAACGC CTGGCTGAGCTGGGTCCGCCAGGCTCCAGGGAAGGGGC TGGAGTGGGTTGGCCGTATTAAAGCAAAGATCGATGAT GGGACAACAACTACGCTGCACCCCGTGAAAGGCAGATT GGGACAACAACTACGCTGCACCCTGAAAGGCAGATT | MDFGLSWIFLAAILK GVPCEVQLVESGGGL VKPGGSLRLSCAASG FTFNNAWLSWVRQAP GKGLEWVGRIKSKID DGTTNYAAPVKGRFT ISRDDSKNTLYLQMN | GFTFNNAWLS SEQ ID NO: 294 | RIKSKIDDGTTNYAAPVKG SEQ ID NO: 295 | LFLWFGELRDY SEQ ID NO: 296 |

TABLE 16-continued

Variable region sequences of further antibodies. CDRs are as identified by IMGT.

| Ab name | VH nucleotide | VH amino acid | HCDR1 | HCDR2 | HCDR3 |
|---|---|---|---|---|---|
| | CACCATCTCAAGAGATGATTCAAAAAACACGCTATATC TGCAAATGAACGCTGCAAACCGAGGACACCAGCCTG TATTACTGTGTTCCTCCCTATTCCTATGGTTCGGGAGTT AAGGGACTACTGGGGCCAGGGAACCCTGGTCACCGTCT CCTCAGC SEQ ID NO: 292 | GLQTEDTAVYYCSSL FLWFGELRDYWGQGT LVTVSS SEQ ID NO: 293 | | | |
| CL-141810 | ATGGCCTGGGCTCTGCTCCTCAACCTCCTCACTCAGGACACAGGGTC CTGGGCCCAATCTGCCCTGACTCAGCCTCCCTGTCTGTGTCCGGGTC TGACAGTCGATCACCATCTCCTGCACTGGAACCAGCAGTGATGTTGGTGGT TCTAAGTATGTCTCCTGGTACCAACAGCACCCAGGCAAAGCCCCCAAACT CATGATTTATGATGTCAGTAAGCGGCCCTCAGGGGTTTCTAATCGCTTCT CTGGCTCCAAGTCTGGCAACACGGCCTCCCTGACAATCTCTGGGCTCCAG GCTGAGGACGAGGCTGATTATTACTGTTGCTGTTATGCAGGTAGTAGCAC TTGGGTGTTCGGCGGAGGGACCAAACTGACCGTCCTAGG SEQ ID NO: 297 | MAWALLLLNLLTQDTGSWAQSA LTQPASVSGSPGQSITISCTGT SSDVGGSKYVSWYQQHPGKAPK LMIYDVSKRPSGVSNRFSGSKS GNTASLTISGLQAEDEADYYCC SYAGSSTWVFGGGTKLTVL SEQ ID NO: 298 | TGTSSDVGGSKYVS SEQ ID NO: 299 | DVSKRPS SEQ ID NO: 7 | CSYAGSSTWV SEQ ID NO: 10 |
| CL-141805 | ATGGCCTGGGCTCTGCTGCTCCTCCTCAACCTCCTCACTCAGGACACAGGGTC CTGGGCCCAGTCTGCCCTGACTCAGCCTGCCTCCGTGTCTGGGTCTCCTG GACAGTCGATCACCATCTCCTGCACTGGAACCAGCAGTGATGTGGTGTT TATAACTACGTCTCCTGGTTCCAACAGCACCCCAGGCAAAGCCCCCAAACT CATGATTTATGATGTCAGTAAGCGGCCCTCAGGGGTTTCTAATCGCTTCT CTGGCTCCAAGTCTGGCAACACGGCCTCCCTGACAATCTCTGGGCTCCAG GCTGAGGACGAGGCTGATTATTACTGTTGCTGTTATGCAGGTAGTAGCAC TTGGGTGTTCGGCGGAGGGACCAACCTGACCGTCCTAGG SEQ ID NO: 300 | MAWALLLLNLLTQDTGSWAQSA LTQPASVSGSPGQSITISCTGT SSDVGVYNYVSWFQQHPGKAPK LMIYDVSKRPSGVSNRFSGSKS GNTASLTISGLQAEDEADYYCC SYAGSSTWVFGGGTNLTVL SEQ ID NO: 301 | TGTSSDVGVYNYVS SEQ ID NO: 8 | NVSKRPS SEQ ID NO: 9 | CSYAGSSTWV SEQ ID NO: 10 |
| CL-141806 | ATGGCCTGGGCTCTGCTGCTCCTCCTCAACCTCCTCACTCAGGACACAGGGTC CTGGGCCCAGTCTGCCCTGACTCAGCCTGCCTCCGTGTCTGGGTCTCCTG GACAGTCGATCACCATCTCCTGCACTGGAACCAGCAGTGATGTTGGTAGT TACAACCATGTCTCCTGGTACCAACAGCACCCAGGCAAAGCCCCAAACT CATGATTTATGATGTCAGTAAGCGGCCCTCAGGGGATGTCTGATCGCTTCT CTGGCTCCAAGTCTGGCAACACGGCCTCCCTGACAATCTCTGGGCTCCAG GCTGAGGACGAGGCTGATTATTACTGTTGCTGTTATGCAGGTAGTAGTAC TTGGGTGTTCGGCGGAGGGACCAAGTTGACCGTCCTAGG SEQ ID NO: 302 | MAWALLLLNLLTQDTGSWAQSA LTQPASVSGSPGQSITISCTGT SSDVGSYNHVSWYQQHPGKAPK LMIYDVSKRPSGMSDRFSGSKS GNTASLTISGLQAEDEADYYCC SYAGSSTWVFGGGTKLTVL SEQ ID NO: 303 | TGTSSDVGSYNHVS SEQ ID NO: 63 | DVSKRPS SEQ ID NO: 39 | CSYAGSSTWV SEQ ID NO: 10 |
| CL-141795 | ATGGCCTGGGCTCTGCTGCTCCTCCTCAACCTCCTCACTCAGGACACAGGGTC CTGGGCCCAGTCTGCCCTGACTCAGCCTGCCTCCGTGTCTGGGTCTCCTG GACAGTCGATCACCATCTCCTGCACTGGAACCAGCAGTGATGTTGGTGGT TATAACTATGTCTCCTGGTACCAACAGCACCCCAGGCAAAGCCCCCAAACT CATGATTTATGATGTCAGTAAGCGGCCCTCAGGGGTTTCTAATCGCTTCT CTGGCTCCAAGTCTGGCAACACGGCCTCCCTGACAATCTCTGGGCTCCAG GCTGAGGACGAGGCTGATTATTACTGTTGCTGTTATGCAGGTAGTAGCAC TTGGGTGTTCGGCGGAGGGACCAAGCTGACCGTCCTAGG SEQ ID NO: 304 | MAWALLLLNLLTQDTGSWAQSA LTQPASVSGSPGQSITISCTGT SSDVGYNYVSWYQQHPGKAPK LMIYDVSKRPSGVSNRFSGSKS GNTASLTISGLQAEDEADYYCC SYAGSSTWVFGGGTKLTVL SEQ ID NO: 305 | TGTSSDVGGYNYVS SEQ ID NO: 112 | DVSKRPS SEQ ID NO: 39 | CSYAGSSTWV SEQ ID NO: 10 |
| CL-141798 | ATGGCCTGGGCTCTGCTGCTCCTCCTCAACCTCCTCACTCAGGACACAGGGTC CTGGGCCCAGTCAGTCTGCCCTGACTCAGCCTGCCTCCGTGTCTGGGTCTCCTG | MAWALLLLNLLTQDTGSWAQSA LTQPASVSGSPGQSITISCTGT | TGTSSDVGGYNYVS SEQ ID NO: 112 | DVSKRPS SEQ ID NO: 39 | CSYAGNTTWV SEQ ID NO: 308 |

TABLE 16-continued

Variable region sequences of further antibodies. CDRs are as identified by IMGT.

| Ab name | VH nucleotide | VH amino acid | HCDR1 | HCDR2 | HCDR3 |
|---|---|---|---|---|---|
| | GACAGTCGATCACCATCTCCTGCACTGGAACCAGCAGTGATGTTGGTGGT TATAACTATGTCTCCTGGTACCAACAGCACCCAGGCAAGGCCCCCAAACT CATGATTTATGATGTCAGTAAGCGGCCCTCAGGGGTTTCTAATCGCTTCT CTGTCTCCAAGTCTGGCAACACGGCCTCCCTGACAATCTCTGGGCTCCAG GCTGAGGACGAGGCTGATTATTACTGCTGCTCATATGCAGGTAATTACCAC TTGGGTGTTCGGCGGAGGGACCAAACTGACCGTCCTAGG SEQ ID NO: 306 | SSDVGGYNYVSWYQQHPGKAPK LMIYDVSKRPSGVSNRFSVSKS GNTASLTISGLQAEDEADYYCC SYAGNTTWVFGGGTKLTVL SEQ ID NO: 307 | | | |
| CL-141763 | ATGGCCTGGGCTCTGCTGCTCCTCAACCTCCTCACTCAGGACACAGGGTC CTGGGCCCAGTCTGCCCTGACTCAGCCTGTCTCCGTGTCTGGGTCTCCTG GACAGTCGATCACCATCTCCTGCACTGGAACCAGCAGTGATGTTGGTGGT TATAACTATGTCTCCTGGTACCAACAGCACCCAGGCAAGGCCCCCAAACT CATGATTTATGATGTCAGTAAGCGGCCCTCAGGGGTTTCTGATCGCTTCT CTGGCTCCAAGTCTGGCAACACGGCCTCCCTGACAATCTCTGGGCTCCAG GCTGAGGACGAGGCTGATTATTACTGCTGCTCATATGCAGGTAGTAGAAC TTGGGTGTTCGGCGGAGGGACCAAGCTGACCGTCCTAGG SEQ ID NO: 309 | MAWALLLLNLLTQDTGSWAQSA LTQPASVSGSPGQSITISCTGT SSNVGGYNYVSWYQQHPGKAPK LMIYDVSKRPSGVSDRFSGSKS GNTASLTISGLQAEDEADYYCC SYAGSRTWVFGGGTKLTVL SEQ ID NO: 310 | TGTSSNVGGYNYVS SEQ ID NO: 311 | DVSKRPS SEQ ID NO: 39 | CSYAGSRTWV SEQ ID NO: 312 |
| CL-141764 | ATGGCCTGGGCTCTGCTGCTCCTCAACCTCCTCACTCAGGACACAGGGTC CTGGGCCCAGTCTGCCCTGACTCAGCCTGTCCGTGTCTGGGTCTCCTG GACAGTCGATCACCATCTCCTGCACTGAACCAGCAGTGATGTTGGTGGT TATAACTATGTCTCCTGGTACCAACAGCACCCAGGCAAAGCCCCCAAACT CATGATTTATGATGTCAGTAAGCGGCCCTCAGGGGTTTCTGATCGCTTCT CTGGCTCCAAGTCTGGCAACACGGCCTCCCTGACAATCTCTGGGCTCCAG GCTGAGGACGAGGCTGATTATTACTGCTGCTCATATGCAGGTAGTACAGC TTGGGTGTTCGGCGGAGGGACCAAGCTGACCGTCCTAGG SEQ ID NO: 313 | MAWALLLLNLLTQDTGSWAQSA LTQPASVSGSPGQSITISCTGT SSDVGGYNYVSWYQQHPGKAPK LMIYDVSKRPSGVSDRFSGSKS GNTASLTISGLQAEDEADYYCC SYAGTSTWVFGGGTKLTVL SEQ ID NO: 314 | TGTSSDVGGYNYVS SEQ ID NO: 112 | DVSKRPS SEQ ID NO: 39 | CSYAGTSTWV SEQ ID NO: 315 |
| CL-141765 | ATGGCCTGGGCTCTGCTGCTCCTCAACCTCCTCACTCAGGACACAGGGTC CTGGGCCCAGTCTGCCCTGACTCAGCCTGCCTCCGTGTCTGGGTCTCTG GACAGTCGATCACCATCTCCTGCACTGGAACCAGCAGTGATGTTGGTGGT TATACTATGTCTCCTGGTACCAACAGCACCCAGGCAAAGCCCCCAAACT CATGATTTATGATGTCAGTAAGCGGCCCTCAGGGGTTTCTGACATCGCTTCT CTGCTCCAAGTCTGGCAACACGGCCTCCCTGACAATCTCTGGGCTCCAG GCTGAGGACGAGACTGATTATTACTGCTGCTCATATGCAGGTAGTAGAAC TTGGGTGTTCGGCGGAGGGACCAAGCTGACCGTCCTAGG SEQ ID NO: 316 | MAWALLLLNLLTQDTGSWAQSA LTQPASVSGSPGQSITISCTGT SSNVGGYNYVSWYQQHPGKAPK LMIYDVSKRPSGVSDRFSGSKS GNTASLTISGLQAEDETDYYCC SYAGSRTWVFGGGTKLTVL SEQ ID NO: 317 | TGTSSNVGGYNYVS SEQ ID NO: 311 | DVSKRPS SEQ ID NO: 39 | CSYAGSRTWV SEQ ID NO: 312 |
| CL-141766 | ATGGCCTGGGCTCTGCTGCTCCTCAACCTCCTCACTCAGGACACAGGGTC CTGGGCCCAGTCTGCCCTGACTCAGCCTTCCTCTGTGTCTGGGTCTCTG GACAGTCGATCACCTTCTCCTGCACTGGAACCAGCAGTGATGTTGGTAGT TATAATCATGTCTCCTGGTACCAACAGCACCCAGGCAAGGCCCCCAAACT CATGATTTATGATGTCAGTAAGCGGCCCTCAATCGCTTCT CTGGCTCCAAGTCTGGCAACACGGCCTCCCTGACAATCTCTGGGCTCCAG GCTGAGGACGAGGCTGATTATTACTGCTGCTCATATGCAGGTAGTAGCAC TTGGGTGTTCGGCGGAGGGACCAAGCTGACCGTCCTAGG SEQ ID NO: 318 | MAWALLLLNLLTQDTGSWAQSA LTQPASVSGSPGQSITFSCTGT SSDVGSYNHVSWYQQHPGKAPK LMIYDVSKRPSGVSNRFSGSKS GNTASLTISGLQAEDEADYYCC SYAGSSTWVFGGGTKLTVL SEQ ID NO: 319 | TGTSSDVGSYNHVS SEQ ID NO: 63 | DVSKRPS SEQ ID NO: 39 | CSYAGSSTWV SEQ ID NO: 10 |

TABLE 16-continued

Variable region sequences of further antibodies. CDRs are as identified by IMGT.

| Ab name | VH nucleotide | VH amino acid | HCDR1 | HCDR2 | HCDR3 |
|---|---|---|---|---|---|
| CL-141768 | ATGGCCTGGGCTCTGCTGCTCCTCAACCTCCTCACTCAGGACACAGGGTC CTGGGCCCAGTCTGCCCTGACTCAGCCTGCCTCCGTGTCTGGGTCTCCTG GACAGTCGATCACCATCTCCTGCACTGGAACCAGCAGTGATGTTGGTGGT TATAACTATGTCTCCTGGTACCAACAGCACCCAGGCAAAGCCCCCAAACT CATGATTTATGATGTCAGTAAGCGGCCCTCAGGGGTTTCTAATCGCTTCT CTGGCTCCAAGTCTGCAACAGGCTCTCCTCACAATCTCTGGGCTCCAG GCTGAGGACGAGGCTGATTATTACTGCTGTTCATATGCAGGTAGTAGCAC TTGGGTGTTCGGCGGAGGGACCAAGCTGACCGTCCTAGG SEQ ID NO: 320 | MAWALLLLNLLTQDTGSWAQSA LTQPASVSGSPGQSITISCTGT SSDVGGYNYVSWYQQHPGKAPK LMIYDVSKRPSGVSNRFSGSKS GNTASLTISGLQAEDEADYYCC SYAGSSTWVFGGGTKLTVL SEQ ID NO: 422 | TGTSSDVGGYNYVS SEQ ID NO: 112 | DVSKRPS SEQ ID NO: 39 | CSYAGSSTWV SEQ ID NO: 10 |
| CL-141799 | ATGGCCTGGGCTCTGCTGCTCCTCAACCTCCTCACTCAGGACACAGGGTC CTGGGCCCAGTCTGCCCTGACTCAGCCTGCCTCCGTGTCTGGGTCTCCTG GACAGTCGATCACCATCTCCTGCACTGGAACCAGCAGTGATGTTGGTGCT TATAAGTATGTCTCCTGGTACCAACAGCACCCAGGCAAAGCCCCAAACT CATGATTTATGATGTCAATACGGGCCCTCAGGGGTTTCTACTCGCTTCT CTGCCTCCAAGTCTGCAACACGGCTCTCCTGACAGTCTCTGGGCTCCAG GCTGAGGACGAGGCTGTTTATTACTGCTCTTCATATGCAGGTAGTAGCAC TTGGGTGTTCGGCGGAGGGACCAAGCTGACCGTCCTAGG SEQ ID NO: 321 | MAWALLLLNLLTQDTGSWAQSA LTQPASVSGSPGQSITISCTGT SSDVGAYKYVSWYQQHPGKAPK LMIYDVNTRPSGVSTRFSASKS GNTASLTVSGLQAEDEAVYYCS SYAGSSTWVFGGGTKLTVL SEQ ID NO: 322 | TGTSSDVGAYKYVS SEQ ID NO: 92 | DVNTRPS SEQ ID NO: 29 | SSYAGSSTWV SEQ ID NO: 30 |
| CL-141800 | ATGGCCTGGGCTCTGCTGCTCCTCAACCTCCTCACTCAGGACACAGGGTC CTGGGCCCAGTCTGCCCTGACTCAGCCTGCCTCCGTGTCTGGGTCTCCTG GACAGTCGATCACCATCTCCTGCACTGGAACCAGCAGTGATGTTGGTGGT TATAAAAATGTCTCCTGGTACCAACAGCACCCAGGCAAAGCCCCCAAACT CATGATTTATGATGTCAGTAAGCGGCCCCCAGGGGTTTCTAATCGCTTCT CTGGCTCCAAGTCTGCAACAGGCTCTCCTGACAGTCTCTGGGCTCCAG GCTGAGGACGAGGCTGATTATTACTGCTGTTCATATGCAGGTAGTAGCAC TTGGGTGTTCGGCGGAGGGACCAAACTGACCGTCCTAGG SEQ ID NO: 323 | MAWALLLLNLLTQDTGSWAQSA LTQPASVSGSPGQSITISCTGT SSDVGGYKNVSWYQQHPGKAPK LMIYDVSKRPPGVSNRFSGSKS GNTASLTVSGLQAEDEADYYCC SYAGSSTWVFGGGTKLTVL SEQ ID NO: 324 | TGTSSDVGGYKNVS SEQ ID NO: 325 | DVSKRPP SEQ ID NO: 326 | CSYAGSSTWV SEQ ID NO: 10 |
| CL-141802 | ATGGCCTGGGCTCTGCTGCTCCTCAACCTCCTCACTCAGGACACAGGGTC CTGGGCCCAGTCTGCCCTGACTCAGCCTGCCTCCGTGTCTGGGTCTCCTG GACAGTCGATCACCATCTCCTGCACTGGAACCAGCAGTGATGTTGGTGCT TATAACTATGTCTCCTGGTACCAACAGCACCCAGGCAAAGCCCCCAAACT CATGATTTATGATGTCAGTAAGCGGCCCTCAGGGGTTTCTAATCGCTTCT CTGGCTCCAAGTCTGACAACAGGCTCTCCTGACAGTCTCTGGGCTCCAG GCTGAGGACGAGGCTGTTTATTACTGCTCTTATGCAGGTAGTAGCAC TTGGGTGTTCGGCGGAGGGACCAAGCTGACCGTCCTAGG SEQ ID NO: 327 | MAWALLLLNLLTQDTGSWAQSA LTQPASVSGSPGQSITISCTGT SSDVGAYNYVSWYQQHPGKAPK LMISDVSKRPSGVSNRFSGSKS DNTASLTVSGLQAEDEAVYYCC SYAGSSTWVFGGGTKLTVL SEQ ID NO: 328 | TGTSSDVGAYNYVS SEQ ID NO: 161 | DVSKRPS SEQ ID NO: 39 | CSYAGSSTWV SEQ ID NO: 10 |
| CL-141804 | ATGGCCTGGGCTCTGCTGCTCCTCAACCTCCTCACTCAGGACACAGGGTC CTGGGCCCAGTCTGCCCTGCCTCAGCCTGACTCAGCCAGTGATGTTGGTGGT TATAACTATGTCTCCTGGTACCAACAGCACCCAGGCAAAGCCCCCAAACT | MAWALLLLNLLTQDTGSWAQSA LTQPASVSGSPGQSITISCTGT SSDVGYNYVSWYQQHPGKAPK LMIYDVSKWPSGVSNRFSGSKS | TGTSSDVGYNYVS SEQ ID NO: 426 | DVSKWPS SEQ ID NO: 331 | CSYAGSSTWV SEQ ID NO: 10 |

TABLE 16-continued

Variable region sequences of further antibodies. CDRs are as identified by IMGT.

| Ab name | VH nucleotide | VH amino acid | HCDR1 | HCDR2 | HCDR3 |
|---|---|---|---|---|---|
| | CATGATTTATGATGTCAGTAAGTGCCCTCAGGGGTTTCTAATCGCTTCT CTGGCTCCAAGTCTGCCAACATCTCTGGCCTCCCTGACAATCTCTGGGCTCCAG GCAGTTGATGATGTCTGATTATTACTGCTCATATGCAGGTAGCAC TTGGGTGTTCGGCGGAGGGACCAAGCTGACCGTCCTAGG SEQ ID NO: 329 | GNTASLTISGLQAEDEADYYCC SYAGSSTWVFGGGTRLTVL SEQ ID NO: 330 | | | |
| CL-141792 | ATGGCCTGGGCTCTGCTGCTCCTCAACCTCCTCACTCAGGACACAGGGTC CTGGGCCCAGTCTGCCCTGACTCAGCCTGCCTCCGTGTCTGGGTCTCCTG GACAGTCGATCACCATCTCTGCACTGGAACCAGCAGTGATGTTGGTAGT TATAACCATGTCTCTGGTACCAACAACCAGCCAGCAAAGCCCCCAAACT CATGATTTATGATGTCAGTAAGCGCCCTCAGGGGTTTCTAATCGCTTCT CTGGCTCCAAGTCTGGCAACACGGCCTCCCTGACAATCTCTGGGCTCCAG GCTGAGGACGAGGCTGATTATTACTGCTCATATGCAGGTAGTAGCAC TTGGGTGTTCGGCGGAGGGACCAAGCTGACCGTCCTAGG SEQ ID NO: 332 | MAWALLLLLNLLTQDTGSWAQSA LTQPASVSGSPGQSITISCTGT SSDVGSYNHVSWYQQHPGKAPK LMIYDVSKRPSGVSNRFSGSKS GNTASLTISGLQAEDEADYYCC SYAGSSTWVFGGGTKLTVL SEQ ID NO: 333 | TGTSSDVGSYNHVS SEQ ID NO: 63 | SYNYVS DVSKRPS SEQ ID NO: 39 | CSYAGSSTWV SEQ ID NO: 10 |
| CL-141793 | ATGGCCTGGGCTCTGCTGCTCCTCAACCTCCTCACTCAGGACACAGGGTC CTGGGCCCAGTCTGCCCTGACTCAGCCTGCCTCCGTGTCTGGGTCTCCTG GACAGTCGATCACCATCTCTGCACTGGAACCAGCAGTGATGTTGGTGGT TATAACTATGTCTCTGGTACCAACAACCGGCCCTCAGGGGTTTCTAATCGCTTCT CTGGCTCCAAGTCTGGCAACACGGCCTCCCTGACAATCTCTGGGCTCCAG GCTGAGGACGAGGCTGATTATTACTGCTCATATGCAGGTAGTAGCAC TTGGGTGTTCGGCGGAGGGACCAAGCCAAGCTGACCGTCCTAGG SEQ ID NO: 334 | MAWALLLLLNLLTQDTGSWAQSA LTQPASVSGSPGQSITISCTGT SSDVGGYNYVSWYQQHPGKAPK LMIYDVSKRPSGVSNRFSGSKS GNTASLTISGLQAEDEADYYCC SYAGSSTWVFGGGTKLTVL SEQ ID NO: 422 | TGTSSDVGGYNYVS SEQ ID NO: 426 | SYNYVS DVSKRPS SEQ ID NO: 39 | CSYAGSSTWV SEQ ID NO: 10 |
| CL-141794 | ATGGCCTGGGCTCTGCTGCTCCTCAACCTCCTCACTCAGGACACAGGGTC CTGGGCCCAGTCTGCCCTGACTCAGCCTGCCTCCGTGTCTGGGTCTCCTG GACAGTCGATCACCATCTCTGCACTGGAACCAGCAGTGATGTTGGTGGT TATAACTATGTCTCTGGTACCAACAACCAGCCAGCAAAGCCCCCAAACT CATGATTTATGATGTCAGTAAGCGCCCTCAGGGGTTTCTAATCGCTTCT CTGGCTCCAAGTCTGGCAACACGGCCTCCCTGACAATCTCTGGGCTCCAG GCTGAGGACGAGGCTGATTATTACTGCTCATATGCAGGTAGTAGCAC TTGGGTGTTCGGCGGAGGGACCAAGCTGACCGTCCTAGG SEQ ID NO: 335 | MAWALLLLLNLLTQDTGSWAQSA LTQPASVSGSPGQSITISCTGT SSDVGGYNYVSWYQQHPGKAPK LMIYDVSKRPSGVSNRFSGSKS GNTASLTISGLQAEDEADYYCC SYAGSSTWVFGGGTKLTVL SEQ ID NO: 422 | TGTSSDVGGYNYVS SEQ ID NO: 426 | SYNYVS DVSKRPS SEQ ID NO: 39 | CSYAGSSTWV SEQ ID NO: 10 |
| CL-141769 | ATGGCCTGGGCTCTGCTGCTCCTCAACCTCCTCACTCAGGACACAGGGTC CTGGGCCCAGTCTGCCCTGACTCAGCCTGCCTCCGTGTCTGGGTCTCCTG GACAGTCGATCACCATCTCTGCACTGGAACCAGCAATGATGTTGGTGTT TATAACCATGTCTCTGGTACCAACAACCAGCCAGCAAAGCCCCAAACT CATGATTTATGATGAGTCAGTAAGCGCCCTCAGGGGTTTCTAATCGCTTCT CTGCCTCCAAGTCTGGCAACACGGCCTCCCTGACAATCTCTGGGCTCCAG GCTGAGGACGAGAGAGTGATTATTACTGCTCATATGCAGGTAGTAGCAC TTGGGTGTTCGGCGGAGGGACCAAGCTGACCGTCCTAGG SEQ ID NO: 336 | MAWALLLLLNLLTQDTGSWAQSA LTQPDSVSGSPGQSITISCTGT SNDVGVYNHVSWYQQHPGKAPK LMIYDVSKRPSGVSNRFSGSKS GNTASLTISGLQAEDESDYYCC SYAGSSTWVFGGGTKLTVL SEQ ID NO: 337 | TGTSNDVGVYNHVS SEQ ID NO: 77 | SYNYVS DVSKRPS SEQ ID NO: 39 | CSYAGSSTWV SEQ ID NO: 10 |
| CL-141770 | ATGGCCTGGGCTCTGCTGCTCCTGCTCCTCAACCTCCTCACTCAGGACACAGGGTC CTGGGCCCAGTCTGCCCTGACTCAGCCTGCCTCCGTGTCTGGGTCTCCC GACAGTCGATCACCATCTCCTGCACTGGAACCAGCAGTGATGTTGTTCC | MAWALLLLLNLLTQDTGSWAQSA LTQPASVSGSPGQSITISCTGT SSDVGSYNHVSWYQQHPGKAPQ | TGTSSDVGSYNHVS SEQ ID NO: 63 | SYNYVS DVSKRPS SEQ ID NO: 39 | CSYVGSSSWV SEQ ID NO: |

TABLE 16-continued

Variable region sequences of further antibodies. CDRs are as identified by IMGT.

| Ab name | VH nucleotide | VH amino acid | HCDR1 | HCDR2 | HCDR3 |
|---|---|---|---|---|---|
| | TATAACCATGTCTCCTGGTACCAACAGCACCCAGGCAAAGCCCCCCAACT CATGATTTATGATGTCAGTAAGCGGCCCTCAGGGGTTTCTGATCGCTTCT CTGGCTCCAAGTCTGGCAACACCGCCTCCCTGACAATCTCTGGGCTCCAG GCTGAGGACGAGGCTGAGTATTACTGCTGTGTCATATGTGGGTAGTAGCTC TTGGGTGTTCGGCGGAGGGACCAAGCTGACCGTCCTAGG SEQ ID NO: 338 | LMIYDVSKRPSGVSDRFSGSKS GNTASLTISGLQAEDEAEYYCC SYVGSSWVLGGGTKLTVL SEQ ID NO: 339 | | | |
| CL-141772 | ATGGCCTGGGCTCTGCTGCTCCTCAACCTCCTCACTCAGGACACAGGGTC CTGGGCCCAGTCTGCCCTGACTCAGCCTCGCTCCGTGTCTGGGTCTCCTG GACAGTCGATCACCATCTCCTGCACTGGAACCAGCAGTGATTTGGTGGT TATAACTATGTCTCCTGGTACCAACAGCACCCAGGCAAAGCCCCCAAACT CATGATTTATGATGTCAGTAAGCGGCCCTCAGGGGTTTCTAATCGCTTCT CTGGCTCCAAGTCTGGCAACACGGCCTCCCTGACAATCTCTGGGCTCCAG GCTGAGGACGAGGCTGATTATTACTGCTGCTCATATGCAGGTAGTAGCAC TTGGGTGTTCGGCGGAGGGACCAAGCTGACCGTCCTAGG SEQ ID NO: 341 | MAWALLLLNLLTQDTGSWAQSA LTQPASVSGSPGQSITISCTGT SSDVGGYNYVSWYQQHPGKAPK LMIYDVSKRPSGVSDRFSGSKS GNTASLTISGLQAEDEADYYCC SYAGSSTWVFGGGTKLTVL SEQ ID NO: 342 | TGTSSDVGGYNYVS SEQ ID NO: 426 | DVSKRPS SEQ ID NO: 39 | CSYAGSSTWV SEQ ID NO: 10 |
| CL-141773 | ATGGCCTGGGCTCTGCTGCTCCTCAACCTCCTCACTCAGGACACAGGGTC CTGGGCCCAGTCTGCCCTGACTCAGCCTCGCTCCGTGTCTGGGTCTCCTG GACAGTCGATCACCATCTCCTGCACTGGAACCACCAGTGATGTGGTGGT TATAACTATGTCTCCTGGTACCAACAGCACCCAGGCAAAGCCCCCAAATT CATGATTTATGATGTCAATGAGCGGCCCTCAGGGGTTTCCAATCGCTTCT CTGGCTCCAAGTCTGGCAACACGGCCTCCCTGACAATCTCTGGGCTCCAG GCTGAGGACGAGGCTGATTATTACTGCTGCTCATATGCAGGTAGTAGCAC TTGGGTGTTCGGCGGAGGGACCAAGCTGACCGTCCTAGG SEQ ID NO: 343 | MAWALLLLNLLTQDTGSWAQSA LTQPASVSGSPGQSITISCTGT ISDVGGYNYVSWYQQHPGKAPK LMIYDVNERPSGVSNRFSGSKS GNTASLTISGLQAEDEADYYCC SYAGSSTWVFGGGTKLTVL SEQ ID NO: 344 | TGTISDVGGYNYVS SEQ ID NO: 345 | DVNERPS SEQ ID NO: 346 | CSYAGSSTWV SEQ ID NO: 10 |
| CL-141776 | ATGGCCTGGGCTCTGCTGCTCCTCAACCTCCTCACTCAGGACACAGGGTC CTGGGCCCAGTCTGCCCTGACTCAGCCTCAGCTCCGTGTCTGGGTCTCCTG GACAGTCGATCACCATCTCCTGCACTGGAACCAGCAGTGATGTGGTGGT TATAACTATGTCTCCTGGTACCAACAGCACCCAGGCAAAGCCCCAAATT CATGATTTATGATGTCAGTAAGCGGCCCTCAATCGCTTCT CTGGCTCCAAGTCTGGCAACACGGCCTCCCTGACAATCTCTGGGCTCCAG GCTGAGGACGAGGCTGATTATTACTGCTGCTCATATGCAGGTAGTAGCAC TTGGGTGTTCGGCGGAGGGACCAAGCTGACCGTCCTAGG SEQ ID NO: 347 | MAWALLLLNLLTQDTGSWAQSA LTQPASVSGSPGQSITISCTGT SSDVGGYNYVSWYQQHPGKAPK FMIYDVSKRPSGVSNRFSGSKS GNTASLTISGLQAEDEADYYCC SYAGSSTWVFGGGTKLTVL SEQ ID NO: 348 | TGTSSDVGGYNYVS SEQ ID NO: 426 | DVSKRPS SEQ ID NO: 39 | CSYAGSSTWV SEQ ID NO: 10 |
| CL-141777 | ATGGCCTGGGCTCTGCTGCTCCTCAACCTCCTCACTCAGGACACAGGGTC CTGGGCCCAGTCTGATCACCAGCCTCGCTCCGTGTCTGGGTCTCCTG GACAGTCGATCACCATCTCCTGCACTGGAACCAGCAGTGATGTTGGTAGT TATAACCATGTCTCCTGGTACCAACAATACCCAGGCAAAGCCCCCAAACT CCTGATTTATGATGTCAGTAAGCGGCCCTCAGGGGTTTCTAATCGCTTCT CTGGCTCCAAGTCTGGCAACACGGCCTCCCTGACAATCTATGGGCTCCAG GCTGAGGACGAGGCTGATTATTACTGCTGCTCATATGTAGGTAGCAGCAC TTGGGTGTTCGGCGGAGGGACCAAGCTGACCGTCCTAGG SEQ ID NO: 349 | MAWALLLLNLLTQDTGSWAQSA LTQPASVSGSPGQSITISCTGT SSDVGSYNHVSWYQQYPGKAPK LLIYDVSKRPSGVSNRFSGSKS GNTASLTIYGLQAEDEADYYCC SYVGSSTWVFGGGTKLTVL SEQ ID NO: 350 | TGTSSDVGSYNHVS SEQ ID NO: 63 | DVSKRPS SEQ ID NO: 39 | CSVVGSSTWV SEQ ID NO: 10 |
| CL-141779 | ATGGCCTGGGCTCTGCTGCTCCTCAACCTCCTCACTCAGGACACAGGGTC CTGGGCCCAGTCAGTCTGCCCTGACTCAGCCTCGTCTGGGTCTCCTG | MAWALLLLNLLTQDTGSWAQSA LTQPASVSGSPGQSITISCTGT | TGTSSDVGGYNYVS SEQ ID NO: 112 | VVSKRPS SEQ ID NO: 157 | CSYAGSSTWV SEQ ID NO: 10 |

TABLE 16-continued

Variable region sequences of further antibodies. CDRs are as identified by IMGT.

| Ab name | VH nucleotide | VH amino acid | HCDR1 | HCDR2 | HCDR3 |
|---|---|---|---|---|---|
| | GACAGTCGATCACCATCTCCTGCACTGGAACCAGCAGTGATGTTGGTGGT TATAACTATGTCTCCTGGTACCAACAGCACCCAGGCAAAGCCCCAAACT CATGATTTATGTTGTCAGTGGAGTCCCTGGGGTTTCTAATCGCTTCT CTGGCTCCAAGTCTGGCAACACGGCCTCCCTGACAATCTCTGGGCTCCAG GCTGAGGACGAGGCTGATTATTACTGCTCATATGCAGGTAGTAGCAC TTGGGTGTTCGGCGGAGGGACCAAGCTGACCGTCCTAGG SEQ ID NO: 351 | SSDVGGNYYVSWYQQHPGKAPK LMIYVVSKRPSGVSNRFSGSKS GNTASLTISGLQAEDEADYYCC SYAGSSTWVFGGGTKLTVL SEQ ID NO: 352 | | | |
| CL-141781 | ATGGCCTGGGCTCTGCTGCTCCTCAACCTCCTCACTCAGGACACAGGGTC CTGGGCCCAGTCCGTGCTGACTCAGCCTGCCTCCGTGTCTGGGTCTCCTG GACAGTCGATCACCATCTCCTGCACTGGAACCAGCAGTGATGTTGGTGGT TATAACCATGTCTCTCTGGTACCAACAGCACCCCAGGCAAAGCCCCAAACT CATGATTTATGATGTCAGTGGAGTCCGGGGTTTCTAATCGCTTCT CTGGCTCCAAGTCTGGCAACACGGCCTCCCTGACAATCTCTGGGCTCCAG GCTGAGGACGAGGCTGATTATTACTGCTCATATGTAGGTAATAGCGC TTGGGTGTTCGGCGGAGGGACCAAACTGACCGTCCTAGG SEQ ID NO: 355 | MAWALLLLNLLTQDTGSWAQSA LTQPDSVSGSPGQSITISCTGT SNDVGVYNHVSWYQQHPGKAPK LMIYVVSKRPSGVSNRFSGSKS GNTASLTISGLQAEDEADYYCC SYVGNSAWVFGGGTKLTVL SEQ ID NO: 354 | TGTSNDVGVYNHVS SEQ ID NO: 77 | DVSKRPS SEQ ID NO: 39 | CSVVGNSAWV SEQ ID NO: 78 |
| CL-141783 | ATGGCCTGGGCTCTGCTGCTCCTCAACCTCCTCACTCAGGACACAGGGTC CTGGGCCCAGTCCGTGCTGACTCAGCCTGCCTCCGTGTCTGGGTCTCCTG GACAGTCGATCACCATCTCCTGCACTGGAACCAGCAGTGATGTGGTTCC TATAACCATGTCTCTCTGGTACCAACAGCACCCCAGGCAAAGCCCCAAACT CATGATTTATGATGTCAGTAAGCGGCCCTCAGGGGTTTCTGATCGCTTCT CTGGCTCCAAGTCTGGCAACACGGCCTCCCTGACAATCTCTGGGCTCCAG GCTGAGGACGAGGCTGATTATTACTGCTCATATGTGGGTAGTAGCAC TTGGGTGTTCGGCGGAGGGACCAAGCTGACCGTCCTAGG SEQ ID NO: 357 | MAWALLLLNLLTQDTGSWAQSA LTQPASVSGSPGQSITISCTGT SSDVGSYNHVSWYQQHPGKAPK LMIYDVSTRPSGVSDRFSGSKS GNTASLTISGLQAEDEADYYCC SYVGSSTWVFGGGTKLTVL SEQ ID NO: 356 | TGTSSDVGSYNHVS SEQ ID NO: 63 | DVSKRPS SEQ ID NO: 39 | CSVVGSSTWV SEQ ID NO: 70 |
| CL-141784 | ATGGCCTGGGCTCTGCTGCTCCTCAACCTCCTCACTCAGGACACAGGGTC CTGGGCCCAGTCCGTGCTGACTCAGCCTGCCTCCGTGTCTGGGTCTCCTG GACAGTCGATCACCATCTCCTGCACTGGAACCAGCAGTGATGTTGGTTCT TATAACCATGTCTCTCTGGTACCAACAGCACCCAGGCAAAGCCCCAAACT CATGATTTATGATGTCAGTACGCGGCCCTCAGGGGTTTCTAATCGCTTCT CTGGCTCCAAGTCTGGCAACACGGCCTCCCTGACAATCTCTGGGCTCCAG GCTGAGGACGAGGCTGATTATTACTGCTCATATGCAGGTAGTAGCAC TTGGGTGTTCGGCGGAGGGACCAAAATGACCGTCCTAGG SEQ ID NO: 360 | MAWALLLLNLLTQDTGSWAQSA LTQPASVSGSPGQSITISCTGT SSDVGSYNHVSWYQQHPGKAPK LMIYDVSTRPSGVSNRFSGSKS GNTASLTISGLQAEDEADYYCC SYAGSSTWVFGGGTKMTVL SEQ ID NO: 358 | TGTSSDVGSYNHVS SEQ ID NO: 63 | DVSTRPS SEQ ID NO: 359 | CSYAGSSTWV SEQ ID NO: 10 |
| CL-141785 | ATGGCCTGGGCTCTGCTGCTCCTCAACCTCCTCACTCAGGACACAGGGTC CTGGGCCCAGTCCGTGCTGACTCAGCCTGCCTCCGTGTCTGGGTCTCCTG GACAGTCGATCACCATCTCCTGCACTGGAACCAGCAGTGATGTTGGTAGT TATAACTATGTCTCCTGGTACCAACAGCACCCCAGGCAAAGCCCCAAATT CATGATTTATGATGTCAGTAAGCGGCCCTCGATCGCTTCT CTGGCTCCAAGTCTGGCAACAATCTCTGGCTCCAG GCTGAGGACGAGGCTGATTATTACTGCTCATATGCAGGTAGTAGCAC TTGGGTGTTCGGCGGAGGGACCAAGCTGACCGTCCTTGG SEQ ID NO: 362 | MAWALLLLNLLTQDTGSWAQSA LTQPASVSGSPGQSITISCTGT SSDVGSYNYVSWYQQHPGKAPK FMIYDVSKRPSGVSDRFSGSKS GNTASLTISGLQAEDEADYYCC SYAGSSTWVFGGGTKLTVL SEQ ID NO: 361 | TGTSSDVGSYNYVS SEQ ID NO: 38 | DVSKRPS SEQ ID NO: 39 | CSYAGSSTWV SEQ ID NO: 10 |

TABLE 16-continued

Variable region sequences of further antibodies. CDRs are as identified by IMGT.

| Ab name | VH nucleotide | VH amino acid | HCDR1 | HCDR2 | HCDR3 |
|---|---|---|---|---|---|
| CL-141786 | ATGGCCTGGCTCTGCTCTTCCTCAACCTCCTGCTCCTGACTCAGGACACAGGGTCCTGGGCCCAGTCTGTCTGACTCAGCCGTCCTCCCTGCTCTGGGCTCCTGGACAGTCGATCACCATCTCCTGCACTGGAACCAGCAGTGATGTTGGTAATTATAACCATGTCTCCTGGTACCAACAGCACCCAGACAAAGCCCCCAAACTCATGATTTATGATGTCAATAAGCGGCCCTCAGGGATTTCTAATCGCTTCTCTGGCTCCAAGTCTGGCAACACGGCCTCCCTGACAATCTCTGGGCTCCAGGCTGAGGACGAGGCTGATTATTACTGCTGCTCATATGCAGGTAGTAGTACTTGGGTGTTCGGCGGAGGGACCAAGCTGACCGTCCTAGG SEQ ID NO: 364 | MAWALLLLNLLTQDTGSWAQSV LTQPASVSGPPGQSITISCTGT SSDVGNYNHVSWYQQHPDKAPK LMIYDVNKRPSGISNRFSGSKS GNTASLTISGLQAEDEADYYCC SYAGSSTWVFGGGTKLTVL SEQ ID NO: 363 | TGTSSDVGNYNHV SEQ ID NO: 164 | YDVNKRPS SEQ ID NO: 19 | CSYAGSSTWV SEQ ID NO: 10 |
| CL-141787 | ATGGCCTGGCTCTGCTCTTCCTCAACCTCCTGCTCCTGACTCAGGACACAGGGTCCTGGGCCCAGTCTGTCCCTGACTCAGCCGTCCTCCCTGTCTGGGCTCCTGGACAGTCGATCACCATCTCCTGCACTGGAACCAGCAGTGATGTTGGCGGTTATAACTATGTCTCCTGGTACCAACAGCACCCCAAAATCATGATTTATGATGTCAGTAAGCGGCCCTCAGGGTTTCTAATCGCTTCTCTGGCTCCAAGTCTGGCAACACGGCCTCCCTGACAATCTCTGGGCTCCAGGCTGAGGACGAGGCTGATTATTACTGCTGCTCATATGCAGGTAGTAGTACTTGGGTGTTCGGCGGAGGGACCAAGCTGACCGTCCTAGG SEQ ID NO: 365 | MAWALLLLNLLTQDTGSWAQSA LTQPASVSGSPGQSITISCTGT SSDVGGYNYVSWYQQHPGKAPK FMIYDVSKRPSGVSNRFSGSKS GNTASLTISGLQAEDEADYYCC SYAGSSTWVFGGGTKLTVL SEQ ID NO: 348 | TGTSSDVGGYNYVS SEQ ID NO: 112 | DVSKRPS SEQ ID NO: 39 | CSYAGSSTWV SEQ ID NO: 10 |
| CL-141789 | ATGGCCTGGCTCTGCTCTTCCTCAACCTCCTGCTCCTGACTCAGGACACAGGGTCCTGGGCCCAGTCTGTCCCTGACTCAGCCGTCCTCCCTGTCTGGGCTCCTGGACAGTCGATCACCATCTCCTGCACTGGAACCAGCAGCCCCAAATTATATGCTCTCTGGTACCAACAGCACCCCCAAATTCATGATTTCTGATGTCAGTAAGCGGCCCTCAGGGTTTCTAATCTCTGGCTCCAAGTCTGGCAATAATGGCCTCCCTGACAATCTCTGGGCTCCAGGCTGAGGACGAGGCTGATTATTACTGCTGCTCATATGCAGGTAGTAGTACTTGGGTGTTCGGCGGAGGGACCAAGCTGACCCGTCCTTGG SEQ ID NO: 367 | MAWALLLLNLLTQDTGSWAQSA LTQPASVSGSPGQSITISCTGT SSDVGSYNYVSWYQQHPGKVPK FMISDVSKRPSGISDRFSGSKS GNTASLTISGLQAEDEADYYCC SYAGGSSTWVFGGGTKLTVL SEQ ID NO: 366 | TGTSSDVGSYNYVS SEQ ID NO: 28 | DVSKRPS SEQ ID NO: 39 | CSYAGGSSTWV SEQ ID NO: 105 |
| CL-141790 | ATGGCCTGGCTCTGCTCTTCCTCAACCTCCTGCTCCTGACTCAGGACACAGGATCCTGGGCCCAGTCTGTCTGACTCAGCCGTCCTCCCTGCTCTGGGCTCCTGGACAGTCGATCACCATCTCCTGCACTGGAACCAGCAGTGATGTTGGTAATTATAACCATGTCTCCTGGTACCAACAGCACCCAGACAAAGCCCCCAAACTCATGATTTATGATGTCAATAAGCGGCCCTCAGGGATTTCTAATCGCTTCTCTGGCTCCAAGTCTGGCAACACGGCCTCCCTGACAATCTCTGGGCTCCAGGCTGAGGACGAGGCTGATTATTACTGCTGCTCATATGCAGGTAGTAGCACTTGGGTGTTCGGCGGAGGGACCAAGCTGACCGTCCTAAG SEQ ID NO: 369 | MAWALLLLNLLTQDTGSWAQSA LTQPASVSGPPGQSITISCTGT SSDVGNYNHVSWYQQHPDKAPK LMIYDVSKRPSGVSNRFSGSKS GNTASLTISGLQAEDEADYYCC SYAGSSTWVFGGGTKLTVL SEQ ID NO: 368 | TGTSSDVGNYNHV SEQ ID NO: 164 | DVSKRPS SEQ ID NO: 39 | CSYAGSSTWV SEQ ID NO: 10 |
| CL-141791 | ATGGCCTGGCTCTGCTCTTCCTCAACCTCCTGCTCCTGACTCAGCCGTCCTGGGCCCAGTCGATCACCATCTCCTGCACTGGAACCAGCAATGATGTTGGTGTTTATAACCATGTCTCCTGGTACCAAGCAGCACCCCCAAACTCATGATTTATGATGTCAGTAAGCGGCCCTCAGGGTTTCTAATCGCTTCTCTGGCTCCAAGTCTGGCAACACGGCCTCCCTGACAATCTCTGGGCTCCAGGCTGAGGACGAGGCTGATTATTACTGCTGCTCATATGTAGGTAGTAGCGCTTGGGTGTTCGGCGGAGGGACCAATCTGACCGTCCTAGG SEQ ID NO: 371 | MAWALLLLNLLTQDTGSWAQSA LTQPASVSGSPGQSITISCTGT SNDVGVYNHVSWYQQHPGKAPK LMIYDVSKRPSGVSNRFSGSKS GNTASLTISGLQAEDEADYYCC SYVGSSAWVFGGGTNLTVL SEQ ID NO: 370 | TGTSNDVGVYNHVS SEQ ID NO: 77 | DVSKRPS SEQ ID NO: 39 | CSVVGSSAWV SEQ ID NO: 83 |

TABLE 16-continued

Variable region sequences of further antibodies. CDRs are as identified by IMGT.

| Ab name | VH nucleotide | VH amino acid | HCDR1 | HCDR2 | HCDR3 |
|---|---|---|---|---|---|
| CL-141778 | ATGGCCTGGACCCCTCTGCTCACTCTCCTCACTCTTTGCATAGGTTC TGTGTTTCTCTGAGTCAGTCACCCTGTCTGTCTGTGCCTTGG GACAGACAGTCAGGATCACATGCCAAGGAGACAGCCTCAGAAGCTATTGT ACAAGTTGGTACCAGCAGAAGCCAGGACAGGCCCCTGTACTTGTCATCTA TGGTGAAAACAACCGGCCCTCAGGGATCCCAGACCGATTCTCTGGCTCCA GCTCAGGAAACACAGCTTCCTGACCATCACTGGGCTCAGGCGAAGAT GAGGCTGACTATTACTGTAACTCCCGGGACAGCAGTGGTAACCATCTGGT GTTCGGCGGAGGGACCAAGCTGACCGTCCTAGG SEQ ID NO: 376 | MAWTPLWLTLLTLCIGSVVSSE LTQDPAVSVALGQTVRITCQGD SLRSYCTSWYQQKPGQAPVLVI YGENNRPSGIPDRFSGSSSGNT ASLTITGAQAEDEADYCNSRD SSGNHLVFGGGTKLTVL SEQ ID NO: 372 | QGDSLRSYCTS SEQ ID NO: 373 | GENNRPS SEQ ID NO: 374 | NSRDSSGNHLV SEQ ID NO: 375 |
| CL-141780 | ATGGCCTGGACCCCCTCTGCTCACTCTCCTCACTCTTTGCATAGGTTC TGTGTTTCTCTGAGTCAGTCACCCTGTCTGTGTCTGTGGCCTTGG GACAGACAGTCAGGATCACATGCCAAGGAGACAGCCTCAGAATCTATTAT GCAAACTACAGCAGAAGCCAGGACAGGCCCCCTGTACTTGTCATCTA TGGTAAAAACAACCGGCCCTCAGGGATCCCAGACCGATTCTCTGGCTCCA ACTCAGGAAACACAGCTTCCTGACCATCACTGGGCTCAGGCGAAGAT GAGGCTGACTATTACTGTAACTCCCGGGACAGCAGTGGTAACCATCTGGT GTTCGGCGGAGGGACCAAACTGACCGTCCTAGG SEQ ID NO: 380 | MAWTPLWLTLLTLCIGSVVSSE LTQDPAVSVALGQTVRITCQGD SLRIYYANWYQQKPGQAPVLVI YGKNNRPSGIPDRFSGSNSGNT ASLTITGAQAEDEADYCNSRD SSGNHLVFGGGTKLTVL SEQ ID NO: 377 | QGDSLRIYYAN SEQ ID NO: 378 | GKNNRPS SEQ ID NO: 379 | NSRDSSGNHLV SEQ ID NO: 375 |
| CL-141771 | ATGGCCTGGACCCCCTCTCTGGCTCACTCTCCTCACTCTTTGCATAGGTTC TGTGTTTCTCTGAGTCAGTCACCCTGTCTGTCTGTGCCTTGG GACAGACAGTCAGGATCCAGGAGACAGCAGCCTCAGAAGCTATTAT GCAAACTACAGCAGAAGCCAGGACAGGCCCCTGTATTTGTCATCTA TGGTAAAAACAACCGGCCCTCAGGGATCCCAGACCGATTCTCTGGCTCCA GCTCAGGAAACACAGCTTCCTGACCATCACCGGGACCAGCAGCGAAGAT GAGGCTGACTATTACTGTAACTCCCGGGACAGCAGTGGTAACCATCTGGT GTTCGGCGGAGGGACCAAGCTGACCGTCCTAGG SEQ ID NO: 383 | MAWTPLWLTLLTLCIGSVVSSE LTQDPAVSVALGQTVRITCQGD SLRSYASWYQQKPGQAPVFVI YGKNNRPSGIPDRFSGSSSGNT ASLTITGAQAEDEADYCNSRD SSGNHLVFGGGTKLTVL SEQ ID NO: 381 | QGDSLRSYAS SEQ ID NO: 382 | GKNNRPS SEQ ID NO: 379 | NSRDSSGNHLV SEQ ID NO: 375 |
| CL-141814 | ATGGACATGAGAGTCCTCGCTCAGCTCCTGGGGCTCCTGCTGCTCTGTTT CCCAGGTGCCAGATGCCAGATGACCCAGTCCCAGTCCCATCCTCACTGT CTGCATCTGTCGGAGACAGAGTCACCATCACTTGTCGGCGAGTCAGGAC ATTAGGAATTATTTAGCCTGGTTTCAGCAGAAACCAGGGAAAGCCCCTAA GTCCCTGATCTATGCTGCATCCACTTTGCAATCTGGGGTCCCATCAAGT TCAGCGGCAGTGGATCTGGACAGATTTCACTCTCACCATCAGCAGCCTG CAGCCTGAAGATTTTGCAACTTATTACTGCCAACAGTATAATCGTTCCCC ATTCACTTTCGGCCCTGGGACCAGAGTGGATATCAAACG SEQ ID NO: 388 | MDMRVLAQLLGLLLLCFPGARC DIQMTQSPSSLSASVGDRVTIT CRASQDIRNYLAWFQQKPGKAP KSLIYAASTLQSGVPSKFSGSG SGTDFTLTISSLQPEDFATYYC QQYNRSPFTFGPGTRVDIK SEQ ID NO: 384 | RASQDIRNYLA SEQ ID NO: 385 | AASTLQS SEQ ID NO: 386 | QQYNRSPFT SEQ ID NO: 387 |
| CL-141813 | ATGGACATGAGAGTCCTCGCTCAGCTCCTGGGGCTCCTGCTGCTCTGTTT CCCAGGTGCCAGATGCCAGATGACCCAGTCCCAGTCCCATCCTCACTGT CTGCATCTGTAGGAGACAGAGTCACCATCACGTGTCGGCGAGTCAGGAC ATTAGCAATTATTTAGCCTGGATTCAGCAGAAACCCAGGGAAAGCCCCTAA GTCCCTGATCTATGCTGCGTCCACCTTGCAAAGTGGGGTCCCATCAAAGT SEQ ID NO: | MDMRVLAQLLGLLLLCFPGARC DIQMTQSPSSLSASVGDRVTIT CRASQDISNYLAWIQQKPGKAP KSLIYAASTLQSGVPSKFSGSG SGTDFTLTISSLQPEDFATYYC | RASQDISNYLA SEQ ID NO: 390 | AASTLQS SEQ ID NO: 386 | QQYHTYPFT SEQ ID NO: 391 |

TABLE 16-continued

Variable region sequences of further antibodies. CDRs are as identified by IMGT.

| Ab name | VH nucleotide | VH amino acid | HCDR1 | HCDR2 | HCDR3 |
|---|---|---|---|---|---|
| | TCAGCGGCAGTGGATCTGGGACAGATTTCACTCTCACCATCAGCAGCCTG CAGCCTGAAGATTTTGCAACTTATTACTGTCAACAGTATCATACTTACCC ATTCACTTTCGGCCCTGGGACCAAAGTGGATATCAAACG SEQ ID NO: 392 | QQYHTYPFTFGPGTKVDIK SEQ ID NO: 389 | | | |
| CL-141812 | ATGGACATGAGAGTCCTCGCTCAGCTCCTGGGGCTCCTGCTGCTCTGTTT CCCAGGTGCCAGATGTGACATCCAGATGACCCAGTCTCCATCCTCACTGT CTGCATCTGTAGGAGACAGAGTCACCATCACTTGTCGGGCGAGTCAGGGC ATTAGCAATTATTTAGCCTGGTTTCAGCAGAAACCAGGGAAAGCCCCTAA GTCCCTGATCTATGCTGCATCCAGTTTGCAAAGTGGGGTCCCATCAAAAT TCAGCGGCAGTGGATCTGGGACAGATTTCACTCTCACCATCAGCAGCCTG CAGCCTGAAGATTTTGCAACTTATTACTGCCAACAGTATAATAGTTACCC ATTCACTTTCGGCCCTGGGACCAAAGTGGATATCAAACG SEQ ID NO: 397 | MDMRVLAQLLGLLLLCFPGARC DIQMTQSPSSLSASVGDRVTIT CRASQGISNYLAWFQQKPGKAP KSLIYAASSLQSGVPSKFSGSG SGTDFTLTISSLQPEDFATYYC QQYNSYPFTFGPGTKVDIK SEQ ID NO: 393 | RASQGISNYLA SEQ ID NO: 394 | AASSLQS SEQ ID NO: 395 | QQYNSYPFT SEQ ID NO: 396 |

TABLE 17

Closest germline gene segment sequences

| Antibody name | H chain v segment | H chain d segment | H chain j segment | L chain v segment | L chain j segment |
|---|---|---|---|---|---|
| CL-141810 | IGHV3-23 | IGHD3-10 | IGHJ6 | IGLV2-23 | IGLJ3 |
| CL-141805 | IGHV1-3 | IGHD3-10 | IGHJ6 | IGLV2-23 | IGLJ3 |
| CL-141806 | IGHV1-3 | IGHD3-10 | IGHJ6 | IGLV2-23 | IGLJ3 |
| CL-141795 | IGHV1-3 | IGHD3-10 | IGHJ4 | IGLV2-23 | IGLJ3 |
| CL-141798 | IGHV3-20 | IGHD3-9 | IGHJ6 | IGLV2-23 | IGLJ3 |
| CL-141763 | IGHV3-13 | IGHD3-10 | IGHJ6 | IGLV2-23 | IGLJ3 |
| CL-141764 | IGHV6-1 | IGHD1-26 | IGHJ3 | IGLV2-23 | IGLJ3 |
| CL-141765 | IGHV3-13 | IGHD3-10 | IGHJ6 | IGLV2-23 | IGLJ3 |
| CL-141766 | IGHV1-3 | IGHD3-10 | IGHJ6 | IGLV2-23 | IGLJ3 |
| CL-141768 | IGHV3-23 | IGHD1-26 | IGHJ5 | IGLV2-23 | IGLJ3 |
| CL-141799 | IGHV1-3 | IGHD4-11 | IGHJ6 | IGLV2-23 | IGLJ3 |
| CL-141800 | IGHV1-3 | IGHD3-22 | IGHJ4 | IGLV2-23 | IGLJ3 |
| CL-141802 | IGHV1-3 | IGHD2-2 | IGHJ6 | IGLV2-23 | IGLJ3 |
| CL-141804 | IGHV4-4 | IGHD3-10 | IGHJ5 | IGLV2-23 | IGLJ3 |
| CL-141792 | IGHV1-3 | IGHD3-22 | IGHJ6 | IGLV2-23 | IGLJ3 |
| CL-141793 | IGHV6-1 | IGHD1-26 | IGHJ4 | IGLV2-23 | IGLJ3 |
| CL-141794 | IGHV6-1 | IGHD1-26 | IGHJ4 | IGLV2-23 | IGLJ3 |
| CL-141769 | IGHV1-3 | IGHD3-9 | IGHJ6 | IGLV2-23 | IGLJ3 |
| CL-141770 | IGHV1-3 | IGHD3-9 | IGHJ6 | IGLV2-23 | IGLJ3 |
| CL-141772 | IGHV1-3 | IGHD2-2 | IGHJ6 | IGLV2-23 | IGLJ3 |
| CL-141773 | IGHV2-5 | IGHD4-23 | IGHJ6 | IGLV2-23 | IGLJ3 |
| CL-141776 | IGHV1-3 | IGHD2-2 | IGHJ6 | IGLV2-23 | IGLJ3 |
| CL-141777 | IGHV1-3 | IGHD3-10 | IGHJ6 | IGLV2-23 | IGLJ3 |
| CL-141779 | IGHV1-3 | IGHD3-9 | IGHJ6 | IGLV2-23 | IGLJ3 |
| CL-141781 | IGHV1-3 | IGHD3-9 | IGHJ6 | IGLV2-23 | IGLJ3 |
| CL-141783 | IGHV1-3 | IGHD3-9 | IGHJ6 | IGLV2-23 | IGLJ3 |
| CL-141784 | IGHV1-3 | IGHD3-10 | IGHJ6 | IGLV2-23 | IGLJ3 |
| CL-141785 | IGHV1-3 | IGHD2-2 | IGHJ6 | IGLV2-23 | IGLJ3 |
| CL-141786 | IGHV1-3 | IGHD3-22 | IGHJ6 | IGLV2-23 | IGLJ3 |
| CL-141787 | IGHV1-3 | IGHD2-2 | IGHJ6 | IGLV2-23 | IGLJ3 |
| CL-141789 | IGHV1-3 | IGHD2-2 | IGHJ6 | IGLV2-23 | IGLJ3 |
| CL-141790 | IGHV1-3 | IGHD3-10 | IGHJ6 | IGLV2-23 | IGLJ3 |
| CL-141791 | IGHV1-3 | IGHD3-9 | IGHJ6 | IGLV2-23 | IGLJ3 |
| CL-141778 | IGHV3-15 | IGHD6-19 | IGHJ4 | IGLV3-19 | IGLJ3 |
| CL-141780 | IGHV3-15 | IGHD6-19 | IGHJ4 | IGLV3-19 | IGLJ3 |
| CL-141771 | IGHV3-15 | IGHD6-19 | IGHJ4 | IGLV3-19 | IGLJ3 |
| CL-141814 | IGHV3-15 | IGHD3-10 | IGHJ4 | IGKV1-16 | IGKJ3 |
| CL-141813 | IGHV3-15 | IGHD3-10 | IGHJ4 | IGKV1-16 | IGKJ3 |
| CL-141812 | IGHV3-15 | IGHD3-10 | IGHJ4 | IGKV1-16 | IGKJ3 |
| Ab-c82 | IGHV1-3 | IGHD3-10 | IGHJ6 | IGLV2-23 | IGLJ3 |
| Ab-c152 | IGHV1-3 | IGHD3-10 | IGHJ4 | IGLV2-23 | IGLJ3 |
| Ab-c194 | IGHV1-3 | IGHD6-19 | IGHJ6 | IGLV2-14 | IGLJ3 |
| Ab-c265 | IGHV1-2 | IGHD6-19 | IGHJ6 | IGKV4-1 | IGKJ1 |
| Ab-c1281 | IGHV1-3 | IGHD2-2 | IGHJ6 | IGLV2-23 | IGLJ3 |
| Ab-c1315 | IGHV1-3 | IGHD2-2 | IGHJ6 | IGLV2-23 | IGLJ3 |
| Ab-c1731 | IGHV1-3 | IGHD2-2 | IGHJ6 | IGLV2-23 | IGLJ3 |

TABLE 18

Variable region sequences of additionally selected anti-CSP antibodies
This table identifies the VH, VL and CDR sequences of the antibodies described in Example 18: Ab-c82, Ab-c152, Ab-c194, Ab-c265, Ab-c1281, Ab-c1315 and Ab-c1731. These antibodies all represent antibodies of the present invention, as do antibodies comprising the CDRs (HCDRs and/or LCDRs), the VH domain and/or the VL domain of any of these antibodies.

| Antibody | | Sequence |
|---|---|---|
| Ab-c82 | VH nucleotide (SEQ ID NO: 1) | ATGGACTGGACCTGGAGGATCCTCTTTTTGGTGGCAGCAGCCACAGGTG CCCACTCCCAGGTCCAGCTTGTGCAGTCTGGGGCTGAGGTGAAGAAGCC TGGGGCCTCAGTGAAGGTTTCCTGCAAGGCTTCTGGATACACCTTCACA AACTATGCTATGCATTGGGTGCGCCAGGCCCCCGGACAAAGGCTTGAGT GGATGGGATGGATCAACGCTGGCAATGGTAATACAAAATATTCACAAAA TTTCCAGGGCAGAGTCACCATTACCAGGGACACATCCGCGAGCACAGCC TACATGGAGCTGAGCAGCCTGAGATCTGAAGACACGGCTGTGTATTACT GTGCGAGAGATGAATACTATGCTTCGGGGAGTTATTATGACTACTACTA CTACGGTATGGACGTCTGGGGCCAAGGGACCACGGTCACCGTCACCTCA GC |
| | VH amino acid (SEQ ID NO: 182) | MDWTWRILFLVAAATGAHSQVQLVQSGAEVKKPGASVKVSCKASGYTFT NYAMHWVRQAPGQRLEWMGWINAGNGNTKYSQNFQGRVTITRDTSASTA YMELSSLRSEDTAVYYCARDEYYASGSYYDYYYYGMDVWGQGTTVTVTS |
| | HCDR1 IMGT (SEQ ID NO: 399) | GYTFTNYA |
| | HCDR2 IMGT (SEQ ID NO: 400) | INAGNGNT |
| | HCDR3 IMGT (SEQ ID NO: 401) | ARDEYYASGSYYDYYYYGMDV |
| | HCDR1 Kabat (SEQ ID NO: 402) | NYAMH |
| | HCDR2 Kabat | WINAGNGNTKYSQNFQG |

TABLE 18-continued

Variable region sequences of additionally selected anti-CSP antibodies
This table identifies the VH, VL and CDR sequences of the antibodies described in Example 18: Ab-c82, Ab-c152, Ab-c194, Ab-c265, Ab-c1281, Ab-c1315 and Ab-c1731. These antibodies all represent antibodies of the present invention, as do antibodies comprising the CDRs (HCDRs and/or LCDRs), the VH domain and/or the VL domain of any of these antibodies.

| Antibody | | Sequence |
|---|---|---|
| | (SEQ ID NO: 403) HCDR3 Kabat | DEYYASGSYYDYYYYGMDV |
| | (SEQ ID NO: 404) VL nucleotide (SEQ ID NO: 405) | ATGGCCTGGGCTCTGCTGCTCCTCAACCTCCTCACTCAGGACACAGGGT CCTGGGCCCAGTCTGCCCTGACTCAGCCTGCCTCCGTGTCTGGGTCTCC TGGACAGTCGATCACCATCTCCTGCACTGGAACCAGCAGTGATGTTGGT GTTTATAACTATGTCTCCTGGTTCCAACAGCACCCAGGCAAAGCCCCCA AACTCATGATTTATAATGTCAGTAAGCGGCCCTCAGGGGTTTCTAATCG CTTCTCTGGCTCCAAGTCTGGCAACACGGCCTCCCTGACAATCTCTGGG CTCCAGGCTGAGGACGAGGCTGATTATTACTGCTGCTCATATGCAGGTA GTAGCACTTGGGTGTTCGGCGGAGGGACCAACCTGACCGTCCTAGG |
| | VL amino acid (SEQ ID NO: 406) | MAWALLLLNLLTQDTGSWAQSALTQPASVSGSPGQSITISCTGTSSDVG VYNYVSWFQQHPGKAPKLMIYNVSKRPSGVSNRFSGSKSGNTASLTISG LQAEDEADYYCCSYAGSSTWVFGGGTNLTVL |
| | LCDR1 IMGT (SEQ ID NO: 407) | SSDVGVYNY |
| | LCDR2 IMGT (SEQ ID NO: 408) | NVS |
| | LCDR3 IMGT (SEQ ID NO: 409) | CSYAGSSTWV |
| | LCDR1 Kabat (SEQ ID NO: 410) | TGTSSDVGVYNYVS |
| | LCDR2 Kabat (SEQ ID NO: 411) | NVSKRPS |
| | LCDR3 Kabat (SEQ ID NO: 412) | CSYAGSSTWV |
| Ab-c152 | VH nucleotide (SEQ ID NO: 413 | ATGGACTGGACCTGGAGGATCCTCTTTTTGGTGGCAGCAGCCACAGGTG CCCACTCCCAGGTCCAGCTTGTGCAGTCTGGGGCTGAGGTGAAGAAGCC TGGGGCCTCAGTGAAGGTTTCGTGCAAGGCTTCTGGATACACCTTCACT AGCTATGCTATGCATTGGGTGCGCCAGGCCCCCGGACAAAGGCTTGAGT GGATGGGATGGATCAACGCTGGCAATGGTAACACAAAATATTCACAGAA GTTCCAGGGCAGAGTCACCATTACCAGGGACACATCCGCGAGCACAGCC TACATGGAGCTGAGCAGCCTGAGATCTGAAGACACGGCTGTGTATTACT GTGCGAGAGGGGGATCGAGGGACTACTGGGGCCAGGGAACCCTGGTCAC CGTCTCCTCAGC |
| | VH amino acid (SEQ ID NO: 414) | MDWTWRILFLVAAATGAHSQVQLVQSGAEVKKPGASVKVSCKASGYTFT SYAMHWVRQAPGQRLEWMGWINAGNGNTKYSQKFQGRVTITRDTSASTA YMELSSLRSEDTAVYYCARGGSRDYWGQGTLVTVSS |
| | HCDR1 IMGT (SEQ ID NO: 415) | GYTFTSYA |
| | HCDR2 IMGT (SEQ ID NO: 416) | INAGNGNT |
| | HCDR3 IMGT (SEQ ID NO: 417) | ARGGSRDY |
| | HCDR1 Kabat | SYAMH |

TABLE 18-continued

Variable region sequences of additionally selected anti-CSP antibodies
This table identifies the VH, VL and CDR sequences of the antibodies described in Example 18: Ab-c82, Ab-c152, Ab-c194, Ab-c265, Ab-c1281, Ab-c1315 and Ab-c1731. These antibodies all represent antibodies of the present invention, as do antibodies comprising the CDRs (HCDRs and/or LCDRs), the VH domain and/or the VL domain of any of these antibodies.

| Antibody | | Sequence |
|---|---|---|
| | (SEQ ID NO: 418) | |
| | HCDR2 Kabat (SEQ ID NO: 419) | WINAGNGNTKYSQKFQG |
| | HCDR3 Kabat (SEQ ID NO: 420) | GGSRDY |
| | VL nucleotide (SEQ ID NO: 421) | ATGGCCTGGGCTCTGCTGCTCCTCAACCTCCTCACTCAGGACACAGGGT CCTGGGCCCAGTCTGCCCTGACTCAGCCTGCCTCCGTGTCTGGGTCTCC TGGACAGTCGATCACCATCTCCTGCACTGGAACCAGCAGTGATGTTGGT GGTTATAACTATGTCTCCTGGTACCAACAGCACCCAGGCAAAGCCCCCA AACTCATGATTTATGATGTCAGTAAGCGGCCCTCAGGGGTTTCTAATCG CTTCTCTGGCTCCAAGTCTGGCAACACGGCCTCCTGACAATCTCTGGG CTCCAGGCTGAGGACGAGGCTGATTATTACTGCTGCTCATATGCAGGTA GTAGCACTTGGGTGTTCGGCGGAGGGACCAAGCTGACCGTCCTAGG |
| | VL amino acid (SEQ ID NO: 422) | MAWALLLLNLLTQDTGSWAQSALTQPASVSGSPGQSITISCTGTSSDVG GYNYVSWYQQHPGKAPKLMIYDVSKRPSGVSNRFSGSKSGNTASLTISG LQAEDEADYYCCSYAGSSTWVFGGGTKLTVL |
| | LCDR1 IMGT (SEQ ID NO: 423) | SSDVGGYNY |
| | LCDR2 IMGT (SEQ ID NO: 424) | DVS |
| | LCDR3 IMGT (SEQ ID NO: 425) | CSYAGSSTWV |
| | LCDR1 Kabat (SEQ ID NO: 426) | TGTSSDVGGYNYVS |
| | LCDR2 Kabat (SEQ ID NO: 427) | DVSKRPS |
| | LCDR3 Kabat (SEQ ID NO: 428) | CSYAGSSTWV |
| Ab-c194 | VH nucleotide (SEQ ID NO: 429) | ATGGACTGGACCTGGAGGATCCTCTTTTTGGTGGCAGCAGCCACAGGTG CCCACTCCCAGGTCCAACTTGTGCAGTCTGGGGCTGAGGTGAAGAAGCC TGGGGCCTCAGTGAAGGTTTCCTGCAAGGCTTCTGGATACACCTTCATT AGATATACTTTGCATTGGGTGTGCCAGGCCCCCGGACAAAGGCTTGAGT GGATGGGATGGATCAATGTTGGCAATGGTGACACAAAATATTCACAGAA GTTCCAGGGCAGAGTCACCCTTACCAGGGACACATCCGCGAGTACAGCC TACATGGAGGTGAGCAGTTTGAGATCTGAAGACACGGCTGTGTATTACT GTGCGAGAGAGGGTATAGCAGTGGCCGGAACGGGAAAGTACTACAACTT CTACGGGATGGACGTCTGGGGCCAAGGGACCACGGTCACCGTCTCCTCA GC |
| | VH amino acid (SEQ ID NO: 430) | MDWTWRILFLVAAATGAHSQVQLVQSGAEVKKPGASVKVSCKASGYTFI RYTLHWVCQAPGQRLEWMGWINVGNGDTKYSQKFQGRVTLTRDTSASTA YMEVSSLRSEDTAVYYCAREGIAVAGTGKYYNFYGMDVWGQGTTVTVSS |
| | HCDR1 IMGT (SEQ ID NO: 431) | GYTFIRYT |
| | HCDR2 IMGT (SEQ ID NO: 432) | INVGNGDT |
| | HCDR3 IMGT | AREGIAVAGTGKYYNFYGMDV |

TABLE 18-continued

Variable region sequences of additionally selected anti-CSP antibodies
This table identifies the VH, VL and CDR sequences of the antibodies described in Example 18: Ab-c82, Ab-c152, Ab-c194, Ab-c265, Ab-c1281, Ab-c1315 and Ab-c1731. These antibodies all represent antibodies of the present invention, as do antibodies comprising the CDRs (HCDRs and/or LCDRs), the VH domain and/or the VL domain of any of these antibodies.

| Antibody | | Sequence |
|---|---|---|
| | (SEQ ID NO: 433) HCDR1 Kabat | |
| | (SEQ ID NO: 434) HCDR2 Kabat | RYTLH |
| | (SEQ ID NO: 435) HCDR3 Kabat | WINVGNGDTKYSQKFQG |
| | (SEQ ID NO: 436) | EGIAVAGTGKYYNFYGMDV |
| | VL nucleotide (SEQ ID NO: 437) | ATGGCCTGGGCTCTGCTGCTCCTCACCCTCCTCACTCAGGGCACAGGGT CCTGGGCCCAGTCTGCCCTGACTCAGCCTGCCTCCGTGTCTGGGTCTCC TGGACAGTCGATCACCATCTCCTGCACTGGAACCAGCAGTGACGTTGGT GGTTTTAACTATGTCTCCTGGTACCAACAGCACCCAGGCAAAGCCCCCA CACTCATGATTTATGAGGTCACTTTTCGGCCCTCAGGGGTTTCTAATCG CTTCTCTGGCTCCAAGTCTGGCAACACGGCCTCCTGACCATCTCTGGG CTCCAGGCTGAGGACGAGGCTGATTATTACTGCAGCTCATATATAAGCG GCAACACTTGGGTGTTCGGCGGAGGGACCAAGCTGACCGTCCTAGG |
| | VL amino acid (SEQ ID NO: 438) | MAWALLLLTLLTQGTGSWAQSALTQPASVSGSPGQSITISCTGTSSDVG GFNYVSWYQQHPGKAPTLMIYEVTFRPSGVSNRFSGSKSGNTASLTISG LQAEDEADYYCSSYISGNTWVFGGGTKLTVL |
| | LCDR1 IMGT (SEQ ID NO: 439) | SSDVGGFNY |
| | LCDR2 IMGT (SEQ ID NO: 440) | EVT |
| | LCDR3 IMGT (SEQ ID NO: 441) | SSYISGNTWV |
| | LCDR1 Kabat (SEQ ID NO: 442) | TGTSSDVGGFNYVS |
| | LCDR2 Kabat (SEQ ID NO: 443) | EVTFRPS |
| | LCDR3 Kabat (SEQ ID NO: 444) | SSYISGNTWV |
| Ab-c265 | VH nucleotide (SEQ ID NO: 445) | ATGGACTGGACCTGGAGGATCCTCTTCTTGGTGGCAGCAGCCACAGGAG CCCACTCCCAGGTGCAGCTGGTGCAGTCTGGGGCTGAGGTGAAGAAGCC TGGGGCCTCAGTGAAGGTCTCCTGCAAGGCTTCTGGATACACCTTCACC GCCTACTATATACACTGGGTGCGACAGGCCCCTGGACAAGGGCTTGAGT GGATGGGATGGATCAACCCTAACAGTGGTGGCACAAACTATGCACAGAA GTTTCAGGACTGGGTCACCATGACCAGGGACACGTCCATCACCACAGCC TACATGGAGCTGAGTAGACTGAAATCTGACGACACGGCCATATATTACT GTGCGAGAGACGGGGAGGCTGGTACGAACTACTACTACGGTATGGACGT CTGGGGCCAAGGGACCACGGTCACCGTCTCCTCAGC |
| | VH amino acid (SEQ ID NO: 446) | MDWTWRILFLVAAATGAHSQVQLVQSGAEVKKPGASVKVSCKASGYTFT AYYIHWVRQAPGQGLEWMGWINPNSGGTNYAQKFQDWVTMTRDTSITTA YMELSRLKSDDTAIYYCARDGEAGTNYYYGMDVWGQGTTVTVSS |
| | HCDR1 IMGT (SEQ ID NO: 447) | GYTFTAYY |
| | HCDR2 IMGT | INPNSGGT |

TABLE 18-continued

Variable region sequences of additionally selected anti-CSP antibodies
This table identifies the VH, VL and CDR sequences of the antibodies described in Example 18: Ab-c82, Ab-c152, Ab-c194, Ab-c265, Ab-c1281, Ab-c1315 and Ab-c1731. These antibodies all represent antibodies of the present invention, as do antibodies comprising the CDRs (HCDRs and/or LCDRs), the VH domain and/or the VL domain of any of these antibodies.

| Antibody | | Sequence |
|---|---|---|
| | (SEQ ID NO: 448) HCDR3 IMGT | ARDGEAGTNYYYGMDV |
| | (SEQ ID NO: 449) HCDR1 Kabat | AYYIH |
| | (SEQ ID NO: 450) HCDR2 Kabat | WINPNSGGTNYAQKFQD |
| | (SEQ ID NO: 451) HCDR3 Kabat | DGEAGTNYYYGMDV |
| | VL nucleotide (SEQ ID NO: 452) | ATGGTGTTGCAGACCCAGGTCTTCATTTCTCTGTTGCTCTGGATCTCTG GTGCCTACGGGGACATCGTGATGACCCAGTCTCCAGACTCCCTGGCTGT GTCTCTGGGCGAGAGGGCCACCATCAACTGCAAGTCCAGTCAGAGTGTT TTATACAGCTCCAACAATAAGAACTACTTGGCTTGGTACCAGCAGAAAC CAGGACAGCCTCCTAAGCTGCTCATTTACTGGGCATCTACCCGGGAATC CGGGGTCCCTGACCGATTCAGTGGCAGCGGGTCTGGGACAGATTTCGCT CTCACCATCAGCAGCCTGCAGGCTGAAGATGTGGCAGTTTATTACTGTC AGCAATATTATAGTACTCCGTGGACGTTCGGCCAAGGGACCAAGGTGGA AATCAAACG |
| | VL amino acid (SEQ ID NO: 453) | MVLQTQVFISLLLWISGAYGDIVMTQSPDSLAVSLGERATINCKSSQSV LYSSNNKNYLAWYQQKPGQPPKLLIYWASTRESGVPDRFSGSGSGTDFA LTISSLQAEDVAVYYCQQYYSTPWTFGQGTKVEIK |
| | LCDR1 IMGT (SEQ ID NO: 454) | QSVLYSSNNKNY |
| | LCDR2 IMGT (SEQ ID NO: 455) | WAS |
| | LCDR3 IMGT (SEQ ID NO: 456) | QQYYSTPWT |
| | LCDR1 Kabat (SEQ ID NO: 457) | KSSQSVLYSSNNKNYLA |
| | LCDR2 Kabat (SEQ ID NO: 458) | WASTRES |
| | LCDR3 Kabat (SEQ ID NO: 459) | QQYYSTPWT |
| Ab-c1281 | VH nucleotide (SEQ ID NO: 460) | ATGGACTGGACCTGGAGGATCCTCTTTTTGGTGGCAGCAGCCGCAGGTG CCCACTCCCAGGTCCAGCTTGTGCAGTCTGGGGCTGAGGTGAAGAAGCC TGGGGCCTCAGTGAAGGTTTCCTGCAAGGCTTCTGGATTCACCTTCACT GACTATGCTATGCATTGGGTGCGCCAGGCCCCCGGACAAAGGCTTGAGT GGATGGGTTGGATCAACGCTGGCAATGGTTACACAAAATATTCACAGAA GTTCCAGGTCAGACTCACCATTACCAGGGACACATTCGCGAGCACAGTC TACATGGAGCTGAGCAGCCTGAGATCTGAAGACACGGCTGTGTATTACT GTGCGAGAGATGGGTTTTGTCCTAGTACCACTTGCTCTGGTTACTACGG TATGGACGTCTGGGGCCAAGGGACCACGGTCACCGTCTCCTCAGC |
| | VH amino acid (SEQ ID NO: 461) | MDWTWRILFLVAAAAGAHSQVQLVQSGAEVKKPGASVKVSCKASGFTFT DYAMHWVRQAPGQRLEWMGWINAGNGYTKYSQKFQVRLTITRDTFASTV YMELSSLRSEDTAVYYCARDGFCPSTTCSGYYGMDVWGQGTTVTVSS |
| | HCDR1 IMGT | GFTFTDYA |

TABLE 18-continued

Variable region sequences of additionally selected anti-CSP antibodies
This table identifies the VH, VL and CDR sequences of the antibodies described in Example 18: Ab-c82, Ab-c152, Ab-c194, Ab-c265, Ab-c1281, Ab-c1315 and Ab-c1731. These antibodies all represent antibodies of the present invention, as do antibodies comprising the CDRs (HCDRs and/or LCDRs), the VH domain and/or the VL domain of any of these antibodies.

| Antibody | Sequence |
|---|---|
| (SEQ ID NO: 463) HCDR2 IMGT | |
| (SEQ ID NO: 464) HCDR3 IMGT | INAGNGYT |
| (SEQ ID NO: 465) HCDR1 Kabat | ARDGFCPSTTCSGYYGMDV |
| (SEQ ID NO: 466) HCDR2 Kabat | DYAMH |
| (SEQ ID NO: 467) HCDR3 Kabat | WINAGNGYTKYSQKFQV |
| (SEQ ID NO: 468) VL nucleotide (SEQ ID NO: 469) | DGFCPSTTCSGYYGMDV |
| VL nucleotide (SEQ ID NO: 469) | ATGGCCTGGGCTCTGCTGCTCCTCAACCTCCTCACTCAGGACACAGGGT CCTGGGCCCAGTCTGCCCTGACTCAGCCTGCCTCCGTGTCTGGGTCTCC TGGACAGTCGATCACCATCTCCTGCACTGGAACCAGCAGTGATGTTGGT GCTTATAACTATGTCTCCTGGTACCAACAGCACCCAGGCAAAGCCCCCA AACTCATGATTTATGATGTCAATACGCGGCCCTCAGGGGTTTCTACTCG CTTCTCTGCCTCCAAGTCTGGCAACACGGCCTCCCTGACAGTCTCTGGG CTCCAGGCTGAGGACGAGGCTGTTTATTACTGCTCCTCATATGCAGGTA GTAGCACTTGGATTTTCGGCGGAGGGACCAAGCTGACCGTCCTAGG |
| VL amino acid (SEQ ID NO: 470) | MAWALLLLNLLTQDTGSWAQSALTQPASVSGSPGQSITISCTGTSSDVG AYNYVSWYQQHPGKAPKLMIYDVNTRPSGVSTRFSASKSGNTASLTVSG LQAEDEAVYYCSSYAGSSTWIFGGGTKLTVL |
| LCDR1 IMGT (SEQ ID NO: 471) | SSDVGAYNY |
| LCDR2 IMGT (SEQ ID NO: 472) | DVN |
| LCDR3 IMGT (SEQ ID NO: 473) | SSYAGSSTWI |
| LCDR1 Kabat (SEQ ID NO: 474) | TGTSSDVGAYNYVS |
| LCDR2 Kabat (SEQ ID NO: 475) | DVNTRPS |
| LCDR3 Kabat (SEQ ID NO: 476) | SSYAGSSTWI |
| Ab-c1315 VH nucleotide (SEQ ID NO: 477) | ATGGACTGGACCTGGAGGATCCTCTTTTTGGTGGCAGCAGCCGCAGGTG CCCACTCCCAGGTCCAGCTTGTGCAGTCTGGGGCTGAGGTGAAGAAGCC TGGGGCCTCAGTGAAGGTTTCCTGCAAGGCTTCTGGATTCACCTTCACT GACTATGCTATGCATTGGGTGCGCCAGGCCCCCGGACAAAGGCTTGAGT GGATGGGTTGGATCAACGCTGGCAATGGTTACACAAAATATTCACAGCA GTTCCAGGTCAGACTCACCATTACCAGGGACACATTCGCGAGCACAGTC |

TABLE 18-continued

Variable region sequences of additionally selected anti-CSP antibodies
This table identifies the VH, VL and CDR sequences of the antibodies described in Example 18: Ab-c82, Ab-c152, Ab-c194, Ab-c265, Ab-c1281, Ab-c1315 and Ab-c1731. These antibodies all represent antibodies of the present invention, as do antibodies comprising the CDRs (HCDRs and/or LCDRs), the VH domain and/or the VL domain of any of these antibodies.

| Antibody | Sequence |
|---|---|
| | TACATGGAGCTGAGCAGCCTGACATCTGAAGACACGGCTGTGTATTACT |
| | GTGCGAGAGATGGGTTTTGTCCTAGTACCACTTGCTCTGGTTACTACGG |
| | TATGGACGTCTGGGGCCAAGGGACCACGGTCACCGTCTCCTCAGC |
| VH amino acid (SEQ ID NO: 478) | MDWTWRILFLVAAAAGAHSQVQLVQSGAEVKKPGASVKVSCKASGFTFT DYAMHWVRQAPGQRLEWMGWINAGNGYTKYSQQFQVRLTITRDTFASTV YMELSSLTSEDTAVYYCARDGFCPSTTCSGYYGMDVWGQGTTVTSS |
| HCDR1 IMGT (SEQ ID NO: 479) | GFTFTDYA |
| HCDR2 IMGT (SEQ ID NO: 480) | INAGNGYT |
| HCDR3 IMGT (SEQ ID NO: 481) | ARDGFCPSTTCSGYYGMDV |
| HCDR1 Kabat (SEQ ID NO: 482) | DYAMH |
| HCDR2 Kabat (SEQ ID NO: 483) | WINAGNGYTKYSQQFQV |
| HCDR3 Kabat (SEQ ID NO: 484) | DGFCPSTTCSGYYGMDV |
| VL nucleotide (SEQ ID NO: 485) | ATGGCCTGGGCTCTGCTGCTCCTCAACCTCCTCACTCAGGACACAGGGT CCTGGGCCCAGTCTGCCCTGACTCAGCCTGCCTCCGTGTCTGGGTCTCC TGGACAGTCGATCACCATCTCCTGCACTGGAACCAGCAGTGATGTTGGT GCTTATAACTATGTCTCCTGGTACCAACAGCACCCAGGCAAAGCCCCCA AACTCATGATTTATGATGTCAATACGCGGCCCTCAGGGGTTTCTACTCG CTTCTCTGCCTCCAAGTCTGGCAACACGGCCTCCCTGACAGTCTCTGGG CTCCAGGCTGAGGACGAGGCTGTTTATTACTGCTCCTCATATGCAGGTA GTAGCACTTGGATTTTCGGCGGAGGGACCAAGCTGACCGTCCTAGG |
| VL amino acid (SEQ ID NO: 486) | MAWALLLLNLLTQDTGSWAQSALTQPASVSGSPGQSITISCTGTSSDVG AYNYVSWYQQHPGKAPKLMIYDVNTRPSGVSTRFSASKSGNTASLTVSG LQAEDEAVYYCSSYAGSSTWIFGGGTKLTVL |
| LCDR1 IMGT (SEQ ID NO: 487) | SSDVGAYNY |
| LCDR2 IMGT (SEQ ID NO: 488) | DVN |
| LCDR3 IMGT (SEQ ID NO: 489) | SSYAGSSTWI |
| LCDR1 Kabat (SEQ ID NO: 490) | TGTSSDVGAYNYVS |
| LCDR2 Kabat (SEQ ID NO: 491) | DVNTRPS |
| LCDR3 Kabat (SEQ ID NO: 492) | SSYAGSSTWI |
| Ab-c1731 VH nucleotide (SEQ ID NO: 493) | ATGGACTGGACCTGGAGGATCCTCTTTTTGGTGGCAGCAGCCACAGGTG CCCACTCCCAGGTCCAGCTTGTGCAGTCTGGGGCTGAGGTGAAGAAGCC TGGGGCCTCAGTGAAGGTTTCCTGTAAGGCTTCTGGATACATCTTTATT |

TABLE 18-continued

Variable region sequences of additionally selected anti-CSP antibodies
This table identifies the VH, VL and CDR sequences of the antibodies described in Example 18: Ab-c82, Ab-c152, Ab-c194, Ab-c265, Ab-c1281, Ab-c1315 and Ab-c1731. These antibodies all represent antibodies of the present invention, as do antibodies comprising the CDRs (HCDRs and/or LCDRs), the VH domain and/or the VL domain of any of these antibodies.

| Antibody | Sequence |
|---|---|
| | AACTATGCTATGCAATGGGTGCGCCAGGCCCCCGGACAAAGGCTTGAGT<br>GGATGGGATGGATCAACGCTGGCAACGGTTACACAAAATATTCACAGAA<br>GTTCCAGGGCAGAGTCACCATCACCAGGGACATATCCGCGAGCACAGTC<br>TACATGGAGCTGAGCAGCCTGAGATCTGAAGACACGGCTGTGTATTACT<br>GTGCGAGAGATGGATTTTGTAGGACAACCAGCTGCTCCGACCACTACGG<br>TATGGACGTCTGGGGCCAAGGGACCACGGTCACCGTCTCCTCAGC |
| VH amino acid (SEQ ID NO: 494) | MDWTWRILFLVAAATGAHSQVQLVQSGAEVKKPGASVKVSCKASGYIFI<br>NYAMQWVRQAPGQRLEWMGWINAGNGYTKYSQKFQGRVTITRDISASTV<br>YMELSSLRSEDTAVYYCARDGFCRTTSCSDHYGMDVWGQGTTVTVSS |
| HCDR1 IMGT (SEQ ID NO: 495) | GYIFINYA |
| HCDR2 IMGT (SEQ ID NO: 496) | INAGNGYT |
| HCDR3 IMGT (SEQ ID NO: 497) | ARDGFCRTTSCSDHYGMDV |
| HCDR1 Kabat (SEQ ID NO: 498) | NYAMQ |
| HCDR2 Kabat (SEQ ID NO: 499) | WINAGNGYTKYSQKFQG |
| HCDR3 Kabat (SEQ ID NO: 500) | DGFCRTTSCSDHYGMDV |
| VL nucleotide (SEQ ID NO: 501) | ATGGCCTGGGCTCTGCTGCTCCTCAACCTCCTCACTCAGGACACAGGGT<br>CCTGGGCCCAGTCTGCCCTGACTCAGCCTGCCTCCGTGTCTGGGTCTCC<br>TGGACAGTCGATCACCATCTCCTGCACTGGAACCAGCAGTGATGTTGGT<br>GGTTATAACTATGTCTCCTGGTACCAACAACACCCAGGCAAAGCCCCCA<br>AACTCATGATTTATGATGTCAGTAAGCGGCCCTCAGGGGTTTCTGATCG<br>CTTCTCTGGCTCCAAGTCTGGCAACACGGCCTCCCTGACAATCTCTGGG<br>CTCCAGACTGAGGACGAGGCTGATTTTTACTGCTGCTCATATGCAGGTA<br>GTAGCACTTGGGTGTTCGGCGGAGGGACCAAGCTGACCGTCCTAGG |
| VL amino acid (SEQ ID NO: 502) | MAWALLLLNLLTQDTGSWAQSALTQPASVSGSPGQSITISCTGTSSDVG<br>GYNYVSWYQQHPGKAPKLMIYDVSKRPSGVSDRFSGSKSGNTASLTISG<br>LQTEDEADFYCCSYAGSSTWVFGGGTKLTVL |
| LCDR1 IMGT (SEQ ID NO: 503) | SSDVGGYNY |
| LCDR2 IMGT (SEQ ID NO: 504) | DVS |
| LCDR3 IMG (SEQ ID NO: 505) | CSYAGSSTWV |
| LCDR1 Kabat (SEQ ID NO: 506) | TGTSSDVGGYNYVS |
| LCDR2 Kabat (SEQ ID NO: 507) | DVSKRPS |
| LCDR3 Kabat (SEQ ID NO: 508) | CSYAGSSTWV |

What is claimed is:

1. An isolated antibody that specifically binds the circumsporozoite protein (CSP) of *Plasmodium falciparum*, comprising the heavy and light chain complementarity determining regions of antibody 666 (SEQ ID Nos: 3-5 and 8-10, respectively), antibody 667 (SEQ ID Nos: 13-15 and 18-20, respectively), antibody 668 (SEQ ID Nos: 23-25 and 28-30, respectively) or antibody 669 (SEQ ID Nos: 33-35 and 38-40, respectively).

2. The antibody according to claim 1, wherein the antibody is an IgG.

3. The antibody according to claim 2, wherein the antibody is a human IgG1.

4. The antibody according to claim 2, wherein the IgG comprises a CH2 domain having "YTE" mutations to extend the in vivo half-life of the antibody, the YTE mutations being tyrosine at residue 252, threonine at residue 254 and glutamic acid at residue 256, numbered according to the EU index of Kabat.

5. A composition comprising an isolated antibody according to claim 1 and a pharmaceutically acceptable excipient.

6. The antibody according to claim 1, comprising the heavy and light chain complementarity determining regions of antibody 666 (SEQ ID Nos: 3-5 and 8-10, respectively).

7. The antibody according to claim 1, comprising the heavy and light chain complementarity determining regions of antibody 667 (SEQ ID Nos: 13-15 and 18-20, respectively).

8. The antibody according to claim 1, comprising the heavy and light chain complementarity determining regions of antibody 668 (SEQ ID Nos: 23-25 and 28-30, respectively).

9. The antibody according to claim 1, comprising the heavy and light chain complementarity determining regions of antibody 669 (SEQ ID Nos: 33-35 and 38-40, respectively).

10. An isolated antibody comprising the VH domain of antibody 666 (SEQ ID NO: 2), and the VL domain of antibody 666 (SEQ ID NO: 7).

11. An isolated antibody comprising the VH domain of antibody 667 (SEQ ID NO: 12), and the VL domain of antibody 667 (SEQ ID NO: 17).

12. An isolated antibody comprising the VH domain of antibody 668 (SEQ ID NO: 22), and the VL domain of antibody 668 (SEQ ID NO: 27).

13. An isolated antibody comprising the VH domain of antibody 669 (SEQ ID NO: 32), and the VL domain of antibody 669 (SEQ ID NO: 37).

* * * * *

SEQUENCE LISTING

<160> NUMBER OF SEQ ID NOS: 546

<210> SEQ ID NO 1
<211> LENGTH: 443
<212> TYPE: DNA
<213> ORGANISM: Homo sapiens

<400> SEQUENCE: 1

| | |
|---|---|
| atggactgga cctggaggat cctcttttg gtggcagcag ccacaggtgc ccactcccag | 60 |
| gtccagcttg tgcagtctgg ggctgaggtg aagaagcctg gggcctcagt gaaggtttcc | 120 |
| tgcaaggctt ctggatacac cttcacaaac tatgctatgc attgggtgcg ccaggccccc | 180 |
| ggacaaaggc ttgagtggat gggatggatc aacgctggca atggtaatac aaaatattca | 240 |
| caaaatttcc agggcagagt caccattacc aggacacat ccgcgagcac agcctacatg | 300 |
| gagctgagca gcctgagatc tgaagacacg gctgtgtatt actgtgcgag agatgaatac | 360 |
| tatgcttcgg ggagttatta tgactactac tactacggta tggacgtctg gggccaaggg | 420 |
| accacggtca ccgtcacctc agc | 443 |

<210> SEQ ID NO 2
<211> LENGTH: 128
<212> TYPE: PRT
<213> ORGANISM: Homo sapiens

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Asn Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Glu Tyr Tyr Ala Ser Gly Ser Tyr Tyr Asp Tyr Tyr Tyr
            100                 105                 110

Tyr Gly Met Asp Val Trp Gly Gln Gly Thr Thr Val Thr Val Thr Ser
        115                 120                 125

<210> SEQ ID NO 3
<211> LENGTH: 10
<212> TYPE: PRT
<213> ORGANISM: Homo sapiens

<400> SEQUENCE: 3

Gly Tyr Thr Phe Thr Asn Tyr Ala Met His
1               5                   10

<210> SEQ ID NO 4
<211> LENGTH: 17
<212> TYPE: PRT
<213> ORGANISM: Homo sapiens

<400> SEQUENCE: 4

Trp Ile Asn Ala Gly Asn Gly Asn Thr Lys Tyr Ser Gln Asn Phe Gln
1               5                   10                  15

Gly

<210> SEQ ID NO 5
<211> LENGTH: 19
<212> TYPE: PRT
<213> ORGANISM: Homo sapiens

<400> SEQUENCE: 5

Asp Glu Tyr Tyr Ala Ser Gly Ser Tyr Tyr Asp Tyr Tyr Tyr Gly
1               5                   10                  15

Met Asp Val

<210> SEQ ID NO 6
<211> LENGTH: 389
<212> TYPE: DNA
<213> ORGANISM: Homo sapiens

<400> SEQUENCE: 6
atggcctggg ctctgctgct cctcaacctc ctcactcagg acacagggtc ctgggcccag      60
tctgccctga ctcagcctgc ctccgtgtct gggtctcctg gacagtcgat caccatctcc     120
tgcactggaa ccagcagtga tgttggtgtt tataactatg tctcctggtt ccaacagcac     180
ccaggcaaag cccccaaact catgatttat aatgtcagta agcggccctc agggggtttct    240 aatcgcttct ctggctccaa gtctggcaac acggcctccc tgacaatctc tgggctccag     300
gctgaggacg aggctgatta ttactgctgc tcatatgcag gtagtagcac ttgggtgttc     360
ggcggaggga ccaacctgac cgtcctagg                                        389

<210> SEQ ID NO 7
<211> LENGTH: 110
<212> TYPE: PRT
<213> ORGANISM: Homo sapiens

<400> SEQUENCE: 7

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Val Tyr
            20                  25                  30

Asn Tyr Val Ser Trp Phe Gln Gln His Pro Gly Lys Ala Pro Lys Leu
        35                  40                  45

Met Ile Tyr Asn Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Trp Val Phe Gly Gly Gly Thr Asn Leu Thr Val Leu
            100                 105                 110

<210> SEQ ID NO 8
<211> LENGTH: 14
<212> TYPE: PRT
<213> ORGANISM: Homo sapiens

<400> SEQUENCE: 8

Thr Gly Thr Ser Ser Asp Val Gly Val Tyr Asn Tyr Val Ser
1               5                   10

```
<210> SEQ ID NO 9
<211> LENGTH: 7
<212> TYPE: PRT
<213> ORGANISM: Homo sapiens

<400> SEQUENCE: 9

Asn Val Ser Lys Arg Pro Ser
1               5

<210> SEQ ID NO 10
<211> LENGTH: 10
<212> TYPE: PRT
<213> ORGANISM: Homo sapiens

<400> SEQUENCE: 10

Cys Ser Tyr Ala Gly Ser Ser Thr Trp Val
1               5                   10

<210> SEQ ID NO 11
<211> LENGTH: 443
<212> TYPE: DNA
<213> ORGANISM: Homo sapiens

<400> SEQUENCE: 11
atggactgga cctggagggt cctcttttg gtggcagcag ccacaggtgc ccactcccag      60
gtccagcttg tgcagtctgg ggctgaggtg aagaagcctg ggcctcagt gaaggtttcc     120 tgcagggctt ctggatacac cttcactaac tatgctatgc attgggtgcg ccaggccccc    180
ggacaaaggc ttgagtggat gggatggatc aacgctggca atggttacac aaaatattca    240
cagaagttcc aggacagagt caccattacc agggacacat ccgcgaccac agcctacatg    300
gagctgagca gcctgagatc tgaagacacg gctatgtatt actgtgcgag agattctttt    360
tacgatattt tgagtgggcc agtctatcac tactacggta tggacgtctg gggccaaggg    420
accacggtca ccgtctcctc agc                                            443

<210> SEQ ID NO 12
<211> LENGTH: 128
<212> TYPE: PRT
<213> ORGANISM: Homo sapiens

<400> SEQUENCE: 12

Gln Val Gln Leu Val Gln Ser Gly Ala Glu Val Lys Lys Pro Gly Ala
1               5                   10                  15

Ser Val Lys Val Ser Cys Arg Ala Ser Gly Tyr Thr Phe Thr Asn Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Tyr Thr Lys Tyr Ser Gln Lys Phe
        50                  55                  60

Gln Asp Arg Val Thr Ile Thr Arg Asp Thr Ser Ala Thr Thr Ala Tyr
65                  70                  75                  80

Met Glu Leu Ser Ser Leu Arg Ser Glu Asp Thr Ala Met Tyr Tyr Cys
                85                  90                  95

Ala Arg Asp Ser Phe Tyr Asp Ile Leu Ser Gly Pro Val Tyr His Tyr
            100                 105                 110

Tyr Gly Met Asp Val Trp Gly Gln Gly Thr Thr Val Thr Val Ser Ser
        115                 120                 125

<210> SEQ ID NO 13
```

-continued

```
<211> LENGTH: 10
<212> TYPE: PRT
<213> ORGANISM: Homo sapiens

<400> SEQUENCE: 13

Gly Tyr Thr Phe Thr Asn Tyr Ala Met His
1               5                   10

<210> SEQ ID NO 14
<211> LENGTH: 17
<212> TYPE: PRT
<213> ORGANISM: Homo sapiens

<400> SEQUENCE: 14

Trp Ile Asn Ala Gly Asn Gly Tyr Thr Lys Tyr Ser Gln Lys Phe Gln
1               5                   10                  15

Asp

<210> SEQ ID NO 15
<211> LENGTH: 19
<212> TYPE: PRT
<213> ORGANISM: Homo sapiens

<400> SEQUENCE: 15

Asp Ser Phe Tyr Asp Ile Leu Ser Gly Pro Val Tyr His Tyr Tyr Gly
1               5                   10                  15

Met Asp Val

<210> SEQ ID NO 16
<211> LENGTH: 389
<212> TYPE: DNA
<213> ORGANISM: Homo sapiens

<400> SEQUENCE: 16
atggcctggg ctctgctgct cctcaacctc ctcactcagg ccacagggtc ctgggcccag       60
tctgccctga ctcagcctga ctccgtgtct gggtctcctg gacagtcgat caccatctcc      120
tgcactggaa ccagcaatga tgttggtatt tataaccatg tctcctggta ccaacagcac      180
ccaggcaaag cccccaaact catgatttat gatgtcaata gcggcccctc agggatttct      240
aatcgcttct ctggctccaa gtctggcgac acggcctccc tgacaatctc tgggctccag      300
gctgaggacg aggctgatta ttactgctgc tcatatgcag gtagtagcgc ttgggtgttc      360
ggcggaggga ccaaattgac cgtccttgg                                        389

<210> SEQ ID NO 17
<211> LENGTH: 110
<212> TYPE: PRT
<213> ORGANISM: Homo sapiens

<400> SEQUENCE: 17

Gln Ser Ala Leu Thr Gln Pro Asp Ser Val Ser Gly Ser Pro Gly Gln
1               5                   10                  15

Ser Ile Thr Ile Ser Cys Thr Gly Thr Ser Asn Asp Val Gly Ile Tyr
                20                  25                  30

Asn His Val Ser Trp Tyr Gln Gln His Pro Gly Lys Ala Pro Lys Leu
            35                  40                  45

Met Ile Tyr Asp Val Asn Lys Arg Pro Ser Gly Ile Ser Asn Arg Phe
        50                  55                  60

Ser Gly Ser Lys Ser Gly Asp Thr Ala Ser Leu Thr Ile Ser Gly Leu
65                  70                  75                  80
```

Gln Ala Glu Asp Glu Ala Asp Tyr Tyr Cys Cys Ser Tyr Ala Gly Ser
                85                  90                  95

Ser Ala Trp Val Phe Gly Gly Gly Thr Lys Leu Thr Val Leu
            100                 105                 110

<210> SEQ ID NO 18
<211> LENGTH: 14
<212> TYPE: PRT
<213> ORGANISM: Homo sapiens

<400> SEQUENCE: 18

Thr Gly Thr Ser Asn Asp Val Gly Ile Tyr Asn His Val Ser
1               5                   10

<210> SEQ ID NO 19
<211> LENGTH: 7
<212> TYPE: PRT
<213> ORGANISM: Homo sapiens

<400> SEQUENCE: 19

Asp Val Asn Lys Arg Pro Ser
1               5

<210> SEQ ID NO 20
<211> LENGTH: 10
<212> TYPE: PRT
<213> ORGANISM: Homo sapiens

<400> SEQUENCE: 20

Cys Ser Tyr Ala Gly Ser Ser Ala Trp Val
1               5                   10

<210> SEQ ID NO 21
<211> LENGTH: 437
<212> TYPE: DNA
<213> ORGANISM: Homo sapiens

<400> SEQUENCE: 21
atggactgga cctggaggat cctcttttg gtggcagcag ccgcaggtgc ccactcccag      60
gtccagcttg tgcagtctgg ggctgaggtg aagaagcctg ggcctcagt gaaggtttcc     120 tgcaaggctt ctggattcac cttcactgac tatgctatgc attgggtgcg ccaggccccc    180
ggacaaaggc ttgagtggat gggctggatc aacgctggca atggttacac aaaatattca    240
cagaagttcc aggacagact caccattacc agggacacat cgcgagcac agtctacatg     300 gagctgagca gcctgagatc tgaagacacg actgtgtatt actgtgcgag atgggtt      360 tgtcctagta acacttgttc tggttactac ggtatggacg tctggggcca agggaccacg    420
gtcaccgtct cctcagc                                                   437

<210> SEQ ID NO 22
<211> LENGTH: 126
<212> TYPE: PRT
<213> ORGANISM: Homo sapiens

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asp Tyr
            20                  25                  30

Ala Met His Trp Val Arg Gln Ala Pro Gly Gln Arg Leu Glu Trp Met

```
            35                  40                  45
Gly Trp Ile Asn Ala Gly Asn Gly Tyr Thr Lys Tyr Ser Gln Lys Phe
    50                  55                  60

Gln Asp Arg Leu Thr Ile Thr Arg Asp Thr Phe Ala Ser Thr Val Tyr
65                  70                  75                  80

Met Glu Leu Ser Ser Leu Arg Ser Glu Asp Thr Thr Val Tyr Tyr Cys
                85                  90                  95

Ala Arg Asp Gly Phe Cys Pro Ser Asn Thr Cys Ser Gly Tyr Tyr Gly
            100                 105                 110

Met Asp Val Trp Gly Gln Gly Thr Thr Val Thr Val Ser Ser
        115                 120                 125

<210> SEQ ID NO 23
<211> LENGTH: 10
<212> TYPE: PRT
<213> ORGANISM: Homo sapiens

<400> SEQUENCE: 23

Gly Phe Thr Phe Thr Asp Tyr Ala Met His
1               5                   10

<210> SEQ ID NO 24
<211> LENGTH: 17
<212> TYPE: PRT
<213> ORGANISM: Homo sapiens

<400> SEQUENCE: 24

Trp Ile Asn Ala Gly Asn Gly Tyr Thr Lys Tyr Ser Gln Lys Phe Gln
1               5                   10                  15

Asp

<210> SEQ ID NO 25
<211> LENGTH: 17
<212> TYPE: PRT
<213> ORGANISM: Homo sapiens

<400> SEQUENCE: 25

Asp Gly Phe Cys Pro Ser Asn Thr Cys Ser Gly Tyr Tyr Gly Met Asp
1               5                   10                  15

Val

<210> SEQ ID NO 26
<211> LENGTH: 389
<212> TYPE: DNA
<213> ORGANISM: Homo sapiens

<400> SEQUENCE: 26
atggcctggg ctctgctgct cctcaacctc ctcactcagg acacagggtc ctgggcccag    60
tctgccctga ctcagcctgc ctccgtgtct gggtctcctg gacagtcgat caccatctcc   120
tgcactggaa ccagcagtga tgttggttct tataactatg tctcctggta ccaacagcac   180
ccaggcaaag cccccaaact catgatttat gatgtcaata cgcggccctc agggggtttct   240 attcgcttct ctgcctccaa gtctggcaac acggcctccc tgacagtctc tgggctccag   300
gctgaggacg aggctgttta ttactgctcc tcatatgcag gtagtagcac ttgggtgttc   360
ggcggaggga ccaagctgac cgtcctagg                                      389

<210> SEQ ID NO 27
<211> LENGTH: 110
```

```
<212> TYPE: PRT
<213> ORGANISM: Homo sapiens

<400> SEQUENCE: 27

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Ser Trp Tyr Gln Gln His Pro Gly Lys Ala Pro Lys Leu
        35                  40                  45

Met Ile Tyr Asp Val Asn Thr Arg Pro Ser Gly Val Ser Ile Arg Phe
    50                  55                  60

Ser Ala Ser Lys Ser Gly Asn Thr Ala Ser Leu Thr Val Ser Gly Leu
65                  70                  75                  80

Gln Ala Glu Asp Glu Ala Val Tyr Tyr Cys Ser Ser Tyr Ala Gly Ser
                85                  90                  95

Ser Thr Trp Val Phe Gly Gly Gly Thr Lys Leu Thr Val Leu
            100                 105                 110

<210> SEQ ID NO 28
<211> LENGTH: 14
<212> TYPE: PRT
<213> ORGANISM: Homo sapiens

<400> SEQUENCE: 28

Thr Gly Thr Ser Ser Asp Val Gly Ser Tyr Asn Tyr Val Ser
1               5                   10

<210> SEQ ID NO 29
<211> LENGTH: 7
<212> TYPE: PRT
<213> ORGANISM: Homo sapiens

<400> SEQUENCE: 29

Asp Val Asn Thr Arg Pro Ser
1               5

<210> SEQ ID NO 30
<211> LENGTH: 10
<212> TYPE: PRT
<213> ORGANISM: Homo sapiens

<400> SEQUENCE: 30

Ser Ser Tyr Ala Gly Ser Ser Thr Trp Val
1               5                   10

<210> SEQ ID NO 31
<211> LENGTH: 437
<212> TYPE: DNA
<213> ORGANISM: Homo sapiens

<400> SEQUENCE: 31
atggactgga cctggaggat cctctttttg gtggcagcag ccacaggtgc ccactcccag      60
gtccagcttg tgcagtctgg ggctgaggtg aagaagcctg ggcctcagt  gagggtttcc     120 tgcaaggctt ctggattcac cttcactagt tatgctatgc attgggtgcg ccaggccccc     180
ggacaaaggc ttgagtggat gggatggatc aacgctggca atggtcacac aaaatattca     240
cagaagttcc aggacagagt cgccattacc agggacacat ccgcgaccac agtctacatg     300
gacctgagca gcctgagatc tgaagacacg gctgtgtatt actgtacgag agatggattt     360
```
tgtactagta ccacctgctc cgaccactac ggtatggacg tctggggcca agggaccacg      420
gtcaccgtct cctcagc                                                     437

<210> SEQ ID NO 32
<211> LENGTH: 126
<212> TYPE: PRT
<213> ORGANISM: Homo sapiens

<400> SEQUENCE: 32

Gln Val Gln Leu Val Gln Ser Gly Ala Glu Val Lys Lys Pro Gly Ala
1               5                   10                  15

Ser Val Arg Val Ser Cys Lys Ala Ser Gly Phe Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly His Thr Lys Tyr Ser Gln Lys Phe
    50                  55                  60

Gln Asp Arg Val Ala Ile Thr Arg Asp Thr Ser Ala Thr Thr Val Tyr
65                  70                  75                  80

Met Asp Leu Ser Ser Leu Arg Ser Glu Asp Thr Ala Val Tyr Tyr Cys
                85                  90                  95

Thr Arg Asp Gly Phe Cys Thr Ser Thr Cys Ser Asp His Tyr Gly
            100                 105                 110

Met Asp Val Trp Gly Gln Gly Thr Thr Val Thr Val Ser Ser
        115                 120                 125

<210> SEQ ID NO 33
<211> LENGTH: 10
<212> TYPE: PRT
<213> ORGANISM: Homo sapiens

<400> SEQUENCE: 33

Gly Phe Thr Phe Thr Ser Tyr Ala Met His
1               5                   10

<210> SEQ ID NO 34
<211> LENGTH: 17
<212> TYPE: PRT
<213> ORGANISM: Homo sapiens

<400> SEQUENCE: 34

Trp Ile Asn Ala Gly Asn Gly His Thr Lys Tyr Ser Gln Lys Phe Gln
1               5                   10                  15

Asp

<210> SEQ ID NO 35
<211> LENGTH: 17
<212> TYPE: PRT
<213> ORGANISM: Homo sapiens

<400> SEQUENCE: 35

Asp Gly Phe Cys Thr Ser Thr Cys Ser Asp His Tyr Gly Met Asp
1               5                   10                  15

Val

<210> SEQ ID NO 36
<211> LENGTH: 389
<212> TYPE: DNA
<213> ORGANISM: Homo sapiens

<400> SEQUENCE: 36

```
atggcctggg ctctgctgct cctcaacctc ctcactcagg acacagggtc ctgggcccag    60
tctgccctga ctcagcctgc ctccgtgtct gggtctcctg gacagtcgat caccatctcc   120
tgcactggaa ccagcagtga tgttggtagt tataactatg tctcctggta ccaacagcac   180
ccaggcaaag cccccaaatt catgatttat gatgtcagta agcggccctc agggg tttct   240
aatcgcttct ctggctccaa gtctggcaac acggcctccc tgacaatctc tgggctccag   300
gctgaggacg aggctgatta ttactgctgc tcatatgcag gtagtagcac ttgggtgttc   360
ggcggaggga ccaagctgac cgtccttgg                                     389
```

<210> SEQ ID NO 37
<211> LENGTH: 110
<212> TYPE: PRT
<213> ORGANISM: Homo sapiens

<400> SEQUENCE: 37

```
Gln Ser Ala Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Ser Tyr
            20                  25                  30
Asn Tyr Val Ser Trp Tyr Gln Gln His Pro Gly Lys Ala Pro Lys Phe
        35                  40                  45
Met Ile Tyr Asp Val Ser Lys Arg Pro Ser Gly Val Ser Asn Arg Phe
    50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Cys Ser Tyr Ala Gly Ser
                85                  90                  95
Ser Thr Trp Val Phe Gly Gly Gly Thr Lys Leu Thr Val Leu
            100                 105                 110
```

<210> SEQ ID NO 38
<211> LENGTH: 14
<212> TYPE: PRT
<213> ORGANISM: Homo sapiens

<400> SEQUENCE: 38

```
Thr Gly Thr Ser Ser Asp Val Gly Ser Tyr Asn Tyr Val Ser
1               5                   10
```

<210> SEQ ID NO 39
<211> LENGTH: 7
<212> TYPE: PRT
<213> ORGANISM: Homo sapiens

<400> SEQUENCE: 39

```
Asp Val Ser Lys Arg Pro Ser
1               5
```

<210> SEQ ID NO 40
<211> LENGTH: 10
<212> TYPE: PRT
<213> ORGANISM: Homo sapiens

<400> SEQUENCE: 40

```
Cys Ser Tyr Ala Gly Ser Ser Thr Trp Val
1               5                   10
```

<210> SEQ ID NO 41
<211> LENGTH: 1260
<212> TYPE: DNA
<213> ORGANISM: Artificial Sequence
<220> FEATURE:
<223> OTHER INFORMATION: Synethetic

<400> SEQUENCE: 41

```
cgaattgggg atcgatccac tagttaatta acgcgatgta aggtaccata tgctgtttca      60
agaatatcag tgctatggca gcagcagcaa cacccgtgtg ctgaacgagc tgaactatga     120
taacgcgggc accaacctgt ataacgagct ggaaatgaac tattacggca agcaggaaaa     180
ctggtacagc ctgaaaaaaa acagccgtag cctgggcgaa aacgatgatg caacaacaa      240
caacggcgat aacggccgtg aaggcaaaga tgaagataaa cgcgacggca taacgaaga      300
taacgagaaa ctgcgtaaac cgaaacacaa aaaactgaaa cagccgggcg atggcaatcc     360
ggaccctaat gcgaatccaa atgtcgaccc taatgccaat ccgaatgtag atccgaacgc     420
gaatccgaac gtggatccaa atgcaaatcc caatgccaat ccaaatgcaa acccaaacgc     480
gaatcccaat gccaatccca cgcaaatccc aaatgcgaac ccaaatgcaa atcccaacgc     540
aaatcccaat gcgaaccccca tgccaatccc aacgcaaatc caaatgcca accctaatgc     600
aaatccaaat gctaatccaa atgtagatcc taacgctaac ccaaatgcta accctaacgc     660
aaaccctaat gccaatccta tgccaatccc aaacgcaat ccgaacgcga acccaaatgc      720
caaccctaac gcgaatccta tgccaatccc caatgccaat ccaaatgcca atccgaacgc     780
gaatccgaat gcgaatccga atgctaaccc taatgccaac cccaatgcca accccaatgc     840
taatcccaac gcaaacccta caaaaaacaa ccagggcaac ggccagggcc ataacatgcc     900
gaacgatccg aaccgtaacg tggatgaaaa cgcgaacgcg aacaacgcgg tgaaaaacaa     960
caacaacgaa gaaccgagcg ataaacacat cgaaaaatac ctgaaaaaga tccagaacag    1020
cctgagcacc gaatggtctc cgtgcagcgt gacctgcggc aacggcattc aggtgcgtat    1080
taaaccgggc agcgcgaaca aaccgaaaga tgagctggat tacgaaaacg acatcgaaaa    1140
aaaaatctgc aaaatggaaa atgcagcag cgtgtttaac gtggtgaaca gcagcattgg    1200
cctgattctg aacatcatca tcatcatca ctaaccgctc gagcggagct cttacatcgc    1260
```

<210> SEQ ID NO 42
<211> LENGTH: 394
<212> TYPE: PRT
<213> ORGANISM: Artificial Sequence
<220> FEATURE:
<223> OTHER INFORMATION: Synthetic

<400> SEQUENCE: 42

Met Leu Phe Gln Glu Tyr Gln Cys Tyr Gly Ser Ser Ser Asn Thr Arg
1               5                   10                  15

Val Leu Asn Glu Leu Asn Tyr Asp Asn Ala Gly Thr Asn Leu Tyr Asn
            20                  25                  30

Glu Leu Glu Met Asn Tyr Tyr Gly Lys Gln Glu Asn Trp Tyr Ser Leu
        35                  40                  45

Lys Lys Asn Ser Arg Ser Leu Gly Glu Asn Asp Asp Gly Asn Asn
    50                  55                  60

Asn Gly Asp Asn Gly Arg Glu Gly Lys Asp Glu Asp Lys Arg Asp Gly
65                  70                  75                  80

Asn Asn Glu Asp Asn Glu Lys Leu Arg Lys Pro Lys His Lys Lys Leu
                85                  90                  95

-continued

```
Lys Gln Pro Gly Asp Gly Asn Pro Asp Pro Asn Ala Asn Pro Asn Val
            100                 105                 110

Asp Pro Asn Ala Asn Pro Asn Val Asp Pro Asn Ala Asn Pro Asn Val
        115                 120                 125

Asp Pro Asn Ala Asn Pro Asn Ala Asn Pro Asn Ala Asn Pro Asn Ala
    130                 135                 140

Asn Pro Asn Ala Asn Pro Asn Ala Asn Pro Asn Ala Asn Pro Asn Ala
145                 150                 155                 160

Asn Pro Asn Ala Asn Pro Asn Ala Asn Pro Asn Ala Asn Pro Asn Ala
            165                 170                 175

Asn Pro Asn Ala Asn Pro Asn Ala Asn Pro Asn Ala Asn Pro Asn Val
        180                 185                 190

Asp Pro Asn Ala Asn Pro Asn Ala Asn Pro Asn Ala Asn Pro Asn Ala
    195                 200                 205

Asn Pro Asn Ala Asn Pro Asn Ala Asn Pro Asn Ala Asn Pro Asn Ala
210                 215                 220

Asn Pro Asn Ala Asn Pro Asn Ala Asn Pro Asn Ala Asn Pro Asn Ala
225                 230                 235                 240

Asn Pro Asn Ala Asn Pro Asn Ala Asn Pro Asn Ala Asn Pro Asn Ala
            245                 250                 255

Asn Pro Asn Ala Asn Pro Asn Ala Asn Pro Asn Ala Asn Pro Asn Lys
        260                 265                 270

Asn Asn Gln Gly Asn Gly Gln Gly His Asn Met Pro Asn Asp Pro Asn
    275                 280                 285

Arg Asn Val Asp Glu Asn Ala Asn Ala Asn Asn Ala Val Lys Asn Asn
290                 295                 300

Asn Asn Glu Glu Pro Ser Asp Lys His Ile Glu Lys Tyr Leu Lys Lys
305                 310                 315                 320

Ile Gln Asn Ser Leu Ser Thr Glu Trp Ser Pro Cys Ser Val Thr Cys
            325                 330                 335

Gly Asn Gly Ile Gln Val Arg Ile Lys Pro Gly Ser Ala Asn Lys Pro
        340                 345                 350

Lys Asp Glu Leu Asp Tyr Glu Asn Asp Ile Glu Lys Lys Ile Cys Lys
    355                 360                 365

Met Glu Lys Cys Ser Ser Val Phe Asn Val Val Asn Ser Ser Ile Gly
370                 375                 380

Leu Ile Leu Glu His His His His His His
385                 390

<210> SEQ ID NO 43
<211> LENGTH: 388
<212> TYPE: PRT
<213> ORGANISM: Plasmodium falciparum

<400> SEQUENCE: 43

Met Leu Phe Gln Glu Tyr Gln Cys Tyr Gly Ser Ser Ser Asn Thr Arg
1               5                   10                  15

Val Leu Asn Glu Leu Asn Tyr Asp Asn Ala Gly Thr Asn Leu Tyr Asn
            20                  25                  30

Glu Leu Glu Met Asn Tyr Tyr Gly Lys Gln Glu Asn Trp Tyr Ser Leu
        35                  40                  45

Lys Lys Asn Ser Arg Ser Leu Gly Glu Asn Asp Asp Gly Asn Asn Asn
    50                  55                  60

Asn Gly Asp Asn Gly Arg Glu Gly Lys Asp Glu Asp Lys Arg Asp Gly
65                  70                  75                  80
```

```
Asn Asn Glu Asp Asn Glu Lys Leu Arg Lys Pro Lys His Lys Lys Leu
                85                  90                  95
Lys Gln Pro Gly Asp Gly Asn Pro Asp Pro Asn Ala Asn Pro Asn Val
            100                 105                 110
Asp Pro Asn Ala Asn Pro Asn Val Asp Pro Asn Ala Asn Pro Asn Val
        115                 120                 125
Asp Pro Asn Ala Asn Pro Asn Ala Asn Pro Asn Ala Asn Pro Asn Ala
    130                 135                 140
Asn Pro Asn Ala Asn Pro Asn Ala Asn Pro Asn Ala Asn Pro Asn Ala
145                 150                 155                 160
Asn Pro Asn Ala Asn Pro Asn Ala Asn Pro Asn Ala Asn Pro Asn Ala
                165                 170                 175
Asn Pro Asn Ala Asn Pro Asn Ala Asn Pro Asn Ala Asn Pro Asn Val
            180                 185                 190
Asp Pro Asn Ala Asn Pro Asn Ala Asn Pro Asn Ala Asn Pro Asn Ala
        195                 200                 205
Asn Pro Asn Ala Asn Pro Asn Ala Asn Pro Asn Ala Asn Pro Asn Ala
    210                 215                 220
Asn Pro Asn Ala Asn Pro Asn Ala Asn Pro Asn Ala Asn Pro Asn Ala
225                 230                 235                 240
Asn Pro Asn Ala Asn Pro Asn Ala Asn Pro Asn Ala Asn Pro Asn Ala
                245                 250                 255
Asn Pro Asn Ala Asn Pro Asn Ala Asn Pro Asn Ala Asn Pro Asn Lys
            260                 265                 270
Asn Asn Gln Gly Asn Gly Gln Gly His Asn Met Pro Asn Asp Pro Asn
        275                 280                 285
Arg Asn Val Asp Glu Asn Ala Asn Ala Asn Asn Ala Val Lys Asn Asn
    290                 295                 300
Asn Asn Glu Glu Pro Ser Asp Lys His Ile Glu Lys Tyr Leu Lys Lys
305                 310                 315                 320
Ile Gln Asn Ser Leu Ser Thr Glu Trp Ser Pro Cys Ser Val Thr Cys
                325                 330                 335
Gly Asn Gly Ile Gln Val Arg Ile Lys Pro Gly Ser Ala Asn Lys Pro
            340                 345                 350
Lys Asp Glu Leu Asp Tyr Glu Asn Asp Ile Glu Lys Lys Ile Cys Lys
        355                 360                 365
Met Glu Lys Cys Ser Ser Val Phe Asn Val Val Asn Ser Ser Ile Gly
    370                 375                 380
Leu Ile Leu Glu
385

<210> SEQ ID NO 44
<211> LENGTH: 160
<212> TYPE: PRT
<213> ORGANISM: Artificial Sequence
<220> FEATURE:
<223> OTHER INFORMATION: Synthetic

<400> SEQUENCE: 44

Asn Ala Asn Pro Asn Ala Asn Pro Asn Ala Asn Pro Asn Ala Asn Pro
1               5                   10                  15
Asn Ala Asn Pro Asn Ala Asn Pro Asn Ala Asn Pro Asn Ala Asn Pro
            20                  25                  30
Asn Ala Asn Pro Asn Ala Asn Pro Asn Ala Asn Pro Asn Ala Asn Pro
        35                  40                  45
```

Asn Ala Asn Pro Asn Ala Asn Pro Asn Ala Asn Pro Asn Ala Asn Pro
        50                  55                  60

Asn Ala Asn Pro Asn Ala Asn Pro Asn Ala Asn Pro Asn Ala Asn Pro
65                  70                  75                  80

Asn Ala Asn Pro Asn Ala Asn Pro Asn Ala Asn Pro Asn Ala Asn Pro
            85                  90                  95

Asn Ala Asn Pro Asn Ala Asn Pro Asn Ala Asn Pro Asn Ala Asn Pro
        100                 105                 110

Asn Ala Asn Pro Asn Ala Asn Pro Asn Ala Asn Pro Asn Ala Asn Pro
        115                 120                 125

Asn Ala Asn Pro Asn Ala Asn Pro Asn Ala Asn Pro Asn Ala Asn Pro
        130                 135                 140

Asn Ala Asn Pro Asn Ala Asn Pro Asn Ala Asn Pro Asn Ala Asn Pro
145                 150                 155                 160

<210> SEQ ID NO 45
<211> LENGTH: 40
<212> TYPE: PRT
<213> ORGANISM: Artificial Sequence
<220> FEATURE:
<223> OTHER INFORMATION: Synthetic

<400> SEQUENCE: 45

Asn Ala Asn Pro Asn Ala Asn Pro Asn Ala Asn Pro Asn Ala Asn Pro
1               5                   10                  15

Asn Ala Asn Pro Asn Ala Asn Pro Asn Ala Asn Pro Asn Ala Asn Pro
            20                  25                  30

Asn Ala Asn Pro Asn Ala Asn Pro
        35                  40

<210> SEQ ID NO 46
<211> LENGTH: 16
<212> TYPE: PRT
<213> ORGANISM: Artificial Sequence
<220> FEATURE:
<223> OTHER INFORMATION: Synthetic

<400> SEQUENCE: 46

Asn Ala Asn Pro Asn Ala Asn Pro Asn Ala Asn Pro Asn Ala Asn Pro
1               5                   10                  15

<210> SEQ ID NO 47
<211> LENGTH: 4
<212> TYPE: PRT
<213> ORGANISM: Artificial Sequence
<220> FEATURE:
<223> OTHER INFORMATION: Synthetic

<400> SEQUENCE: 47

Asn Ala Asn Pro
1

<210> SEQ ID NO 48
<211> LENGTH: 11
<212> TYPE: PRT
<213> ORGANISM: Homo sapiens

<400> SEQUENCE: 48

Gly Cys Cys Ala Gly Thr Cys Thr Ala Thr Cys
1               5                   10

```
<210> SEQ ID NO 49
<211> LENGTH: 13
<212> TYPE: PRT
<213> ORGANISM: Homo sapiens

<400> SEQUENCE: 49

Thr Gly Gly Gly Thr Thr Thr Thr Gly Thr Cys Cys Thr
1               5                   10

<210> SEQ ID NO 50
<211> LENGTH: 12
<212> TYPE: PRT
<213> ORGANISM: Homo sapiens

<400> SEQUENCE: 50

Ala Cys Thr Thr Gly Thr Thr Cys Thr Gly Gly Thr
1               5                   10

<210> SEQ ID NO 51
<211> LENGTH: 24
<212> TYPE: PRT
<213> ORGANISM: Artificial Sequence
<220> FEATURE:
<223> OTHER INFORMATION: Synthetic

<400> SEQUENCE: 51

Met Asp Pro Lys Gly Ser Leu Ser Trp Arg Ile Leu Leu Phe Leu Ser
1               5                   10                  15

Leu Ala Phe Glu Leu Ser Tyr Gly
            20

<210> SEQ ID NO 52
<211> LENGTH: 20
<212> TYPE: PRT
<213> ORGANISM: Artificial Sequence
<220> FEATURE:
<223> OTHER INFORMATION: Synthetic

<400> SEQUENCE: 52

Met Ser Val Pro Thr Gln Val Leu Gly Leu Leu Leu Leu Trp Leu Thr
1               5                   10                  15

Asp Ala Arg Cys
            20

<210> SEQ ID NO 53
<211> LENGTH: 20
<212> TYPE: PRT
<213> ORGANISM: Artificial Sequence
<220> FEATURE:
<223> OTHER INFORMATION: Synthetic

<400> SEQUENCE: 53

Met Glu Thr Asp Thr Leu Leu Leu Trp Val Leu Leu Leu Trp Val Pro
1               5                   10                  15

Gly Ser Thr Gly
            20

<210> SEQ ID NO 54
<211> LENGTH: 5
<212> TYPE: PRT
<213> ORGANISM: Homo sapiens

<400> SEQUENCE: 54

Asn Tyr Ala Met His
1               5
```

<210> SEQ ID NO 55
<211> LENGTH: 7
<212> TYPE: PRT
<213> ORGANISM: Homo sapiens

<400> SEQUENCE: 55

Gly Tyr Thr Phe Thr Asn Tyr
1               5

<210> SEQ ID NO 56
<211> LENGTH: 6
<212> TYPE: PRT
<213> ORGANISM: Homo sapiens

<400> SEQUENCE: 56

Asn Ala Gly Asn Gly Asn
1               5

<210> SEQ ID NO 57
<211> LENGTH: 5
<212> TYPE: PRT
<213> ORGANISM: Homo sapiens

<400> SEQUENCE: 57

Asp Tyr Ala Met His
1               5

<210> SEQ ID NO 58
<211> LENGTH: 7
<212> TYPE: PRT
<213> ORGANISM: Homo sapiens

<400> SEQUENCE: 58

Gly Tyr Thr Phe Thr Ser Tyr
1               5

<210> SEQ ID NO 59
<211> LENGTH: 5
<212> TYPE: PRT
<213> ORGANISM: Homo sapiens

<400> SEQUENCE: 59

Ser Tyr Ala Met His
1               5

<210> SEQ ID NO 60
<211> LENGTH: 10
<212> TYPE: PRT
<213> ORGANISM: Homo sapiens

<400> SEQUENCE: 60

Gly Tyr Thr Phe Thr Ser Tyr Ala Met His
1               5                   10

<210> SEQ ID NO 61
<211> LENGTH: 17
<212> TYPE: PRT
<213> ORGANISM: Homo sapiens

<400> SEQUENCE: 61

Trp Ile Asn Ala Gly Asn Gly Asn Thr Lys Tyr Ser Gln Lys Phe Gln
1               5                   10                  15

Gly

<210> SEQ ID NO 62
<211> LENGTH: 19
<212> TYPE: PRT
<213> ORGANISM: Homo sapiens

<400> SEQUENCE: 62

Asp Asn Tyr Tyr Asp Ser Gly Ser Tyr Tyr Asp Tyr Tyr Tyr Gly
1               5                   10                  15

Met Asp Val

<210> SEQ ID NO 63
<211> LENGTH: 14
<212> TYPE: PRT
<213> ORGANISM: Homo sapiens

<400> SEQUENCE: 63

Thr Gly Thr Ser Ser Asp Val Gly Ser Tyr Asn His Val Ser
1               5                   10

<210> SEQ ID NO 64
<211> LENGTH: 443
<212> TYPE: PRT
<213> ORGANISM: Homo sapiens

<400> SEQUENCE: 64

Ala Thr Gly Gly Ala Cys Thr Gly Gly Ala Cys Cys Thr Gly Gly
1               5                   10                  15

Gly Gly Ala Thr Cys Cys Thr Cys Thr Thr Thr Thr Thr Gly Gly Thr
                20                  25                  30

Gly Gly Cys Ala Gly Cys Ala Gly Cys Ala Cys Ala Gly Gly Thr
                35                  40                  45

Gly Cys Cys Cys Ala Cys Thr Cys Cys Cys Ala Gly Gly Thr Cys Cys
                50                  55                  60

Ala Gly Cys Thr Thr Gly Thr Gly Cys Ala Gly Thr Cys Thr Gly Gly
65                  70                  75                  80

Gly Gly Cys Thr Gly Ala Gly Gly Thr Gly Ala Ala Gly Ala Ala Gly
                85                  90                  95

Cys Cys Thr Gly Gly Gly Cys Cys Thr Cys Ala Gly Thr Gly Ala
                100                 105                 110

Ala Gly Gly Thr Thr Cys Cys Thr Gly Cys Ala Ala Gly Gly Cys
                115                 120                 125

Thr Thr Cys Thr Gly Gly Ala Thr Ala Cys Ala Cys Cys Thr Thr Cys
    130                 135                 140

Ala Cys Thr Ala Gly Thr Thr Ala Thr Gly Cys Thr Ala Thr Gly Cys
145                 150                 155                 160

Ala Thr Thr Gly Gly Gly Thr Gly Cys Gly Cys Ala Gly Gly Cys
                165                 170                 175

Cys Cys Cys Cys Gly Gly Ala Cys Ala Ala Gly Gly Cys Thr Thr
                180                 185                 190

Gly Ala Gly Thr Gly Gly Ala Thr Gly Gly Gly Ala Thr Gly Ala
                195                 200                 205

Thr Cys Ala Ala Cys Gly Cys Thr Gly Gly Cys Ala Thr Gly Gly
                210                 215                 220

Thr Ala Ala Cys Ala Cys Ala Ala Ala Thr Ala Thr Thr Cys Ala
225                 230                 235                 240

Cys Ala Gly Ala Ala Gly Thr Thr Cys Cys Ala Gly Gly Gly Cys Gly

```
                    245                 250                 255
Gly Ala Gly Thr Cys Ala Cys Cys Ala Thr Thr Ala Cys Cys Ala Gly
                260                 265                 270
Gly Gly Ala Cys Ala Cys Ala Thr Cys Cys Gly Cys Gly Ala Gly Cys
            275                 280                 285
Ala Cys Ala Gly Cys Cys Thr Ala Cys Ala Thr Gly Gly Ala Gly Cys
        290                 295                 300
Thr Gly Ala Gly Cys Ala Gly Cys Cys Thr Gly Ala Gly Ala Thr Cys
305                 310                 315                 320
Thr Gly Ala Ala Gly Ala Cys Ala Cys Gly Gly Cys Thr Gly Thr Ala
                325                 330                 335
Thr Ala Thr Thr Ala Cys Thr Gly Thr Gly Cys Gly Ala Gly Ala Gly
                340                 345                 350
Ala Cys Ala Ala Thr Thr Ala Cys Thr Ala Thr Gly Ala Thr Thr Cys
            355                 360                 365
Gly Gly Gly Gly Ala Gly Thr Thr Ala Thr Thr Ala Thr Gly Ala Cys
        370                 375                 380
Thr Ala Cys Thr Ala Cys Thr Ala Cys Thr Ala Cys Gly Gly Thr Ala
385                 390                 395                 400
Thr Gly Gly Ala Cys Gly Thr Cys Thr Gly Gly Gly Gly Cys Cys Ala
                405                 410                 415
Ala Gly Gly Gly Ala Cys Cys Ala Cys Gly Gly Thr Cys Ala Cys Cys
                420                 425                 430
Gly Thr Cys Thr Cys Cys Thr Cys Ala Gly Cys
                435                 440

<210> SEQ ID NO 65
<211> LENGTH: 128
<212> TYPE: PRT
<213> ORGANISM: Homo sapiens

<400> SEQUENCE: 65

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Ala Met His Trp Val Arg Gln Ala Pro Gly Gln Arg Leu Glu Trp Met
        35                  40                  45
Gly Trp Ile Asn Ala Gly Asn Gly Asn Thr Lys Tyr Ser Gln Lys Phe
    50                  55                  60
Gln Gly Gly Val Thr Ile Thr Arg Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asp Asn Tyr Tyr Asp Ser Gly Ser Tyr Tyr Asp Tyr Tyr
            100                 105                 110
Tyr Gly Met Asp Val Trp Gly Gln Gly Thr Thr Val Thr Val Ser Ser
        115                 120                 125

<210> SEQ ID NO 66
<211> LENGTH: 389
<212> TYPE: PRT
<213> ORGANISM: Homo sapiens

<400> SEQUENCE: 66

Ala Thr Gly Gly Cys Cys Thr Gly Gly Gly Cys Thr Cys Thr Gly Cys
```

```
1               5                   10                  15
Thr Gly Cys Thr Cys Cys Thr Cys Ala Ala Cys Cys Thr Cys Cys Thr
                20                  25                  30
Cys Ala Cys Thr Cys Ala Gly Gly Ala Cys Ala Cys Ala Gly Gly Gly
                35                  40                  45
Thr Cys Cys Thr Gly Gly Cys Cys Cys Ala Gly Thr Cys Thr Gly
       50                   55                  60
Cys Cys Cys Thr Gly Ala Cys Thr Cys Ala Gly Cys Cys Thr Gly Cys
65                  70                  75                  80
Cys Thr Cys Cys Gly Thr Gly Thr Cys Thr Gly Gly Thr Cys Thr
                    85                  90                  95
Cys Cys Thr Gly Gly Ala Cys Ala Gly Thr Cys Gly Ala Thr Cys Ala
                100                 105                 110
Cys Cys Thr Thr Cys Thr Cys Cys Thr Gly Cys Ala Cys Thr Gly Gly
                115                 120                 125
Ala Ala Cys Cys Ala Gly Cys Ala Gly Thr Gly Ala Thr Gly Thr Thr
                130                 135                 140
Gly Gly Thr Ala Gly Thr Thr Ala Thr Ala Ala Thr Cys Ala Thr Gly
145                 150                 155                 160
Thr Cys Thr Cys Cys Thr Gly Gly Thr Ala Cys Cys Ala

<400> SEQUENCE: 67

Gln Ser Ala Leu Thr Gln Pro Ala Ser Val Ser Gly Ser Pro Gly Gln
1               5                   10                  15

Ser Ile Thr Phe Ser Cys Thr Gly Thr Ser Ser Asp Val Gly Ser Tyr
            20                  25                  30

Asn His Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Trp Val Phe Gly Gly Gly Thr Lys Leu Thr Val Leu
            100                 105                 110

<210> SEQ ID NO 68
<211> LENGTH: 17
<212> TYPE: PRT
<213> ORGANISM: Homo sapiens

<400> SEQUENCE: 68

Trp Ile Asn Ala Gly Asn Gly Tyr Thr Lys Tyr Ser Gln Lys Phe Gln
1               5                   10                  15

Gly

<210> SEQ ID NO 69
<211> LENGTH: 19
<212> TYPE: PRT
<213> ORGANISM: Homo sapiens

<400> SEQUENCE: 69

Asp Asn Tyr Tyr Asp Ser Gly Ser Tyr Tyr Glu Tyr Cys Tyr Tyr Gly
1               5                   10                  15

Met Asp Val

<210> SEQ ID NO 70
<211> LENGTH: 10
<212> TYPE: PRT
<213> ORGANISM: Homo sapiens

<400> SEQUENCE: 70

Cys Ser Tyr Val Gly Ser Ser Thr Trp Val
1               5                   10

<210> SEQ ID NO 71
<211> LENGTH: 443
<212> TYPE: PRT
<213> ORGANISM: Homo sapiens

<400> SEQUENCE: 71

Ala Thr Gly Gly Ala Cys Thr Gly Gly Ala Cys Cys Thr Gly Gly Ala
1               5                   10                  15

Gly Gly Ala Thr Cys Cys Thr Cys Thr Thr Thr Cys Thr Gly Gly Thr
            20                  25                  30

Gly Gly Cys Ala Gly Cys Ala Gly Cys Ala Cys Ala Gly Gly Thr
        35                  40                  45

Gly Cys Cys Cys Ala Cys Thr Cys Cys Cys Ala Gly Gly Thr Cys Cys

```
                50                  55                  60
Ala Gly Cys Thr Thr Gly Thr Gly Cys Ala Gly Thr Cys Thr Gly Gly
 65                  70                  75                  80

Gly Gly Cys Thr Gly Ala Gly Thr Gly Ala Ala Gly Ala Ala Gly
                 85                  90                  95

Cys Cys Thr Gly Gly Gly Cys Thr Cys Ala Gly Thr Gly Ala
                100                 105                 110

Ala Gly Gly Thr Thr Thr Cys Thr Gly Cys Ala Ala Gly Gly Cys
                115                 120                 125

Gly Thr Cys Thr Gly Gly Ala Thr Ala Cys Ala Cys Thr Thr Cys
            130                 135                 140

Ala Cys Gly Ala Ala Cys Thr Ala Thr Gly Cys Thr Ala Thr Gly Cys
145                 150                 155                 160

Ala Thr Thr Gly Gly Gly Thr Gly Cys Gly Cys Ala Gly Cys
                165                 170                 175

Cys Cys Cys Cys Gly Gly Ala Cys Ala Ala Gly Gly Cys Thr Thr
            180                 185                 190

Gly Ala Gly Thr Gly Gly Ala Thr Gly Gly Ala Thr Gly Gly Ala
                195                 200                 205

Thr Cys Ala Ala Cys Gly Cys Thr Gly Gly Cys Ala Ala Thr Gly Gly
            210                 215                 220

Thr Thr Ala Cys Ala Cys Ala Ala Ala Thr Ala Thr Thr Cys Ala
225                 230                 235                 240

Cys Ala Gly Ala Ala Gly Thr Thr Cys Ala Gly Gly Gly Cys Ala
                245                 250                 255

Gly Ala Gly Thr Cys Ala Cys Cys Ala Thr Thr Ala Thr Cys Ala Gly
            260                 265                 270

Gly Gly Ala Cys Ala Cys Ala Thr Cys Thr Gly Cys Gly Ala Cys Cys
                275                 280                 285

Ala Cys Ala Gly Cys Cys Thr Ala Thr Ala Thr Gly Gly Ala Gly Cys
290                 295                 300

Thr Gly Ala Gly Cys Ala Gly Cys Cys Thr Gly Ala Gly Ala Thr Cys
305                 310                 315                 320

Thr Gly Ala Ala Gly Ala Cys Ala Cys Gly Gly Cys Thr Gly Thr Gly
            325                 330                 335

Thr Ala Thr Thr Ala Cys Thr Gly Thr Cys Gly Ala Gly Ala Gly
            340                 345                 350

Ala Thr Ala Ala Thr Thr Ala Thr Thr Ala Thr Gly Ala Thr Thr Cys
            355                 360                 365

Gly Gly Gly Gly Ala Gly Thr Thr Ala Thr Gly Cys Thr Ala Ala
370                 375                 380

Thr Ala Cys Thr Gly Cys Thr Ala Cys Thr Ala Cys Gly Gly Thr Ala
385                 390                 395                 400

Thr Gly Gly Ala Cys Gly Thr Cys Thr Gly Gly Gly Gly Cys Cys Ala
                405                 410                 415

Ala Gly Gly Gly Ala Cys Cys Ala Cys Gly Gly Thr Cys Ala Cys Cys
                420                 425                 430

Gly Thr Cys Thr Cys Cys Thr Cys Ala Gly Cys
            435                 440

<210> SEQ ID NO 72
<211> LENGTH: 128
<212> TYPE: PRT
<213> ORGANISM: Homo sapiens
```

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Tyr Thr Lys Tyr Ser Gln Lys Phe
    50                  55                  60

Gln Gly Arg Val Thr Ile Ile Arg Asp Thr Ser Ala Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asn Tyr Tyr Asp Ser Gly Ser Tyr Tyr Glu Tyr Cys Tyr
            100                 105                 110

Tyr Gly Met Asp Val Trp Gly Gln Gly Thr Thr Val Thr Val Ser Ser
        115                 120                 125

<210> SEQ ID NO 73
<211> LENGTH: 389
<212> TYPE: PRT
<213> ORGANISM: Homo sapiens

<400> SEQUENCE: 73

Ala Thr Gly Gly Cys Cys Thr Gly Gly Cys Thr Cys Thr Gly Cys
1               5                   10                  15

Thr Gly Cys Thr Cys Cys Thr Cys Ala Ala Cys Cys Thr Cys Cys Thr
            20                  25                  30

Cys Ala Cys Thr Cys Ala Gly Gly Ala Cys Ala Cys Ala Gly Gly Gly
        35                  40                  45

Thr Cys Cys Thr Gly Gly Gly Cys Cys Cys Ala Gly Thr Cys Thr Gly
    50                  55                  60

Cys Cys Cys Thr Gly Ala Cys Thr Cys Ala Gly Cys Cys Thr Cys Gly
65                  70                  75                  80

Cys Thr Cys Cys Gly Thr Gly Thr Cys Thr Gly Gly Gly Thr Cys Thr
                85                  90                  95

Cys Cys Thr Gly Gly Ala Cys Ala Gly Thr Cys Gly Ala Thr Cys Ala
            100                 105                 110

Cys Cys Ala Thr Cys Thr Cys Cys Thr Gly Cys Ala Cys Thr Gly Gly
        115                 120                 125

Ala Ala Cys Cys Ala Gly Cys Ala Gly Thr Gly Ala Thr Gly Thr Thr
    130                 135                 140

Gly Gly Thr Ala Gly Thr Thr Ala Thr Ala Ala Cys Cys Ala Thr Gly
145                 150                 155                 160

Thr Cys Thr Cys Cys Thr Gly Gly Thr Ala Cys Cys Ala Ala Cys Ala
                165                 170                 175

Ala Thr Ala Cys Cys Cys Ala Gly Gly Cys Ala Ala Ala Gly Cys Cys
            180                 185                 190

Cys Cys Cys Ala Ala Cys Thr Cys Thr Gly Ala Thr Thr Thr
            195                 200                 205

Ala Thr Gly Ala Thr Gly Thr Cys Ala Gly Thr Ala Ala Gly Cys Gly
        210                 215                 220

Gly Cys Cys Cys Thr Cys Ala Gly Gly Gly Thr Thr Thr Cys Thr
225                 230                 235                 240

```
Ala Ala Thr Cys Gly Cys Thr Thr Cys Thr Cys Thr Gly Gly Cys Thr
            245                 250                 255

Cys Cys Ala Ala Gly Thr Cys Thr Gly Gly Cys Ala Ala Cys Ala Cys
            260                 265                 270

Gly Gly Cys Cys Thr Cys Cys Thr Gly Ala Cys Ala Ala Thr Cys
            275                 280                 285

Thr Ala Thr Gly Gly Gly Cys Thr Cys Ala Gly Gly Cys Thr Gly
            290                 295                 300

Ala Gly Gly Ala Cys Gly Ala Gly Cys Thr Gly Ala Thr Thr Ala
305                 310                 315                 320

Thr Thr Ala Cys Thr Gly Cys Thr Gly Cys Thr Cys Ala Thr Ala Thr
            325                 330                 335

Gly Thr Ala Gly Gly Thr Ala Gly Cys Ala Gly Cys Ala Cys Thr Thr
            340                 345                 350

Gly Gly Gly Thr Gly Thr Thr Cys Gly Gly Cys Gly Gly Ala Gly Gly
            355                 360                 365

Gly Ala Cys Cys Ala Ala Gly Cys Thr Gly Ala Cys Cys Gly Thr Cys
            370                 375                 380

Cys Thr Ala Gly Gly
385

<210> SEQ ID NO 74
<211> LENGTH: 110
<212> TYPE: PRT
<213> ORGANISM: Homo sapiens

<400> SEQUENCE: 74

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn His Val Ser Trp Tyr Gln Gln Tyr Pro Gly Lys Ala Pro Lys Leu
        35                  40                  45

Leu Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Tyr Gly Leu
65                  70                  75                  80

Gln Ala Glu Asp Glu Ala Asp Tyr Tyr Cys Cys Ser Tyr Val Gly Ser
                85                  90                  95

Ser Thr Trp Val Phe Gly Gly Gly Thr Lys Leu Thr Val Leu
            100                 105                 110

<210> SEQ ID NO 75
<211> LENGTH: 10
<212> TYPE: PRT
<213> ORGANISM: Homo sapiens

<400> SEQUENCE: 75

Gly Tyr Thr Phe Ser Asn Tyr Ala Met His
1               5                   10

<210> SEQ ID NO 76
<211> LENGTH: 19
<212> TYPE: PRT
<213> ORGANISM: Homo sapiens

<400> SEQUENCE: 76
```

```
Asp Ser Phe Tyr Asp Ile Leu Thr Gly Pro Val Tyr His Tyr Gly
1               5                   10                  15

Met Asp Val

<210> SEQ ID NO 77
<211> LENGTH: 14
<212> TYPE: PRT
<213> ORGANISM: Homo sapiens

<400> SEQUENCE: 77

Thr Gly Thr Ser Asn Asp Val Gly Val Tyr Asn His Val Ser
1               5                   10

<210> SEQ ID NO 78
<211> LENGTH: 10
<212> TYPE: PRT
<213> ORGANISM: Homo sapiens

<400> SEQUENCE: 78

Cys Ser Tyr Val Gly Asn Ser Ala Trp Val
1               5                   10

<210> SEQ ID NO 79
<211> LENGTH: 443
<212> TYPE: PRT
<213> ORGANISM: Homo sapiens

<400> SEQUENCE: 79

Ala Thr Gly Gly Ala Cys Thr Gly Gly Ala Cys Cys Thr Gly Ala
1               5                   10                  15

Gly Gly Gly Thr Cys Cys Thr Cys Thr Thr Thr Thr Gly Gly Thr
                20                  25                  30

Gly Gly Cys Ala Gly Cys Ala Gly Cys Cys Ala Cys Ala Gly Gly
                35                  40                  45

Gly Cys Cys Cys Ala Cys Thr Cys Cys Ala Gly Gly Thr Cys Cys
            50                  55                  60

Ala Gly Cys Thr Thr Gly Thr Gly Cys Ala Gly Thr Cys Thr Gly
65                  70                  75                  80

Gly Gly Cys Thr Gly Ala Gly Gly Thr Gly Ala Ala Gly Ala Ala
                85                  90                  95

Cys Cys Thr Gly Gly Gly Gly Cys Cys Thr Cys Ala Gly Thr Gly
                100                 105                 110

Ala Gly Gly Thr Thr Thr Cys Cys Thr Gly Cys Ala Gly Gly Cys
                115                 120                 125

Thr Thr Cys Thr Gly Gly Ala Thr Ala Cys Ala Cys Cys Thr Cys
                130                 135                 140

Ala Gly Thr Ala Ala Thr Thr Ala Thr Gly Cys Thr Ala Thr Gly
145                 150                 155                 160

Ala Thr Thr Gly Gly Gly Thr Gly Cys Gly Cys Ala Gly Gly Cys
                165                 170                 175

Cys Cys Cys Cys Gly Gly Ala Cys Ala Ala Gly Gly Cys Thr Thr
                180                 185                 190

Gly Ala Gly Thr Gly Gly Ala Thr Gly Gly Ala Thr Gly Gly Ala
                195                 200                 205

Thr Cys Ala Ala Cys Gly Cys Thr Gly Gly Cys Ala Ala Thr Gly Gly
            210                 215                 220

Thr Thr Ala Cys Ala Cys Ala Ala Ala Thr Ala Thr Cys Ala
225                 230                 235                 240
```

```
Cys Ala Gly Ala Ala Gly Thr Cys Cys Ala Gly Ala Cys Ala
                245                 250                 255

Gly Ala Gly Thr Cys Ala Cys Cys Ala Thr Thr Ala Cys Ala Gly
            260                 265                 270

Gly Gly Ala Cys Ala Cys Ala Thr Cys Cys Gly Cys Gly Ala Cys Cys
        275                 280                 285

Ala Cys Ala Gly Cys Cys Thr Ala Cys Ala Thr Gly Gly Ala Ala Cys
    290                 295                 300

Thr Gly Ala Gly Cys Ala Gly Cys Cys Thr Gly Ala Gly Ala Thr Cys
305                 310                 315                 320

Thr Gly Ala Ala Gly Ala Cys Ala Cys Gly Gly Cys Thr Ala Thr Gly
                325                 330                 335

Thr Ala Thr Thr Ala Cys Thr Gly Thr Thr Cys Gly Ala Gly Ala Gly
            340                 345                 350

Ala Thr Thr Cys Thr Thr Thr Thr Ala Cys Gly Ala Thr Ala Thr
        355                 360                 365

Thr Thr Thr Gly Ala Cys Thr Gly Gly Gly Cys Cys Ala Gly Thr Cys
    370                 375                 380

Thr Ala Thr Cys Ala Cys Thr Ala Cys Thr Ala Cys Gly Gly Thr Ala
385                 390                 395                 400

Thr Gly Gly Ala Cys Gly Thr Cys Thr Gly Gly Gly Cys Cys Ala
                405                 410                 415

Ala Gly Gly Gly Ala Cys Cys Ala Cys Gly Gly Thr Cys Ala Cys Cys
            420                 425                 430

Gly Thr Cys Thr Cys Cys Thr Cys Ala Gly Cys
        435                 440
```

<210> SEQ ID NO 80
<211> LENGTH: 128
<212> TYPE: PRT
<213> ORGANISM: Homo sapiens

<400> SEQUENCE: 80

```
Gln Val Gln Leu Val Gln Ser Gly Ala Glu Val Lys Lys Pro Gly Ala
1               5                   10                  15

Ser Val Lys Val Ser Cys Arg Ala Ser Gly Tyr Thr Phe Ser Asn Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Tyr Thr Lys Tyr Ser Gln Lys Phe
    50                  55                  60

Gln Asp Arg Val Thr Ile Thr Arg Asp Thr Ser Ala Thr Thr Ala Tyr
65                  70                  75                  80

Met Glu Leu Ser Ser Leu Arg Ser Glu Asp Thr Ala Met Tyr Tyr Cys
                85                  90                  95

Ser Arg Asp Ser Phe Tyr Asp Ile Leu Thr Gly Pro Val Tyr His Tyr
            100                 105                 110

Tyr Gly Met Asp Val Trp Gly Gln Gly Thr Thr Val Thr Val Ser Ser
        115                 120                 125
```

<210> SEQ ID NO 81
<211> LENGTH: 389
<212> TYPE: PRT
<213> ORGANISM: Homo sapiens

<400> SEQUENCE: 81

Ala Thr Gly Gly Cys Cys Thr Gly Gly Cys Thr Cys Thr Gly Cys
1               5                   10                  15

Thr Gly Cys Thr Cys Cys Thr Cys Ala Ala Cys Cys Thr Cys Cys Thr
            20                  25                  30

Cys Ala Cys Thr Cys Ala Gly Gly Ala Cys Ala Cys Ala Gly Gly Gly
        35                  40                  45

Thr Cys Cys Thr Gly Gly Cys Cys Ala Gly Thr Cys Thr Gly
    50                  55                  60

Cys Cys Cys Thr Gly Ala Cys Thr Cys Ala Gly Cys Cys Thr Gly Ala
65              70                  75                  80

Cys Thr Cys Cys Gly Thr Gly Thr Cys Thr Gly Gly Thr Cys Thr
            85                  90                  95

Cys Cys Thr Gly Gly Ala Cys Ala Gly Thr Cys Gly Ala Thr Cys Ala
            100                 105                 110

Cys Cys Ala Thr Cys Thr Cys Cys Thr Gly Cys Ala Cys Thr Gly Gly
        115                 120                 125

Ala Ala Cys Cys Ala Gly Cys Ala Ala Thr Gly Ala Thr Gly Thr Thr
        130                 135                 140

Gly Gly Thr Gly Thr Thr Thr Ala Thr Ala Ala Cys Cys Ala Thr Gly
145                 150                 155                 160

Thr Cys Thr Cys Cys Thr Gly Gly Thr Ala Cys Cys Ala Ala Cys Ala
            165                 170                 175

Gly Cys Ala Cys Cys

<212> TYPE: PRT
<213> ORGANISM: Homo sapiens

<400> SEQUENCE: 82

Gln Ser Ala Leu Thr Gln Pro Asp Ser Val Ser Gly Ser Pro Gly Gln
1               5                   10                  15

Ser Ile Thr Ile Ser Cys Thr Gly Thr Ser Asn Asp Val Gly Val Tyr
            20                  25                  30

Asn His Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Val Gly Asn
                85                  90                  95

Ser Ala Trp Val Phe Gly Gly Gly Thr Lys Leu Thr Val Leu
            100                 105                 110

<210> SEQ ID NO 83
<211> LENGTH: 10
<212> TYPE: PRT
<213> ORGANISM: Homo sapiens

<400> SEQUENCE: 83

Cys Ser Tyr Val Gly Ser Ser Ala Trp Val
1               5                   10

<210> SEQ ID NO 84
<211> LENGTH: 443
<212> TYPE: PRT
<213> ORGANISM: Homo sapiens

<400> SEQUENCE: 84

Ala Thr Gly Gly Ala Cys Thr Gly Gly Ala Cys Cys Thr Gly Gly Ala
1               5                   10                  15

Gly Gly Gly Thr Cys Cys Thr Cys Thr Thr Thr Thr Thr Gly Gly Thr
            20                  25                  30

Gly Gly Cys Ala Gly Cys Ala Gly Cys Ala Cys Ala Gly Gly Thr
        35                  40                  45

Gly Cys Cys Cys Ala Cys Thr Cys Cys Cys Ala Gly Gly Thr Cys Cys
    50                  55                  60

Ala Gly Cys Thr Thr Gly Thr Gly Cys Ala Gly Thr Cys Thr Gly Gly
65                  70                  75                  80

Gly Gly Cys Thr Gly Ala Gly Gly Thr Gly Ala Ala Gly Ala Ala Gly
                85                  90                  95

Cys Cys Thr Gly Gly Gly Cys Cys Thr Cys Ala Gly Thr Gly Ala
            100                 105                 110

Ala Gly Gly Thr Thr Cys Cys Thr Gly Cys Ala Gly Gly Gly Cys
        115                 120                 125

Thr Thr Cys Thr Gly Gly Ala Thr Ala Cys Ala Cys Cys Thr Cys
    130                 135                 140

Ala Cys Thr Ala Ala Cys Thr Ala Thr Gly Gly Thr Ala Thr Gly Cys
145                 150                 155                 160

Ala Thr Thr Gly Gly Thr Gly Cys Gly Cys Ala Gly Gly Cys
            165                 170                 175

Cys Cys Cys Cys Gly Gly Ala Cys Ala Ala Ala Gly Gly Cys Thr Thr

```
                    180                 185                 190
Gly Ala Gly Thr Gly Gly Ala Thr Gly Gly Ala Thr Gly Gly Ala
                195                 200                 205
Thr Cys Ala Ala Cys Gly Cys Thr Gly Gly Cys Ala Ala Thr Gly Gly
            210                 215                 220
Thr Thr Ala Cys Ala Cys Ala Ala Gly Thr Ala Thr Thr Cys Ala
225                 230                 235                 240
Cys Ala Gly Ala Ala Gly Thr Thr Cys Cys Ala Gly Gly Ala Cys Ala
                245                 250                 255
Gly Ala Gly Thr Cys Ala Cys Ala Thr Thr Ala Cys Cys Ala Gly Gly
            260                 265                 270
Gly Gly Ala Cys Ala Cys Ala Thr Cys Cys Gly Cys Gly Ala Cys Cys
            275                 280                 285
Ala Cys Ala Gly Cys Cys Ala Cys Ala Thr Gly Gly Ala Ala Cys
            290                 295                 300
Thr Gly Ala Gly Cys Ala Gly Cys Cys Thr Gly Ala Gly Ala Thr Cys
305                 310                 315                 320
Thr Gly Ala Ala Gly Ala Cys Ala Cys Gly Gly Cys Thr Ala Thr Gly
                325                 330                 335
Thr Ala Thr Thr Ala Cys Thr Gly Thr Gly Cys Gly Ala Gly Ala Gly
                340                 345                 350
Ala Thr Thr Cys Thr Thr Thr Thr Ala Cys Gly Ala Thr Ala Thr
            355                 360                 365
Thr Thr Thr Gly Ala Cys Thr Gly Gly Gly Cys Cys Ala Gly Thr Cys
370                 375                 380
Thr Ala Thr Cys Ala Cys Thr Ala Cys Thr Ala Cys Gly Gly Thr Ala
385                 390                 395                 400
Thr Gly Gly Ala Cys Gly Thr Cys Thr Gly Gly Gly Cys Cys Ala
                405                 410                 415
Ala Gly Gly Gly Ala Cys Cys Ala Cys Gly Gly Thr Cys Ala Cys Cys
            420                 425                 430
Gly Thr Cys Thr Cys Cys Thr Cys Ala Gly Cys
        435                 440

<210> SEQ ID NO 85
<211> LENGTH: 128
<212> TYPE: PRT
<213> ORGANISM: Homo sapiens

<400> SEQUENCE: 85

Gln Val Gln Leu Val Gln Ser Gly Ala Glu Val Lys Lys Pro Gly Ala
1               5                   10                  15
Ser Val Lys Val Ser Cys Arg Ala Ser Gly Tyr Thr Phe Thr Asn Tyr
            20                  25                  30
Ala Met His Trp Val Arg Gln Ala Pro Gly Gln Arg Leu Glu Trp Met
        35                  40                  45
Gly Trp Ile Asn Ala Gly Asn Gly Tyr Thr Lys Tyr Ser Gln Lys Phe
    50                  55                  60
Gln Asp Arg Val Thr Ile Thr Arg Asp Thr Ser Ala Thr Thr Ala His
65                  70                  75                  80
Met Glu Leu Ser Ser Leu Arg Ser Glu Asp Thr Ala Met Tyr Tyr Cys
                85                  90                  95
Ala Arg Asp Ser Phe Tyr Asp Ile Leu Thr Gly Pro Val Tyr His Tyr
            100                 105                 110
```

Tyr Gly Met Asp Val Trp Gly Gln Gly Thr Thr Val Thr Val Ser Ser
            115                 120                 125

<210> SEQ ID NO 86
<211> LENGTH: 389
<212> TYPE: PRT
<213> ORGANISM: Homo sapiens

<400> SEQUENCE: 86

Ala Thr Gly Gly Cys Cys Thr Gly Gly Cys Thr Cys Thr Gly Cys
1               5                   10                  15

Thr Gly Cys Thr Cys Cys Thr Cys Ala Ala Cys Cys Thr Cys Thr
                20                  25                  30

Cys Ala Cys Thr Cys Ala Gly Gly Ala Cys Ala Cys Ala Gly Gly
                35                  40                  45

Thr Cys Cys Thr Gly Gly Gly Cys Cys Cys Ala Gly Gly Thr Gly
            50                  55                  60

Cys Cys Cys Thr Gly Ala Cys Thr Cys Ala Gly Cys Cys Thr Gly Ala
65                      70                  75                  80

Cys Thr Cys Cys Gly Thr Gly Thr Cys Thr Gly Gly Gly Thr Cys Thr
                        85                  90                  95

Cys Cys Thr Gly Gly Ala Cys Ala Gly Thr Cys Gly Ala Thr Cys Ala
                100                 105                 110

Cys Cys Ala Thr Cys Thr Cys Cys Thr Gly Cys Ala Cys Thr Gly Gly
                115                 120                 125

Ala Ala Cys Cys Ala Gly Cys Ala Ala Thr Gly Ala Thr Gly Thr Thr
                130                 135                 140

Gly Gly Thr Gly Thr Thr Thr Ala Thr Ala Ala Cys Cys Ala Thr Gly
145                 150                 155                 160

Thr Cys Thr Cys Cys Thr Gly Gly Thr Ala Cys Cys Ala Ala Cys Ala
                165                 170                 175

Gly Cys Ala Cys Cys Cys Ala Gly Gly Cys Ala Ala Ala Gly Cys Cys
                180                 185                 190

Cys Cys Cys Ala Ala Ala Cys Thr Cys Ala Thr Gly Ala Thr Thr Thr
                195                 200                 205

Ala Thr Gly Ala Thr Gly Thr Cys Ala Gly Thr Ala Ala Gly Cys Gly
                210                 215                 220

Gly Cys Cys Cys Thr Cys Ala Gly Gly Gly Thr Thr Thr Cys Thr
225                 230                 235                 240

Ala Ala Thr Cys Gly Cys Thr Thr Cys Thr Cys Thr Gly Gly Cys Thr
                        245                 250                 255

Cys Cys Ala Ala Gly Thr Cys Thr Gly Gly Cys Ala Ala Cys Ala Cys
                        260                 265                 270

Gly Gly Cys Cys Thr Cys Cys Cys Thr Gly Ala Cys Ala Thr Cys
                275                 280                 285

Thr Cys Thr Gly Gly Gly Cys Thr Cys Cys Ala Gly Gly Cys Thr Gly
                290                 295                 300

Ala Gly Gly Ala Cys Gly Ala Gly Gly Cys Thr Gly Ala Thr Thr Ala
305                 310                 315                 320

Thr Thr Ala Cys Thr Gly Cys Thr Gly Cys Thr Cys Ala Thr Ala Thr
                325                 330                 335

Gly Thr Ala Gly Gly Thr Ala Gly Thr Ala Gly Cys Gly Cys Thr Thr
                340                 345                 350

Gly Gly Gly Thr Gly Thr Thr Cys Gly Gly Cys Gly Gly Ala Gly Gly
                355                 360                 365

```
Gly Ala Cys Cys Ala Ala Thr Cys Thr Gly Ala Cys Cys Gly Thr Cys
    370                 375                 380

Cys Thr Ala Gly Gly
385

<210> SEQ ID NO 87
<211> LENGTH: 110
<212> TYPE: PRT
<213> ORGANISM: Homo sapiens

<400> SEQUENCE: 87

Gln Ser Ala Leu Thr Gln Pro Asp Ser Val Ser Gly Ser Pro Gly Gln
1               5                   10                  15

Ser Ile Thr Ile Ser Cys Thr Gly Thr Ser Asn Asp Val Gly Val Tyr
            20                  25                  30

Asn His Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Val Gly Ser
                85                  90                  95

Ser Ala Trp Val Phe Gly Gly Thr Asn Leu Thr Val Leu
            100                 105                 110

<210> SEQ ID NO 88
<211> LENGTH: 443
<212> TYPE: PRT
<213> ORGANISM: Homo sapiens

<400> SEQUENCE: 88

Ala Thr Gly Gly Ala Cys Thr Gly Gly Ala Cys Cys Thr Gly Gly Ala
1               5                   10                  15

Gly Gly Gly Thr Cys Cys Thr Cys Thr Thr Thr Thr Thr Gly Gly Thr
            20                  25                  30

Gly Gly Cys Ala Gly Cys Ala Gly Cys Cys Ala Cys Ala Gly Gly Thr
        35                  40                  45

Gly Cys Cys Cys Ala Cys Thr Cys Cys Cys Ala Gly Gly Thr Cys Cys
    50                  55                  60

Ala Gly Cys Thr Thr Gly Thr Gly Cys Ala Gly Thr Cys Thr Gly Gly
65                  70                  75                  80

Gly Gly Cys Thr Gly Ala Gly Gly Thr Gly Ala Ala Gly Ala Ala Gly
                85                  90                  95

Cys Cys Thr Gly Gly Gly Cys Thr Cys Ala Gly Thr Gly Ala
            100                 105                 110

Ala Gly Gly Thr Thr Thr Cys Cys Thr Gly Cys Ala Gly Gly Gly Cys
        115                 120                 125

Thr Thr Cys Thr Gly Gly Ala Thr Ala Cys Ala Cys Cys Thr Thr Cys
    130                 135                 140

Ala Cys Thr Ala Ala Cys Thr Ala Thr Gly Thr Ala Thr Gly Cys
145                 150                 155                 160

Ala Thr Thr Gly Gly Gly Thr Gly Cys Gly Cys Ala Gly Gly Cys
                165                 170                 175

Cys Cys Cys Cys Gly Gly Ala Cys Ala Ala Gly Gly Cys Thr Thr
            180                 185                 190
```

Gly Ala Gly Thr Gly Ala Thr Gly Gly Ala Thr Gly Gly Ala
            195                 200                 205

Thr Cys Ala Ala Cys Gly Cys Thr Gly Gly Cys Ala Ala Thr Gly Gly
210                 215                 220

Thr Thr Ala Cys Ala Cys Ala Ala Ala Thr Ala Thr Thr Cys Ala
225                 230                 235                 240

Cys Ala Gly Ala Ala Gly Thr Thr Cys Ala Gly Gly Ala Cys Ala
                245                 250                 255

Gly Ala Thr Thr Cys Ala Cys Cys Ala Thr Ala Cys Cys Ala Gly
                260                 265                 270

Gly Gly Ala Cys Ala Cys Ala Thr Cys Gly Cys Gly Ala Cys Cys
                275                 280                 285

Ala Cys Ala Gly Cys Cys Thr Ala Cys Ala Thr Gly Gly Ala Cys
                290                 295                 300

Thr Gly Ala Gly Cys Ala Gly Cys Cys Thr Gly Ala Gly Ala Thr Cys
305                 310                 315                 320

Thr Gly Ala Ala Gly Ala Cys Ala Cys Gly Gly Cys Thr Gly Thr Ala
                325                 330                 335

Thr Ala Thr Thr Ala Cys Thr Gly Thr Gly Cys Gly Ala Gly Ala Gly
                340                 345                 350

Ala Thr Thr Cys Thr Thr Thr Thr Thr Ala Cys Gly Ala Thr Ala Thr
                355                 360                 365

Thr Thr Thr Gly Ala Cys Thr Gly Gly Gly Cys Cys Ala Gly Thr Cys
                370                 375                 380

Thr Ala Thr Cys Ala Cys Thr Ala Cys Thr Ala Cys Gly Gly Thr Ala
385                 390                 395                 400

Thr Gly Gly Ala Cys Gly Thr Cys Thr Gly Gly Gly Cys Cys Ala
                405                 410                 415

Ala Gly Gly Gly Ala Cys Cys Ala Cys Gly Gly Thr Cys Ala Cys Cys
                420                 425                 430

Gly Thr Cys Thr Cys Cys Thr Cys Ala Gly Cys
                435                 440

<210> SEQ ID NO 89
<211> LENGTH: 128
<212> TYPE: PRT
<213> ORGANISM: Homo sapiens

<400> SEQUENCE: 89

Gln Val Gln Leu Val Gln Ser Gly Ala Glu Val Lys Lys Pro Gly Ala
1               5                   10                  15

Ser Val Lys Val Ser Cys Arg Ala Ser Gly Tyr Thr Phe Thr Asn Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Tyr Thr Lys Tyr Ser Gln Lys Phe
        50                  55                  60

Gln Asp Arg Phe Thr Ile Thr Arg Asp Thr Ser Ala Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Phe Tyr Asp Ile Leu Thr Gly Pro Val Tyr His Tyr
                100                 105                 110

Tyr Gly Met Asp Val Trp Gly Gln Gly Thr Thr Val Thr Val Ser Ser

<210> SEQ ID NO 90
<211> LENGTH: 389
<212> TYPE: PRT
<213> ORGANISM: Homo sapiens

<400> SEQUENCE: 90

Ala Thr Gly Gly Cys Cys Thr Gly Gly Cys Thr Cys Thr Gly Cys
1               5                   10                  15

Thr Gly Cys Thr Cys Cys Thr Cys Ala Ala Cys Cys Thr Cys Cys Thr
            20                  25                  30

Cys Ala Cys Thr Cys Ala Gly Gly Ala Cys Ala Cys Ala Gly Gly Gly
            35                  40                  45

Thr Cys Cys Thr Gly Gly Cys Cys Ala Gly Thr Cys Thr Gly
    50                  55                  60

Cys Cys Cys Thr Gly Ala Cys Thr Cys Ala Gly Cys Cys Thr Gly Ala
65                  70                  75                  80

Cys Thr Cys Cys Gly Thr Gly Thr Cys Thr Gly Gly Gly Thr Cys Thr
                85                  90                  95

Cys Cys Thr Gly Gly Ala Cys Ala Gly Thr Cys Gly Ala Thr Cys Ala
                100                 105                 110

Cys Cys Ala Thr Cys Thr Cys Cys Thr Gly Cys Ala Cys Thr Gly Gly
                115                 120                 125

Ala Ala Cys Cys Ala Gly Cys Ala Ala Thr Gly Ala Thr Gly Thr Thr
            130                 135                 140

Gly Gly Thr Gly Thr Thr Ala Thr Ala Ala Cys Cys Ala Thr Gly
145                 150                 155                 160

Thr Cys Thr Cys Cys Thr Gly Gly Thr Ala Cys Cys Ala Ala Cys Ala
                165                 170                 175

Gly Cys Ala Cys Cys Cys Ala Gly Gly Cys Ala Ala Ala Gly Cys Cys
            180                 185                 190

Cys Cys Cys Ala Ala Ala Cys Thr Cys Ala Thr Gly Ala Thr Thr Thr
                195                 200                 205

Ala Thr Gly Ala Thr Gly Thr Cys Ala Gly Thr Ala Ala Gly Cys Gly
            210                 215                 220

Gly Cys Cys Cys Thr Cys Ala Gly Gly Gly Thr Thr Thr Cys Thr
225                 230                 235                 240

Ala Ala Thr Cys Gly Cys Thr Thr Cys Thr Cys Thr Gly Gly Cys Thr
                245                 250                 255

Cys Cys Ala Ala Gly Thr Cys Thr Gly Gly Cys Ala Ala Cys Ala Cys
            260                 265                 270

Gly Gly Cys Cys Thr Cys Cys Cys Thr Gly Ala Cys Ala Ala Thr Cys
            275                 280                 285

Thr Cys Thr Gly Gly Gly Cys Thr Cys Cys Ala Gly Gly Cys Thr Gly
            290                 295                 300

Ala Gly Gly Ala Cys Gly Ala Gly Gly Cys Thr Gly Ala Thr Thr Ala
305                 310                 315                 320

Thr Thr Ala Cys Thr Gly Cys Thr Gly Cys Thr Cys Ala Thr Ala Thr
                325                 330                 335

Gly Cys Ala Gly Gly Thr Ala Gly Thr Ala Gly Cys Ala Cys Thr Thr
            340                 345                 350

Gly Gly Gly Thr Gly Thr Thr Cys Gly Gly Cys Gly Gly Ala Gly Gly
            355                 360                 365

Gly Ala Cys Cys Ala Ala Gly Cys Thr Gly Ala Cys Cys Gly Thr Cys
            370                 375                 380

Cys Thr Ala Gly Gly
385

<210> SEQ ID NO 91
<211> LENGTH: 110
<212> TYPE: PRT
<213> ORGANISM: Homo sapiens

<400> SEQUENCE: 91

Gln Ser Ala Leu Thr Gln Pro Asp Ser Val Ser Gly Ser Pro Gly Gln
1               5                   10                  15

Ser Ile Thr Ile Ser Cys Thr Gly Thr Ser Asn Asp Val Gly Val Tyr
            20                  25                  30

Asn His Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ser Asp Tyr Tyr Cys Ser Tyr Ala Gly Ser
                85                  90                  95

Ser Thr Trp Val Phe Gly Gly Thr Lys Leu Thr Val Leu
            100                 105                 110

<210> SEQ ID NO 92
<211> LENGTH: 14
<212> TYPE: PRT
<213> ORGANISM: Homo sapiens

<400> SEQUENCE: 92

Thr Gly Thr Ser Ser Asp Val Gly Ala Tyr Lys Tyr Val Ser
1               5                   10

<210> SEQ ID NO 93
<211> LENGTH: 437
<212> TYPE: PRT
<213> ORGANISM: Homo sapiens

<400> SEQUENCE: 93

Ala Thr Gly Gly Ala Cys Thr Gly Gly Ala Cys Cys Thr Gly Gly Ala
1               5                   10                  15

Gly Gly Ala Thr Cys Cys Thr Cys Thr Thr Thr Thr Thr Gly Gly Thr
            20                  25                  30

Gly Gly Cys Ala Gly Cys Ala Gly Cys Cys Gly Cys Ala Gly Gly Thr
        35                  40                  45

Gly Cys Cys Cys Ala Cys Thr Cys Cys Cys Ala Gly Gly Thr Cys Cys
    50                  55                  60

Ala Gly Cys Thr Thr Gly Thr Gly Cys Ala Gly Thr Cys Thr Gly Gly
65                  70                  75                  80

Gly Gly Cys Thr Gly Ala Gly Gly Thr Gly Ala Ala Gly Ala Ala Gly
                85                  90                  95

Cys Cys Thr Gly Gly Gly Gly Cys Cys Thr Cys Ala Gly Thr Gly Ala
            100                 105                 110

Ala Gly Gly Thr Thr Thr Cys Cys Thr Gly Cys Ala Ala Gly Gly Cys
        115                 120                 125

Thr Thr Cys Thr Gly Gly Ala Thr Ala Cys Ala Cys Cys Thr Thr Cys

```
                130             135             140
Ala Cys Thr Gly Ala Cys Thr Ala Cys Gly Cys Thr Ala Thr Gly Cys
145                 150                 155                 160

Ala Thr Thr Gly Gly Thr Gly Cys Gly Cys Cys Ala Gly Gly Cys
                165                 170                 175

Cys Cys Cys Cys Gly Gly Ala Cys Ala Ala Gly Gly Cys Thr Thr
            180                 185                 190

Gly Ala Gly Thr Gly Gly Ala Thr Gly Gly Gly Thr Thr Gly Gly Ala
                195                 200                 205

Thr Cys Ala Ala Cys Gly Cys Thr Gly Gly Cys Ala Ala Thr Gly Gly
210                 215                 220

Thr Thr Ala Cys Ala Cys Ala Ala Ala Thr Ala Thr Thr Cys Ala
225                 230                 235                 240

Cys Ala Gly Ala Ala Gly Thr Thr Cys Cys Ala Gly Gly Ala Cys Ala
                245                 250                 255

Gly Ala Cys Thr Cys Ala Cys Cys Ala Thr Thr Ala Cys Cys Ala Gly
                260                 265                 270

Gly Gly Ala Cys Ala Cys Ala Thr Thr Cys Gly Cys Gly Ala Gly Cys
                275                 280                 285

Ala Cys Ala Gly Thr Cys Thr Ala Cys Ala Thr Gly Gly Ala Gly Cys
                290                 295                 300

Thr Gly Ala Gly Cys Ala Gly Cys Cys Thr Gly Ala Gly Ala Thr Cys
305                 310                 315                 320

Thr Gly Ala Ala Gly Ala Cys Ala Cys Gly Gly Cys Thr Gly Thr Gly
                325                 330                 335

Thr Ala Thr Thr Ala Cys Thr Gly Thr Gly Cys Gly Ala Gly Ala Gly
                340                 345                 350

Ala Thr Gly Gly Gly Thr Thr Thr Thr Gly Thr Cys Cys Thr Ala Gly
                355                 360                 365

Thr Ala Ala Cys Ala Cys Thr Thr Gly Thr Thr Cys Thr Gly G

Gln Asp Arg Leu Thr Ile Thr Arg Asp Thr Phe Ala Ser Thr Val Tyr
65                  70                  75                  80

Met Glu Leu Ser Ser Leu Arg Ser Glu Asp Thr Thr Val Tyr Tyr Cys
                85                  90                  95

Ala Arg Asp Gly Phe Cys Pro Ser Asn Thr Cys Ser Gly Tyr Tyr Gly
            100                 105                 110

Met Asp Val Trp Gly Gln Gly Thr Thr Val Thr Val Ser Ser
            115                 120                 125

<210> SEQ ID NO 95
<211> LENGTH: 389
<212> TYPE: PRT
<213> ORGANISM: Homo sapiens

<400> SEQUENCE: 95

Ala Thr Gly Gly Cys Cys Thr Gly Gly Cys Thr Cys Thr Gly Cys
1               5                   10                  15

Thr Gly Cys Thr Cys Cys Thr Cys Ala Ala Cys Cys Thr Cys Cys Thr
                20                  25                  30

Cys Ala Cys Thr Cys Ala Gly Gly Ala Cys Ala Cys Ala Gly Gly Gly
            35                  40                  45

Thr Cys Cys Thr Gly Gly Cys Cys Cys Ala Gly Thr Cys Thr Gly
    50                  55                  60

Cys Cys Cys Thr Gly Ala Cys Thr Cys Ala Gly Cys Cys Thr Gly Cys
65                  70                  75                  80

Cys Thr Cys Cys Gly Thr Gly Thr Cys Thr Gly Gly Gly Thr Cys Thr
            85                  90                  95

Cys Cys Thr Gly Gly Ala Cys Ala Gly Thr Cys Gly Ala Thr Cys Ala
            100                 105                 110

Cys Cys Ala Thr Cys Thr Cys Cys Thr Gly Cys Ala Cys Thr Gly Gly
            115                 120                 125

Ala Ala Cys Cys Ala Gly Cys Ala Gly Thr Gly Ala Thr Gly Thr Thr
130                 135                 140

Gly Gly Thr Gly Cys Thr Thr Ala Thr Ala Ala Gly Thr Ala Thr Gly
145                 150                 155                 160

Thr Cys Thr Cys Cys Thr Gly Gly Thr Ala Cys Cys Ala Ala Cys Ala
            165                 170                 175

Gly Cys Ala Cys Cys Cys Ala Gly Gly Cys Ala Ala Gly Cys Cys
            180                 185                 190

Cys Cys Cys Ala Ala Ala Cys Thr Cys Ala Thr Gly Ala Thr Thr Thr
            195                 200                 205

Ala Thr Gly Ala Thr Gly Thr Cys Ala Ala Thr Ala Cys Gly Cys Gly
210                 215                 220

Gly Cys Cys Cys Thr Cys Ala Gly Gly Gly Thr Thr Thr Cys Thr
225                 230                 235                 240

Ala Cys Thr Cys Gly Cys Thr Cys Thr Cys Thr Gly Cys Cys Thr
            245                 250                 255

Cys Cys Ala Ala Gly Thr Cys Thr Gly Gly Cys Ala Ala Cys Ala Cys
            260                 265                 270

Gly Gly Cys Cys Thr Cys Cys Thr Gly Ala Cys Ala Gly Thr Cys
            275                 280                 285

Thr Cys Thr Gly Gly Gly Cys Thr Cys Ala Gly Gly Cys Thr Gly
            290                 295                 300

Ala Gly Gly Ala Cys Gly Ala Gly Gly Cys Thr Gly Thr Thr Thr Ala
305                 310                 315                 320

Thr Thr Ala Cys Thr Gly Cys Thr Cys Thr Cys Ala Thr Ala Thr
                325                 330                 335

Gly Cys Ala Gly Gly Thr Ala Gly Thr Ala Gly Cys Ala Cys Thr Thr
            340                 345                 350

Gly Gly Gly Thr Gly Thr Thr Cys Gly Cys Gly Ala Gly Gly
        355                 360                 365

Gly Ala Cys Cys Ala Ala Gly Cys Thr Gly Ala Cys Cys Gly Thr Cys
    370                 375                 380

Cys Thr Ala Gly Gly
385

<210> SEQ ID NO 96
<211> LENGTH: 110
<212> TYPE: PRT
<213> ORGANISM: Homo sapiens

<400> SEQUENCE: 96

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
            20                  25                  30

Lys Tyr Val Ser Trp Tyr Gln Gln His Pro Gly Lys Ala Pro Lys Leu
        35                  40                  45

Met Ile Tyr Asp Val Asn Thr Arg Pro Ser Gly Val Ser Thr Arg Phe
    50                  55                  60

Ser Ala Ser Lys Ser Gly Asn Thr Ala Ser Leu Thr Val Ser Gly Leu
65                  70                  75                  80

Gln Ala Glu Asp Glu Ala Val Tyr Tyr Cys Ser Ser Tyr Ala Gly Ser
                85                  90                  95

Ser Thr Trp Val Phe Gly Gly Gly Thr Lys Leu Thr Val Leu
            100                 105                 110

<210> SEQ ID NO 97
<211> LENGTH: 10
<212> TYPE: PRT
<213> ORGANISM: Homo sapiens

<400> SEQUENCE: 97

Gly Phe Thr Phe Ile Ser Tyr Ala Met His
1               5                   10

<210> SEQ ID NO 98
<211> LENGTH: 17
<212> TYPE: PRT
<213> ORGANISM: Homo sapiens

<400> SEQUENCE: 98

Trp Ile Asn Ala Gly Asp Gly His Thr Lys Tyr Ser Gln Lys Phe Gln
1               5                   10                  15

Asp

<210> SEQ ID NO 99
<211> LENGTH: 17
<212> TYPE: PRT
<213> ORGANISM: Homo sapiens

<400> SEQUENCE: 99

Asp Gly Phe Cys Thr Thr Thr Thr Cys Ser Asp His Tyr Gly Met Asp
1               5                   10                  15

Val

<210> SEQ ID NO 100
<211> LENGTH: 437
<212> TYPE: PRT
<213> ORGANISM: Homo sapiens

<400> SEQUENCE: 100

```
Ala Thr Gly Gly Ala Cys Thr Gly Gly Ala Cys Cys Thr Gly Gly Ala
1               5                   10                  15

Gly Gly Ala Thr Cys Cys Thr Cys Thr Thr Thr Thr Thr Gly Gly Thr
            20                  25                  30

Gly Gly Cys Ala Gly Cys Ala Gly Cys Ala Cys Ala Gly Gly Thr
        35                  40                  45

Gly Cys Cys Cys Ala Cys Thr Cys Cys Ala Gly Gly Thr Cys Cys
    50                  55                  60

Ala Gly Cys Thr Thr Gly Thr Gly Cys Ala Gly Thr Cys Thr Gly Gly
65                  70                  75                  80

Gly Gly Cys Thr Gly Ala Gly Gly Thr Gly Ala Ala Gly Ala Ala Gly
            85                  90                  95

Cys Cys Thr Gly Gly Gly Gly Cys Cys Thr Cys Ala Gly Thr Gly Ala
            100                 105                 110

Gly Gly Gly Thr Thr Thr Cys Cys Thr Gly Cys Ala Ala Gly Gly Cys
            115                 120                 125

Thr Thr Cys Thr Gly Gly Ala Thr Thr Cys Ala Cys Cys Thr Thr Cys
        130                 135                 140

Ala Thr Thr Ala Gly Thr Thr Ala Thr Gly Cys Thr Ala Thr Gly Cys
145                 150                 155                 160

Ala Thr Thr Gly Gly Gly Thr Gly Cys Gly Cys Cys Ala Gly Gly Cys
            165                 170                 175

Cys Cys Cys Cys Gly Gly Ala Cys Ala Ala Gly Gly Gly Cys Thr Thr
            180                 185                 190

Gly Ala Gly Thr Gly Gly Ala Thr Gly Gly Gly Ala Thr Gly Gly Ala
            195                 200                 205

Thr Cys Ala Ala Cys Gly Cys Thr Gly Gly Cys Gly Ala Thr Gly Gly
        210                 215                 220

Thr Cys Ala Cys Ala Cys Ala Ala Ala Thr Ala Thr Thr Cys Ala
225                 230                 235                 240

Cys Ala Gly Ala Ala Gly Thr Thr Cys Ala Gly Gly Ala Cys Ala
            245                 250                 255

Gly Ala Gly Thr Cys Gly Cys Cys Ala Thr Thr Ala Cys Cys Ala Gly
            260                 265                 270

Gly Gly Ala Cys Ala Cys Ala Thr Cys Cys Gly Cys Ala Cys Cys
        275                 280                 285

Ala Cys Ala Gly Thr Cys Thr Ala Cys Ala Gly Gly Ala Cys Cys
        290                 295                 300

Thr Gly Ala Gly Cys Ala Gly Cys Cys Thr Gly Ala Gly Ala Thr Cys
305                 310                 315                 320

Thr Gly Ala Ala Gly Ala Cys Ala Cys Gly Gly Cys Thr Gly Thr Gly
            325                 330                 335

Thr Ala Thr Thr Ala Cys Thr Gly Thr Cys Gly Ala Gly Ala Gly
        340                 345                 350

Ala Thr Gly Gly Ala Thr Thr Thr Thr Gly Thr Ala Cys Thr Ala Cys
            355                 360                 365
```

```
Thr Ala Cys Cys Ala Cys Thr Gly Thr Cys Cys Gly Ala Cys
    370                 375                 380

Cys Ala Cys Thr Ala Cys Gly Gly Thr Ala Thr Gly Gly Ala Cys Gly
385                 390                 395                 400

Thr Cys Thr Gly Gly Gly Cys Cys Ala Ala Gly Gly Gly Ala Cys
                405                 410                 415

Cys Ala Cys Gly Gly Thr Cys Ala Cys Cys Gly Thr Cys Thr Cys Cys
                420                 425                 430

Thr Cys Ala Gly Cys
        435
```

<210> SEQ ID NO 101
<211> LENGTH: 126
<212> TYPE: PRT
<213> ORGANISM: Homo sapiens

<400> SEQUENCE: 101

```
Gln Val Gln Leu Val Gln Ser Gly Ala Glu Val Lys Lys Pro Gly Ala
1               5                   10                  15

Ser Val Arg Val Ser Cys Lys Ala Ser Gly Phe Thr Phe Ile Ser Tyr
            20                  25                  30

Ala Met His Trp Val Arg Gln Ala Pro Gly Gln Gly Leu Glu Trp Met
        35                  40                  45

Gly Trp Ile Asn Ala Gly Asp Gly His Thr Lys Tyr Ser Gln Lys Phe
    50                  55                  60

Gln Asp Arg Val Ala Ile Thr Arg Asp Thr Ser Ala Thr Thr Val Tyr
65                  70                  75                  80

Met Asp Leu Ser Ser Leu Arg Ser Glu Asp Thr Ala Val Tyr Tyr Cys
                85                  90                  95

Ser Arg Asp Gly Phe Cys Thr Thr Thr Cys Ser Asp His Tyr Gly
            100                 105                 110

Met Asp Val Trp Gly Gln Gly Thr Thr Val Thr Val Ser Ser
        115                 120                 125
```

<210> SEQ ID NO 102
<211> LENGTH: 389
<212> TYPE: PRT
<213> ORGANISM: Homo sapiens

<400> SEQUENCE: 102

```
Ala Thr Gly Gly Cys Cys Thr Gly Gly Cys Thr Cys Thr Gly Cys
1               5                   10                  15

Thr Gly Cys Thr Cys Cys Thr Cys Ala Ala Cys Cys Thr Cys Cys Thr
            20                  25                  30

Cys Ala Cys Thr Cys Ala Gly Gly Ala Cys Ala Cys Ala Gly Gly Gly
        35                  40                  45

Thr Cys Cys Thr Gly Gly Gly Cys Cys Cys Ala Gly Thr Cys Thr Gly
    50                  55                  60

Cys Cys Cys Thr Gly Ala Cys Thr Cys Ala Gly Cys Cys Thr Gly Cys
65                  70                  75                  80

Cys Thr Cys Cys Gly Thr Gly Thr Cys Thr Gly Gly Gly Thr Cys Thr
                85                  90                  95

Cys Cys Thr Gly Gly Ala Cys Ala Gly Thr Cys Gly Ala Thr Cys Ala
            100                 105                 110

Cys Cys Ala Thr Cys Thr Cys Cys Thr Gly Cys Ala Cys Thr Gly Gly
        115                 120                 125
```

```
Ala Ala Cys Cys Ala Gly Cys Ala Gly Thr Gly Ala Thr Gly Thr Thr
            130                 135                 140

Gly Gly Thr Ala Gly Thr Thr Ala Thr Ala Ala Cys Thr Ala Thr Gly
145                 150                 155                 160

Thr Cys Thr Cys Cys Thr Gly Gly Thr Ala Cys Cys Ala Ala Cys Ala
                165                 170                 175

Gly Cys Ala Cys Cys Ala Gly Gly Cys Ala Ala Gly Cys Cys
            180                 185                 190

Cys Cys Cys Ala Ala Ala Thr Thr Cys Ala Thr Gly Ala Thr Thr Thr
        195                 200                 205

Ala Thr Gly Ala Thr Gly Thr Cys Ala Gly Thr Ala Ala Gly Cys Gly
    210                 215                 220

Gly Cys Cys Cys Thr Cys Ala Gly Gly Gly Thr Thr Thr Cys Thr Thr
225                 230                 235                 240

Gly Ala Thr Cys Gly Cys Thr Thr Cys Thr Cys Thr Gly Gly Cys Thr
                245                 250                 255

Cys Cys Ala Ala Gly Thr Cys Thr Gly Gly Cys Ala Ala Cys Ala Cys
            260                 265                 270

Gly Gly Cys Cys Thr Cys Cys Cys Thr Gly Ala Cys Ala Ala Thr Cys
        275                 280                 285

Thr Cys Thr Gly Gly Gly Cys Thr Cys Cys Ala Gly Gly Cys Thr Gly
    290                 295                 300

Ala Gly Gly Ala Cys Gly Ala Gly Gly Cys Thr Gly Ala Thr Thr Ala
305                 310                 315                 320

Thr Thr Ala Cys Thr Gly Cys Thr Gly Cys Thr Cys Ala Thr Ala Thr
                325                 330                 335

Gly Cys Ala Gly Gly Thr Ala Gly Thr Ala Gly Cys Ala Cys Thr Thr
            340                 345                 350

Gly Gly Gly Thr Gly Thr Thr Cys Gly Gly Cys Gly Gly Ala Gly Gly
        355                 360                 365

Gly Ala Cys Cys Ala Ala Gly Cys Thr Gly Ala Cys Cys Gly Thr Cys
    370                 375                 380

Cys Thr Thr Gly Gly
385

<210> SEQ ID NO 103
<211> LENGTH: 110
<212> TYPE: PRT
<213> ORGANISM: Homo sapiens

<400> SEQUENCE: 103

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Ser Trp Tyr Gln Gln His Pro Gly Lys Ala Pro Lys Phe
        35                  40                  45

Met Ile Tyr Asp Val Ser Lys Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Trp Val Phe Gly Gly Gly Thr Lys Leu Thr Val Leu
            100                 105                 110
```

100        105        110

<210> SEQ ID NO 104
<211> LENGTH: 10
<212> TYPE: PRT
<213> ORGANISM: Homo sapiens

<400> SEQUENCE: 104

Gly Phe Thr Phe Thr Ser Tyr Ala Ile Gln
1               5                   10

<210> SEQ ID NO 105
<211> LENGTH: 10
<212> TYPE: PRT
<213> ORGANISM: Homo sapiens

<400> SEQUENCE: 105

Cys Ser Tyr Ala Gly Gly Ser Thr Trp Val
1               5                   10

<210> SEQ ID NO 106
<211> LENGTH: 437
<212> TYPE: PRT
<213> ORGANISM: Homo sapiens

<400> SEQUENCE: 106

Ala Thr Gly Gly Ala Cys Thr Gly Gly Ala Cys Cys Thr Gly Ala
1               5                   10                  15

Gly Gly Ala Thr Cys Cys Thr Cys Thr Thr Thr Thr Gly Gly Thr
                20                  25                  30

Gly Gly Cys Ala Gly Cys Ala Gly Cys Ala Cys Ala Gly Gly Thr
                35                  40                  45

Gly Cys Cys Cys Ala Cys Thr Cys Cys Ala Gly Gly Thr Cys Cys
    50                  55                  60

Ala Gly Cys Thr Thr Gly Thr Gly Cys Ala Gly Thr Cys Thr Gly
65                  70                  75                  80

Gly Gly Cys Thr Gly Ala Gly Gly Thr Gly Ala Ala Gly Ala Ala
                85                  90                  95

Cys Cys Thr Gly Gly Gly Cys Cys Thr Cys Ala Gly Thr Gly Ala
                100                 105                 110

Gly Gly Gly Thr Thr Thr Cys Cys Thr Gly Cys Ala Ala Gly Ala Cys
    115                 120                 125

Thr Thr Cys Thr Gly Gly Ala Thr Thr Cys Ala Cys Cys Thr Cys
    130                 135                 140

Ala Cys Thr Ala Gly Thr Thr Ala Thr Gly Cys Thr Ala Thr Ala Cys
145                 150                 155                 160

Ala Gly Thr Gly Gly Gly Thr Gly Cys Gly Cys Ala Gly Gly Cys
                165                 170                 175

Cys Cys Cys Cys Gly Gly Ala Cys Ala Ala Gly Gly Gly Cys Thr Thr
            180                 185                 190

Gly Ala Gly Thr Gly Gly Ala Thr Gly Gly Ala Thr Gly Gly Ala
        195                 200                 205

Thr Cys Ala Ala Cys Gly Cys Thr Gly Gly Cys Ala Thr Gly Gly
        210                 215                 220

Thr Cys Ala Cys Ala Cys Gly Ala Ala Thr Ala Thr Thr Cys Ala
225                 230                 235                 240

Cys Ala Gly Ala Ala Gly Thr Thr Cys Cys Ala Gly Gly Ala Cys Ala
            245                 250                 255

```
Gly Ala Gly Thr Cys Gly Thr Cys Ala Thr Thr Ala Cys Cys Ala Gly
            260                 265                 270

Gly Gly Ala Cys Ala Cys Ala Thr Cys Cys Gly Cys Gly Ala Cys Cys
            275                 280                 285

Ala Cys Ala Gly Thr Cys Thr Ala Cys Ala Thr Gly Gly Ala Cys Cys
            290                 295                 300

Thr Gly Ala Gly Cys Ala Gly Cys Cys Thr Gly Ala Gly Ala Thr Cys
305                 310                 315                 320

Thr Gly Ala Ala Gly Ala Cys Ala Cys Gly Gly Cys Thr Gly Thr Gly
                325                 330                 335

Thr Ala Thr Thr Ala Cys Thr Gly Thr Ala Cys Gly Ala Gly Ala Gly
            340                 345                 350

Ala Thr Gly Gly Ala Thr Thr Thr Thr Gly Thr Ala Cys Thr Ala Cys
            355                 360                 365

Gly Ala Cys Cys Ala Cys Cys Thr Gly Cys Thr Cys Cys Gly Ala Cys
            370                 375                 380

Cys Ala Cys Thr Ala Cys Gly Gly Thr Ala Thr Gly Gly Ala Cys Gly
385                 390                 395                 400

Thr Cys Thr Gly Gly Gly Gly Cys Cys Ala Ala Gly Gly Gly Ala Cys
                405                 410                 415

Cys Ala Cys Gly Gly Thr Cys Ala Cys Cys Gly Thr Cys Thr Cys Cys
            420                 425                 430

Thr Cys Ala Gly Cys
        435

<210> SEQ ID NO 107
<211> LENGTH: 126
<212> TYPE: PRT
<213> ORGANISM: Homo sapiens

<400> SEQUENCE: 107

Gln Val Gln Leu Val Gln Ser Gly Ala Glu Val Lys Lys Pro Gly Ala
1               5                   10                  15

Ser Val Arg Val Ser Cys Lys Thr Ser Gly Phe Thr Phe Thr Ser Tyr
            20                  25                  30

Ala Ile Gln Trp Val Arg Gln Ala Pro Gly Gln Gly Leu Glu Trp Met
        35                  40                  45

Gly Trp Ile Asn Ala Gly Asp Gly His Thr Lys Tyr Ser Gln Lys Phe
    50                  55                  60

Gln Asp Arg Val Val Ile Thr Arg Asp Thr Ser Ala Thr Thr Val Tyr
65                  70                  75                  80

Met Asp Leu Ser Ser Leu Arg Ser Glu Asp Thr Ala Val Tyr Tyr Cys
                85                  90                  95

Thr Arg Asp Gly Phe Cys Thr Thr Thr Cys Ser Asp His Tyr Gly
            100                 105                 110

Met Asp Val Trp Gly Gln Gly Thr Thr Val Thr Val Ser Ser
        115                 120                 125

<210> SEQ ID NO 108
<211> LENGTH: 389
<212> TYPE: PRT
<213> ORGANISM: Homo sapiens

<400> SEQUENCE: 108

Ala Thr Gly Gly Cys Cys Thr Gly Gly Gly Cys Thr Cys Thr Gly Cys
1               5                   10                  15
```

Thr Gly Cys Thr Cys Cys Thr Cys Ala Ala Cys Cys Thr Cys Cys Thr
                20                  25                  30
Cys Ala Cys Thr Cys Ala Gly Gly Ala Cys Ala Cys Ala Gly Gly Gly
            35                  40                  45
Thr Cys Thr Cys Thr Gly Gly Gly Cys Cys Cys Ala Gly Thr Cys Gly
        50                  55                  60
Cys Cys Cys Thr Gly Ala Cys Thr Cys Ala Gly Cys Cys Thr Gly Cys
65                  70                  75                  80
Cys Thr Cys Cys Gly Thr Gly Thr Cys Thr Gly Gly Gly Thr Cys Thr
                85                  90                  95
Cys Cys Thr Gly Gly Ala Cys Ala Gly Thr Cys Gly Ala Thr Cys Ala
                100                 105                 110
Cys Cys Ala Thr Cys Thr Cys Cys Thr Gly Cys Ala Cys Thr Gly Gly
            115                 120                 125
Ala Ala Cys Cys Ala Gly Cys Ala Gly Thr Gly Ala Thr Gly Thr Thr
        130                 135                 140
Gly Gly Thr Ala Gly Thr Thr Ala Thr Ala Ala Cys Thr Ala Thr Gly
145                 150                 155                 160
Thr Cys Thr Cys Cys Thr Gly Gly Thr Ala Cys Cys Ala Ala Cys Ala
                165                 170                 175
Gly Cys Ala Cys Cys Cys Ala Gly Gly C

<400> SEQUENCE: 109

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Ser Trp Tyr Gln Gln His Pro Gly Lys Val Pro Lys Phe
        35                  40                  45

Met Ile Ser Asp Val Ser Lys Arg Pro Ser Gly Ile Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Gly
                85                  90                  95

Ser Thr Trp Val Phe Gly Gly Gly Thr Lys Leu Thr Val Leu
            100                 105                 110

<210> SEQ ID NO 110
<211> LENGTH: 10
<212> TYPE: PRT
<213> ORGANISM: Homo sapiens

<400> SEQUENCE: 110

Gly Phe Thr Phe Thr Asn Tyr Ala Met His
1               5                   10

<210> SEQ ID NO 111
<211> LENGTH: 17
<212> TYPE: PRT
<213> ORGANISM: Homo sapiens

<400> SEQUENCE: 111

Asp Gly Phe Cys Ser Thr Thr Cys Ser Asp His Tyr Gly Met Asp
1               5                   10                  15

Val

<210> SEQ ID NO 112
<211> LENGTH: 14
<212> TYPE: PRT
<213> ORGANISM: Homo sapiens

<400> SEQUENCE: 112

Thr Gly Thr Ser Ser Asp Val Gly Gly Tyr Asn Tyr Val Ser
1               5                   10

<210> SEQ ID NO 113
<211> LENGTH: 437
<212> TYPE: PRT
<213> ORGANISM: Homo sapiens

<400> SEQUENCE: 113

Ala Thr Gly Gly Ala Cys Thr Gly Gly Ala Cys Cys Thr Gly Gly Ala
1               5                   10                  15

Gly Gly Ala Thr Cys Cys Thr Cys Thr Thr Cys Thr Thr Gly Gly Thr
            20                  25                  30

Gly Gly Cys Ala Gly Cys Ala Gly Cys Cys Ala Cys Ala Gly Gly Thr
        35                  40                  45

Gly Cys Cys Cys Ala Cys Thr Cys Cys Ala Gly Gly Thr Cys Cys
    50                  55                  60

Ala Gly Cys Thr Thr Gly Thr Gly Cys Ala Gly Thr Cys Thr Gly Gly

```
                65                  70                  75                  80
Gly Gly Cys Thr Gly Ala Gly Thr Gly Ala Ala Gly Ala Ala Cys
                    85                  90                  95
Cys Cys Thr Gly Gly Gly Cys Cys Thr Cys Ala Gly Thr Gly Ala
                    100                 105                 110
Ala Gly Gly Thr Thr Thr Cys Thr Gly Cys Ala Ala Gly Gly Cys
                    115                 120                 125
Thr Thr Cys Thr Gly Gly Ala Thr Thr Cys Ala Cys Cys Thr Cys
                    130                 135                 140
Ala Cys Thr Ala Ala Cys Thr Ala Thr Gly Cys Thr Ala Thr Gly
145                 150                 155                 160
Ala Thr Thr Gly Gly Thr Gly Cys Gly Cys Ala Gly Gly Cys
                    165                 170                 175
Cys Cys Cys Cys Gly Gly Ala Cys Ala Ala Gly Gly Cys Thr Thr
                    180                 185                 190
Gly Ala Gly Thr Gly Gly Ala Thr Gly Gly Gly Ala Thr Gly Ala
                    195                 200                 205
Thr Cys Ala Ala Cys Gly Cys Thr Gly Gly Cys Ala Ala Thr Gly Gly
210                 215                 220
Thr Cys Ala Cys Ala Cys Ala Ala Ala Thr Ala Thr Cys Ala
225                 230                 235                 240
Cys Ala Gly Ala Ala Gly Thr Thr Cys Ala Gly Gly Ala Cys Ala
                    245                 250                 255
Gly Ala Gly Thr Cys Ala Cys Cys Ala Thr Thr Ala Cys Cys Ala
                    260                 265                 270
Gly Gly Ala Cys Ala Cys Ala Thr Cys Cys Gly Cys Gly Ala Cys Cys
                275                 280                 285
Ala Cys Ala Gly Cys Cys Thr Ala Cys Ala Thr Gly Ala Ala Cys
                    290                 295                 300
Thr Gly Ala Gly Cys Ala Gly Cys Cys Thr Gly Ala Gly Ala Thr Cys
305                 310                 315                 320
Thr Gly Ala Ala Gly Ala Cys Ala Cys Gly Gly Cys Thr Gly Thr
                    325                 330                 335
Thr Ala Thr Thr Ala Cys Thr Gly Thr Cys Gly Ala Gly Ala Gly
                    340                 345                 350
Ala Thr Gly Gly Ala Thr Thr Thr Gly Thr Ala Gly Thr Ala Cys
                    355                 360                 365
Thr Ala Cys Cys Ala Cys Thr Gly Cys Thr Cys Cys Gly Ala Cys
                    370                 375                 380
Cys Ala Cys Thr Ala Cys Gly Gly Thr Ala Thr Gly Gly Ala Cys Gly
385                 390                 395                 400
Thr Cys Thr Gly Gly Gly Gly Cys Ala Ala Gly Gly Gly Ala Cys
                    405                 410                 415
Cys Ala Cys Gly Gly Thr Cys Ala Cys Cys Gly Thr Cys Thr Cys
                    420                 425                 430
Thr Cys Ala Gly Cys
        435

<210> SEQ ID NO 114
<211> LENGTH: 126
<212> TYPE: PRT
<213> ORGANISM: Homo sapiens

<400> SEQUENCE: 114
```

Gln Val Gln Leu Val Gln Ser Gly Ala Glu Val Lys Asn Pro Gly Ala
1               5                   10                  15

Ser Val Lys Val Ser Cys Lys Ala Ser Gly Phe Thr Phe Thr Asn Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly His Thr Lys Tyr Ser Gln Lys Phe
50                  55                  60

Gln Asp Arg Val Ala Ile Thr Arg Asp Thr Ser Ala Thr Thr Ala Tyr
65                  70                  75                  80

Met Glu Leu Ser Ser Leu Arg Ser Glu Asp Thr Ala Val Tyr Tyr Cys
                85                  90                  95

Ser Arg Asp Gly Phe Cys Ser Thr Thr Thr Cys Ser Asp His Tyr Gly
                100                 105                 110

Met Asp Val Trp Gly Gln Gly Thr Thr Val Thr Val Ser Ser
            115                 120                 125

<210> SEQ ID NO 115
<211> LENGTH: 389
<212> TYPE: PRT
<213> ORGANISM: Homo sapiens

<400> SEQUENCE: 115

Ala Thr Gly Gly Cys Thr Gly Gly Cys Thr Cys Thr Gly Cys
1               5                   10                  15

Thr Gly Cys Thr Cys Cys Thr Cys Ala Ala Cys Cys Thr Cys Cys Thr
            20                  25                  30

Cys Ala Cys Thr Cys Ala Gly Gly Ala Cys Ala Cys Ala Gly Gly Gly
        35                  40                  45

Thr Cys Cys Thr Gly Gly Gly Cys Cys Cys Ala Gly Cys Thr Gly Gly
50                  55                  60

Cys Cys Cys Thr Gly Ala Cys Thr Cys Ala Gly Cys Cys Thr Gly Cys
65                  70                  75                  80

Cys Thr Cys Cys Gly Thr Gly Thr Cys Thr Gly Gly Gly Thr Cys Thr
                85                  90                  95

Cys Cys Thr Gly Gly Ala Cys Ala Gly Thr Cys Gly Ala Thr Cys Ala
                100                 105                 110

Cys Cys Ala Thr Cys Thr Cys Cys Thr Gly Cys Ala Cys Thr Gly Gly
                115                 120                 125

Ala Ala Cys Cys Ala Gly Cys Ala Gly Thr Gly Ala Thr Gly Thr Thr
                130                 135                 140

Gly Gly Thr Gly Gly Thr Thr Ala Thr Ala Ala Cys Thr Ala Thr Gly
145                 150                 155                 160

Thr Cys Thr Cys Cys Thr Gly Gly Thr Ala Cys Cys Ala Ala Cys Ala
                165                 170                 175

Gly Cys Ala Cys Cys Cys Ala Gly Gly Cys Ala Ala Gly Cys Cys
                180                 185                 190

Cys Cys Cys Ala Ala Ala Thr Cys Ala Thr Gly Ala Thr Thr Thr
                195                 200                 205

Ala Thr Gly Ala Thr Gly Thr Cys Ala Gly Thr Ala Ala Gly Cys Gly
                210                 215                 220

Gly Cys Cys Cys Thr Cys Ala Gly Gly Gly Gly Thr Thr Thr Cys Cys
225                 230                 235                 240

Ala Ala Thr Cys Gly Cys Thr Thr Cys Thr Cys Thr Gly Gly Cys Thr
                245                 250                 255

```
Cys Cys Ala Ala Gly Thr Cys Thr Gly Gly Cys Ala Ala Cys Ala Cys
            260                 265                 270

Gly Gly Cys Cys Thr Cys Cys Thr Gly Ala Cys Ala Ala Thr Cys
            275                 280                 285

Thr Cys Thr Gly Gly Gly Cys Thr Cys Cys Ala Gly Gly Cys Thr Gly
            290                 295                 300

Ala Gly Gly Ala Cys Gly Ala Gly Gly Cys Thr Gly Ala Thr Thr Ala
305                 310                 315                 320

Thr Thr Ala Cys Thr Gly Cys Thr Gly Cys Thr Cys Ala Thr Ala Thr
            325                 330                 335

Gly Cys Ala Gly Gly Thr Ala Gly Thr Ala Gly Cys Ala Cys Thr Thr
            340                 345                 350

Gly Gly Gly Thr Gly Thr Thr Cys Gly Gly Cys Gly Gly Ala Gly Gly
            355                 360                 365

Gly Ala Cys Cys Ala Ala Gly Cys Thr Gly Ala Cys Cys Gly Thr Cys
            370                 375                 380

Cys Thr Ala Gly Gly
385

<210> SEQ ID NO 116
<211> LENGTH: 110
<212> TYPE: PRT
<213> ORGANISM: Homo sapiens

<400> SEQUENCE: 116

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Phe
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Trp Val Phe Gly Gly Gly Thr Lys Leu Thr Val Leu
            100                 105                 110

<210> SEQ ID NO 117
<211> LENGTH: 10
<212> TYPE: PRT
<213> ORGANISM: Homo sapiens

<400> SEQUENCE: 117

Gly Phe Thr Phe Thr Ser His Ala Ile His
1               5                   10

<210> SEQ ID NO 118
<211> LENGTH: 437
<212> TYPE: PRT
<213> ORGANISM: Homo sapiens

<400> SEQUENCE: 118

Ala Thr Gly Gly Ala Cys Thr Gly Gly Ala Cys Cys Thr Gly Gly Ala
1               5                   10                  15
```

```
Gly Gly Ala Thr Cys Cys Thr Cys Thr Thr Thr Thr Gly Gly Thr
            20                  25                  30

Gly Gly Cys Ala Gly Cys Ala Gly Cys Ala Cys Ala Gly Gly Thr
            35                  40                  45

Gly Cys Cys Cys Ala Cys Thr Cys Cys Ala Gly Gly Thr Cys Cys
    50                  55                  60

Ala Gly Cys Thr Thr Gly Thr Gly Cys Ala Gly Thr Cys Gly Gly
65                  70                  75                  80

Gly Gly Cys Thr Gly Ala Gly Thr Gly Ala Ala Gly Ala Ala Gly
                85                  90                  95

Cys Cys Thr Gly Gly Gly Cys Cys Thr Cys Ala Gly Thr Gly Ala
            100                 105                 110

Ala Gly Gly Thr Thr Thr Cys Thr Gly Cys Ala Ala Gly Gly Cys
            115                 120                 125

Thr Thr Cys Thr Gly Gly Ala Thr Thr Cys Ala Cys Cys Thr Cys
    130                 135                 140

Ala Cys Thr Ala Gly Cys Cys Ala Thr Gly Cys Thr Ala Thr Cys
145                 150                 155                 160

Ala Thr Thr Gly Gly Gly Thr Gly Cys Gly Cys Ala Gly Gly Cys
            165                 170                 175

Cys Cys Cys Cys Gly Gly Ala Cys Ala Ala Gly Gly Cys Thr Thr
            180                 185                 190

Gly Ala Gly Thr Gly Gly Ala Thr Gly Gly Ala Thr Gly Gly Ala
            195                 200                 205

Thr Cys Ala Ala Cys Gly Cys Thr Gly Gly Cys Ala Ala Thr Gly
    210                 215                 220

Thr Thr Ala Cys Ala Cys Ala Ala Ala Thr Ala Thr Thr Cys Ala
225                 230                 235                 240

Cys Ala Gly Ala Ala Gly Thr Thr Cys Ala Gly Gly Ala Cys Ala
            245                 250                 255

Gly Ala Gly Thr Cys Gly Cys Cys Ala Thr Thr Ala Cys

<210> SEQ ID NO 119
<211> LENGTH: 126
<212> TYPE: PRT
<213> ORGANISM: Homo sapiens

<400> SEQUENCE: 119

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser His
            20                  25                  30

Ala Ile His Trp Val Arg Gln Ala Pro Gly Gln Arg Leu Glu Trp Met
        35                  40                  45

Gly Trp Ile Asn Ala Gly Asn Gly Tyr Thr Lys Tyr Ser Gln Lys Phe
    50                  55                  60

Gln Asp Arg Val Ala Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asp Gly Phe Cys Ser Thr Thr Cys Ser Asp His Tyr Gly
            100                 105                 110

Met Asp Val Trp Gly Gln Gly Thr Thr Val Thr Val Ser Ser
        115                 120                 125
```

<210> SEQ ID NO 120
<211> LENGTH: 389
<212> TYPE: PRT
<213> ORGANISM: Homo sapiens

<400> SEQUENCE: 120

```
Ala Thr Gly Gly Cys Thr Gly Gly Cys Thr Cys Thr Gly Cys
1               5                   10                  15

Thr Gly Cys Thr Cys Cys Thr Cys Ala Ala Cys Cys Thr Cys Cys Thr
            20                  25                  30

Cys Ala Cys Thr Cys Ala Gly Gly Ala Cys Ala Cys Ala Gly Gly Gly
        35                  40                  45

Thr Cys Cys Thr Gly Gly Gly Cys Cys Ala Gly Thr Cys Thr Gly
    50                  55                  60

Cys Cys Cys Thr Gly Ala Cys Thr Cys Ala Gly Cys Cys Thr Gly Cys
65                  70                  75                  80

Cys Thr Cys Cys Gly Thr Gly Thr Cys Thr Gly Gly Gly Thr Cys Thr
                85                  90                  95

Cys Cys Thr Gly Gly Ala Cys Ala Gly Thr Cys Gly Ala Thr Cys Ala
            100                 105                 110

Cys Cys Ala Thr Cys Thr Cys Cys Thr Gly Cys Ala Cys Thr Gly Gly
        115                 120                 125

Ala Ala Cys Cys Ala Gly Cys Ala Gly Thr Gly Ala Thr Gly Thr Thr
    130                 135                 140

Gly Gly Cys Gly Gly Thr Thr Ala Thr Ala Ala Cys Thr Ala Thr Gly
145                 150                 155                 160

Thr Cys Thr Cys Cys Thr Gly Gly Thr Ala Cys Cys Ala Ala Cys Ala
                165                 170                 175

Gly Cys Ala Cys Cys Cys Ala Gly Gly Cys Ala Ala Ala Gly Cys Cys
            180                 185                 190

Cys Cys Cys Ala Ala Ala Thr Thr Cys Ala Thr Gly Ala Thr Thr Thr
```

```
                195                 200                 205
Ala Thr Gly Ala Thr Gly Thr Cys Ala Gly Thr Ala Ala Gly Cys Gly
    210                 215                 220

Gly Cys Cys Cys Thr Cys Ala Gly Gly Gly Thr Thr Thr Cys Thr
225                 230                 235                 240

Ala Ala Thr Cys Gly Cys Thr Cys Thr Cys Thr Gly Gly Cys Thr
                245                 250                 255

Cys Cys Ala Ala Gly Thr Cys Thr Gly Gly Cys Ala Ala Cys Ala Cys
                260                 265                 270

Gly Gly Cys Cys Thr Cys Cys Thr Gly Ala Cys Ala Ala Thr Cys
            275                 280                 285

Thr Cys Thr Gly Gly Gly Cys Thr Cys Ala Gly Gly Cys Thr Gly
    290                 295                 300

Ala Gly Gly Ala Cys Gly Ala Gly Gly Cys Thr Gly Ala Thr Thr Ala
305                 310                 315                 320

Thr Thr Ala Cys Thr Gly Cys Thr Gly Cys Thr Cys Ala Thr Ala Thr
                325                 330                 335

Gly Cys Ala Gly Gly Thr Ala Gly Thr Ala Gly Cys Ala Cys Thr Thr
            340                 345                 350

Gly Gly Gly Thr Gly Thr Thr Cys Gly Gly Cys Gly Gly Ala Gly Gly
    355                 360                 365

Gly Ala Cys Cys Ala Ala Gly Cys Thr Gly Ala Cys Cys Gly Thr Cys
370                 375                 380

Cys Thr Ala Gly Gly
385

<210> SEQ ID NO 121
<211> LENGTH: 110
<212> TYPE: PRT
<213> ORGANISM: Homo sapiens

<400> SEQUENCE: 121

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Phe
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Trp Val Phe Gly Gly Gly Thr Lys Leu Thr Val Leu
            100                 105                 110

<210> SEQ ID NO 122
<211> LENGTH: 10
<212> TYPE: PRT
<213> ORGANISM: Homo sapiens

<400> SEQUENCE: 122

Gly Tyr Ile Phe Ile Asn Tyr Ala Met Gln
1               5                   10
```

```
<210> SEQ ID NO 123
<211> LENGTH: 17
<212> TYPE: PRT
<213> ORGANISM: Homo sapiens

<400> SEQUENCE: 123

Asp Gly Phe Cys Arg Thr Thr Ser Cys Ser Asp His Tyr Gly Met Asp
1               5                   10                  15

Val

<210> SEQ ID NO 124
<211> LENGTH: 437
<212> TYPE: PRT
<213> ORGANISM: Homo sapiens

<400> SEQUENCE: 124

Ala Thr Gly Gly Ala Cys Thr Gly Gly Ala Cys Cys Thr Gly Gly Ala
1               5                   10                  15

Gly Gly Ala Thr Cys Cys Thr Cys Thr Thr Thr Thr Gly Gly Thr
                20                  25                  30

Gly Gly Cys Ala Gly Cys Ala Gly Cys Ala Cys Ala Gly Gly Thr
            35                  40                  45

Gly Cys Cys Ala Cys Thr Cys Cys Ala Gly Gly Thr Cys Cys
        50                  55                  60

Ala Gly Cys Thr Thr Gly Thr Cys Ala Gly Thr Cys Thr Gly Gly
65                  70                  75                  80

Gly Gly Cys Thr Gly Ala Gly Gly Thr Gly Ala Ala Gly Ala Ala Gly
                85                  90                  95

Cys Cys Thr Gly Gly Gly Cys Cys Thr Cys Ala Gly Thr Gly Ala
            100                 105                 110

Ala Gly Gly Thr Thr Thr Cys Cys Thr Gly Cys Ala Ala Gly Gly Cys
                115                 120                 125

Thr Thr Cys Thr Gly Gly Ala Thr Ala Cys Ala Thr Cys Thr Thr Thr
            130                 135                 140

Ala Thr Thr Ala Ala Cys Thr Ala Thr Gly Cys Thr Ala Thr Gly Cys
145                 150                 155                 160

Ala Ala Thr Gly Gly Gly Thr Gly Cys Gly Cys Ala Gly Gly Cys
                165                 170                 175

Cys Cys Cys Cys Gly Gly Ala Cys Ala Ala Gly Gly Cys Thr Thr
            180                 185                 190

Gly Ala Gly Thr Gly Gly Ala Thr Gly Gly Gly Ala Thr Gly Ala
                195                 200                 205

Thr Cys Ala Ala Cys Gly Cys Thr Gly Gly Cys Ala Ala Cys Gly Gly
            210                 215                 220

Thr Thr Ala Cys Ala Cys Ala Ala Ala Thr Ala Thr Cys Ala
225                 230                 235                 240

Cys Ala Gly Ala Ala Gly Thr Thr Cys Ala Gly Gly Gly Cys Ala
                245                 250                 255

Gly Ala Gly Thr Cys Ala Cys Ala Thr Cys Ala Cys Cys Ala Gly
            260                 265                 270

Gly Gly Ala Cys Ala Thr Ala Cys Cys Gly Cys Gly Ala Gly Cys
            275                 280                 285

Ala Cys Ala Gly Thr Ala Thr Ala Cys Ala Thr Gly Ala Gly Cys
        290                 295                 300

Thr Gly Ala Gly Cys Ala Gly Cys Cys Thr Gly Ala Gly Ala Thr Cys
305                 310                 315                 320
```

Thr Gly Ala Ala Gly Ala Cys Ala Cys Gly Gly Cys Thr Gly Thr Gly
            325                 330                 335

Thr Ala Thr Thr Ala Cys Thr Gly Thr Gly Cys Gly Ala Gly Ala Gly
            340                 345                 350

Ala Thr Gly Gly Ala Thr Thr Thr Thr Gly Thr Ala Gly Gly Ala Cys
            355                 360                 365

Ala Ala Cys Cys Ala Gly Cys Thr Gly Cys Thr Cys Cys Gly Ala Cys
            370                 375                 380

Cys Ala Cys Thr Ala Cys Gly Gly Thr Ala Thr Gly Gly Ala Cys Gly
385                 390                 395                 400

Thr Cys Thr Gly Gly Gly Gly Cys Cys Ala Ala Gly Gly Ala Ala Cys
            405                 410                 415

Cys Ala Cys Gly Gly Thr Cys Ala Cys Cys Gly Thr Cys Thr Cys Cys
            420                 425                 430

Thr Cys Ala Gly Cys
            435

<210> SEQ ID NO 125
<211> LENGTH: 126
<212> TYPE: PRT
<213> ORGANISM: Homo sapiens

<400> SEQUENCE: 125

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ile Asn Tyr
            20                  25                  30

Ala Met Gln Trp Val Arg Gln Ala Pro Gly Gln Arg Leu Glu Trp Met
        35                  40                  45

Gly Trp Ile Asn Ala Gly Asn Gly Tyr Thr Lys Tyr Ser Gln Lys Phe
    50                  55                  60

Gln Gly Arg Val Thr Ile Thr Arg Asp Ile Ser Ala Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Phe Cys Arg Thr Thr Ser Cys Ser Asp His Tyr Gly
            100                 105                 110

Met Asp Val Trp Gly Gln Gly Thr Thr Val Thr Val Ser Ser
        115                 120                 125

<210> SEQ ID NO 126
<211> LENGTH: 389
<212> TYPE: PRT
<213> ORGANISM: Homo sapiens

<400> SEQUENCE: 126

Ala Thr Gly Gly Cys Cys Thr Gly Gly Cys Thr Cys Thr Gly Cys
1               5                   10                  15

Thr Gly Cys Thr Cys Cys Thr Cys Ala Ala Cys Cys Thr Cys Cys Thr
            20                  25                  30

Cys Ala Cys Thr Cys Ala Gly Gly Ala Cys Ala Cys Ala Gly Gly Gly
            35                  40                  45

Thr Cys Cys Thr Gly Gly Gly Cys Cys Cys Ala Gly Thr Cys Thr Gly
    50                  55                  60

Cys Cys Cys Thr Gly Ala Cys Thr Cys Ala Gly Cys Cys Thr Gly Cys
65                  70                  75                  80

```
Cys Thr Cys Cys Gly Thr Gly Thr Cys Thr Gly Gly Gly Thr Cys Thr
85 90 95

Cys Cys Thr Gly Gly Ala Cys Ala Gly Thr Cys Gly Ala Thr Cys Ala
100 105 110

Cys Cys Ala Thr Cys Thr Cys Cys Thr Gly Cys Ala Cys Thr Gly Gly
115 120 125

Ala Ala Cys Cys Ala Gly Cys Ala Gly Thr Gly Ala Thr Gly Thr Thr
130 135 140

Gly Gly Thr Gly Gly Thr Thr Ala Thr Ala Ala Cys Thr Ala Thr Gly
145 150 155 160

Thr Cys Thr Cys Cys Thr Gly Gly Thr Ala Cys Cys Ala Ala Cys Ala
165 170 175

Ala Cys Ala Cys Cys Cys Ala Gly Gly Cys Ala Ala Ala Gly Cys Cys
180 185 190

Cys Cys Cys Ala Ala Ala Cys Thr Cys Ala Thr Gly Ala Thr Thr Thr
195 200 205

Ala Thr Gly Ala Thr Gly Thr Cys Ala Gly Thr Ala Ala Gly Cys Gly
210 215 220

Gly Cys Cys Cys Thr Cys Ala Gly Gly Gly Gly Thr Thr Thr Cys Thr
225 230 235 240

Gly Ala Thr Cys Gly Cys Thr Thr Cys Thr Cys Thr Gly Gly Cys Thr
245 250 255

Cys Cys Ala Ala Gly Thr Cys Thr Gly Gly Cys Ala Ala Cys Ala Cys
260 265 270

Gly Gly Cys Cys Thr Cys Cys Cys Thr Gly Ala Cys Ala Ala Thr Cys
275 280 285

Thr Cys Thr Gly Gly Gly Cys Thr Cys Cys Ala Gly Ala Cys Thr Gly
290 295 300

Ala Gly Gly Ala Cys Gly Ala Gly Gly Cys Thr Gly Ala Thr Thr Thr
305 310 315 320

Thr Thr Ala Cys Thr Gly Cys Thr Gly Cys Thr Cys Ala Thr Ala Thr
325 330 335

Gly Cys Ala Gly Gly Thr Ala Gly Thr Ala Gly Cys Ala Cys Thr Thr
340 345 350

Gly Gly Gly Thr Gly Thr Thr Cys Gly Gly Cys Gly Gly Ala Gly Gly
355 360 365

Gly Ala Cys Cys Ala Ala Gly Cys Thr Gly Ala Cys Cys Gly Thr Cys
370 375 380

Cys Thr Ala Gly Gly
385

<210> SEQ ID NO 127
<211> LENGTH: 110
<212> TYPE: PRT
<213> ORGANISM: Homo sapiens

<400> SEQUENCE: 127

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Asp Val Ser Lys Arg Pro Ser Gly Val Ser Asp Arg Phe

```
                50                  55                  60
Ser Gly Ser Lys Ser Gly Asn Thr Ala Ser Leu Thr Ile Ser Gly Leu
 65                  70                  75                  80

Gln Thr Glu Asp Glu Ala Asp Phe Tyr Cys Cys Ser Tyr Ala Gly Ser
                 85                  90                  95

Ser Thr Trp Val Phe Gly Gly Gly Thr Lys Leu Thr Val Leu
            100                 105                 110

<210> SEQ ID NO 128
<211> LENGTH: 10
<212> TYPE: PRT
<213> ORGANISM: Homo sapiens

<400> SEQUENCE: 128

Gly Phe Ile Phe Ile Asn Tyr Ala Met Gln
 1               5                  10

<210> SEQ ID NO 129
<211> LENGTH: 17
<212> TYPE: PRT
<213> ORGANISM: Homo sapiens

<400> SEQUENCE: 129

Asp Gly Phe Cys Ser Thr Thr Cys Ser Asp His Tyr Gly Met Asp
 1               5                  10                  15

Val

<210> SEQ ID NO 130
<211> LENGTH: 437
<212> TYPE: PRT
<213> ORGANISM: Homo sapiens

<400> SEQUENCE: 130

Ala Thr Gly Gly Ala Cys Thr Gly Gly Ala Cys Cys Thr Gly Gly Ala
 1               5                  10                  15

Gly Gly Ala Thr Cys Cys Thr Cys Thr Thr Thr Thr Gly Gly Thr
                20                  25                  30

Gly Gly Cys Ala Gly Cys Ala Gly Cys Ala Cys Ala Gly Gly Thr
             35                  40                  45

Gly Thr Cys Cys Ala Cys Thr Cys Cys Ala Gly Gly Thr Cys Cys
             50                  55                  60

Ala Gly Cys Thr Thr Gly Thr Gly Cys Ala Gly Thr Cys Thr Gly Gly
 65                  70                  75                  80

Gly Gly Cys Thr Gly Ala Gly Gly Thr Gly Ala Ala Gly Ala Ala Gly
                 85                  90                  95

Cys Cys Thr Gly Gly Gly Cys Thr Cys Ala Gly Thr Gly Ala
            100                 105                 110

Ala Gly Gly Thr Thr Cys Cys Thr Gly Cys Ala Ala Gly Gly Cys
            115                 120                 125

Thr Thr Cys Thr Gly Gly Ala Thr Thr Cys Ala Thr Cys Thr Thr Thr
            130                 135                 140

Ala Thr Thr Ala Ala Cys Thr Ala Thr Gly Cys Thr Ala Thr Gly Cys
145                 150                 155                 160

Ala Ala Thr Gly Gly Gly Thr Gly Cys Gly Ala Cys Ala Gly Gly Cys
                165                 170                 175

Cys Cys Cys Cys Gly Gly Ala Cys Ala Ala Gly Gly Cys Thr Thr
            180                 185                 190
```

Gly Ala Gly Thr Gly Gly Ala Thr Gly Gly Gly Ala Thr Gly Gly Ala
            195                 200                 205

Thr Cys Ala Ala Cys Gly Cys Thr Gly Gly Cys Ala Ala Cys Gly Gly
            210                 215                 220

Thr Thr Ala Cys Ala Cys Ala Ala Ala Thr Ala Thr Thr Cys Ala
225                 230                 235                 240

Cys Ala Gly Ala Ala Thr Thr Cys Ala Gly Gly Cys Ala
            245                 250                 255

Gly Ala Gly Thr Cys Ala Cys Cys Ala Thr Cys Ala Cys Ala Gly
            260                 265                 270

Gly Gly Ala Cys Ala Thr Ala Thr Cys Gly Cys Gly Ala Ala Cys
            275                 280                 285

Ala Cys Ala Gly Thr Cys Thr Ala Cys Ala Thr Gly Gly Ala Gly Cys
            290                 295                 300

Thr Gly Ala Gly Cys Ala Gly Cys Cys Thr Gly Ala Gly Ala Thr Cys
305                 310                 315                 320

Thr Gly Ala Ala Gly Ala Cys Ala Cys Gly Gly Cys Thr Gly Thr Gly
                325                 330                 335

Thr Ala Thr Thr Ala Cys Thr Gly Thr Gly Cys Gly Ala Gly Ala Gly
            340                 345                 350

Ala Thr Gly Gly Ala Thr Thr Thr Thr Gly Thr Ala Gly Thr Ala Cys
            355                 360                 365

Ala Ala Cys Cys Ala Cys Cys Thr Gly Cys Thr Cys Cys Gly Ala Cys
            370                 375                 380

Cys Ala Cys Thr Ala Cys Gly Gly Thr Ala Thr Gly Gly Ala Cys Gly
385                 390                 395                 400

Thr Cys Thr Gly Gly Gly Gly Cys Cys Ala Ala Gly Gly Gly Ala Cys
                405                 410                 415

Cys Ala Cys Gly Gly Thr Cys Ala Cys Cys Gly Thr Cys Thr Cys Cys
            420                 425                 430

Thr Cys Ala Gly Cys
            435

<210> SEQ ID NO 131
<211> LENGTH: 126
<212> TYPE: PRT
<213> ORGANISM: Homo sapiens

<400> SEQUENCE: 131

Gln Val Gln Leu Val Gln Ser Gly Ala Glu Val Lys Lys Pro Gly Ala
1               5                   10                  15

Ser Val Lys Val Ser Cys Lys Ala Ser Gly Phe Ile Phe Ile Asn Tyr
            20                  25                  30

Ala Met Gln Trp Val Arg Gln Ala Pro Gly Gln Arg Leu Glu Trp Met
        35                  40                  45

Gly Trp Ile Asn Ala Gly Asn Gly Tyr Thr Lys Tyr Ser Gln Lys Phe
    50                  55                  60

Gln Gly Arg Val Thr Ile Thr Arg Asp Ile Ser Ala Asn Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Phe Cys Ser Thr Thr Cys Ser Asp His Tyr Gly
            100                 105                 110

Met Asp Val Trp Gly Gln Gly Thr Thr Val Thr Val Ser Ser
        115                 120                 125

<210> SEQ ID NO 132
<211> LENGTH: 389
<212> TYPE: PRT
<213> ORGANISM: Homo sapiens

<400> SEQUENCE: 132

```
Ala Thr Gly Gly Cys Cys Thr Gly Gly Cys Thr Cys Thr Gly Cys
1               5                   10                  15

Thr Gly Cys Thr Cys Cys Thr Cys Ala Cys Cys Thr Cys Cys Thr
                20                  25                  30

Cys Ala Cys Thr Cys Ala Gly Gly Ala Cys Ala Cys Ala Gly Gly
                35                  40                  45

Thr Cys Cys Thr Gly Gly Cys Cys Ala Gly Thr Cys Thr Gly Gly
                50                  55                  60

Cys Cys Cys Thr Gly Ala Cys Thr Cys Ala Gly Cys Cys Gly Cys
65                  70                  75                  80

Cys Thr Cys Cys Gly Thr Gly Thr Cys Thr Gly Gly Gly Thr Cys
                85                  90                  95

Cys Cys Thr Gly Gly Ala Cys Ala Gly Thr Cys Gly Ala Thr Cys
                100                 105                 110

Cys Cys Ala Thr Cys Thr Cys Cys Thr Gly Cys Ala Cys Thr Gly Gly
                115                 120                 125

Ala Ala Cys Cys Ala Gly Cys Ala Gly Thr Gly Ala Thr Gly Thr Thr
                130                 135                 140

Gly Gly Thr Gly Gly Thr Thr Ala Thr Ala Ala Cys Thr Ala Thr Gly
145                 150                 155                 160

Thr Cys Thr Cys Cys Thr Gly Gly Thr Ala Cys Cys Ala Ala Cys Ala
                165                 170                 175

Ala Cys Ala Cys Cys Cys Ala Gly Gly Cys Ala Ala Ala Gly Cys Cys
                180                 185                 190

Cys Cys Cys Ala Ala Ala Cys Thr Cys Ala Thr Gly Ala Thr Thr Thr
                195                 200                 205

Ala Thr Gly Ala Thr Gly Thr Cys Ala Gly Thr Ala Ala Gly Cys Gly
                210                 215                 220

Gly Cys Cys Cys Thr Cys Ala Gly Gly Gly Thr Thr Thr Cys Thr
225                 230                 235                 240

Gly Ala Thr Cys Gly Cys Thr Thr Cys Thr Cys Thr Gly Gly Cys Thr
                245                 250                 255

Cys Cys Ala Ala Gly Thr Cys Thr Gly Gly Cys Ala Ala Cys Ala Cys
                260                 265                 270

Gly Gly Cys Cys Thr Cys Cys Cys Thr Gly Ala Cys Ala Ala Thr Cys
                275                 280                 285

Thr Cys Thr Gly Gly Gly Cys Thr Cys Cys Ala Gly Ala Cys Thr Gly
                290                 295                 300

Ala Gly Gly Ala Cys Gly Ala Gly Gly Cys Thr Gly Ala Thr Thr Ala
305                 310                 315                 320

Thr Thr Ala Cys Thr Gly Cys Thr Gly Cys Thr Cys Ala Thr Ala Thr
                325                 330                 335

Gly Cys Ala Gly Gly Thr Ala Gly Thr Ala Gly Cys Ala Thr Thr Thr
                340                 345                 350

Gly Gly Gly Thr Gly Thr Thr Cys Gly Gly Cys Gly Gly Ala Gly Gly
                355                 360                 365

Gly Ala Cys Cys Ala Ala Gly Cys Thr Gly Ala Cys Cys Gly Thr Cys
```

Cys Thr Ala Gly Gly
385

<210> SEQ ID NO 133
<211> LENGTH: 110
<212> TYPE: PRT
<213> ORGANISM: Homo sapiens

<400> SEQUENCE: 133

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Cys Ser Tyr Ala Gly Ser
                85                  90                  95

Ser Thr Trp Val Phe Gly Gly Gly Thr Lys Leu Thr Val Leu
            100                 105                 110

<210> SEQ ID NO 134
<211> LENGTH: 10
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Tyr or Phe
<220> FEATURE:
<221> NAME/KEY: MISC_FEATURE
<222> LOCATION: (6)..(6)
<223> OTHER INFORMATION: Xaa is Asn or Asp

<400> SEQUENCE: 134

Gly Xaa Thr Phe Thr Xaa Tyr Ala Met His
1               5                   10

<210> SEQ ID NO 135
<211> LENGTH: 13
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is Asn or Ser
<220> FEATURE:
<221> NAME/KEY: MISC_FEATURE
<222> LOCATION: (9)..(9)
<223> OTHER INFORMATION: Xaa is Ile or Ser
<220> FEATURE:
<221> NAME/KEY: MISC_FEATURE
<222> LOCATION: (12)..(12)
<223> OTHER INFORMATION: Xaa is His or Tyr-Val

<400> SEQUENCE: 135

Thr Gly Thr Ser Xaa Asp Val Gly Xaa Tyr Asn Xaa Ser
1               5                   10

<210> SEQ ID NO 136
<211> LENGTH: 7

```
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Thr or Lys

<400> SEQUENCE: 136

Asp Val Asn Xaa Arg Pro Ser
1               5

<210> SEQ ID NO 137
<211> LENGTH: 10
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Cys or Ser
<220> FEATURE:
<221> NAME/KEY: MISC_FEATURE
<222> LOCATION: (8)..(8)
<223> OTHER INFORMATION: Xaa is Ala or Thr

<400> SEQUENCE: 137

Xaa Ser Tyr Ala Gly Ser Ser Xaa Trp Val
1               5                   10

<210> SEQ ID NO 138
<211> LENGTH: 6
<212> TYPE: PRT
<213> ORGANISM: Homo sapiens

<400> SEQUENCE: 138

Asn Ala Gly Asn Gly Tyr
1               5

<210> SEQ ID NO 139
<211> LENGTH: 7
<212> TYPE: PRT
<213> ORGANISM: Homo sapiens

<400> SEQUENCE: 139

Gly Tyr Thr Phe Ser Asn Tyr
1               5

<210> SEQ ID NO 140
<211> LENGTH: 7
<212> TYPE: PRT
<213> ORGANISM: Homo sapiens

<400> SEQUENCE: 140

Gly Phe Thr Phe Thr Asp Tyr
1               5

<210> SEQ ID NO 141
<211> LENGTH: 7
<212> TYPE: PRT
<213> ORGANISM: Homo sapiens

<400> SEQUENCE: 141

Gly Phe Thr Phe Thr Ser Tyr
1               5

<210> SEQ ID NO 142
<211> LENGTH: 6
<212> TYPE: PRT
```

<213> ORGANISM: Homo sapiens

<400> SEQUENCE: 142

Asn Ala Gly Asn Gly His
1               5

<210> SEQ ID NO 143
<211> LENGTH: 7
<212> TYPE: PRT
<213> ORGANISM: Homo sapiens

<400> SEQUENCE: 143

Gly Phe Thr Phe Ile Ser Tyr
1               5

<210> SEQ ID NO 144
<211> LENGTH: 6
<212> TYPE: PRT
<213> ORGANISM: Homo sapiens

<400> SEQUENCE: 144

Asn Ala Gly Asp Gly His
1               5

<210> SEQ ID NO 145
<211> LENGTH: 5
<212> TYPE: PRT
<213> ORGANISM: Homo sapiens

<400> SEQUENCE: 145

Ser Tyr Ala Ile Gln
1               5

<210> SEQ ID NO 146
<211> LENGTH: 7
<212> TYPE: PRT
<213> ORGANISM: Homo sapiens

<400> SEQUENCE: 146

Gly Phe Thr Phe Thr Asn Tyr
1               5

<210> SEQ ID NO 147
<211> LENGTH: 5
<212> TYPE: PRT
<213> ORGANISM: Homo sapiens

<400> SEQUENCE: 147

Ser His Ala Ile His
1               5

<210> SEQ ID NO 148
<211> LENGTH: 7
<212> TYPE: PRT
<213> ORGANISM: Homo sapiens

<400> SEQUENCE: 148

Gly Phe Thr Phe Thr Ser His
1               5

<210> SEQ ID NO 149
<211> LENGTH: 5
<212> TYPE: PRT
<213> ORGANISM: Homo sapiens

```
<400> SEQUENCE: 149

Asn Tyr Ala Met Gln
1               5

<210> SEQ ID NO 150
<211> LENGTH: 7
<212> TYPE: PRT
<213> ORGANISM: Homo sapiens

<400> SEQUENCE: 150

Gly Tyr Ile Phe Ile Asn Tyr
1               5

<210> SEQ ID NO 151
<211> LENGTH: 7
<212> TYPE: PRT
<213> ORGANISM: Homo sapiens

<400> SEQUENCE: 151

Gly Phe Ile Phe Ile Asn Tyr
1               5

<210> SEQ ID NO 152
<211> LENGTH: 19
<212> TYPE: PRT
<213> ORGANISM: Homo sapiens

<400> SEQUENCE: 152

Asp Asn Phe Phe Glu Ser Ser Gly Tyr Tyr Ser Tyr Tyr Phe Tyr Gly
1               5                   10                  15

Met Asp Val

<210> SEQ ID NO 153
<211> LENGTH: 17
<212> TYPE: PRT
<213> ORGANISM: Homo sapiens

<400> SEQUENCE: 153

Trp Ile Asn Ala Gly Asn Gly Tyr Thr Lys Tyr Ser Gln Arg Phe Gln
1               5                   10                  15

Gly

<210> SEQ ID NO 154
<211> LENGTH: 10
<212> TYPE: PRT
<213> ORGANISM: Homo sapiens

<400> SEQUENCE: 154

Cys Ser Tyr Val Gly Ser Ser Thr Trp Ile
1               5                   10

<210> SEQ ID NO 155
<211> LENGTH: 19
<212> TYPE: PRT
<213> ORGANISM: Homo sapiens

<400> SEQUENCE: 155

Asp Asn Phe Tyr Gly Ser Gly Thr Tyr Phe Ser Tyr Phe Phe Tyr His
1               5                   10                  15

Met Asp Val

<210> SEQ ID NO 156
```

<210> SEQ ID NO 156
<211> LENGTH: 10
<212> TYPE: PRT
<213> ORGANISM: Homo sapiens

<400> SEQUENCE: 156

Gly Tyr Thr Phe Thr Asn Tyr Ala Ile His
1               5                   10

<210> SEQ ID NO 157
<211> LENGTH: 7
<212> TYPE: PRT
<213> ORGANISM: Homo sapiens

<400> SEQUENCE: 157

Val Val Ser Lys Arg Pro Ser
1               5

<210> SEQ ID NO 158
<211> LENGTH: 17
<212> TYPE: PRT
<213> ORGANISM: Homo sapiens

<400> SEQUENCE: 158

Asp Gly Phe Cys Pro Ser Thr Thr Cys Ser Gly Tyr Tyr Gly Met Asp
1               5                   10                  15

Val

<210> SEQ ID NO 159
<211> LENGTH: 17
<212> TYPE: PRT
<213> ORGANISM: Homo sapiens

<400> SEQUENCE: 159

Trp Ile Asn Ala Gly Asn Gly Tyr Thr Lys Tyr Ser Gln Lys Phe Gln
1               5                   10                  15

Val

<210> SEQ ID NO 160
<211> LENGTH: 10
<212> TYPE: PRT
<213> ORGANISM: Homo sapiens

<400> SEQUENCE: 160

Ser Ser Tyr Ala Gly Ser Ser Thr Trp Ile
1               5                   10

<210> SEQ ID NO 161
<211> LENGTH: 14
<212> TYPE: PRT
<213> ORGANISM: Homo sapiens

<400> SEQUENCE: 161

Thr Gly Thr Ser Ser Asp Val Gly Ala Tyr Asn Tyr Val Ser
1               5                   10

<210> SEQ ID NO 162
<211> LENGTH: 17
<212> TYPE: PRT
<213> ORGANISM: Homo sapiens

<400> SEQUENCE: 162

Trp Ile Asn Ala Gly Asn Gly Tyr Thr Lys Tyr Ser Gln Gln Phe Gln
1               5                   10                  15

Val

<210> SEQ ID NO 163
<211> LENGTH: 19
<212> TYPE: PRT
<213> ORGANISM: Homo sapiens

<400> SEQUENCE: 163

Asp Asn Tyr Tyr Asp Ser Asn Val Tyr Asn Ser Tyr Tyr Phe Tyr Gly
1               5                   10                  15

Met Asp Val

<210> SEQ ID NO 164
<211> LENGTH: 14
<212> TYPE: PRT
<213> ORGANISM: Homo sapiens

<400> SEQUENCE: 164

Thr Gly Thr Ser Ser Asp Val Gly Asn Tyr Asn His Val Ser
1               5                   10

<210> SEQ ID NO 165
<211> LENGTH: 19
<212> TYPE: PRT
<213> ORGANISM: Homo sapiens

<400> SEQUENCE: 165

Asp Gln Tyr Tyr Asp Ile Leu Thr Pro Tyr Tyr Tyr Tyr Tyr Gly
1               5                   10                  15

Met Asp Val

<210> SEQ ID NO 166
<211> LENGTH: 17
<212> TYPE: PRT
<213> ORGANISM: Homo sapiens

<400> SEQUENCE: 166

Asp Gly Tyr Cys Ser Ser Thr Ser Cys Tyr Gly Tyr Tyr Gly Met Asp
1               5                   10                  15

Val

<210> SEQ ID NO 167
<211> LENGTH: 10
<212> TYPE: PRT
<213> ORGANISM: Homo sapiens

<400> SEQUENCE: 167

Gly Phe Thr Phe Ser Ser Tyr Ala Met His
1               5                   10

<210> SEQ ID NO 168
<211> LENGTH: 21
<212> TYPE: PRT
<213> ORGANISM: Homo sapiens

<400> SEQUENCE: 168

Asp Gln Tyr Tyr Asp Ile Leu Lys Gly Tyr Tyr Asn Val Asp Tyr Tyr
1               5                   10                  15

Tyr Gly Met Asp Val
            20

<210> SEQ ID NO 169

```
<211> LENGTH: 21
<212> TYPE: PRT
<213> ORGANISM: Homo sapiens

<400> SEQUENCE: 169

Asp Asn Tyr Phe Asp Ser Ser Val Tyr Asp Ser Ser Tyr Tyr Phe Tyr
1               5                   10                  15

Tyr Gly Met Asp Val
            20

<210> SEQ ID NO 170
<211> LENGTH: 17
<212> TYPE: PRT
<213> ORGANISM: Homo sapiens

<400> SEQUENCE: 170

Trp Ile Asn Ala Gly Asn Gly Tyr Thr Lys Tyr Ser Gln Asn Phe Gln
1               5                   10                  15

Gly

<210> SEQ ID NO 171
<211> LENGTH: 18
<212> TYPE: PRT
<213> ORGANISM: Homo sapiens

<400> SEQUENCE: 171

Asp Glu Tyr Tyr Glu Ser Gly Ser Ser Asn Tyr Tyr Tyr Gly Met
1               5                   10                  15

Asp Val

<210> SEQ ID NO 172
<211> LENGTH: 17
<212> TYPE: PRT
<213> ORGANISM: Homo sapiens

<400> SEQUENCE: 172

Trp Ile Asn Ala Gly Asn Gly Tyr Thr Lys Tyr Ser Gln Thr Phe Gln
1               5                   10                  15

Gly

<210> SEQ ID NO 173
<211> LENGTH: 21
<212> TYPE: PRT
<213> ORGANISM: Homo sapiens

<400> SEQUENCE: 173

Asp Gln Phe Tyr Glu Thr Leu Thr Gly Tyr Tyr Asn Val Tyr Tyr
1               5                   10                  15

Tyr Gly Met Asp Val
            20

<210> SEQ ID NO 174
<211> LENGTH: 17
<212> TYPE: PRT
<213> ORGANISM: Homo sapiens

<400> SEQUENCE: 174

Trp Ile Asn Ala Gly Asn Gly Tyr Thr Lys Tyr Ser Gln Met Phe Gln
1               5                   10                  15

Asp
```

```
<210> SEQ ID NO 175
<211> LENGTH: 18
<212> TYPE: PRT
<213> ORGANISM: Homo sapiens

<400> SEQUENCE: 175

Asp Glu Tyr Tyr Asp Ser Gly Ser Ser Asn Tyr Tyr Tyr Gly Met
1               5                   10                  15
Asp Val

<210> SEQ ID NO 176
<211> LENGTH: 416
<212> TYPE: DNA
<213> ORGANISM: Homo sapiens

<400> SEQUENCE: 176
atggagtttg ggctgagctg gcttttctt gtggctattt taaaaggtgt ccagtgtgag      60
gtgcagctgg tggagtctgg gggaggcttg gtacagccgg ggggtccct gagactctcc     120 tgtgcagcct ctggattcac ctttagcagc tatgccatga gctgggtccg ccaggctcca    180
gggaaggggc tggagtgggt ctcaggtatt agtggtagtg gtggtagcac atactacgca    240
gactccgaga agggccggtt caccatctcc agagacaatt ccaagaacac gctgtatctg    300
caaatgaaca gcctgagagg cgaggacacg gccgtatatt attgtgcgaa agcctattac    360
tatggttcgg ggatggacgt ctggggccaa gggaccacgg tcaccgtctc ctcagc        416

<210> SEQ ID NO 177
<211> LENGTH: 138
<212> TYPE: PRT
<213> ORGANISM: Homo sapiens

<400> SEQUENCE: 177

Met Glu Phe Gly Leu Ser Trp Leu Phe Leu Val Ala Ile Leu Lys Gly
1               5                   10                  15

Val Gln Cys Glu Val Gln Leu Val Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Ser Tyr Ala Met Ser Trp Val Arg Gln Ala Pro Gly Lys Gly Leu
        50                  55                  60

Glu Trp Val Ser Gly Ile Ser Gly Ser Gly Gly Ser Thr Tyr Tyr Ala
65                  70                  75                  80

Asp Ser Glu Lys Gly Arg Phe Thr Ile Ser Arg Asp Asn Ser Lys Asn
                85                  90                  95

Thr Leu Tyr Leu Gln Met Asn Ser Leu Arg Gly Glu Asp Thr Ala Val
            100                 105                 110

Tyr Tyr Cys Ala Lys Ala Tyr Tyr Tyr Gly Ser Gly Met Asp Val Trp
        115                 120                 125

Gly Gln Gly Thr Thr Val Thr Val Ser Ser
    130                 135

<210> SEQ ID NO 178
<211> LENGTH: 10
<212> TYPE: PRT
<213> ORGANISM: Homo sapiens

<400> SEQUENCE: 178

Gly Phe Thr Phe Ser Ser Tyr Ala Met Ser
1               5                   10
```

<210> SEQ ID NO 179
<211> LENGTH: 17
<212> TYPE: PRT
<213> ORGANISM: Homo sapiens

<400> SEQUENCE: 179

Gly Ile Ser Gly Ser Gly Gly Ser Thr Tyr Tyr Ala Asp Ser Glu Lys
1               5                   10                  15
Gly

<210> SEQ ID NO 180
<211> LENGTH: 10
<212> TYPE: PRT
<213> ORGANISM: Homo sapiens

<400> SEQUENCE: 180

Ala Tyr Tyr Tyr Gly Ser Gly Met Asp Val
1               5                   10

<210> SEQ ID NO 181
<211> LENGTH: 584
<212> TYPE: DNA
<213> ORGANISM: Homo sapiens

<400> SEQUENCE: 181
atggactgga cctggaggat cctctttttg gtggcagcag ccacaggtgc ccactcccag      60
gtccagcttg tgcagtctgg ggctgaggtg aagaagcctg ggccctcagt gaaggtttcc     120
tgcaaggctt ctggatacac cttcactagt tatgctatgc attgggtgcg ccaggccccc     180
ggacaaaggc ttgagtggat gggatggatc aacgctggca atggtaacac aaaatattca     240
cagaagttcc agggcgtttc ctgcaaggct tctggataca ccttcacaaa ctatgctatg     300
cattgggtgc gccaggcccc cggacaaagg cttgagtgga tgggatggat caacgctggc     360
aatggtaata caaaatattc acaaaatttc cagggcagag tcaccattac cagggacaca     420
tccgcgagca cagcctacat ggagctgagc agcctgagat ctgaagacac ggctgtgtat     480
tactgtgcga gagatgaata ctatgcttcg gggagttatt atgactacta ctactacggt     540
atggacgtct ggggccaagg gaccacggtc accgtcacct cagc                     584

<210> SEQ ID NO 182
<211> LENGTH: 147
<212> TYPE: PRT
<213> ORGANISM: Homo sapiens

<400> SEQUENCE: 182

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Asn Tyr Ala Met His Trp Val Arg Gln Ala Pro Gly Gln Arg Leu
        50                  55                  60

Glu Trp Met Gly Trp Ile Asn Ala Gly Asn Gly Asn Thr Lys Tyr Ser
65                  70                  75                  80

Gln Asn Phe Gln Gly Arg Val Thr Ile Thr Arg Asp Thr Ser Ala Ser
                85                  90                  95

```
Thr Ala Tyr Met Glu Leu Ser Ser Leu Arg Ser Glu Asp Thr Ala Val
                100                 105                 110
Tyr Tyr Cys Ala Arg Asp Glu Tyr Tyr Ala Ser Gly Ser Tyr Tyr Asp
            115                 120                 125
Tyr Tyr Tyr Tyr Gly Met Asp Val Trp Gly Gln Gly Thr Thr Val Thr
        130                 135                 140
Val Thr Ser
145
```

<210> SEQ ID NO 183
<211> LENGTH: 584
<212> TYPE: DNA
<213> ORGANISM: Homo sapiens

<400> SEQUENCE: 183

```
atggactgga cctggaggat cctcttttgg gtggcagcag ccacaggtgc ccactcccag      60
gtccagcttg tgcagtctgg ggctgaggtg aagaagcctg ggcctcagt gaaggtttcc     120
tgcaaggctt ctggatacac cttcactagt tatgctatgc attgggtgcg ccaggccccc    180
ggacaaaggc ttgagtggat gggatggatc aacgctggca atggtaacac aaaatattca    240
cagaagttcc agggcgtttc ctgcaaggct tctggataca ccttcactaa ctatgctata    300
cattgggtgc gccaggcccc cggacaaagg cttgagtgga tgggatggat caacgctggc    360
aatggtaaca caaaatattc acagaagttc agggcagag tcaccattac agggacaca     420
tccgcgagca cagcctacat ggagctgagc agcctgagat ctgaagacac ggctgtgtat    480
tactgtgcga gagataattt ctatggttcg gggacttatt tttcgtactt cttctaccat    540
atggacgtct ggggccaagg gaccacggtc accgtctcct cagc                     584
```

<210> SEQ ID NO 184
<211> LENGTH: 147
<212> TYPE: PRT
<213> ORGANISM: Homo sapiens

<400> SEQUENCE: 184

```
Met Asp Trp Thr Trp Arg Ile Leu Phe Leu Val Ala Ala Ala Thr Gly
1               5                   10                  15
Ala His Ser Gln Val Gln Leu Val Gln Ser Gly Ala Glu Val Lys Lys
                20                  25                  30
Pro Gly Ala Ser Val Lys Val Ser Cys Lys Ala Ser Gly Tyr Thr Phe
            35                  40                  45
Thr Asn Tyr Ala Ile His Trp Val Arg Gln Ala Pro Gly Gln Arg Leu
    50                  55                  60
Glu Trp Met Gly Trp Ile Asn Ala Gly Asn Gly Asn Thr Lys Tyr Ser
65                  70                  75                  80
Gln Lys Phe Gln Gly Arg Val Thr Ile Thr Arg Asp Thr Ser Ala Ser
                85                  90                  95
Thr Ala Tyr Met Glu Leu Ser Ser Leu Arg Ser Glu Asp Thr Ala Val
                100                 105                 110
Tyr Tyr Cys Ala Arg Asp Asn Phe Tyr Gly Ser Gly Thr Tyr Phe Ser
            115                 120                 125
Tyr Phe Phe Tyr His Met Asp Val Trp Gly Gln Gly Thr Thr Val Thr
        130                 135                 140
Val Ser Ser
145
```

<210> SEQ ID NO 185
<211> LENGTH: 545
<212> TYPE: DNA
<213> ORGANISM: Homo sapiens

<400> SEQUENCE: 185

```
atggactgga cctggaggat cctcttttg gtggcagcag ccacaggtgc ccactcccag      60
gtccagcttg tgcagtctgg ggctgaggtg aagaagcctg ggcctcagt gaaggtttcc     120
tgcaaggctt ctggatacac cttcactagt tatgctatgc attgggtgcg ccaggcccc     180
ggacaaaggc ttgagtggat gggatggatc aacgctggca atggtaacac aaaatattca    240
cagaagttcc agggcgtttc gtgcaaggct tctggataca ccttcactag ctatgctatg    300
cattgggtgc gccaggcccc cggacaaagg cttgagtgga tgggatggat caacgctggc    360
aatggtaaca caaaatattc acagaagttc cagggcagag tcaccattac cagggacaca    420
tccgcgagca cagcctacat ggagctgagc agcctgagat ctgaagacac ggctgtgtat    480
tactgtgcga gaggggatc gagggactac tggggccagg gaaccctggt caccgtctcc    540
tcagc                                                                545
```

<210> SEQ ID NO 186
<211> LENGTH: 134
<212> TYPE: PRT
<213> ORGANISM: Homo sapiens

<400> SEQUENCE: 186

```
Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Ser Tyr Ala Met His Trp Val Arg Gln Ala Pro Gly Gln Arg Leu
        50                  55                  60

Glu Trp Met Gly Trp Ile Asn Ala Gly Asn Gly Asn Thr Lys Tyr Ser
65                  70                  75                  80

Gln Lys Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Gly Ser Arg Asp Tyr Trp Gly Gln Gly Thr
        115                 120                 125

Leu Val Thr Val Ser Ser
    130
```

<210> SEQ ID NO 187
<211> LENGTH: 6
<212> TYPE: PRT
<213> ORGANISM: Homo sapiens

<400> SEQUENCE: 187

```
Gly Gly Ser Arg Asp Tyr
1               5
```

<210> SEQ ID NO 188
<211> LENGTH: 425
<212> TYPE: DNA
<213> ORGANISM: Homo sapiens -continued

<400> SEQUENCE: 188

```
atggagtttg ggctgagctg ggttttcctt gttgctattt taaaaggtgt ccagtgtgag    60
gtgcagctgg tggagtctgg gggaggtgtg gtacggcctg gggggtccct gagactctcc   120
tgtgcagcct ctggattcac ctttgatgat tatggcatga gctgggtccg ccaaggtcca   180
gggaaggggc tggagtgggt ctctggtatt aattggaatg gtggtaacac aggttatgca   240
gactctgtga aggccgatt caccatctcc agagacaacg ccaagaactc cctgtatttg   300
caaatgaata gtctgagagc cgaggacacg gccttgtatt actgtgcgag agggttacga   360
tattttgact ggttagtcgg tatggacgtc tggggccaag gaccacggt caccgtctcc   420
tcagc                                                               425
```

<210> SEQ ID NO 189
<211> LENGTH: 141
<212> TYPE: PRT
<213> ORGANISM: Homo sapiens

<400> SEQUENCE: 189

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Val Val Arg
            20                  25                  30

Pro Gly Gly Ser Leu Arg Leu Ser Cys Ala Ala Ser Gly Phe Thr Phe
        35                  40                  45

Asp Asp Tyr Gly Met Ser Trp Val Arg Gln Gly Pro Gly Lys Gly Leu
    50                  55                  60

Glu Trp Val Ser Gly Ile Asn Trp Asn Gly Gly Asn Thr Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Arg Gly Leu Arg Tyr Phe Asp Trp Leu Val Gly Met
        115                 120                 125

Asp Val Trp Gly Gln Gly Thr Thr Val Thr Val Ser Ser
    130                 135                 140

<210> SEQ ID NO 190
<211> LENGTH: 10
<212> TYPE: PRT
<213> ORGANISM: Homo sapiens

<400> SEQUENCE: 190

Gly Phe Thr Phe Asp Asp Tyr Gly Met Ser
1               5                   10

<210> SEQ ID NO 191
<211> LENGTH: 17
<212> TYPE: PRT
<213> ORGANISM: Homo sapiens

<400> SEQUENCE: 191

Gly Ile Asn Trp Asn Gly Gly Asn Thr Gly Tyr Ala Asp Ser Val Lys
1               5                   10                  15

Gly

<210> SEQ ID NO 192

```
<211> LENGTH: 13
<212> TYPE: PRT
<213> ORGANISM: Homo sapiens

<400> SEQUENCE: 192

Gly Leu Arg Tyr Phe Asp Trp Leu Val Gly Met Asp Val
1               5                  10

<210> SEQ ID NO 193
<211> LENGTH: 434
<212> TYPE: DNA
<213> ORGANISM: Homo sapiens

<400> SEQUENCE: 193
atggagttgg ggctgagctg ggttttcctt gttgctatat tagaaggtgt ccagtgtgag      60
gtgcagctgg tggagtctgg gggaggcttg gtacagcctg ggggtccct gagactctcc     120 tgtgcagcct ctggattccc cttcagtaac tacgacatgc actgggtccg ccaagttaca    180
ggaaaaggtc tggagtgggt ctcagctatt ggtactgctg gtgacacata ctatccagac    240
tccgtgaagg gccgattcac catctccaga gacaatgcca agaactcctt gtttcttcaa    300
atgaacagcc tgagagccgg ggacacggct gtgtattact gtgcaagagg ggggggttcg    360
gggacttatt cctactacta ctactacggt atggacgtct ggggccaagg gaccacggtc    420
accgtctcct cagc                                                      434

<210> SEQ ID NO 194
<211> LENGTH: 144
<212> TYPE: PRT
<213> ORGANISM: Homo sapiens

<400> SEQUENCE: 194

Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Pro Phe
        35                  40                  45

Ser Asn Tyr Asp Met His Trp Val Arg Gln Val Thr Gly Lys Gly Leu
    50                  55                  60

Glu Trp Val Ser Ala Ile Gly Thr Ala Gly Asp Thr Tyr Tyr Pro Asp
65                  70                  75                  80

Ser Val Lys Gly Arg Phe Thr Ile Ser Arg Asp Asn Ala Lys Asn Ser
                85                  90                  95

Leu Phe Leu Gln Met Asn Ser Leu Arg Ala Gly Asp Thr Ala Val Tyr
            100                 105                 110

Tyr Cys Ala Arg Gly Gly Gly Ser Gly Thr Tyr Ser Tyr Tyr Tyr Tyr
        115                 120                 125

Tyr Gly Met Asp Val Trp Gly Gln Gly Thr Thr Val Thr Val Ser Ser
    130                 135                 140

<210> SEQ ID NO 195
<211> LENGTH: 10
<212> TYPE: PRT
<213> ORGANISM: Homo sapiens

<400> SEQUENCE: 195

Gly Phe Pro Phe Ser Asn Tyr Asp Met His
1               5                   10
```

<210> SEQ ID NO 196
<211> LENGTH: 16
<212> TYPE: PRT
<213> ORGANISM: Homo sapiens

<400> SEQUENCE: 196

Ala Ile Gly Thr Ala Gly Asp Thr Tyr Tyr Pro Asp Ser Val Lys Gly
1               5                   10                  15

<210> SEQ ID NO 197
<211> LENGTH: 17
<212> TYPE: PRT
<213> ORGANISM: Homo sapiens

<400> SEQUENCE: 197

Gly Gly Gly Ser Gly Thr Tyr Ser Tyr Tyr Tyr Tyr Gly Met Asp
1               5                   10                  15

Val

<210> SEQ ID NO 198
<211> LENGTH: 428
<212> TYPE: DNA
<213> ORGANISM: Homo sapiens

<400> SEQUENCE: 198

```
atgtctgtct ccttcctcat cttcctgccc gtgctgggcc tcccatgggg tgtcctgtca    60
caggtacagc tgcagcagtc aggtccagga ctggtgaagc cctcgcagac cctctcactc   120
acctgtgcca tctccgggga cagtgtctct agcaacagtg ctgcttggaa ctggatcagg   180
cagtccccat cgagaggcct tgagtggctg ggaaggacat actacaggtc aagtggtat    240
aatgattatt cagtatctgt gaaaagtcga ataaccatca cccagacac atccaagaac   300
cagttctccc tgcaactgaa ctctgtgact cccgaggaca cggctgtgta ttactgtgca   360
agaaagtggg agctacttga tgcttttgat gtctggggcc aagggacaat ggtcaccgtc   420
tcttcagc                                                           428
```

<210> SEQ ID NO 199
<211> LENGTH: 142
<212> TYPE: PRT
<213> ORGANISM: Homo sapiens

<400> SEQUENCE: 199

Met Ser Val Ser Phe Leu Ile Phe Leu Pro Val Leu Gly Leu Pro Trp
1               5                   10                  15

Gly Val Leu Ser Gln Val Gln Leu Gln Gln Ser Gly Pro Gly Leu Val
                20                  25                  30

Lys Pro Ser Gln Thr Leu Ser Leu Thr Cys Ala Ile Ser Gly Asp Ser
            35                  40                  45

Val Ser Ser Asn Ser Ala Ala Trp Asn Trp Ile Arg Gln Ser Pro Ser
        50                  55                  60

Arg Gly Leu Glu Trp Leu Gly Arg Thr Tyr Tyr Arg Ser Lys Trp Tyr
65                  70                  75                  80

Asn Asp Tyr Ser Val Ser Val Lys Ser Arg Ile Thr Ile Asn Pro Asp
                85                  90                  95

Thr Ser Lys Asn Gln Phe Ser Leu Gln Leu Asn Ser Val Thr Pro Glu
            100                 105                 110

Asp Thr Ala Val Tyr Tyr Cys Ala Arg Lys Trp Glu Leu Leu Asp Ala
        115                 120                 125

Phe Asp Val Trp Gly Gln Gly Thr Met Val Thr Val Ser Ser
    130                 135                 140

<210> SEQ ID NO 200
<211> LENGTH: 12
<212> TYPE: PRT
<213> ORGANISM: Homo sapiens

<400> SEQUENCE: 200

Gly Asp Ser Val Ser Ser Asn Ser Ala Ala Trp Asn
1               5                   10

<210> SEQ ID NO 201
<211> LENGTH: 18
<212> TYPE: PRT
<213> ORGANISM: Homo sapiens

<400> SEQUENCE: 201

Arg Thr Tyr Tyr Arg Ser Lys Trp Tyr Asn Asp Tyr Ser Val Ser Val
1               5                   10                  15

Lys Ser

<210> SEQ ID NO 202
<211> LENGTH: 10
<212> TYPE: PRT
<213> ORGANISM: Homo sapiens

<400> SEQUENCE: 202

Lys Trp Glu Leu Leu Asp Ala Phe Asp Val
1               5                   10

<210> SEQ ID NO 203
<211> LENGTH: 434
<212> TYPE: DNA
<213> ORGANISM: Homo sapiens

<400> SEQUENCE: 203
atggagttgg ggctgagctg ggttttcctt gttgctatat tagaaggtgt ccagtgtgag    60
gtgcagctgg tggagtctgg gggaggcttg gtacagccgg ggggtccct gagactctcc    120
tgtgcatcct ctggattccc cttcagtaac tacgacatgc actgggtccg ccaagttaca   180
ggaaaaggtc tggagtgggt ctcagctatt ggtactgctg gtgacacata ctatccagac   240
tccgtgaagg gccgattcac catctccaga gacaatgcca agaactcctt gtttcttcaa   300
atgaacagcc tgagagccgg ggacacggct gtgtattact gtgcaagagg ggggggttcg   360
gggacttatt cctactacta ctactacggt atggacgtct ggggccaagg gaccacggtc    420
accgtctcct cagc                                                      434

<210> SEQ ID NO 204
<211> LENGTH: 144
<212> TYPE: PRT
<213> ORGANISM: Homo sapiens

<400> SEQUENCE: 204

Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ser Ser Gly Phe Pro Phe
        35                  40                  45

Ser Asn Tyr Asp Met His Trp Val Arg Gln Val Thr Gly Lys Gly Leu
    50                  55                  60

Glu Trp Val Ser Ala Ile Gly Thr Ala Gly Asp Thr Tyr Tyr Pro Asp
65                  70                  75                  80

Ser Val Lys Gly Arg Phe Thr Ile Ser Arg Asp Asn Ala Lys Asn Ser
                85                  90                  95

Leu Phe Leu Gln Met Asn Ser Leu Arg Ala Gly Asp Thr Ala Val Tyr
                100                 105                 110

Tyr Cys Ala Arg Gly Gly Ser Gly Thr Tyr Ser Tyr Tyr Tyr Tyr
        115                 120                 125

Tyr Gly Met Asp Val Trp Gly Gln Gly Thr Thr Val Thr Val Ser Ser
        130                 135                 140

<210> SEQ ID NO 205
<211> LENGTH: 584
<212> TYPE: DNA
<213> ORGANISM: Homo sapiens

<400> SEQUENCE: 205
atggactgga cctggaggat cctcttttg gtggcagcag ccacaggtgc ccactcccag     60
gtccagcttg tgcagtctgg ggctgaggtg aagaagcctg ggcctcagt gaaggtttcc    120
tgcaaggctt ctggatacac cttcactagt tatgctatgc attgggtgcg ccaggccccc   180
ggacaaaggc ttgagtggat gggatggatc aacgctggca atggtaacac aaaatattca   240
cagaagttcc aggcgtttc ctgcaaggct tctggataca ccttcactag ttatgctatg    300
cattgggtgc gccaggcccc cggacaaagg cttgagtgga tgggatggat caacgctggc   360
aatggtaaca caaaatattc acagaagttc agggcggag tcaccattac agggacaca    420
tccgcgagca gcctacat ggagctgagc agcctgagat ctgaagacac ggctgtatat     480
tactgtgcga gagacaatta ctatgattcg ggagttatt atgactacta ctactacggt    540
atggacgtct ggggccaagg gaccacggtc accgtctcct cagc                    584

<210> SEQ ID NO 206
<211> LENGTH: 147
<212> TYPE: PRT
<213> ORGANISM: Homo sapiens

<400> SEQUENCE: 206

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Ser Tyr Ala Met His Trp Val Arg Gln Ala Pro Gly Gln Arg Leu
    50                  55                  60

Glu Trp Met Gly Trp Ile Asn Ala Gly Asn Gly Asn Thr Lys Tyr Ser
65                  70                  75                  80

Gln Lys Phe Gln Gly Gly Val Thr Ile Thr Arg Asp Thr Ser Ala Ser
                85                  90                  95

Thr Ala Tyr Met Glu Leu Ser Ser Leu Arg Ser Glu Asp Thr Ala Val
                100                 105                 110

Tyr Tyr Cys Ala Arg Asp Asn Tyr Tyr Asp Ser Gly Ser Tyr Tyr Asp
            115                 120                 125

```
Tyr Tyr Tyr Tyr Gly Met Asp Val Trp Gly Gln Gly Thr Thr Val Thr
    130                 135                 140
Val Ser Ser
145
```

<210> SEQ ID NO 207
<211> LENGTH: 425
<212> TYPE: DNA
<213> ORGANISM: Homo sapiens

<400> SEQUENCE: 207

```
atggagtttg ggctgagctg gcttttctt gtggctattt taaaaggtgt ccagtgtgag     60
gtgcagctgg tggagtctgg gggaggcttg gtacagcctg gggggtccct gagactctcc   120
tgtgcagcct ctggattcac ctttagtagc tatgccatga gctgggtccg ccaggctcca   180
gggaaggggc tggagtgggt ctcagctatt agtggtagtg gtggtagcac atactacgca   240
gactccgtga agggccggtt caccatctcc agagacaatt ccaagaacac gctgtatctg   300
caaatgaaca gcctgagagc cgaggacacg gccgtatatt actgtgcgaa agaggggagt   360
gggagctact acggagactg gttcgacccc tggggccagg aaccctggt caccgtctcc    420 tcagc                                                               425
```

<210> SEQ ID NO 208
<211> LENGTH: 141
<212> TYPE: PRT
<213> ORGANISM: Homo sapiens

<400> SEQUENCE: 208

```
Met Glu Phe Gly Leu Ser Trp Leu Phe Leu Val Ala Ile Leu Lys Gly
1               5                  10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Glu Gly Ser Gly Ser Tyr Tyr Gly Asp Trp Phe
        115                 120                 125

Asp Pro Trp Gly Gln Gly Thr Leu Val Thr Val Ser Ser
    130                 135                 140
```

<210> SEQ ID NO 209
<211> LENGTH: 17
<212> TYPE: PRT
<213> ORGANISM: Homo sapiens

<400> SEQUENCE: 209

```
Ala Ile Ser Gly Ser Gly Gly Ser Thr Tyr Tyr Ala Asp Ser Val Lys
1               5                  10                  15

Gly
```

```
<210> SEQ ID NO 210
<211> LENGTH: 13
<212> TYPE: PRT
<213> ORGANISM: Homo sapiens

<400> SEQUENCE: 210

Glu Gly Ser Gly Ser Tyr Tyr Gly Asp Trp Phe Asp Pro
1               5                   10

<210> SEQ ID NO 211
<211> LENGTH: 437
<212> TYPE: DNA
<213> ORGANISM: Homo sapiens

<400> SEQUENCE: 211
atggactgga cctggaggat cctcttttg gtggcagcag ccgcaggtgc ccactcccag      60
gtccagcttg tgcagtctgg ggctgaggtg aagaagcctg ggcctcagt gaaggtttcc    120 tgcaaggctt ctggattcac cttcactgac tacgctatgc attgggtgcg ccaggccccc    180
ggacaaaggc ttgagtggat gggttggatc aacgctggca atggttacac aaaatattca    240
cagaagttcc aggacagact caccattacc agggacacat tcgcgagcac agtctacatg    300
gagctgagca gcctgagatc tgaagacacg actgtgtatt actgtgcgag agatgggttt    360
tgtcctagta acacttgttc tggttactac ggtatggacg tctggggcca agggaccacg    420
gtcaccgtct cctcagc                                                    437

<210> SEQ ID NO 212
<211> LENGTH: 145
<212> TYPE: PRT
<213> ORGANISM: Homo sapiens

<400> SEQUENCE: 212

Met Asp Trp Thr Trp Arg Ile Leu Phe Leu Val Ala Ala Ala Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Thr Asp Tyr Ala Met His Trp Val Arg Gln Ala Pro Gly Gln Arg Leu
    50                  55                  60

Glu Trp Met Gly Trp Ile Asn Ala Gly Asn Gly Tyr Thr Lys Tyr Ser
65              70                  75                  80

Gln Lys Phe Gln Asp Arg Leu Thr Ile Thr Arg Asp Thr Phe Ala Ser
            85                  90                  95

Thr Val Tyr Met Glu Leu Ser Ser Leu Arg Ser Glu Asp Thr Thr Val
        100                 105                 110

Tyr Tyr Cys Ala Arg Asp Gly Phe Cys Pro Ser Asn Thr Cys Ser Gly
    115                 120                 125

Tyr Tyr Gly Met Asp Val Trp Gly Gln Gly Thr Thr Val Thr Val Ser
    130                 135                 140

Ser
145

<210> SEQ ID NO 213
<211> LENGTH: 425
<212> TYPE: DNA
<213> ORGANISM: Homo sapiens

<400> SEQUENCE: 213
```

```
atggactgga cctggaggat cctcttcttg gtggcagcag ccacaggtga ccactcccag    60
gtccagcttg tgcagtctgg ggctgaggtg aagaagcctg gggcctcagt gaaggtttcc   120
tgcaaggctt ctggatacac cttcacaaac tatactatac attgggtgcg ccaggtcccc   180
ggacaaaggc ttgagtggat gggatggatc aacggtggca atggtaacac aaaatattca   240
cagaagttcc agggcagagt cactattaac aggacacat ccgcgaacac agcctacatg    300
gagctgagca gcctgagatc tgaagacacg gttgtgtatt actgtgcgag agatcagtat   360
tactatgata gtagtggtta ttttgactac tggggccagg aaccctggt caccgtctcc    420 tcagc                                                                425
```

<210> SEQ ID NO 214
<211> LENGTH: 141
<212> TYPE: PRT
<213> ORGANISM: Homo sapiens

<400> SEQUENCE: 214

```
Met Asp Trp Thr Trp Arg Ile Leu Phe Leu Val Ala Ala Thr Gly
1               5                   10                  15

Asp His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Thr Ile His Trp Val Arg Gln Val Pro Gly Gln Arg Leu
    50                  55                  60

Glu Trp Met Gly Trp Ile Asn Gly Gly Asn Gly Asn Thr Lys Tyr Ser
65                  70                  75                  80

Gln Lys Phe Gln Gly Arg Val Thr Ile Asn Arg Asp Thr Ser Ala Asn
                85                  90                  95

Thr Ala Tyr Met Glu Leu Ser Ser Leu Arg Ser Glu Asp Thr Val Val
            100                 105                 110

Tyr Tyr Cys Ala Arg Asp Gln Tyr Tyr Tyr Asp Ser Ser Gly Tyr Phe
        115                 120                 125

Asp Tyr Trp Gly Gln Gly Thr Leu Val Thr Val Ser Ser
    130                 135                 140
```

<210> SEQ ID NO 215
<211> LENGTH: 10
<212> TYPE: PRT
<213> ORGANISM: Homo sapiens

<400> SEQUENCE: 215

```
Gly Tyr Thr Phe Thr Asn Tyr Thr Ile His
1               5                   10
```

<210> SEQ ID NO 216
<211> LENGTH: 17
<212> TYPE: PRT
<213> ORGANISM: Homo sapiens

<400> SEQUENCE: 216

```
Trp Ile Asn Gly Gly Asn Gly Asn Thr Lys Tyr Ser Gln Lys Phe Gln
1               5                   10                  15

Gly
```

<210> SEQ ID NO 217
<211> LENGTH: 13

<212> TYPE: PRT
<213> ORGANISM: Homo sapiens

<400> SEQUENCE: 217

Asp Gln Tyr Tyr Tyr Asp Ser Ser Gly Tyr Phe Asp Tyr
1               5                   10

<210> SEQ ID NO 218
<211> LENGTH: 437
<212> TYPE: DNA
<213> ORGANISM: Homo sapiens

<400> SEQUENCE: 218

```
atggactgga cctggaggat cctcttttg gtggcagcag ccgcaggtgc ccactcccag      60
gtccagcttg tgcagtctgg gactgaggtg aagaagcctg ggcctcagt gaaggtttcc    120 tgcaaggctt ctggattcac cttcagtagc tatgctatgc attgggtgcg ccaggccccc    180
ggacaaaggc ttgagtggat gggatggatc aacgctggca atggcaacac aaaatattca    240
cagaagttcc agggcagagt caccattacc agggacacgt ccgcgagcac agcctacatg    300
gagctgagca gcctgagatc tgaagacacg gctgtgtatt actgtgcgag agatgggtat    360
tgtagtagta ccagctgcta tggctactac ggtatggacg tctggggcca agggaccacg    420
gtcaccgtct cctcagc                                                   437
```

<210> SEQ ID NO 219
<211> LENGTH: 145
<212> TYPE: PRT
<213> ORGANISM: Homo sapiens

<400> SEQUENCE: 219

Met Asp Trp Thr Trp Arg Ile Leu Phe Leu Val Ala Ala Ala Gly
1               5                   10                  15

Ala His Ser Gln Val Gln Leu Val Gln Ser Gly Thr Glu Val Lys Lys
                20                  25                  30

Pro Gly Ala Ser Val Lys Val Ser Cys Lys Ala Ser Gly Phe Thr Phe
            35                  40                  45

Ser Ser Tyr Ala Met His Trp Val Arg Gln Ala Pro Gly Gln Arg Leu
    50                  55                  60

Glu Trp Met Gly Trp Ile Asn Ala Gly Asn Gly Asn Thr Lys Tyr Ser
65                  70                  75                  80

Gln Lys Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Gly Tyr Cys Ser Ser Thr Ser Cys Tyr Gly
        115                 120                 125

Tyr Tyr Gly Met Asp Val Trp Gly Gln Gly Thr Thr Val Thr Val Ser
    130                 135                 140

Ser
145

<210> SEQ ID NO 220
<211> LENGTH: 443
<212> TYPE: DNA
<213> ORGANISM: Homo sapiens

<400> SEQUENCE: 220

```
atgaaacacc tgtggttctt cctcctcctg gtggcagctc ccagatgggt cctgtctcag      60
```

```
gtgcagctgc aggagtcggg cccaggactg gtgaagcctt cggggaccct gtccctcacc      120
tgcgctgtct ctggtgactc catcagcagt agtaactggt ggagttgggt ccgccagccc      180
ccagggaagg ggctggagtg gattggggaa atctatcata gtgggaacac caactacaac      240
ccgtccctca agagtcgagt caccatatca gtagacaggc caagaaccag ttctccctg       300 aacctgaact ctgtgaccgc cgcggacacg gccgtgtatt actgtgcgag aggacgcccc      360
ctctcttatg gttcgggcag ttattataac ctcaactggt tcgacccctg gggccagggg      420
accctggtca ccgtctcctc agc                                               443
```

<210> SEQ ID NO 221
<211> LENGTH: 147
<212> TYPE: PRT
<213> ORGANISM: Homo sapiens
<400> SEQUENCE: 221

```
Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Gly Thr Leu Ser Leu Thr Cys Ala Val Ser Gly Asp Ser Ile
        35                  40                  45

Ser Ser Ser Asn Trp Trp Ser Trp Val Arg Gln Pro Pro Gly Lys Gly
    50                  55                  60

Leu Glu Trp Ile Gly Glu Ile Tyr His Ser Gly Asn Thr Asn Tyr Asn
65                  70                  75                  80

Pro Ser Leu Lys Ser Arg Val Thr Ile Ser Val Asp Arg Ser Lys Asn
                85                  90                  95

Gln Phe Ser Leu Asn Leu Asn Ser Val Thr Ala Ala Asp Thr Ala Val
            100                 105                 110

Tyr Tyr Cys Ala Arg Gly Arg Pro Leu Ser Tyr Gly Ser Gly Ser Tyr
        115                 120                 125

Tyr Asn Leu Asn Trp Phe Asp Pro Trp Gly Gln Gly Thr Leu Val Thr
    130                 135                 140

Val Ser Ser
145
```

<210> SEQ ID NO 222
<211> LENGTH: 11
<212> TYPE: PRT
<213> ORGANISM: Homo sapiens
<400> SEQUENCE: 222

```
Gly Asp Ser Ile Ser Ser Ser Asn Trp Trp Ser
1               5                   10
```

<210> SEQ ID NO 223
<211> LENGTH: 16
<212> TYPE: PRT
<213> ORGANISM: Homo sapiens
<400> SEQUENCE: 223

```
Glu Ile Tyr His Ser Gly Asn Thr Asn Tyr Asn Pro Ser Leu Lys Ser
1               5                   10                  15
```

<210> SEQ ID NO 224
<211> LENGTH: 19
<212> TYPE: PRT

<213> ORGANISM: Homo sapiens

<400> SEQUENCE: 224

Gly Arg Pro Leu Ser Tyr Gly Ser Gly Ser Tyr Tyr Asn Leu Asn Trp
1               5                   10                  15

Phe Asp Pro

<210> SEQ ID NO 225
<211> LENGTH: 590
<212> TYPE: DNA
<213> ORGANISM: Homo sapiens

<400> SEQUENCE: 225
atggactgga cctggaggat cctcttttg gtggcagcag ccacaggtgc ccactcccag     60
gtccagcttg tgcagtctgg ggctgaggtg aagaagcctg gggcctcagt gaaggtttcc    120
tgcaaggctt ctggatacac cttcactagt tatgctatgc attgggtgcg ccaggccccc    180
ggacaaaggc ttgagtggat gggatggatc aacgctggca atggtaacac aaaatattca    240
cagaagttcc agggcgtttc tgcaaggct tctggataca ccttcactag ttatgctatg     300
cattgggtgc gccaggcccc cggacaaagg cttgagtgga tgggatggat caacgctggc    360
aatggttaca caaaatattc acagaacttc cagggcagag tcaccattac agggacaca     420 tccgcgagca cagcctacat ggagctgagc agcctgagat ctgaagacac ggctgtgtat    480
tactgtgcga gagataatta ctttgatagt agtgtttatg actcttctta ctacttctac    540
tacggtatgg acgtctgggg ccaagggacc acggtcaccg tctcctcagc                590

<210> SEQ ID NO 226
<211> LENGTH: 149
<212> TYPE: PRT
<213> ORGANISM: Homo sapiens

<400> SEQUENCE: 226

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Ala Met His Trp Val Arg Gln Ala Pro Gly Gln Arg Leu
    50                  55                  60

Glu Trp Met Gly Trp Ile Asn Ala Gly Asn Gly Tyr Thr Lys Tyr Ser
65                  70                  75                  80

Gln Asn Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Asn Tyr Phe Asp Ser Ser Val Tyr Asp Ser
        115                 120                 125

Ser Tyr Tyr Phe Tyr Tyr Gly Met Asp Val Trp Gly Gln Gly Thr Thr
    130                 135                 140

Val Thr Val Ser Ser
145

<210> SEQ ID NO 227
<211> LENGTH: 434
<212> TYPE: DNA

<213> ORGANISM: Homo sapiens

<400> SEQUENCE: 227

| | |
|---|---|
| atgtctgtct ccttcctcat cttcctgccc gtgctgggcc tcccatgggg tgtcctgtca | 60 |
| caggtacagc tgcagcagtc aggtccagga ctggtgaagc cctcgcagac cctctcactc | 120 |
| acctgtgcca tctccgggga cagtgtctct agcaacagtg ctgcttggaa ctggatcagg | 180 |
| cagtccccat cgagaggcct tgagtggctg ggaaggacat actacaggtc caagtggtat | 240 |
| aatgattatg cagtatctgt gaaaagtcga ataaccttca acccagacac atccaagaac | 300 |
| cagttctccc tgcagctgaa ctctgtgact cccgaggaca cggctgtgta ttactgtgca | 360 |
| agagaggggg tgggagctat tacgtctcac tttgactact ggggccaggg aaccctggtc | 420 |
| accgtctcct cagc | 434 |

<210> SEQ ID NO 228
<211> LENGTH: 144
<212> TYPE: PRT
<213> ORGANISM: Homo sapiens

<400> SEQUENCE: 228

Met Ser Val Ser Phe Leu Ile Phe Leu Pro Val Leu Gly Leu Pro Trp
1               5                   10                  15
Gly Val Leu Ser Gln Val Gln Leu Gln Gln Ser Gly Pro Gly Leu Val
            20                  25                  30
Lys Pro Ser Gln Thr Leu Ser Leu Thr Cys Ala Ile Ser Gly Asp Ser
        35                  40                  45
Val Ser Ser Asn Ser Ala Ala Trp Asn Trp Ile Arg Gln Ser Pro Ser
    50                  55                  60
Arg Gly Leu Glu Trp Leu Gly Arg Thr Tyr Tyr Arg Ser Lys Trp Tyr
65                  70                  75                  80
Asn Asp Tyr Ala Val Ser Val Lys Ser Arg Ile Thr Phe Asn Pro Asp
                85                  90                  95
Thr Ser Lys Asn Gln Phe Ser Leu Gln Leu Asn Ser Val Thr Pro Glu
            100                 105                 110
Asp Thr Ala Val Tyr Tyr Cys Ala Arg Glu Gly Val Gly Ala Ile Thr
        115                 120                 125
Ser His Phe Asp Tyr Trp Gly Gln Gly Thr Leu Val Thr Val Ser Ser
    130                 135                 140

<210> SEQ ID NO 229
<211> LENGTH: 12
<212> TYPE: PRT
<213> ORGANISM: Homo sapiens

<400> SEQUENCE: 229

Glu Gly Val Gly Ala Ile Thr Ser His Phe Asp Tyr
1               5                   10

<210> SEQ ID NO 230
<211> LENGTH: 434
<212> TYPE: DNA
<213> ORGANISM: Homo sapiens

<400> SEQUENCE: 230

| | |
|---|---|
| atgtctgtct ccttcctcat cttcctgccc gtgctgggcc tcccatgggg tgtcctgtca | 60 |
| caggtacagc tgcagcagtc aggtccagga ctggtgaagc cctcgcagac cctctcactc | 120 |
| acctgtgcca tctccgggga cagtgtctct agcaaccgtg ctgcttggaa ctggatcagg | 180 |

```
cagtccccat cgagaggcct tgagtggctg ggaaggacat actacaggtc caagtggtat      240
aatgattatg cagtatctgt gaaaagtcga ataaccttca acccagacac atccaagaac      300
cagttctccc tgcagctgaa ctctgtgact cccgaggaca cggctgtgta ttactgtgca      360 agagagggg tgggagctat tacgtctcac tttgactact ggggccaggg aaccctggtc       420
accgtctcct cagc                                                        434
```

```
<210> SEQ ID NO 231
<211> LENGTH: 144
<212> TYPE: PRT
<213> ORGANISM: Homo sapiens

<400> SEQUENCE: 231
```

Met Ser Val Ser Phe Leu Ile Phe Leu Pro Val Leu Gly Leu Pro Trp
1               5                   10                  15

Gly Val Leu Ser Gln Val Gln Leu Gln Gln Ser Gly Pro Gly Leu Val
            20                  25                  30

Lys Pro Ser Gln Thr Leu Ser Leu Thr Cys Ala Ile Ser Gly Asp Ser
        35                  40                  45

Val Ser Ser Asn Arg Ala Ala Trp Asn Trp Ile Arg Gln Ser Pro Ser
    50                  55                  60

Arg Gly Leu Glu Trp Leu Gly Arg Thr Tyr Tyr Arg Ser Lys Trp Tyr
65                  70                  75                  80

Asn Asp Tyr Ala Val Ser Val Lys Ser Arg Ile Thr Phe Asn Pro Asp
                85                  90                  95

Thr Ser Lys Asn Gln Phe Ser Leu Gln Leu Asn Ser Val Thr Pro Glu
            100                 105                 110

Asp Thr Ala Val Tyr Tyr Cys Ala Arg Glu Gly Val Gly Ala Ile Thr
        115                 120                 125

Ser His Phe Asp Tyr Trp Gly Gln Gly Thr Leu Val Thr Val Ser Ser
    130                 135                 140

```
<210> SEQ ID NO 232
<211> LENGTH: 12
<212> TYPE: PRT
<213> ORGANISM: Homo sapiens

<400> SEQUENCE: 232
```

Gly Asp Ser Val Ser Ser Asn Arg Ala Ala Trp Asn
1               5                   10

```
<210> SEQ ID NO 233
<211> LENGTH: 18
<212> TYPE: PRT
<213> ORGANISM: Homo sapiens

<400> SEQUENCE: 233
```

Arg Thr Tyr Tyr Arg Ser Lys Trp Tyr Asn Asp Tyr Ala Val Ser Val
1               5                   10                  15

Lys Ser

```
<210> SEQ ID NO 234
<211> LENGTH: 443
<212> TYPE: DNA
<213> ORGANISM: Homo sapiens

<400> SEQUENCE: 234
```

```
atggactgga cctggagggt cctcttttg gtggcagcag ccacaggtgc ccactcccag       60
```

```
gtccagcttg tgcagtctgg ggctgaggtg aagaagcctg gggcctcagt gaaggtttcc      120
tgcagggctt ctggatacac cttcactaac tatgctatgc attgggtgcg ccaggccccc      180
ggacaaaggc ttgagtggat gggatggatc aacgctggca atggttacac aaaatattca      240
cagaagttcc aggacagatt caccattacc agggacacat ccgcgaccac agcctacatg      300
gaactgagca gcctgagatc tgaagacacg gctgtatatt actgtgcgag agattctttt      360
tacgatattt tgactgggcc agtctatcac tactacggta tggacgtctg gggccaaggg      420
accacggtca ccgtctcctc agc                                              443
```

```
<210> SEQ ID NO 235
<211> LENGTH: 147
<212> TYPE: PRT
<213> ORGANISM: Homo sapiens

<400> SEQUENCE: 235
```

```
Met Asp Trp Thr Trp Arg Val Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Arg Ala Ser Gly Tyr Thr Phe
        35                  40                  45

Thr Asn Tyr Ala Met His Trp Val Arg Gln Ala Pro Gly Gln Arg Leu
    50                  55                  60

Glu Trp Met Gly Trp Ile Asn Ala Gly Asn Gly Tyr Thr Lys Tyr Ser
65                  70                  75                  80

Gln Lys Phe Gln Asp Arg Phe Thr Ile Thr Arg Asp Thr Ser Ala Thr
                85                  90                  95

Thr Ala Tyr Met Glu Leu Ser Ser Leu Arg Ser Glu Asp Thr Ala Val
            100                 105                 110

Tyr Tyr Cys Ala Arg Asp Ser Phe Tyr Asp Ile Leu Thr Gly Pro Val
        115                 120                 125

Tyr His Tyr Tyr Gly Met Asp Val Trp Gly Gln Gly Thr Thr Val Thr
    130                 135                 140

Val Ser Ser
145
```

```
<210> SEQ ID NO 236
<211> LENGTH: 449
<212> TYPE: DNA
<213> ORGANISM: Homo sapiens

<400> SEQUENCE: 236
atggactgga cctggaggat cctcttttg gtggcagcag ccacaggtgc ccactcccag        60
gtccaacttg tgcagtctgg ggctgaggtg aagaagcctg gggcctcagt gaaggtttcc      120
tgcaaggctt ctggatacac cttcactaac tatgctatac attgggtgcg ccaggccccc      180
ggacaaagtc ttgtgtggat gggatggatc aacgctggca atggttacac aaaatattca      240
cagatgttcc aggacagagt cgccattact agggacacat ccgcgaacac agcctacatg      300
gagctgagca gcctgagatc tggagacacg gctgtgtatt actgtgcgag agatcagttt      360
tacgagactt tgactggtta ttataacgtg tactactact acggtatgga cgtctggggc      420
caagggacca cggtcgccgt ctcctcagc                                        449
```

```
<210> SEQ ID NO 237
```

<211> LENGTH: 149
<212> TYPE: PRT
<213> ORGANISM: Homo sapiens

<400> SEQUENCE: 237

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Ala Ile His Trp Val Arg Gln Ala Pro Gly Gln Ser Leu
    50                  55                  60

Val Trp Met Gly Trp Ile Asn Ala Gly Asn Gly Tyr Thr Lys Tyr Ser
65                  70                  75                  80

Gln Met Phe Gln Asp Arg Val Ala Ile Thr Arg Asp Thr Ser Ala Asn
                85                  90                  95

Thr Ala Tyr Met Glu Leu Ser Ser Leu Arg Ser Gly Asp Thr Ala Val
            100                 105                 110

Tyr Tyr Cys Ala Arg Asp Gln Phe Tyr Glu Thr Leu Thr Gly Tyr Tyr
        115                 120                 125

Asn Val Tyr Tyr Tyr Gly Met Asp Val Trp Gly Gln Gly Thr Thr
    130                 135                 140

Val Ala Val Ser Ser
145

<210> SEQ ID NO 238
<211> LENGTH: 437
<212> TYPE: DNA
<213> ORGANISM: Homo sapiens

<400> SEQUENCE: 238
atggactgga cctggaggat cctcttttg gtggcagcag ccacaggtgt ccactcccag      60
gtccagcttg tgcagtctgg ggctgagtg aagaagcctg gggcctcagt gaaggtttcc     120
tgcaaggctt ctggattcat ctttattaac tatgctatgc aatgggtgcg ccaggccccc     180
ggacaaaggc ttgagtggat gggatggatc aacgctggca acggttacac aaaatattca     240
cagaaattcc agggcagagt caccatcacc agggacatat ccgcgaacac agtctacatg     300
gagctgagca gcctgagatc tgaagacacg gctgtgtatt actgtgcgag agatggattt     360
tgtagtacaa ccacctgctc cgaccactac ggtatggacg tctggggcca agggaccacg     420
gtcaccgtct cctcagc                                                   437

<210> SEQ ID NO 239
<211> LENGTH: 145
<212> TYPE: PRT
<213> ORGANISM: Homo sapiens

<400> SEQUENCE: 239

Met Asp Trp Thr Trp Arg Ile Leu Phe Leu Val Ala Ala Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Ile Phe
        35                  40                  45

Ile Asn Tyr Ala Met Gln Trp Val Arg Gln Ala Pro Gly Gln Arg Leu
    50                  55                  60

Glu Trp Met Gly Trp Ile Asn Ala Gly Asn Gly Tyr Thr Lys Tyr Ser
65                  70                  75                  80

Gln Lys Phe Gln Gly Arg Val Thr Ile Thr Arg Asp Ile Ser Ala Asn
            85                  90                  95

Thr Val Tyr Met Glu Leu Ser Ser Leu Arg Ser Glu Asp Thr Ala Val
                100                 105                 110

Tyr Tyr Cys Ala Arg Asp Gly Phe Cys Ser Thr Thr Cys Ser Asp
            115                 120                 125

His Tyr Gly Met Asp Val Trp Gly Gln Gly Thr Thr Val Thr Val Ser
    130                 135                 140

Ser
145

<210> SEQ ID NO 240
<211> LENGTH: 437
<212> TYPE: DNA
<213> ORGANISM: Homo sapiens

<400> SEQUENCE: 240
atggactgga cctggaggat cctcttttg gtggcagcag ccacaggtgc ccactcccag      60
gtccagcttg tgcagtctgg ggctgaggtg aagaaccctg gggcctcagt gaaggtttcc    120
tgcaaggctt ctggattcac cttcactaac tatgctatgc attgggtgcg ccaggccccc    180
ggacaaaggc ttgagtggat gggatggatc aacgctggca atggtcacac aaaatattca    240
cagaagttcc aggacagagt cgccattacc agggacacat ccgcgaccac agcctacatg    300
gaactgagca gcctgagatc tgaagacacg gctgtgtatt actgttcgag agatggattt    360
tgtagtacta ccacctgctc cgaccactac ggtatggacg tctggggcca agggaccacg    420
gtcaccgtct cctcagc                                                   437

<210> SEQ ID NO 241
<211> LENGTH: 145
<212> TYPE: PRT
<213> ORGANISM: Homo sapiens

<400> SEQUENCE: 241

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Asn
                20                  25                  30

Pro Gly Ala Ser Val Lys Val Ser Cys Lys Ala Ser Gly Phe Thr Phe
            35                  40                  45

Thr Asn Tyr Ala Met His Trp Val Arg Gln Ala Pro Gly Gln Arg Leu
    50                  55                  60

Glu Trp Met Gly Trp Ile Asn Ala Gly Asn Gly His Thr Lys Tyr Ser
65                  70                  75                  80

Gln Lys Phe Gln Asp Arg Val Ala Ile Thr Arg Asp Thr Ser Ala Thr
            85                  90                  95

Thr Ala Tyr Met Glu Leu Ser Ser Leu Arg Ser Glu Asp Thr Ala Val
                100                 105                 110

Tyr Tyr Cys Ser Arg Asp Gly Phe Cys Ser Thr Thr Cys Ser Asp
            115                 120                 125

His Tyr Gly Met Asp Val Trp Gly Gln Gly Thr Thr Val Thr Val Ser
    130                 135                 140

Ser

<210> SEQ ID NO 242
<211> LENGTH: 12
<212> TYPE: PRT
<213> ORGANISM: Homo sapiens

<400> SEQUENCE: 242

Gly Phe Ala Leu Ser Thr Ser Gly Val Gly Val Gly
1               5                   10

<210> SEQ ID NO 243
<211> LENGTH: 16
<212> TYPE: PRT
<213> ORGANISM: Homo sapiens

<400> SEQUENCE: 243

Leu Ile Tyr Trp Asp Asp Asp Lys Arg Tyr Ser Pro Ser Leu Lys Ser
1               5                   10                  15

<210> SEQ ID NO 244
<211> LENGTH: 13
<212> TYPE: PRT
<213> ORGANISM: Homo sapiens

<400> SEQUENCE: 244

Lys Asp Tyr Gly Asp Tyr Tyr Tyr Tyr Asp Met Asp Val
1               5                   10

<210> SEQ ID NO 245
<211> LENGTH: 437
<212> TYPE: DNA
<213> ORGANISM: Homo sapiens

<400> SEQUENCE: 245
atggactgga cctggaggat cctcttttg gtggcagcag ccacaggtgc ccactcccag      60
gtccagcttg tgcagtctgg ggctgaggtg aagaaccctg ggcctcagt gaaggtttcc     120 tgcaaggctt ctggattcac cttcactaac tatgctatgc attgggtgcg ccaggccccc    180
ggacaaaggc ttgagtggat gggatggatc aacgctggca atggtcacac aaaatattca    240
cagaagttcc aggacagagt cgccattacc agggacacat ccgcgaccac agcctacatg    300
gaactgagca gcctgagatc tgaagacacg gctgtgtatt actgttcgag agatggattt    360
tgtagtacta ccacctgctc cgaccactac ggtatggacg tctggggcca agggaccacg    420
gtcaccgtct cctcagc                                                   437

<210> SEQ ID NO 246
<211> LENGTH: 584
<212> TYPE: DNA
<213> ORGANISM: Homo sapiens

<400> SEQUENCE: 246
atggactgga cctggaggat cctcttttg gtggcagcag ccacaggtgc ccactcccag      60
gtccagcttg tgcagtctgg ggctgaggtg aagaagcctg ggcctcagt gaaggtttcc     120 tgcaaggctt ctggatacac cttcactagt tatgctatgc attgggtgcg ccaggccccc    180
ggacaaaggc ttgagtggat gggatggatc aacgctggca atggtaacac aaaatattca    240
cagaagttcc agggcgtttc ctgcaaggcg tctggataca ccttcacgaa ctatgctatg    300
cattgggtgc gccaggcccc cggacaaagg cttgagtgga tgggatggat caacgctggc    360

```
aatggttaca caaaatattc acagaagttc agggcagag tcaccattat cagggacaca    420
tctgcgacca cagcctatat ggagctgagc agcctgagat ctgaagacac ggctgtgtat    480
tactgtgcga gagataatta ttatgattcg ggagttatt atgaatactg ctactacggt    540
atggacgtct ggggccaagg gaccacggtc accgtctcct cagc                     584
```

<210> SEQ ID NO 247
<211> LENGTH: 147
<212> TYPE: PRT
<213> ORGANISM: Homo sapiens

<400> SEQUENCE: 247

```
Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Ala Met His Trp Val Arg Gln Ala Pro Gly Gln Arg Leu
    50                  55                  60

Glu Trp Met Gly Trp Ile Asn Ala Gly Asn Gly Tyr Thr Lys Tyr Ser
65                  70                  75                  80

Gln Lys Phe Gln Gly Arg Val Thr Ile Ile Arg Asp Thr Ser Ala Thr
                85                  90                  95

Thr Ala Tyr Met Glu Leu Ser Ser Leu Arg Ser Glu Asp Thr Ala Val
            100                 105                 110

Tyr Tyr Cys Ala Arg Asp Asn Tyr Tyr Asp Ser Gly Ser Tyr Tyr Glu
        115                 120                 125

Tyr Cys Tyr Tyr Gly Met Asp Val Trp Gly Gln Gly Thr Thr Val Thr
    130                 135                 140

Val Ser Ser
145
```

<210> SEQ ID NO 248
<211> LENGTH: 584
<212> TYPE: DNA
<213> ORGANISM: Homo sapiens

<400> SEQUENCE: 248

```
atggactgga cctggaggat cctcttttg gtggcagcag ccacaggtgc ccactcccag     60
gtccagcttg tgcagtctgg ggctgaggtg aagaagcctg ggcctcagt gaaggtttcc    120 tgcaaggctt ctggatacac cttcactagt tatgctatgc attgggtgcg ccaggccccc    180
ggacaaaggc ttgagtggat gggatggat aacgctggca atggtaacac aaaatattca    240
cagaagttcc agggcgtttc ctgcaaggct tctggataca ccttcactag ctatgctatg    300
cattgggtgc gccaggcccc cggacaaagg cttgagtgga tgggatggat caacgctggc    360
aatggtaaca caaaatattc acagaagttc agggcagag tcaccattac cagggacaca    420
tccgcgagca cagcctacat ggagctgagc agcctgagat ctgaagacac ggctgtgtat    480
tactgtgcga gagatcagta ttacgatatt ttgactccat attactacta ctactacggt    540
atggacgtct ggggccaagg gaccacggtc accgtctcct cagc                     584
```

<210> SEQ ID NO 249
<211> LENGTH: 147
<212> TYPE: PRT
<213> ORGANISM: Homo sapiens

<400> SEQUENCE: 249

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Ala Met His Trp Val Arg Gln Ala Pro Gly Gln Arg Leu
    50                  55                  60

Glu Trp Met Gly Trp Ile Asn Ala Gly Asn Gly Asn Thr Lys Tyr Ser
65              70                  75                  80

Gln Lys Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Gln Tyr Tyr Asp Ile Leu Thr Pro Tyr Tyr
        115                 120                 125

Tyr Tyr Tyr Tyr Gly Met Asp Val Trp Gly Gln Gly Thr Thr Val Thr
    130                 135                 140

Val Ser Ser
145

<210> SEQ ID NO 250
<211> LENGTH: 443
<212> TYPE: DNA
<213> ORGANISM: Homo sapiens

<400> SEQUENCE: 250
atggactgga cctggagggt cctcttttg gtggcagcag ccacaggtgc ccactcccag      60
gtccagcttg tgcagtctgg ggctgaggtg aagaagcctg gggcctcagt gaaggtttcc     120
tgcagggctt ctggatacac cttcagtaat tatgctatgc attgggtgcg ccaggccccc     180
ggacaaaggc ttgagtggat gggatggatc aacgctggca atggttacac aaaatattca     240
cagaagttcc aggacagagt caccattacc agggacacat ccgcgaccac agcctacatg     300
gaactgagca gcctgagatc tgaagacacg gctatgtatt actgttcgag agattctttt     360
tacgatattt tgactgggcc agtctatcac tactacggta tggacgtctg gggccaaggg     420
accacggtca ccgtctcctc agc                                             443

<210> SEQ ID NO 251
<211> LENGTH: 147
<212> TYPE: PRT
<213> ORGANISM: Homo sapiens

<400> SEQUENCE: 251

Met Asp Trp Thr Trp Arg Val Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Arg Ala Ser Gly Tyr Thr Phe
        35                  40                  45

Ser Asn Tyr Ala Met His Trp Val Arg Gln Ala Pro Gly Gln Arg Leu
    50                  55                  60

Glu Trp Met Gly Trp Ile Asn Ala Gly Asn Gly Tyr Thr Lys Tyr Ser
65              70                  75                  80

```
Gln Lys Phe Gln Asp Arg Val Thr Ile Thr Arg Asp Thr Ser Ala Thr
                85                  90                  95

Thr Ala Tyr Met Glu Leu Ser Ser Leu Arg Ser Glu Asp Thr Ala Met
            100                 105                 110

Tyr Tyr Cys Ser Arg Asp Ser Phe Tyr Asp Ile Leu Thr Gly Pro Val
        115                 120                 125

Tyr His Tyr Tyr Gly Met Asp Val Trp Gly Gln Gly Thr Thr Val Thr
    130                 135                 140

Val Ser Ser
145

<210> SEQ ID NO 252
<211> LENGTH: 449
<212> TYPE: DNA
<213> ORGANISM: Homo sapiens

<400> SEQUENCE: 252
atggactgga cctggaggat cctctttttg gtggcagcag ccacaggtgt ccactcccag      60
gtccaacttg tgcagtctgg ggctgaggtg aagaagcctg ggcctcagt aaagctttcc     120 tgcaaggctt ctggatacac cttcactaac tatgctatgc attgggtgcg ccaggcccc     180 ggacaaagtc ttgagtggat gggatggatc aacgctggca atggttacac aaaatattca     240
cagaagttcc agggcagagt caccattact agggacacat ccgcgaacac agcctacatg     300
gatctgagca gcctgagatc tgaagacacg gctgtgtatt actgtgcgag agatcagtat     360
tacgatattt tgaaaggtta ttataacgtg gactactact acggtatgga cgtctggggc     420
caagggacca cggtcgccgt ctcctcagc                                       449

<210> SEQ ID NO 253
<211> LENGTH: 149
<212> TYPE: PRT
<213> ORGANISM: Homo sapiens

<400> SEQUENCE: 253

Met Asp Trp Thr Trp Arg Ile Leu Phe Leu Val Ala Ala Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Leu Ser Cys Lys Ala Ser Gly Tyr Thr Phe
        35                  40                  45

Thr Asn Tyr Ala Met His Trp Val Arg Gln Ala Pro Gly Gln Ser Leu
    50                  55                  60

Glu Trp Met Gly Trp Ile Asn Ala Gly Asn Gly Tyr Thr Lys Tyr Ser
65                  70                  75                  80

Gln Lys Phe Gln Gly Arg Val Thr Ile Thr Arg Asp Thr Ser Ala Asn
                85                  90                  95

Thr Ala Tyr Met Asp Leu Ser Ser Leu Arg Ser Glu Asp Thr Ala Val
            100                 105                 110

Tyr Tyr Cys Ala Arg Asp Gln Tyr Tyr Asp Ile Leu Lys Gly Tyr Tyr
        115                 120                 125

Asn Val Asp Tyr Tyr Gly Met Asp Val Trp Gly Gln Gly Thr Thr
    130                 135                 140

Val Ala Val Ser Ser
145
```

-continued

<210> SEQ ID NO 254
<211> LENGTH: 440
<212> TYPE: DNA
<213> ORGANISM: Homo sapiens

<400> SEQUENCE: 254

```
atggactgga cctggaggat cctcttttg gtggcagcag ccacaggtgc ccactcccag      60
gtccagcttg tgcagtctgg ggctgaggtg aagaaccctg gggcctcatt gaaagtttcc    120
tgcaaggctt ctggatacac cttcactaat tatgctatgc attgggtgcg ccaggccccc    180
ggacaaaggc ttgagtggat gggatggatc aacgctggca atggttacac aaaatattca    240
cagaccttcc agggcagagt caccattacc agggacacat acgcgagtac agcctacatg    300
gagctgagca gcctgagatc tgaagacacg gctgtatatt actgtgtgag agatgaatat    360
tatgagtcgg ggagttccaa ctactactac tatggtatgg acgtctgggg ccaagggacc    420
acggtcaccg tctcctcagc                                                 440
```

<210> SEQ ID NO 255
<211> LENGTH: 146
<212> TYPE: PRT
<213> ORGANISM: Homo sapiens

<400> SEQUENCE: 255

```
Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Asn
            20                  25                  30

Pro Gly Ala Ser Leu Lys Val Ser Cys Lys Ala Ser Gly Tyr Thr Phe
        35                  40                  45

Thr Asn Tyr Ala Met His Trp Val Arg Gln Ala Pro Gly Gln Arg Leu
    50                  55                  60

Glu Trp Met Gly Trp Ile Asn Ala Gly Asn Gly Tyr Thr Lys Tyr Ser
65                  70                  75                  80

Gln Thr Phe Gln Gly Arg Val Thr Ile Thr Arg Asp Thr Tyr Ala Ser
                85                  90                  95

Thr Ala Tyr Met Glu Leu Ser Ser Leu Arg Ser Glu Asp Thr Ala Val
            100                 105                 110

Tyr Tyr Cys Val Arg Asp Glu Tyr Tyr Glu Ser Gly Ser Ser Asn Tyr
        115                 120                 125

Tyr Tyr Tyr Gly Met Asp Val Trp Gly Gln Gly Thr Thr Val Thr Val
    130                 135                 140

Ser Ser
145
```

<210> SEQ ID NO 256
<211> LENGTH: 437
<212> TYPE: DNA
<213> ORGANISM: Homo sapiens

<400> SEQUENCE: 256

```
atggactgga cctggaggat cctcttttg gtggcagcag ccacaggtgc ccactcccag      60
gtccagcttg tgcagtctgg ggctgaggtg aagaagcctg gggcctcagt gagggtttcc    120
tgcaaggctt ctggattcac cttcattagt tatgctatgc attgggtgcg ccaggccccc    180
ggacaagggc ttgagtggat gggatggatc aacgctggcg atggtcacac aaaatattca    240
cagaagttcc aggacagagt cgccattacc agggacacat ccgcgaccac agtctacatg    300
```

```
gacctgagca gcctgagatc tgaagacacg gctgtgtatt actgttcgag agatggattt    360
tgtactacta ccacctgttc cgaccactac ggtatggacg tctggggcca agggaccacg    420
gtcaccgtct cctcagc                                                   437

<210> SEQ ID NO 257
<211> LENGTH: 145
<212> TYPE: PRT
<213> ORGANISM: Homo sapiens

<400> SEQUENCE: 257

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Arg Val Ser Cys Lys Ala Ser Gly Phe Thr Phe
            35                  40                  45

Ile Ser Tyr Ala Met His Trp Val Arg Gln Ala Pro Gly Gln Gly Leu
        50                  55                  60

Glu Trp Met Gly Trp Ile Asn Ala Gly Asp Gly His Thr Lys Tyr Ser
65                  70                  75                  80

Gln Lys Phe Gln Asp Arg Val Ala Ile Thr Arg Asp Thr Ser Ala Thr
                85                  90                  95

Thr Val Tyr Met Asp Leu Ser Ser Leu Arg Ser Glu Asp Thr Ala Val
                100                 105                 110

Tyr Tyr Cys Ser Arg Asp Gly Phe Cys Thr Thr Thr Cys Ser Asp
            115                 120                 125

His Tyr Gly Met Asp Val Trp Gly Gln Gly Thr Thr Val Thr Val Ser
        130                 135                 140

Ser
145

<210> SEQ ID NO 258
<211> LENGTH: 443
<212> TYPE: DNA
<213> ORGANISM: Homo sapiens

<400> SEQUENCE: 258
atggactgga cctggaggat cctcttttg gtggcagcag ccacaggtgc ccactcccag    60
gtccagcttt tgcagtctgg ggctgaggtg aagaagcctg ggcctcagt gaaggtttcc    120 tgcaaggctt ctggatacac cttcactaac tatgctatgc attggttgcg ccaggccccc    180
ggacaaaggc ttgagtggat gggatggatc aacgctggca tggttacac aaaatattca    240 cagaagttcc agggcagagt caccataacc agggacacat ccgcgaccac agcctacatg    300
gacctgagca gcctgagatc tgaagacacg gctgtttact actgtgcgag agataattac    360
tatgatagta atgtttataa ttccttactac ttctacggta tggacgtctg gggccaaggg    420
accacggtca ccgtctcctc agc                                            443

<210> SEQ ID NO 259
<211> LENGTH: 147
<212> TYPE: PRT
<213> ORGANISM: Homo sapiens

<400> SEQUENCE: 259

Met Asp Trp Thr Trp Arg Ile Leu Phe Leu Val Ala Ala Ala Thr Gly
1               5                   10                  15
```

```
Ala His Ser Gln Val Gln Leu Leu Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Ala Met His Trp Leu Arg Gln Ala Pro Gly Gln Arg Leu
    50                  55                  60

Glu Trp Met Gly Trp Ile Asn Ala Gly Asn Gly Tyr Thr Lys Tyr Ser
65                  70                  75                  80

Gln Lys Phe Gln Gly Arg Val Thr Ile Thr Arg Asp Thr Ser Ala Thr
                85                  90                  95

Thr Ala Tyr Met Asp Leu Ser Ser Leu Arg Ser Glu Asp Thr Ala Val
            100                 105                 110

Tyr Tyr Cys Ala Arg Asp Asn Tyr Tyr Asp Ser Asn Val Tyr Asn Ser
        115                 120                 125

Tyr Tyr Phe Tyr Gly Met Asp Val Trp Gly Gln Gly Thr Thr Val Thr
    130                 135                 140

Val Ser Ser
145

<210> SEQ ID NO 260
<211> LENGTH: 578
<212> TYPE: DNA
<213> ORGANISM: Homo sapiens

<400> SEQUENCE: 260
atggactgga cctggaggat cctcttttg gtggcagcag ccacaggtgc ccactcccag      60
gtccagcttg tgcagtctgg ggctgaggtg aagaagcctg ggcctcagt gaaggtttcc    120 tgcaaggctt ctggatacac cttcactagt tatgctatgc attgggtgcg ccaggccccc    180
ggacaaaggc ttgagtggat gggatggatc aacgctggca atggtaacac aaaatattca    240
cagaagttcc agggcgtttc ctgcaaggct tctggattca ccttcactag ccatgctata    300
cattgggtgc gccaggcccc cggacaaagg cttgagtgga tgggatggat caacgctggc    360
aatggttaca aaaatattc acagaagttc aggacagag tcgccattac agggacaca    420 tccgcgagca cagcctacat ggagctgagc agcctgagat ctgaagacac ggctgtgtat    480
tactgtacga gagatggatt ttgtagtact accacctgct ccgaccacta cggtatggac    540
gtctggggcc aagggaccac ggtcaccgtc tcctcagc                            578

<210> SEQ ID NO 261
<211> LENGTH: 145
<212> TYPE: PRT
<213> ORGANISM: Homo sapiens

<400> SEQUENCE: 261

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Thr Ser His Ala Ile His Trp Val Arg Gln Ala Pro Gly Gln Arg Leu
    50                  55                  60

Glu Trp Met Gly Trp Ile Asn Ala Gly Asn Gly Tyr Thr Lys Tyr Ser
65                  70                  75                  80

Gln Lys Phe Gln Asp Arg Val Ala Ile Thr Arg Asp Thr Ser Ala Ser
```

```
                        85                  90                  95

Thr Ala Tyr Met Glu Leu Ser Ser Leu Arg Ser Glu Asp Thr Ala Val
                    100                 105                 110

Tyr Tyr Cys Thr Arg Asp Gly Phe Cys Ser Thr Thr Cys Ser Asp
                115                 120                 125

His Tyr Gly Met Asp Val Trp Gly Gln Gly Thr Thr Val Thr Val Ser
            130                 135                 140

Ser
145

<210> SEQ ID NO 262
<211> LENGTH: 437
<212> TYPE: DNA
<213> ORGANISM: Homo sapiens

<400> SEQUENCE: 262
atggactgga cctggaggat cctcttttg gtggcagcag ccacaggtgc ccactcccag      60
gtccagcttg tgcagtctgg ggctgaggtg aagaagcctg gggcctcagt gagggtttcc     120
tgcaagactt ctggattcac cttcactagt tatgctatac agtgggtgcg ccaggccccc     180
ggacaagggc ttgagtggat gggatggatc aacgctggcg atggtcacac gaaatattca     240
cagaagttcc aggacagagt cgtcattacc agggacacat ccgcgaccac agtctacatg     300
gacctgagca gcctgagatc tgaagacacg gctgtgtatt actgtacgag agatggattt     360
tgtactacga ccacctgctc cgaccactac ggtatggacg tctggggcca agggaccacg     420
gtcaccgtct cctcagc                                                    437

<210> SEQ ID NO 263
<211> LENGTH: 145
<212> TYPE: PRT
<213> ORGANISM: Homo sapiens

<400> SEQUENCE: 263

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Arg Val Ser Cys Lys Thr Ser Gly Phe Thr Phe
            35                  40                  45

Thr Ser Tyr Ala Ile Gln Trp Val Arg Gln Ala Pro Gly Gln Gly Leu
        50                  55                  60

Glu Trp Met Gly Trp Ile Asn Ala Gly Asp Gly His Thr Lys Tyr Ser
65                  70                  75                  80

Gln Lys Phe Gln Asp Arg Val Val Ile Thr Arg Asp Thr Ser Ala Thr
                85                  90                  95

Thr Val Tyr Met Asp Leu Ser Ser Leu Arg Ser Glu Asp Thr Ala Val
                    100                 105                 110

Tyr Tyr Cys Thr Arg Asp Gly Phe Cys Thr Thr Thr Cys Ser Asp
                115                 120                 125

His Tyr Gly Met Asp Val Trp Gly Gln Gly Thr Thr Val Thr Val Ser
            130                 135                 140

Ser
145

<210> SEQ ID NO 264
<211> LENGTH: 440
```

```
<212> TYPE: DNA
<213> ORGANISM: Homo sapiens

<400> SEQUENCE: 264
atggactgga cctggaggat cctcttttg gtggcagcag ccacaggtgc ccactcccag    60
gtccagcttg tgcagtctgg ggctgaggtg aagaggcctg gggcctcagt gaaaatttcc   120
tgcaaggctt ctggatacac cttcactaac tatgctatac attgggtgcg ccaggccccc   180
ggacaaaggc ttgagtggat ggggtggatc aacgctggca atggttacac aaaatattca   240
cagaagttcc agggcagagt caccattacc aggacacat ccgcgacctc agcctacctg    300
gagctgtaca gcctgatatc tgaagacacg gctgtatatt actgtgtgag agatgaatac   360
tatgattcgg gagttccaa ctactactac tatggtatgg acgtctgggg ccaagggacc    420
acggtcaccg tctcctcagc                                                440

<210> SEQ ID NO 265
<211> LENGTH: 146
<212> TYPE: PRT
<213> ORGANISM: Homo sapiens

<400> SEQUENCE: 265

Met Asp Trp Thr Trp Arg Ile Leu Phe Leu Val Ala Ala Thr Gly
 1               5                  10                  15

Ala His Ser Gln Val Gln Leu Val Gln Ser Gly Ala Glu Val Lys Arg
             20                  25                  30

Pro Gly Ala Ser Val Lys Ile Ser Cys Lys Ala Ser Gly Tyr Thr Phe
         35                  40                  45

Thr Asn Tyr Ala Ile His Trp Val Arg Gln Ala Pro Gly Gln Arg Leu
     50                  55                  60

Glu Trp Met Gly Trp Ile Asn Ala Gly Asn Gly Tyr Thr Lys Tyr Ser
 65                  70                  75                  80

Gln Lys Phe Gln Gly Arg Val Thr Ile Thr Arg Asp Thr Ser Ala Thr
                 85                  90                  95

Ser Ala Tyr Leu Glu Leu Tyr Ser Leu Ile Ser Glu Asp Thr Ala Val
            100                 105                 110

Tyr Tyr Cys Val Arg Asp Glu Tyr Tyr Asp Ser Gly Ser Ser Asn Tyr
        115                 120                 125

Tyr Tyr Tyr Gly Met Asp Val Trp Gly Gln Gly Thr Thr Val Thr Val
    130                 135                 140

Ser Ser
145

<210> SEQ ID NO 266
<211> LENGTH: 443
<212> TYPE: DNA
<213> ORGANISM: Homo sapiens

<400> SEQUENCE: 266
atggactgga cctggagggt cctcttttg gtggcagcag ccacaggtgc ccactcccag     60
gtccagcttg tgcagtctgg ggctgaggtg aagaagcctg gggcctcagt gaaggtttcc   120
tgcagggctt ctggatacac cttcactaac tatgctatgc attgggtgcg ccaggccccc   180
ggacaaaggc ttgagtggat gggatggatc aacgctggca atggttacac aaagtattca   240
cagaagttcc aggacagagt caccattacc aggacacat ccgcgaccac agcccacatg    300
gaactgagca gcctgagatc tgaagacacg gctatgtatt actgtgcgag agattctttt   360
```

```
tacgatattt tgactgggcc agtctatcac tactacggta tggacgtctg gggccaaggg    420
accacggtca ccgtctcctc agc                                            443
```

<210> SEQ ID NO 267
<211> LENGTH: 147
<212> TYPE: PRT
<213> ORGANISM: Homo sapiens

<400> SEQUENCE: 267

```
Met Asp Trp Thr Trp Arg Val Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Arg Ala Ser Gly Tyr Thr Phe
        35                  40                  45

Thr Asn Tyr Ala Met His Trp Val Arg Gln Ala Pro Gly Gln Arg Leu
    50                  55                  60

Glu Trp Met Gly Trp Ile Asn Ala Gly Asn Gly Tyr Thr Lys Tyr Ser
65                  70                  75                  80

Gln Lys Phe Gln Asp Arg Val Thr Ile Thr Arg Asp Thr Ser Ala Thr
                85                  90                  95

Thr Ala His Met Glu Leu Ser Ser Leu Arg Ser Glu Asp Thr Ala Met
            100                 105                 110

Tyr Tyr Cys Ala Arg Asp Ser Phe Tyr Asp Ile Leu Thr Gly Pro Val
        115                 120                 125

Tyr His Tyr Tyr Gly Met Asp Val Trp Gly Gly Thr Thr Val Thr
    130                 135                 140

Val Ser Ser
145
```

<210> SEQ ID NO 268
<211> LENGTH: 443
<212> TYPE: DNA
<213> ORGANISM: Homo sapiens

<400> SEQUENCE: 268

```
atggactgga cctggagggt cctcttttg gtggcagcag ccacaggtgc ccactcccag     60
gtccagcttg tgcagtctgg ggctgaggtg aagaagcctg gggcctcagt gaaggtttcc   120
tgcagggctt ctggatacac cttcactaac tatgctatgc attgggtgcg ccaggccccc   180
ggacaaaggc ttgagtggat gggatggatc aacgctggca atggttacac aaagtattca   240
cagaagttcc aggacagagt caccattacc agggacacat ccgcgaccac agcccacatg   300
gaactgagca gcctgagatc tgaagacacg gctatgtatt actgtgcgag agattctttt   360
tacgatattt tgactgggcc agtctatcac tactacggta tggacgtctg gggccaaggg   420
accacggtca ccgtctcctc agc                                           443
```

<210> SEQ ID NO 269
<211> LENGTH: 419
<212> TYPE: DNA
<213> ORGANISM: Homo sapiens

<400> SEQUENCE: 269

```
atggagtttg gctgagttg gatttaccct gctgctattt taaaaggtgt ccagtgtgag     60
gtgcagctgg tggagtctgg gggggcttg gtaaagcctg gggggtccct tagtctctcc   120
tgtacagcct ctggattcac tttcaataac gcctggatga gctgggtccg ccaggctcca   180
```

```
gggaaggggc tggagtgggt tggccgtatt aaaagcaaaa ctgatggtgg gacaacagac      240
tacgctgcac ccgtgaaagg cagattcacc atctcaagag atgattcaaa aaccacgctg      300
tctctgcgaa tgaacagcct gaaaaccgag gacacggccg tgtattactg tgccacaggc      360
agtggctggt cccactttga ctactggggc cagggaaccc tggtcaccgt ctcctcagc       419
```

<210> SEQ ID NO 270
<211> LENGTH: 139
<212> TYPE: PRT
<213> ORGANISM: Homo sapiens

<400> SEQUENCE: 270

```
Met Glu Phe Gly Leu Ser Trp Ile Tyr Leu Ala Ala Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Ser Leu Ser Cys Thr Ala Ser Gly Phe Thr Phe
        35                  40                  45

Asn Asn Ala Trp Met Ser Trp Val Arg Gln Ala Pro Gly Lys Gly Leu
    50                  55                  60

Glu Trp Val Gly Arg Ile Lys Ser Lys Thr Asp Gly Gly Thr Thr Asp
65                  70                  75                  80

Tyr Ala Ala Pro Val Lys Gly Arg Phe Thr Ile Ser Arg Asp Asp Ser
                85                  90                  95

Lys Thr Thr Leu Ser Leu Arg Met Asn Ser Leu Lys Thr Glu Asp Thr
            100                 105                 110

Ala Val Tyr Tyr Cys Ala Thr Gly Ser Gly Trp Ser His Phe Asp Tyr
        115                 120                 125

Trp Gly Gln Gly Thr Leu Val Thr Val Ser Ser
    130                 135
```

<210> SEQ ID NO 271
<211> LENGTH: 10
<212> TYPE: PRT
<213> ORGANISM: Homo sapiens

<400> SEQUENCE: 271

```
Gly Phe Thr Phe Asn Asn Ala Trp Met Ser
1               5                   10
```

<210> SEQ ID NO 272
<211> LENGTH: 19
<212> TYPE: PRT
<213> ORGANISM: Homo sapiens

<400> SEQUENCE: 272

```
Arg Ile Lys Ser Lys Thr Asp Gly Gly Thr Thr Asp Tyr Ala Ala Pro
1               5                   10                  15

Val Lys Gly
```

<210> SEQ ID NO 273
<211> LENGTH: 9
<212> TYPE: PRT
<213> ORGANISM: Homo sapiens

<400> SEQUENCE: 273

```
Gly Ser Gly Trp Ser His Phe Asp Tyr
1               5
```

<210> SEQ ID NO 274
<211> LENGTH: 419
<212> TYPE: DNA
<213> ORGANISM: Homo sapiens

<400> SEQUENCE: 274

```
atggagtttg ggctgagctg gattttcctt actgctattt taaaaggtgt ccagtgtgag    60
gtgcagctgg tggagtctgg gggaggcttg gtaaagcctg gggggtccct tagactctcc   120
tgtgcagcct ctggattcac tttcagtaac gcctggatga gctgggtccg ccaggctcca   180
gggaaggggc tggagtgggt tggccgtgtt aaaagcaaaa ctgatggtgg gacaacagac   240
tacgctgcac ccgtgaaagg cagattcacc atctcaagag atgattcaaa aaacacgctg   300
tatctgcaaa tgaacagcct gaaaaccgag gacacagccg tgtattactg taccacaggc   360
agtgactggt cccactttga ctactggggc cagggaaccc tggtcaccgt ctcctcagc    419
```

<210> SEQ ID NO 275
<211> LENGTH: 139
<212> TYPE: PRT
<213> ORGANISM: Homo sapiens

<400> SEQUENCE: 275

Met Glu Phe Gly Leu Ser Trp Ile Phe Leu Thr Ala Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asn Ala Trp Met Ser Trp Val Arg Gln Ala Pro Gly Lys Gly Leu
    50                  55                  60

Glu Trp Val Gly Arg Val Lys Ser Lys Thr Asp Gly Gly Thr Thr Asp
65                  70                  75                  80

Tyr Ala Ala Pro Val Lys Gly Arg Phe Thr Ile Ser Arg Asp Asp Ser
                85                  90                  95

Lys Asn Thr Leu Tyr Leu Gln Met Asn Ser Leu Lys Thr Glu Asp Thr
            100                 105                 110

Ala Val Tyr Tyr Cys Thr Thr Gly Ser Asp Trp Ser His Phe Asp Tyr
        115                 120                 125

Trp Gly Gln Gly Thr Leu Val Thr Val Ser Ser
    130                 135

<210> SEQ ID NO 276
<211> LENGTH: 10
<212> TYPE: PRT
<213> ORGANISM: Homo sapiens

<400> SEQUENCE: 276

Gly Phe Thr Phe Ser Asn Ala Trp Met Ser
1               5                   10

<210> SEQ ID NO 277
<211> LENGTH: 19
<212> TYPE: PRT
<213> ORGANISM: Homo sapiens

<400> SEQUENCE: 277

Arg Val Lys Ser Lys Thr Asp Gly Gly Thr Thr Asp Tyr Ala Ala Pro
1               5                   10                  15

Val Lys Gly

<210> SEQ ID NO 278
<211> LENGTH: 9
<212> TYPE: PRT
<213> ORGANISM: Homo sapiens

<400> SEQUENCE: 278

Gly Ser Asp Trp Ser His Phe Asp Tyr
1               5

<210> SEQ ID NO 279
<211> LENGTH: 419
<212> TYPE: DNA
<213> ORGANISM: Homo sapiens

<400> SEQUENCE: 279

```
atggagtttg ggctgagctg gattttcctt gctggtattt taaaaggtgt ccagtgtgag      60
gtgcagctgg tggagtctgg gggaggcttg gtaaagcctg ggggtccct  tagactctcc     120 tgtgcagcct ctggattcac tttcagtaac gcctggatga actgggtccg ccaggccca     180 gggaaggggc tggagtgggt tggccgtatt aaaagcaaaa ctgaaggtgg acaacagac      240 tacgctgcac ccgtgaaagg cagattcacc atctcaagag atgattcaaa aaacacgctg    300
tatctgcaaa tgaatagcct gaaaaccgaa gacacagccg tgtattactg taccacaggc    360
agtgactgga cccactttga ctactggggc cagggaaccc tggtcaccgt ctcctcagc     419
```

<210> SEQ ID NO 280
<211> LENGTH: 139
<212> TYPE: PRT
<213> ORGANISM: Homo sapiens

<400> SEQUENCE: 280

Met Glu Phe Gly Leu Ser Trp Ile Phe Leu Ala Gly Ile Leu Lys Gly
1               5                   10                  15

Val Gln Cys Glu Val Gln Leu Val Glu Ser Gly Gly Gly Leu Val Lys
                20                  25                  30

Pro Gly Gly Ser Leu Arg Leu Ser Cys Ala Ala Ser Gly Phe Thr Phe
            35                  40                  45

Ser Asn Ala Trp Met Asn Trp Val Arg Gln Ala Pro Gly Lys Gly Leu
        50                  55                  60

Glu Trp Val Gly Arg Ile Lys Ser Lys Thr Glu Gly Gly Thr Thr Asp
65                  70                  75                  80

Tyr Ala Ala Pro Val Lys Gly Arg Phe Thr Ile Ser Arg Asp Asp Ser
                85                  90                  95

Lys Asn Thr Leu Tyr Leu Gln Met Asn Ser Leu Lys Thr Glu Asp Thr
            100                 105                 110

Ala Val Tyr Tyr Cys Thr Thr Gly Ser Asp Trp Thr His Phe Asp Tyr
        115                 120                 125

Trp Gly Gln Gly Thr Leu Val Thr Val Ser Ser
    130                 135

<210> SEQ ID NO 281
<211> LENGTH: 10
<212> TYPE: PRT
<213> ORGANISM: Homo sapiens

<400> SEQUENCE: 281

Gly Phe Thr Phe Ser Asn Ala Trp Met Asn

<210> SEQ ID NO 282
<211> LENGTH: 19
<212> TYPE: PRT
<213> ORGANISM: Homo sapiens

<400> SEQUENCE: 282

Arg Ile Lys Ser Lys Thr Glu Gly Gly Thr Thr Asp Tyr Ala Ala Pro
1               5                   10                  15
Val Lys Gly

<210> SEQ ID NO 283
<211> LENGTH: 9
<212> TYPE: PRT
<213> ORGANISM: Homo sapiens

<400> SEQUENCE: 283

Gly Ser Asp Trp Thr His Phe Asp Tyr
1               5

<210> SEQ ID NO 284
<211> LENGTH: 425
<212> TYPE: DNA
<213> ORGANISM: Homo sapiens

<400> SEQUENCE: 284

```
atggagtttg ggctgagctg gattttcctt gctgctattt taaaaggtgt ccagtgtgag      60
gtgcaactgg tggagtctgg gggaggcttg gtaaagcctg gggggtccct tagactgtcc     120
tgtgcagcct ctggattcac tttcagtgac gcctggatga cctgggtccg ccaggctcca     180
gggaaggggc tggagtgggt tggccgtatt aaaagcaaaa ctgatgatgg acaacagac      240
tacgctgcac ccgtgaaagg cagattcacc atctcaagag atgattcaaa aaacacgctg     300
tatctgcaaa tgaacagcct gaaaaccgag gacacagccg tttattactg tacctcccta     360
ttactatggt tcggggagtt aagggactac tggggccagg aaccctggt caccgtctcc      420
tcagc                                                                 425
```

<210> SEQ ID NO 285
<211> LENGTH: 141
<212> TYPE: PRT
<213> ORGANISM: Homo sapiens

<400> SEQUENCE: 285

Met Glu Phe Gly Leu Ser Trp Ile Phe Leu Ala Ala Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Ala Trp Met Thr Trp Val Arg Gln Ala Pro Gly Lys Gly Leu
    50                  55                  60

Glu Trp Val Gly Arg Ile Lys Ser Lys Thr Asp Asp Gly Thr Thr Asp
65                  70                  75                  80

Tyr Ala Ala Pro Val Lys Gly Arg Phe Thr Ile Ser Arg Asp Asp Ser
                85                  90                  95

Lys Asn Thr Leu Tyr Leu Gln Met Asn Ser Leu Lys Thr Glu Asp Thr
            100                 105                 110

Ala Val Tyr Tyr Cys Thr Ser Leu Leu Leu Trp Phe Gly Glu Leu Arg
            115                 120                 125

Asp Tyr Trp Gly Gln Gly Thr Leu Val Thr Val Ser Ser
        130                 135                 140

<210> SEQ ID NO 286
<211> LENGTH: 10
<212> TYPE: PRT
<213> ORGANISM: Homo sapiens

<400> SEQUENCE: 286

Gly Phe Thr Phe Ser Asp Ala Trp Met Thr
1               5                   10

<210> SEQ ID NO 287
<211> LENGTH: 19
<212> TYPE: PRT
<213> ORGANISM: Homo sapiens

<400> SEQUENCE: 287

Arg Ile Lys Ser Lys Thr Asp Asp Gly Thr Thr Asp Tyr Ala Ala Pro
1               5                   10                  15

Val Lys Gly

<210> SEQ ID NO 288
<211> LENGTH: 11
<212> TYPE: PRT
<213> ORGANISM: Homo sapiens

<400> SEQUENCE: 288

Leu Leu Leu Trp Phe Gly Glu Leu Arg Asp Tyr
1               5                   10

<210> SEQ ID NO 289
<211> LENGTH: 425
<212> TYPE: DNA
<213> ORGANISM: Homo sapiens

<400> SEQUENCE: 289
atggagtttg ggctgagctg gattttcctt gctgctattt taaaaggtgt ccagtgtgag      60
gtgcagctgg tggaatctgg gggaggcttg ataaagcctg gggggtccct tagactctcc     120
tgtgcagcct ctggattcac tttcagtaac gcctggatga cctgggtccg ccaggctcca     180 gggaagggc tggagtgggt tggccgtatt aaaagcaaaa ctgatgatgg gacaaccgac      240
tacgctgcac ccgtgaaagg cagattcacc atctcaagaa atgattcaaa aacacgctg     300 tatctgcaaa tgaacagcct gaaaaccgag gacacagccg tctattactg tacctcccta     360
ttactctggt tcggggagtt aagggactac tggggccagg gaaccctggt caccgtctcc     420
tcagc                                                                425

<210> SEQ ID NO 290
<211> LENGTH: 141
<212> TYPE: PRT
<213> ORGANISM: Homo sapiens

<400> SEQUENCE: 290

Met Glu Phe Gly Leu Ser Trp Ile Phe Leu Ala Ala Ile Leu Lys Gly
1               5                   10                  15

Val Gln Cys Glu Val Gln Leu Val Glu Ser Gly Gly Gly Leu Ile Lys
            20                  25                  30

Pro Gly Gly Ser Leu Arg Leu Ser Cys Ala Ala Ser Gly Phe Thr Phe
        35                  40                  45

Ser Asn Ala Trp Met Thr Trp Val Arg Gln Ala Pro Gly Lys Gly Leu
 50                  55                  60

Glu Trp Val Gly Arg Ile Lys Ser Lys Thr Asp Asp Gly Thr Thr Asp
 65                  70                  75                  80

Tyr Ala Ala Pro Val Lys Gly Arg Phe Thr Ile Ser Arg Asn Asp Ser
                 85                  90                  95

Lys Asn Thr Leu Tyr Leu Gln Met Asn Ser Leu Lys Thr Glu Asp Thr
            100                 105                 110

Ala Val Tyr Tyr Cys Thr Ser Leu Leu Leu Trp Phe Gly Glu Leu Arg
            115                 120                 125

Asp Tyr Trp Gly Gln Gly Thr Leu Val Thr Val Ser Ser
130                 135                 140

<210> SEQ ID NO 291
<211> LENGTH: 10
<212> TYPE: PRT
<213> ORGANISM: Homo sapiens

<400> SEQUENCE: 291

Gly Phe Thr Phe Ser Asn Ala Trp Met Thr
1               5                   10

<210> SEQ ID NO 292
<211> LENGTH: 425
<212> TYPE: DNA
<213> ORGANISM: Homo sapiens

<400> SEQUENCE: 292
atggactttg gctgagctg attttcctt gctgctattt taaaaggtgt cccgtgtgag      60
gtgcagttgg tggagtctgg gggaggcttg gtaaagcctg gggggtccct tagactctcc    120
tgtgcagcct ctggattcac tttcaataac gcctggttga gctgggtccg ccaggctcca    180
gggaaggggc tggagtgggt tggccgtatt aaaagcaaaa ttgatgatgg acaacaaac     240 tacgctgcac ccgtgaaagg cagattcacc atctcaagag atgattcaaa aaacacgcta    300
tatctgcaaa tgaacggcct gcaaaccgag gacacagccg tgtattactg ttcctcccta    360
ttcctatggt tcggggagtt aagggactac tggggccagg gaaccctggt caccgtctcc    420
tcagc                                                               425

<210> SEQ ID NO 293
<211> LENGTH: 141
<212> TYPE: PRT
<213> ORGANISM: Homo sapiens

<400> SEQUENCE: 293

Met Asp Phe Gly Leu Ser Trp Ile Phe Leu Ala Ala Ile Leu Lys Gly
1               5                   10                  15

Val Pro Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
            35                  40                  45

Asn Asn Ala Trp Leu Ser Trp Val Arg Gln Ala Pro Gly Lys Gly Leu
 50                  55                  60

Glu Trp Val Gly Arg Ile Lys Ser Lys Ile Asp Asp Gly Thr Thr Asn
 65                  70                  75                  80

Tyr Ala Ala Pro Val Lys Gly Arg Phe Thr Ile Ser Arg Asp Asp Ser
                85                  90                  95

Lys Asn Thr Leu Tyr Leu Gln Met Asn Gly Leu Gln Thr Glu Asp Thr
            100                 105                 110

Ala Val Tyr Tyr Cys Ser Ser Leu Phe Leu Trp Phe Gly Glu Leu Arg
        115                 120                 125

Asp Tyr Trp Gly Gln Gly Thr Leu Val Thr Val Ser Ser
    130                 135                 140

<210> SEQ ID NO 294
<211> LENGTH: 10
<212> TYPE: PRT
<213> ORGANISM: Homo sapiens

<400> SEQUENCE: 294

Gly Phe Thr Phe Asn Asn Ala Trp Leu Ser
1               5                   10

<210> SEQ ID NO 295
<211> LENGTH: 19
<212> TYPE: PRT
<213> ORGANISM: Homo sapiens

<400> SEQUENCE: 295

Arg Ile Lys Ser Lys Ile Asp Asp Gly Thr Thr Asn Tyr Ala Ala Pro
1               5                   10                  15

Val Lys Gly

<210> SEQ ID NO 296
<211> LENGTH: 11
<212> TYPE: PRT
<213> ORGANISM: Homo sapiens

<400> SEQUENCE: 296

Leu Phe Leu Trp Phe Gly Glu Leu Arg Asp Tyr
1               5                   10

<210> SEQ ID NO 297
<211> LENGTH: 389
<212> TYPE: DNA
<213> ORGANISM: Homo sapiens

<400> SEQUENCE: 297
atggcctggg ctctgctgct cctcaacctc ctcactcagg acacagggtc ctgggcccaa      60
tctgccctga ctcagcctgc tccgtgtct gggtctcctg gacagtcgat caccatctcc     120
tgcactggaa ccagcagtga tgttggtggt tctaagtatg tctcctggta ccaacagcac     180
ccaggcaaag cccccaaact catgatttat gatgtcagta gcggccctc aggggtttct     240 aatcgcttct ctggctccaa gtctggcaac acggcctccc tgacaatctc tgggctccag     300
gctgaggacg aggctgatta ttactgctgc tcatatgcag gtagtagcac ttgggtgttc     360
ggcggaggga ccaaactgac cgtcctagg                                       389

<210> SEQ ID NO 298
<211> LENGTH: 129
<212> TYPE: PRT
<213> ORGANISM: Homo sapiens

<400> SEQUENCE: 298

Met Ala Trp Ala Leu Leu Leu Leu Asn Leu Leu Thr Gln Asp Thr Gly
1               5                   10                  15

-continued

```
Ser Trp Ala Gln Ser Ala Leu Thr Gln Pro Ala Ser Val Ser Gly Ser
         20                  25                  30

Pro Gly Gln Ser Ile Thr Ile Ser Cys Thr Gly Thr Ser Ser Asp Val
         35                  40                  45

Gly Gly Ser Lys Tyr Val Ser Trp Tyr Gln Gln His Pro Gly Lys Ala
     50                  55                  60

Pro Lys Leu Met Ile Tyr Asp Val Ser Lys Arg Pro Ser Gly Val Ser
 65                  70                  75                  80

Asn Arg Phe Ser Gly Ser Lys Ser Gly Asn Thr Ala Ser Leu Thr Ile
                 85                  90                  95

Ser Gly Leu Gln Ala Glu Asp Glu Ala Asp Tyr Tyr Cys Cys Ser Tyr
            100                 105                 110

Ala Gly Ser Ser Thr Trp Val Phe Gly Gly Gly Thr Lys Leu Thr Val
        115                 120                 125

Leu
```

<210> SEQ ID NO 299
<211> LENGTH: 14
<212> TYPE: PRT
<213> ORGANISM: Homo sapiens

<400> SEQUENCE: 299

```
Thr Gly Thr Ser Ser Asp Val Gly Gly Ser Lys Tyr Val Ser
 1               5                  10
```

<210> SEQ ID NO 300
<211> LENGTH: 389
<212> TYPE: DNA
<213> ORGANISM: Homo sapiens

<400> SEQUENCE: 300

```
atggcctggg ctctgctgct cctcaacctc ctcactcagg acacagggtc ctgggcccag      60
tctgccctga ctcagcctgc tccgtgtct gggtctcctg gacagtcgat caccatctcc     120
tgcactggaa ccagcagtga tgttggtgtt tataactatg tctcctggtt ccaacagcac     180
ccaggcaaag cccccaaact catgatttat aatgtcagta gcggccctc agggtttct     240
aatcgcttct ctggctccaa gtctggcaac acggcctccc tgacaatctc tgggctccag     300
gctgaggacg aggctgatta ttactgctgc tcatatgcag gtagtagcac ttgggtgttc     360
ggcggaggga ccaacctgac cgtcctagg                                      389
```

<210> SEQ ID NO 301
<211> LENGTH: 129
<212> TYPE: PRT
<213> ORGANISM: Homo sapiens

<400> SEQUENCE: 301

```
Met Ala Trp Ala Leu Leu Leu Asn Leu Leu Thr Gln Asp Thr Gly
 1               5                  10                  15

Ser Trp Ala Gln Ser Ala Leu Thr Gln Pro Ala Ser Val Ser Gly Ser
         20                  25                  30

Pro Gly Gln Ser Ile Thr Ile Ser Cys Thr Gly Thr Ser Ser Asp Val
         35                  40                  45

Gly Val Tyr Asn Tyr Val Ser Trp Phe Gln Gln His Pro Gly Lys Ala
     50                  55                  60

Pro Lys Leu Met Ile Tyr Asn Val Ser Lys Arg Pro Ser Gly Val Ser
 65                  70                  75                  80
```

Asn Arg Phe Ser Gly Ser Lys Ser Gly Asn Thr Ala Ser Leu Thr Ile
            85                  90                  95

Ser Gly Leu Gln Ala Glu Asp Glu Ala Asp Tyr Tyr Cys Cys Ser Tyr
            100                 105                 110

Ala Gly Ser Ser Thr Trp Val Phe Gly Gly Gly Thr Asn Leu Thr Val
            115                 120                 125

Leu

<210> SEQ ID NO 302
<211> LENGTH: 389
<212> TYPE: DNA
<213> ORGANISM: Homo sapiens

<400> SEQUENCE: 302
atggcctggg ctctgctgct cctcaacctc ctcactcagg acacagggtc ctgggcccag      60
tctgccctga ctcagcctgc ctccgtgtct gggtctcctg gacagtcgat caccatctcc     120
tgcactggaa ccagcagtga tgttggtagt tacaacatgt ctcctggta ccaacagcac      180 ccaggcaaag cccccaaact catgatatat gatgtcagta agcggccctc cggatgtct      240 gatcgcttct ctggctccaa gtctggcaac acggcctccc tgacaatctc tgggctccag    300
gctgaggacg aggctgatta ttactgctgc tcatatgcag gtagtagtac ttgggtgttc    360
ggcggaggga ccaagttgac cgtcctagg                                      389

<210> SEQ ID NO 303
<211> LENGTH: 129
<212> TYPE: PRT
<213> ORGANISM: Homo sapiens

<400> SEQUENCE: 303

Met Ala Trp Ala Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
            35                  40                  45

Gly Ser Tyr Asn His Val Ser Trp Tyr Gln Gln His Pro Gly Lys Ala
        50                  55                  60

Pro Lys Leu Met Ile Tyr Asp Val Ser Lys Arg Pro Ser Gly Met Ser
65                  70                  75                  80

Asp Arg Phe Ser Gly Ser Lys Ser Gly Asn Thr Ala Ser Leu Thr Ile
            85                  90                  95

Ser Gly Leu Gln Ala Glu Asp Glu Ala Asp Tyr Tyr Cys Cys Ser Tyr
            100                 105                 110

Ala Gly Ser Ser Thr Trp Val Phe Gly Gly Gly Thr Lys Leu Thr Val
            115                 120                 125

Leu

<210> SEQ ID NO 304
<211> LENGTH: 389
<212> TYPE: DNA
<213> ORGANISM: Homo sapiens

<400> SEQUENCE: 304
atggcctggg ctctgctgct cctcaacctc ctcactcagg acacagggtc ctgggcccag      60
tctgccctga ctcagcctgc ctccgtgtct gggtctcctg gacagtcgat caccatctcc     120

```
tgcactggaa ccagcagtga tgttggtggt tataactatg tctcctggta ccaacagcac       180
ccaggcaaag cccccaaact catgatttat gatgtcagta agcggccctc aggggtttct       240
aatcgcttct ctggctccaa gtctggcaac acggcctccc tgacaatctc tgggctccag       300
gctgaggacg aggctgatta ttactgctgc tcatatgcag gtagtagcac ttgggtgttc       360
ggcggaggga ccaagctgac cgtcctagg                                         389
```

<210> SEQ ID NO 305
<211> LENGTH: 129
<212> TYPE: PRT
<213> ORGANISM: Homo sapiens
<400> SEQUENCE: 305

```
Met Ala Trp Ala Leu Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
        35                  40                  45

Gly Gly Tyr Asn Tyr Val Ser Trp Tyr Gln Gln His Pro Gly Lys Ala
    50                  55                  60

Pro Lys Leu Met Ile Tyr Asp Val Ser Lys Arg Pro Ser Gly Val Ser
65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Cys Ser Tyr
            100                 105                 110

Ala Gly Ser Ser Thr Trp Val Phe Gly Gly Gly Thr Lys Leu Thr Val
        115                 120                 125

Leu
```

<210> SEQ ID NO 306
<211> LENGTH: 389
<212> TYPE: DNA
<213> ORGANISM: Homo sapiens
<400> SEQUENCE: 306

```
atggcctggg ctctgctgct cctcaacctc ctcactcagg acacagggtc ctgggcccag       60
tctgccctga ctcagcctgc ctccgtgtct gggtctcctg gacagtcgat caccatctcc       120
tgcactggaa ccagcagtga tgttggtggt tataactatg tctcctggta ccaacagcac       180
ccaggcaaag cccccaaact catgatttat gatgtcagta agcggccctc aggggtttct       240
aatcgcttct ctgtctccaa gtctggcaac acggcctccc tgacaatctc tgggctccag       300
gctgaggacg aggctgatta ttactgctgc tcatatgcag gtaataccac ttgggtgttc       360
ggcggaggga ccaaactgac cgtcctagg                                         389
```

<210> SEQ ID NO 307
<211> LENGTH: 129
<212> TYPE: PRT
<213> ORGANISM: Homo sapiens
<400> SEQUENCE: 307

```
Met Ala Trp Ala Leu Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
```

```
            20                  25                  30
Pro Gly Gln Ser Ile Thr Ile Ser Cys Thr Gly Thr Ser Ser Asp Val
            35                  40                  45

Gly Gly Tyr Asn Tyr Val Ser Trp Tyr Gln Gln His Pro Gly Lys Ala
        50                  55                  60

Pro Lys Leu Met Ile Tyr Asp Val Ser Lys Arg Pro Ser Gly Val Ser
65                  70                  75                  80

Asn Arg Phe Ser Val Ser Lys Ser Gly Asn Thr Ala Ser Leu Thr Ile
                85                  90                  95

Ser Gly Leu Gln Ala Glu Asp Glu Ala Asp Tyr Tyr Cys Cys Ser Tyr
            100                 105                 110

Ala Gly Asn Thr Thr Trp Val Phe Gly Gly Gly Thr Lys Leu Thr Val
            115                 120                 125

Leu

<210> SEQ ID NO 308
<211> LENGTH: 10
<212> TYPE: PRT
<213> ORGANISM: Homo sapiens

<400> SEQUENCE: 308

Cys Ser Tyr Ala Gly Asn Thr Thr Trp Val
1               5                   10

<210> SEQ ID NO 309
<211> LENGTH: 389
<212> TYPE: DNA
<213> ORGANISM: Homo sapiens

<400> SEQUENCE: 309
atggcctggg ctctgctgct cctcaacctc ctcactcagg acacagggtc ctgggcccag    60
tctgccctga ctcagcctgc ctccgtgtct gggtctcctg gacagtcgat caccatctcc   120
tgcactggaa ccagcagtaa tgttggtggt tataactatg tctcctggta ccaacagcac   180
ccaggcaaag cccccaaaact catgatttat gatgtcagta agcggccctc aggggtttct   240
gatcgcttct ctggctccaa gtctggcaac acggcctccc tgacaatctc tgggctccag   300
gctgaggacg aggctgatta ttactgctgc tcatatgcag gtagtagaac ttgggtgttc   360
ggcggaggga ccaagctgac cgtcctagg                                      389

<210> SEQ ID NO 310
<211> LENGTH: 129
<212> TYPE: PRT
<213> ORGANISM: Homo sapiens

<400> SEQUENCE: 310

Met Ala Trp Ala Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Ile Ser Cys Thr Gly Thr Ser Ser Asn Val
            35                  40                  45

Gly Gly Tyr Asn Tyr Val Ser Trp Tyr Gln Gln His Pro Gly Lys Ala
        50                  55                  60

Pro Lys Leu Met Ile Tyr Asp Val Ser Lys Arg Pro Ser Gly Val Ser
65                  70                  75                  80

Asp Arg Phe Ser Gly Ser Lys Ser Gly Asn Thr Ala Ser Leu Thr Ile
```

```
                    85                  90                  95

Ser Gly Leu Gln Ala Glu Asp Glu Ala Asp Tyr Tyr Cys Cys Ser Tyr
            100                 105                 110

Ala Gly Ser Arg Thr Trp Val Phe Gly Gly Gly Thr Lys Leu Thr Val
            115                 120                 125

Leu

<210> SEQ ID NO 311
<211> LENGTH: 14
<212> TYPE: PRT
<213> ORGANISM: Homo sapiens

<400> SEQUENCE: 311

Thr Gly Thr Ser Ser Asn Val Gly Gly Tyr Asn Tyr Val Ser
1               5                   10

<210> SEQ ID NO 312
<211> LENGTH: 10
<212> TYPE: PRT
<213> ORGANISM: Homo sapiens

<400> SEQUENCE: 312

Cys Ser Tyr Ala Gly Ser Arg Thr Trp Val
1               5                   10

<210> SEQ ID NO 313
<211> LENGTH: 389
<212> TYPE: DNA
<213> ORGANISM: Homo sapiens

<400> SEQUENCE: 313
atggcctggg ctctgctgct cctcaacctc ctcactcagg acacagggtc ctgggcccag      60
tctgccctga ctcagcctgc tccgtgtct gggtctcctg gacagtcgat caccatctcc     120
tgcactggaa ccagcagtga tgttggtggt tataactatg tctcctggta ccaacagcac     180
ccaggcaaag ccccaaaact catgatttat gatgtcagta agcggccctc aggggtttct     240
aatcgcttct ctggctccaa gtctggcaac acggcctccc tgacaatctc tgggctccag     300
gctgaggacg aggctgatta ttgctgctgc tcatatgcag gtactagcac ttgggtgttc     360
ggcggaggga ccaagctgac cgtcctagg                                       389

<210> SEQ ID NO 314
<211> LENGTH: 129
<212> TYPE: PRT
<213> ORGANISM: Homo sapiens

<400> SEQUENCE: 314

Met Ala Trp Ala Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
        35                  40                  45

Gly Gly Tyr Asn Tyr Val Ser Trp Tyr Gln Gln His Pro Gly Lys Ala
    50                  55                  60

Pro Lys Leu Met Ile Tyr Asp Val Ser Lys Arg Pro Ser Gly Val Ser
65                  70                  75                  80

Asn Arg Phe Ser Gly Ser Lys Ser Gly Asn Thr Ala Ser Leu Thr Ile
                85                  90                  95
```

Ser Gly Leu Gln Ala Glu Asp Glu Ala Asp Tyr Cys Cys Cys Ser Tyr
            100                 105                 110

Ala Gly Thr Ser Thr Trp Val Phe Gly Gly Gly Thr Lys Leu Thr Val
            115                 120                 125

Leu

<210> SEQ ID NO 315
<211> LENGTH: 10
<212> TYPE: PRT
<213> ORGANISM: Homo sapiens

<400> SEQUENCE: 315

Cys Ser Tyr Ala Gly Thr Ser Thr Trp Val
1               5                   10

<210> SEQ ID NO 316
<211> LENGTH: 389
<212> TYPE: DNA
<213> ORGANISM: Homo sapiens

<400> SEQUENCE: 316
atggcctggg ctctgctgct cctcaacctc ctcactcagg acacagggtc ctgggcccag      60
tctgccctga ctcagcctgc ctccgtgtct gggtctcctg gacagtcgat caccatctcc     120
tgcactggaa ccagcagtaa tgttggtggt tataactatg tctcctggta ccaacagcac     180
ccaggcaaag cccccaaact catgatttat gatgtcagta agcggccctc aggggtttct     240
gatcgcttct ctggctccaa gtctggcaac acggcctccc tgacaatctc tgggctccag     300
gctgaggacg agactgatta ttactgctgc tcatatgcag gtagtagaac ttgggtgttc     360
ggcggaggga ccaagctgac cgtcctagg                                       389

<210> SEQ ID NO 317
<211> LENGTH: 129
<212> TYPE: PRT
<213> ORGANISM: Homo sapiens

<400> SEQUENCE: 317

Met Ala Trp Ala Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Ile Ser Cys Thr Gly Thr Ser Ser Asn Val
            35                  40                  45

Gly Gly Tyr Asn Tyr Val Ser Trp Tyr Gln Gln His Pro Gly Lys Ala
    50                  55                  60

Pro Lys Leu Met Ile Tyr Asp Val Ser Lys Arg Pro Ser Gly Val Ser
65                  70                  75                  80

Asp Arg Phe Ser Gly Ser Lys Ser Gly Asn Thr Ala Ser Leu Thr Ile
                85                  90                  95

Ser Gly Leu Gln Ala Glu Asp Glu Thr Asp Tyr Tyr Cys Cys Ser Tyr
            100                 105                 110

Ala Gly Ser Arg Thr Trp Val Phe Gly Gly Gly Thr Lys Leu Thr Val
            115                 120                 125

Leu

<210> SEQ ID NO 318
<211> LENGTH: 389

```
<212> TYPE: DNA
<213> ORGANISM: Homo sapiens

<400> SEQUENCE: 318
atggcctggg ctctgctgct cctcaacctc ctcactcagg acacagggtc ctgggcccag      60
tctgccctga ctcagcctgc ctccgtgtct gggtctcctg gacagtcgat caccttctcc     120
tgcactggaa ccagcagtga tgttggtagt tataatcatg tctcctggta ccaacagcac     180
ccaggcaaag cccccaaact catgatttat gatgtcagta agcggccctc aggggtttct     240
aatcgcttct ctggctccaa gtctggcaac acggcctccc tgacaatctc tgggctccag     300
gctgaggacg aggctgatta ttactgctgc tcatatgcag gtagtagcac ttgggtgttc     360
ggcggaggga ccaagctgac cgtcctagg                                      389

<210> SEQ ID NO 319
<211> LENGTH: 129
<212> TYPE: PRT
<213> ORGANISM: Homo sapiens

<400> SEQUENCE: 319
```

Met Ala Trp Ala Leu Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Phe Ser Cys Thr Gly Thr Ser Ser Asp Val
        35                  40                  45

Gly Ser Tyr Asn His Val Ser Trp Tyr Gln Gln His Pro Gly Lys Ala
    50                  55                  60

Pro Lys Leu Met Ile Tyr Asp Val Ser Lys Arg Pro Ser Gly Val Ser
65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Cys Ser Tyr
            100                 105                 110

Ala Gly Ser Ser Thr Trp Val Phe Gly Gly Gly Thr Lys Leu Thr Val
        115                 120                 125

Leu

```
<210> SEQ ID NO 320
<211> LENGTH: 389
<212> TYPE: DNA
<213> ORGANISM: Homo sapiens

<400> SEQUENCE: 320
atggcctggg ctctgctgct cctcaacctc ctcactcagg acacagggtc ctgggcccag      60
tctgccctga ctcagcctgc ctccgtgtct gggtctcctg gacagtcgat caccatctcc     120
tgcactggaa ccagcagtga tgttggtggt ataactatg tctcctggta ccaacagcac      180
ccaggcaaag cccccaaact catgatttat gatgtcagta agcggccctc aggggtttct     240
aatcgcttct ctggctccaa gtctggcaac acggcctccc tgacaatctc tgggctccag     300
gctgaggacg aggctgatta ttactgctgc tcatatgcag gtagtagcac ttgggtgttc     360
ggcggaggga ccaagctgac cgtcctagg                                      389

<210> SEQ ID NO 321
<211> LENGTH: 389
<212> TYPE: DNA
```

<213> ORGANISM: Homo sapiens

<400> SEQUENCE: 321

| | | |
|---|---|---|
| atggcctggg ctctgctgct cctcaacctc ctcactcagg acacagggtc ctgggcccag | 60 |
| tctgccctga ctcagcctgc ctccgtgtct gggtctcctg gacagtcgat caccatctcc | 120 |
| tgcactggaa ccagcagtga tgttggtgct tataagtatg tctcctggta ccaacagcac | 180 |
| ccaggcaaag cccccaaact catgatttat gatgtcaata cgcggccctc aggggtttct | 240 |
| actcgcttct ctgcctccaa gtctggcaac acggcctccc tgacagtctc tgggctccag | 300 |
| gctgaggacg aggctgttta ttactgctcc tcatatgcag gtagtagcac ttgggtgttc | 360 |
| ggcggaggga ccaagctgac cgtcctagg | 389 |

<210> SEQ ID NO 322
<211> LENGTH: 129
<212> TYPE: PRT
<213> ORGANISM: Homo sapiens

<400> SEQUENCE: 322

Met Ala Trp Ala Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
        35                  40                  45

Gly Ala Tyr Lys Tyr Val Ser Trp Tyr Gln Gln His Pro Gly Lys Ala
    50                  55                  60

Pro Lys Leu Met Ile Tyr Asp Val Asn Thr Arg Pro Ser Gly Val Ser
65                  70                  75                  80

Thr Arg Phe Ser Ala Ser Lys Ser Gly Asn Thr Ala Ser Leu Thr Val
                85                  90                  95

Ser Gly Leu Gln Ala Glu Asp Glu Ala Val Tyr Tyr Cys Ser Ser Tyr
            100                 105                 110

Ala Gly Ser Ser Thr Trp Val Phe Gly Gly Gly Thr Lys Leu Thr Val
        115                 120                 125

Leu

<210> SEQ ID NO 323
<211> LENGTH: 389
<212> TYPE: DNA
<213> ORGANISM: Homo sapiens

<400> SEQUENCE: 323

| | | |
|---|---|---|
| atggcctggg ctctgctgct cctcaacctc ctcactcagg acacagggtc ctgggcccag | 60 |
| tctgccctga ctcagcctgc ctccgtgtct gggtctcctg gacagtcgat caccatctcc | 120 |
| tgcactggaa ccagcagtga tgttggtggt tataaaaatg tctcctggta ccaacagcac | 180 |
| ccaggcaaag cccccaaact catgatttat gatgtcagta gcggccccc aggggtttct | 240 |
| aatcgcttct ctggctccaa gtctggcaac acggcctccc tgacagtctc tgggctccag | 300 |
| gctgaggacg aggctgatta ttactgctgc tcatatgcag gtagtagcac ttgggtgttc | 360 |
| ggcggaggga ccaaactgac cgtcctagg | 389 |

<210> SEQ ID NO 324
<211> LENGTH: 129
<212> TYPE: PRT
<213> ORGANISM: Homo sapiens

<400> SEQUENCE: 324

Met Ala Trp Ala Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
        35                  40                  45

Gly Gly Tyr Lys Asn Val Ser Trp Tyr Gln Gln His Pro Gly Lys Ala
    50                  55                  60

Pro Lys Leu Met Ile Tyr Asp Val Ser Lys Arg Pro Pro Gly Val Ser
65                  70                  75                  80

Asn Arg Phe Ser Gly Ser Lys Ser Gly Asn Thr Ala Ser Leu Thr Val
                85                  90                  95

Ser Gly Leu Gln Ala Glu Asp Glu Ala Asp Tyr Tyr Cys Cys Ser Tyr
            100                 105                 110

Ala Gly Ser Ser Thr Trp Val Phe Gly Gly Thr Lys Leu Thr Val
        115                 120                 125

Leu

<210> SEQ ID NO 325
<211> LENGTH: 14
<212> TYPE: PRT
<213> ORGANISM: Homo sapiens

<400> SEQUENCE: 325

Thr Gly Thr Ser Ser Asp Val Gly Gly Tyr Lys Asn Val Ser
1               5                   10

<210> SEQ ID NO 326
<211> LENGTH: 7
<212> TYPE: PRT
<213> ORGANISM: Homo sapiens

<400> SEQUENCE: 326

Asp Val Ser Lys Arg Pro Pro
1               5

<210> SEQ ID NO 327
<211> LENGTH: 389
<212> TYPE: DNA
<213> ORGANISM: Homo sapiens

<400> SEQUENCE: 327
atggcctggg ctctgctgct cctcaacctc ctcactcagg acacagggtc ctgggcccag      60
tctgccctga ctcagcctgc ctccgtgtct gggtctcctg gacagtcgat caccatctcc     120
tgcactggaa ccagcagtga tgttggtgct ataactatg tctcctggta ccaacagcac      180
ccaggcaaag cccccaaact catgatttct gatgtcagta agcggccctc agggggttct     240
aatcgcttct ctggctccaa gtctgacaac acggcctccc tgacagtctc tgggctccag     300
gctgaggacg aggctgttta ttactgctgc tcatatgcag gtagtagcac ttgggtgttc     360
ggcggaggga ccaagctgac cgtcctagg                                       389

<210> SEQ ID NO 328
<211> LENGTH: 129
<212> TYPE: PRT
<213> ORGANISM: Homo sapiens

<400> SEQUENCE: 328

Met Ala Trp Ala Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
        35                  40                  45

Gly Ala Tyr Asn Tyr Val Ser Trp Tyr Gln Gln His Pro Gly Lys Ala
    50                  55                  60

Pro Lys Leu Met Ile Ser Asp Val Ser Lys Arg Pro Ser Gly Val Ser
65                  70                  75                  80

Asn Arg Phe Ser Gly Ser Lys Ser Asp Asn Thr Ala Ser Leu Thr Val
                85                  90                  95

Ser Gly Leu Gln Ala Glu Asp Glu Ala Val Tyr Tyr Cys Cys Ser Tyr
            100                 105                 110

Ala Gly Ser Ser Thr Trp Val Phe Gly Gly Gly Thr Lys Leu Thr Val
        115                 120                 125

Leu

<210> SEQ ID NO 329
<211> LENGTH: 389
<212> TYPE: DNA
<213> ORGANISM: Homo sapiens

<400> SEQUENCE: 329
atggcctggg ctctgctgct cctcaacctc ctcactcagg acacagggtc ctgggcccag    60
tctgccctga ctcagcctgc ctccgtgtct gggtctcctg gacagtcgat caccatctcc   120
tgcactggaa ccagcagtga tgttggtggt tataactatg tctcctggta ccaacagcac   180
ccaggcaaag cccccaaact catgatttat gatgtcagta agtggccctc aggggtttct   240
aatcgcttct ctggctccaa gtctggcaac acggcctccc tgacaatctc tgggctccag   300
gctgaggacg aggctgatta ttactgctgc tcatatgcag gtagtagcac ttgggtgttc   360
ggcggaggga ccaggctgac cgtcctagg                                     389

<210> SEQ ID NO 330
<211> LENGTH: 129
<212> TYPE: PRT
<213> ORGANISM: Homo sapiens

<400> SEQUENCE: 330

Met Ala Trp Ala Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
        35                  40                  45

Gly Gly Tyr Asn Tyr Val Ser Trp Tyr Gln Gln His Pro Gly Lys Ala
    50                  55                  60

Pro Lys Leu Met Ile Tyr Asp Val Ser Lys Trp Pro Ser Gly Val Ser
65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Cys Ser Tyr
            100                 105                 110

```
Ala Gly Ser Ser Thr Trp Val Phe Gly Gly Gly Thr Arg Leu Thr Val
        115                 120                 125
Leu

<210> SEQ ID NO 331
<211> LENGTH: 7
<212> TYPE: PRT
<213> ORGANISM: Homo sapiens

<400> SEQUENCE: 331

Asp Val Ser Lys Trp Pro Ser
1               5

<210> SEQ ID NO 332
<211> LENGTH: 389
<212> TYPE: DNA
<213> ORGANISM: Homo sapiens

<400> SEQUENCE: 332
atggcctggg ctctgctgct cctcaacctc ctcactcagg acacagggtc ctgggcccag    60
tctgccctga ctcagcctgc ctccgtgtct gggtctcctg gacagtcgat caccatctcc   120
tgcactggaa ccagcagtga tgttggtagt tataaccatg tctcctggta ccaacaacac   180
ccaggcaaag cccccaaact catgatttat gatgtcagta agcggccctc aggggtttct   240
aatcgcttct ctggctccaa gtctggcaac acggcctccc tgacaatctc tgggctccag   300
gctgaggacg aggctgatta ttactgctgc tcatatgcag gtagtagcac ttgggtgttc   360
ggcggaggga ccaagctgac cgtcctagg                                     389

<210> SEQ ID NO 333
<211> LENGTH: 129
<212> TYPE: PRT
<213> ORGANISM: Homo sapiens

<400> SEQUENCE: 333

Met Ala Trp Ala Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
                20                  25                  30

Pro Gly Gln Ser Ile Thr Ile Ser Cys Thr Gly Thr Ser Ser Asp Val
            35                  40                  45

Gly Ser Tyr Asn His Val Ser Trp Tyr Gln Gln His Pro Gly Lys Ala
        50                  55                  60

Pro Lys Leu Met Ile Tyr Asp Val Ser Lys Arg Pro Ser Gly Val Ser
65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Cys Ser Tyr
            100                 105                 110

Ala Gly Ser Ser Thr Trp Val Phe Gly Gly Gly Thr Lys Leu Thr Val
        115                 120                 125

Leu

<210> SEQ ID NO 334
<211> LENGTH: 389
<212> TYPE: DNA
<213> ORGANISM: Homo sapiens

<400> SEQUENCE: 334
```

```
atggcctggg ctctgctgct cctcaacctc ctcactcagg acacagggtc ctgggcccag      60
tctgccctga ctcagcctgc ctccgtgtct gggtctcctg gacagtcgat caccatctcc     120
tgcactggaa ccagcagtga tgttggtggt tataactatg tctcctggta ccaacagcac     180
ccaggcaaag cccccaaact catgatttat gatgtcagta gcggccctca gggggtttct     240
aatcgcttct ctggctccaa gtctggcaac acggcctccc tgacaatctc tgggctccag     300
gctgaggacg aggctgatta ttactgctgc tcatatgcag gtagtagcac ttgggtgttc     360
ggcggaggga ccaagctgac cgtcctagg                                       389
```

<210> SEQ ID NO 335
<211> LENGTH: 389
<212> TYPE: DNA
<213> ORGANISM: Homo sapiens
<400> SEQUENCE: 335

```
atggcctggg ctctgctgct cctcaacctc ctcactcagg acacagggtc ctgggcccag      60
tctgccctga ctcagcctgc ctccgtgtct gggtctcctg gacagtcgat caccatctcc     120
tgcactggaa ccagcagtga tgttggtggt tataactatg tctcctggta ccaacagcac     180
ccaggcaaag cccccaaact catgatttat gatgtcagta gcggccctca gggggtttct     240
aatcgcttct ctggctccaa gtctggcaac acggcctccc tgacaatctc tgggctccag     300
gctgaggacg aggctgatta ttactgctgc tcatatgcag gtagtagcac ttgggtgttc     360
ggcggaggga ccaagctgac cgtcctagg                                       389
```

<210> SEQ ID NO 336
<211> LENGTH: 389
<212> TYPE: DNA
<213> ORGANISM: Homo sapiens
<400> SEQUENCE: 336

```
atggcctggg ctctgctgct cctcaacctc ctcactcagg acacagggtc ctgggcccag      60
tctgccctga ctcagcctga ctccgtgtct gggtctcctg gacagtcgat caccatctcc     120
tgcactggaa ccagcaatga tgttggtgtt tataaccatg tctcctggta ccaacagcac     180
ccaggcaaag cccccaaact catgatttat gatgtcagta gcggccctca gggggtttct     240
aatcgcttct ctggctccaa gtctggcaac acggcctccc tgacaatctc tgggctccag     300
gctgaggacg agagtgatta ttactgctgc tcatatgcag gtagtagcac ttgggtgttc     360
ggcggaggga ccaagctgac cgtcctagg                                       389
```

<210> SEQ ID NO 337
<211> LENGTH: 129
<212> TYPE: PRT
<213> ORGANISM: Homo sapiens
<400> SEQUENCE: 337

```
Met Ala Trp Ala Leu Leu Leu Asn Leu Leu Thr Gln Asp Thr Gly
1               5                   10                  15

Ser Trp Ala Gln Ser Ala Leu Thr Gln Pro Asp Ser Val Ser Gly
                20                  25                  30

Pro Gly Gln Ser Ile Thr Ile Ser Cys Thr Gly Thr Ser Asn Asp Val
                35                  40                  45

Gly Val Tyr Asn His Val Ser Trp Tyr Gln Gln His Pro Gly Lys Ala
        50                  55                  60
```

```
Pro Lys Leu Met Ile Tyr Asp Val Ser Lys Arg Pro Ser Gly Val Ser
 65                  70                  75                  80

Asn Arg Phe Ser Gly Ser Lys Ser Gly Asn Thr Ala Ser Leu Thr Ile
                 85                  90                  95

Ser Gly Leu Gln Ala Glu Asp Glu Ser Asp Tyr Tyr Cys Cys Ser Tyr
            100                 105                 110

Ala Gly Ser Ser Thr Trp Val Phe Gly Gly Gly Thr Lys Leu Thr Val
        115                 120                 125

Leu
```

<210> SEQ ID NO 338
<211> LENGTH: 389
<212> TYPE: DNA
<213> ORGANISM: Homo sapiens

<400> SEQUENCE: 338

```
atggcctggg ctctgctgct cctcaacctc ctcactcagg acacagggtc ctgggcccag    60
tctgccctga ctcaacctgc ctccgtgtct gggtctcctg gacagtcgat caccatctcc   120
tgcactggaa ccagcagtga tgttggttcc tataaccatg tctcctggta ccaacagcac   180
ccaggcaaag cccccccaact catgatttat gatgtcagta gcggccctc aggggtttct   240 gatcgcttct ctggctccaa gtctggcaac acggcctccc tgacaatctc tgggctccag   300
gctgaggacg aggctgagta ttactgctgc tcatatgtgg gtagtagctc ttgggtgctc   360
ggcggaggga ccaagctgac cgtcctagg                                     389
```

<210> SEQ ID NO 339
<211> LENGTH: 129
<212> TYPE: PRT
<213> ORGANISM: Homo sapiens

<400> SEQUENCE: 339

```
Met Ala Trp Ala Leu Leu Leu Leu Asn Leu Leu Thr Gln Asp Thr Gly
 1               5                  10                  15

Ser Trp Ala Gln Ser Ala Leu Thr Gln Pro Ala Ser Val Ser Gly Ser
                20                  25                  30

Pro Gly Gln Ser Ile Thr Ile Ser Cys Thr Gly Thr Ser Ser Asp Val
            35                  40                  45

Gly Ser Tyr Asn His Val Ser Trp Tyr Gln Gln His Pro Gly Lys Ala
        50                  55                  60

Pro Gln Leu Met Ile Tyr Asp Val Ser Lys Arg Pro Ser Gly Val Ser
 65                  70                  75                  80

Asp Arg Phe Ser Gly Ser Lys Ser Gly Asn Thr Ala Ser Leu Thr Ile
                 85                  90                  95

Ser Gly Leu Gln Ala Glu Asp Glu Ala Glu Tyr Tyr Cys Cys Ser Tyr
            100                 105                 110

Val Gly Ser Ser Trp Val Leu Gly Gly Gly Thr Lys Leu Thr Val
        115                 120                 125

Leu
```

<210> SEQ ID NO 340
<211> LENGTH: 10
<212> TYPE: PRT
<213> ORGANISM: Homo sapiens

<400> SEQUENCE: 340

```
Cys Ser Tyr Val Gly Ser Ser Ser Trp Val
 1               5                  10
```

<210> SEQ ID NO 341
<211> LENGTH: 389
<212> TYPE: DNA
<213> ORGANISM: Homo sapiens

<400> SEQUENCE: 341
atggcctggg ctctgctgct cctcaacctc ctcactcagg acacagggtc ctgggcccag      60
tctgccctga ctcagcctgc tccgtgtct gggtctcctg dacagtcgat caccatctcc     120
tgcactggaa ccagcagtga tgttggtggt tataactatg tctcctggta ccaacaacac     180
ccaggcaaag cccccaaact catgatttat gatgtcagta agcggccctc aggggtttct     240
gatcgcttct ctggctccaa gtctggcaac acggcctccc tgacaatctc tgggctccag     300
actgaggacg aggctgatta ttactgctgc tcatatgcag gtagtagcac ttgggtgttc     360
ggcggaggga ccaagctgac cgtcctagg                                       389

<210> SEQ ID NO 342
<211> LENGTH: 129
<212> TYPE: PRT
<213> ORGANISM: Homo sapiens

<400> SEQUENCE: 342

Met Ala Trp Ala Leu Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
        35                  40                  45

Gly Gly Tyr Asn Tyr Val Ser Trp Tyr Gln Gln His Pro Gly Lys Ala
    50                  55                  60

Pro Lys Leu Met Ile Tyr Asp Val Ser Lys Arg Pro Ser Gly Val Ser
65                  70                  75                  80

Asp Arg Phe Ser Gly Ser Lys Ser Gly Asn Thr Ala Ser Leu Thr Ile
                85                  90                  95

Ser Gly Leu Gln Thr Glu Asp Glu Ala Asp Tyr Tyr Cys Cys Ser Tyr
            100                 105                 110

Ala Gly Ser Ser Thr Trp Val Phe Gly Gly Thr Lys Leu Thr Val
        115                 120                 125

Leu

<210> SEQ ID NO 343
<211> LENGTH: 389
<212> TYPE: DNA
<213> ORGANISM: Homo sapiens

<400> SEQUENCE: 343
atggcctggg ctctgctgct cctcaacctc ctcactcagg acacagggtc ctgggcccag      60
tctgccctga ctcagcctgt ctccgtgtct gggtctcctg dacagtcgct caccatctcc     120
tgcactggaa ccatcagtga tgttggtggt tataactatg tctcctggta ccaacagcac     180
ccaggcaaag cccccaaact catgatttat gatgtcaatg agcggccctc aggggtttct     240
aatcgcttct ctggctccaa gtctggcaac acggcctccc tgacaatctc tgggctccag     300
gctgaggacg aggctgatta ttactgctgc tcatatgcag gtagtagcac ttgggtgttc     360
ggcggaggga ccaagctgac cgtcctagg                                       389

<210> SEQ ID NO 344
<211> LENGTH: 129
<212> TYPE: PRT
<213> ORGANISM: Homo sapiens

<400> SEQUENCE: 344

```
Met Ala Trp Ala Leu Leu Leu Asn Leu Leu Thr Gln Asp Thr Gly
1               5                   10                  15
Ser Trp Ala Gln Ser Ala Leu Thr Gln Pro Val Ser Val Ser Gly Ser
            20                  25                  30
Pro Gly Gln Ser Leu Thr Ile Ser Cys Thr Gly Thr Ile Ser Asp Val
        35                  40                  45
Gly Gly Tyr Asn Tyr Val Ser Trp Tyr Gln Gln His Pro Gly Lys Ala
    50                  55                  60
Pro Lys Leu Met Ile Tyr Asp Val Asn Glu Arg Pro Ser Gly Val Ser
65                  70                  75                  80
Asn Arg Phe Ser Gly Ser Lys Ser Gly Asn Thr Ala Ser Leu Thr Ile
                85                  90                  95
Ser Gly Leu Gln Ala Glu Asp Glu Ala Asp Tyr Tyr Cys Cys Ser Tyr
            100                 105                 110
Ala Gly Ser Ser Thr Trp Val Phe Gly Gly Gly Thr Lys Leu Thr Val
        115                 120                 125
Leu
```

<210> SEQ ID NO 345
<211> LENGTH: 14
<212> TYPE: PRT
<213> ORGANISM: Homo sapiens

<400> SEQUENCE: 345

```
Thr Gly Thr Ile Ser Asp Val Gly Gly Tyr Asn Tyr Val Ser
1               5                   10
```

<210> SEQ ID NO 346
<211> LENGTH: 7
<212> TYPE: PRT
<213> ORGANISM: Homo sapiens

<400> SEQUENCE: 346

```
Asp Val Asn Glu Arg Pro Ser
1               5
```

<210> SEQ ID NO 347
<211> LENGTH: 389
<212> TYPE: DNA
<213> ORGANISM: Homo sapiens

<400> SEQUENCE: 347

```
atggcctggg ctctgctgct cctcaacctc ctcactcagg acacagggtc ctgggcccag      60
tctgccctga ctcagcctgc tccgtgtct gggtctcctg acagtcgat caccatctcc      120
tgcactggaa ccagcagtga tgttggtggt tataactatg tctcctggta ccaacagcac      180
ccaggcaaag cccccaaatt catgatttat gatgtcagta gcggccctc aggggtttcc      240
aatcgcttct ctggctccaa gtctggcaac acggcctccc tgacaatctc tgggctccag      300
gctgaggacg aggctgatta ttactgctgc tcatatgcag gtagtagcac ttgggtgttc      360
ggcggaggga ccaagctgac cgtcctagg                                        389
```

<210> SEQ ID NO 348
<211> LENGTH: 129
<212> TYPE: PRT
<213> ORGANISM: Homo sapiens

<400> SEQUENCE: 348

Met Ala Trp Ala Leu Leu Leu Asn Leu Thr Gln Asp Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
        35                  40                  45

Gly Gly Tyr Asn Tyr Val Ser Trp Tyr Gln Gln His Pro Gly Lys Ala
    50                  55                  60

Pro Lys Phe Met Ile Tyr Asp Val Ser Lys Arg Pro Ser Gly Val Ser
65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Cys Ser Tyr
            100                 105                 110

Ala Gly Ser Ser Thr Trp Val Phe Gly Gly Gly Thr Lys Leu Thr Val
        115                 120                 125

Leu

<210> SEQ ID NO 349
<211> LENGTH: 389
<212> TYPE: DNA
<213> ORGANISM: Homo sapiens

<400> SEQUENCE: 349
atggcctggg ctctgctgct cctcaacctc ctcactcagg acacagggtc ctgggcccag     60
tctgccctga ctcagcctgc ctccgtgtct gggtctcctg gacagtcgat caccatctcc    120
tgcactggaa ccagcagtga tgttggtagt tataaccatg tctcctggta ccaacaatac    180
ccaggcaaag cccccaaact cctgatttat gatgtcagta agcggccctc aggggtttct    240
aatcgcttct ctggctccaa gtctggcaac acggcctccc tgacaatcta tgggctccag    300
gctgaggacg aggctgatta ttactgctgc tcatatgtag gtagcagcac ttgggtgttc    360
ggcggaggga ccaagctgac cgtcctagg                                      389

<210> SEQ ID NO 350
<211> LENGTH: 129
<212> TYPE: PRT
<213> ORGANISM: Homo sapiens

<400> SEQUENCE: 350

Met Ala Trp Ala Leu Leu Leu Asn Leu Thr Gln Asp Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
        35                  40                  45

Gly Ser Tyr Asn His Val Ser Trp Tyr Gln Gln Tyr Pro Gly Lys Ala
    50                  55                  60

Pro Lys Leu Leu Ile Tyr Asp Val Ser Lys Arg Pro Ser Gly Val Ser
65                  70                  75                  80

```
            Asn Arg Phe Ser Gly Ser Lys Ser Gly Asn Thr Ala Ser Leu Thr Ile
                            85                  90                  95

Tyr Gly Leu Gln Ala Glu Asp Glu Ala Asp Tyr Tyr Cys Cys Ser Tyr
                        100                 105                 110

Val Gly Ser Ser Thr Trp Val Phe Gly Gly Gly Thr Lys Leu Thr Val
                    115                 120                 125

Leu

<210> SEQ ID NO 351
            <211> LENGTH: 389
            <212> TYPE: DNA
            <213> ORGANISM: Homo sapiens

<400> SEQUENCE: 351
atggcctggg ctctgctgct cctcaacctc ctcactcagg acacagggtc ctgggcccag     60
tctgccctga ctcagcctgc ctccgtgtct gggtctcctg gacagtcgat caccatctcc    120
tgcactggaa ccagcagtga tgttggtggt tataactatg tctcctggta ccaacagcac    180
ccaggcaaag cccccaaact catgatttat gttgtcagta agcggccctc agggatttct    240
aatcgcttct ctggctccaa gtctggcaac acggcctccc tgacaatctc tgggctccag    300
gctgaggacg aggctgatta ttactgctgc tcatatgcag gtagtagcac ttgggtgttc    360
ggcggaggga ccaagctgac cgtcctagg                                     389

<210> SEQ ID NO 352
            <211> LENGTH: 129
            <212> TYPE: PRT
            <213> ORGANISM: Homo sapiens

<400> SEQUENCE: 352

Met Ala Trp Ala Leu Leu Leu Asn Leu Leu Thr Gln Asp Thr Gly
            1               5                   10                  15

Ser Trp Ala Gln Ser Ala Leu Thr Gln Pro Ala Ser Val Ser Gly Ser
                        20                  25                  30

Pro Gly Gln Ser Ile Thr Ile Ser Cys Thr Gly Thr Ser Ser Asp Val
                    35                  40                  45

Gly Gly Tyr Asn Tyr Val Ser Trp Tyr Gln Gln His Pro Gly Lys Ala
                50                  55                  60

Pro Lys Leu Met Ile Tyr Val Val Ser Lys Arg Pro Ser Gly Val Ser
            65                  70                  75                  80

Asn Arg Phe Ser Gly Ser Lys Ser Gly Asn Thr Ala Ser Leu Thr Ile
                            85                  90                  95

Ser Gly Leu Gln Ala Glu Asp Glu Ala Asp Tyr Tyr Cys Cys Ser Tyr
                        100                 105                 110

Ala Gly Ser Ser Thr Trp Val Phe Gly Gly Gly Thr Lys Leu Thr Val
                    115                 120                 125

Leu

<210> SEQ ID NO 353
            <211> LENGTH: 389
            <212> TYPE: DNA
            <213> ORGANISM: Homo sapiens

<400> SEQUENCE: 353
atggcctggg ctctgctgct cctcaacctc ctcactcagg acacagggtc ctgggcccag     60
tctgccctga ctcagcctga ctccgtgtct gggtctcctg gacagtcgat caccatctcc    120
```

```
tgcactggaa ccagcaatga tgttggtgtt tataaccatg tctcctggta ccaacagcac    180
ccaggcaaag cccccaaact catgatttat gatgtcagta agcggccctc aggggtttct    240
aatcgcttct ctggctccaa gtctggcaac acggcctccc tgacaatctc tgggctccag    300
gctgaggacg aggctgatta ttactgctgc tcatatgtag gtaatagcgc ttgggtgttc    360
ggcggaggga ccaaactgac cgtcctagg                                      389
```

<210> SEQ ID NO 354
<211> LENGTH: 129
<212> TYPE: PRT
<213> ORGANISM: Homo sapiens

<400> SEQUENCE: 354

```
Met Ala Trp Ala Leu Leu Leu Asn Leu Leu Thr Gln Asp Thr Gly
1               5                   10                  15

Ser Trp Ala Gln Ser Ala Leu Thr Gln Pro Asp Ser Val Ser Gly Ser
            20                  25                  30

Pro Gly Gln Ser Ile Thr Ile Ser Cys Thr Gly Thr Ser Asn Asp Val
        35                  40                  45

Gly Val Tyr Asn His Val Ser Trp Tyr Gln Gln His Pro Gly Lys Ala
    50                  55                  60

Pro Lys Leu Met Ile Tyr Asp Val Ser Lys Arg Pro Ser Gly Val Ser
65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Cys Ser Tyr
            100                 105                 110

Val Gly Asn Ser Ala Trp Val Phe Gly Gly Gly Thr Lys Leu Thr Val
        115                 120                 125

Leu
```

<210> SEQ ID NO 355
<211> LENGTH: 389
<212> TYPE: DNA
<213> ORGANISM: Homo sapiens

<400> SEQUENCE: 355

```
atggcctggg ctctgctgct cctcaacctc ctcactcagg acacagggtc ctggcccag     60 tctgccctga ctcagcctgc ctccgtgtct gggtctcctg gacagtcgat caccatctcc    120
tgcactggaa ccagcagtga tgttggttcc tataaccatg tctcctggta ccaacagcac    180
ccaggcaaag cccccaaact catgatttat gatgtcagta agcggccctc aggggtttct    240
gatcgcttct ctggctccaa gtctggcaac acggcctccc tgacaatctc tgggctccag    300
gctgaggacg aggctgatta ttactgctgc tcatatgtgg gtagtagcac ttgggtgttc    360
ggcggaggga ccaagctgac cgtcctagg                                      389
```

<210> SEQ ID NO 356
<211> LENGTH: 129
<212> TYPE: PRT
<213> ORGANISM: Homo sapiens

<400> SEQUENCE: 356

```
Met Ala Trp Ala Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
            20                  25                  30
```

Pro Gly Gln Ser Ile Thr Ile Ser Cys Thr Gly Thr Ser Ser Asp Val
        35                  40                  45

Gly Ser Tyr Asn His Val Ser Trp Tyr Gln Gln His Pro Gly Lys Ala
    50                  55                  60

Pro Lys Leu Met Ile Tyr Asp Val Ser Lys Arg Pro Ser Gly Val Ser
65                  70                  75                  80

Asp Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Cys Ser Tyr
            100                 105                 110

Val Gly Ser Ser Thr Trp Val Phe Gly Gly Gly Thr Lys Leu Thr Val
            115                 120                 125

Leu

<210> SEQ ID NO 357
<211> LENGTH: 389
<212> TYPE: DNA
<213> ORGANISM: Homo sapiens

<400> SEQUENCE: 357
atggcctggg ctctgctgct cctcaacctc ctcactcagg acacagggtc ctgggcccag      60
tctgccctga ctcagcctgc ctccgtgtct gggtctcctg gacagtcgat caccatctcc     120
tgcactggaa ccagcagtga tgttggttct tataaccatg tctcctggta ccaacaacac     180
ccaggcaaag cccccaaact catgatttat gatgtcagta cgcggccctc aggggtttct     240
aatcgcttct ctggctccaa gtctggcaac acggcctccc tgacaatctc tgggctccag     300
gctgaggacg aggctgatta ttactgctgc tcatatgcag gtagtagcac ttgggtgttc     360
ggcggaggga ccaaaatgac cgtcctagg                                       389

<210> SEQ ID NO 358
<211> LENGTH: 129
<212> TYPE: PRT
<213> ORGANISM: Homo sapiens

<400> SEQUENCE: 358

Met Ala Trp Ala Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
        35                  40                  45

Gly Ser Tyr Asn His Val Ser Trp Tyr Gln Gln His Pro Gly Lys Ala
    50                  55                  60

Pro Lys Leu Met Ile Tyr Asp Val Ser Thr Arg Pro Ser Gly Val Ser
65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Cys Ser Tyr
            100                 105                 110

Ala Gly Ser Ser Thr Trp Val Phe Gly Gly Gly Thr Lys Met Thr Val
            115                 120                 125

Leu

<210> SEQ ID NO 359

<210> SEQ ID NO 359
<211> LENGTH: 7
<212> TYPE: PRT
<213> ORGANISM: Homo sapiens

<400> SEQUENCE: 359

Asp Val Ser Thr Arg Pro Ser
1               5

<210> SEQ ID NO 360
<211> LENGTH: 389
<212> TYPE: DNA
<213> ORGANISM: Homo sapiens

<400> SEQUENCE: 360

```
atggcctggg ctctgctgct cctcaacctc ctcactcagg acacagggtc ctgggcccag    60
tctgccctga ctcagcctgc tccgtgtct gggtctcctg acagtcgat caccatctcc     120
tgcactggaa ccagcagtga tgttggtagt tataactatg tctcctggta ccaacagcac    180
ccaggcaaag cccccaaatt catgatttat gatgtcagta agcggccctc aggggtttct    240
gatcgcttct ctggctccaa gtctggcaac acggcctccc tgacaatctc tgggctccag    300
gctgaggacg aggctgatta ttactgctgc tcatatgcag gtagtagcac ttgggtgttc    360
ggcggaggga ccaagctgac cgtccttgg                                      389
```

<210> SEQ ID NO 361
<211> LENGTH: 129
<212> TYPE: PRT
<213> ORGANISM: Homo sapiens

<400> SEQUENCE: 361

Met Ala Trp Ala Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
        35                  40                  45

Gly Ser Tyr Asn Tyr Val Ser Trp Tyr Gln Gln His Pro Gly Lys Ala
    50                  55                  60

Pro Lys Phe Met Ile Tyr Asp Val Ser Lys Arg Pro Ser Gly Val Ser
65                  70                  75                  80

Asp Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Cys Ser Tyr
            100                 105                 110

Ala Gly Ser Ser Thr Trp Val Phe Gly Gly Gly Thr Lys Leu Thr Val
        115                 120                 125

Leu

<210> SEQ ID NO 362
<211> LENGTH: 389
<212> TYPE: DNA
<213> ORGANISM: Homo sapiens

<400> SEQUENCE: 362

```
atggcctggg ctctgctgct cctcaacctc ctcactcagg acacagggtc ctgggcccag    60
tctgtcctga ctcagcctgc tccgtgtct gggcctcctg acagtcgat caccatctcc     120
tgcactggaa ccagcagtga tgttggtaat tataaccatg tctcctggta ccaacagcac    180
```

```
ccagacaaag ccccaaaact catgatttat gatgtcaata agcggccctc agggatttct      240
aatcgcttct ctggctccaa gtctggcaac acggcctccc tgacaatctc tgggctccag      300
gctgaggacg aggctgatta ttactgctgc tcatatgcag gtagtagtac ttgggtgttc      360
ggcggaggga ccaagctgac cgtcctagg                                        389
```

<210> SEQ ID NO 363
<211> LENGTH: 129
<212> TYPE: PRT
<213> ORGANISM: Homo sapiens

<400> SEQUENCE: 363

```
Met Ala Trp Ala Leu Leu Leu Asn Leu Leu Thr Gln Asp Thr Gly
1               5                   10                  15

Ser Trp Ala Gln Ser Val Leu Thr Gln Pro Ala Ser Val Ser Gly Pro
            20                  25                  30

Pro Gly Gln Ser Ile Thr Ile Ser Cys Thr Gly Thr Ser Ser Asp Val
        35                  40                  45

Gly Asn Tyr Asn His Val Ser Trp Tyr Gln Gln His Pro Asp Lys Ala
    50                  55                  60

Pro Lys Leu Met Ile Tyr Asp Val Asn Lys Arg Pro Ser Gly Ile Ser
65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Cys Ser Tyr
            100                 105                 110

Ala Gly Ser Ser Thr Trp Val Phe Gly Gly Gly Thr Lys Leu Thr Val
        115                 120                 125

Leu
```

<210> SEQ ID NO 364
<211> LENGTH: 389
<212> TYPE: DNA
<213> ORGANISM: Homo sapiens

<400> SEQUENCE: 364

```
atggcctggg ctctgctgct cctcaacctc ctcactcagg acacagggtc ctgggcccag      60
tctgccctga ctcagcctgc ctccgtgtct gggtctcctg gacagtcgat caccatctcc      120
tgcactggaa ccagcagtga tgttggcggt tataactatg tctcctggta ccaacagcac      180
ccaggcaaag cccccaaatt catgatttat gatgtcagta agcggccctc aggggtttct      240
aatcgcttct ctggctccaa gtctggcaac acggcctccc tgacaatctc tgggctccag      300
gctgaggacg aggctgatta ttactgctgc tcatatgcag gtagtagcac ttgggtgttc      360
ggcggaggga ccaagctgac cgtcctagg                                        389
```

<210> SEQ ID NO 365
<211> LENGTH: 389
<212> TYPE: DNA
<213> ORGANISM: Homo sapiens

<400> SEQUENCE: 365

```
atggcctggg ctctgctgct cctcaacctc ctcactcagg acacagggtc ctgggcccag      60
tctgccctga ctcagcctgc ctccgtgtct gggtctcctg gacagtcgat caccatctcc      120
tgcactggaa ccagcagtga tgttggtagt tataactatg tctcctggta ccaacagcac      180
ccaggcaaag tccccaaatt catgatttct gatgtcagta agcggccctc aggaatttct      240
```

```
gatcgcttct ctggctccaa gtctggcaat acggcctccc tgacaatctc tgggctccag    300
gctgaggacg aggctgatta ttactgctgc tcatatgcag gtggtagtac ttgggtgttc    360
ggcggaggga ccaagctgac cgtccttgg                                      389
```

<210> SEQ ID NO 366
<211> LENGTH: 129
<212> TYPE: PRT
<213> ORGANISM: Homo sapiens

<400> SEQUENCE: 366

```
Met Ala Trp Ala Leu Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
        35                  40                  45

Gly Ser Tyr Asn Tyr Val Ser Trp Tyr Gln Gln His Pro Gly Lys Val
    50                  55                  60

Pro Lys Phe Met Ile Ser Asp Val Ser Lys Arg Pro Ser Gly Ile Ser
65                  70                  75                  80

Asp Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Cys Ser Tyr
            100                 105                 110

Ala Gly Gly Ser Thr Trp Val Phe Gly Gly Gly Thr Lys Leu Thr Val
        115                 120                 125

Leu
```

<210> SEQ ID NO 367
<211> LENGTH: 389
<212> TYPE: DNA
<213> ORGANISM: Homo sapiens

<400> SEQUENCE: 367

```
atggcctggg ctctgctgct cctcaacctc ctcactcagg acacaggatc ctgggcccag     60
tctgccctga ctcagcctgc ctccgtgtct gggtctcctg gacagtcgat caccatctcc    120
tgcactggaa ccagcagtga tgttggtaat tataaccatg tctcctggta ccaacagcac    180
ccagacaaag cccccaaact catgatttat gatgtcagta agcggccctc agggggtttct   240 aatcgcttct ctggctccaa gtctggcaac acggcctccc tgacaatctc tgggctccag    300
gctgaggacg aggctgatta ttactgctgc tcatatgcag gtagtagcac ttgggtgttc    360
ggcggaggga ccaagctgac cgtcctaag                                       389
```

<210> SEQ ID NO 368
<211> LENGTH: 129
<212> TYPE: PRT
<213> ORGANISM: Homo sapiens

<400> SEQUENCE: 368

```
Met Ala Trp Ala Leu Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
        35                  40                  45
```

-continued

Gly Asn Tyr Asn His Val Ser Trp Tyr Gln Gln His Pro Asp Lys Ala
            50                  55                  60

Pro Lys Leu Met Ile Tyr Asp Val Ser Lys Arg Pro Ser Gly Val Ser
 65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Cys Ser Tyr
                100                 105                 110

Ala Gly Ser Ser Thr Trp Val Phe Gly Gly Gly Thr Lys Leu Thr Val
            115                 120                 125

Leu

<210> SEQ ID NO 369
<211> LENGTH: 389
<212> TYPE: DNA
<213> ORGANISM: Homo sapiens

<400> SEQUENCE: 369
atggcctggg ctctgctgct cctcaacctc ctcactcagg acacagggtc ctgggcccag     60
tctgccctga ctcagcctga ctccgtgtct gggtctcctg gacagtcgat caccatctcc    120
tgcactggaa ccagcaatga tgttggtgtt tataaccatg tctcctggta ccaacagcac    180
ccaggcaaag cccccaaact catgatttat gatgtcagta gcggccctca ggggtttct    240 aatcgcttct ctggctccaa gtctggcaac acggcctccc tgacaatctc tgggctccag    300
gctgaggacg aggctgatta ttactgctgc tcatatgtag gtagtagcgc ttgggtgttc    360
ggcggaggga ccaatctgac cgtcctagg                                      389

<210> SEQ ID NO 370
<211> LENGTH: 129
<212> TYPE: PRT
<213> ORGANISM: Homo sapiens

<400> SEQUENCE: 370

Met Ala Trp Ala Leu Leu Leu Leu Asn Leu Leu Thr Gln Asp Thr Gly
 1               5                  10                  15

Ser Trp Ala Gln Ser Ala Leu Thr Gln Pro Asp Ser Val Ser Gly Ser
            20                  25                  30

Pro Gly Gln Ser Ile Thr Ile Ser Cys Thr Gly Thr Ser Asn Asp Val
        35                  40                  45

Gly Val Tyr Asn His Val Ser Trp Tyr Gln Gln His Pro Gly Lys Ala
    50                  55                  60

Pro Lys Leu Met Ile Tyr Asp Val Ser Lys Arg Pro Ser Gly Val Ser
 65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Cys Ser Tyr
                100                 105                 110

Val Gly Ser Ser Ala Trp Val Phe Gly Gly Gly Thr Asn Leu Thr Val
            115                 120                 125

Leu

<210> SEQ ID NO 371
<211> LENGTH: 383
<212> TYPE: DNA
<213> ORGANISM: Homo sapiens

<400> SEQUENCE: 371

```
atggcctgga cccctctctg gctcactctc ctcactctt gcataggttc tgtggtttct       60
tctgagctga ctcaggaccc tgctgtgtct gtggccttgg gacagacagt caggatcaca      120
tgccaaggag acagcctcag aagctattgt acaagttggt accagcagaa gccaggacag      180
gcccctgtac ttgtcatcta tggtgaaaac aaccggccct cagggatccc agaccgattc      240
tctggctcca gctcaggaaa cacagcttcc ttgaccatca ctggggctca ggcggaagat      300
gaggctgact attactgtaa ctcccgggac agcagtggta accatctggt gttcggcgga      360
gggaccaagc tgaccgtcct agg                                              383
```

<210> SEQ ID NO 372
<211> LENGTH: 127
<212> TYPE: PRT
<213> ORGANISM: Homo sapiens

<400> SEQUENCE: 372

```
Met Ala Trp Thr Pro Leu Trp Leu Thr Leu Leu Thr Leu Cys Ile Gly
1               5                   10                  15
Ser Val Val Ser Ser Glu Leu Thr Gln Asp Pro Ala Val Ser Val Ala
            20                  25                  30
Leu Gly Gln Thr Val Arg Ile Thr Cys Gln Gly Asp Ser Leu Arg Ser
        35                  40                  45
Tyr Cys Thr Ser Trp Tyr Gln Gln Lys Pro Gly Gln Ala Pro Val Leu
    50                  55                  60
Val Ile Tyr Gly Glu Asn Asn Arg Pro Ser Gly Ile Pro Asp Arg Phe
65                  70                  75                  80
Ser Gly Ser Ser Ser Gly Asn Thr Ala Ser Leu Thr Ile Thr Gly Ala
                85                  90                  95
Gln Ala Glu Asp Glu Ala Asp Tyr Tyr Cys Asn Ser Arg Asp Ser Ser
            100                 105                 110
Gly Asn His Leu Val Phe Gly Gly Gly Thr Lys Leu Thr Val Leu
        115                 120                 125
```

<210> SEQ ID NO 373
<211> LENGTH: 11
<212> TYPE: PRT
<213> ORGANISM: Homo sapiens

<400> SEQUENCE: 373

```
Gln Gly Asp Ser Leu Arg Ser Tyr Cys Thr Ser
1               5                   10
```

<210> SEQ ID NO 374
<211> LENGTH: 7
<212> TYPE: PRT
<213> ORGANISM: Homo sapiens

<400> SEQUENCE: 374

```
Gly Glu Asn Asn Arg Pro Ser
1               5
```

<210> SEQ ID NO 375
<211> LENGTH: 11
<212> TYPE: PRT
<213> ORGANISM: Homo sapiens

<400> SEQUENCE: 375

Asn Ser Arg Asp Ser Ser Gly Asn His Leu Val
1               5                   10

<210> SEQ ID NO 376
<211> LENGTH: 383
<212> TYPE: DNA
<213> ORGANISM: Homo sapiens

<400> SEQUENCE: 376
atggcctgga cccctctctg gctcactctc ctcactcttt gcataggttc tgtggtttct     60
tctgagctga ctcaggaccc tgctgtgtct gtggccttgg gacagacagt caggatcaca    120
tgccaaggag acagcctcag aatctattat gcaaactggt accagcagaa gccaggacag    180
gcccctgtac ttgtcatcta tggtaaaaac aaccggccct cagggatccc agaccgattc    240
tctggctcca actcaggaaa cacagcttcc ttgaccatca ctggggctca ggcggaagat    300
gaggctgact attactgtaa ctcccgggac agtagtggta accatctggt gttcggcgga    360
gggaccaaac tgaccgtcct agg                                            383

<210> SEQ ID NO 377
<211> LENGTH: 127
<212> TYPE: PRT
<213> ORGANISM: Homo sapiens

<400> SEQUENCE: 377

Met Ala Trp Thr Pro Leu Trp Leu Thr Leu Leu Thr Leu Cys Ile Gly
1               5                   10                  15

Ser Val Val Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Ile
        35                  40                  45

Tyr Tyr Ala Asn Trp Tyr Gln Gln Lys Pro Gly Gln Ala Pro Val Leu
    50                  55                  60

Val Ile Tyr Gly Lys Asn Asn Arg Pro Ser Gly Ile Pro Asp Arg Phe
65                  70                  75                  80

Ser Gly Ser Asn Ser Gly Asn Thr Ala Ser Leu Thr Ile Thr Gly Ala
                85                  90                  95

Gln Ala Glu Asp Glu Ala Asp Tyr Tyr Cys Asn Ser Arg Asp Ser Ser
            100                 105                 110

Gly Asn His Leu Val Phe Gly Gly Gly Thr Lys Leu Thr Val Leu
        115                 120                 125

<210> SEQ ID NO 378
<211> LENGTH: 11
<212> TYPE: PRT
<213> ORGANISM: Homo sapiens

<400> SEQUENCE: 378

Gln Gly Asp Ser Leu Arg Ile Tyr Tyr Ala Asn
1               5                   10

<210> SEQ ID NO 379
<211> LENGTH: 7
<212> TYPE: PRT
<213> ORGANISM: Homo sapiens

<400> SEQUENCE: 379

Gly Lys Asn Asn Arg Pro Ser
1               5

<210> SEQ ID NO 380
<211> LENGTH: 383
<212> TYPE: DNA
<213> ORGANISM: Homo sapiens

<400> SEQUENCE: 380

```
atggcctgga cccctctctg gctcactctc ctcactcttt gcataggttc tgtggtttct    60
tctgagctga ctcaggaccc tgctgtgtct gtggccttgg gacagacagt caggatcaca   120
tgccaaggag acagcctcag aagctattat gcaagctggt accagcagaa gccaggacag   180
gcccctgtat ttgtcatcta tggtaaaaac aaccggccct cagggatccc agaccgattc   240
tctggctcca gctcaggaaa cacagcttcc ttgaccatca ctggggctca ggcggaagat   300
gaggctgact attactgtaa ctcccgggac agcagtggta accatctggt gttcggcgga   360
gggaccaagc tgaccgtcct agg                                           383
```

<210> SEQ ID NO 381
<211> LENGTH: 127
<212> TYPE: PRT
<213> ORGANISM: Homo sapiens

<400> SEQUENCE: 381

Met Ala Trp Thr Pro Leu Trp Leu Thr Leu Leu Thr Leu Cys Ile Gly
1               5                   10                  15

Ser Val Val Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Ser
        35                  40                  45

Tyr Tyr Ala Ser Trp Tyr Gln Gln Lys Pro Gly Gln Ala Pro Val Phe
    50                  55                  60

Val Ile Tyr Gly Lys Asn Asn Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Asn Ser Arg Asp Ser Ser
            100                 105                 110

Gly Asn His Leu Val Phe Gly Gly Gly Thr Lys Leu Thr Val Leu
        115                 120                 125

<210> SEQ ID NO 382
<211> LENGTH: 11
<212> TYPE: PRT
<213> ORGANISM: Homo sapiens

<400> SEQUENCE: 382

Gln Gly Asp Ser Leu Arg Ser Tyr Tyr Ala Ser
1               5                   10

<210> SEQ ID NO 383
<211> LENGTH: 389
<212> TYPE: DNA
<213> ORGANISM: Homo sapiens

<400> SEQUENCE: 383

```
atggacatga gagtcctcgc tcagctcctg gggctcctgc tgctctgttt cccaggtgcc    60
agatgtgaca tccagatgac ccagtctcca tcctcactgt ctgcatctgt cggagacaga   120
gtcaccatca cttgtcgggc gagtcaggac attaggaatt atttagcctg gtttcagcag   180
```

-continued

```
aaaccaggga aagcccctaa gtccctgatc tatgctgcat ccactttgca gagtggggtc    240
ccatcaaagt tcagcggcag tggatctggg acagatttca ctctcaccat cagcagcctg    300
cagcctgaag attttgcaac ttattactgc caacagtata atcgttcccc attcactttc    360
ggccctggga ccagagtgga tatcaaacg                                      389
```

```
<210> SEQ ID NO 384
<211> LENGTH: 129
<212> TYPE: PRT
<213> ORGANISM: Homo sapiens

<400> SEQUENCE: 384
```

Met Asp Met Arg Val Leu Ala Gln Leu Leu Gly Leu Leu Leu Leu Cys
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Ile Arg Asn Tyr Leu Ala Trp Phe Gln Gln Lys Pro Gly Lys
    50                  55                  60

Ala Pro Lys Ser Leu Ile Tyr Ala Ala Ser Thr Leu Gln Ser Gly Val
65                  70                  75                  80

Pro Ser Lys Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Asn Arg Ser Pro Phe Thr Phe Gly Pro Gly Thr Arg Val Asp Ile
        115                 120                 125

Lys

```
<210> SEQ ID NO 385
<211> LENGTH: 11
<212> TYPE: PRT
<213> ORGANISM: Homo sapiens

<400> SEQUENCE: 385
```

Arg Ala Ser Gln Asp Ile Arg Asn Tyr Leu Ala
1               5                   10

```
<210> SEQ ID NO 386
<211> LENGTH: 7
<212> TYPE: PRT
<213> ORGANISM: Homo sapiens

<400> SEQUENCE: 386
```

Ala Ala Ser Thr Leu Gln Ser
1               5

```
<210> SEQ ID NO 387
<211> LENGTH: 9
<212> TYPE: PRT
<213> ORGANISM: Homo sapiens

<400> SEQUENCE: 387
```

Gln Gln Tyr Asn Arg Ser Pro Phe Thr
1               5

```
<210> SEQ ID NO 388
<211> LENGTH: 389
<212> TYPE: DNA
```

<213> ORGANISM: Homo sapiens

<400> SEQUENCE: 388

```
atggacatga gagtcctcgc tcagctcctg gggctcctgc tgctctgttt cccaggtgcc    60
agatgtgaca tccagatgac ccagtctcca tcctcactgt ctgcatctgt aggagacaga   120
gtcaccatca cgtgtcgggc gagtcaggac attagcaatt atttagcctg gattcagcag   180
aaacctggga agcccctaa gtccctgatc tatgctgcgt ccactttgca aagtggggtc    240
ccatcaaagt tcagcggcag tggatctggg acagatttca ctctcaccat cagcagcctg   300
cagcctgaag attttgcaac ttattactgt caacagtatc atacttaccc attcactttc   360
ggccctggga ccaaagtgga tatcaaacg                                     389
```

<210> SEQ ID NO 389
<211> LENGTH: 129
<212> TYPE: PRT
<213> ORGANISM: Homo sapiens

<400> SEQUENCE: 389

```
Met Asp Met Arg Val Leu Ala Gln Leu Leu Gly Leu Leu Leu Cys
1               5                   10                  15
Phe Pro Gly Ala Arg Cys Asp Ile Gln Met Thr Gln Ser Pro Ser Ser
                20                  25                  30
Leu Ser Ala Ser Val Gly Asp Arg Val Thr Ile Thr Cys Arg Ala Ser
            35                  40                  45
Gln Asp Ile Ser Asn Tyr Leu Ala Trp Ile Gln Gln Lys Pro Gly Lys
        50                  55                  60
Ala Pro Lys Ser Leu Ile Tyr Ala Ala Ser Thr Leu Gln Ser Gly Val
65                  70                  75                  80
Pro Ser Lys Phe Ser Gly Ser Gly Ser Gly Thr Asp Phe Thr Leu Thr
                85                  90                  95
Ile Ser Ser Leu Gln Pro Glu Asp Phe Ala Thr Tyr Tyr Cys Gln Gln
            100                 105                 110
Tyr His Thr Tyr Pro Phe Thr Phe Gly Pro Gly Thr Lys Val Asp Ile
        115                 120                 125
Lys
```

<210> SEQ ID NO 390
<211> LENGTH: 11
<212> TYPE: PRT
<213> ORGANISM: Homo sapiens

<400> SEQUENCE: 390

```
Arg Ala Ser Gln Asp Ile Ser Asn Tyr Leu Ala
1               5                   10
```

<210> SEQ ID NO 391
<211> LENGTH: 9
<212> TYPE: PRT
<213> ORGANISM: Homo sapiens

<400> SEQUENCE: 391

```
Gln Gln Tyr His Thr Tyr Pro Phe Thr
1               5
```

<210> SEQ ID NO 392
<211> LENGTH: 389
<212> TYPE: DNA
<213> ORGANISM: Homo sapiens

<400> SEQUENCE: 392

```
atggacatga gagtcctcgc tcagctcctg gggctcctgc tgctctgttt cccaggtgcc      60
agatgtgaca tccagatgac ccagtctcca tcctcactgt ctgcatctgt aggagacaga    120
gtcaccatca cttgtcgggc gagtcagggc attagcaatt atttagcctg gtttcagcag    180
aaaccaggga agcccctaa gtccctgatc tatgctgcat ccagtttgca aagtggggtc     240
ccatcaaaat tcagcggcag tggatctggg acagatttca ctctcaccat cagcagcctg    300
cagcctgaag attttgcaac ttattactgc caacagtata atagttaccc attcactttc    360
ggccctggga ccaaagtgga tatcaaacg                                       389
```

<210> SEQ ID NO 393
<211> LENGTH: 129
<212> TYPE: PRT
<213> ORGANISM: Homo sapiens

<400> SEQUENCE: 393

```
Met Asp Met Arg Val Leu Ala Gln Leu Leu Gly Leu Leu Leu Leu Cys
1               5                   10                  15
Phe Pro Gly Ala Arg Cys Asp Ile Gln Met Thr Gln Ser Pro Ser Ser
            20                  25                  30
Leu Ser Ala Ser Val Gly Asp Arg Val Thr Ile Thr Cys Arg Ala Ser
        35                  40                  45
Gln Gly Ile Ser Asn Tyr Leu Ala Trp Phe Gln Gln Lys Pro Gly Lys
    50                  55                  60
Ala Pro Lys Ser Leu Ile Tyr Ala Ala Ser Ser Leu Gln Ser Gly Val
65                  70                  75                  80
Pro Ser Lys Phe Ser Gly Ser Gly Ser Gly Thr Asp Phe Thr Leu Thr
                85                  90                  95
Ile Ser Ser Leu Gln Pro Glu Asp Phe Ala Thr Tyr Tyr Cys Gln Gln
            100                 105                 110
Tyr Asn Ser Tyr Pro Phe Thr Phe Gly Pro Gly Thr Lys Val Asp Ile
        115                 120                 125
Lys
```

<210> SEQ ID NO 394
<211> LENGTH: 11
<212> TYPE: PRT
<213> ORGANISM: Homo sapiens

<400> SEQUENCE: 394

```
Arg Ala Ser Gln Gly Ile Ser Asn Tyr Leu Ala
1               5                   10
```

<210> SEQ ID NO 395
<211> LENGTH: 7
<212> TYPE: PRT
<213> ORGANISM: Homo sapiens

<400> SEQUENCE: 395

```
Ala Ala Ser Ser Leu Gln Ser
1               5
```

<210> SEQ ID NO 396
<211> LENGTH: 9
<212> TYPE: PRT
<213> ORGANISM: Homo sapiens

<400> SEQUENCE: 396

Gln Gln Tyr Asn Ser Tyr Pro Phe Thr
1               5

<210> SEQ ID NO 397
<211> LENGTH: 443
<212> TYPE: DNA
<213> ORGANISM: Homo sapiens

<400> SEQUENCE: 397

```
atggactgga cctggaggat cctcttttg gtggcagcag ccacaggtgc ccactcccag    60
gtccagcttg tgcagtctgg ggctgaggtg aagaagcctg gggcctcagt gaaggtttcc   120
tgcaaggctt ctggatacac cttcacaaac tatgctatgc attgggtgcg ccaggccccc   180
ggacaaaggc ttgagtggat gggatggatc aacgctggca atggtaatac aaaatattca   240
caaaatttcc agggcagagt caccattacc agggacacat ccgcgagcac agcctacatg   300
gagctgagca gcctgagatc tgaagacacg gctgtgtatt actgtgcgag agatgaatac   360
tatgcttcgg ggagttatta tgactactac tactacggta tggacgtctg gggccaaggg   420
accacggtca ccgtcacctc agc                                           443
```

<210> SEQ ID NO 398
<211> LENGTH: 147
<212> TYPE: PRT
<213> ORGANISM: Homo sapiens

<400> SEQUENCE: 398

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Ala Met His Trp Val Arg Gln Ala Pro Gly Gln Arg Leu
    50                  55                  60

Glu Trp Met Gly Trp Ile Asn Ala Gly Asn Gly Asn Thr Lys Tyr Ser
65                  70                  75                  80

Gln Asn Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Glu Tyr Tyr Ala Ser Gly Ser Tyr Tyr Asp
        115                 120                 125

Tyr Tyr Tyr Tyr Gly Met Asp Val Trp Gly Gln Gly Thr Thr Val Thr
    130                 135                 140

Val Thr Ser
145

<210> SEQ ID NO 399
<211> LENGTH: 8
<212> TYPE: PRT
<213> ORGANISM: Homo sapiens

<400> SEQUENCE: 399

Gly Tyr Thr Phe Thr Asn Tyr Ala
1               5

<210> SEQ ID NO 400
<211> LENGTH: 8
<212> TYPE: PRT
<213> ORGANISM: Homo sapiens

<400> SEQUENCE: 400

Ile Asn Ala Gly Asn Gly Asn Thr
1               5

<210> SEQ ID NO 401
<211> LENGTH: 21
<212> TYPE: PRT
<213> ORGANISM: Homo sapiens

<400> SEQUENCE: 401

Ala Arg Asp Glu Tyr Tyr Ala Ser Gly Ser Tyr Tyr Asp Tyr Tyr Tyr
1               5                   10                  15

Tyr Gly Met Asp Val
            20

<210> SEQ ID NO 402
<211> LENGTH: 5
<212> TYPE: PRT
<213> ORGANISM: Homo sapiens

<400> SEQUENCE: 402

Asn Tyr Ala Met His
1               5

<210> SEQ ID NO 403
<211> LENGTH: 17
<212> TYPE: PRT
<213> ORGANISM: Homo sapiens

<400> SEQUENCE: 403

Trp Ile Asn Ala Gly Asn Gly Asn Thr Lys Tyr Ser Gln Asn Phe Gln
1               5                   10                  15

Gly

<210> SEQ ID NO 404
<211> LENGTH: 19
<212> TYPE: PRT
<213> ORGANISM: Homo sapiens

<400> SEQUENCE: 404

Asp Glu Tyr Tyr Ala Ser Gly Ser Tyr Tyr Asp Tyr Tyr Tyr Tyr Gly
1               5                   10                  15

Met Asp Val

<210> SEQ ID NO 405
<211> LENGTH: 389
<212> TYPE: DNA
<213> ORGANISM: Homo sapiens

<400> SEQUENCE: 405
atggcctggg ctctgctgct cctcaacctc ctcactcagg acacagggtc ctgggcccag     60
tctgccctga ctcagcctgc ctccgtgtct gggtctcctg gacagtcgat caccatctcc    120
tgcactggaa ccagcagtga tgttggtgtt tataactatg tctcctggtt ccaacagcac    180
ccaggcaaag cccccaaact catgatttat aatgtcagta gcggccctca gggggtttct    240
aatcgcttct ctggctccaa gtctggcaac acggcctccc tgacaatctc tgggctccag    300

-continued

```
gctgaggacg aggctgatta ttactgctgc tcatatgcag gtagtagcac ttgggtgttc    360
ggcggaggga ccaacctgac cgtcctagg                                      389
```

<210> SEQ ID NO 406
<211> LENGTH: 129
<212> TYPE: PRT
<213> ORGANISM: Homo sapiens

<400> SEQUENCE: 406

```
Met Ala Trp Ala Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
        35                  40                  45

Gly Val Tyr Asn Tyr Val Ser Trp Phe Gln Gln His Pro Gly Lys Ala
    50                  55                  60

Pro Lys Leu Met Ile Tyr Asn Val Ser Lys Arg Pro Ser Gly Val Ser
65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Cys Ser Tyr
            100                 105                 110

Ala Gly Ser Ser Thr Trp Val Phe Gly Gly Gly Thr Asn Leu Thr Val
            115                 120                 125

Leu
```

<210> SEQ ID NO 407
<211> LENGTH: 9
<212> TYPE: PRT
<213> ORGANISM: Homo sapiens

<400> SEQUENCE: 407

```
Ser Ser Asp Val Gly Val Tyr Asn Tyr
1               5
```

<210> SEQ ID NO 408
<211> LENGTH: 3
<212> TYPE: PRT
<213> ORGANISM: Homo sapiens

<400> SEQUENCE: 408

```
Asn Val Ser
1
```

<210> SEQ ID NO 409
<211> LENGTH: 10
<212> TYPE: PRT
<213> ORGANISM: Homo sapiens

<400> SEQUENCE: 409

```
Cys Ser Tyr Ala Gly Ser Ser Thr Trp Val
1               5                   10
```

<210> SEQ ID NO 410
<211> LENGTH: 14
<212> TYPE: PRT
<213> ORGANISM: Homo sapiens

<400> SEQUENCE: 410

```
Thr Gly Thr Ser Ser Asp Val Gly Val Tyr Asn Tyr Val Ser
1               5                   10
```

<210> SEQ ID NO 411
<211> LENGTH: 7
<212> TYPE: PRT
<213> ORGANISM: Homo sapiens

<400> SEQUENCE: 411

```
Asn Val Ser Lys Arg Pro Ser
1               5
```

<210> SEQ ID NO 412
<211> LENGTH: 10
<212> TYPE: PRT
<213> ORGANISM: Homo sapiens

<400> SEQUENCE: 412

```
Cys Ser Tyr Ala Gly Ser Ser Thr Trp Val
1               5                   10
```

<210> SEQ ID NO 413
<211> LENGTH: 404
<212> TYPE: DNA
<213> ORGANISM: Homo sapiens

<400> SEQUENCE: 413

```
atggactgga cctggaggat cctcttttg gtggcagcag ccacaggtgc ccactcccag      60
gtccagcttg tgcagtctgg ggctgaggtg aagaagcctg gggcctcagt gaaggtttcg     120
tgcaaggctt ctggatacac cttcactagc tatgctatgc attgggtgcg ccaggccccc    180
ggacaaaggc ttgagtggat gggatggatc aacgctggca atggtaacac aaaatattca    240
cagaagttcc agggcagagt caccattacc agggacacat ccgcgagcac agcctacatg    300
gagctgagca gcctgagatc tgaagacacg gctgtgtatt actgtgcgag aggggatcg     360 agggactact ggggccaggg aaccctggtc accgtctcct cagc                      404
```

<210> SEQ ID NO 414
<211> LENGTH: 134
<212> TYPE: PRT
<213> ORGANISM: Homo sapiens

<400> SEQUENCE: 414

```
Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Ser Tyr Ala Met His Trp Val Arg Gln Ala Pro Gly Gln Arg Leu
    50                  55                  60

Glu Trp Met Gly Trp Ile Asn Ala Gly Asn Gly Asn Thr Lys Tyr Ser
65                  70                  75                  80

Gln Lys Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Gly Ser Arg Asp Tyr Trp Gly Gln Gly Thr
        115                 120                 125
```

Leu Val Thr Val Ser Ser
    130

<210> SEQ ID NO 415
<211> LENGTH: 8
<212> TYPE: PRT
<213> ORGANISM: Homo sapiens

<400> SEQUENCE: 415

Gly Tyr Thr Phe Thr Ser Tyr Ala
1               5

<210> SEQ ID NO 416
<211> LENGTH: 8
<212> TYPE: PRT
<213> ORGANISM: Homo sapiens

<400> SEQUENCE: 416

Ile Asn Ala Gly Asn Gly Asn Thr
1               5

<210> SEQ ID NO 417
<211> LENGTH: 8
<212> TYPE: PRT
<213> ORGANISM: Homo sapiens

<400> SEQUENCE: 417

Ala Arg Gly Gly Ser Arg Asp Tyr
1               5

<210> SEQ ID NO 418
<211> LENGTH: 5
<212> TYPE: PRT
<213> ORGANISM: Homo sapiens

<400> SEQUENCE: 418

Ser Tyr Ala Met His
1               5

<210> SEQ ID NO 419
<211> LENGTH: 17
<212> TYPE: PRT
<213> ORGANISM: Homo sapiens

<400> SEQUENCE: 419

Trp Ile Asn Ala Gly Asn Gly Asn Thr Lys Tyr Ser Gln Lys Phe Gln
1               5                   10                  15

Gly

<210> SEQ ID NO 420
<211> LENGTH: 6
<212> TYPE: PRT
<213> ORGANISM: Homo sapiens

<400> SEQUENCE: 420

Gly Gly Ser Arg Asp Tyr
1               5

<210> SEQ ID NO 421
<211> LENGTH: 389
<212> TYPE: DNA
<213> ORGANISM: Homo sapiens

<400> SEQUENCE: 421

```
atggcctggg ctctgctgct cctcaacctc ctcactcagg acacagggtc ctgggcccag    60
tctgccctga ctcagcctgc ctccgtgtct gggtctcctg gacagtcgat caccatctcc   120
tgcactggaa ccagcagtga tgttggtggt tataactatg tctcctggta ccaacagcac   180
ccaggcaaag cccccaaact catgatttat gatgtcagta gcggccctca gggggtttct   240
aatcgcttct ctggctccaa gtctggcaac acggcctccc tgacaatctc tgggctccag   300
gctgaggacg aggctgatta ttactgctgc tcatatgcag gtagtagcac ttgggtgttc   360
ggcggaggga ccaagctgac cgtcctagg                                     389
```

<210> SEQ ID NO 422
<211> LENGTH: 129
<212> TYPE: PRT
<213> ORGANISM: Homo sapiens

<400> SEQUENCE: 422

Met Ala Trp Ala Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
        35                  40                  45

Gly Gly Tyr Asn Tyr Val Ser Trp Tyr Gln Gln His Pro Gly Lys Ala
    50                  55                  60

Pro Lys Leu Met Ile Tyr Asp Val Ser Lys Arg Pro Ser Gly Val Ser
65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Cys Ser Tyr
            100                 105                 110

Ala Gly Ser Ser Thr Trp Val Phe Gly Gly Gly Thr Lys Leu Thr Val
        115                 120                 125

Leu

<210> SEQ ID NO 423
<211> LENGTH: 9
<212> TYPE: PRT
<213> ORGANISM: Homo sapiens

<400> SEQUENCE: 423

Ser Ser Asp Val Gly Gly Tyr Asn Tyr
1               5

<210> SEQ ID NO 424
<211> LENGTH: 3
<212> TYPE: PRT
<213> ORGANISM: Homo sapiens

<400> SEQUENCE: 424

Asp Val Ser
1

<210> SEQ ID NO 425
<211> LENGTH: 10
<212> TYPE: PRT
<213> ORGANISM: Homo sapiens

<400> SEQUENCE: 425

Cys Ser Tyr Ala Gly Ser Ser Thr Trp Val

<210> SEQ ID NO 426
<211> LENGTH: 14
<212> TYPE: PRT
<213> ORGANISM: Homo sapiens

<400> SEQUENCE: 426

Thr Gly Thr Ser Ser Asp Val Gly Gly Tyr Asn Tyr Val Ser
1               5                   10

<210> SEQ ID NO 427
<211> LENGTH: 7
<212> TYPE: PRT
<213> ORGANISM: Homo sapiens

<400> SEQUENCE: 427

Asp Val Ser Lys Arg Pro Ser
1               5

<210> SEQ ID NO 428
<211> LENGTH: 10
<212> TYPE: PRT
<213> ORGANISM: Homo sapiens

<400> SEQUENCE: 428

Cys Ser Tyr Ala Gly Ser Ser Thr Trp Val
1               5                   10

<210> SEQ ID NO 429
<211> LENGTH: 443
<212> TYPE: DNA
<213> ORGANISM: Homo sapiens

<400> SEQUENCE: 429

```
atggactgga cctggaggat cctcttttg gtggcagcag ccacaggtgc ccactcccag      60
gtccaacttg tgcagtctgg ggctgaggtg aagaagcctg ggcctcagt gaaggtttcc     120
tgcaaggctt ctggatacac cttcattaga tatactttgc attgggtgtg ccaggccccc    180
ggacaaaggc ttgagtggat gggatggatc aatgttggca atggtgacac aaaatattca    240
cagaagttcc agggcagagt caccttacc agggacacat ccgcgagtac agcctacatg    300
gaggtgagca gtttgagatc tgaagacacg gctgtgtatt actgtgcgag agagggtata    360
gcagtggccg aacgggaaa gtactacaac ttctacggga tggacgtctg ggggccaaggg    420
accacggtca ccgtctcctc agc                                            443
```

<210> SEQ ID NO 430
<211> LENGTH: 147
<212> TYPE: PRT
<213> ORGANISM: Homo sapiens

<400> SEQUENCE: 430

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Ile Arg Tyr Thr Leu His Trp Val Cys Gln Ala Pro Gly Gln Arg Leu
    50                  55                  60

```
Glu Trp Met Gly Trp Ile Asn Val Gly Asn Gly Asp Thr Lys Tyr Ser
 65                  70                  75                  80

Gln Lys Phe Gln Gly Arg Val Thr Leu Thr Arg Asp Thr Ser Ala Ser
                 85                  90                  95

Thr Ala Tyr Met Glu Val Ser Ser Leu Arg Ser Glu Asp Thr Ala Val
            100                 105                 110

Tyr Tyr Cys Ala Arg Glu Gly Ile Ala Val Ala Gly Thr Gly Lys Tyr
        115                 120                 125

Tyr Asn Phe Tyr Gly Met Asp Val Trp Gly Gln Gly Thr Thr Val Thr
    130                 135                 140

Val Ser Ser
145

<210> SEQ ID NO 431
<211> LENGTH: 8
<212> TYPE: PRT
<213> ORGANISM: Homo sapiens

<400> SEQUENCE: 431

Gly Tyr Thr Phe Ile Arg Tyr Thr
1               5

<210> SEQ ID NO 432
<211> LENGTH: 8
<212> TYPE: PRT
<213> ORGANISM: Homo sapiens

<400> SEQUENCE: 432

Ile Asn Val Gly Asn Gly Asp Thr
1               5

<210> SEQ ID NO 433
<211> LENGTH: 21
<212> TYPE: PRT
<213> ORGANISM: Homo sapiens

<400> SEQUENCE: 433

Ala Arg Glu Gly Ile Ala Val Ala Gly Thr Gly Lys Tyr Tyr Asn Phe
1               5                  10                  15

Tyr Gly Met Asp Val
            20

<210> SEQ ID NO 434
<211> LENGTH: 5
<212> TYPE: PRT
<213> ORGANISM: Homo sapiens

<400> SEQUENCE: 434

Arg Tyr Thr Leu His
1               5

<210> SEQ ID NO 435
<211> LENGTH: 17
<212> TYPE: PRT
<213> ORGANISM: Homo sapiens

<400> SEQUENCE: 435

Trp Ile Asn Val Gly Asn Gly Asp Thr Lys Tyr Ser Gln Lys Phe Gln
1               5                  10                  15

Gly
```

```
<210> SEQ ID NO 436
<211> LENGTH: 19
<212> TYPE: PRT
<213> ORGANISM: Homo sapiens

<400> SEQUENCE: 436

Glu Gly Ile Ala Val Ala Gly Thr Gly Lys Tyr Tyr Asn Phe Tyr Gly
1               5                   10                  15
Met Asp Val

<210> SEQ ID NO 437
<211> LENGTH: 389
<212> TYPE: DNA
<213> ORGANISM: Homo sapiens

<400> SEQUENCE: 437
atggcctggg ctctgctgct cctcaccctc ctcactcagg gcacagggtc ctgggcccag      60
tctgccctga ctcagcctgc ctccgtgtct gggtctcctg gacagtcgat caccatctcc     120
tgcactggaa ccagcagtga cgttggtggt tttaactatg tctcctggta ccaacagcac     180
ccaggcaaag cccccacact catgatttat gaggtcactt tcggccctc aggggtttct      240 aatcgcttct ctggctccaa gtctggcaac acggcctccc tgaccatctc tgggctccag     300
gctgaggacg aggctgatta ttactgcagc tcatatataa gcggcaacac ttgggtgttc     360
ggcggaggga ccaagctgac cgtcctagg                                       389

<210> SEQ ID NO 438
<211> LENGTH: 129
<212> TYPE: PRT
<213> ORGANISM: Homo sapiens

<400> SEQUENCE: 438

Met Ala Trp Ala Leu Leu Leu Thr Leu Leu Thr Gln Gly Thr Gly
1               5                   10                  15

Ser Trp Ala Gln Ser Ala Leu Thr Gln Pro Ala Ser Val Ser Gly Ser
                20                  25                  30

Pro Gly Gln Ser Ile Thr Ile Ser Cys Thr Gly Thr Ser Ser Asp Val
            35                  40                  45

Gly Gly Phe Asn Tyr Val Ser Trp Tyr Gln Gln His Pro Gly Lys Ala
        50                  55                  60

Pro Thr Leu Met Ile Tyr Glu Val Thr Phe Arg Pro Ser Gly Val Ser
65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Ser Ser Tyr
            100                 105                 110

Ile Ser Gly Asn Thr Trp Val Phe Gly Gly Gly Thr Lys Leu Thr Val
        115                 120                 125

Leu

<210> SEQ ID NO 439
<211> LENGTH: 9
<212> TYPE: PRT
<213> ORGANISM: Homo sapiens

<400> SEQUENCE: 439

Ser Ser Asp Val Gly Gly Phe Asn Tyr
1               5
```

<210> SEQ ID NO 440
<211> LENGTH: 3
<212> TYPE: PRT
<213> ORGANISM: Homo sapiens

<400> SEQUENCE: 440

Glu Val Thr
1

<210> SEQ ID NO 441
<211> LENGTH: 10
<212> TYPE: PRT
<213> ORGANISM: Homo sapiens

<400> SEQUENCE: 441

Ser Ser Tyr Ile Ser Gly Asn Thr Trp Val
1               5                   10

<210> SEQ ID NO 442
<211> LENGTH: 14
<212> TYPE: PRT
<213> ORGANISM: Homo sapiens

<400> SEQUENCE: 442

Thr Gly Thr Ser Ser Asp Val Gly Gly Phe Asn Tyr Val Ser
1               5                   10

<210> SEQ ID NO 443
<211> LENGTH: 7
<212> TYPE: PRT
<213> ORGANISM: Homo sapiens

<400> SEQUENCE: 443

Glu Val Thr Phe Arg Pro Ser
1               5

<210> SEQ ID NO 444
<211> LENGTH: 10
<212> TYPE: PRT
<213> ORGANISM: Homo sapiens

<400> SEQUENCE: 444

Ser Ser Tyr Ile Ser Gly Asn Thr Trp Val
1               5                   10

<210> SEQ ID NO 445
<211> LENGTH: 428
<212> TYPE: DNA
<213> ORGANISM: Homo sapiens

<400> SEQUENCE: 445
atggactgga cctggaggat cctcttcttg gtggcagcag ccacaggagc ccactcccag      60
gtgcagctgg tgcagtctgg ggctgaggtg aagaagcctg ggcctcagt gaaggtctcc     120 tgcaaggctt ctggatacac cttcaccgcc tactatatac actgggtgcg acaggcccct    180
ggacaagggc ttgagtggat gggatggatc aaccctaaca gtggtggcac aaactatgca    240
cagaagtttc aggactgggt caccatgacc agggacacgt ccatcaccac agcctacatg    300
gagctgagta gactgaaatc tgacgacacg gccatatatt actgtgcgag agacggggag    360
gctggtacga actactacta cggtatggac gtctggggcc aagggaccac ggtcaccgtc    420
tcctcagc                                                             428

<210> SEQ ID NO 446
<211> LENGTH: 142
<212> TYPE: PRT
<213> ORGANISM: Homo sapiens

<400> SEQUENCE: 446

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ala Tyr Tyr Ile His Trp Val Arg Gln Ala Pro Gly Gln Gly Leu
    50                  55                  60

Glu Trp Met Gly Trp Ile Asn Pro Asn Ser Gly Gly Thr Asn Tyr Ala
65                  70                  75                  80

Gln Lys Phe Gln Asp Trp Val Thr Met Thr Arg Asp Thr Ser Ile Thr
                85                  90                  95

Thr Ala Tyr Met Glu Leu Ser Arg Leu Lys Ser Asp Asp Thr Ala Ile
            100                 105                 110

Tyr Tyr Cys Ala Arg Asp Gly Glu Ala Gly Thr Asn Tyr Tyr Tyr Gly
        115                 120                 125

Met Asp Val Trp Gly Gln Gly Thr Thr Val Thr Val Ser Ser
    130                 135                 140

<210> SEQ ID NO 447
<211> LENGTH: 8
<212> TYPE: PRT
<213> ORGANISM: Homo sapiens

<400> SEQUENCE: 447

Gly Tyr Thr Phe Thr Ala Tyr Tyr
1               5

<210> SEQ ID NO 448
<211> LENGTH: 8
<212> TYPE: PRT
<213> ORGANISM: Homo sapiens

<400> SEQUENCE: 448

Ile Asn Pro Asn Ser Gly Gly Thr
1               5

<210> SEQ ID NO 449
<211> LENGTH: 16
<212> TYPE: PRT
<213> ORGANISM: Homo sapiens

<400> SEQUENCE: 449

Ala Arg Asp Gly Glu Ala Gly Thr Asn Tyr Tyr Tyr Gly Met Asp Val
1               5                   10                  15

<210> SEQ ID NO 450
<211> LENGTH: 5
<212> TYPE: PRT
<213> ORGANISM: Homo sapiens

<400> SEQUENCE: 450

Ala Tyr Tyr Ile His
1               5

<210> SEQ ID NO 451
<211> LENGTH: 17
<212> TYPE: PRT
<213> ORGANISM: Homo sapiens

<400> SEQUENCE: 451

Trp Ile Asn Pro Asn Ser Gly Gly Thr Asn Tyr Ala Gln Lys Phe Gln
1               5                   10                  15

Asp

<210> SEQ ID NO 452
<211> LENGTH: 14
<212> TYPE: PRT
<213> ORGANISM: Homo sapiens

<400> SEQUENCE: 452

Asp Gly Glu Ala Gly Thr Asn Tyr Tyr Tyr Gly Met Asp Val
1               5                   10

<210> SEQ ID NO 453
<211> LENGTH: 401
<212> TYPE: DNA
<213> ORGANISM: Homo sapiens

<400> SEQUENCE: 453
atggtgttgc agacccaggt cttcatttct ctgttgctct ggatctctgg tgcctacggg      60
gacatcgtga tgacccagtc tccagactcc ctggctgtgt ctctgggcga gagggccacc     120
atcaactgca gtccagtca gagtgtttta tacagctcca acaataagaa ctacttggct      180
tggtaccagc agaaaccagg acagcctcct aagctgctca tttactgggc atctacccgg     240
gaatccgggg tccctgaccg attcagtggc agcgggtctg ggacagattt cgctctcacc     300
atcagcagcc tgcaggctga agatgtggca gtttattact gtcagcaata ttatagtact     360
ccgtggacgt tcggccaagg gaccaaggtg gaaatcaaac g                         401

<210> SEQ ID NO 454
<211> LENGTH: 133
<212> TYPE: PRT
<213> ORGANISM: Homo sapiens

<400> SEQUENCE: 454

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
                20                  25                  30

Val Ser Leu Gly Glu Arg Ala Thr Ile Asn Cys Lys Ser Ser Gln Ser
            35                  40                  45

Val Leu Tyr Ser Ser Asn Asn Lys Asn Tyr Leu Ala Trp Tyr Gln Gln
        50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Ala Leu Thr Ile Ser Ser Leu Gln Ala Glu Asp Val Ala Val Tyr
            100                 105                 110

Tyr Cys Gln Gln Tyr Tyr Ser Thr Pro Trp Thr Phe Gly Gln Gly Thr
        115                 120                 125

Lys Val Glu Ile Lys

<210> SEQ ID NO 455
<211> LENGTH: 12
<212> TYPE: PRT
<213> ORGANISM: Homo sapiens

<400> SEQUENCE: 455

Gln Ser Val Leu Tyr Ser Ser Asn Asn Lys Asn Tyr
1               5                   10

<210> SEQ ID NO 456
<211> LENGTH: 3
<212> TYPE: PRT
<213> ORGANISM: Homo sapiens

<400> SEQUENCE: 456

Trp Ala Ser
1

<210> SEQ ID NO 457
<211> LENGTH: 9
<212> TYPE: PRT
<213> ORGANISM: Homo sapiens

<400> SEQUENCE: 457

Gln Gln Tyr Tyr Ser Thr Pro Trp Thr
1               5

<210> SEQ ID NO 458
<211> LENGTH: 17
<212> TYPE: PRT
<213> ORGANISM: Homo sapiens

<400> SEQUENCE: 458

Lys Ser Ser Gln Ser Val Leu Tyr Ser Ser Asn Asn Lys Asn Tyr Leu
1               5                   10                  15

Ala

<210> SEQ ID NO 459
<211> LENGTH: 7
<212> TYPE: PRT
<213> ORGANISM: Homo sapiens

<400> SEQUENCE: 459

Trp Ala Ser Thr Arg Glu Ser
1               5

<210> SEQ ID NO 460
<211> LENGTH: 9
<212> TYPE: PRT
<213> ORGANISM: Homo sapiens

<400> SEQUENCE: 460

Gln Gln Tyr Tyr Ser Thr Pro Trp Thr
1               5

<210> SEQ ID NO 461
<211> LENGTH: 437
<212> TYPE: DNA
<213> ORGANISM: Homo sapiens

<400> SEQUENCE: 461
atggactgga cctggaggat cctcttttg gtggcagcag ccgcaggtgc ccactcccag    60

```
gtccagcttg tgcagtctgg ggctgaggtg aagaagcctg gggcctcagt gaaggtttcc    120
tgcaaggctt ctggattcac cttcactgac tatgctatgc attgggtgcg ccaggccccc    180
ggacaaaggc ttgagtggat gggttggatc aacgctggca atggttacac aaaatattca    240
cagaagttcc aggtcagact caccattacc agggacacat cgcgagcac agtctacatg    300 gagctgagca gcctgagatc tgaagacacg gctgtgtatt actgtgcgag agatgggttt    360
tgtcctagta ccacttgctc tggttactac ggtatggacg tctggggcca agggaccacg    420
gtcaccgtct cctcagc                                                   437
```

<210> SEQ ID NO 462
<211> LENGTH: 145
<212> TYPE: PRT
<213> ORGANISM: Homo sapiens

<400> SEQUENCE: 462

Met Asp Trp Thr Trp Arg Ile Leu Phe Leu Val Ala Ala Ala Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Phe Thr Phe
            35                  40                  45

Thr Asp Tyr Ala Met His Trp Val Arg Gln Ala Pro Gly Gln Arg Leu
        50                  55                  60

Glu Trp Met Gly Trp Ile Asn Ala Gly Asn Gly Tyr Thr Lys Tyr Ser
65                  70                  75                  80

Gln Lys Phe Gln Val Arg Leu Thr Ile Thr Arg Asp Thr Phe Ala Ser
                85                  90                  95

Thr Val Tyr Met Glu Leu Ser Ser Leu Arg Ser Glu Asp Thr Ala Val
            100                 105                 110

Tyr Tyr Cys Ala Arg Asp Gly Phe Cys Pro Ser Thr Thr Cys Ser Gly
        115                 120                 125

Tyr Tyr Gly Met Asp Val Trp Gly Gln Gly Thr Thr Val Thr Val Ser
    130                 135                 140

Ser
145

<210> SEQ ID NO 463
<211> LENGTH: 8
<212> TYPE: PRT
<213> ORGANISM: Homo sapiens

<400> SEQUENCE: 463

Gly Phe Thr Phe Thr Asp Tyr Ala
1               5

<210> SEQ ID NO 464
<211> LENGTH: 8
<212> TYPE: PRT
<213> ORGANISM: Homo sapiens

<400> SEQUENCE: 464

Ile Asn Ala Gly Asn Gly Tyr Thr
1               5

<210> SEQ ID NO 465
<211> LENGTH: 19
<212> TYPE: PRT

<213> ORGANISM: Homo sapiens

<400> SEQUENCE: 465

Ala Arg Asp Gly Phe Cys Pro Ser Thr Thr Cys Ser Gly Tyr Tyr Gly
1               5                   10                  15

Met Asp Val

<210> SEQ ID NO 466
<211> LENGTH: 5
<212> TYPE: PRT
<213> ORGANISM: Homo sapiens

<400> SEQUENCE: 466

Asp Tyr Ala Met His
1               5

<210> SEQ ID NO 467
<211> LENGTH: 17
<212> TYPE: PRT
<213> ORGANISM: Homo sapiens

<400> SEQUENCE: 467

Trp Ile Asn Ala Gly Asn Gly Tyr Thr Lys Tyr Ser Gln Lys Phe Gln
1               5                   10                  15

Val

<210> SEQ ID NO 468
<211> LENGTH: 17
<212> TYPE: PRT
<213> ORGANISM: Homo sapiens

<400> SEQUENCE: 468

Asp Gly Phe Cys Pro Ser Thr Thr Cys Ser Gly Tyr Tyr Gly Met Asp
1               5                   10                  15

Val

<210> SEQ ID NO 469
<211> LENGTH: 389
<212> TYPE: DNA
<213> ORGANISM: Homo sapiens

<400> SEQUENCE: 469
atggcctggg ctctgctgct cctcaacctc ctcactcagg acacagggtc ctgggcccag    60
tctgccctga ctcagcctgc ctccgtgtct gggtctcctg gacagtcgat caccatctcc   120
tgcactggaa ccagcagtga tgttggtgct tataactatg tctcctggta ccaacagcac   180
ccaggcaaag cccccaaact catgatttat gatgtcaata cgcggccctc agggggtttct   240 actcgcttct ctgcctccaa gtctggcaac acggcctccc tgacagtctc tgggctccag   300
gctgaggacg aggctgttta ttactgctcc tcatatgcag gtagtagcac ttggattttc   360
ggcggaggga ccaagctgac cgtcctagg                                     389

<210> SEQ ID NO 470
<211> LENGTH: 129
<212> TYPE: PRT
<213> ORGANISM: Homo sapiens

<400> SEQUENCE: 470

Met Ala Trp Ala Leu Leu Leu Leu Asn Leu Leu Thr Gln Asp Thr Gly
1               5                   10                  15

```
Ser Trp Ala Gln Ser Ala Leu Thr Gln Pro Ala Ser Val Ser Gly Ser
         20                  25                  30

Pro Gly Gln Ser Ile Thr Ile Ser Cys Thr Gly Thr Ser Ser Asp Val
     35                  40                  45

Gly Ala Tyr Asn Tyr Val Ser Trp Tyr Gln Gln His Pro Gly Lys Ala
 50                  55                  60

Pro Lys Leu Met Ile Tyr Asp Val Asn Thr Arg Pro Ser Gly Val Ser
 65                  70                  75                  80

Thr Arg Phe Ser Ala Ser Lys Ser Gly Asn Thr Ala Ser Leu Thr Val
                 85                  90                  95

Ser Gly Leu Gln Ala Glu Asp Glu Ala Val Tyr Tyr Cys Ser Ser Tyr
            100                 105                 110

Ala Gly Ser Ser Thr Trp Ile Phe Gly Gly Gly Thr Lys Leu Thr Val
        115                 120                 125

Leu

<210> SEQ ID NO 471
<211> LENGTH: 9
<212> TYPE: PRT
<213> ORGANISM: Homo sapiens

<400> SEQUENCE: 471

Ser Ser Asp Val Gly Ala Tyr Asn Tyr
1               5

<210> SEQ ID NO 472
<211> LENGTH: 3
<212> TYPE: PRT
<213> ORGANISM: Homo sapiens

<400> SEQUENCE: 472

Asp Val Asn
1

<210> SEQ ID NO 473
<211> LENGTH: 10
<212> TYPE: PRT
<213> ORGANISM: Homo sapiens

<400> SEQUENCE: 473

Ser Ser Tyr Ala Gly Ser Ser Thr Trp Ile
1               5                   10

<210> SEQ ID NO 474
<211> LENGTH: 14
<212> TYPE: PRT
<213> ORGANISM: Homo sapiens

<400> SEQUENCE: 474

Thr Gly Thr Ser Ser Asp Val Gly Ala Tyr Asn Tyr Val Ser
1               5                   10

<210> SEQ ID NO 475
<211> LENGTH: 7
<212> TYPE: PRT
<213> ORGANISM: Homo sapiens

<400> SEQUENCE: 475

Asp Val Asn Thr Arg Pro Ser
1               5
```

-continued

<210> SEQ ID NO 476
<211> LENGTH: 10
<212> TYPE: PRT
<213> ORGANISM: Homo sapiens

<400> SEQUENCE: 476

Ser Ser Tyr Ala Gly Ser Ser Thr Trp Ile
1               5                   10

<210> SEQ ID NO 477
<211> LENGTH: 437
<212> TYPE: DNA
<213> ORGANISM: Homo sapiens

<400> SEQUENCE: 477

```
atggactgga cctggaggat cctcttttg gtggcagcag ccgcaggtgc ccactcccag      60
gtccagcttg tgcagtctgg ggctgaggtg aagaagcctg gggcctcagt gaaggtttcc    120
tgcaaggctt ctggattcac cttcactgac tatgctatgc attgggtgcg ccaggccccc    180
ggacaaaggc ttgagtggat ggggttggatc aacgctggca atggttacac aaaatattca   240
cagcagttcc aggtcagact caccattacc agggacacat tcgcgagcac agtctacatg   300
gagctgagca gcctgacatc tgaagacacg gctgtgtatt actgtgcgag agatgggttt   360
tgtcctagta ccacttgctc tggttactac ggtatggacg tctggggcca agggaccacg   420
gtcaccgtct cctcagc                                                  437
```

<210> SEQ ID NO 478
<211> LENGTH: 145
<212> TYPE: PRT
<213> ORGANISM: Homo sapiens

<400> SEQUENCE: 478

Met Asp Trp Thr Trp Arg Ile Leu Phe Leu Val Ala Ala Ala Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Thr Asp Tyr Ala Met His Trp Val Arg Gln Ala Pro Gly Gln Arg Leu
    50                  55                  60

Glu Trp Met Gly Trp Ile Asn Ala Gly Asn Gly Tyr Thr Lys Tyr Ser
65                  70                  75                  80

Gln Gln Phe Gln Val Arg Leu Thr Ile Thr Arg Asp Thr Phe Ala Ser
                85                  90                  95

Thr Val Tyr Met Glu Leu Ser Ser Leu Thr Ser Glu Asp Thr Ala Val
            100                 105                 110

Tyr Tyr Cys Ala Arg Asp Gly Phe Cys Pro Ser Thr Thr Cys Ser Gly
        115                 120                 125

Tyr Tyr Gly Met Asp Val Trp Gly Gln Gly Thr Thr Val Thr Val Ser
    130                 135                 140

Ser
145

<210> SEQ ID NO 479
<211> LENGTH: 8
<212> TYPE: PRT
<213> ORGANISM: Homo sapiens

<400> SEQUENCE: 479

```
Gly Phe Thr Phe Thr Asp Tyr Ala
1               5

<210> SEQ ID NO 480
<211> LENGTH: 8
<212> TYPE: PRT
<213> ORGANISM: Homo sapiens

<400> SEQUENCE: 480

Ile Asn Ala Gly Asn Gly Tyr Thr
1               5

<210> SEQ ID NO 481
<211> LENGTH: 19
<212> TYPE: PRT
<213> ORGANISM: Homo sapiens

<400> SEQUENCE: 481

Ala Arg Asp Gly Phe Cys Pro Ser Thr Thr Cys Ser Gly Tyr Tyr Gly
1               5                   10                  15

Met Asp Val

<210> SEQ ID NO 482
<211> LENGTH: 5
<212> TYPE: PRT
<213> ORGANISM: Homo sapiens

<400> SEQUENCE: 482

Asp Tyr Ala Met His
1               5

<210> SEQ ID NO 483
<211> LENGTH: 17
<212> TYPE: PRT
<213> ORGANISM: Homo sapiens

<400> SEQUENCE: 483

Trp Ile Asn Ala Gly Asn Gly Tyr Thr Lys Tyr Ser Gln Gln Phe Gln
1               5                   10                  15

Val

<210> SEQ ID NO 484
<211> LENGTH: 17
<212> TYPE: PRT
<213> ORGANISM: Homo sapiens

<400> SEQUENCE: 484

Asp Gly Phe Cys Pro Ser Thr Thr Cys Ser Gly Tyr Tyr Gly Met Asp
1               5                   10                  15

Val

<210> SEQ ID NO 485
<211> LENGTH: 389
<212> TYPE: DNA
<213> ORGANISM: Homo sapiens

<400> SEQUENCE: 485
atggcctggg ctctgctgct cctcaacctc ctcactcagg acacagggtc ctgggcccag    60
tctgccctga ctcagcctgc ctccgtgtct gggtctcctg gacagtcgat caccatctcc   120
tgcactggaa ccagcagtga tgttggtgct tataactatg tctcctggta ccaacagcac   180
```

```
ccaggcaaag ccccaaaact catgatttat gatgtcaata cgcggccctc agggggtttct    240 actcgcttct ctgcctccaa gtctggcaac acggcctccc tgacagtctc tgggctccag    300
gctgaggacg aggctgttta ttactgctcc tcatatgcag gtagtagcac ttggattttc    360
ggcggaggga ccaagctgac cgtcctagg                                      389
```

<210> SEQ ID NO 486
<211> LENGTH: 129
<212> TYPE: PRT
<213> ORGANISM: Homo sapiens

<400> SEQUENCE: 486

```
Met Ala Trp Ala Leu Leu Leu Asn Leu Leu Thr Gln Asp Thr Gly
1               5                   10                  15

Ser Trp Ala Gln Ser Ala Leu Thr Gln Pro Ala Ser Val Ser Gly
            20                  25                  30

Ser Pro Gly Gln Ser Ile Thr Ile Ser Cys Thr Gly Thr Ser Ser Asp Val
        35                  40                  45

Gly Ala Tyr Asn Tyr Val Ser Trp Tyr Gln Gln His Pro Gly Lys Ala
    50                  55                  60

Pro Lys Leu Met Ile Tyr Asp Val Asn Thr Arg Pro Ser Gly Val Ser
65                  70                  75                  80

Thr Arg Phe Ser Ala Ser Lys Ser Gly Asn Thr Ala Ser Leu Thr Val
                85                  90                  95

Ser Gly Leu Gln Ala Glu Asp Glu Ala Val Tyr Tyr Cys Ser Ser Tyr
            100                 105                 110

Ala Gly Ser Ser Thr Trp Ile Phe Gly Gly Gly Thr Lys Leu Thr Val
            115                 120                 125

Leu
```

<210> SEQ ID NO 487
<211> LENGTH: 9
<212> TYPE: PRT
<213> ORGANISM: Homo sapiens

<400> SEQUENCE: 487

```
Ser Ser Asp Val Gly Ala Tyr Asn Tyr
1               5
```

<210> SEQ ID NO 488
<211> LENGTH: 3
<212> TYPE: PRT
<213> ORGANISM: Homo sapiens

<400> SEQUENCE: 488

```
Asp Val Asn
1
```

<210> SEQ ID NO 489
<211> LENGTH: 10
<212> TYPE: PRT
<213> ORGANISM: Homo sapiens

<400> SEQUENCE: 489

```
Ser Ser Tyr Ala Gly Ser Ser Thr Trp Ile
1               5                   10
```

<210> SEQ ID NO 490
<211> LENGTH: 14
<212> TYPE: PRT

<213> ORGANISM: Homo sapiens

<400> SEQUENCE: 490

Thr Gly Thr Ser Ser Asp Val Gly Ala Tyr Asn Tyr Val Ser
1               5                   10

<210> SEQ ID NO 491
<211> LENGTH: 7
<212> TYPE: PRT
<213> ORGANISM: Homo sapiens

<400> SEQUENCE: 491

Asp Val Asn Thr Arg Pro Ser
1               5

<210> SEQ ID NO 492
<211> LENGTH: 10
<212> TYPE: PRT
<213> ORGANISM: Homo sapiens

<400> SEQUENCE: 492

Ser Ser Tyr Ala Gly Ser Ser Thr Trp Ile
1               5                   10

<210> SEQ ID NO 493
<211> LENGTH: 437
<212> TYPE: DNA
<213> ORGANISM: Homo sapiens

<400> SEQUENCE: 493
atggactgga cctggaggat cctctttttg gtggcagcag ccacaggtgc ccactcccag     60
gtccagcttg tgcagtctgg ggctgaggtg aagaagcctg gggcctcagt gaaggtttcc    120
tgtaaggctt ctggatacat ctttattaac tatgctatgc aatgggtgcg ccaggccccc    180
ggacaaaggc ttgagtggat gggatggatc aacgctggca acggttacac aaaatattca    240
cagaagttcc agggcagagt caccatcacc aggacatat ccgcgagcac agtctacatg     300
gagctgagca gcctgagatc tgaagacacg gctgtgtatt actgtgcgag agatggattt    360
tgtaggacaa ccagctgctc cgaccactac ggtatggacg tctggggcca agggaccacg    420
gtcaccgtct cctcagc                                                   437

<210> SEQ ID NO 494
<211> LENGTH: 145
<212> TYPE: PRT
<213> ORGANISM: Homo sapiens

<400> SEQUENCE: 494

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Ile Phe
            35                  40                  45

Ile Asn Tyr Ala Met Gln Trp Val Arg Gln Ala Pro Gly Gln Arg Leu
        50                  55                  60

Glu Trp Met Gly Trp Ile Asn Ala Gly Asn Gly Tyr Thr Lys Tyr Ser
65                  70                  75                  80

Gln Lys Phe Gln Gly Arg Val Thr Ile Thr Arg Asp Ile Ser Ala Ser
                85                  90                  95

Thr Val Tyr Met Glu Leu Ser Ser Leu Arg Ser Glu Asp Thr Ala Val
            100                 105                 110

Tyr Tyr Cys Ala Arg Asp Gly Phe Cys Arg Thr Thr Ser Cys Ser Asp
        115                 120                 125

His Tyr Gly Met Asp Val Trp Gly Gln Gly Thr Thr Val Thr Val Ser
    130                 135                 140

Ser
145

<210> SEQ ID NO 495
<211> LENGTH: 8
<212> TYPE: PRT
<213> ORGANISM: Homo sapiens

<400> SEQUENCE: 495

Gly Tyr Ile Phe Ile Asn Tyr Ala
1               5

<210> SEQ ID NO 496
<211> LENGTH: 8
<212> TYPE: PRT
<213> ORGANISM: Homo sapiens

<400> SEQUENCE: 496

Ile Asn Ala Gly Asn Gly Tyr Thr
1               5

<210> SEQ ID NO 497
<211> LENGTH: 19
<212> TYPE: PRT
<213> ORGANISM: Homo sapiens

<400> SEQUENCE: 497

Ala Arg Asp Gly Phe Cys Arg Thr Thr Ser Cys Ser Asp His Tyr Gly
1               5                   10                  15

Met Asp Val

<210> SEQ ID NO 498
<211> LENGTH: 5
<212> TYPE: PRT
<213> ORGANISM: Homo sapiens

<400> SEQUENCE: 498

Asn Tyr Ala Met Gln
1               5

<210> SEQ ID NO 499
<211> LENGTH: 17
<212> TYPE: PRT
<213> ORGANISM: Homo sapiens

<400> SEQUENCE: 499

Trp Ile Asn Ala Gly Asn Gly Tyr Thr Lys Tyr Ser Gln Lys Phe Gln
1               5                   10                  15

Gly

<210> SEQ ID NO 500
<211> LENGTH: 17
<212> TYPE: PRT
<213> ORGANISM: Homo sapiens

<400> SEQUENCE: 500

Asp Gly Phe Cys Arg Thr Thr Ser Cys Ser Asp His Tyr Gly Met Asp
1               5                   10                  15

Val

<210> SEQ ID NO 501
<211> LENGTH: 389
<212> TYPE: DNA
<213> ORGANISM: Homo sapiens

<400> SEQUENCE: 501
atggcctggg ctctgctgct cctcaacctc ctcactcagg acacagggtc ctgggcccag      60
tctgccctga ctcagcctgc tccgtgtct gggtctcctg acagtcgat caccatctcc      120 tgcactggaa ccagcagtga tgttggtggt tataactatg tctcctggta ccaacaacac      180
ccaggcaaag cccccaaact catgatttat gatgtcagta gcggccctc aggggtttct      240 gatcgcttct ctggctccaa gtctggcaac acggcctccc tgacaatctc tgggctccag      300
actgaggacg aggctgattt ttactgctgc tcatatgcag gtagtagcac ttgggtgttc      360
ggcggaggga ccaagctgac cgtcctagg                                        389

<210> SEQ ID NO 502
<211> LENGTH: 129
<212> TYPE: PRT
<213> ORGANISM: Homo sapiens

<400> SEQUENCE: 502

Met Ala Trp Ala Leu Leu Leu Asn Leu Leu Thr Gln Asp Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
        35                  40                  45

Gly Gly Tyr Asn Tyr Val Ser Trp Tyr Gln Gln His Pro Gly Lys Ala
    50                  55                  60

Pro Lys Leu Met Ile Tyr Asp Val Ser Lys Arg Pro Ser Gly Val Ser
65                  70                  75                  80

Asp Arg Phe Ser Gly Ser Lys Ser Gly Asn Thr Ala Ser Leu Thr Ile
                85                  90                  95

Ser Gly Leu Gln Thr Glu Asp Glu Ala Asp Phe Tyr Cys Cys Ser Tyr
            100                 105                 110

Ala Gly Ser Ser Thr Trp Val Phe Gly Gly Gly Thr Lys Leu Thr Val
        115                 120                 125

Leu

<210> SEQ ID NO 503
<211> LENGTH: 9
<212> TYPE: PRT
<213> ORGANISM: Homo sapiens

<400> SEQUENCE: 503

Ser Ser Asp Val Gly Gly Tyr Asn Tyr
1               5

<210> SEQ ID NO 504
<211> LENGTH: 3
<212> TYPE: PRT
<213> ORGANISM: Homo sapiens

<400> SEQUENCE: 504

Asp Val Ser
1

<210> SEQ ID NO 505
<211> LENGTH: 10
<212> TYPE: PRT
<213> ORGANISM: Homo sapiens

<400> SEQUENCE: 505

Cys Ser Tyr Ala Gly Ser Ser Thr Trp Val
1               5                   10

<210> SEQ ID NO 506
<211> LENGTH: 14
<212> TYPE: PRT
<213> ORGANISM: Homo sapiens

<400> SEQUENCE: 506

Thr Gly Thr Ser Ser Asp Val Gly Gly Tyr Asn Tyr Val Ser
1               5                   10

<210> SEQ ID NO 507
<211> LENGTH: 7
<212> TYPE: PRT
<213> ORGANISM: Homo sapiens

<400> SEQUENCE: 507

Asp Val Ser Lys Arg Pro Ser
1               5

<210> SEQ ID NO 508
<211> LENGTH: 10
<212> TYPE: PRT
<213> ORGANISM: Homo sapiens

<400> SEQUENCE: 508

Cys Ser Tyr Ala Gly Ser Ser Thr Trp Val
1               5                   10

<210> SEQ ID NO 509
<211> LENGTH: 4
<212> TYPE: PRT
<213> ORGANISM: artificial sequence
<220> FEATURE:
<223> OTHER INFORMATION: synthetic peptide

<400> SEQUENCE: 509

Asn Ala Asn Pro
1

<210> SEQ ID NO 510
<211> LENGTH: 12
<212> TYPE: PRT
<213> ORGANISM: artificial sequence
<220> FEATURE:
<223> OTHER INFORMATION: synthetic peptide

<400> SEQUENCE: 510

Asn Ala Asn Pro Asn Val Asp Pro Asn Ala Asn Pro
1               5                   10

<210> SEQ ID NO 511
<211> LENGTH: 12
<212> TYPE: PRT
<213> ORGANISM: artificial sequence

```
<220> FEATURE:
<223> OTHER INFORMATION: synthetic peptide

<400> SEQUENCE: 511

Lys Leu Lys Gln Pro Gly Asp Gly Asn Pro Asp Pro
1               5                   10

<210> SEQ ID NO 512
<211> LENGTH: 8
<212> TYPE: PRT
<213> ORGANISM: artificial sequence
<220> FEATURE:
<223> OTHER INFORMATION: synthetic peptide

<400> SEQUENCE: 512

Asn Pro Asp Pro Asn Ala Asn Pro
1               5

<210> SEQ ID NO 513
<211> LENGTH: 15
<212> TYPE: PRT
<213> ORGANISM: artificial sequence
<220> FEATURE:
<223> OTHER INFORMATION: Biotinylation tag BirA enzyme substrate peptide

<400> SEQUENCE: 513

Leu His His Ile Leu Asp Ala Gln Lys Met Leu Trp Asn His Arg
1               5                   10                  15

<210> SEQ ID NO 514
<211> LENGTH: 12
<212> TYPE: PRT
<213> ORGANISM: artificial sequence
<220> FEATURE:
<223> OTHER INFORMATION: Biolinker

<400> SEQUENCE: 514

Asp Arg Asn Leu Pro Pro Leu Ala Pro Leu Gly Pro
1               5                   10

<210> SEQ ID NO 515
<211> LENGTH: 6
<212> TYPE: PRT
<213> ORGANISM: artificial sequence
<220> FEATURE:
<223> OTHER INFORMATION: Histidine Tag

<400> SEQUENCE: 515

His His His His His His
1               5

<210> SEQ ID NO 516
<211> LENGTH: 15
<212> TYPE: PRT
<213> ORGANISM: artificial sequence
<220> FEATURE:
<223> OTHER INFORMATION: Synthetic Peptide

<400> SEQUENCE: 516

Lys His Lys Lys Leu Lys Gln Pro Gly Asp Gly Asn Pro Asp Pro
1               5                   10                  15

<210> SEQ ID NO 517
<211> LENGTH: 9
<212> TYPE: PRT
<213> ORGANISM: artificial sequence
<220> FEATURE:
```

<223> OTHER INFORMATION: Synthetic Peptide

<400> SEQUENCE: 517

Lys His Lys Lys Leu Lys Gln Pro Gly
1               5

<210> SEQ ID NO 518
<211> LENGTH: 25
<212> TYPE: PRT
<213> ORGANISM: artificial sequence
<220> FEATURE:
<223> OTHER INFORMATION: Synthetic Peptide

<400> SEQUENCE: 518

Ser Gly Ser Gly Lys Pro Lys His Lys Lys Leu Lys Gln Pro Gly Asp
1               5                   10                  15

Gly Asn Pro Asp Pro Asn Ala Asn Pro
            20                  25

<210> SEQ ID NO 519
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 519

Ser Gly Ser Gly Lys His Lys Lys Leu Lys Gln Pro Gly
1               5                   10

<210> SEQ ID NO 520
<211> LENGTH: 23
<212> TYPE: PRT
<213> ORGANISM: artificial sequence
<220> FEATURE:
<223> OTHER INFORMATION: Synthetic Peptide

<400> SEQUENCE: 520

Ser Gly Ser Gly His Lys Lys Leu Lys Gln Pro Gly Asp Gly Asn Pro
1               5                   10                  15

Asp Pro Asn Ala Asn Pro Asn
            20

<210> SEQ ID NO 521
<211> LENGTH: 12
<212> TYPE: PRT
<213> ORGANISM: artificial sequence
<220> FEATURE:
<223> OTHER INFORMATION: Synthetic Peptide

<400> SEQUENCE: 521

Ser Gly Ser Gly Asn Pro Asp Pro Asn Ala Asn Pro
1               5                   10

<210> SEQ ID NO 522
<211> LENGTH: 16
<212> TYPE: PRT
<213> ORGANISM: artificial sequence
<220> FEATURE:
<223> OTHER INFORMATION: Synthetic Peptide

<400> SEQUENCE: 522

Ser Gly Ser Gly Asp Gly Asn Pro Asp Pro Asn Ala Asn Pro Asn Val
1               5                   10                  15

```
<210> SEQ ID NO 523
<211> LENGTH: 16
<212> TYPE: PRT
<213> ORGANISM: artificial sequence
<220> FEATURE:
<223> OTHER INFORMATION: Synthetic Peptide

<400> SEQUENCE: 523

Ser Gly Ser Gly Ala Gly Asn Pro Asp Pro Asn Ala Asn Pro Asn Val
1               5                   10                  15

<210> SEQ ID NO 524
<211> LENGTH: 16
<212> TYPE: PRT
<213> ORGANISM: artificial sequence
<220> FEATURE:
<223> OTHER INFORMATION: Synthetic Peptide

<400> SEQUENCE: 524

Ser Gly Ser Gly Asp Ala Asn Pro Asp Pro Asn Ala Asn Pro Asn Val
1               5                   10                  15

<210> SEQ ID NO 525
<211> LENGTH: 16
<212> TYPE: PRT
<213> ORGANISM: artificial sequence
<220> FEATURE:
<223> OTHER INFORMATION: Synthetic Peptide

<400> SEQUENCE: 525

Ser Gly Ser Gly Asp Gly Ala Pro Asp Pro Asn Ala Asn Pro Asn Val
1               5                   10                  15

<210> SEQ ID NO 526
<211> LENGTH: 16
<212> TYPE: PRT
<213> ORGANISM: artificial sequence
<220> FEATURE:
<223> OTHER INFORMATION: Synthetic Peptide

<400> SEQUENCE: 526

Ser Gly Ser Gly Asp Gly Asn Ala Asp Pro Asn Ala Asn Pro Asn Val
1               5                   10                  15

<210> SEQ ID NO 527
<211> LENGTH: 16
<212> TYPE: PRT
<213> ORGANISM: artificial sequence
<220> FEATURE:
<223> OTHER INFORMATION: Synthetic Peptide

<400> SEQUENCE: 527

Ser Gly Ser Gly Asp Gly Asn Pro Ala Pro Asn Ala Asn Pro Asn Val
1               5                   10                  15

<210> SEQ ID NO 528
<211> LENGTH: 16
<212> TYPE: PRT
<213> ORGANISM: artificial sequence
<220> FEATURE:
<223> OTHER INFORMATION: Synthetic Peptide

<400> SEQUENCE: 528

Ser Gly Ser Gly Asp Gly Asn Pro Asp Ala Asn Ala Asn Pro Asn Val
1               5                   10                  15

<210> SEQ ID NO 529
```

```
<211> LENGTH: 16
<212> TYPE: PRT
<213> ORGANISM: artificial sequence
<220> FEATURE:
<223> OTHER INFORMATION: Synthetic Peptide

<400> SEQUENCE: 529

Ser Gly Ser Gly Asp Gly Asn Pro Asp Pro Ala Ala Asn Pro Asn Val
1               5                   10                  15

<210> SEQ ID NO 530
<211> LENGTH: 16
<212> TYPE: PRT
<213> ORGANISM: artificial sequence
<220> FEATURE:
<223> OTHER INFORMATION: Synthetic Peptide

<400> SEQUENCE: 530

Ser Gly Ser Gly Asp Gly Asn Pro Asp Pro Asn Lys Asn Pro Asn Val
1               5                   10                  15

<210> SEQ ID NO 531
<211> LENGTH: 16
<212> TYPE: PRT
<213> ORGANISM: artificial sequence
<220> FEATURE:
<223> OTHER INFORMATION: Synthetic Peptide

<400> SEQUENCE: 531

Ser Gly Ser Gly Asp Gly Asn Pro Asp Pro Asn Ala Ala Pro Asn Val
1               5                   10                  15

<210> SEQ ID NO 532
<211> LENGTH: 16
<212> TYPE: PRT
<213> ORGANISM: artificial sequence
<220> FEATURE:
<223> OTHER INFORMATION: Synthetic Peptide

<400> SEQUENCE: 532

Ser Gly Ser Gly Asp Gly Asn Pro Asp Pro Asn Ala Asn Ala Asn Val
1               5                   10                  15

<210> SEQ ID NO 533
<211> LENGTH: 16
<212> TYPE: PRT
<213> ORGANISM: artificial sequence
<220> FEATURE:
<223> OTHER INFORMATION: Synthetic Peptide

<400> SEQUENCE: 533

Ser Gly Ser Gly Asp Gly Asn Pro Asp Pro Asn Ala Asn Pro Ala Val
1               5                   10                  15

<210> SEQ ID NO 534
<211> LENGTH: 16
<212> TYPE: PRT
<213> ORGANISM: artificial sequence
<220> FEATURE:
<223> OTHER INFORMATION: Synthetic Peptide

<400> SEQUENCE: 534

Ser Gly Ser Gly Asp Gly Asn Pro Asp Pro Asn Ala Asn Pro Asn Ala
1               5                   10                  15

<210> SEQ ID NO 535
<211> LENGTH: 12
```

```
<212> TYPE: PRT
<213> ORGANISM: artificial sequence
<220> FEATURE:
<223> OTHER INFORMATION: Synthetic Peptide

<400> SEQUENCE: 535

Asp Gly Asn Pro Asp Pro Asn Lys Asn Pro Asn Val
1               5                   10

<210> SEQ ID NO 536
<211> LENGTH: 12
<212> TYPE: PRT
<213> ORGANISM: artificial sequence
<220> FEATURE:
<223> OTHER INFORMATION: Synthetic Peptide

<400> SEQUENCE: 536

Asp Gly Asn Pro Asp Pro Asn Ala Ala Pro Asn Val
1               5                   10

<210> SEQ ID NO 537
<211> LENGTH: 142
<212> TYPE: PRT
<213> ORGANISM: artificial sequence
<220> FEATURE:
<223> OTHER INFORMATION: Synthetic Peptide

<400> SEQUENCE: 537

Met Asp Thr Leu Cys Ser Thr Leu Leu Leu Thr Ile Pro Ser Trp
1               5                   10                  15

Val Leu Ser Gln Ile Thr Leu Lys Glu Ser Gly Pro Thr Leu Val Lys
            20                  25                  30

Pro Thr Gln Thr Leu Thr Leu Thr Cys Thr Phe Pro Gly Phe Ala Leu
        35                  40                  45

Ser Thr Ser Gly Val Gly Val Gly Trp Ile Arg Gln Pro Pro Gly Lys
    50                  55                  60

Ala Leu Glu Trp Leu Ala Leu Ile Tyr Trp Asp Asp Lys Arg Tyr
65                  70                  75                  80

Ser Pro Ser Leu Lys Ser Arg Leu Thr Ile Thr Lys Asp Thr Ser Lys
                85                  90                  95

Asn Gln Val Val Leu Thr Val Thr Asn Met Asp Pro Val Asp Thr Ala
            100                 105                 110

Thr Tyr Tyr Cys Ala Leu Lys Asp Tyr Gly Asp Tyr Tyr Tyr Asp
        115                 120                 125

Met Asp Val Trp Gly Gln Gly Thr Thr Val Thr Val Ser Ser
    130                 135                 140

<210> SEQ ID NO 538
<211> LENGTH: 1260
<212> TYPE: DNA
<213> ORGANISM: artificial sequence
<220> FEATURE:
<223> OTHER INFORMATION: Complement Sequence

<400> SEQUENCE: 538
gcttaacccc tagctaggtg atcaattaat tgcgctacat tccatggtat acgacaaagt    60
tcttatagtc acgataccgt cgtcgtcgtt gtgggcacac gacttgctcg acttgatact   120
attgcgcccg tggttggaca tattgctcga cctttacttg ataatgccgt tcgtcctttt   180
gaccatgtcg acttttttt tgtcggcatc ggacccgctt ttgctactac cgttgttgtt   240
gttgccgcta ttgccggcac ttccgttttct acttctattt gcgctgccgt tattgcttct   300
```

```
attgctcttt gacgcatttg gctttgtgtt ttttgacttt gtcggcccgc taccgttagg    360
cctgggatta cgcttaggtt tacagctggg attacggtta ggcttacatc taggcttgcg    420
cttaggcttg cacctaggtt tacgtttagg gttacggtta ggtttacgtt tgggtttgcg    480
cttagggtta cggttagggt tgcgtttagg tttacgcttg ggtttacgtt tagggttgcg    540
tttagggtta cgcttgtggt tacggttagg gttgcgttta ggtttacggt tgggattacg    600
tttaggttta cgattaggtt tacatctagg attgcgattg ggtttacgat tgggattgcg    660
tttgggatta cggttaggat tacggttagg tttgcggtta ggcttgcgct tgggtttacg    720
gttgggattg cgcttaggat tacggttagg gttacggtta ggtttacggt taggcttgcg    780
cttaggctta cgcttaggct tacgattggg attacggttg gggttacggt tggggttacg    840
attagggttg cgtttgggat tgttttttgtt ggtcccgttg ccggtcccgg tattgtacgg    900
cttgctaggc ttggcattgc acctactttt gcgcttgcgc ttgttgcgcc actttttgtt    960
gttgttgctt cttggctcgc tatttgtgta gcttttttatg gactttttct aggtcttgtc   1020
ggactcgtgg cttaccagag gcacgtcgca ctggacgccg ttgccgtaag tccacgcata   1080
atttggcccg tcgcgcttgt ttggctttct actcgaccta atgcttttgc cgtagctttt   1140
tttttagacg ttttacctttt ttacgtcgtc gcacaaattg caccacttgt cgtcgtaacc   1200
ggactaagac cttgtagtag tagtagtagt gattggcgag ctcgcctcga aatgtagcg    1260
```

<210> SEQ ID NO 539
<211> LENGTH: 1131
<212> TYPE: DNA
<213> ORGANISM: artificial sequence
<220> FEATURE:
<223> OTHER INFORMATION: Recombinant CSP nucleotide sequence

<400> SEQUENCE: 539

```
acaatggcca gaaagctggc catcctgagc gtgtccagct tcctgttcgt ggaagccctg     60
ttccaggaat accagtgcta cggcagcagc agcaacacca gagtgctgaa cgagctgaac    120
tacgacaacg ccggcaccaa cctgtacaac gagctggaaa tgaactacta cggcaagcag    180
gaaaactggt acagcctgaa gaagaacagc agaagcctgg gcgagaacga cgacggcaac    240
aacgaggaca cgagaagct gcggaagccc aagcacaaga agctgaagca gcccgccgac    300
ggcaatcccg accccaacgc caaccccaac gtggacccta tgccaatcc taatgtggat    360 ccaaacgcta accctaatgt ggaccccaac gcaaatccca tgccaacccc taacgctaac    420
ccaaacgcca atccaaacgc aaaccccaac gctaatccta atgctaatcc caatgcaaac    480
ccaaatgcca atcccaacgc caatccaaat gcaaatccta acgccaaccc caatgctaac    540
cccaacgcca accctaatgc aaaaccaaat gctaacccta acgcaaatcc caacgtggac    600
cccaacgcaa accctaacgc caatccaaat gccaaccct atgccaatcc taacgcaaat    660
cctaatgcta atccaaacgc taatcccaac gccaatccta acgccaaccc caacgccaac    720
ccaaatgcca accccaatgc aaaccctaac gctaatccta acgctaaccc taatgccaat    780
cccaacgcca accccaatgc taatccaaat gccaacccaa caagaacaa ccagggcaac    840 ggccagggcc acaacatgcc caacgacccc aatcggaacg tggacgagaa cgccaatgcc    900
aatagcgccg tgaagaacaa caacaatgag gaacccagcg acaagcacat caaagagtac    960
ctgaacaaga tccagaacag cctgagcacc gagtggtccc cctgcagcgt gacatgcggc   1020
aatggaatcc aagtgcggat caagccccgc agcgccaaca agcccaagga tgagctggac   1080
```
tacgccaatg acatcgagaa gaaaatctgc aagatggaaa agtgcagctc t    1131

<210> SEQ ID NO 540
<211> LENGTH: 415
<212> TYPE: PRT
<213> ORGANISM: artificial sequence
<220> FEATURE:
<223> OTHER INFORMATION: Recombinant CSP amino acid sequence

<400> SEQUENCE: 540

Thr Met Ala Arg Lys Leu Ala Ile Leu Ser Val Ser Phe Leu Phe
1               5                   10                  15

Val Glu Ala Leu Phe Gln Glu Tyr Gln Cys Tyr Gly Ser Ser Asn
                20                  25                  30

Thr Arg Val Leu Asn Glu Leu Asn Tyr Asp Asn Ala Gly Thr Asn Leu
            35                  40                  45

Tyr Asn Glu Leu Glu Met Asn Tyr Tyr Gly Lys Gln Glu Asn Trp Tyr
        50                  55                  60

Ser Leu Lys Lys Asn Ser Arg Ser Leu Gly Glu Asn Asp Asp Gly Asn
65                  70                  75                  80

Asn Glu Asp Asn Glu Lys Leu Arg Lys Pro Lys His Lys Lys Leu Lys
                85                  90                  95

Gln Pro Ala Asp Gly Asn Pro Asp Pro Asn Ala Asn Pro Asn Val Asp
                100                 105                 110

Pro Asn Ala Asn Pro Asn Val Asp Pro Asn Ala Asn Pro Asn Val Asp
            115                 120                 125

Pro Asn Ala Asn Pro Asn Ala Asn Pro Asn Ala Asn Pro Asn Ala Asn
        130                 135                 140

Pro Asn Ala Asn Pro Asn Ala Asn Pro Asn Ala Asn Pro Asn Ala Asn
145                 150                 155                 160

Pro Asn Ala Asn Pro Asn Ala Asn Pro Asn Ala Asn Pro Asn Ala Asn
                165                 170                 175

Pro Asn Ala Asn Pro Asn Ala Asn Pro Asn Ala Asn Pro Asn Ala Asn
            180                 185                 190

Pro Asn Ala Asn Pro Asn Val Asp Pro Asn Ala Asn Pro Asn Ala Asn
        195                 200                 205

Pro Asn Ala Asn Pro Asn Ala Asn Pro Asn Ala Asn Pro Asn Ala Asn
            210                 215                 220

Pro Asn Ala Asn Pro Asn Ala Asn Pro Asn Ala Asn Pro Asn Ala Asn
225                 230                 235                 240

Pro Asn Ala Asn Pro Asn Ala Asn Pro Asn Ala Asn Pro Asn Ala Asn
                245                 250                 255

Pro Asn Ala Asn Pro Asn Ala Asn Pro Asn Ala Asn Pro Asn Ala Asn
            260                 265                 270

Pro Asn Lys Asn Asn Gln Gly Asn Gly Gln Gly His Asn Met Pro Asn
        275                 280                 285

Asp Pro Asn Arg Asn Val Asp Glu Asn Ala Asn Ala Asn Ser Ala Val
        290                 295                 300

Lys Asn Asn Asn Glu Glu Pro Ser Asp Lys His Ile Lys Glu Tyr
305                 310                 315                 320

Leu Asn Lys Ile Gln Asn Ser Leu Ser Thr Glu Trp Ser Pro Cys Ser
                325                 330                 335

Val Thr Cys Gly Asn Gly Ile Gln Val Arg Ile Lys Pro Gly Ser Ala
            340                 345                 350

Asn Lys Pro Lys Asp Glu Leu Asp Tyr Ala Asn Asp Ile Glu Lys Lys

```
                355                 360                 365
Ile Cys Lys Met Glu Lys Cys Ser Ser Gly Ala Pro Gly Ser Leu His
            370                 375                 380

His Ile Leu Asp Ala Gln Lys Met Leu Trp Asn His Arg Asp Arg Asn
385                 390                 395                 400

Leu Pro Pro Leu Ala Pro Leu Gly Pro His His His His His
                405                 410                 415
```

<210> SEQ ID NO 541
<211> LENGTH: 12
<212> TYPE: PRT
<213> ORGANISM: Artificial Sequence
<220> FEATURE:
<223> OTHER INFORMATION: synthetic peptide

<400> SEQUENCE: 541

```
Asp Gly Asn Pro Asp Pro Asn Ala Asn Pro Asn Val
1               5                   10
```

<210> SEQ ID NO 542
<211> LENGTH: 4
<212> TYPE: DNA
<213> ORGANISM: Artificial Sequence
<220> FEATURE:
<223> OTHER INFORMATION: recombinant nucleotide

<400> SEQUENCE: 542 tgaa                                                                    4

<210> SEQ ID NO 543
<211> LENGTH: 6
<212> TYPE: DNA
<213> ORGANISM: Artificial Sequence
<220> FEATURE:
<223> OTHER INFORMATION: recombinant nucleotide

<400> SEQUENCE: 543 ttcttt                                                                  6

<210> SEQ ID NO 544
<211> LENGTH: 13
<212> TYPE: DNA
<213> ORGANISM: Artificial Sequence
<220> FEATURE:
<223> OTHER INFORMATION: recombinant nucleotide

<400> SEQUENCE: 544
tgggttttgt cct                                                         13

<210> SEQ ID NO 545
<211> LENGTH: 11
<212> TYPE: DNA
<213> ORGANISM: Artificial Sequence
<220> FEATURE:
<223> OTHER INFORMATION: recombinant nucleotide

```
<400> SEQUENCE: 545
gccagtctat c                                                          11

<210> SEQ ID NO 546
<211> LENGTH: 12
<212> TYPE: DNA
<213> ORGANISM: Artificial Sequence
<220> FEATURE:
<223> OTHER INFORMATION: recombinant nucleotide

<400> SEQUENCE: 546
acttgttctg gt                                                         12
```